(12) United States Patent
MacCoss et al.

(10) Patent No.: US 8,735,414 B2
(45) Date of Patent: *May 27, 2014

(54) INDOLE DERIVATIVES AND METHODS FOR ANTIVIRAL TREATMENT

(75) Inventors: Malcolm MacCoss, Seakbrook Island, SC (US); F. George Njoroge, Warren, NJ (US); Amin Nomeir, Milford, NJ (US); Guangming Chen, Bridgewater, NJ (US); Song Xiao Huang, New Providence, NJ (US); Ramesh Kakarla, South Glastonbury, CT (US); Gary Mitchell Karp, Princeton Junction, NJ (US); William Joseph Lennox, Bedminster, NJ (US); Chunshi Li, East Brunswick, NJ (US); Ronggang Liu, Berwyn, PA (US); Yalei Liu, Hillsborough, NJ (US); Christie Morrill, Green Brook, NJ (US); Steven D. Paget, Hillsborough, NJ (US); Sean W Smith, New Brunswick, NJ (US); James Takasugi, Lawrenceville, NJ (US); Anthony A. Turpoff, Hillsborough, NJ (US); Hongyu Ren, Dayton, NJ (US); Nanjing Zhang, Princeton, NJ (US); Xiaoyan Zhang, Belle Mead, NJ (US); Jin Zhu, Raritan, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/259,717

(22) PCT Filed: Apr. 5, 2010

(86) PCT No.: PCT/US2010/029923
§ 371 (c)(1),
(2), (4) Date: Mar. 28, 2012

(87) PCT Pub. No.: WO2010/117932
PCT Pub. Date: Oct. 14, 2010

(65) Prior Publication Data
US 2012/0184574 A1    Jul. 19, 2012

Related U.S. Application Data

(60) Provisional application No. 61/166,893, filed on Apr. 6, 2009.

(51) Int. Cl.
| | |
|---|---|
| A61K 31/506 | (2006.01) |
| C07D 401/02 | (2006.01) |
| C07D 405/02 | (2006.01) |
| C07D 209/04 | (2006.01) |

(52) U.S. Cl.
USPC ............ 514/275; 544/331; 546/256; 548/518

(58) Field of Classification Search
None
See application file for complete search history.

(56) References Cited

U.S. PATENT DOCUMENTS

2007/0299068 A1 * 12/2007 Karp et al. ............... 514/235.2

FOREIGN PATENT DOCUMENTS

| EP | 1162196 A1 | 12/2001 |
| WO | 2004065367 A1 | 8/2004 |
| WO | 2006019831 A1 | 2/2006 |
| WO | WO 2006/019831 * | 2/2006 |
| WO | WO 2008137816 A2 * | 11/2008 |
| WO | 2009156462 A2 | 12/2009 |

OTHER PUBLICATIONS

Johnson et al. (Heterocycles, vol. 24, No. B, 1986, 2127-2131).*
Morissette et al., Advanced Drug Delivery Reviews 2004, 56, 275-300.*
Hamdi et al., Solvates of indomethacin. Journal of Thermal Analysis and Calorimetry 2004, 76, 985-1001.*
Tan et al, Nature Review Drug Discovery, 2002, 1, 867-881.*
Schafer et al. Drug Discovery Today 2008, 13 (21/22), 913-916.*
International Search Report for PCT/US2010/029923, mailed Aug. 26, 2010.
Written Opinion for PCT/US2010/029923, mailed Aug. 26, 2010.

* cited by examiner

*Primary Examiner* — Brandon Fetterolf
*Assistant Examiner* — Ana Z Muresan
(74) *Attorney, Agent, or Firm* — Hoffmann & Baron, LLP

(57) ABSTRACT

The present invention is directed to compounds and forms and pharmaceutical compositions thereof useful for treating a viral infection, or for affecting viral activity by modulating viral replication.

15 Claims, No Drawings

INDOLE DERIVATIVES AND METHODS FOR ANTIVIRAL TREATMENT

CROSS-REFERENCE TO RELATED APPLICATIONS

This application is the National Stage of International Application No. PCT/US2010/029923, filed Apr. 5, 2010 which claims benefit to provisional U.S. Ser. No. 61/166,893, filed Apr. 6, 2009, herein incorporated by reference.

This application is related to U.S. patent application Ser. No. 13/259,386, entitled "HCV Inhibitor and Therapeutic Agent Combinations."

GOVERNMENT SUPPORT

The present invention was not made with U.S. Government support.

STATEMENT OF JOINT RESEARCH AGREEMENT

The present invention was made by or on behalf of parties to a joint research agreement that was in effect on or before the date the invention was made, specifically, the present invention was made as a result of activities undertaken within the scope of the joint research agreement to which PTC Therapeutics, Inc. and Schering Corporation are parties.

FIELD OF THE INVENTION

The present invention is directed to compounds, pharmaceutical compositions, and methods of using such compounds or compositions thereof for treating a viral infection, or for affecting viral activity by modulating viral replication. More particularly, the present invention relates to indole compounds or compositions and methods for use thereof for treating or ameliorating Hepatitis C Virus (HCV) infection or disorders or symptoms associated therewith by inhibiting Hepatitis C viral replication.

BACKGROUND OF THE INVENTION

An estimated 170 million people worldwide are reported to be infected with the Hepatitis C virus, the causative agent of hepatitis C. Seventy to eighty percent of HCV infections lead to chronic liver infection, which in turn may result in severe liver disease, including liver fibrosis, cirrhosis, and hepatocellular carcinoma (see Saito I, et al., Hepatitis C virus infection is associated with the development of hepatocellular carcinoma, *Proc Natl Acad Sci USA*, 2003, 87:6547-6549).

Although the treatment outcome is variable among the six major HCV genotypes, only about one-half of all treated patients respond to therapy, suggesting that the virus encodes protein products that may directly or indirectly attenuate the antiviral action of interferon (IFN). IFNs are naturally produced in response to viral infection, and cellular exposure to IFN leads to the induced expression of a variety of IFN-stimulated genes (ISGs), many of which have an antiviral function. ISG action can limit virus replication at multiple points within the replicative cycle.

Compounds and methods for treating Hepatitis C have been disclosed in U.S. patent application Ser. No. 11/653,450, filed Jan. 16, 2007 (having corresponding International Application No. PCT/US2007/00996, filed Jan. 16, 2007), U.S. patent application Ser. No. 11/653,448, filed Jan. 16, 2007 (having corresponding International Application No. PCT/US2007/00923, filed Jan. 16, 2007), each of which are a continuation-in-part of U.S. patent application Ser. No. 11/331,180, filed Jan. 13, 2006, which is a continuation-in-part of U.S. patent application Ser. No. 11/180,961, filed Jul. 14, 2005 (having corresponding International Application No. PCT/US2005/024881, filed Jul. 14, 2005), each of which are incorporated herein by reference in their entirety and for all purposes.

United States Patent Publication 2006/0235028 discloses certain aryl and heteroaryl compounds as 11-beta-hydroxysteroid dehydrogenase type I inhibitors.

All other documents referred to herein are incorporated by reference into the present application as though fully set forth herein.

SUMMARY OF THE INVENTION

The present invention is directed to a compound of Formula (I):

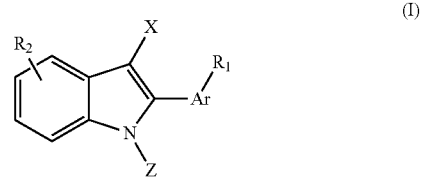

(I)

wherein $R_1$, $R_2$, X, Z and Ar are as defined herein and forms and compositions thereof, and methods of using such compounds, forms or compositions thereof for treating a viral infection, or for affecting viral activity by modulating viral replication.

DETAILED DESCRIPTION OF THE INVENTION

The present invention is directed to a compound of Formula (I):

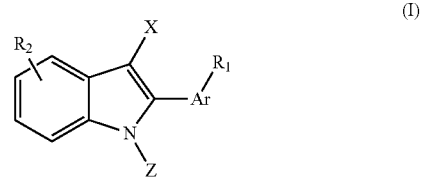

(I)

or a free acid, free base, salt, hydrate, solvate, clathrate, isotopologue, racemate, enantiomer, diastereomer, stereoisomer or polymorph form thereof, wherein X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-amino-carbonyl or $C_{1-8}$alkyl-sulfonyl-;

Ar is heteroaryl or heterocyclyl, each optionally substituted with one or two substituents independently selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, $C_{1-8}$alkoxy-carbonyl, carboxyl, $C_{3-14}$cycloalkyl, $C_{1-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino, $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl, $C_{1-8}$alkyl-carbonyloxy or amino-sulfonyl;

$R_1$ is —N($R_3$)—SO$_2$—$R_4$, —N($R_3$)—SO$_2$—N($R_5$)—$R_6$, —SO$_2$—N($R_5$)—$R_6$ or —SO$_2$—$R_7$;

$R_2$ is one, two, three or four substituents each selected from hydrogen, halogen, hydroxy, cyano, nitro, $C_{1-8}$alkyl, hydroxy-$C_{1-8}$alkyl, halo-$C_{1-8}$alkyl, $C_{2-8}$alkenyl, halo-$C_{2-8}$alkenyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, $C_{1-8}$alkyl-amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkylthio, $C_{1-8}$alkyl-sulfinyl, $C_{1-8}$alkyl-sulfonyl, $C_{1-8}$alkyl-sulfonyl-amino, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

$R_3$ is hydrogen or $C_{1-8}$alkyl, optionally substituted on $C_{1-8}$alkyl with one or more substituents each selected from halogen, hydroxy, cyano, $C_{1-8}$alkoxy, amino or $C_{1-8}$alkyl-amino;

$R_4$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

$R_5$ is hydrogen, $C_{1-8}$alkyl, $C_{1-8}$alkyl-carbonyl- or $C_{3-14}$cycloalkyl, optionally substituted on $C_{1-8}$alkyl with one or more substituents each selected from halogen, hydroxy, cyano or $C_{1-8}$alkoxy;

$R_6$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino; and $R_7$ is $C_{1-8}$alkyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, $C_{3-14}$cycloalkyl and heterocyclyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino.

Embodiments of the present invention include a compound of Formula (I) and forms thereof, wherein X is selected from hydrogen, cyano, carboxyl, amino-carbonyl or $C_{1-8}$alkyl-amino-carbonyl;

Ar is heteroaryl;

Z is $C_{1-8}$alkyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with a substituent selected from cyano, halogen, $C_{1-8}$alkyl, $C_{1-8}$alkoxy, amino or $C_{1-8}$alkyl-amino;

$R_2$ is one, two or three substituents each selected from hydrogen, halogen, hydroxy, cyano, $C_{1-8}$alkyl, hydroxy-$C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy, amino, $C_{1-8}$alkyl-amino, amino-$C_{1-8}$alkyl, $C_{1-8}$alkyl-amino-$C_{1-8}$alkyl, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy or heterocyclyloxy, wherein heteroaryloxy is optionally substituted with a cyano substituent;

$R_3$ is hydrogen or $C_{1-8}$alkyl, optionally substituted on $C_{1-8}$alkyl with one or more substituents each selected from halogen, hydroxy or cyano;

$R_4$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl;

$R_5$ is hydrogen;

$R_6$ is hydrogen, $C_{1-8}$alkyl, hydroxy-$C_{1-8}$alkyl, halo-$C_{1-8}$alkyl, cyano-$C_{1-8}$alkyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from halogen, $C_{1-8}$alkyl or halo-$C_{1-8}$alkyl; and $R_7$ is $C_{1-8}$alkyl or heterocyclyl;

and all other variables are as previously defined.

Embodiments of the present invention include a compound of Formula (I) and forms thereof, wherein X is cyano;

Ar is pyridinyl, pyrimidinyl or pyridazinyl;

Z is $C_{1-8}$alkyl, cyclopropyl, cyclobutyl, cyclopentyl, cyclohexyl, cyclohexenyl, cyclopropyl-methyl, phenyl, thiazolyl, pyridinyl, pyrimidinyl, pyrazinyl, pyridazinyl, triazinyl or tetrahydrofuran, wherein phenyl is optionally substituted with a substituent selected from cyano, halogen, $C_{1-8}$alkyl or $C_{1-8}$alkoxy;

$R_2$ is one, two or three substituents each selected from hydrogen, halogen, hydroxy, cyano, $C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkylthio, $C_{1-8}$alkyl-sulfinyl, $C_{1-8}$alkyl-sulfonyl, cyclopropyl, cyclobutyl, cyclobutoxy, pyridinyloxy, pyrimidinyloxy, pyrazinyloxy or morpholinyl, wherein pyridinyl and pyrazinyl are each optionally substituted with a cyano substituent;

$R_3$ is hydrogen, methyl, ethyl, propyl, isopropyl or tert-butyl, wherein methyl, ethyl, propyl and isopropyl are each optionally substituted with one or more substituents each selected from halogen, hydroxy or cyano;

$R_4$ is $C_{1-8}$alkyl or cyclopropyl;

$R_6$ is hydrogen, $C_{1-8}$alkyl, hydroxy-$C_{1-8}$alkyl, halo-$C_{1-8}$alkyl, cyano-$C_{1-8}$alkyl, cyclopropyl, cyclobutyl or 1-cyclopropyl-ethyl, wherein each instance of cyclopropyl and cyclobutyl is optionally substituted with one or two substituents each selected from halogen, $C_{1-8}$alkyl or halo-$C_{1-8}$alkyl; and $R_7$ is $C_{1-8}$alkyl or piperidinyl;

and all other variables are as previously defined.

Embodiments of the present invention include a compound of Formula (I) and forms thereof, wherein the isotopologue is deuterium.

Embodiments of the present invention include a compound of Formula (I) and forms thereof, wherein $R_2$ is $C_{1-8}$alkyl wherein from 1 to 3 hydrogen atoms are optionally replaced with deuterium;

$R_4$ is $C_{1-8}$alkyl wherein from 1 to 3 hydrogen atoms are optionally replaced with deuterium or halo-$C_{1-8}$alkyl wherein from 1 to 3 hydrogen atoms are optionally replaced with deuterium;

$R_6$ is $C_{1-8}$alkyl wherein from 1 to 3 hydrogen atoms are optionally replaced with deuterium or halo-$C_{1-8}$alkyl wherein from 1 to 3 hydrogen atoms are optionally replaced with deuterium; and $R_7$ is $C_{1-8}$alkyl wherein from 1 to 3 hydrogen atoms are optionally replaced with deuterium or halo-$C_{1-8}$alkyl wherein from 1 to 3 hydrogen atoms are optionally replaced with deuterium.

Embodiments of the present invention include a compound of Formula (I) and forms thereof, wherein Z is methyl, ethyl, 2-hydroxy-ethyl-, propyl, isopropyl, tert-butyl, cyclopropyl, cyclobutyl, cyclopentyl, cyclohexyl, cyclohexenyl, cyclopropyl-methyl, (cyclopropyl, methyl)methyl-, phenyl, thiazolyl, pyridinyl, pyrimidinyl, pyrazinyl, pyridazinyl, pyrazolyl, tetrahydro-2H-pyranyl, 1,6-dihydropyrimidinyl, thienyl, furanyl, oxazolyl, triazinyl or tetrahydrofuran, wherein phenyl, oxazolyl, pyridinyl, pyrimidinyl, pyrazinyl, pyrazolyl, thienyl, furanyl, thiazoyl is optionally substituted with one, two or three substituents each selected from chloro, cyano, nitro, trifluoromethyl, methyl-carbonyl-, methoxy-carbonyl, amino-sulfonyl-, hydroxymethyl-, fluoro, methyl or methoxy;

$R_2$ is one, two or three substituents each selected from hydrogen, chloro, fluoro, bromo, hydroxy, cyano, methyl, ethyl, isopropyl, fluoromethyl, difluoromethyl, trifluoromethyl, difluoroethyl, difluoroethenyl, ethoxy, methoxy, isopropoxy, difluoromethoxy, trifluoromethoxy, difluoroethoxy, trifluoroethoxy, methylthio, isopropylthio, 1-hydroxy-ethyl-, 2-methyl-1,3-dioxolanyl, propenyl, cyclopropyl, cyclobutyl, cyclobutoxy, pyridinyloxy, pyrimidinyloxy, pyrazinyloxy, vinyl, methyl-carbonyl-, or morpholinyl, wherein pyridinyl and pyrazinyl are each optionally substituted with a cyano substituent;

$R_4$ is methyl, ethyl, propyl, isopropyl, tert-butyl or cyclopropyl;

$R_6$ is hydrogen, methyl, ethyl, propyl, isopropyl, tert-butyl, dihydroxyisopropyl, difluoroisopropyl, trifluoroisopropyl, fluoro-tert-butyl, trifluoro-tert-butyl, cyano-methyl, 1-cyano-ethyl, cyclopropyl, cyclobutyl or 1-cyclopropyl-ethyl, wherein each instance of cyclopropyl and cyclobutyl is optionally substituted with one or two substituents each selected from fluoro, methyl or trifluoromethyl;

$R_7$ is methyl, ethyl, propyl, isopropyl, tert-butyl or piperidinyl;

and all other variables are as previously defined.

Embodiments of the present invention include a compound of Formula (I) and forms thereof, wherein X is selected from hydrogen, chloro, cyano, amino-carbonyl, methoxy-carbonyl-, carboxyl-, methyl-amino-carbonyl, ethyl-amino-carbonyl, isopropyl-amino-carbonyl, dimethyl-amino-carbonyl, methyl-sulfonyl or methyl-carbonyl.

Embodiments of the present invention include a compound of Formula (I) and forms thereof, wherein X is cyano.

Embodiments of the present invention include a compound of Formula (I) and forms thereof, wherein Ar is heteroaryl or heterocyclyl.

Embodiments of the present invention include a compound of Formula (I) and forms thereof, wherein Ar is heteroaryl.

Embodiments of the present invention include a compound of Formula (I) and forms thereof, wherein Ar is pyridinyl, pyrimidinyl or pyridazinyl.

Embodiments of the present invention include a compound of Formula (I) and forms thereof, wherein Z is $C_{1-8}$alkyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with a substituent selected from cyano, halogen, $C_{1-8}$alkyl, $C_{1-8}$alkoxy, amino or $C_{1-8}$alkyl-amino.

Embodiments of the present invention include a compound of Formula (I) and forms thereof, wherein Z is $C_{1-8}$alkyl, cyclopropyl, cyclobutyl, cyclopentyl, cyclohexyl, cyclohexenyl, cyclopropyl-methyl, (cyclopropyl, methyl)methyl-, phenyl, thiazolyl, pyridinyl, pyrimidinyl, pyrazinyl, pyridazinyl, pyrazolyl, tetrahydro-2H-pyranyl, 1,6-dihydropyrimidinyl, thienyl, furanyl, oxazolyl, triazinyl or tetrahydrofuran, wherein phenyl, oxazolyl, pyridinyl, pyrimidinyl, pyrazinyl, pyrazolyl, thienyl, furanyl, thiazoyl is optionally substituted with one, two or three substituents each selected from chloro, cyano, nitro, halo-$C_{1-8}$alkyl, $C_{1-8}$alkyl-carbonyl-, $C_{1-8}$alkoxy-carbonyl, amino-sulfonyl, hydroxyl-$C_{1-8}$alkyl-, cyano, halogen, $C_{1-8}$alkyl or $C_{1-8}$alkoxy.

Embodiments of the present invention include a compound of Formula (I) and forms thereof, wherein Z is methyl, ethyl, 2-hydroxy-ethyl-, propyl, isopropyl, tert-butyl, cyclopropyl, cyclobutyl, cyclopentyl, cyclohexyl, cyclohexenyl, cyclopropyl-methyl, (cyclopropyl, methyl)methyl-, phenyl, thiazolyl, pyridinyl, pyrimidinyl, pyrazinyl, pyridazinyl, pyrazolyl, tetrahydro-2H-pyranyl, 1,6-dihydropyrimidinyl, thienyl, furanyl, oxazolyl, triazinyl or tetrahydrofuran, wherein phenyl, oxazolyl, pyridinyl, pyrimidinyl, pyrazinyl, pyrazolyl, thienyl, furanyl, thiazoyl is optionally substituted with one, two or three substituents each selected from chloro, nitro, trifluoromethyl, methyl-carbonyl-, methoxy-carbonyl, amino-sulfonyl, hydroxymethyl-, cyano, fluoro, methyl or methoxy.

Embodiments of the present invention include a compound of Formula (I) and forms thereof, wherein $R_2$ is one, two or three substituents each selected from hydrogen, halogen, hydroxy, cyano, $C_{1-8}$alkyl, hydroxy-$C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy, amino, $C_{1-8}$alkyl-amino, amino-$C_{1-8}$alkyl, $C_{1-8}$alkyl-amino-$C_{1-8}$alkyl, $C_{1-8}$alkylthio, $C_{1-8}$alkyl-sulfinyl, $C_{1-8}$alkyl sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy or heterocyclyloxy, wherein heteroaryloxy is optionally substituted with a cyano substituent.

Embodiments of the present invention include a compound of Formula (I) and forms thereof, wherein $R_2$ is one, two or three substituents each selected from hydrogen, halogen, hydroxy, cyano, $C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyloxy, heteroaryloxy or heterocyclyl, wherein heteroaryloxy is optionally substituted with a cyano substituent.

Embodiments of the present invention include a compound of Formula (I) and forms thereof, wherein $R_2$ is one, two or three substituents each selected from hydrogen, chloro, fluoro, bromo, hydroxy, cyano, methyl, ethyl, isopropyl, fluoromethyl, difluoromethyl, trifluoromethyl, difluoroethyl, difluoroethenyl, ethoxy, methoxy, isopropoxy, difluoromethoxy, trifluoromethoxy, difluoroethoxy, trifluoroethoxy, methylthio, isopropylthio, 1-hydroxy-ethyl-, 2-methyl-1,3-dioxolanyl, propenyl, cyclopropyl, cyclobutyl, cyclobutoxy, pyridinyloxy, pyrimidinyloxy, pyrazinyloxy vinyl, methyl-carbonyl-, or morpholinyl, wherein pyridinyl and pyrazinyl are each optionally substituted with a cyano substituent.

Embodiments of the present invention include a compound of Formula (I) and forms thereof, wherein $R_3$ is hydrogen or $C_{1-8}$alkyl, optionally substituted on $C_{1-8}$alkyl with one or more substituents each selected from halogen, hydroxy or cyano.

Embodiments of the present invention include a compound of Formula (I) and forms thereof, wherein $R_3$ is hydrogen, methyl, ethyl, propyl, isopropyl or tert-butyl, wherein methyl and ethyl are each optionally substituted with one or more substituents each selected from halogen, hydroxy or cyano.

Embodiments of the present invention include a compound of Formula (I) and forms thereof, wherein $R_4$ is $C_{1-8}$alkyl, halo-$C_{1-8}$alkyl, $C_{1-8}$alkoxy, halo-$C_{1-8}$alkoxy, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl.

Embodiments of the present invention include a compound of Formula (I) and forms thereof, wherein $R_4$ is $C_{1-8}$alkyl or $C_{3-14}$cycloalkyl.

Embodiments of the present invention include a compound of Formula (I) and forms thereof, wherein $R_4$ is $C_{1-8}$alkyl or cyclopropyl.

Embodiments of the present invention include a compound of Formula (I) and forms thereof, wherein $R_4$ is methyl, ethyl, propyl, isopropyl, tert-butyl or cyclopropyl.

Embodiments of the present invention include a compound of Formula (I) and forms thereof, wherein $R_5$ is hydrogen.

Embodiments of the present invention include a compound of Formula (I) and forms thereof, wherein $R_6$ is hydrogen, $C_{1-8}$alkyl, hydroxy-$C_{1-8}$alkyl, halo-$C_{1-8}$alkyl, cyano-$C_{1-8}$alkyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino.

Embodiments of the present invention include a compound of Formula (I) and forms thereof, wherein $R_6$ is hydrogen, $C_{1-8}$alkyl, hydroxy-$C_{1-8}$alkyl, halo-$C_{1-8}$alkyl, cyano-$C_{1-8}$alkyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from halogen, $C_{1-8}$alkyl or halo-$C_{1-8}$alkyl.

Embodiments of the present invention include a compound of Formula (I) and forms thereof, wherein $R_6$ is hydrogen, methyl, ethyl, propyl, isopropyl, tert-butyl, dihydroxyisopropyl, difluoroisopropyl, trifluoroisopropyl, fluoro-tert-butyl, trifluoro-tert-butyl, cyano-methyl, 1-cyano-ethyl, cyclopropyl, cyclobutyl, cyclobutyl-methyl-, 1-(trifluoromethyl)ethyl-, 1-(trifluoromethyl)isopropyl, 1-(trifluoromethyl)propyl, pyrimidinyl, phenyl or 1-cyclopropyl-ethyl, wherein each instance of cyclopropyl and cyclobutyl is optionally substituted with one or two substituents each selected from fluoro, methyl or trifluoromethyl.

Embodiments of the present invention include a compound of Formula (I) and forms thereof, wherein $R_7$ is $C_{1-8}$alkyl or heterocyclyl.

Embodiments of the present invention include a compound of Formula (I) and forms thereof, wherein $R_7$ is $C_{1-8}$alkyl or piperidinyl.

Embodiments of the present invention include a compound of Formula (I) and forms thereof, wherein $R_7$ is methyl, ethyl, propyl, isopropyl, tert-butyl or piperidinyl.

Embodiments of the present invention include a compound of Formula (I) and forms thereof, wherein $R_7$ is piperidinyl.

Embodiments of the present invention include a compound of Formula (I), selected from a compound of Formula (Ia):

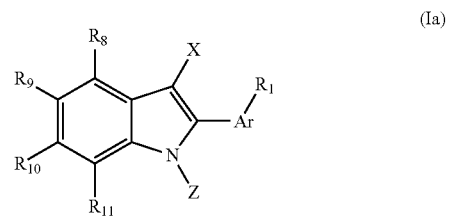

(Ia)

or a free acid, free base, salt, hydrate, solvate, clathrate, isotopologue, racemate, enantiomer, diastereomer, stereoisomer or polymorph form thereof, wherein $R_8$ is hydrogen, halogen or $C_{1-8}$alkoxy;

$R_9$ is hydrogen, halogen, hydroxy, cyano, nitro, $C_{1-8}$alkyl, halo-$C_{1-8}$alkyl, $C_{1-8}$alkoxy, halo-$C_{1-8}$alkoxy, $C_{1-8}$alkyl-carbonyl, $C_{1-8}$alkoxy-carbonyl, amino, $C_{1-8}$alkyl-amino, amino-$C_{1-8}$alkyl, $C_{1-8}$alkyl-amino-$C_{1-8}$alkyl, $C_{1-8}$alkylthio, $C_{3-14}$cycloalkyl, $C_{3-14}$cycloalkyl-$C_{1-8}$alkoxy, aryl, aryl-$C_{1-8}$alkoxy, heteroaryl, heteroaryl-$C_{1-8}$alkoxy, heterocyclyl or heterocyclyl-$C_{1-8}$alkoxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

$R_{10}$ is hydrogen, halogen, hydroxy, cyano, nitro, $C_{1-8}$alkyl, halo-$C_{1-8}$alkyl, $C_{2-8}$alkenyl, halo-$C_{2-8}$alkenyl, hydroxy-$C_{1-8}$alkyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkoxy, amino, $C_{1-8}$alkyl-amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkylthio, $C_{1-8}$alkyl-sulfinyl, $C_{1-8}$alkyl-sulfonyl, $C_{1-8}$alkyl-sulfonyl-amino, $C_{3-14}$cycloalkyl, $C_{3-14}$cycloalkyl-$C_{1-8}$alkoxy, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$ alkyl, heterocyclyl-$C_{1-8}$alkoxy, heterocyclyloxy or heterocyclyl-carbonyloxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl; and $R_{11}$ is hydrogen, halogen, hydroxy, cyano, nitro, $C_{1-8}$alkyl, halo-$C_{1-8}$alkyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy or $C_{1-8}$alkyl-carbonyloxy-$C_{1-8}$alkyl;

and all other variables are as previously defined.

Embodiments of the present invention include a compound of Formula (Ia) and forms thereof, wherein $R_8$ is hydrogen or halogen;

$R_9$ is hydrogen, halogen, hydroxy, cyano, $C_{1-8}$alkyl, halo-$C_{1-8}$alkyl, $C_{1-8}$alkoxy, halo-$C_{1-8}$alkoxy, $C_{1-8}$alkylthio or $C_{3-14}$cycloalkyl;

$R_{10}$ is hydrogen, halogen, hydroxy, cyano, $C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkylthio, $C_{3-14}$cycloalkyl, $C_{3-14}$cycloalkyloxy, heteroaryloxy or heterocyclyl, wherein heteroaryloxy is optionally substituted with a cyano substituent; and $R_{11}$ is hydrogen or halogen;

and all other variables are as previously defined.

Embodiments of the present invention include a compound of Formula (Ia) and forms thereof, wherein $R_9$ is hydrogen, halogen, hydroxy, cyano, $C_{1-8}$alkyl, halo-$C_{1-8}$alkyl, $C_{1-8}$alkoxy, halo-$C_{1-8}$alkoxy, $C_{1-8}$alkylthio or cyclopropyl; and $R_{10}$ is hydrogen, halogen, hydroxy, cyano, $C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkylthio, cyclopropyl, cyclobutyl, cyclobutoxy, pyridinyloxy, pyrimidinyloxy, pyrazinyloxy or morpholinyl, wherein pyridinyl and pyrazinyl are optionally substituted with a cyano substituent;

and all other variables are as previously defined.

Embodiments of the present invention include a compound of Formula (Ia) and forms thereof, wherein $R_8$ is hydrogen, fluoro or methoxy;

$R_9$ is hydrogen, chloro, fluoro, bromo, hydroxy, cyano, methyl, ethyl, fluoromethyl, difluoromethyl, difluoroethyl, methoxy, difluoromethoxy, trifluoromethoxy, methylthio or cyclopropyl;

$R_{10}$ is hydrogen, bromo, chloro, fluoro, hydroxy, cyano, methyl, ethyl, isopropyl, fluoromethyl, difluoromethyl, difluoroethyl, difluoroethenyl, methoxy, ethoxy, isopropoxy, difluoromethoxy, trifluoromethoxy, fluoroethoxy, difluoroethoxy, trifluoroethoxy, methylthio, isopropylthio, methyl-carbonyl, vinyl, propenyl, 1-hydroxy-ethyl, 2-methyl-1,3-dioxolanyl, propenyl, cyclopropyl, cyclobutyl, cyclobutoxy, pyridinyloxy, pyrimidinyloxy, pyrazinyloxy or morpholinyl, wherein pyridinyl and pyrazinyl are optionally substituted with a cyano substituent; and $R_{11}$ is hydrogen, chloro, fluoro or methyl;

and all other variables are as previously defined.

In one embodiment of the present invention, a compound of Formula (I) or a free acid, free base, salt, hydrate, solvate, clathrate, isotopologue, racemate, enantiomer, diastereomer, stereoisomer or polymorph form thereof is selected from:

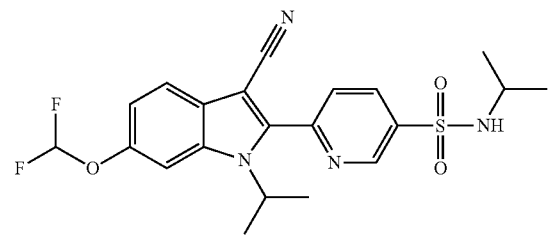

1

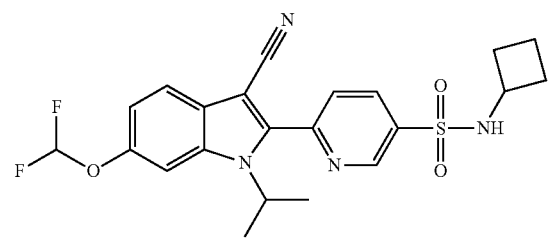

2

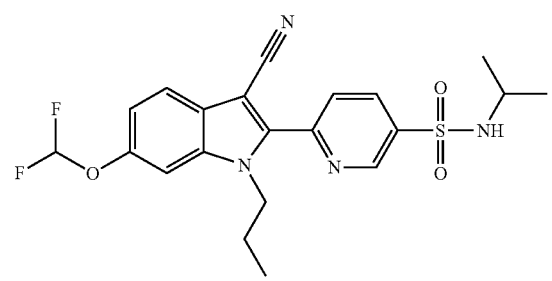

3

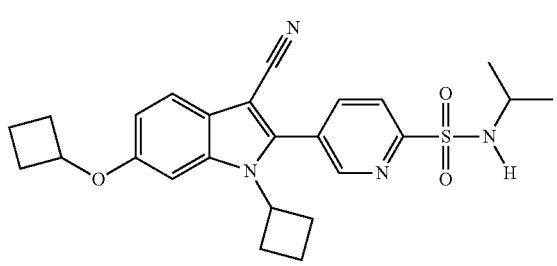

4

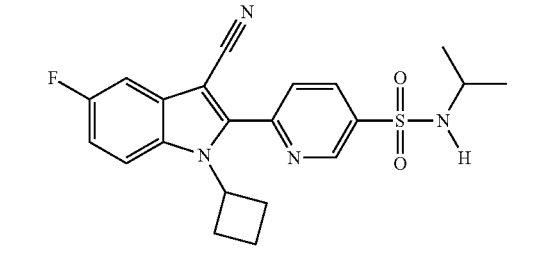

5

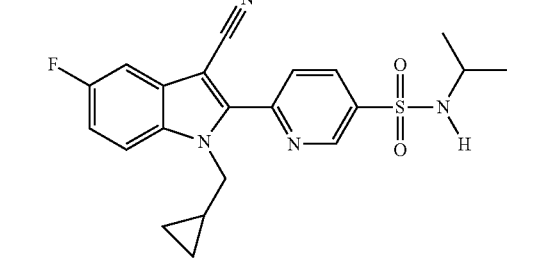

6

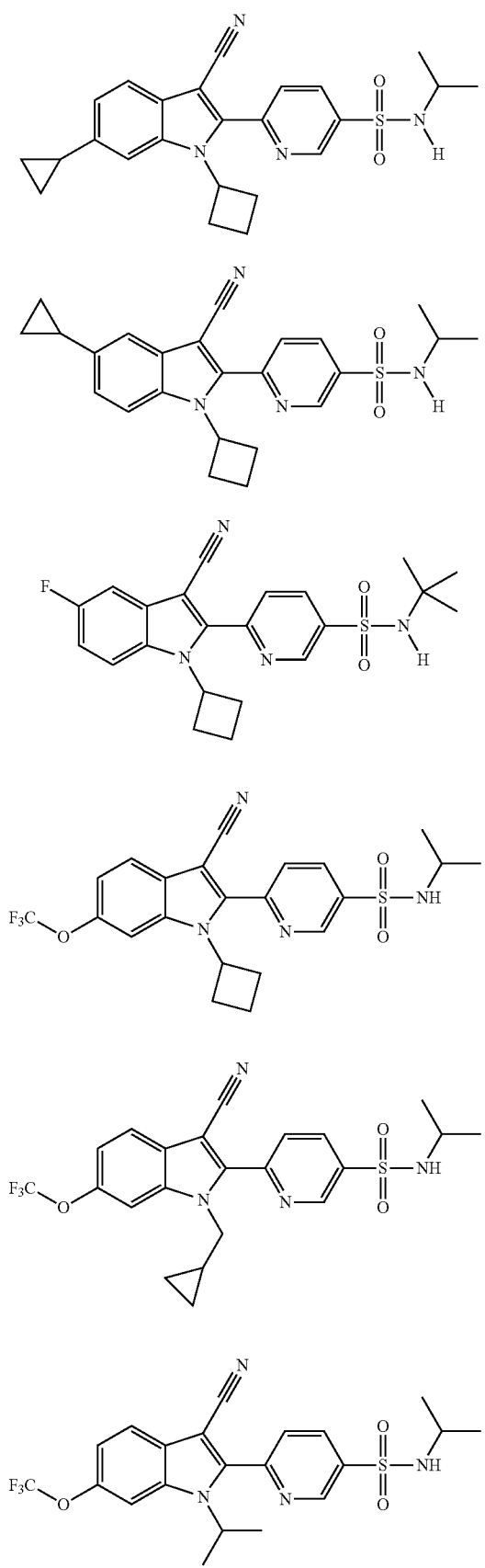

19
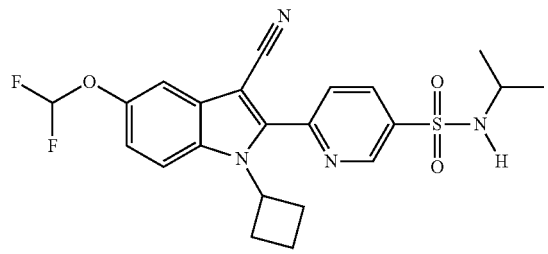
20
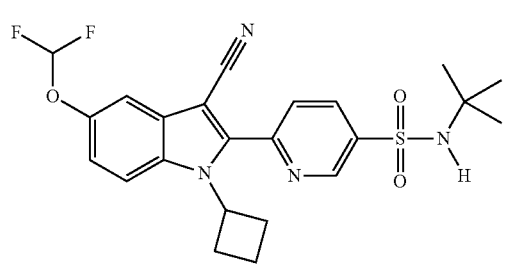
21
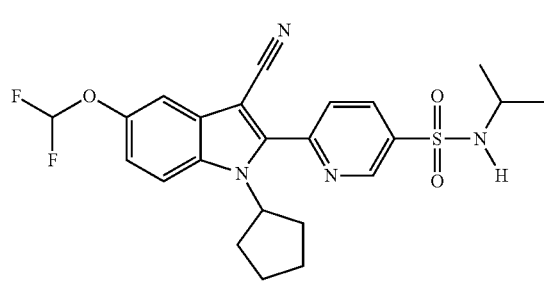
22
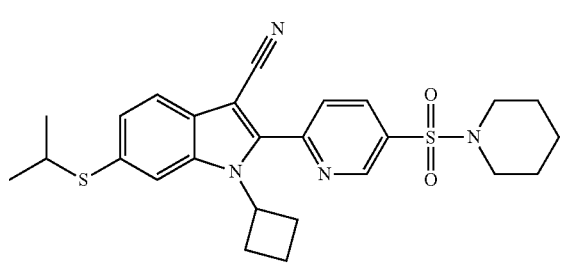
23
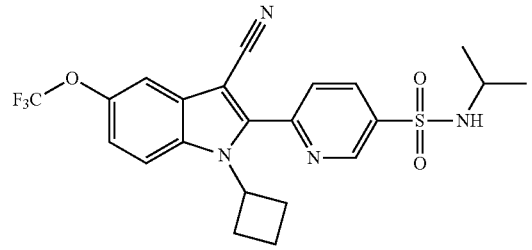
24
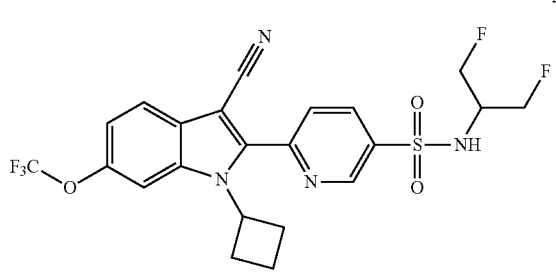
25
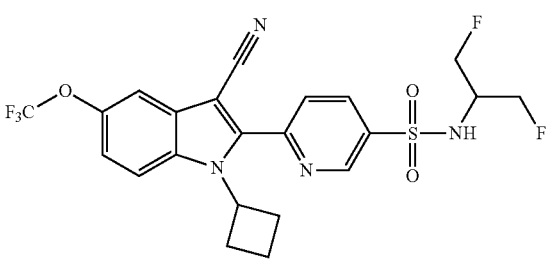
26
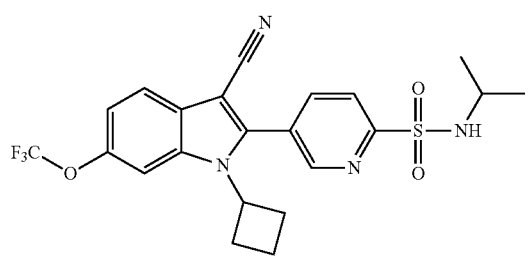
27
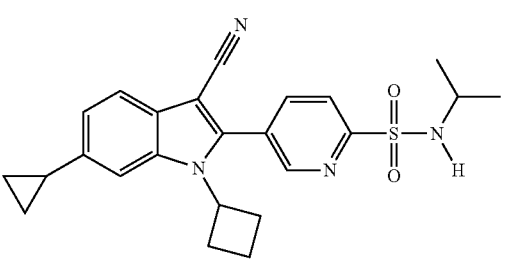
28
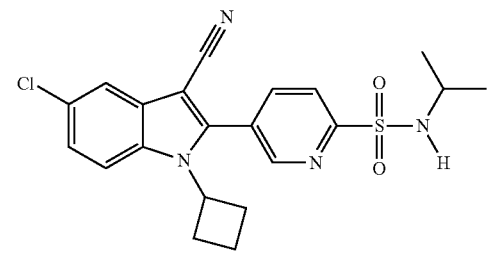
29
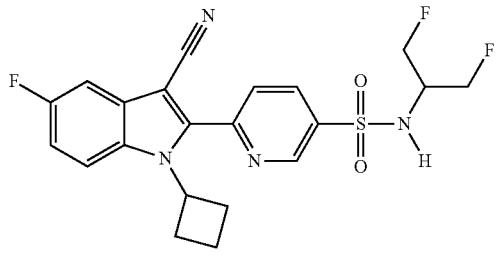
30
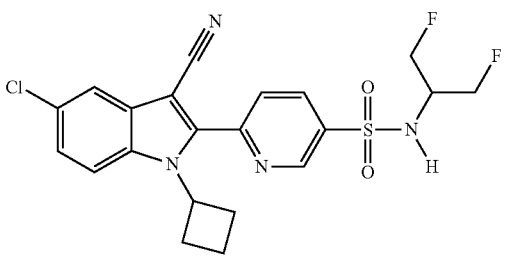

-continued
31
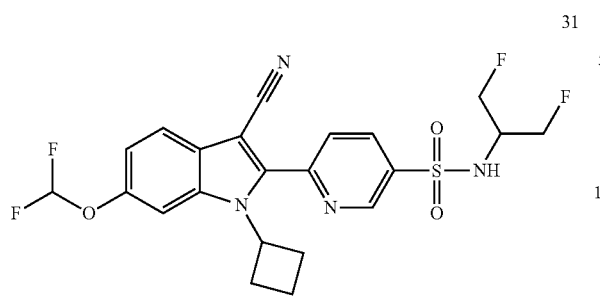
32
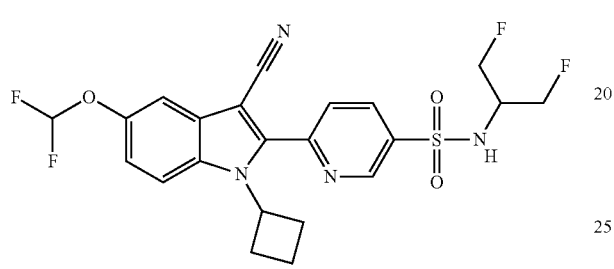
33
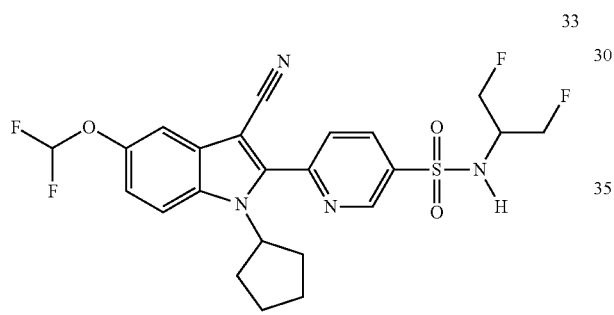
34
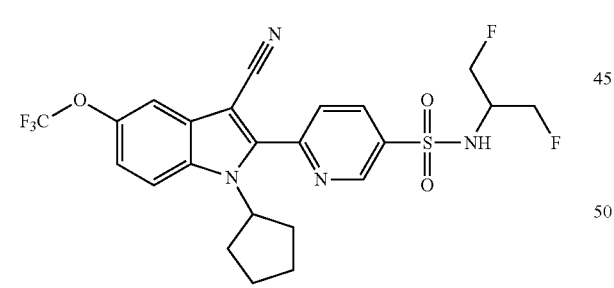
35
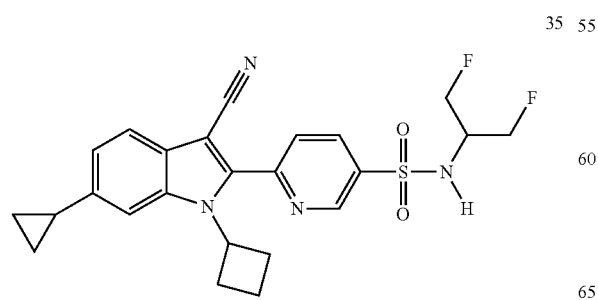
-continued
36
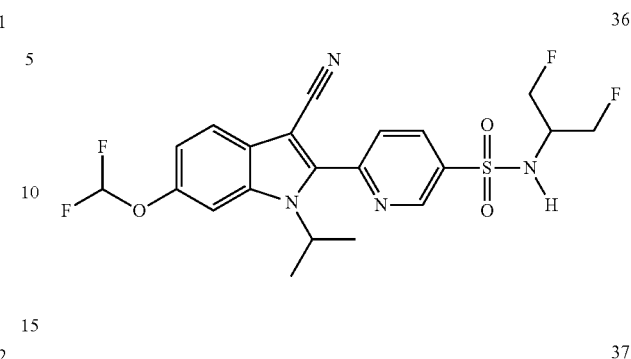
37
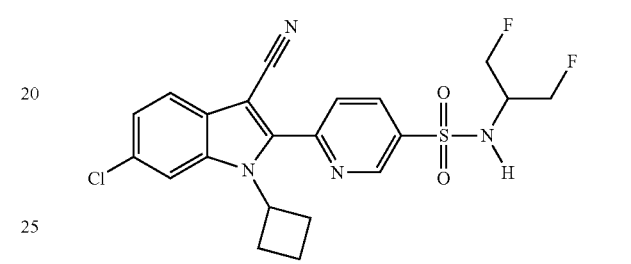
38
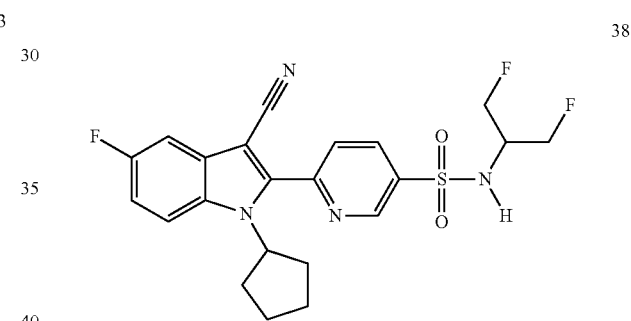
39
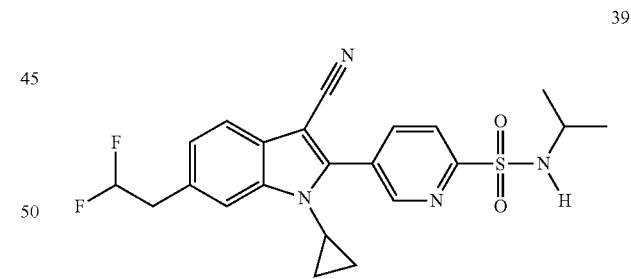
40
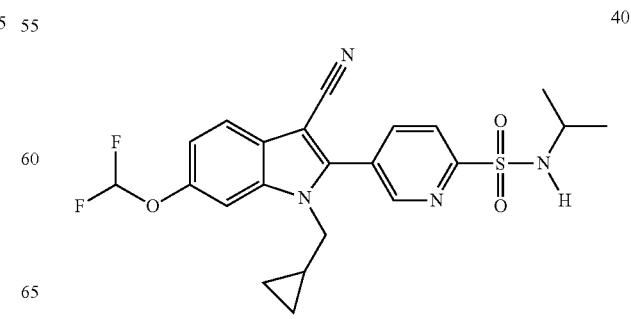

41
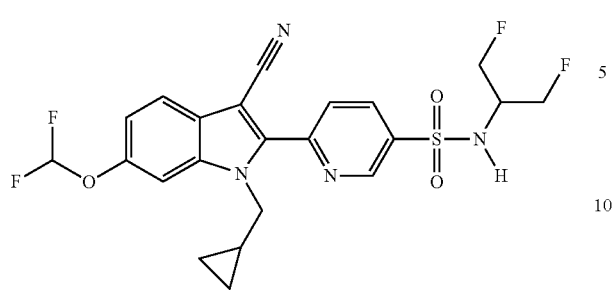
42
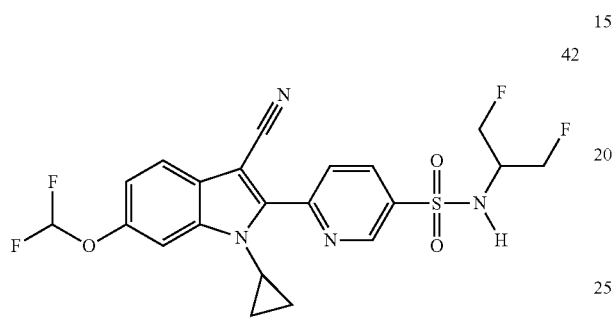
43
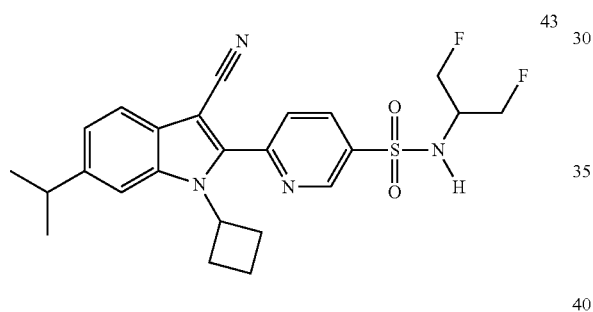
44
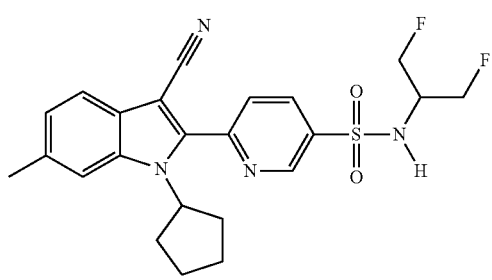
45
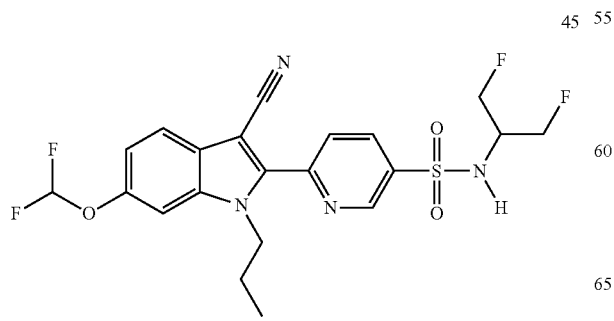
46
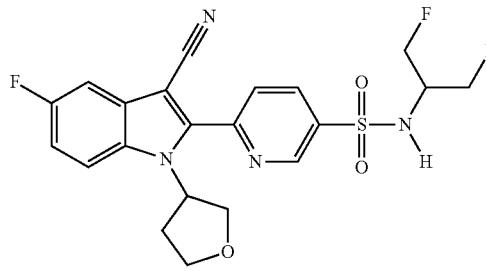
47
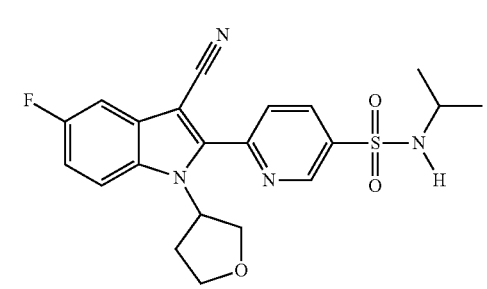
48
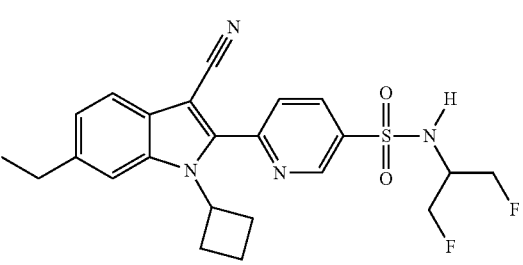
49
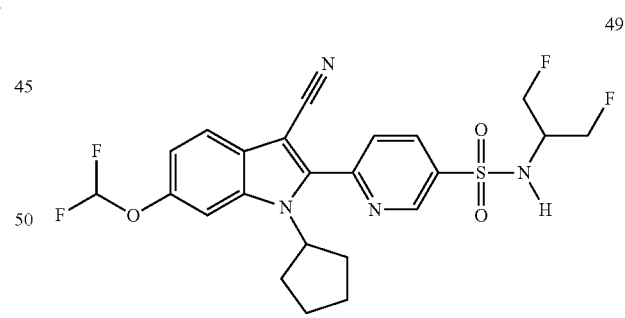
50
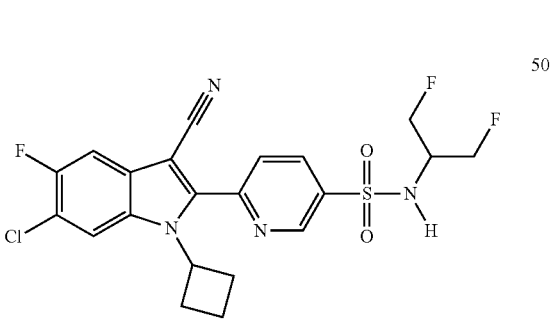

51
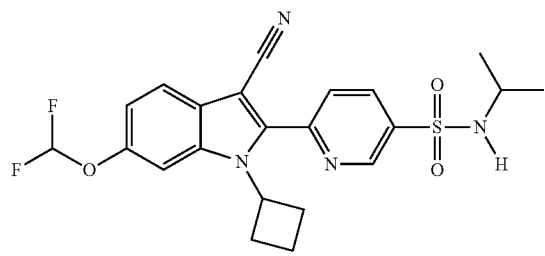
52
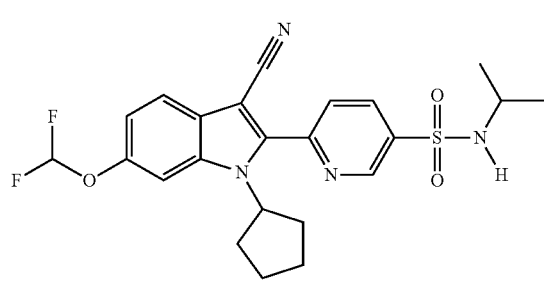
53
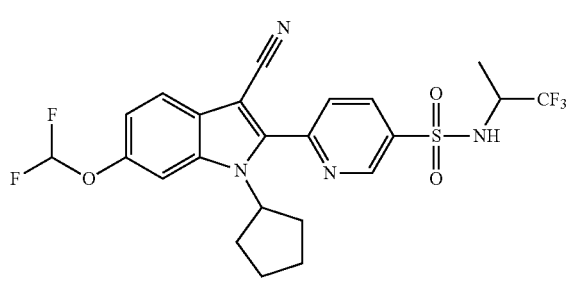
54
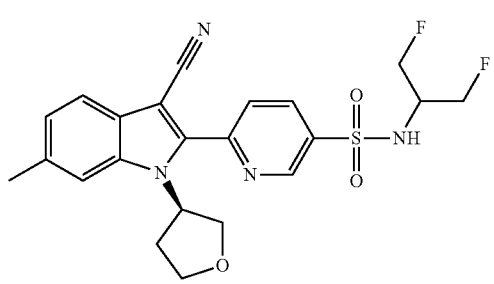
55
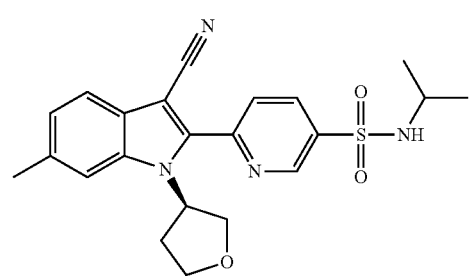
56
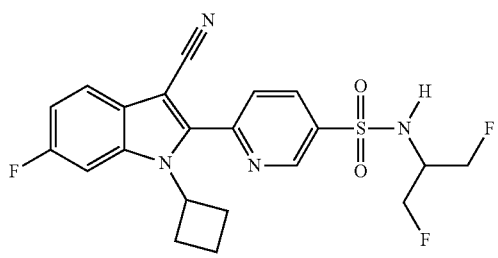
57
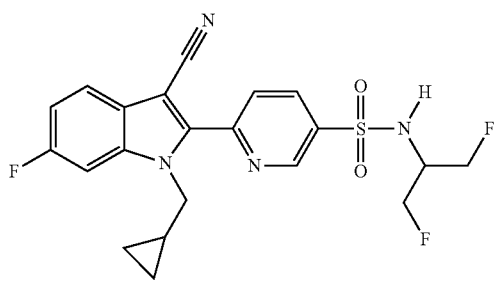
58
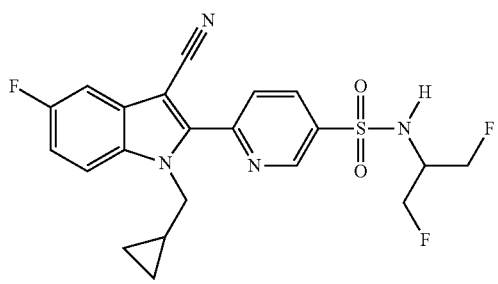
59
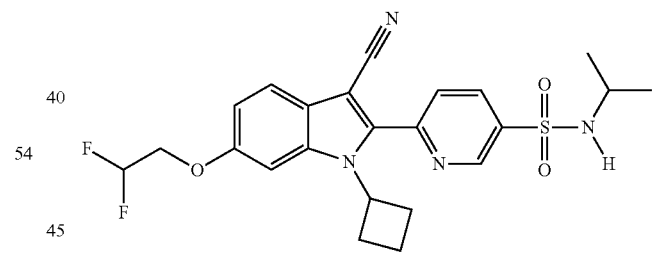
60
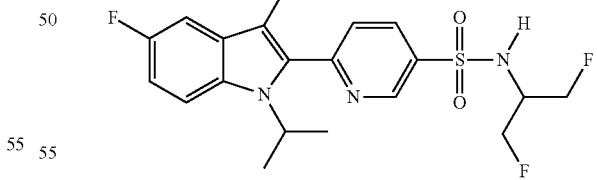
61
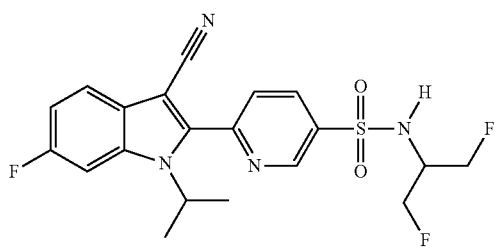

62
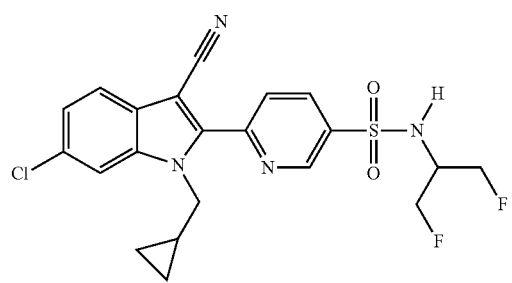
63
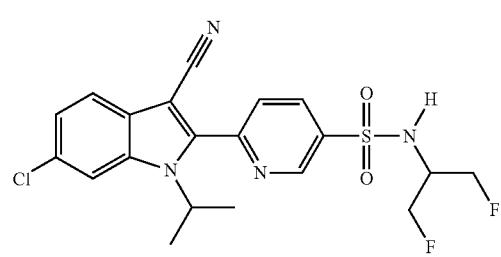
64
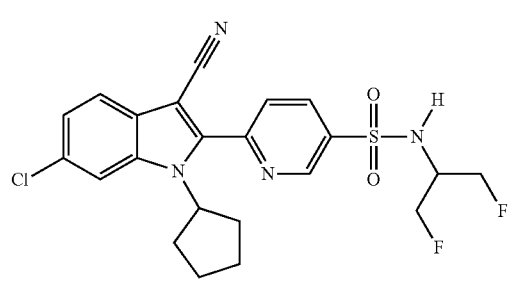
65
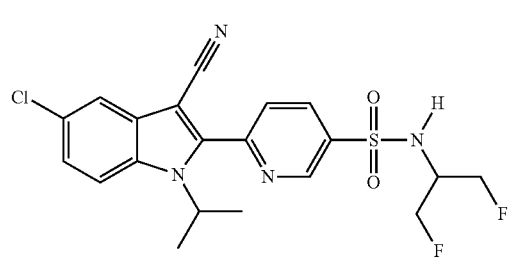
66
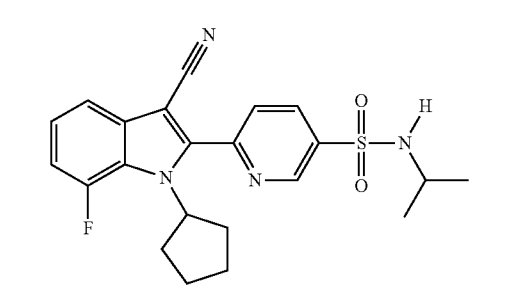
67
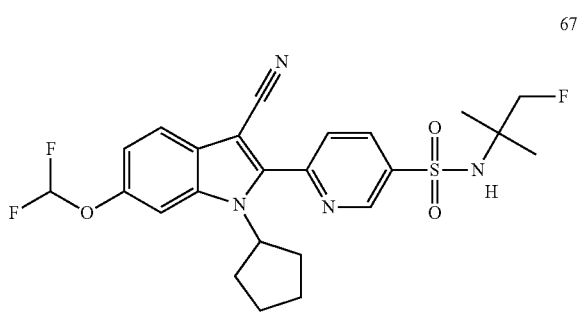
68
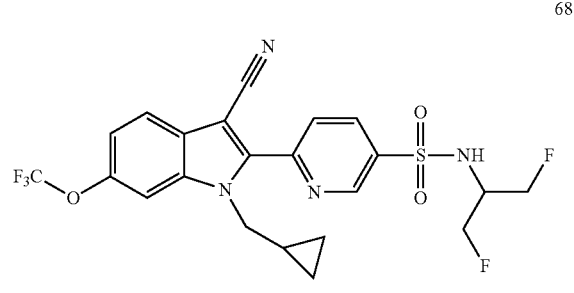
69
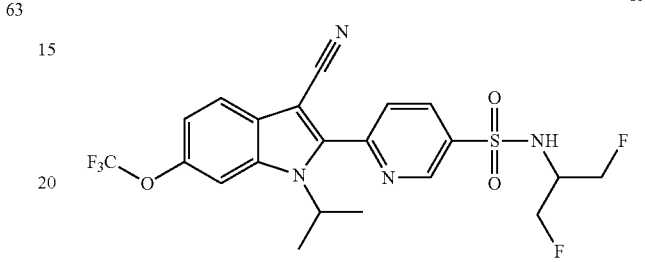
70
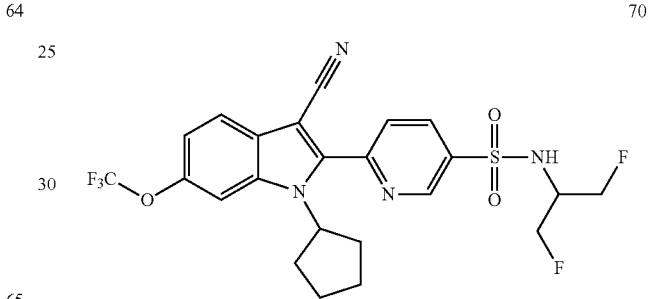
71
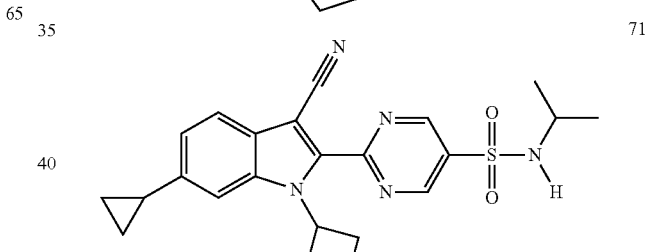
72
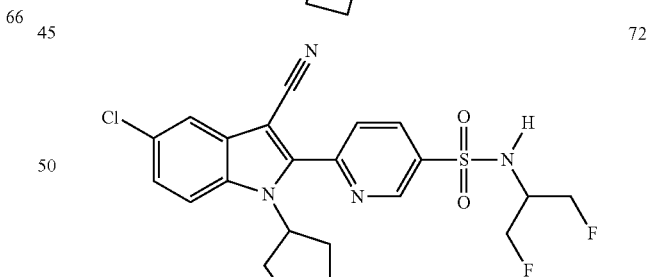
73
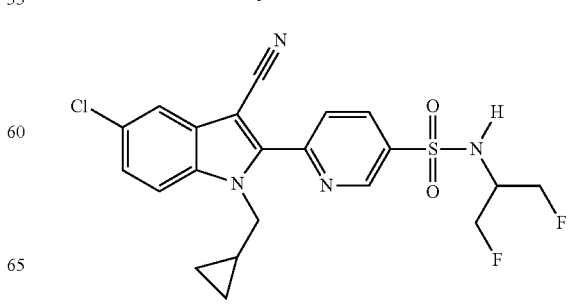

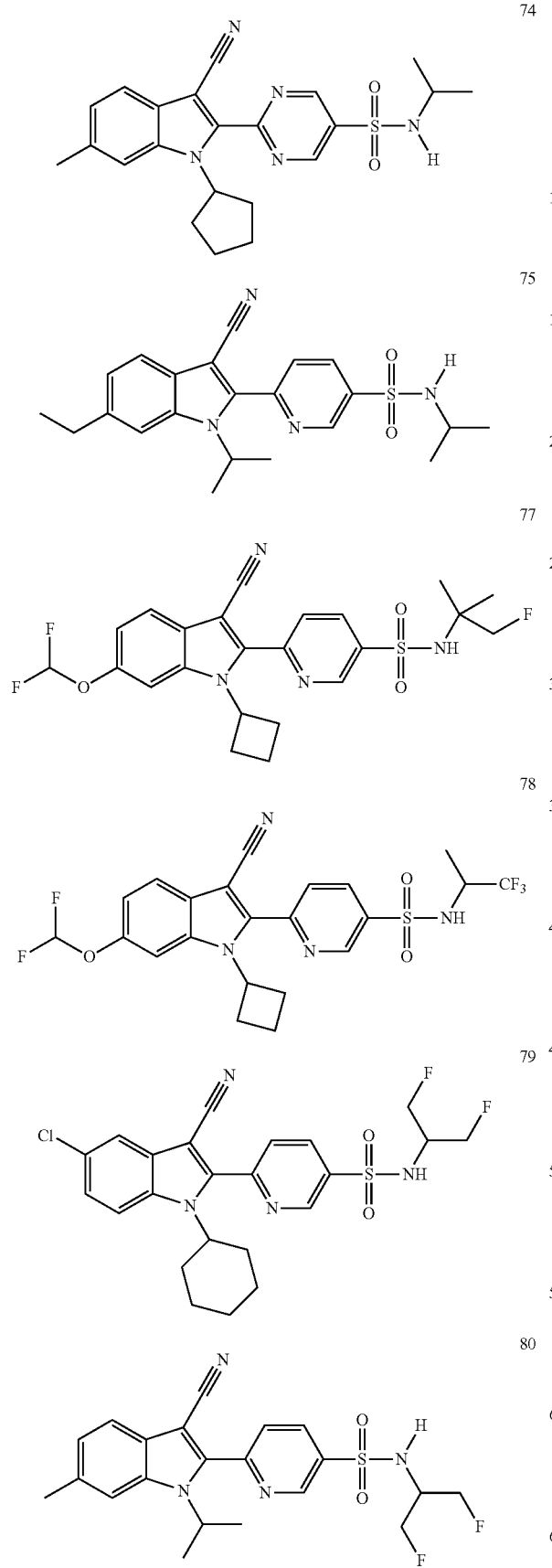

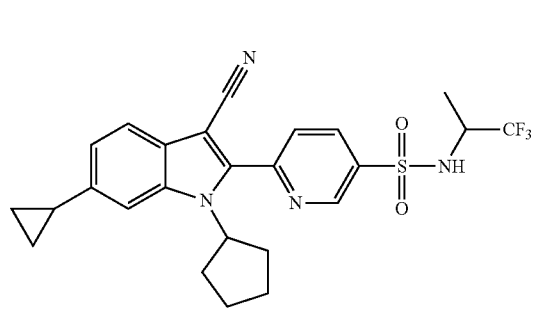
86
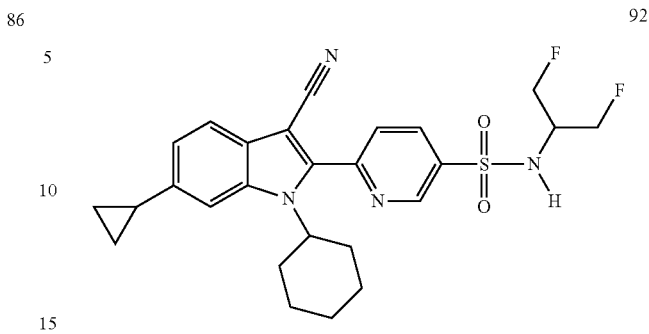
92
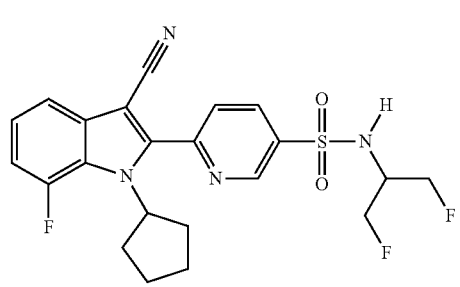
87
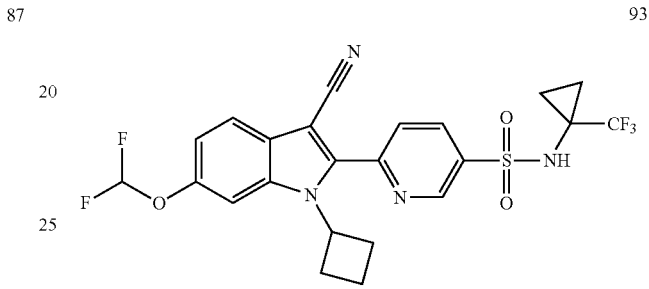
93
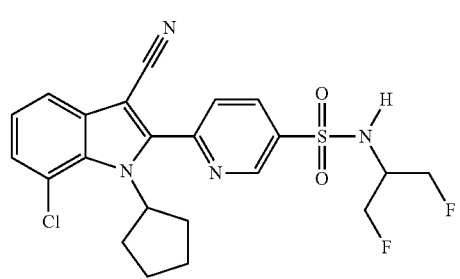
88
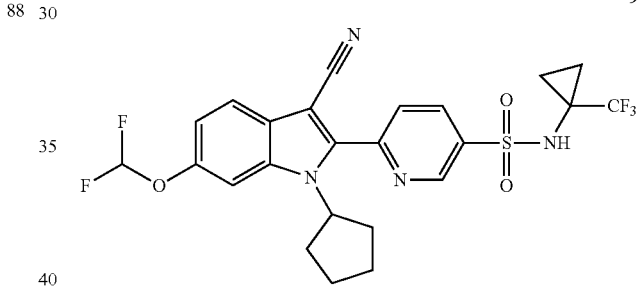
94
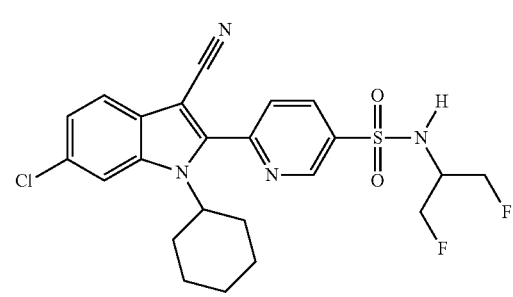
89
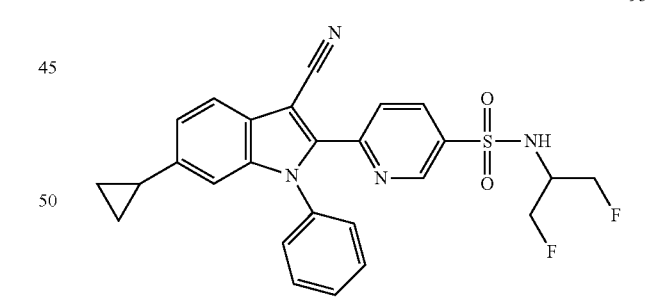
95
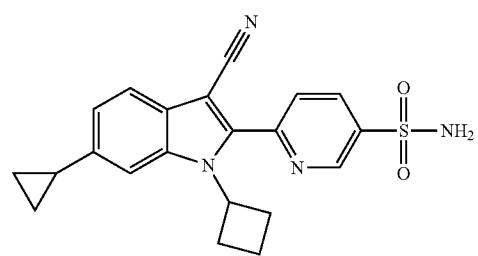
90
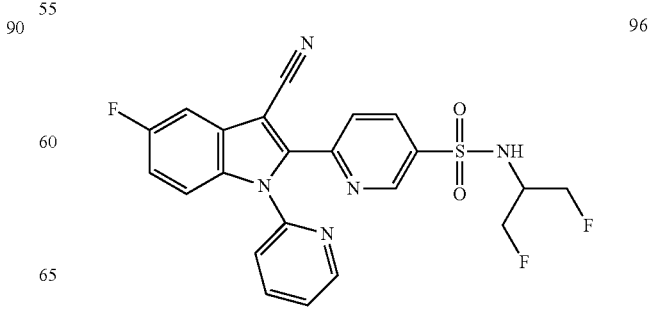
96

97
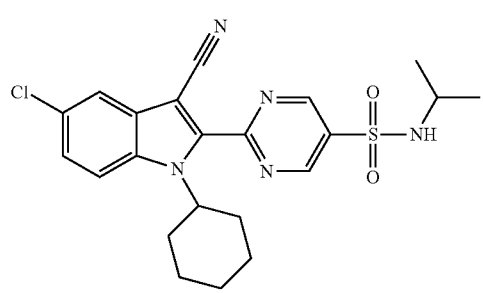
98
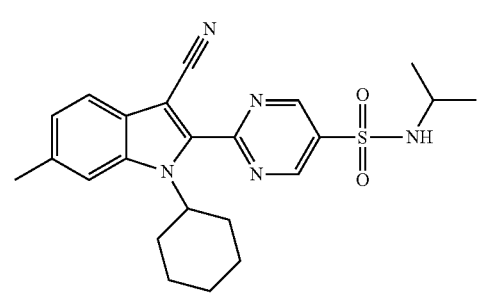
99
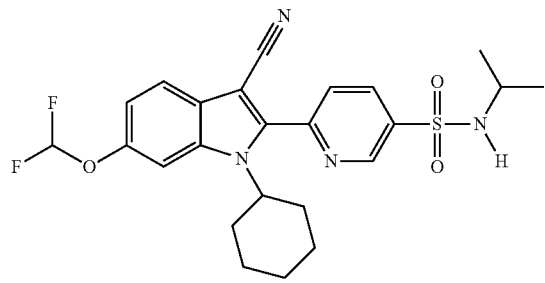
100
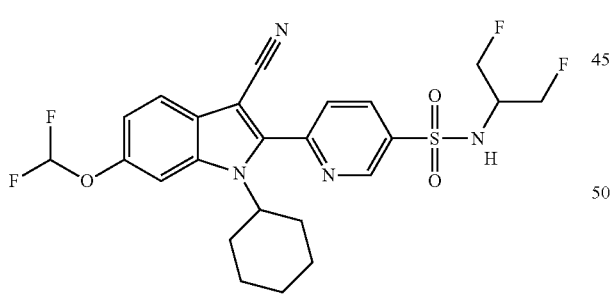
101
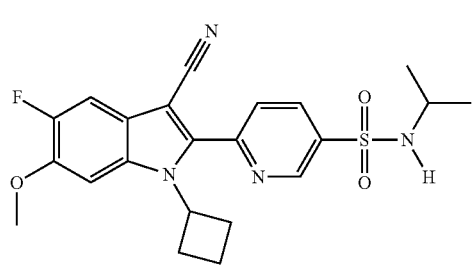
102
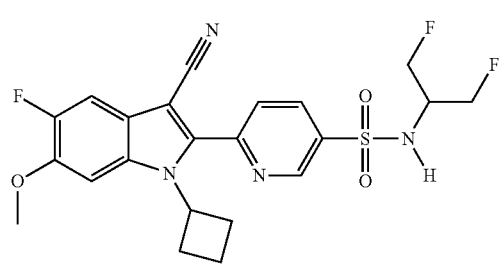
103
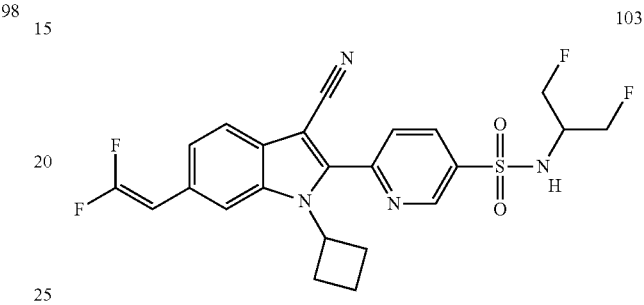
104
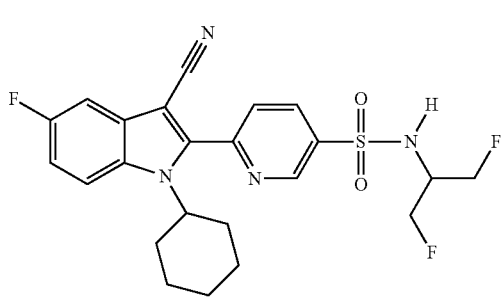
105
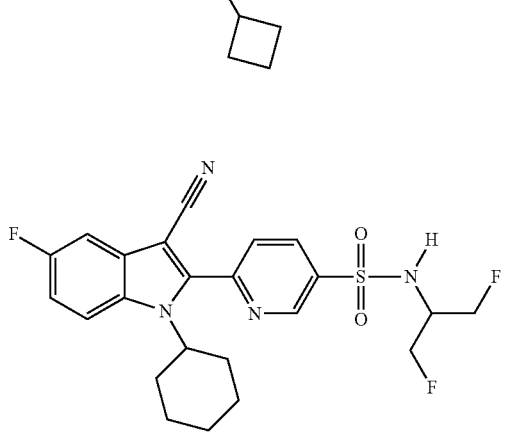
106
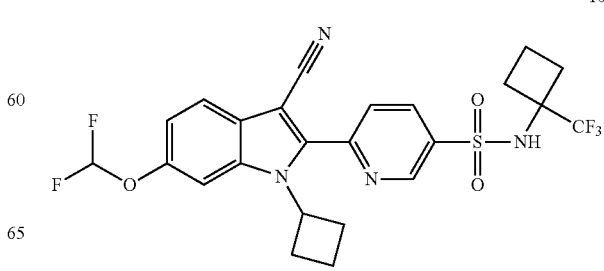

107
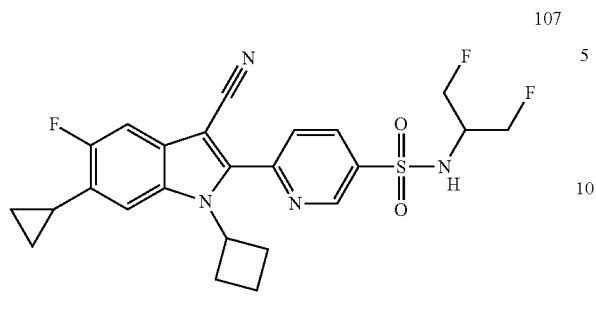
112
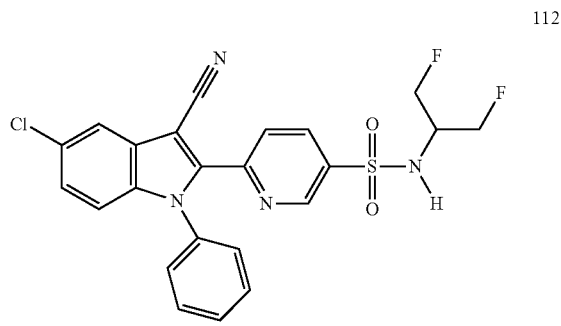
108
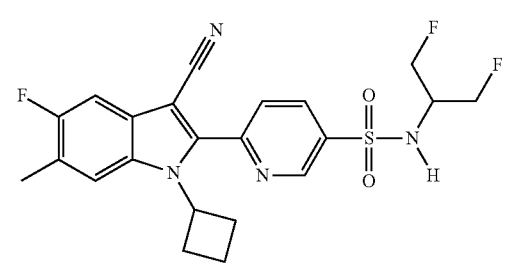
113
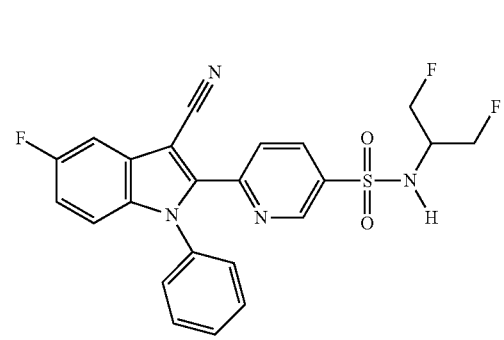
109
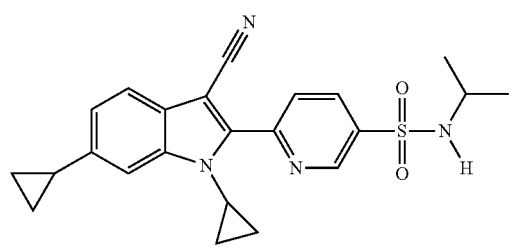
114
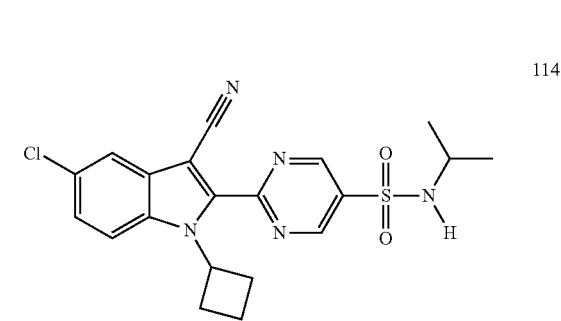
110
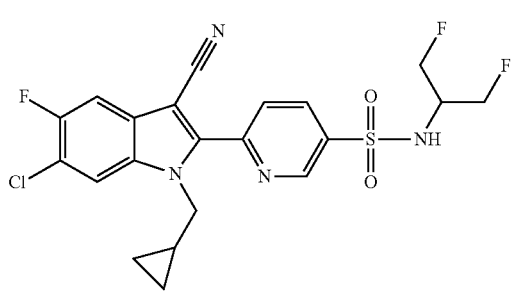
115
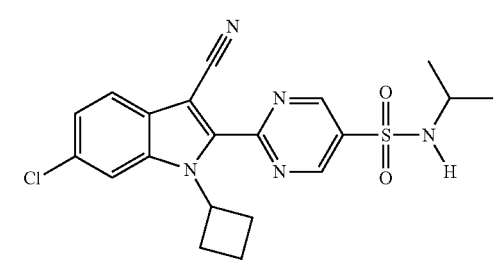
111
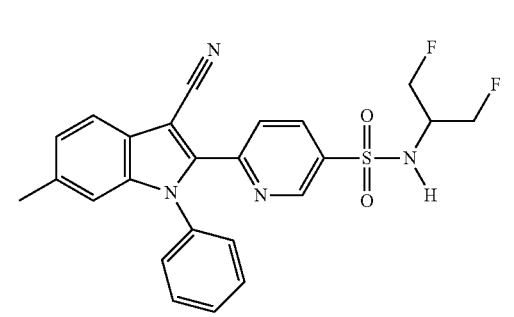
116
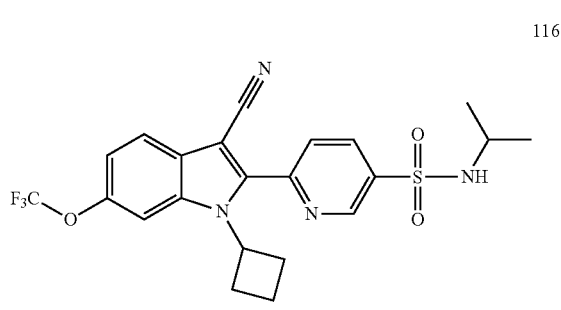

117 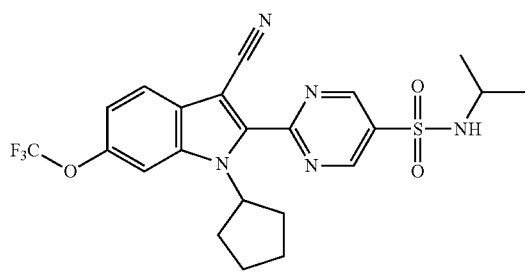
118 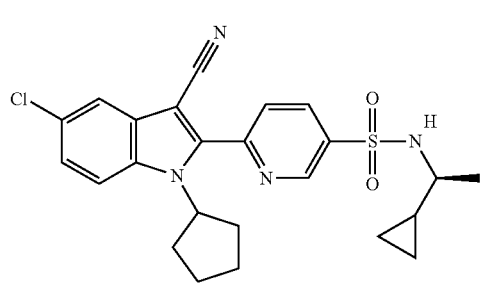
119 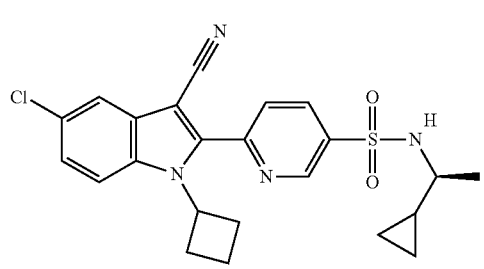
120 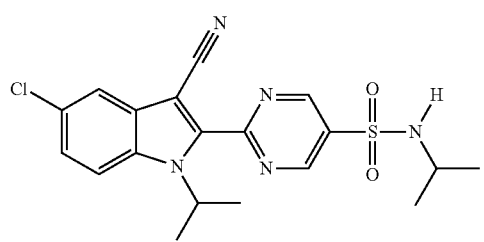
121 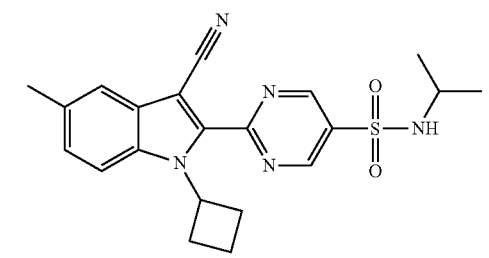
122 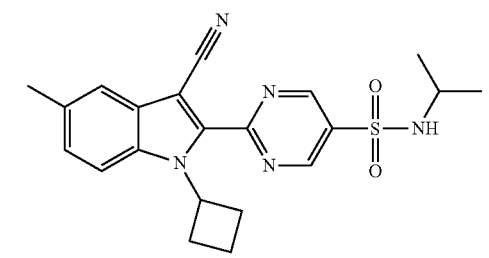
123 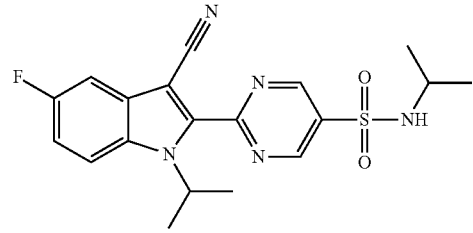
124 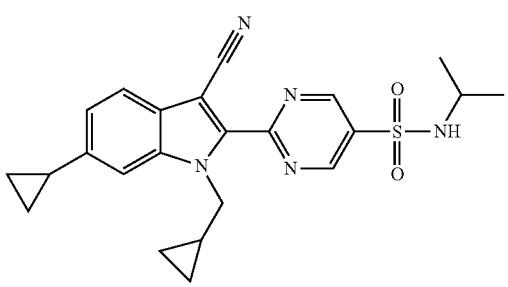
125 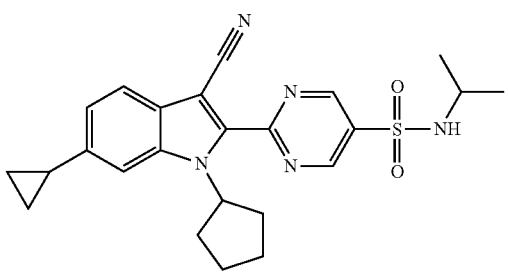
126 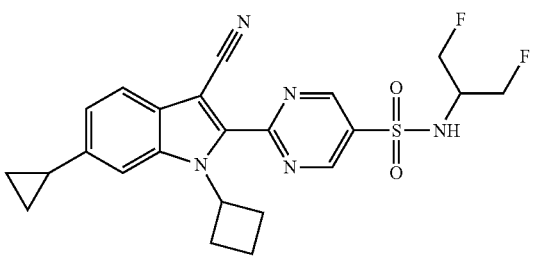
127 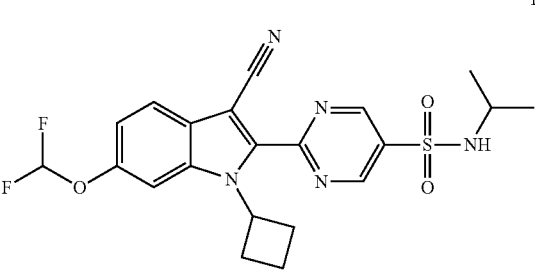

128
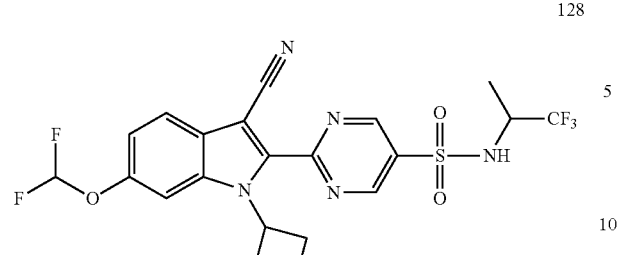
129
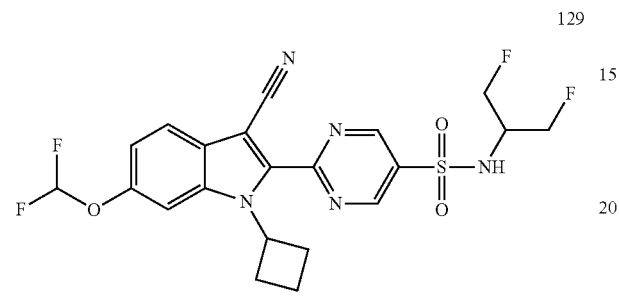
130
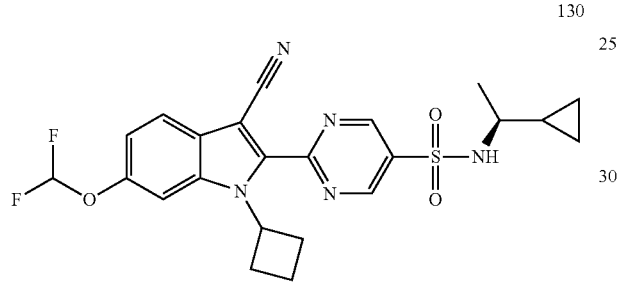
131
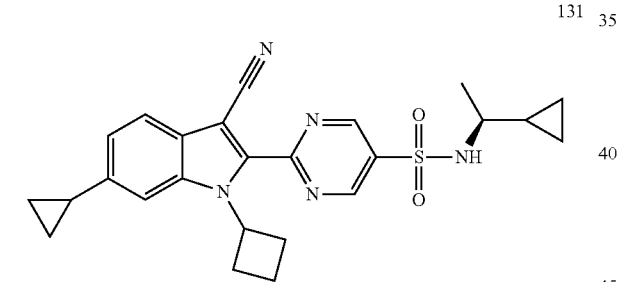
132
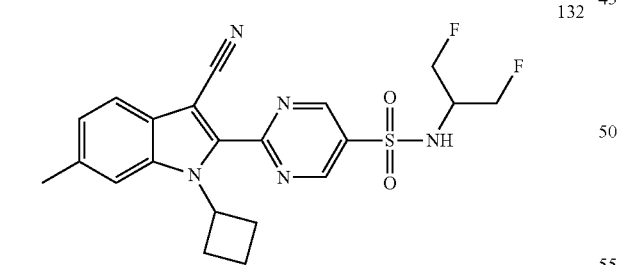
133
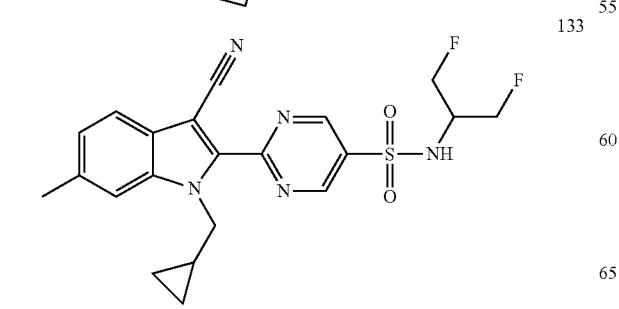
134
135
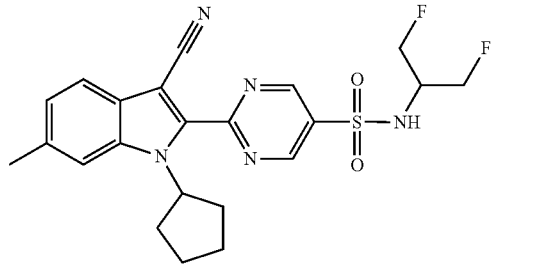
136
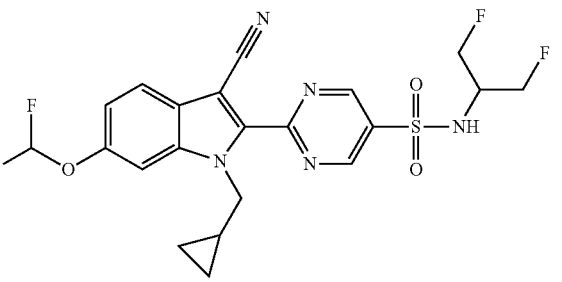
137
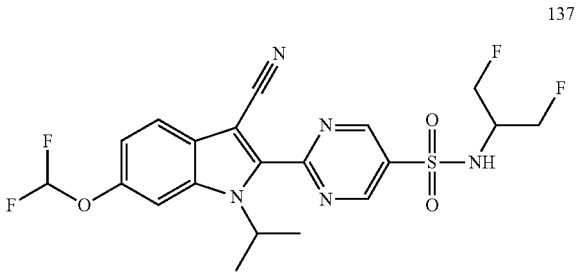
138
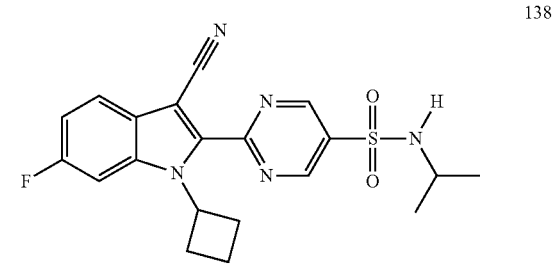
139
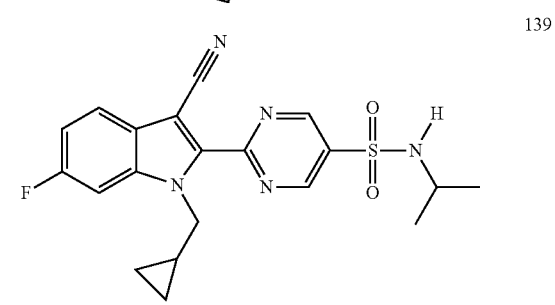

140
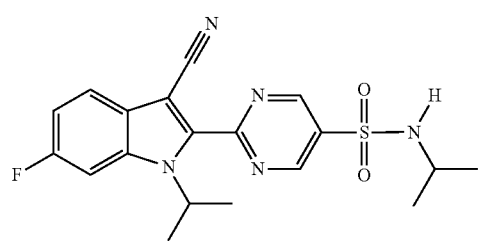
141
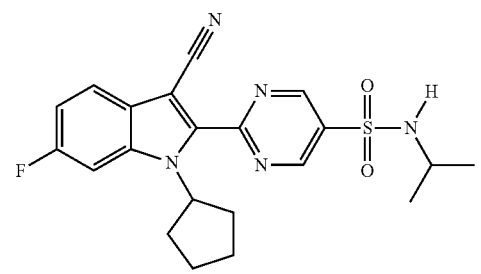
142
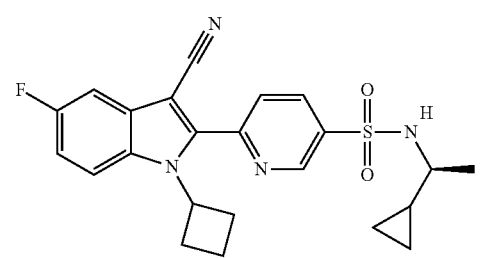
143
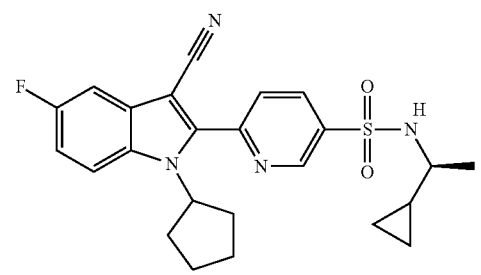
144
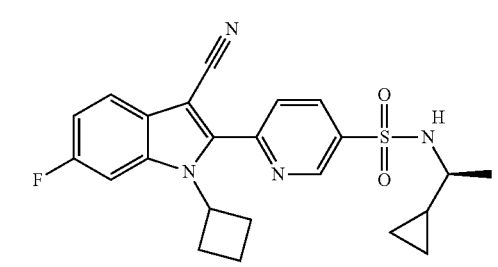
145
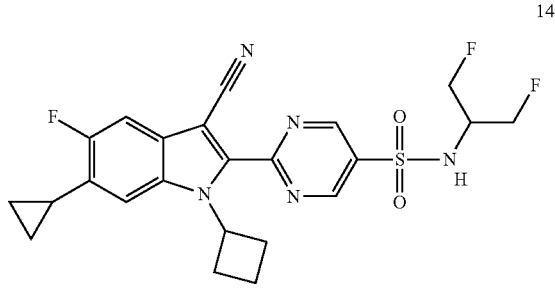
146
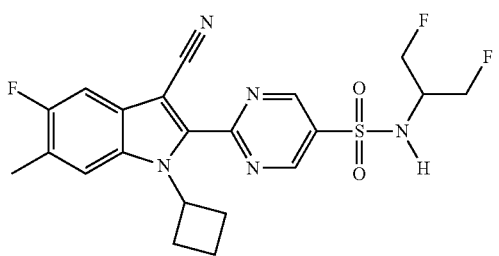
147
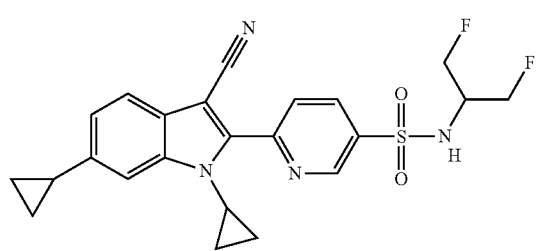
148
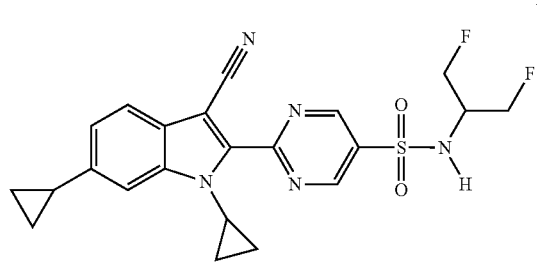
149
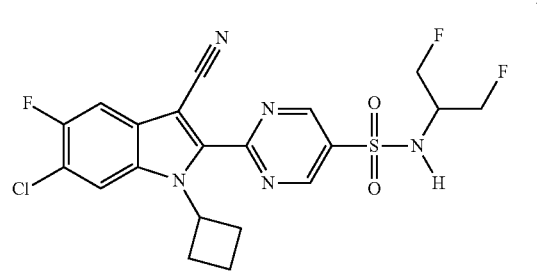
150
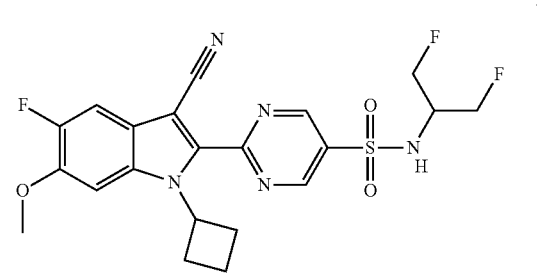
151
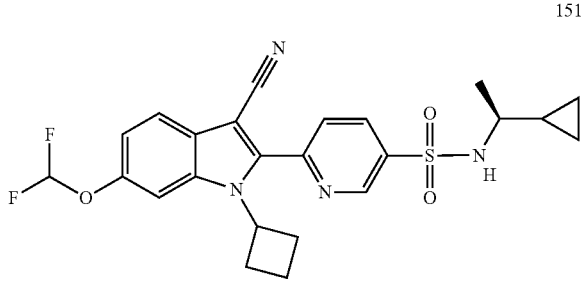

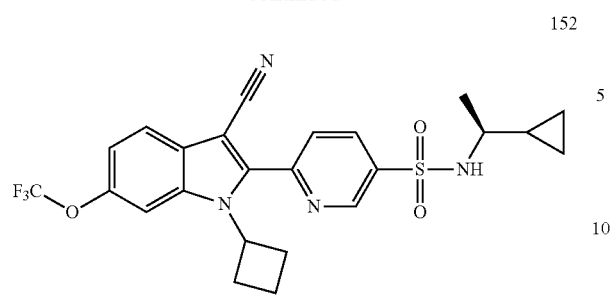
152
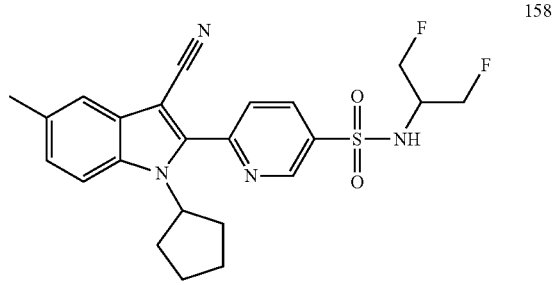
158
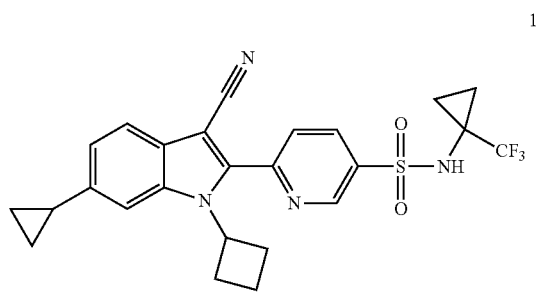
153
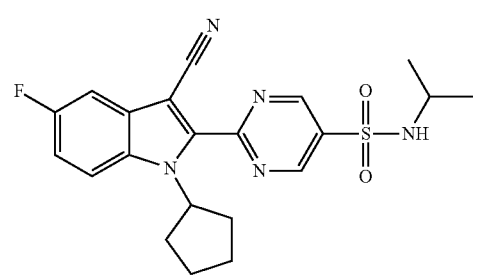
159
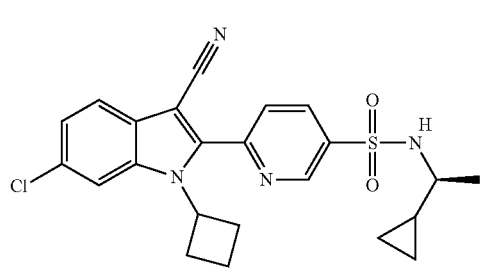
154
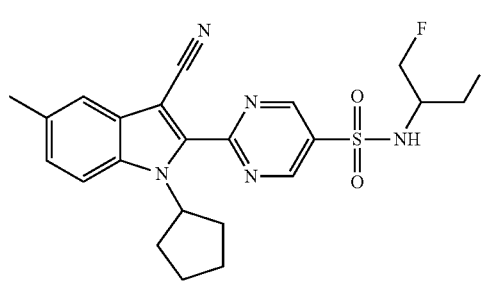
160
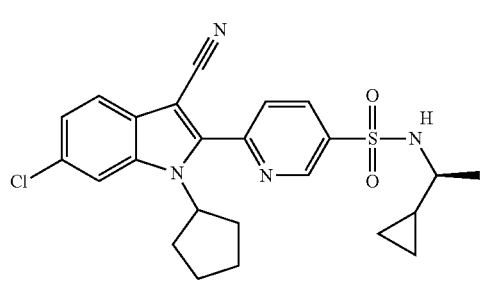
155
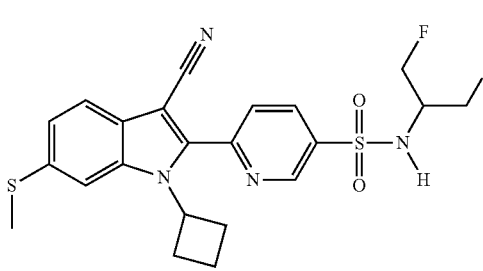
161
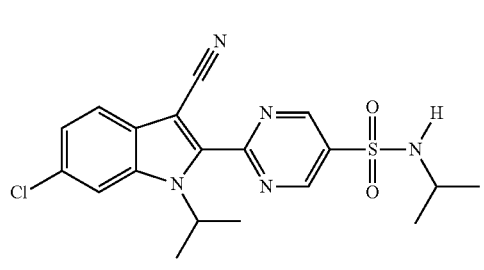
156
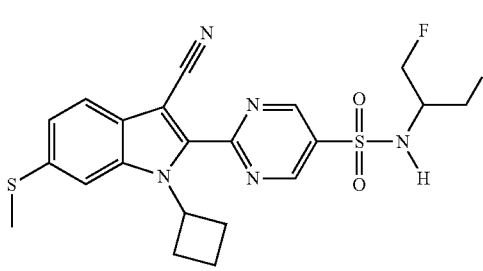
162
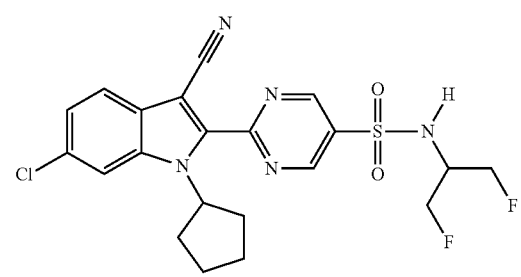
157
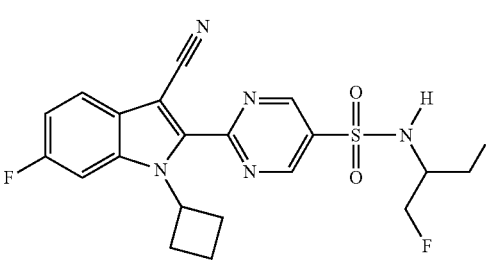
163

-continued
164
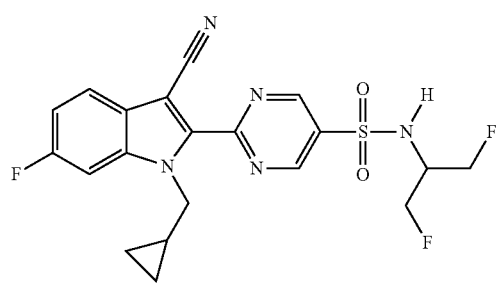
165
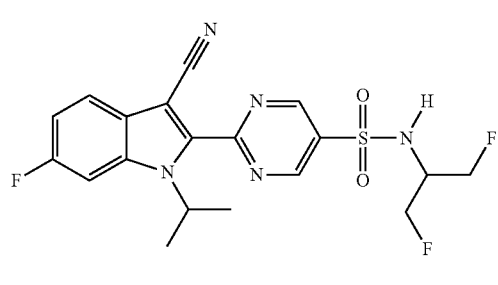
166
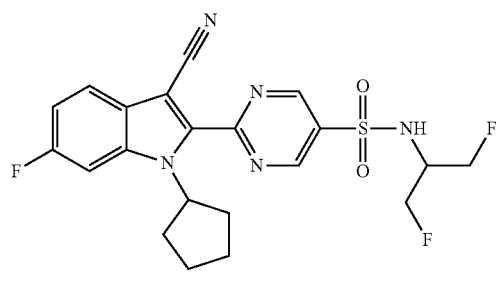
167
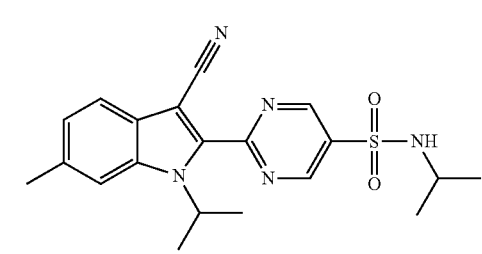
168
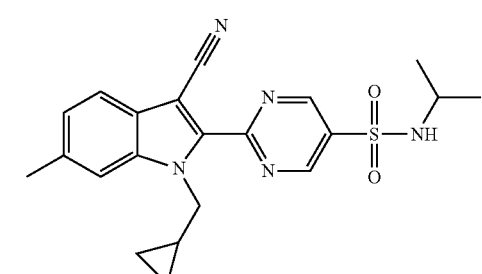
169
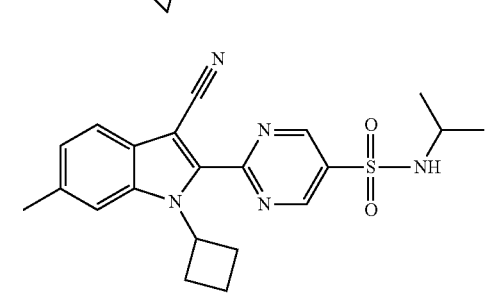
-continued
170
171
172
173
174

175
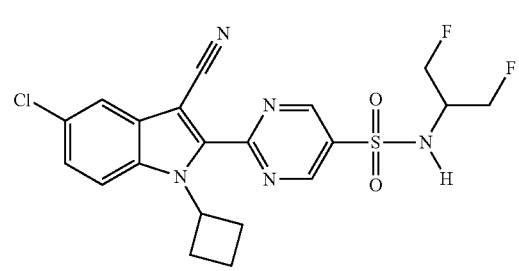
176
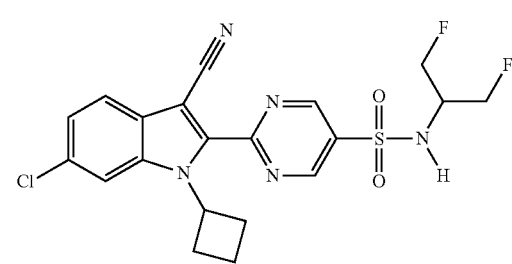
177
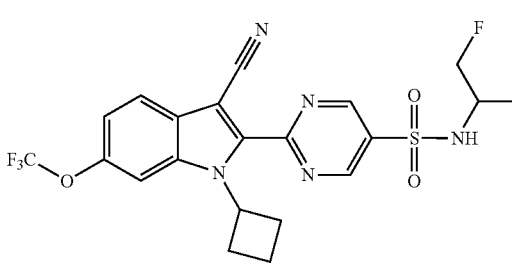
178
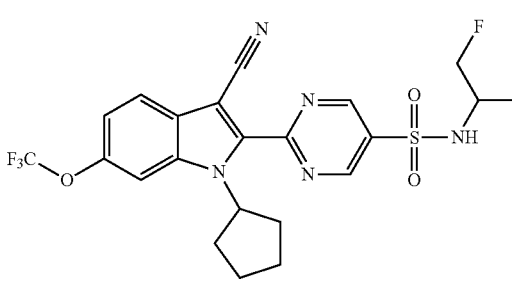
179
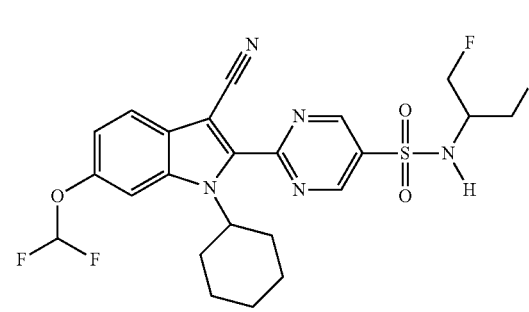
180
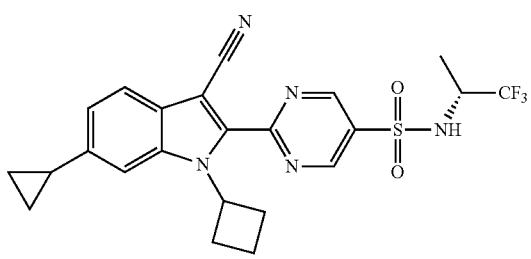
181
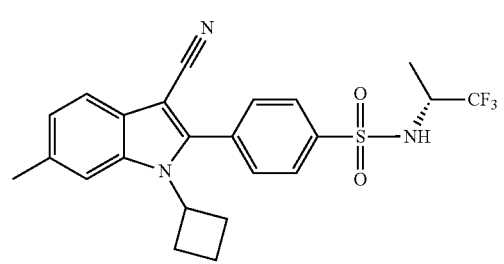
182
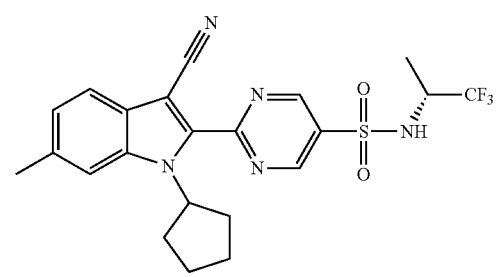
183
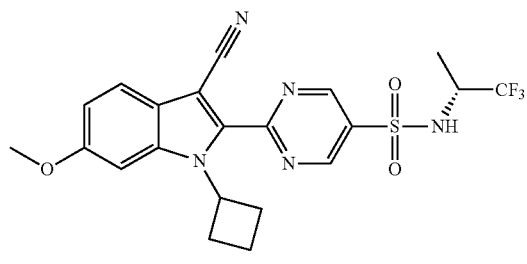
184
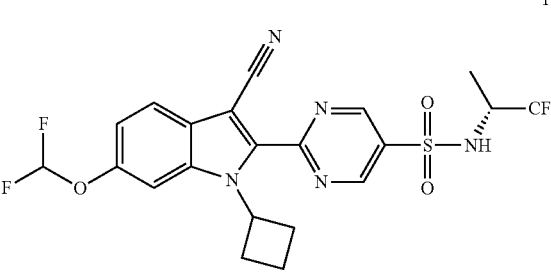
185
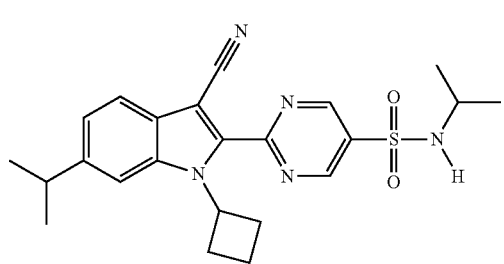

186
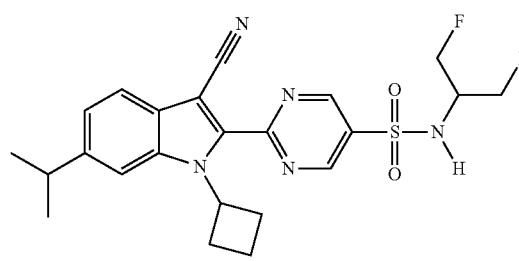
187
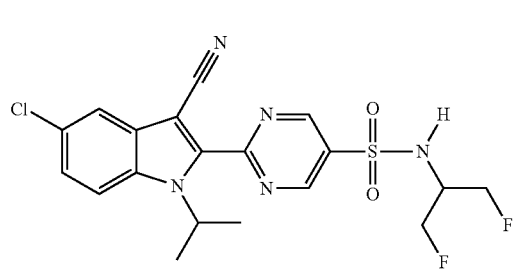
188
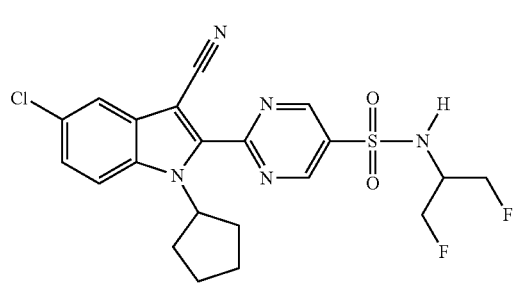
189
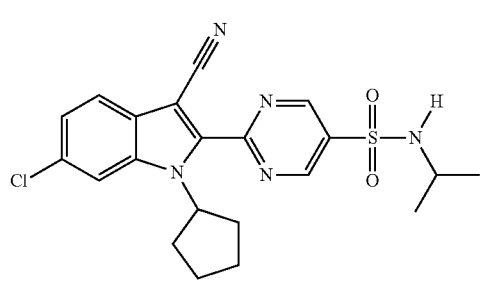
190
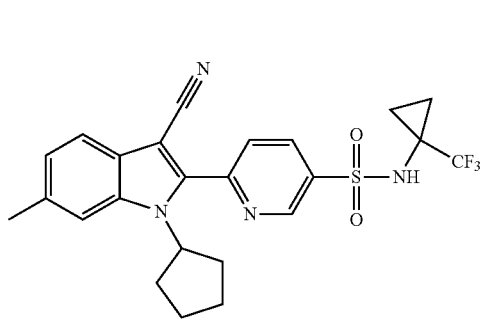
191
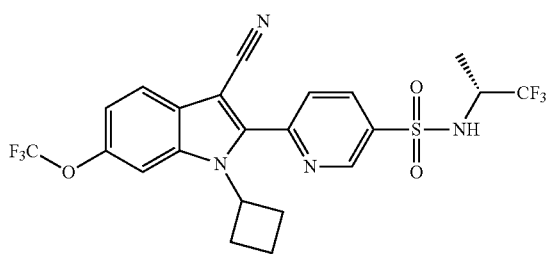
192
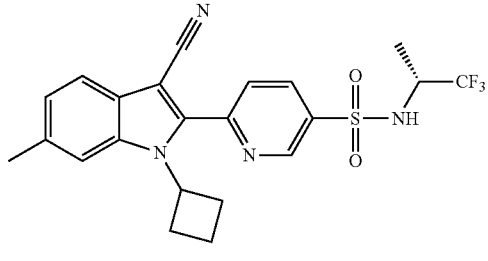
193
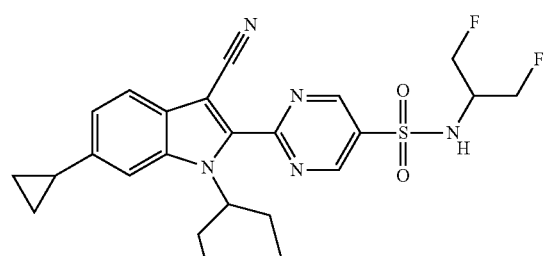
194
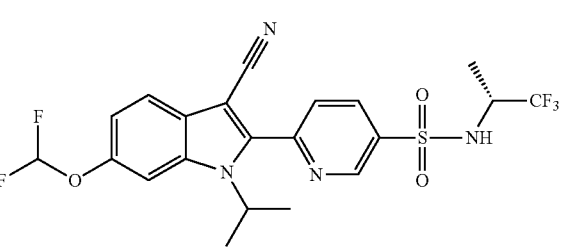
195
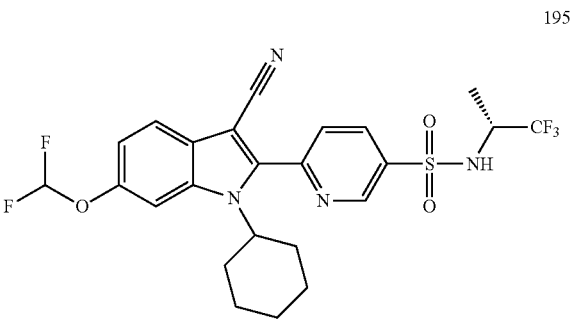

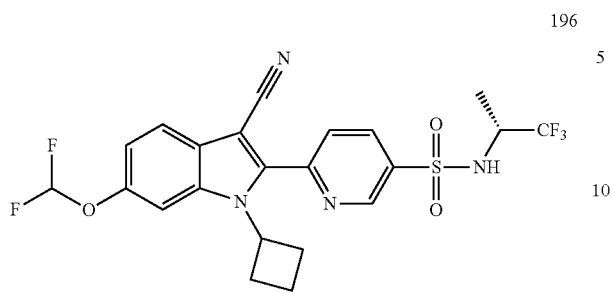
196
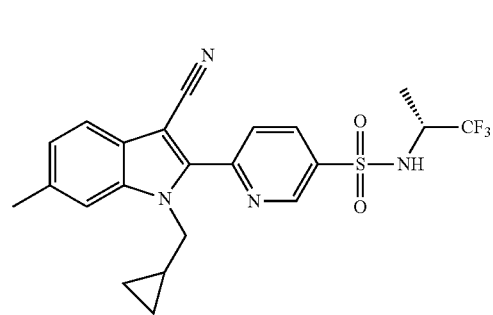
197
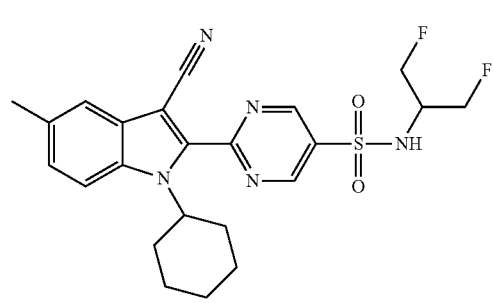
198
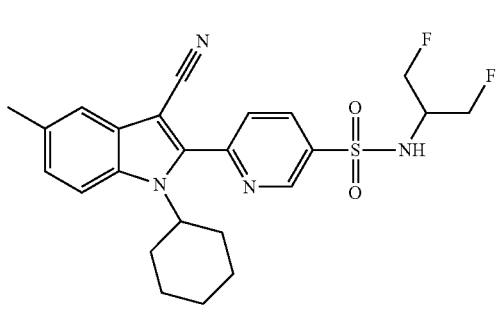
199
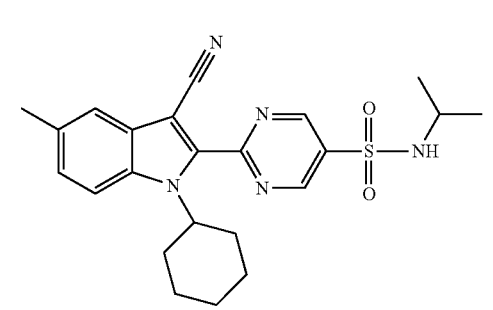
200
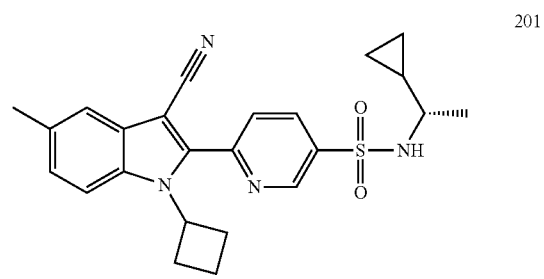
201
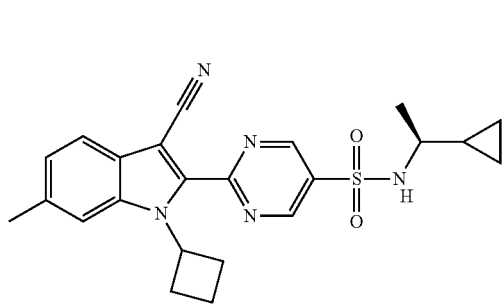
202
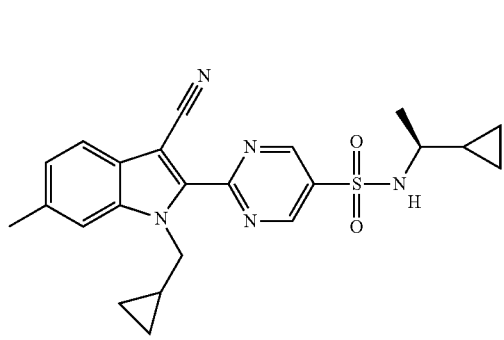
203
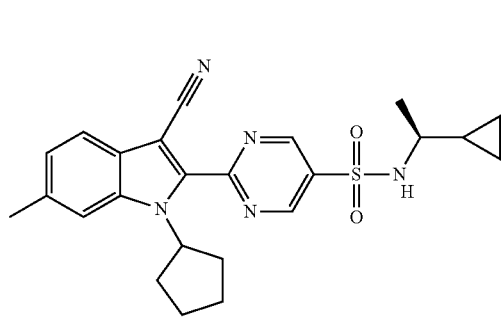
204
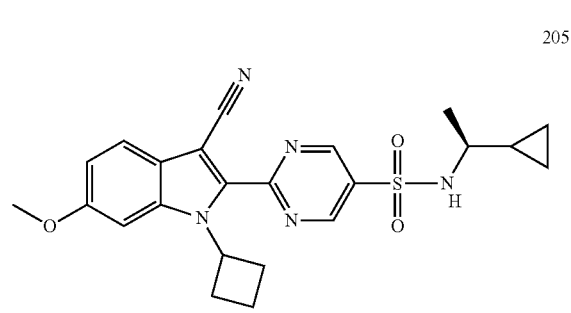
205

206 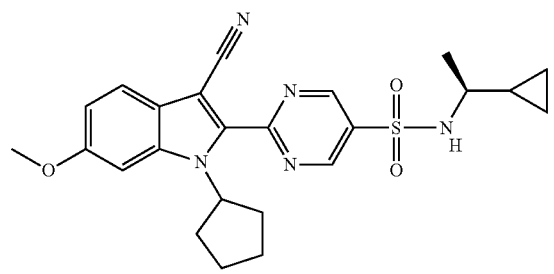
207 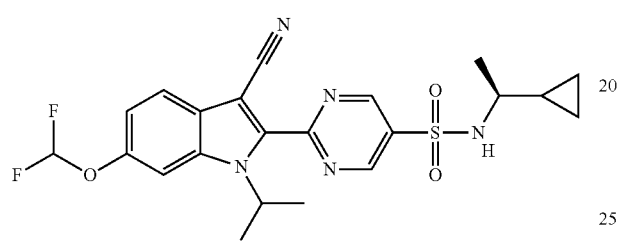
208 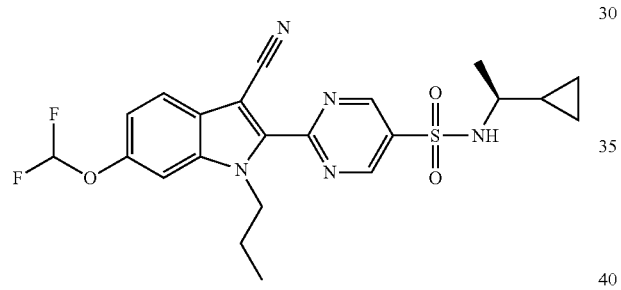
209 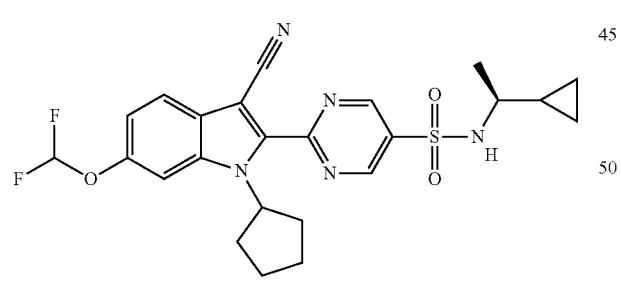
210 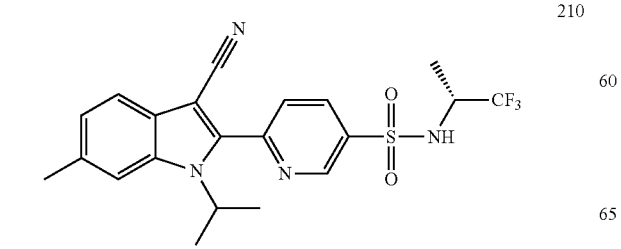
211 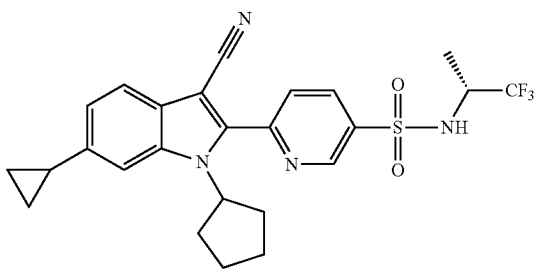
212 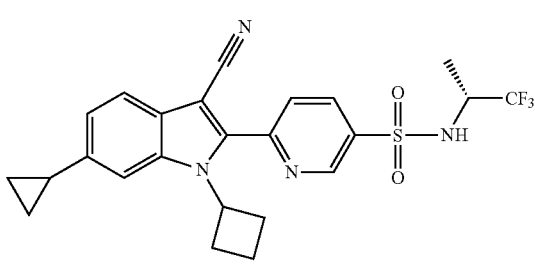
213 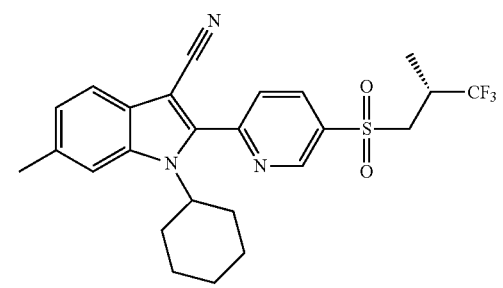
214 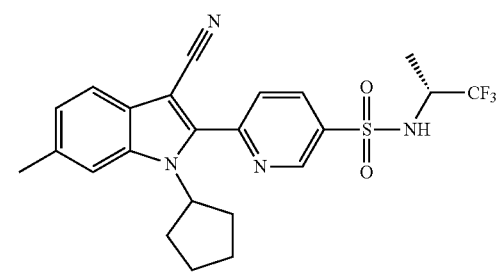
215 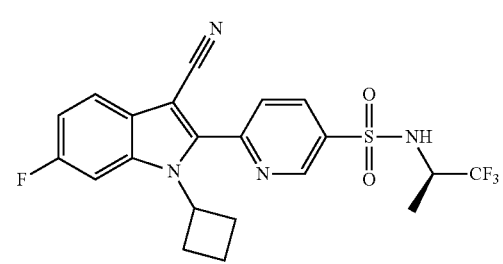

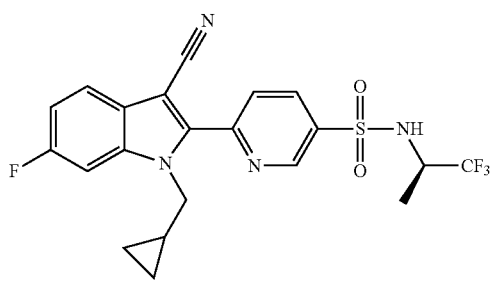
216
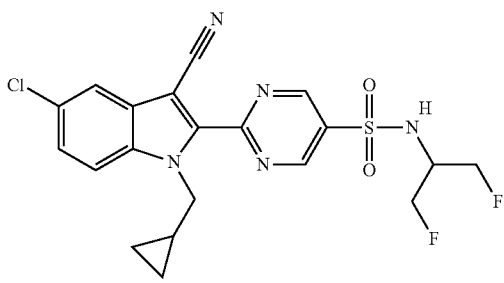
221
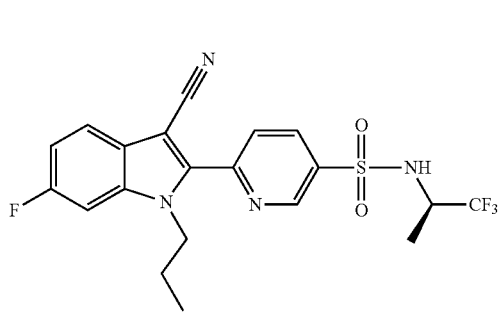
217
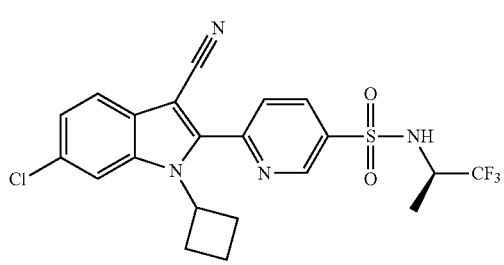
222
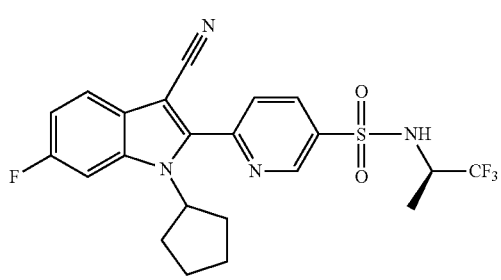
218
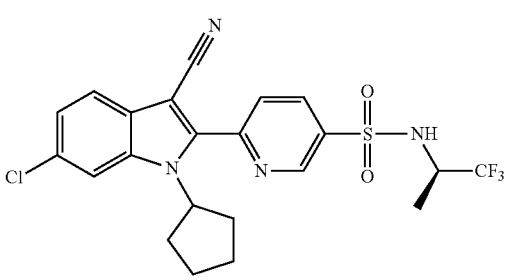
223
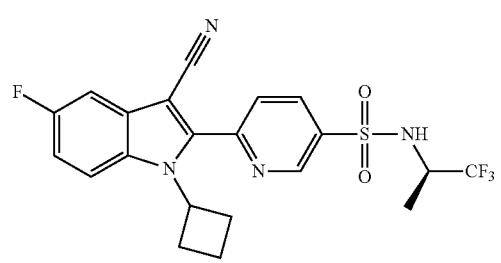
219
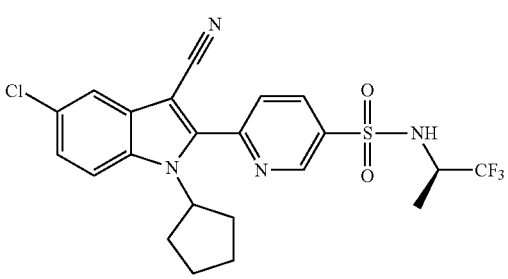
224
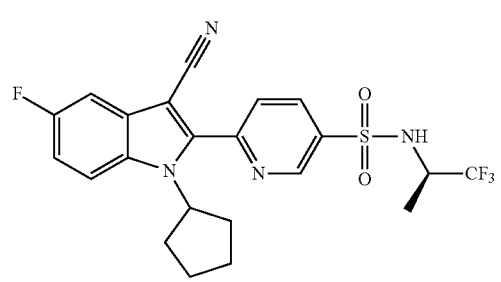
220
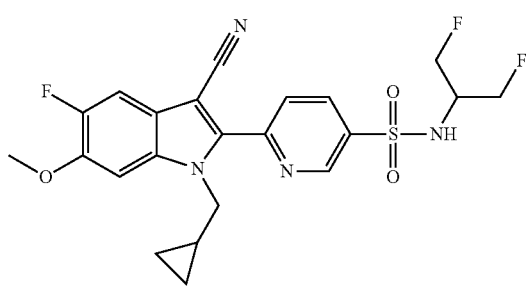
225

226 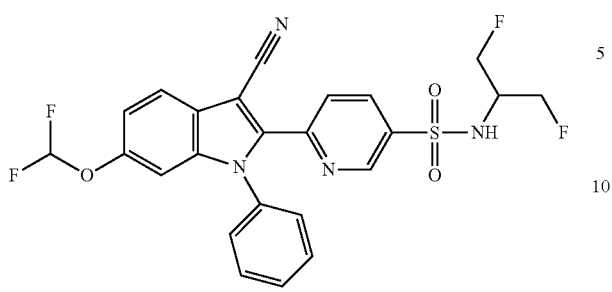
227 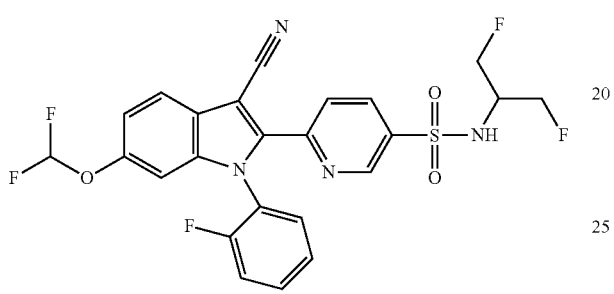
228 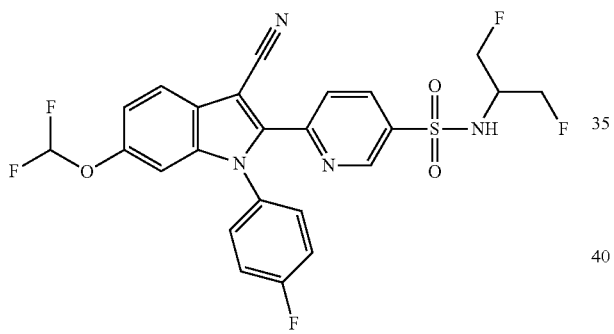
229 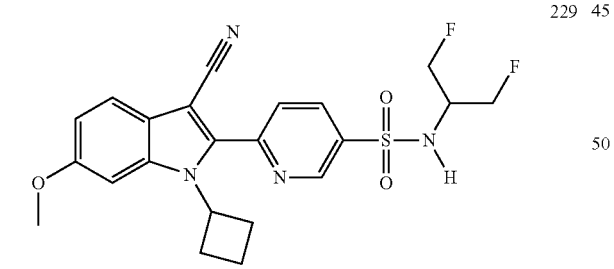
230 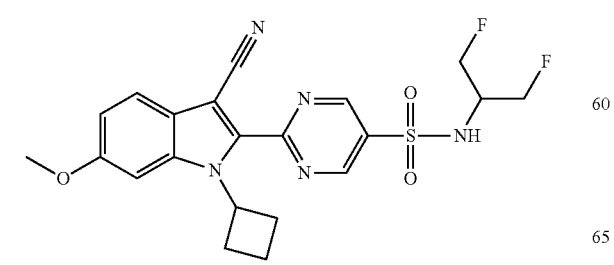
231 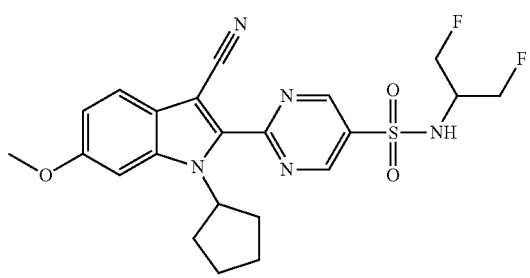
232 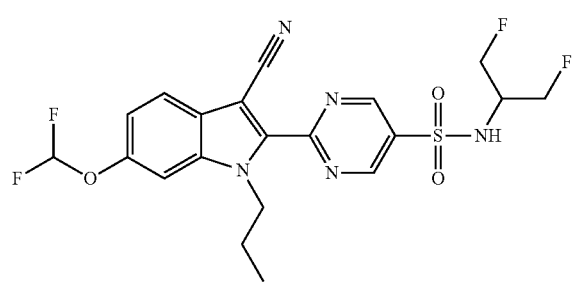
233 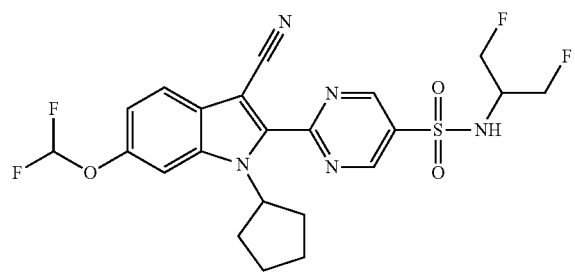
234 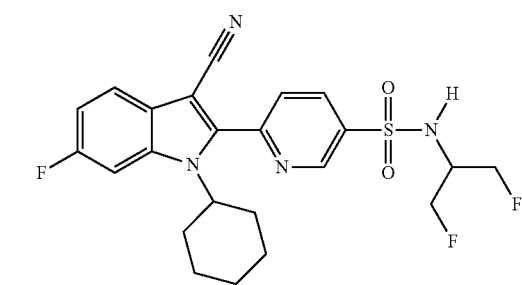
235 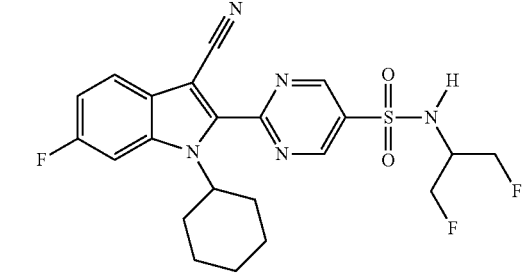

236 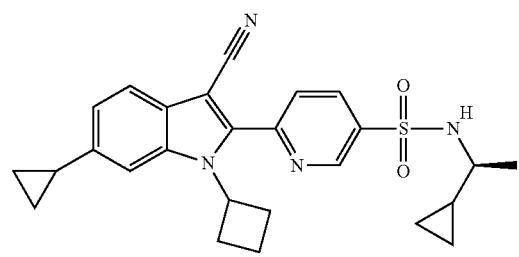
237 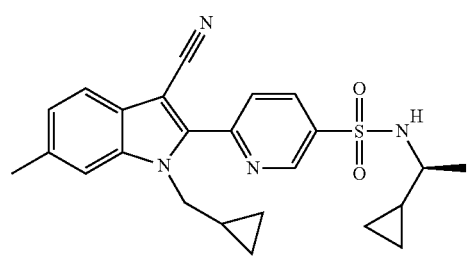
238 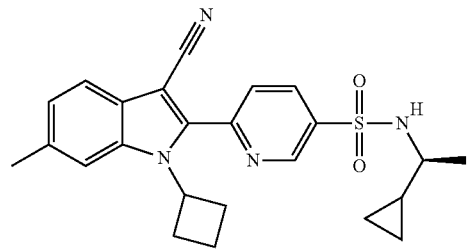
239 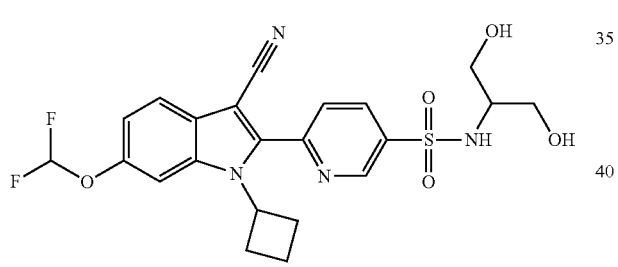
240 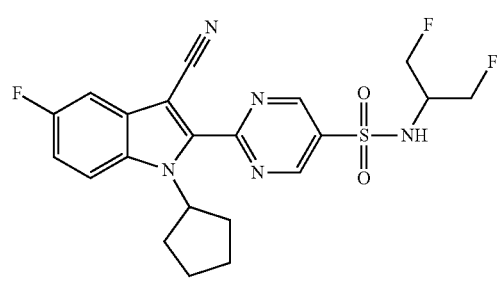
241 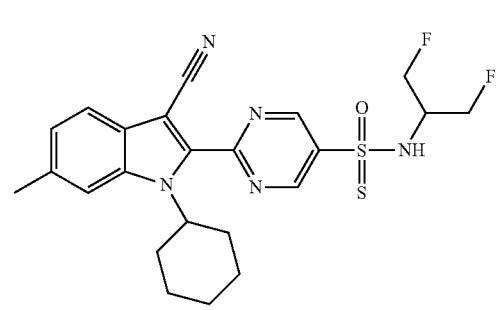
242 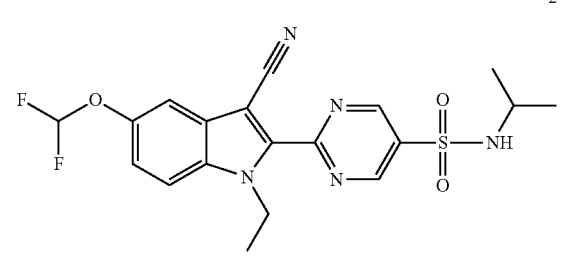
243 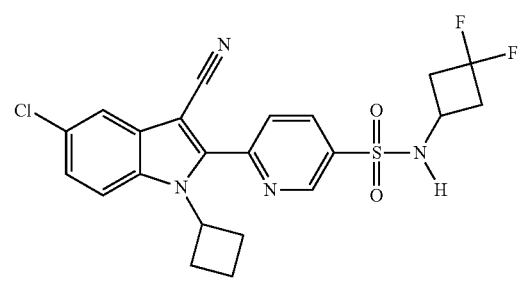
244 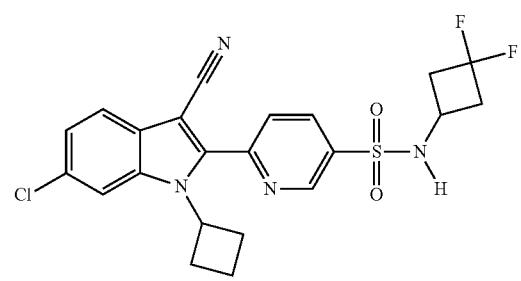
245 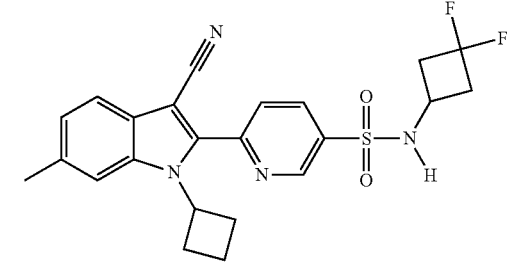
246 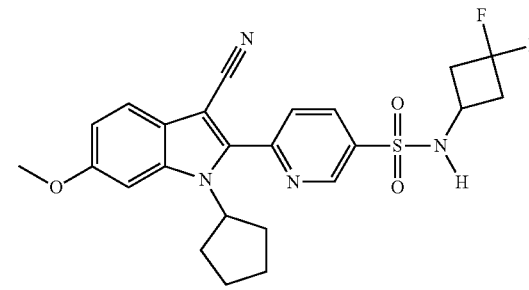

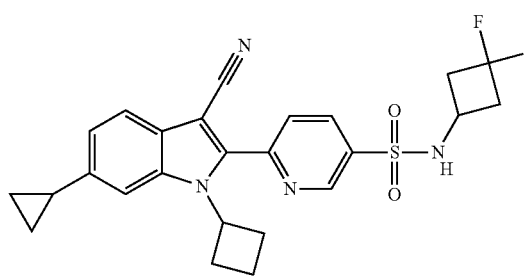
247
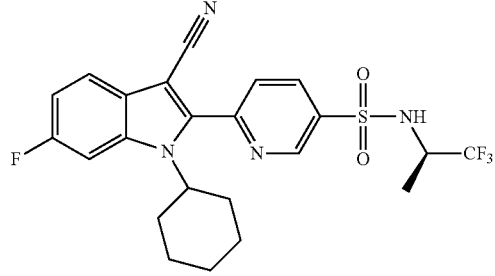
252
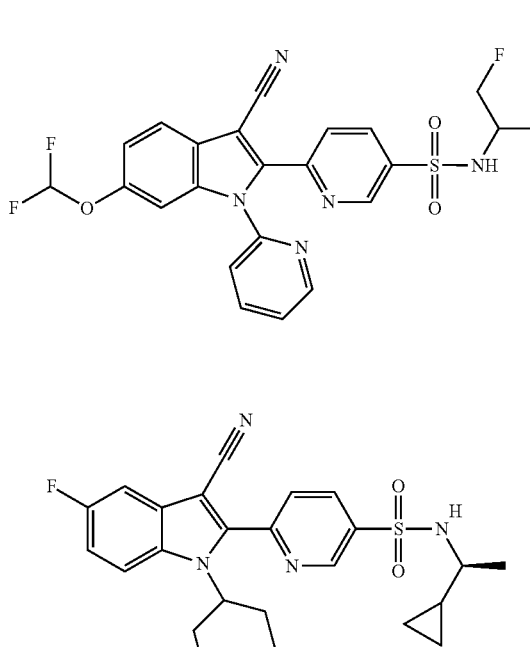
248
249
250
251
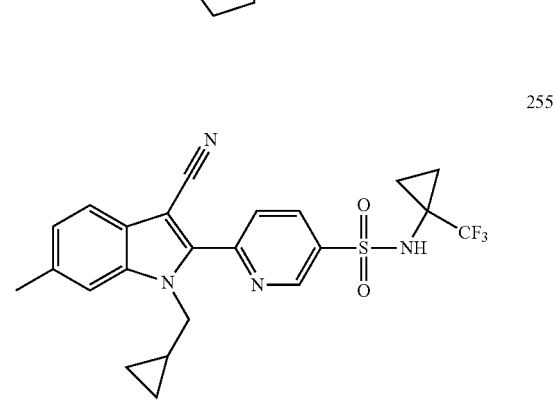
253
254
255
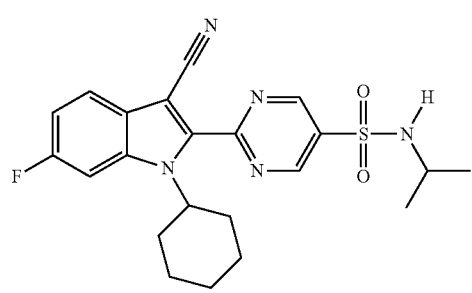
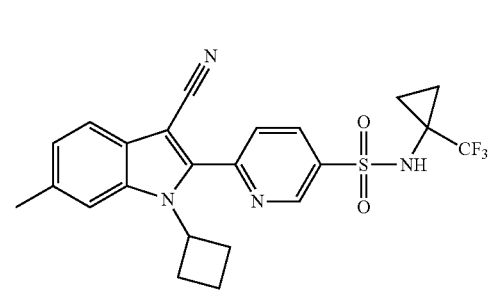
256

257 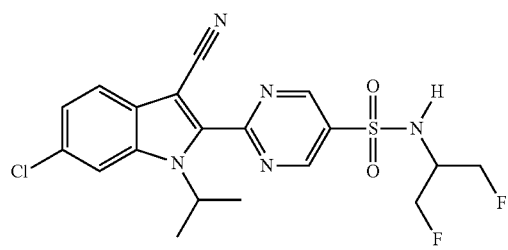
258 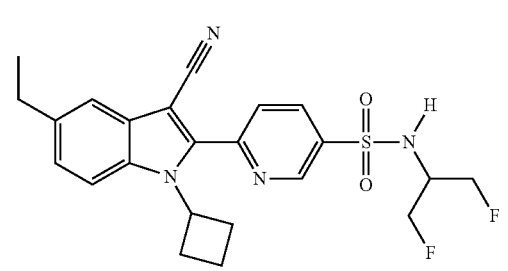
259 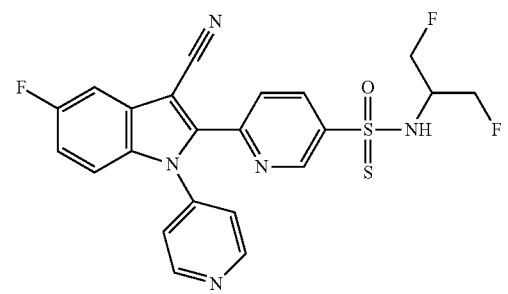
260 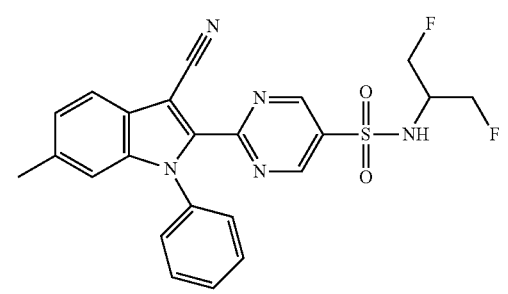
261 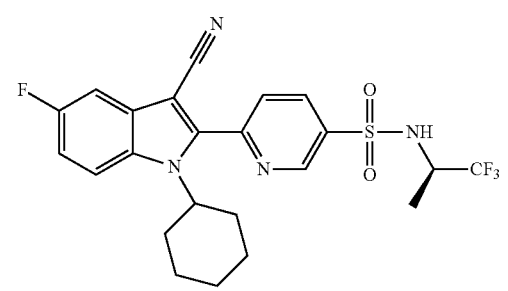
262 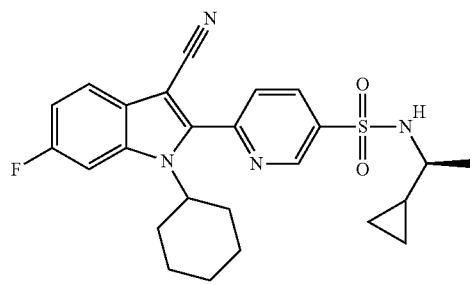
263 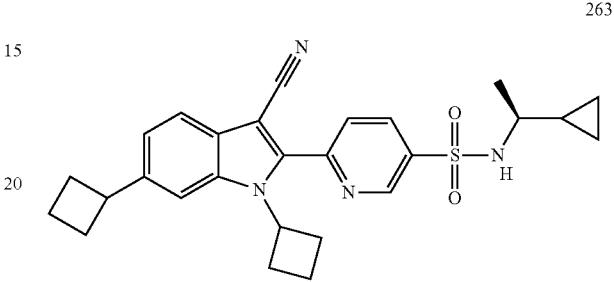
264 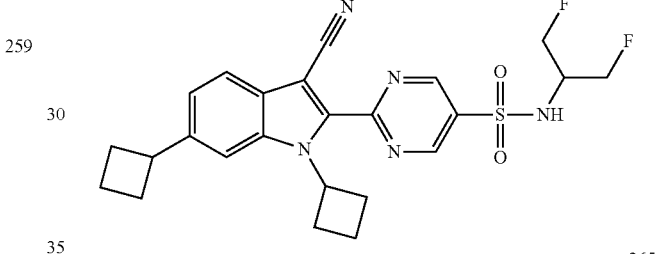
265 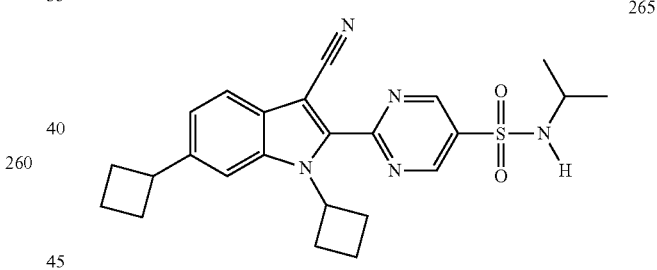
266
267 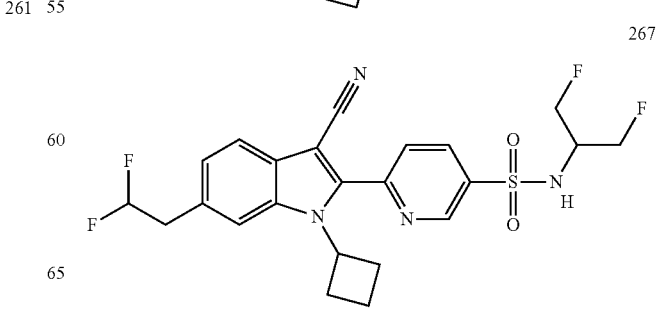

268
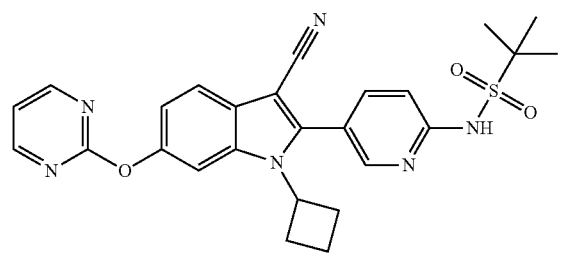
269
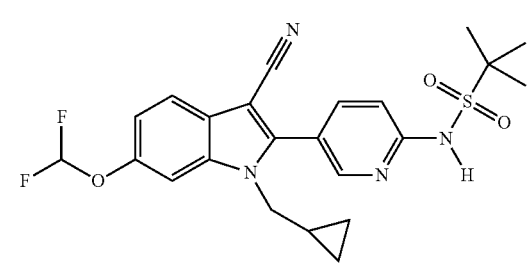
270
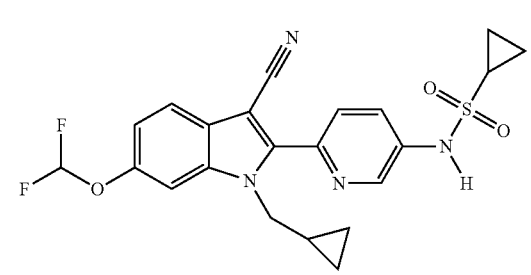
271
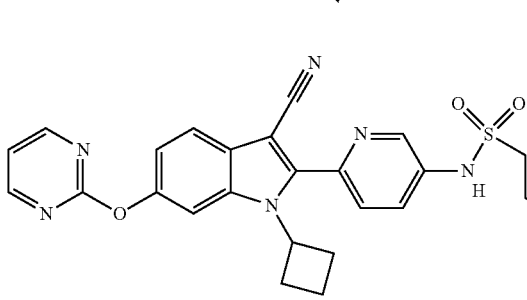
272
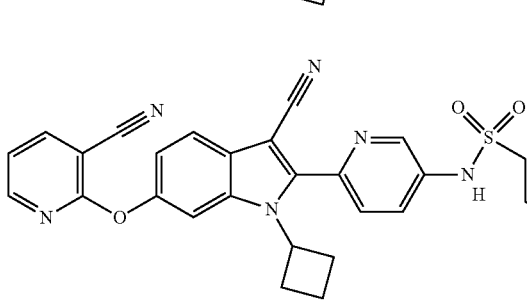
273
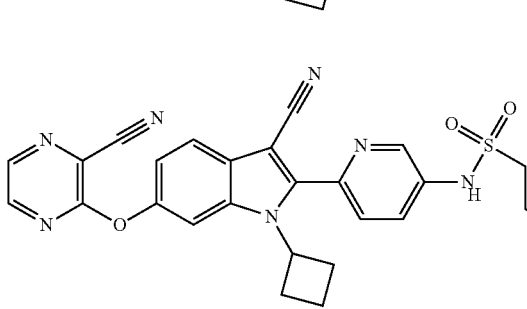
274
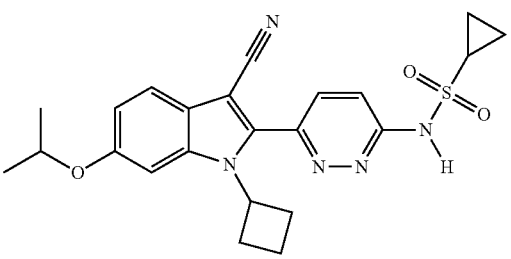
275
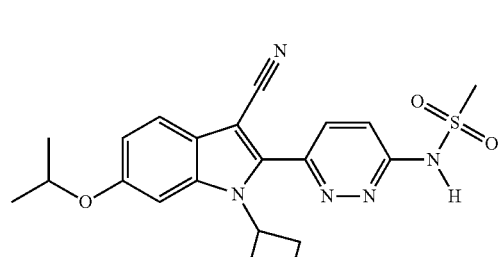
276
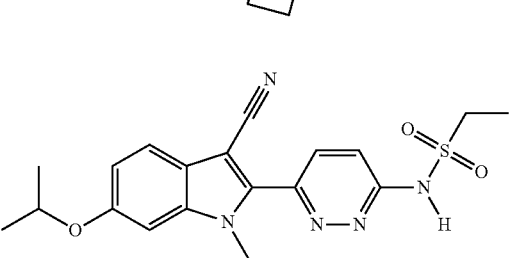
277
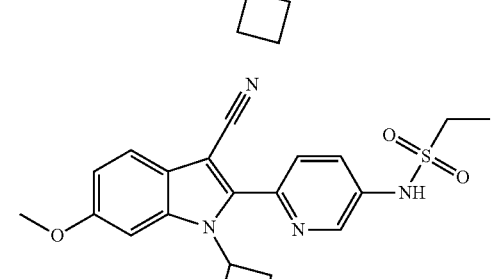
278
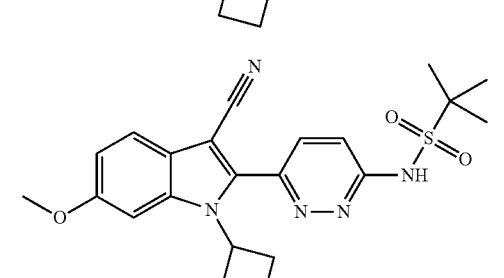
279
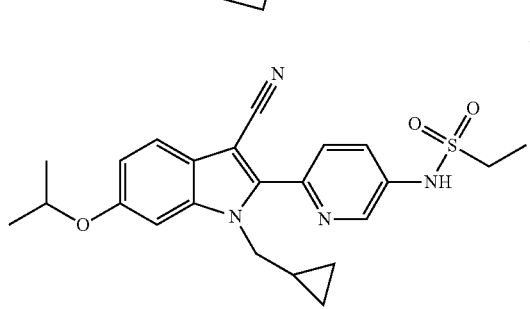

280
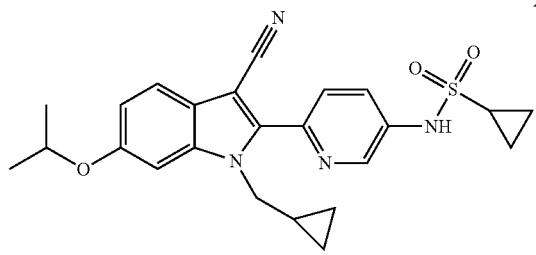
281
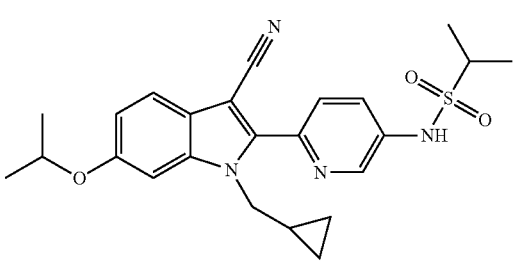
282
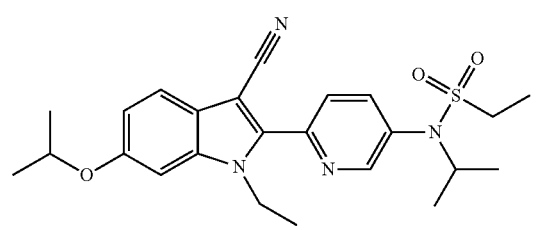
283
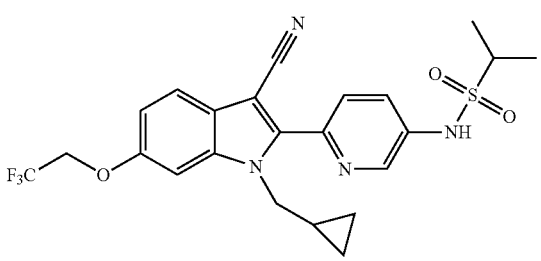
284
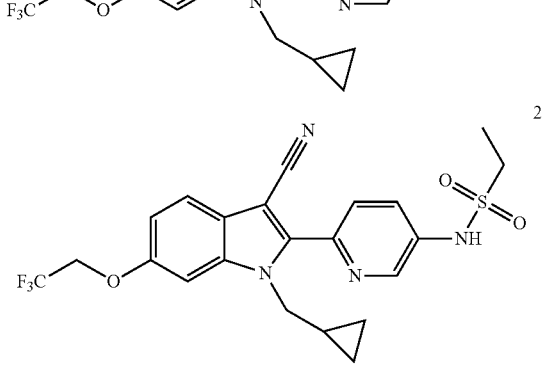
285
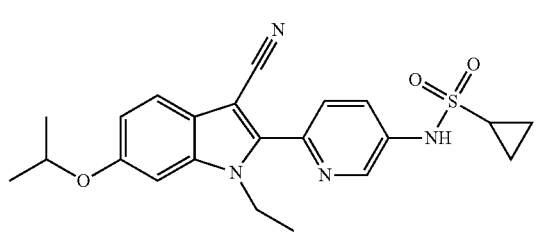
286
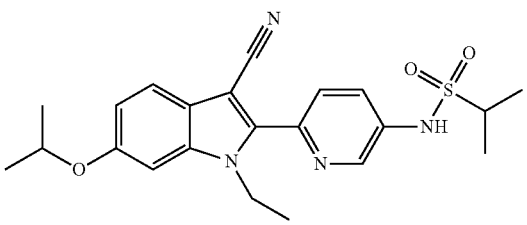
287
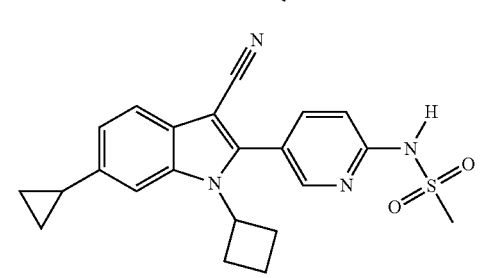
288
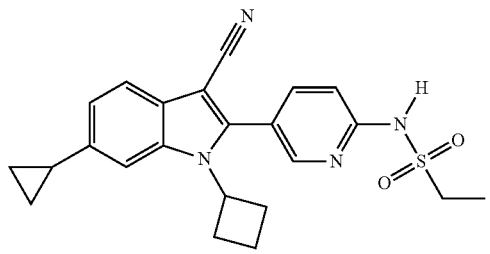
289
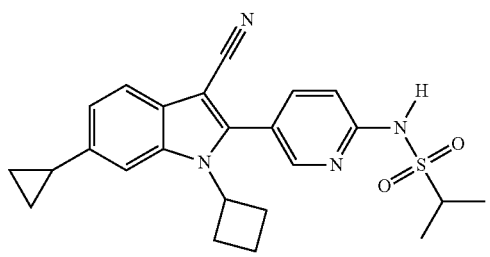
290
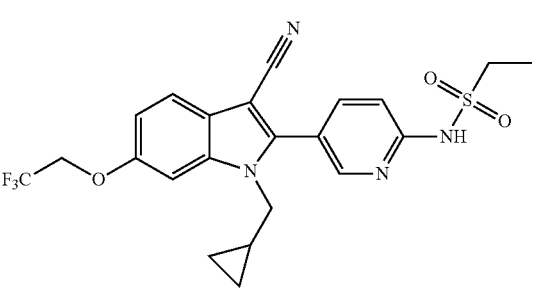
291
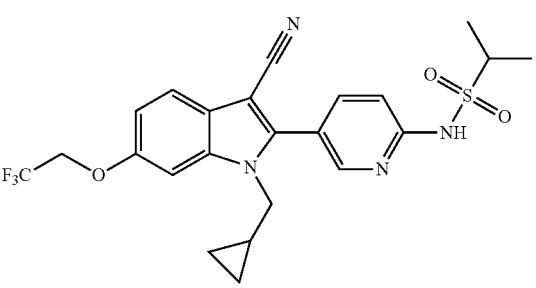

292 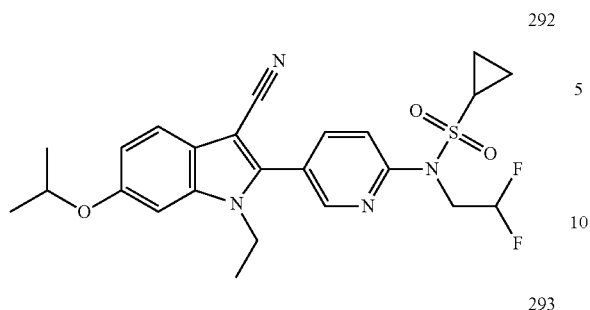
293 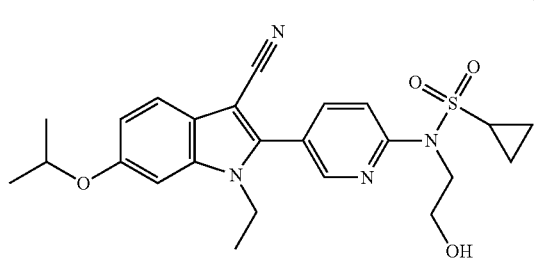
294 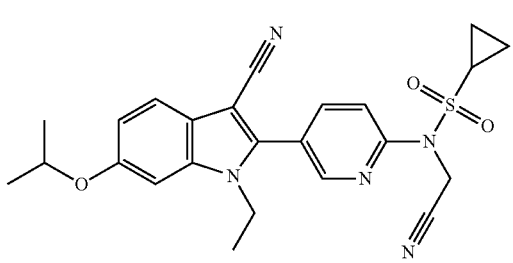
295 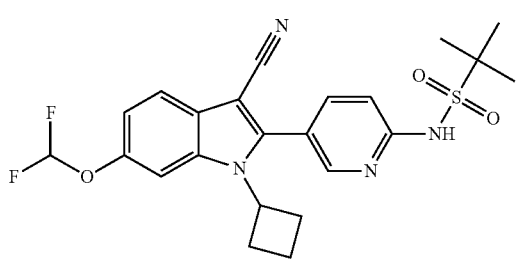
296 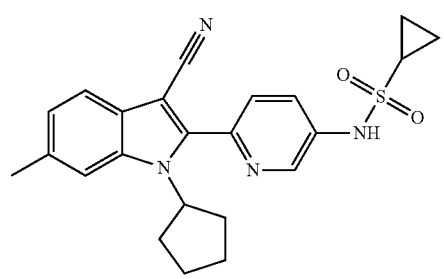
297 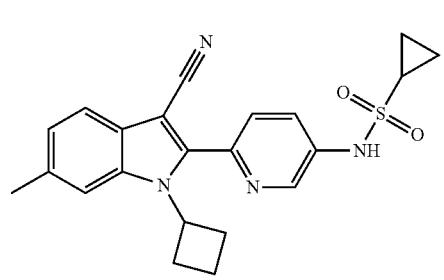
298 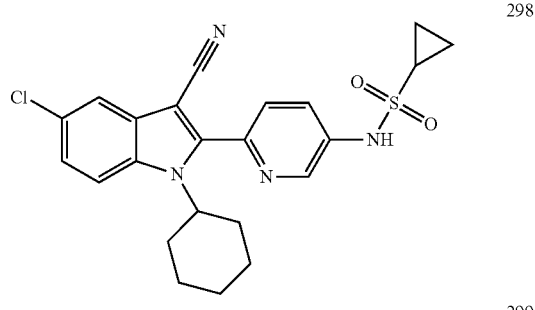
299 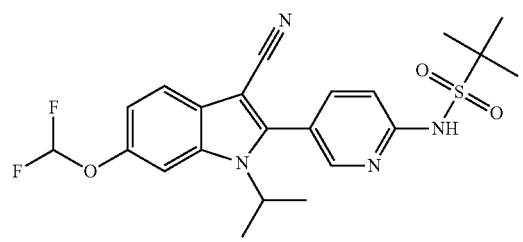
300 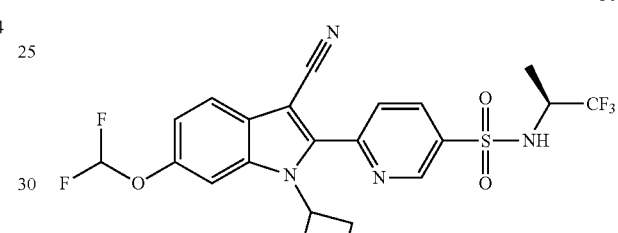
301 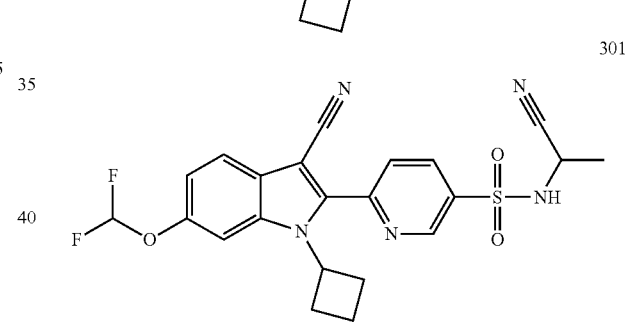
302 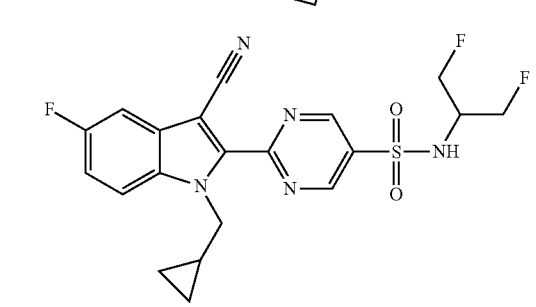
303 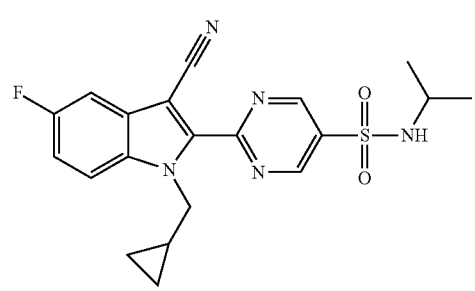

-continued
304
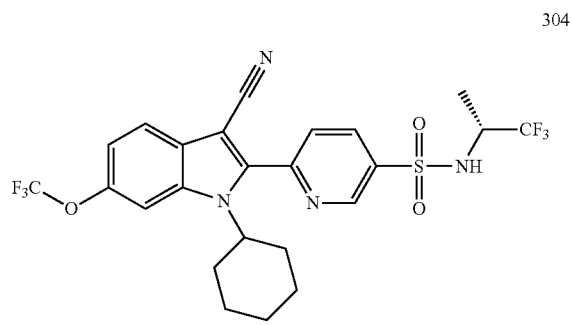
305
309
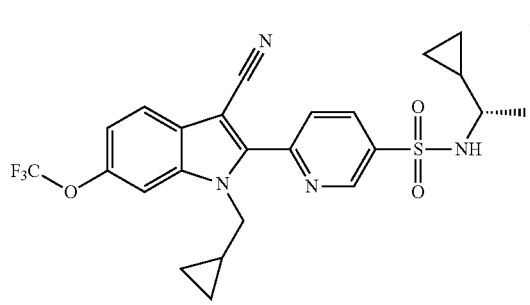
310
306
307
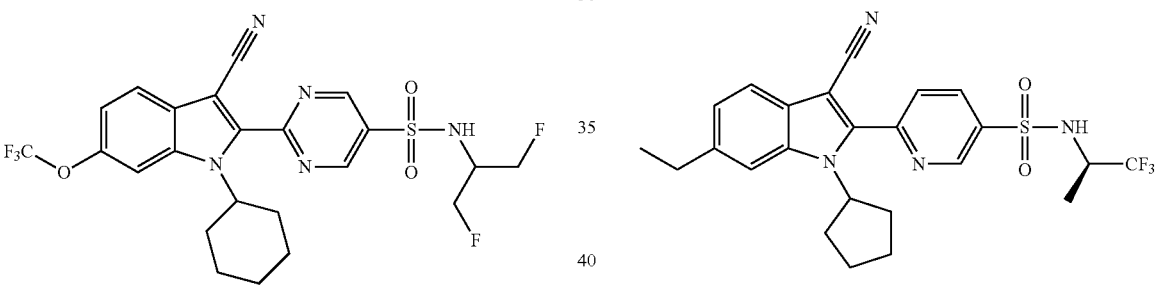
311
312
308
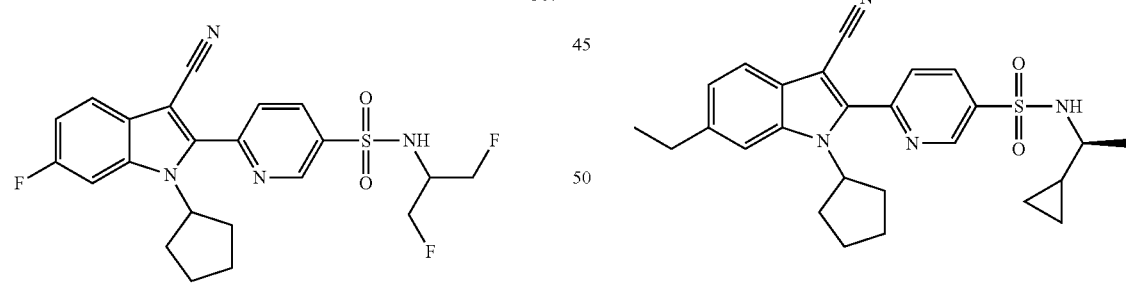
313
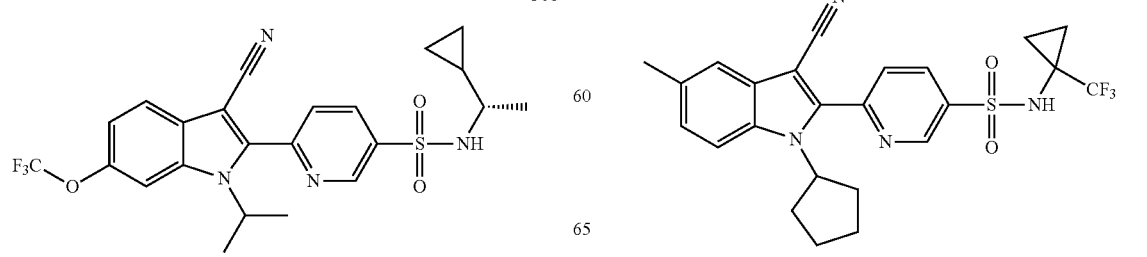

314 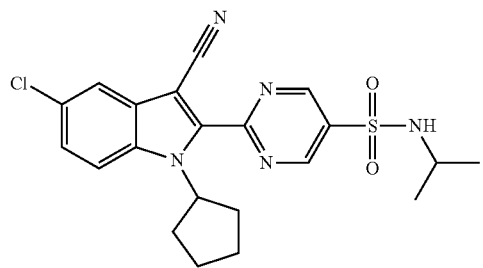
315 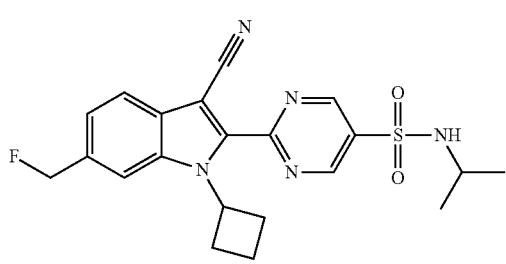
316 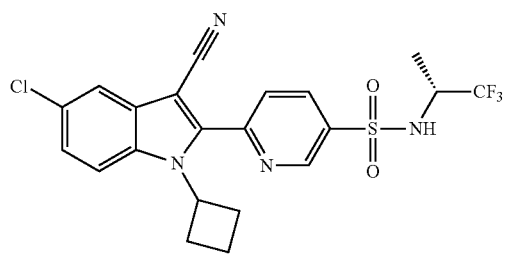
317 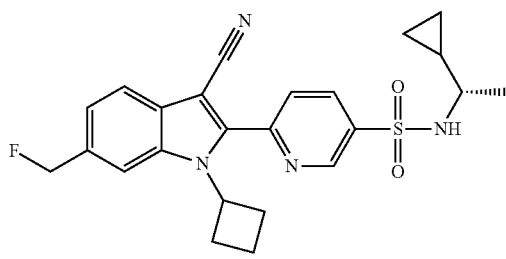
318 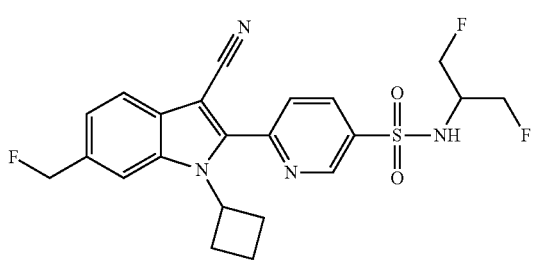
319 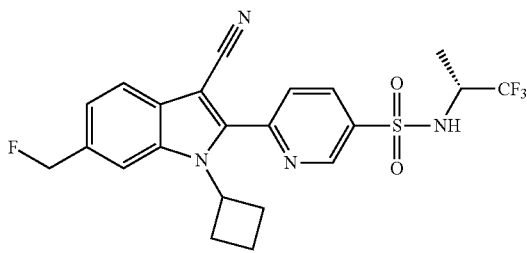
320 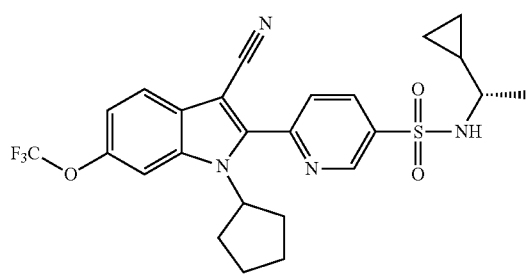
321 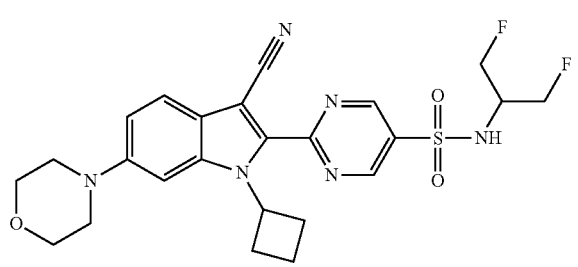
322 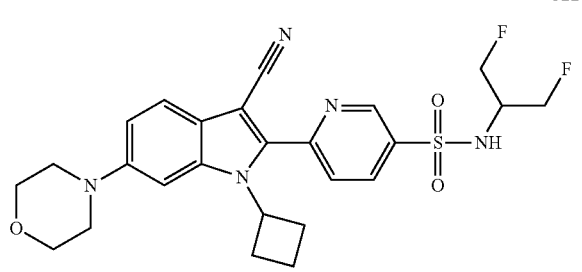
323 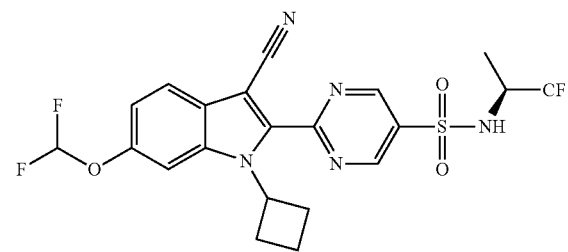
324 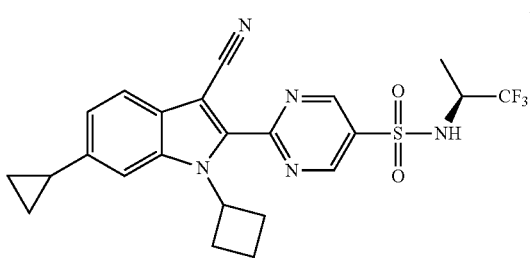

325
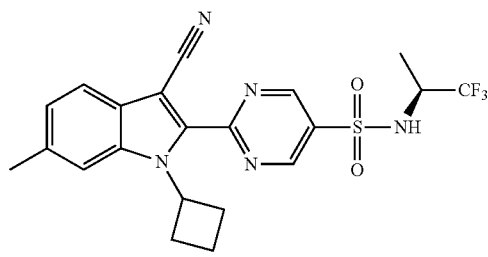
326
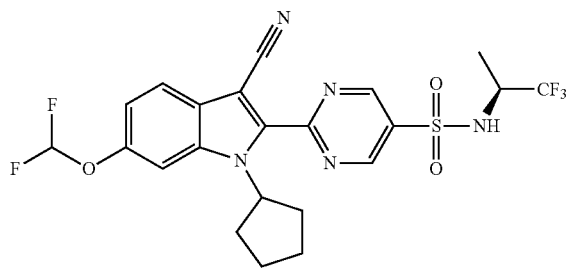
327
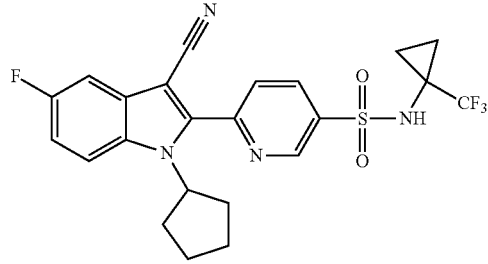
328
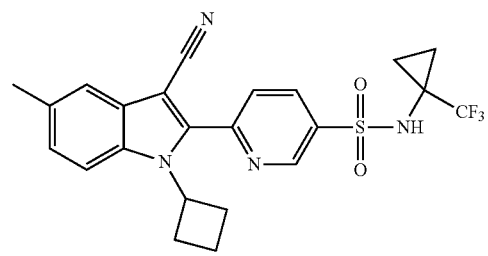
329
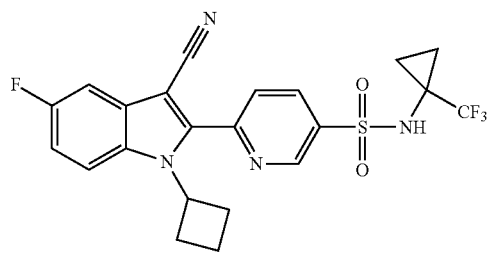
330
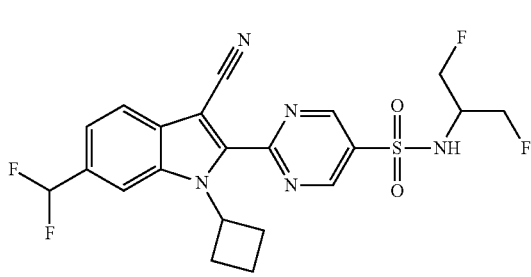
331
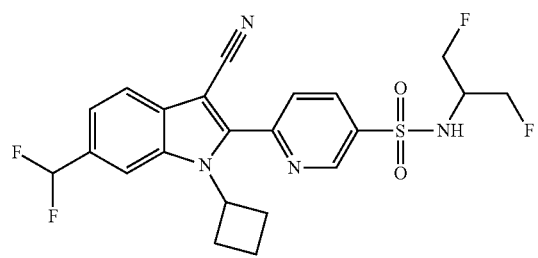
332
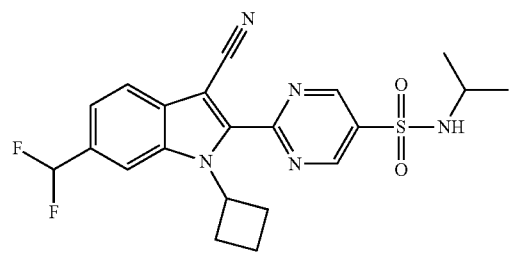
333
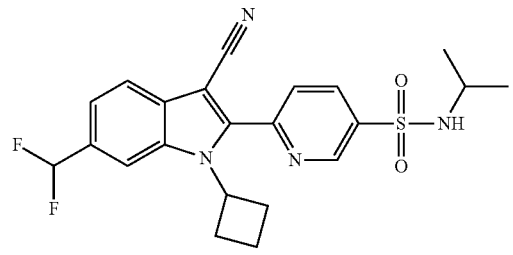
334
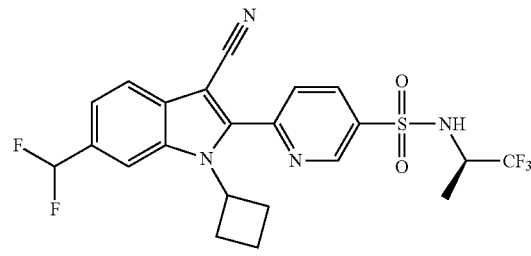
335
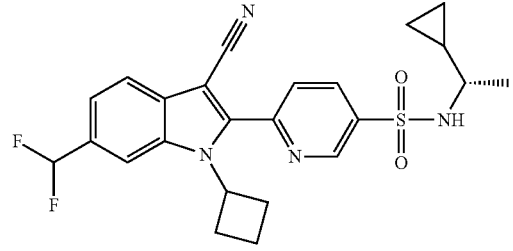

336 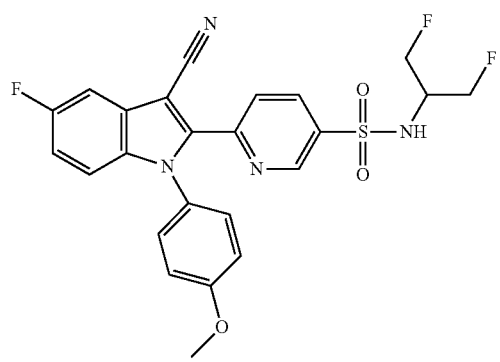
337 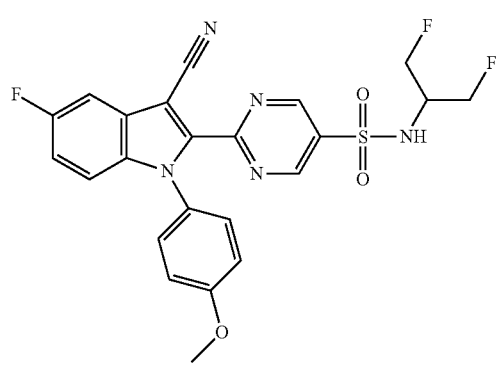
338 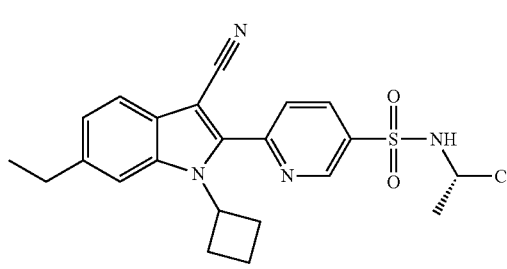
339 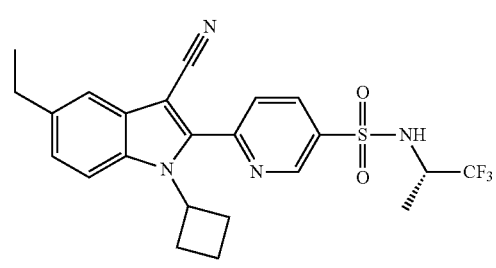
340 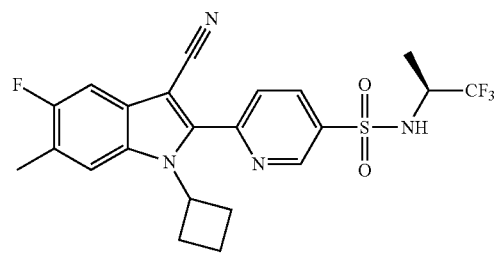
341 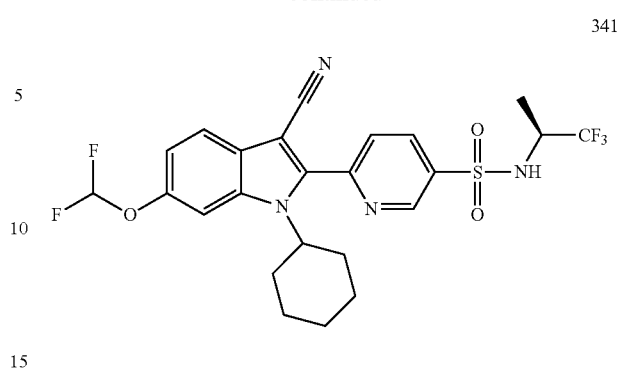
342 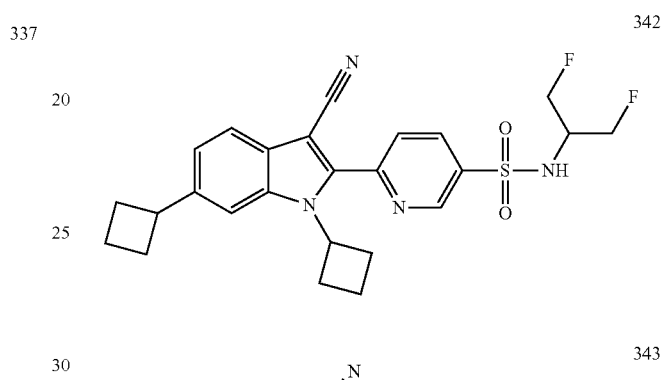
343 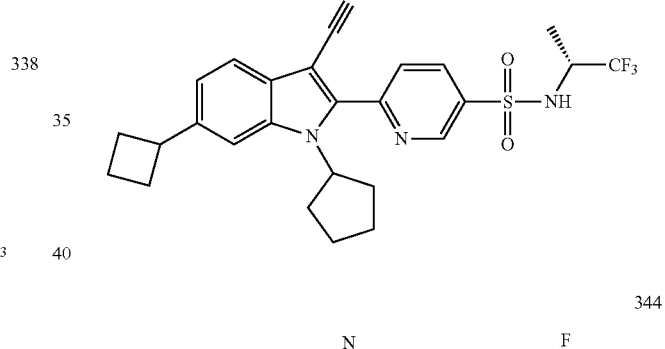
344 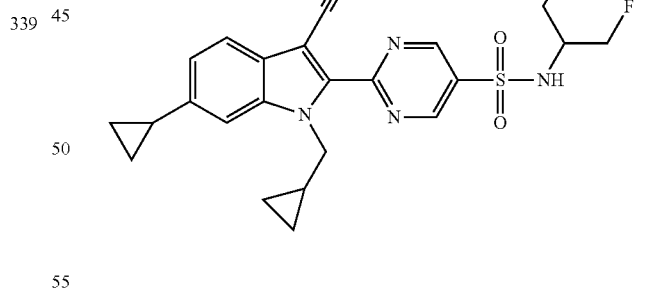
345 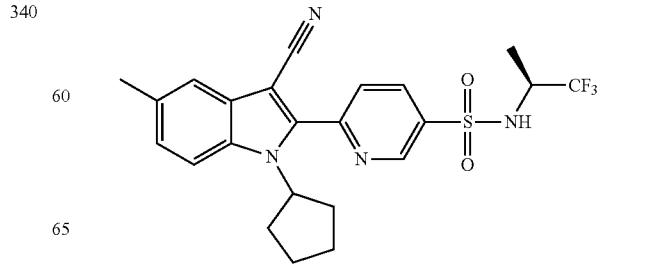

346 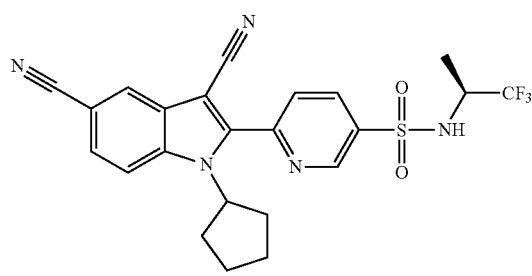
347 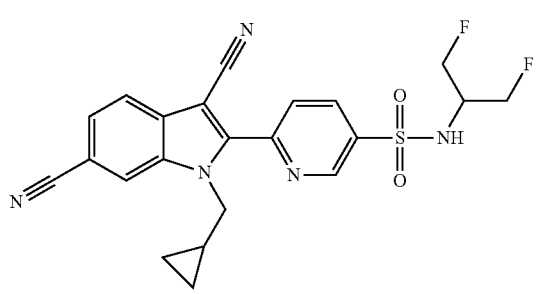
348 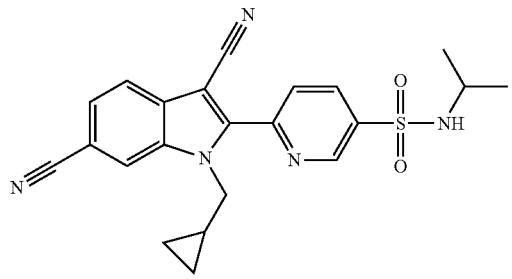
349 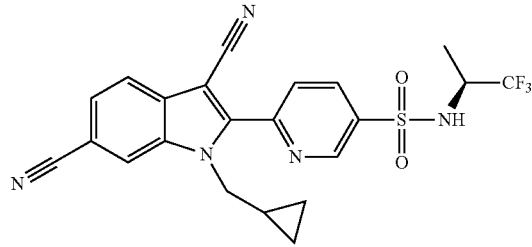
350 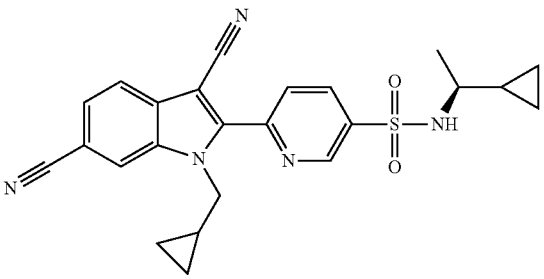
351 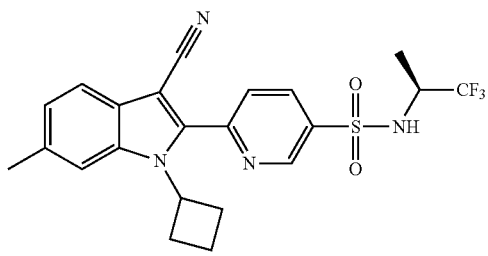
352 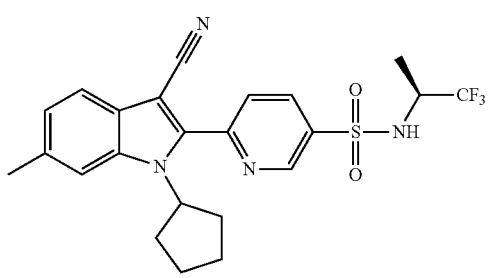
353 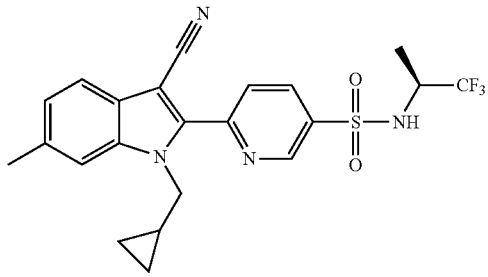
354 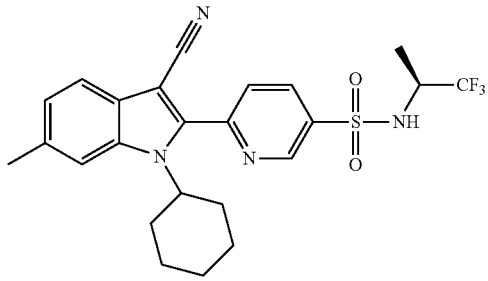
355 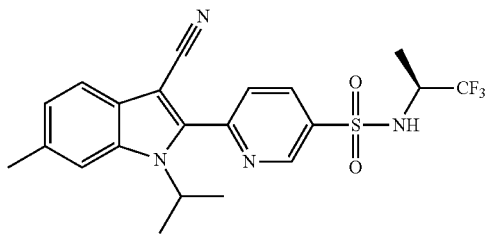

356
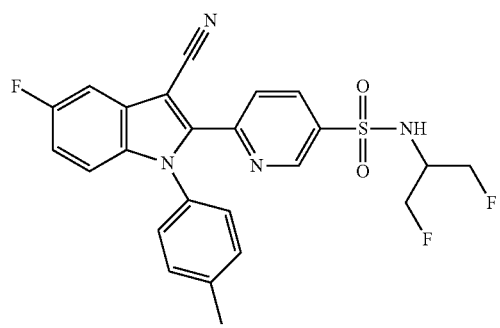
357
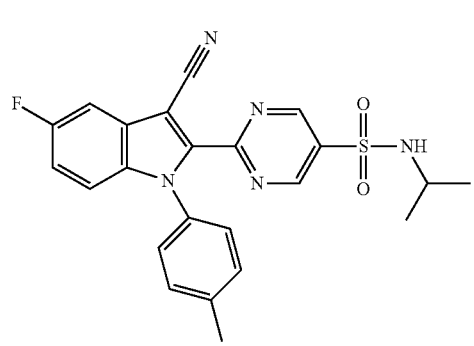
358
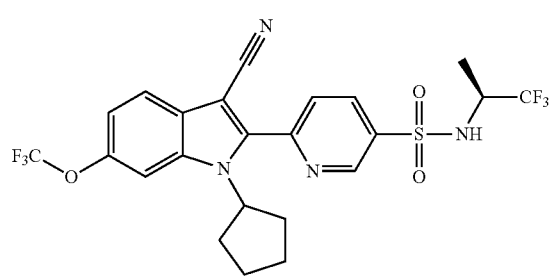
359
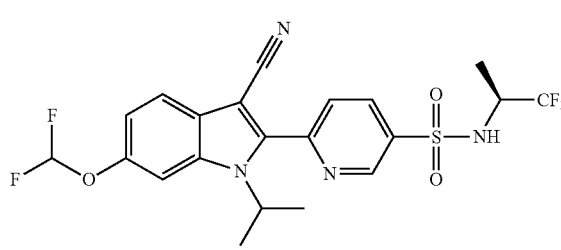
360
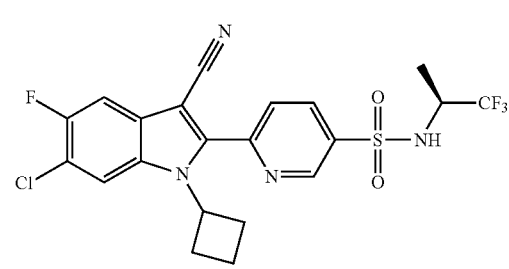
361
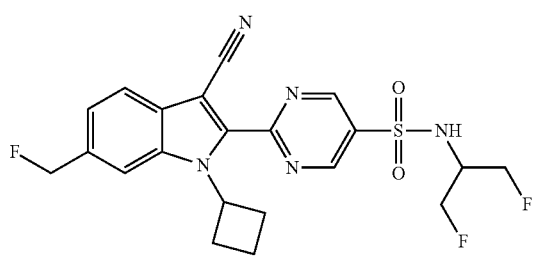
362
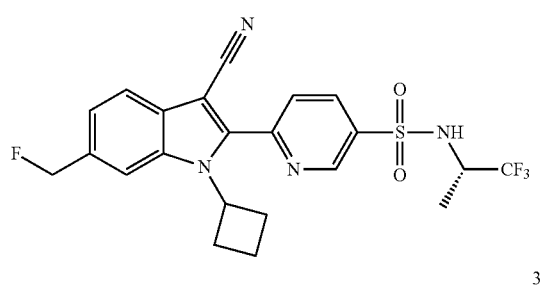
363
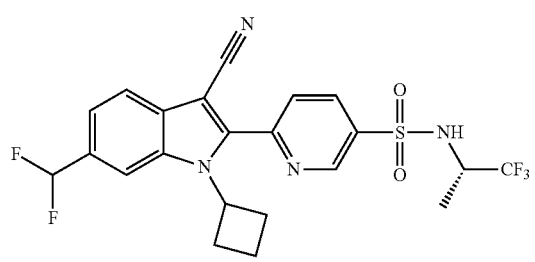
364
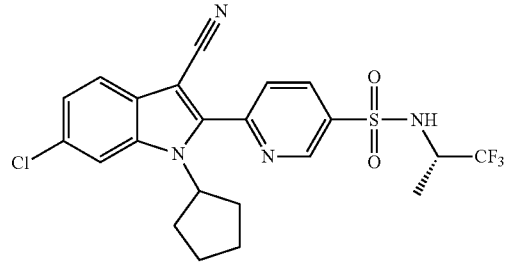
365
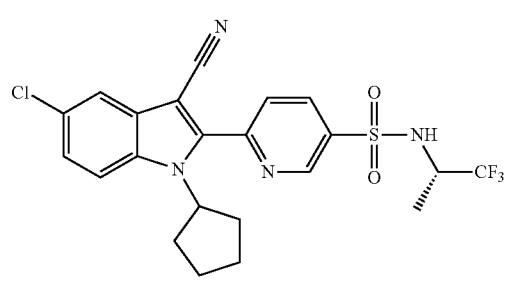
367
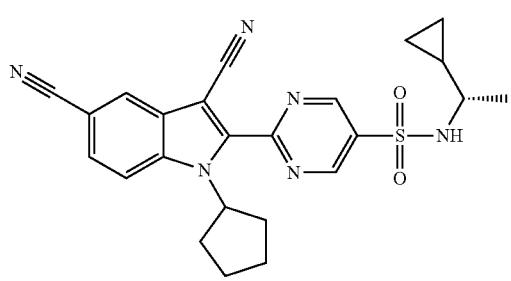

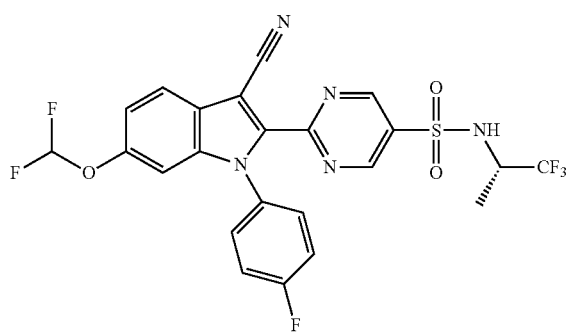
368
369
370
371
372
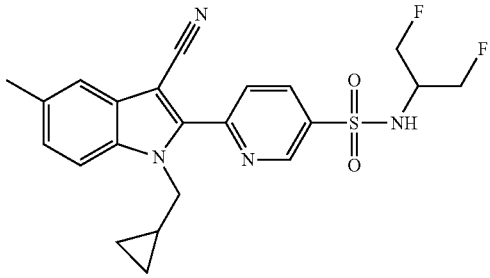
373
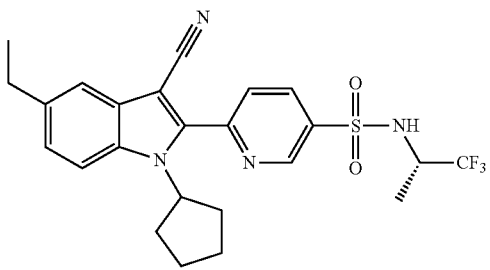
374
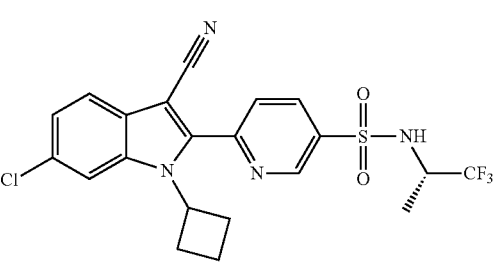
375
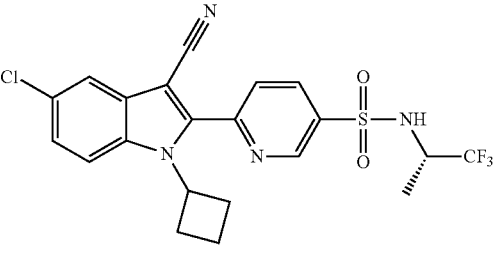
376
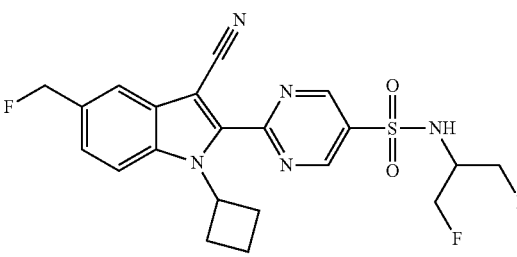
377
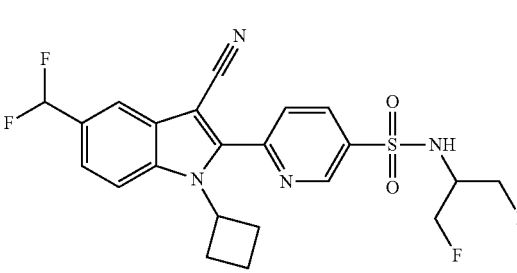
378

379 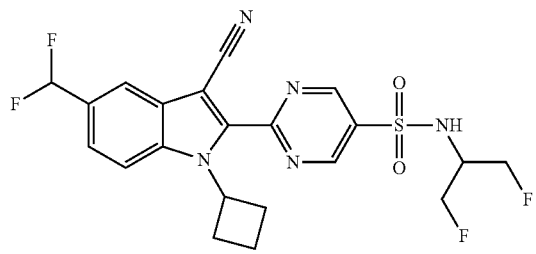
380 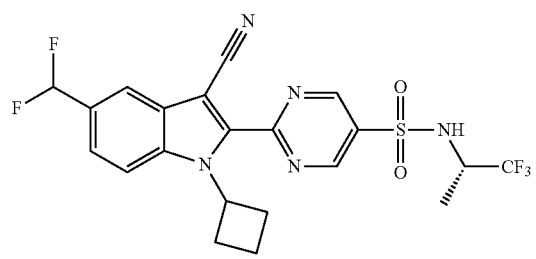
381 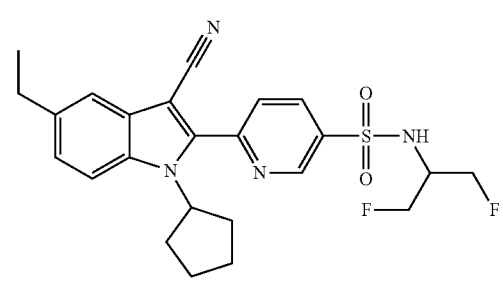
382 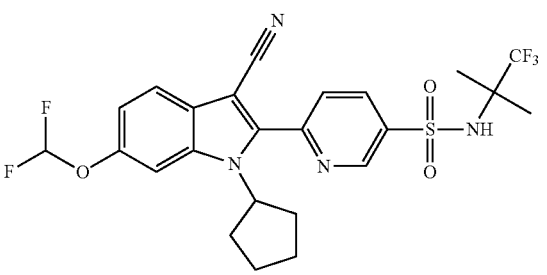
383 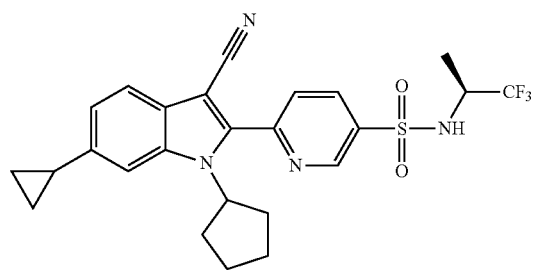
384 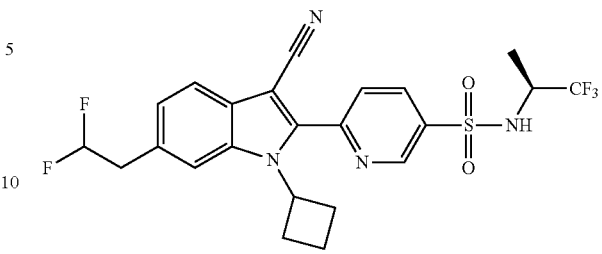
385 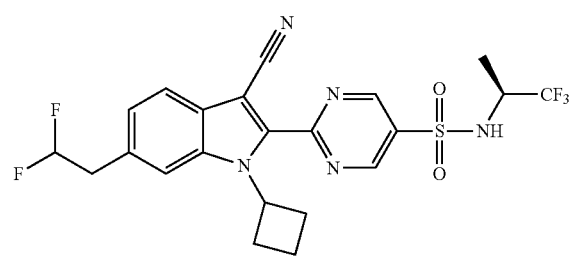
386 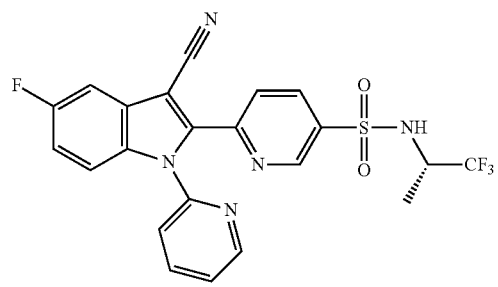
387 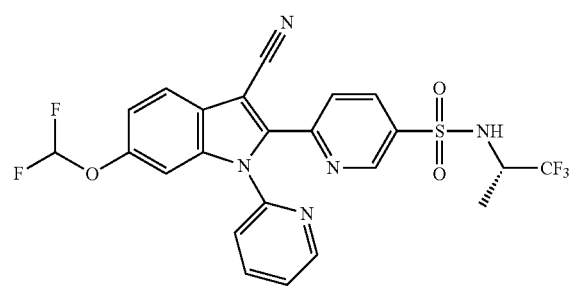
388 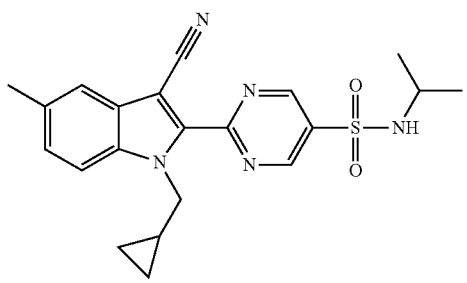

389
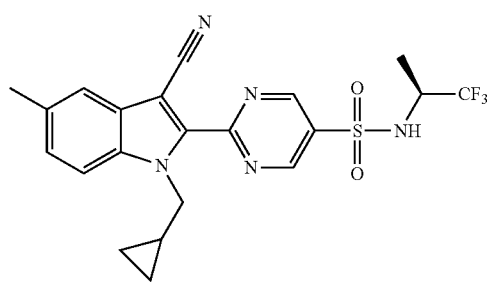
390
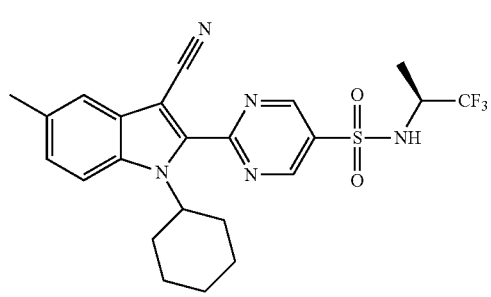
391
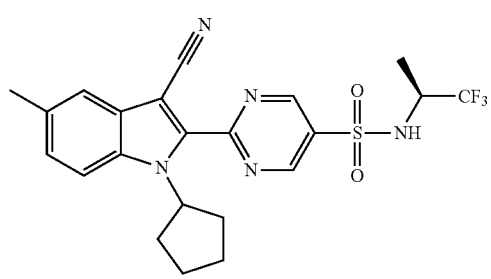
392
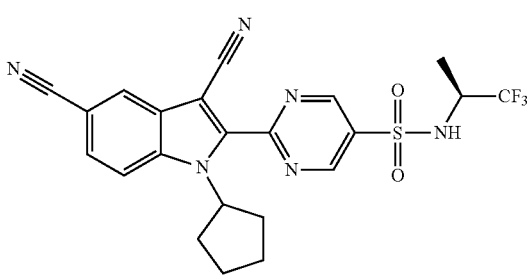
393
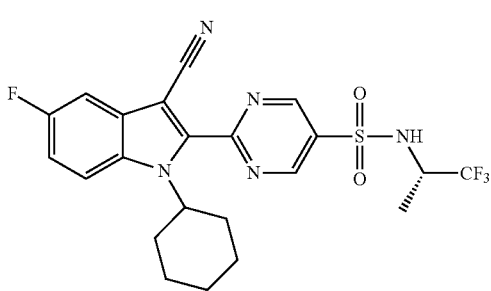
394
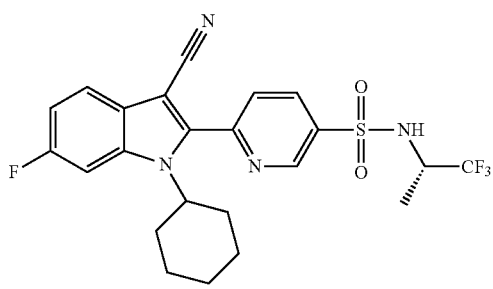
395
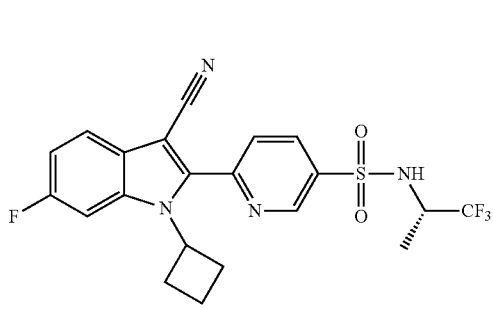
396
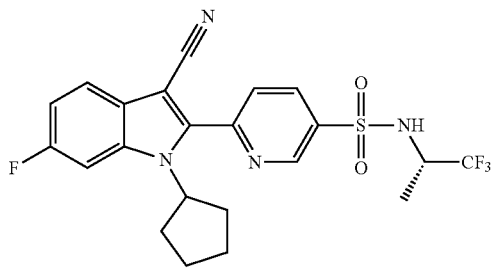
397
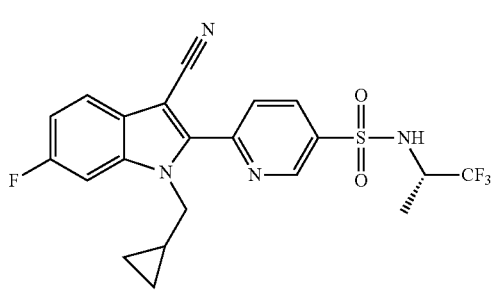
398
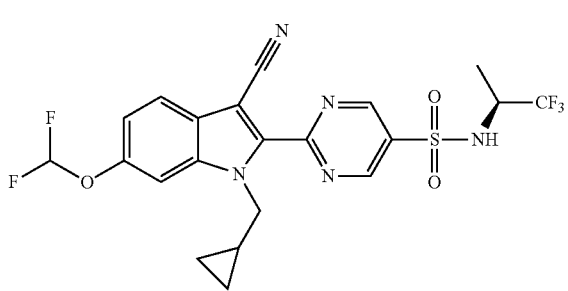

399
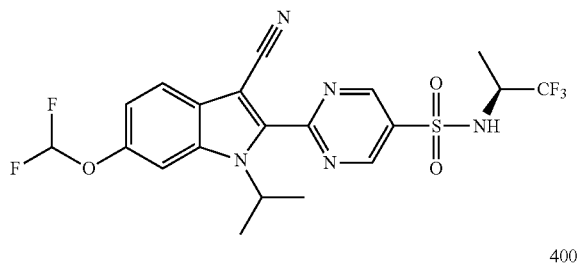
400
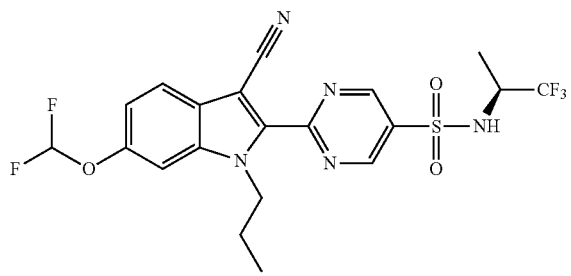
401
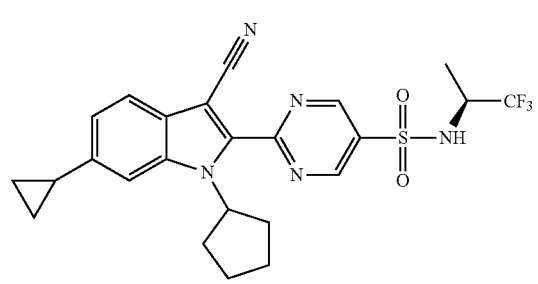
402
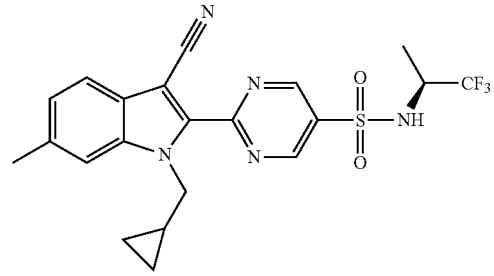
403
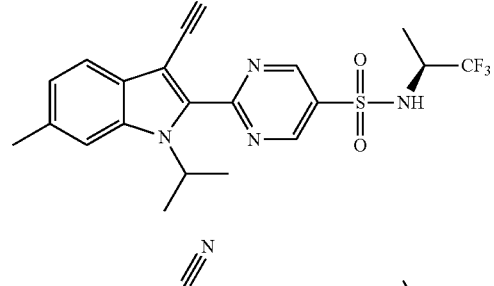
405
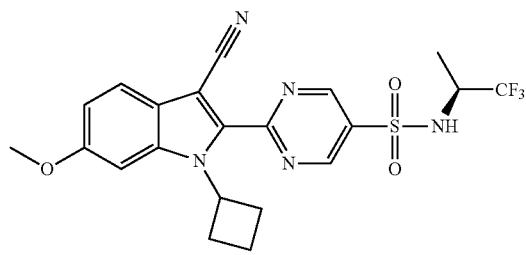
406
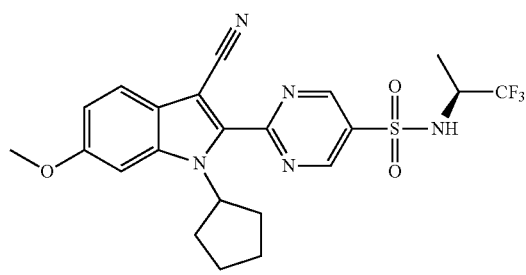
407
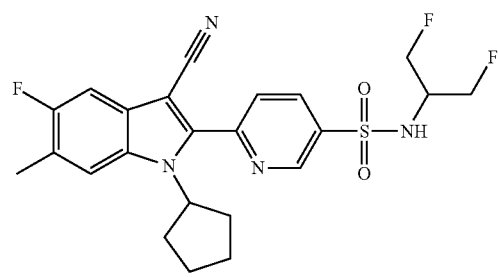
408
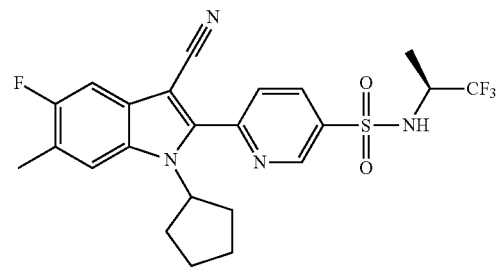
409
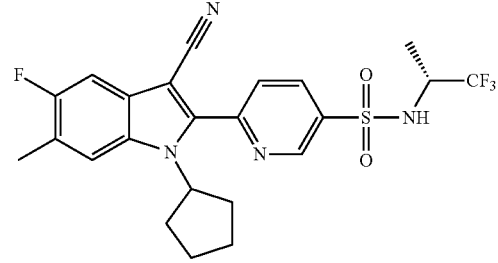

| | |
|---|---|
| 410 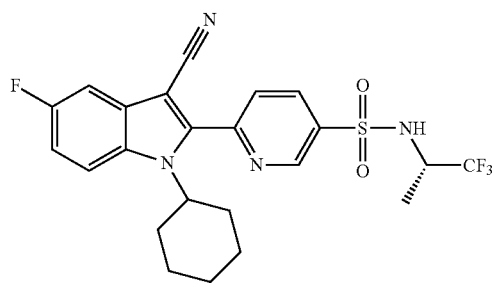 | 415 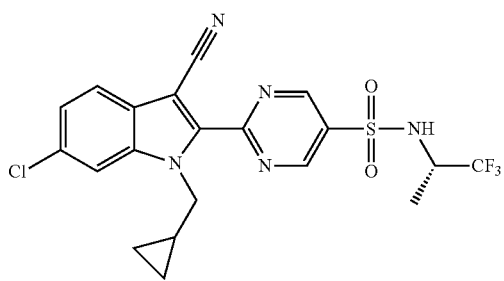 |
| 411 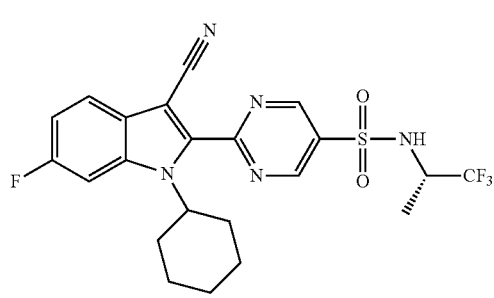 | 416 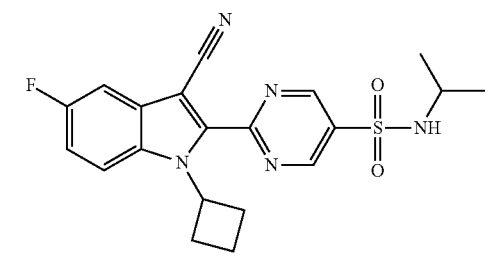 |
| 412 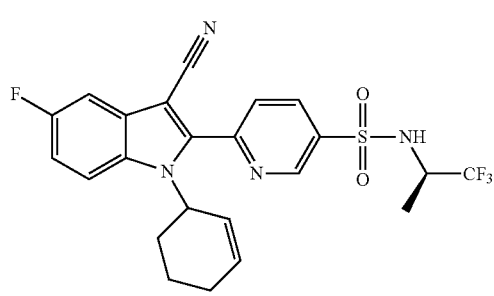 | 417 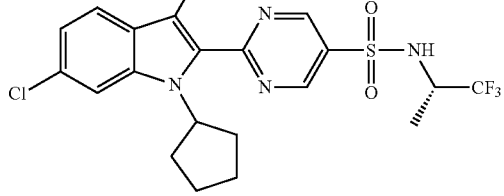 |
| 413 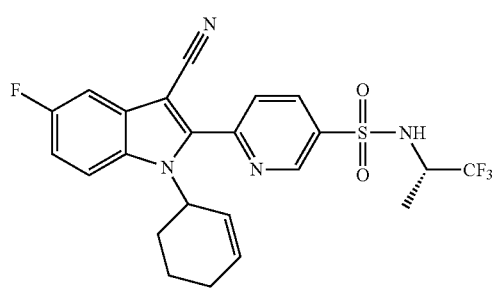 | 418 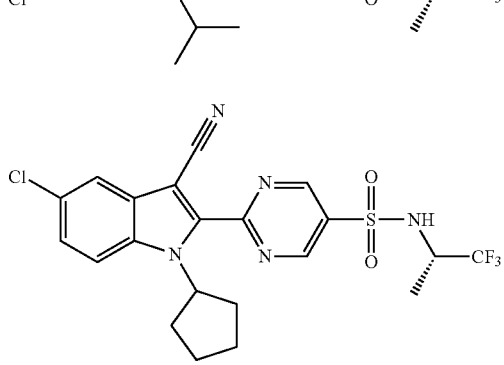 |
| 414 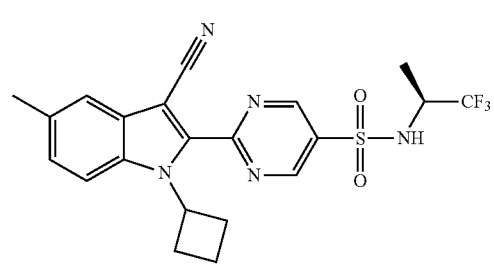 | 419 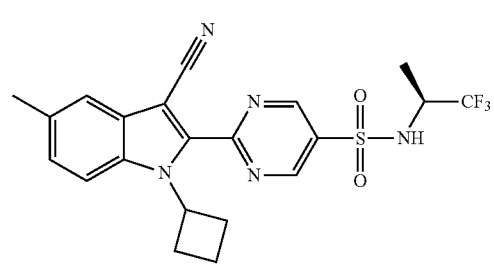 |
| | 420 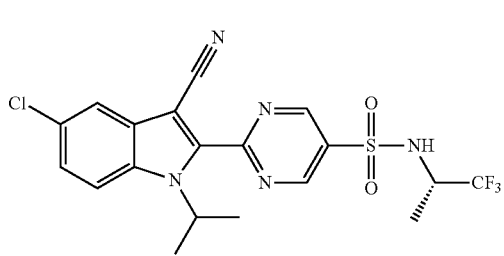 |

| | |
|---|---|
| 421 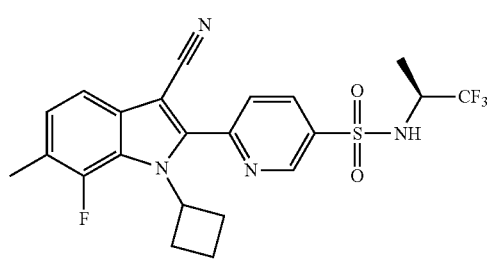 | 427 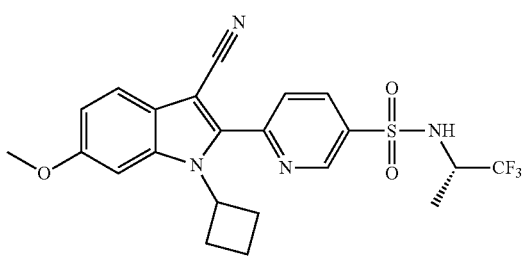 |
| 422 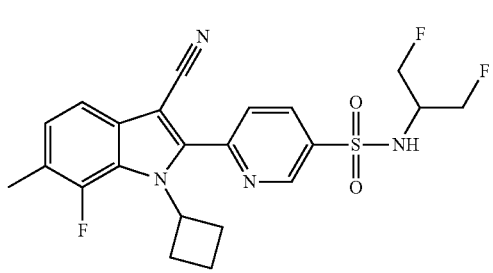 | 428 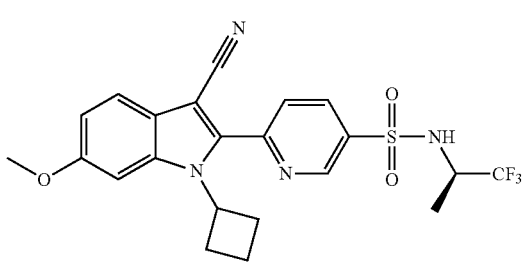 |
| 423 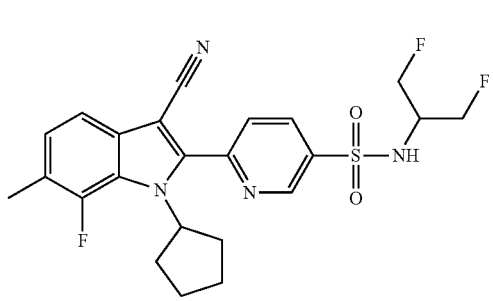 | 429 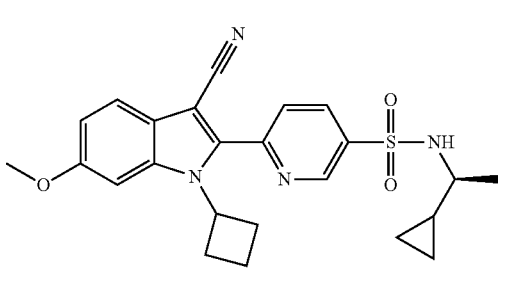 |
| 424 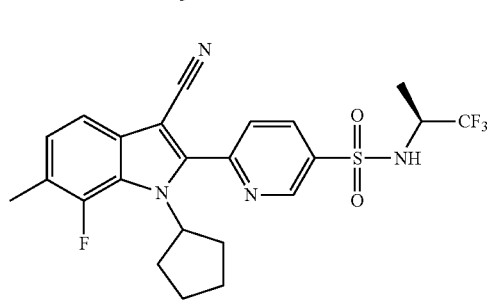 | 430 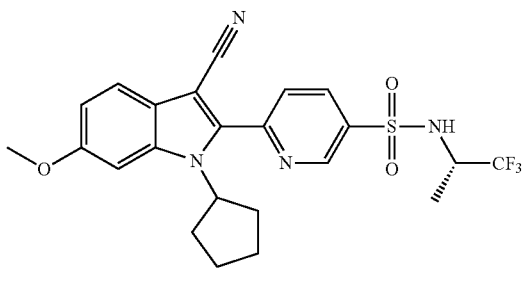 |
| 425 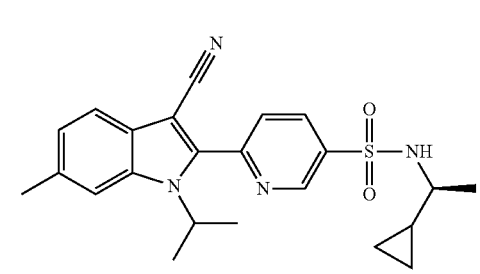 | 431 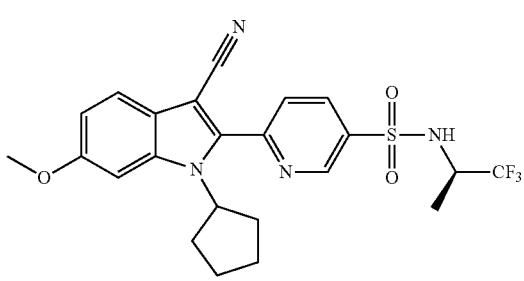 |
| 426 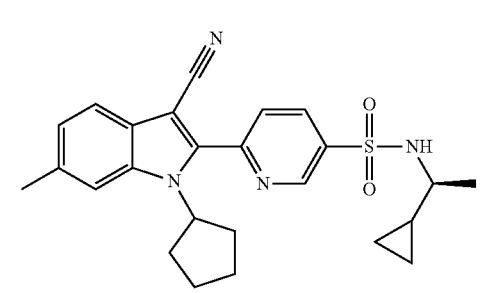 | 432 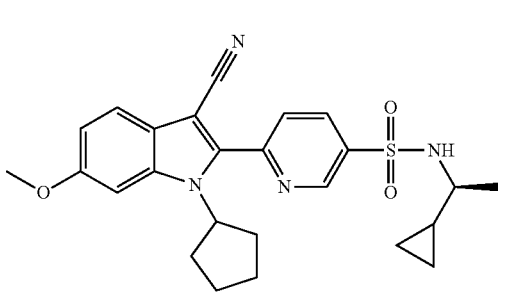 |

433
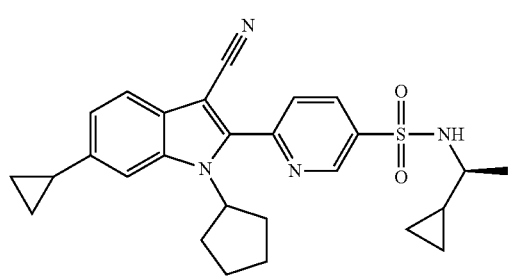
434
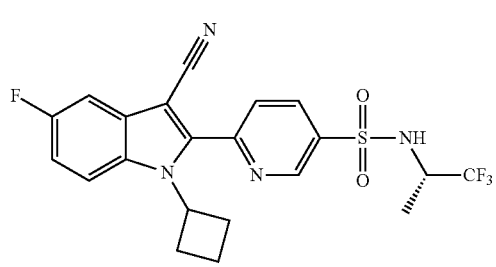
435
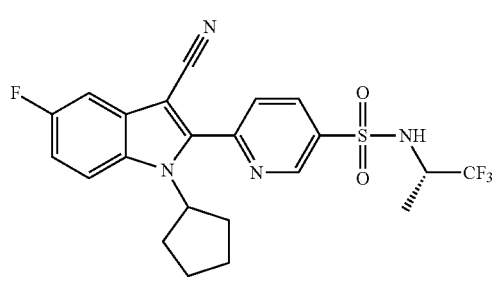
436
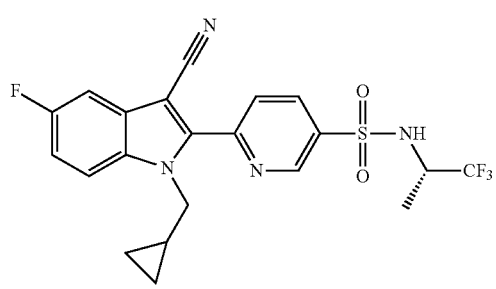
437
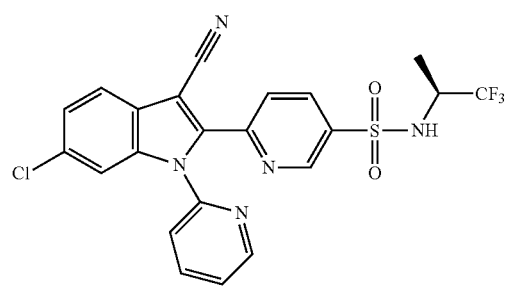
438
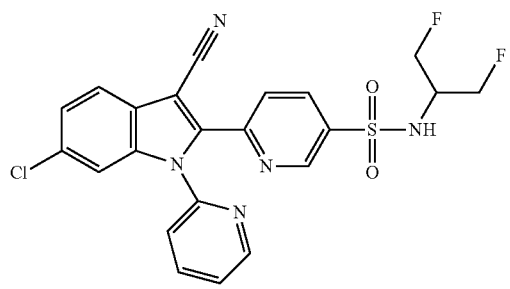
439
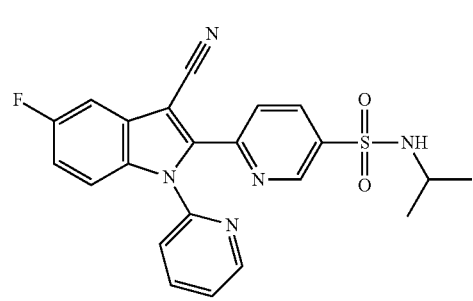
440
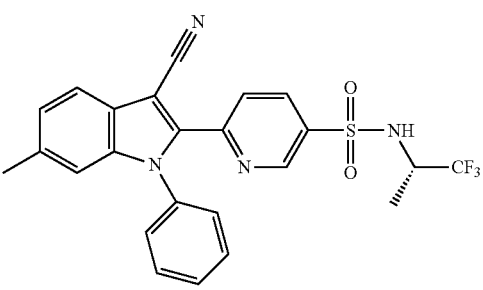
441
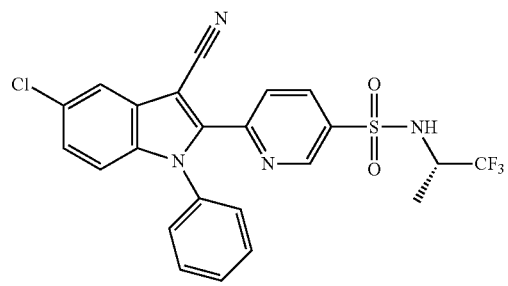
442
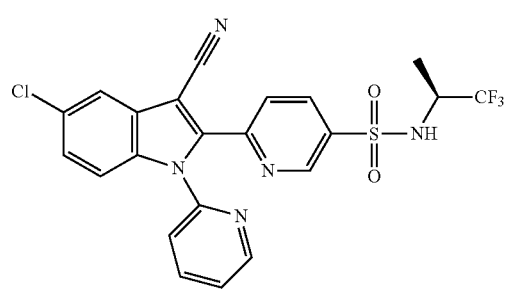

443 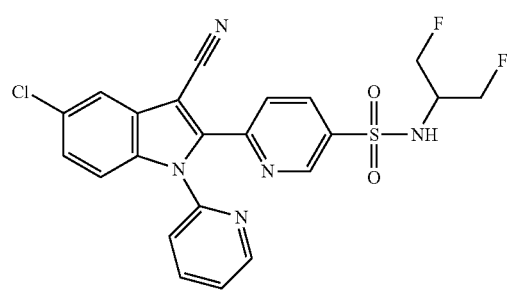
444 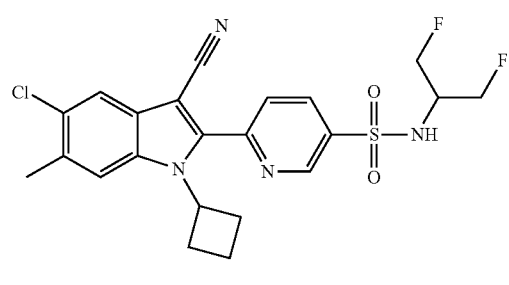
445 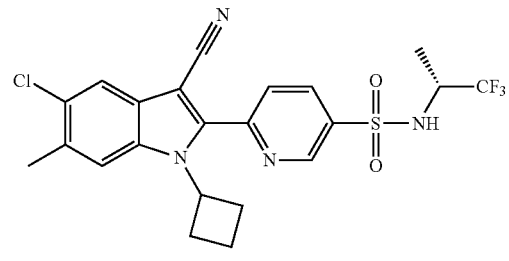
446 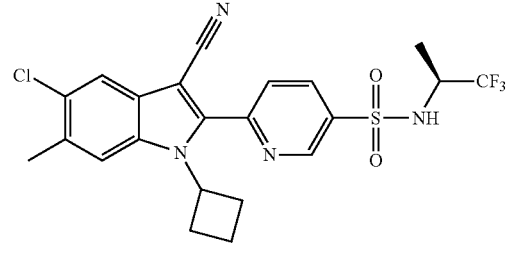
447 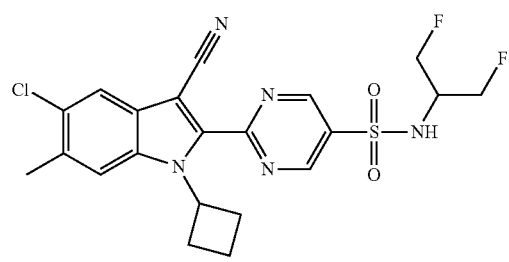
448 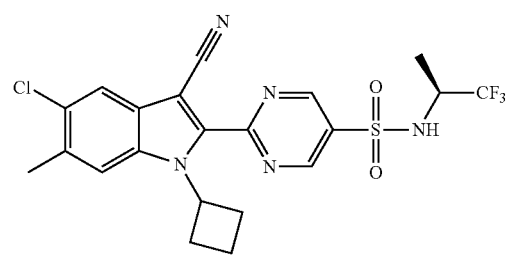
449 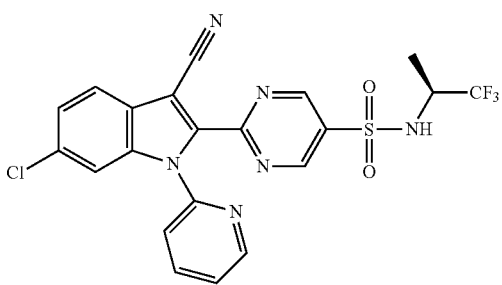
450 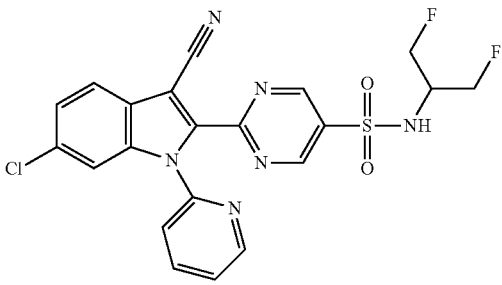
451 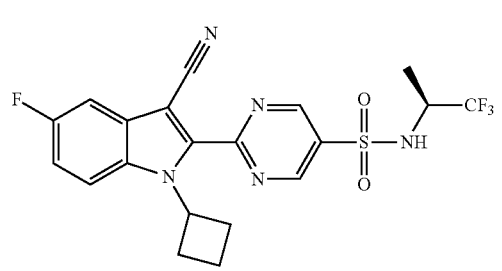
452 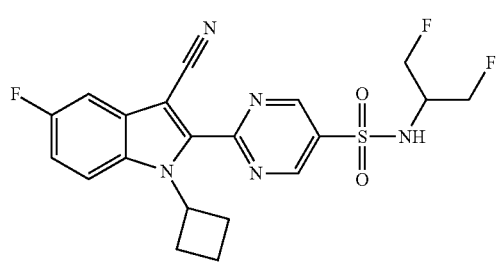
453 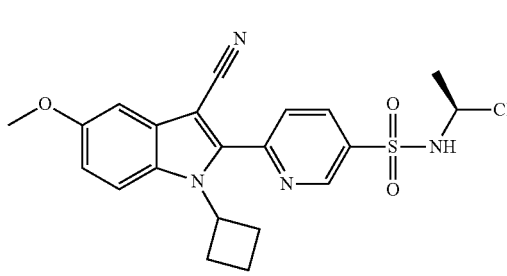
454 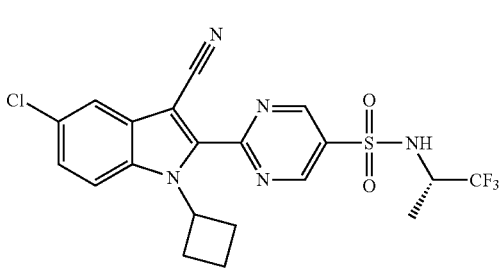

455 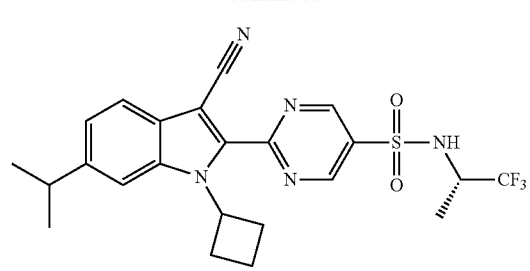
456 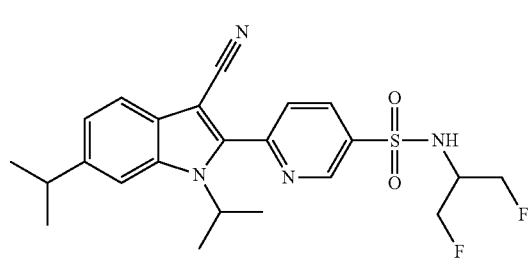
457 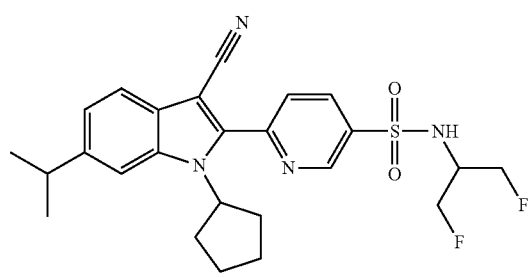
458 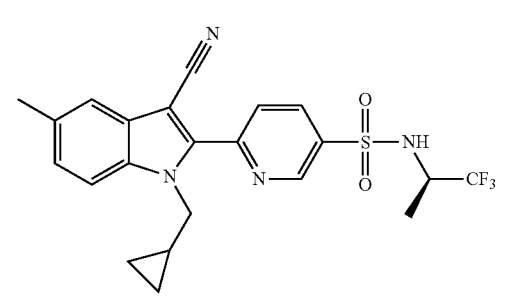
459 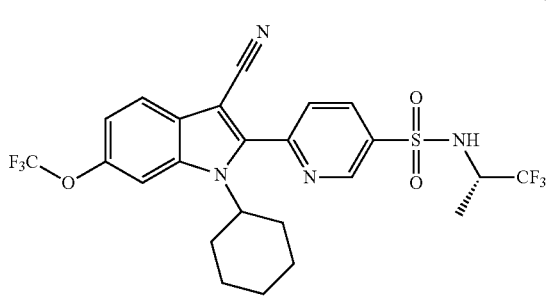
460 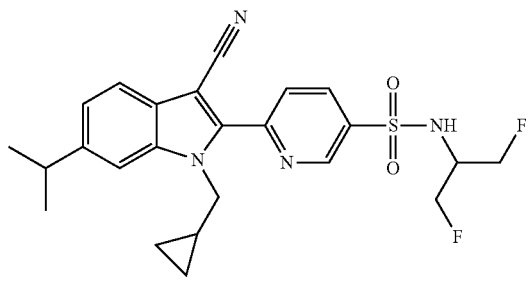
461 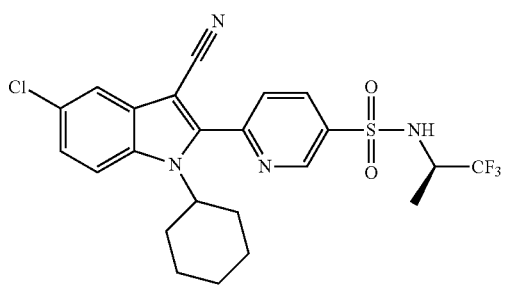
462 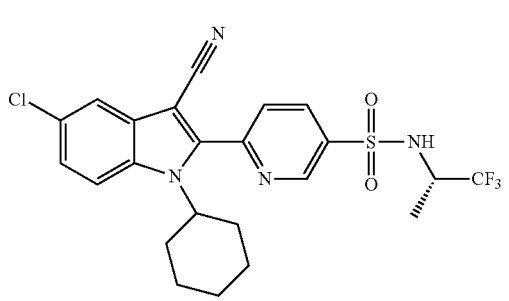
463 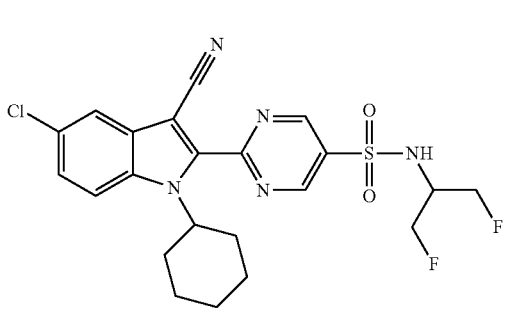
464 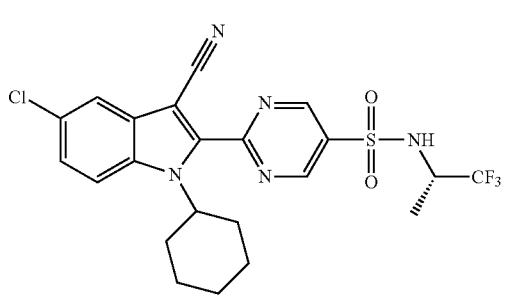

-continued
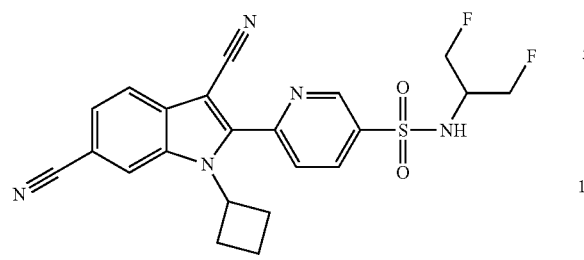
465
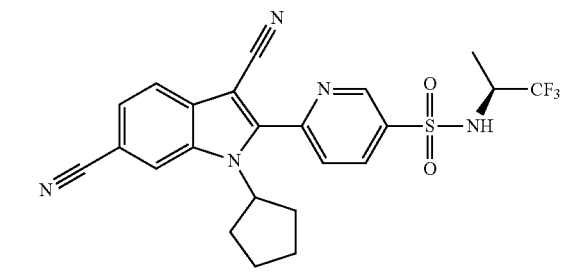
470
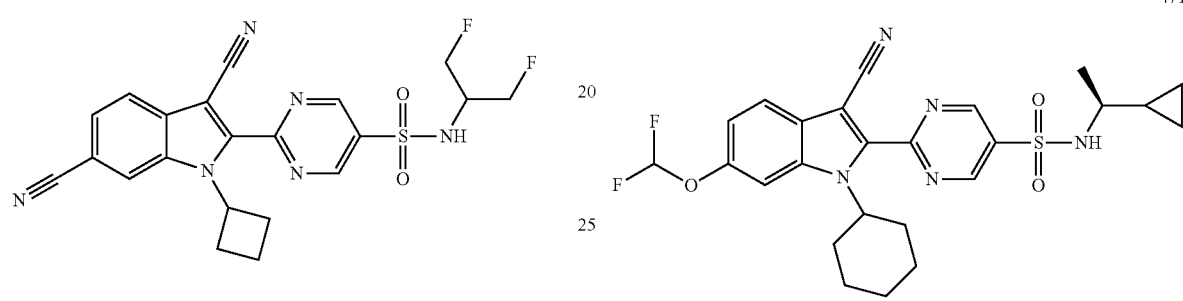
466
471
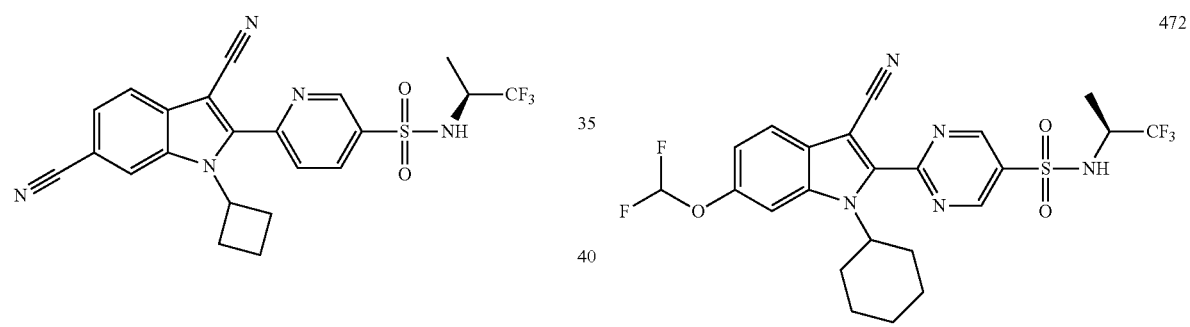
467
472
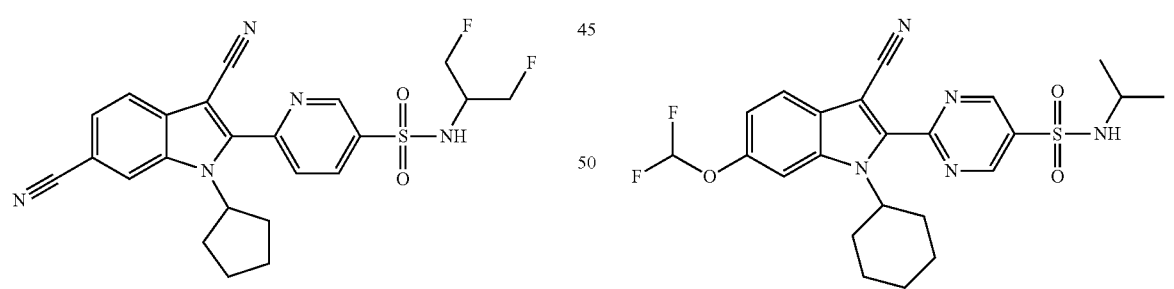
468
473
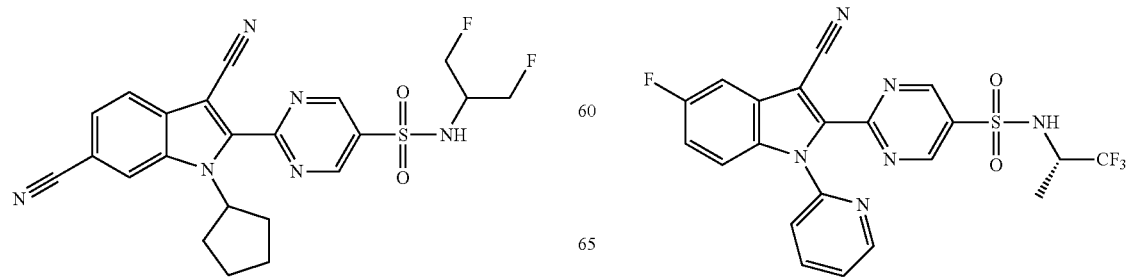
469
474

| 475 | 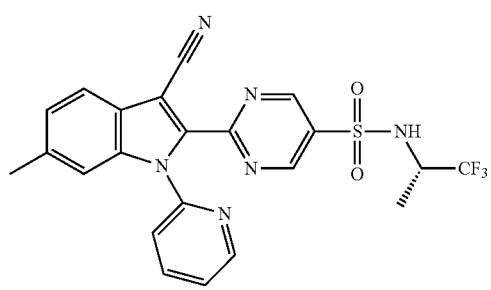 | 480 | 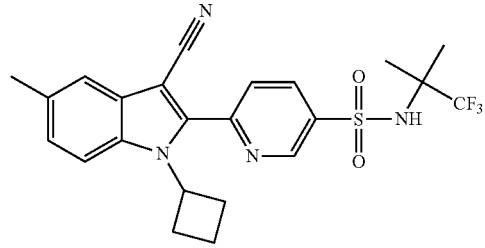 |
| 476 | 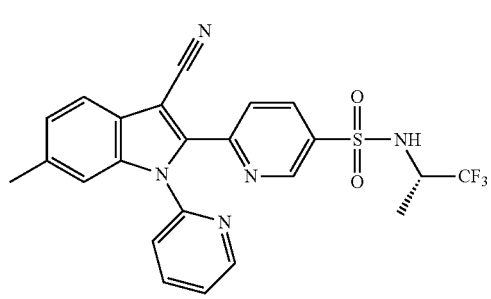 | 481 | 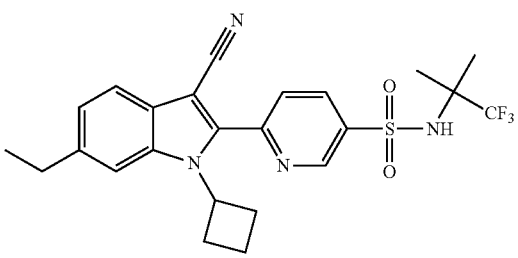 |
| 477 | 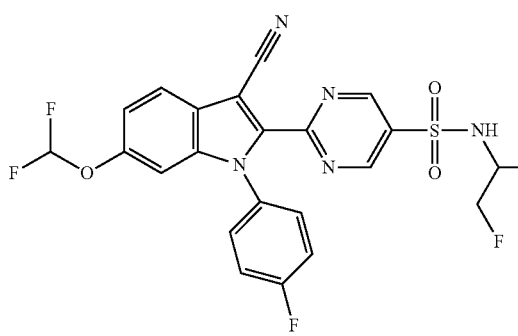 | 482 | 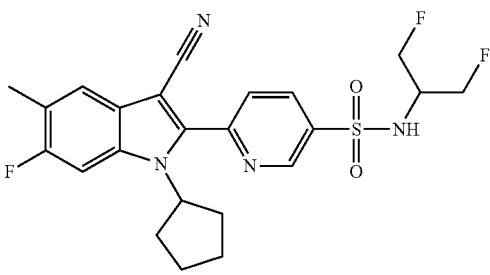 |
|     |                      | 483 | 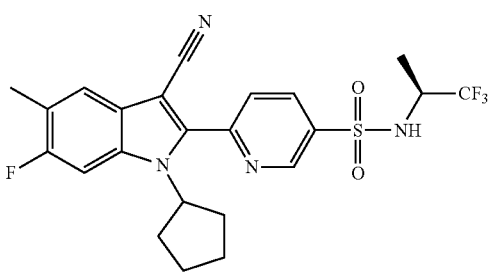 |
| 478 | 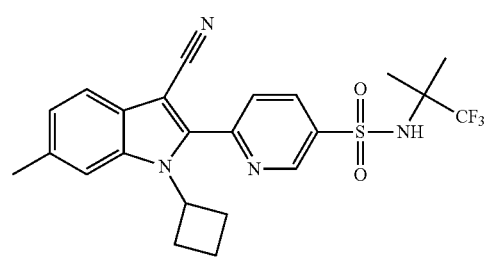 | 484 | 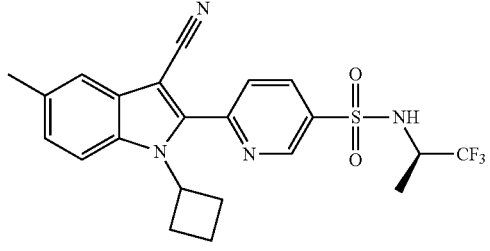 |
| 479 | 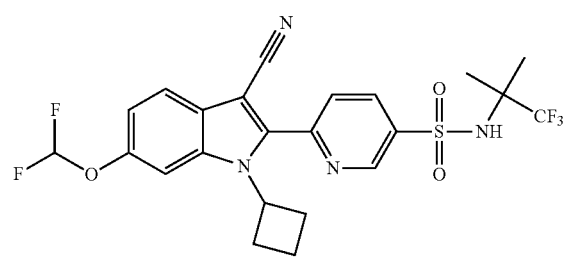 | 485 | 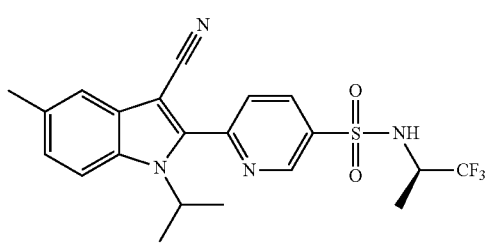 |

99
-continued
486
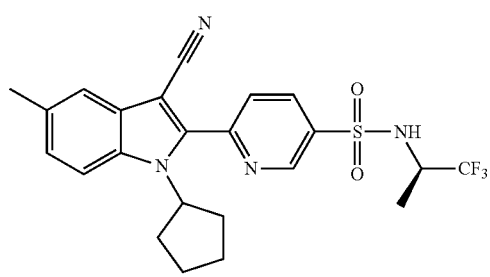
487
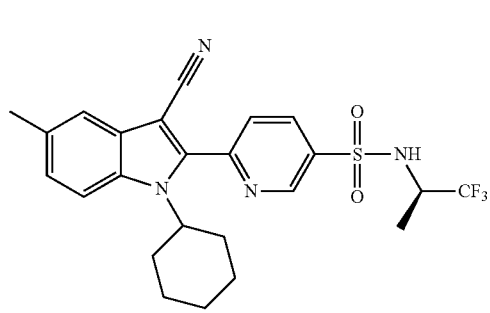
488
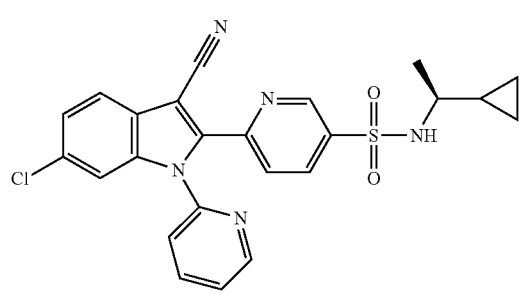
489
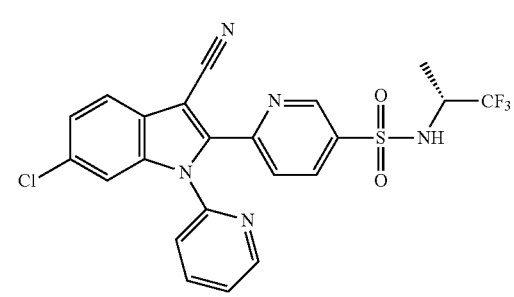
490
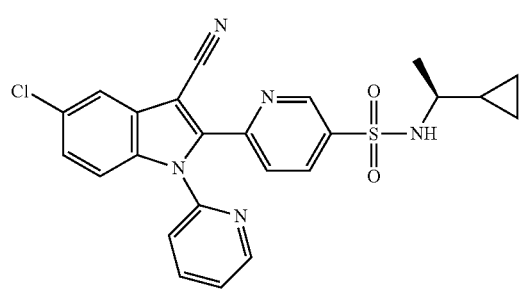
100
-continued
491
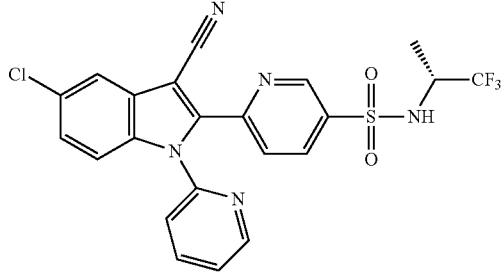
492
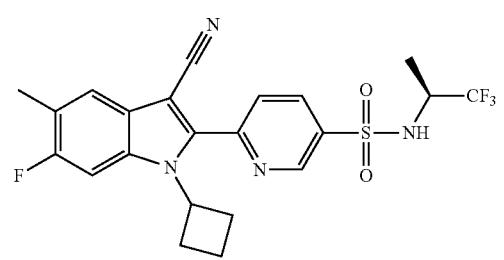
493
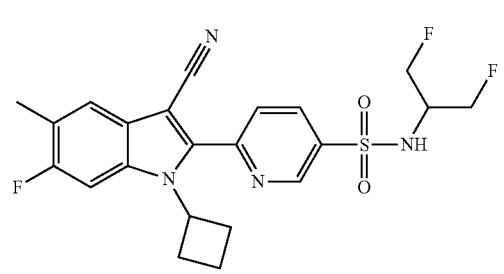
494
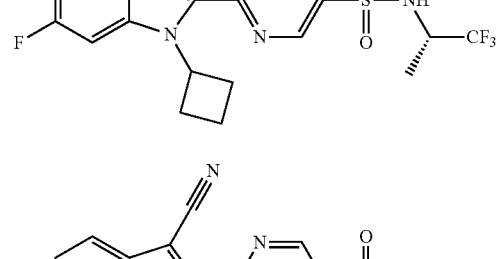
495
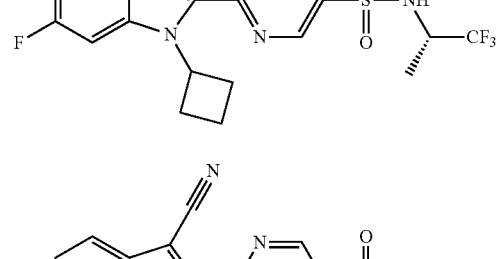
496
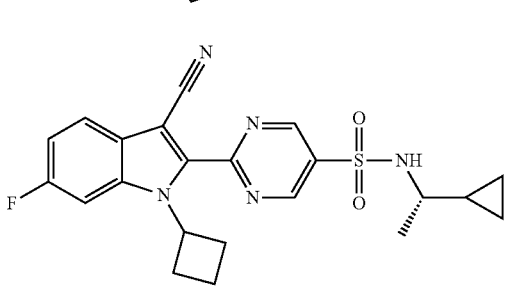

101
-continued
497
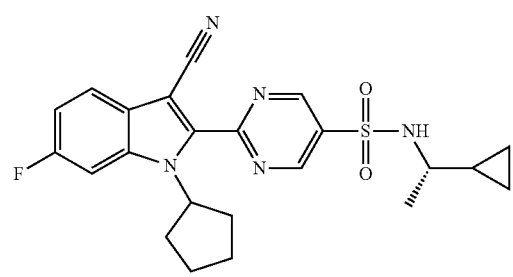
498
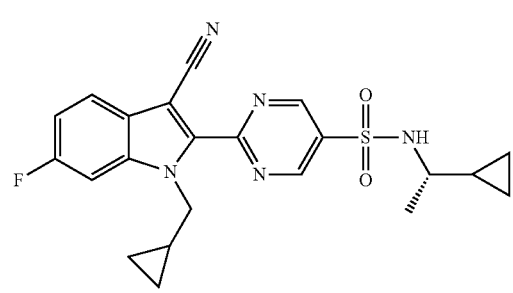
499
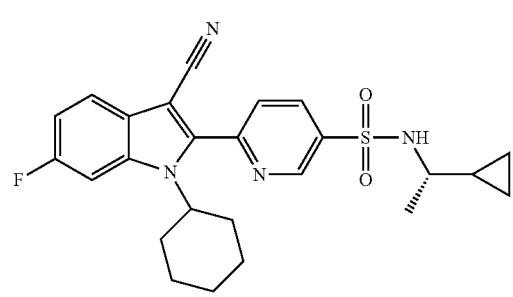
500
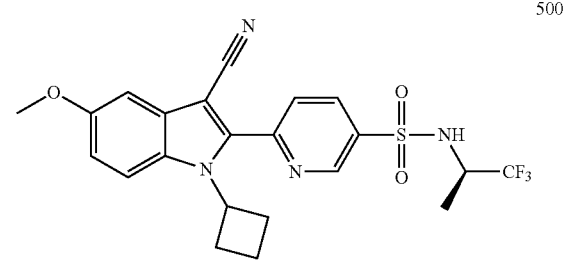
501
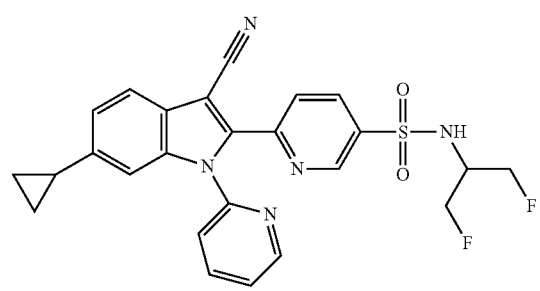
102
-continued
502
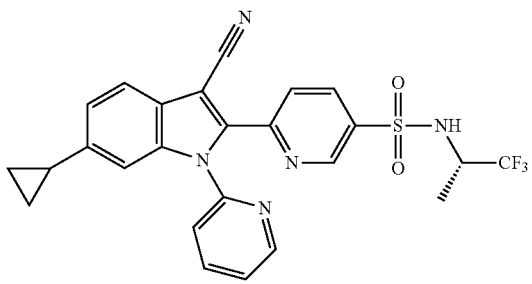
503
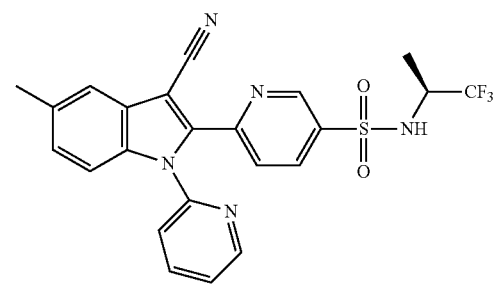
504
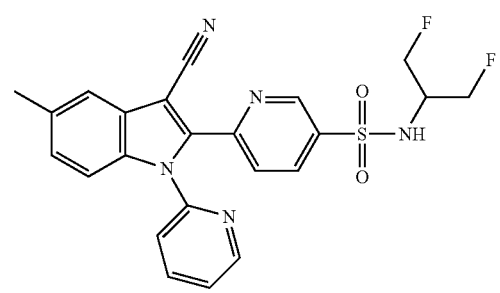
505
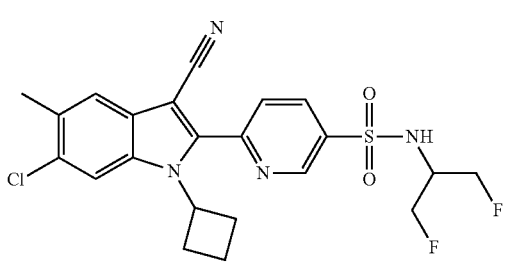
506
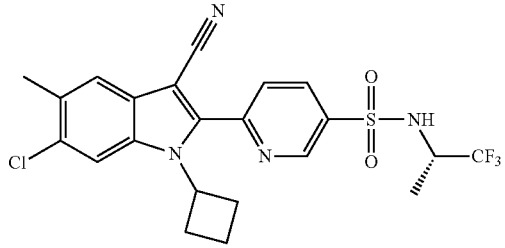
507
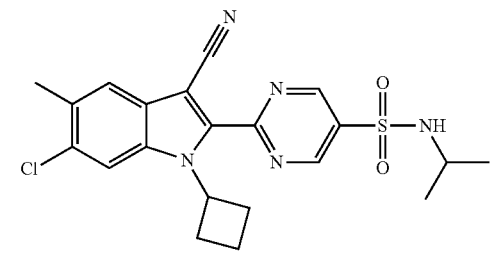

508
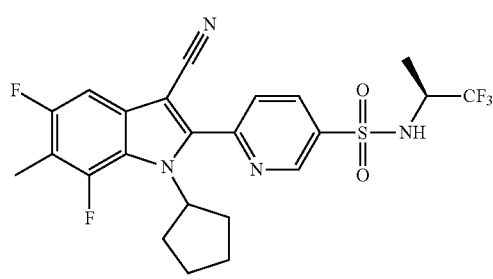
509
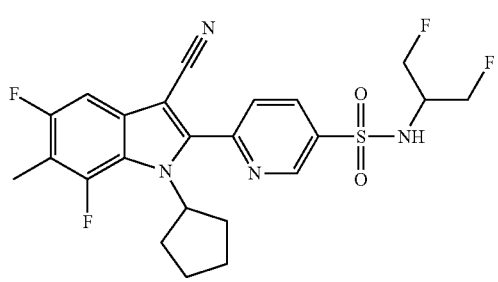
510
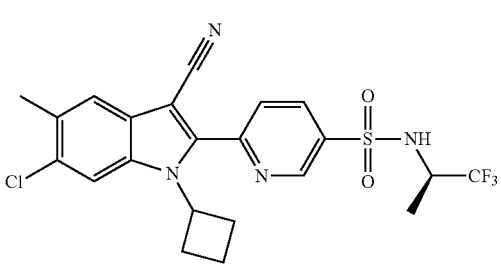
511
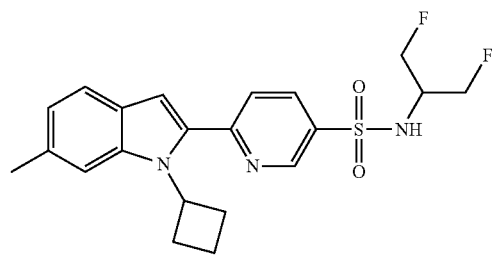
512
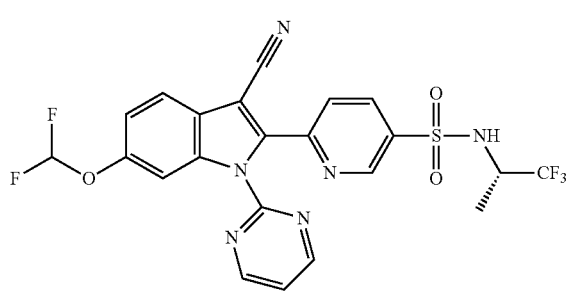
513
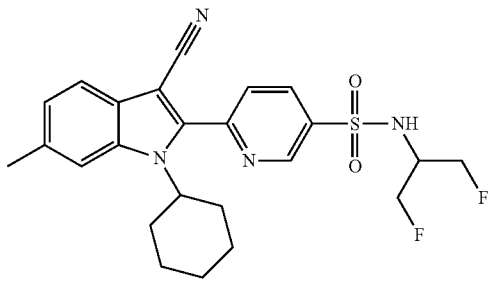
514
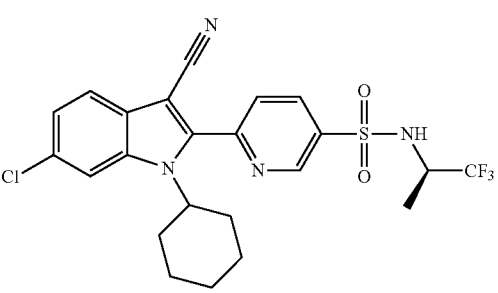
515
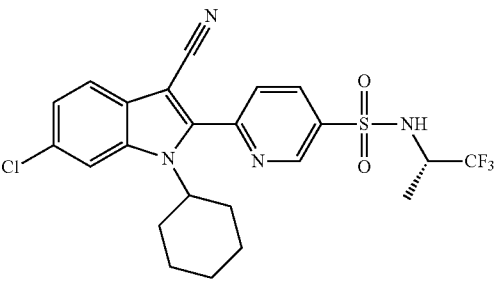
516
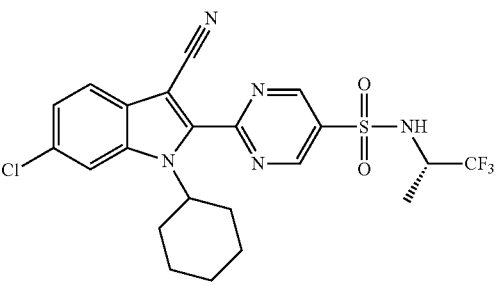
517
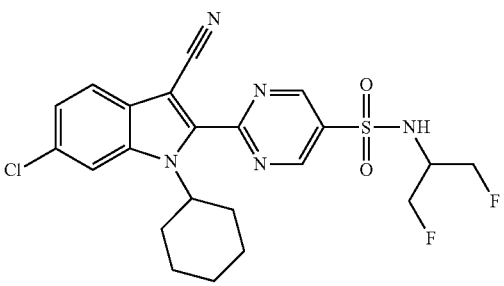

518
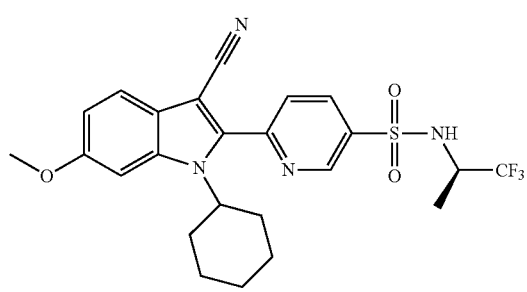
519
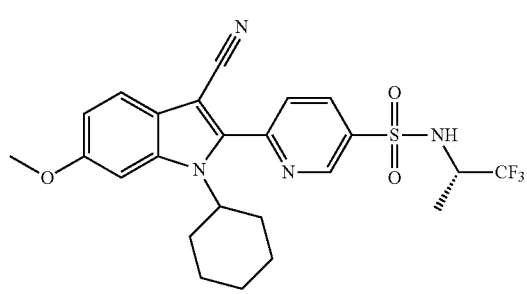
520
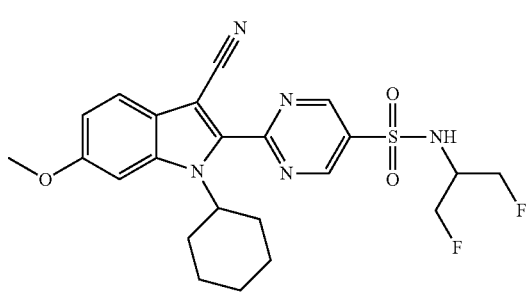
521
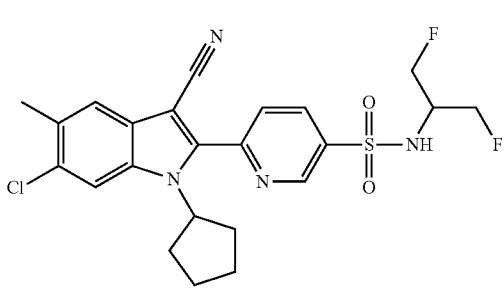
522
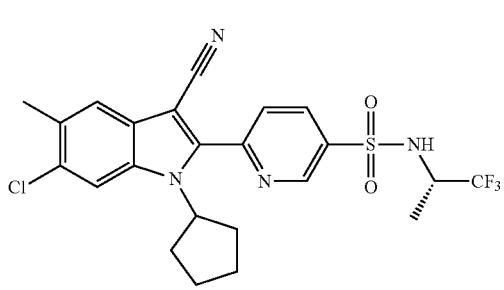
523
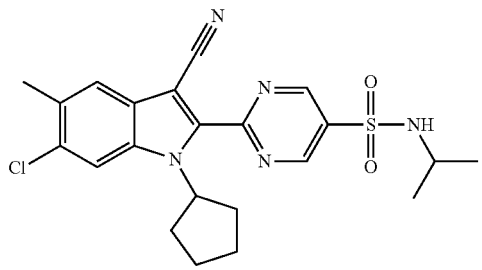
524
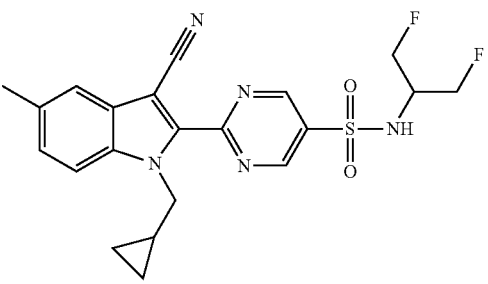
525
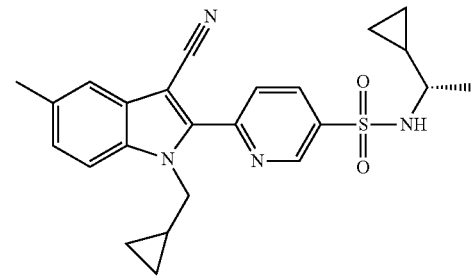
526
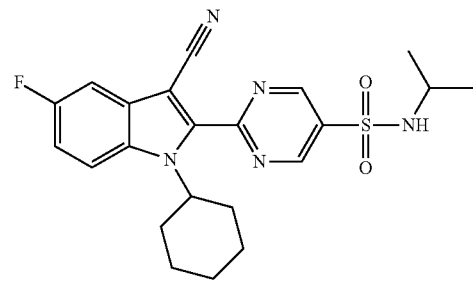
527
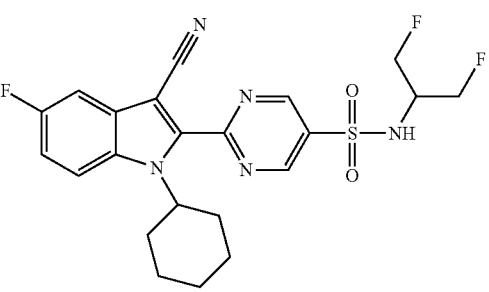

528
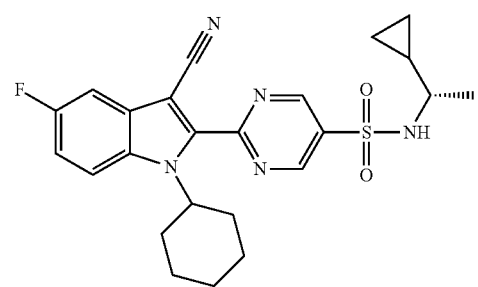
529
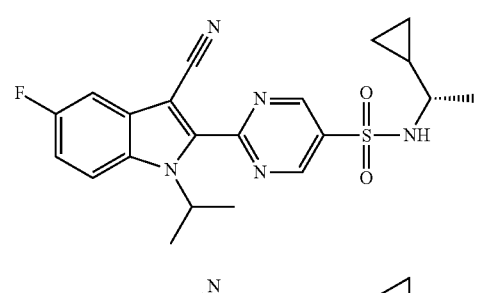
530
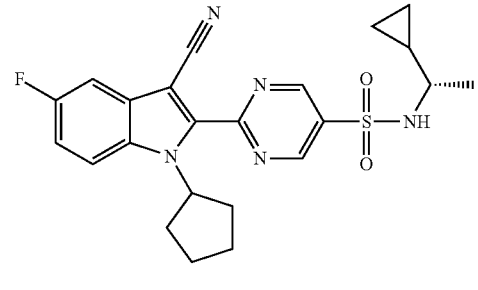
531
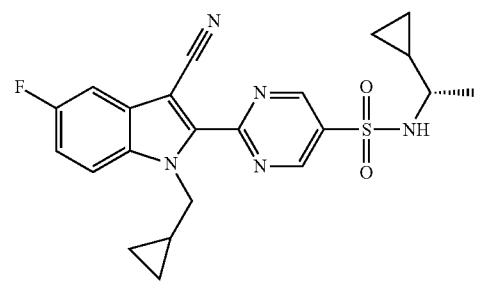
532
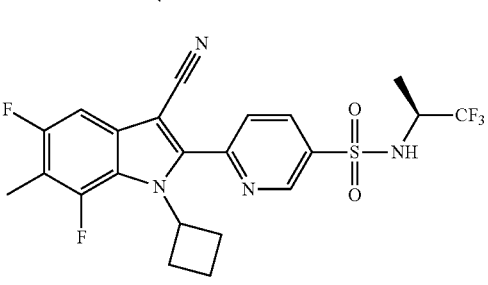
533
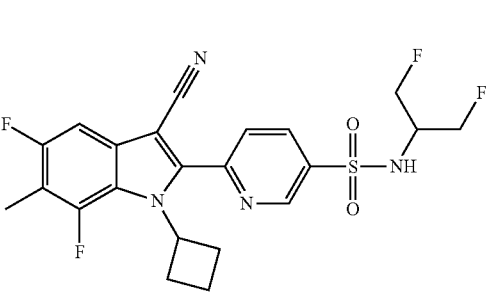
534
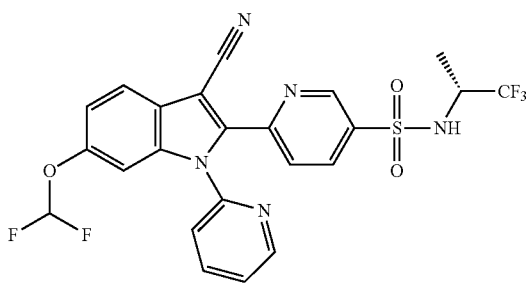
535
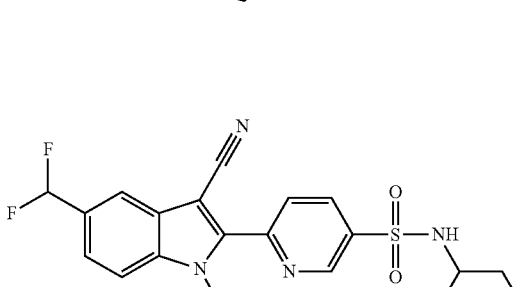
536
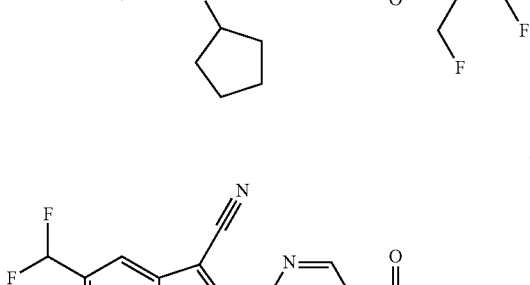
537
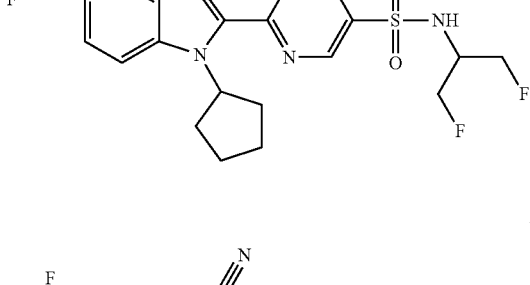
538
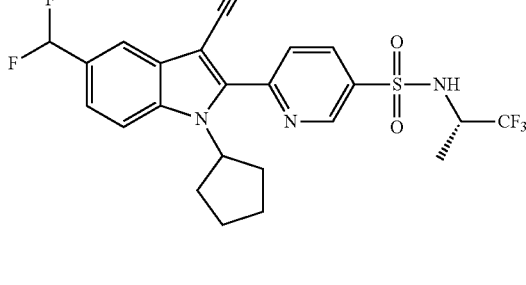
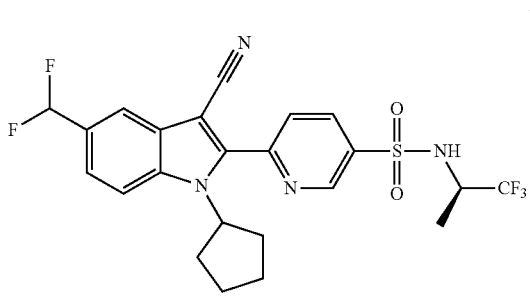

539
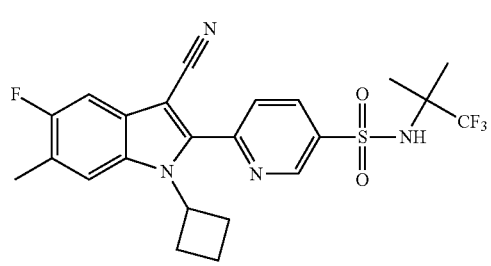
540
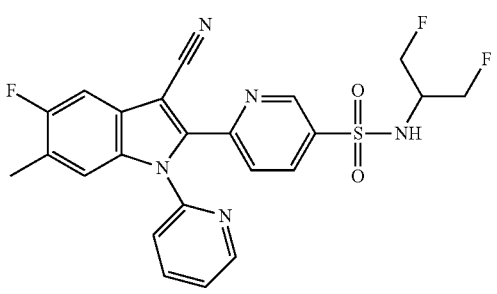
541
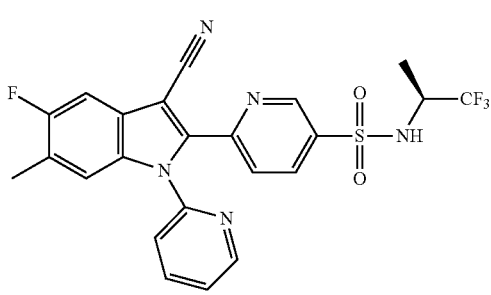
542
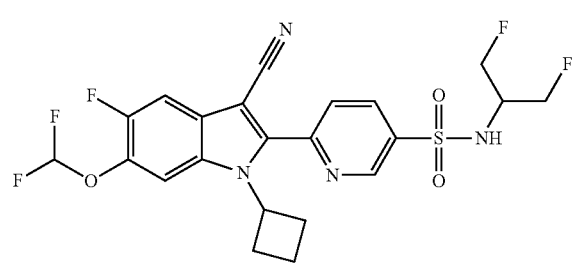
543
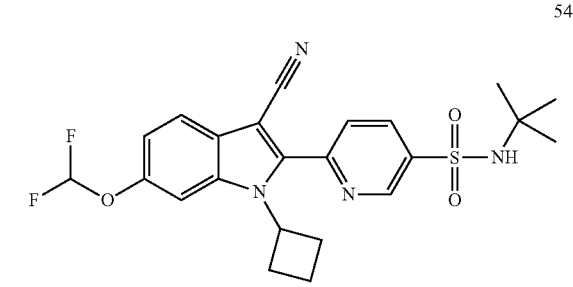
544
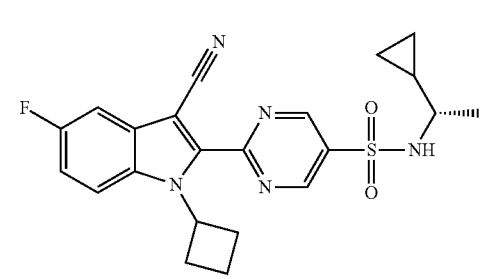
545
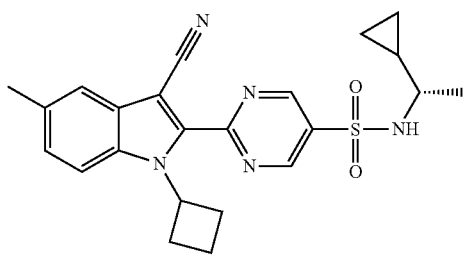
546
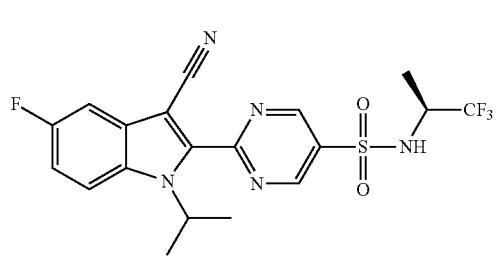
547
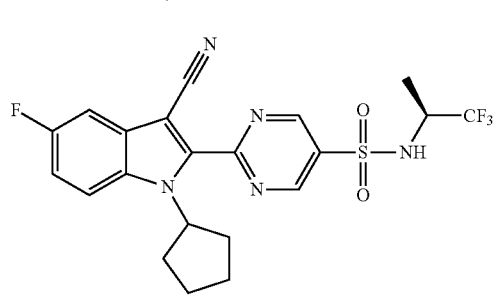
548
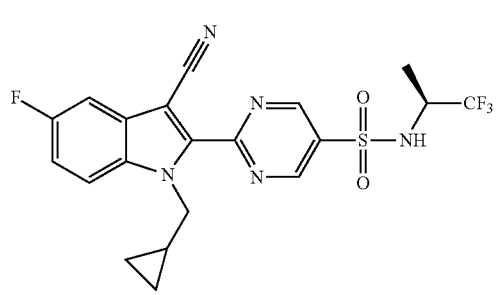
549
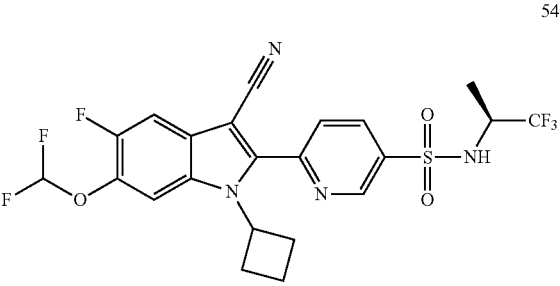
550
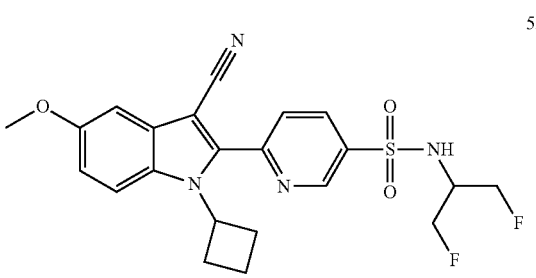

111
-continued
551
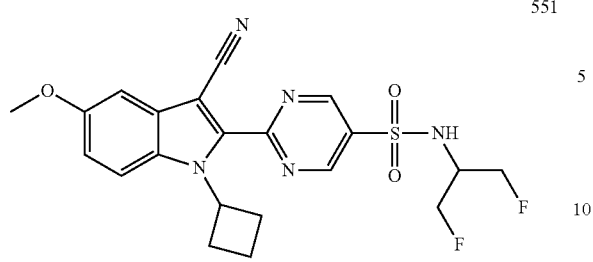
552
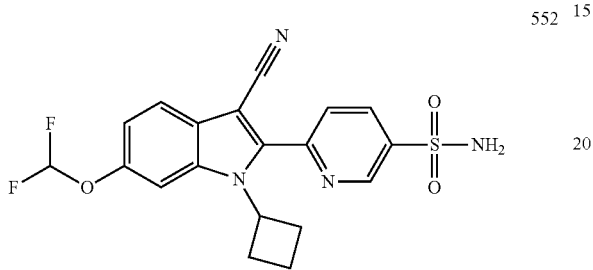
553
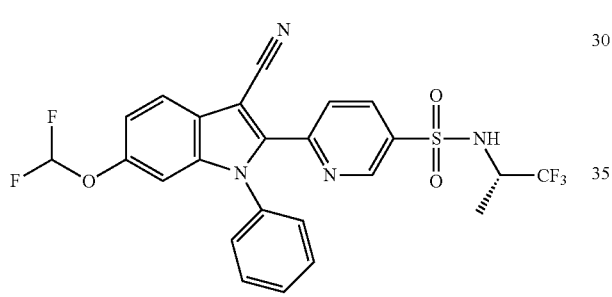
554
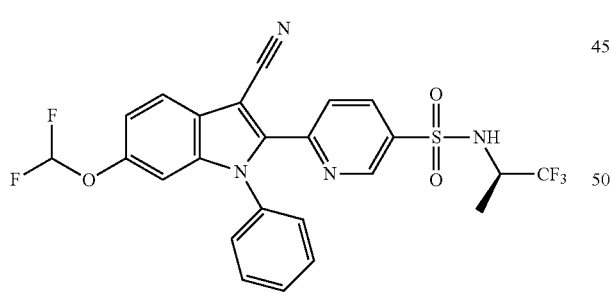
555
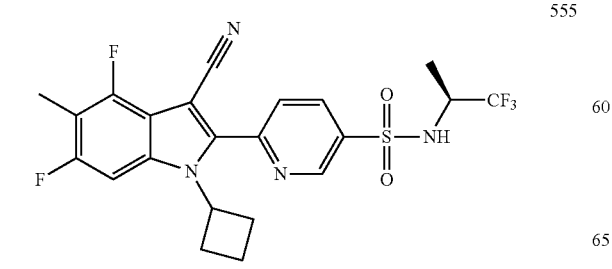
112
-continued
556
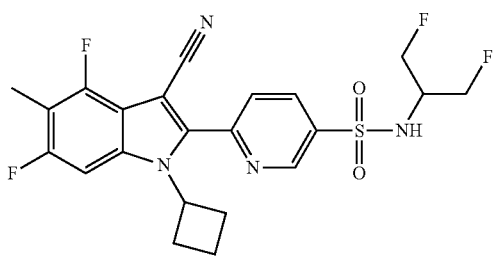
557
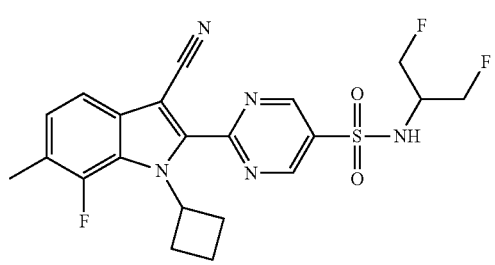
558
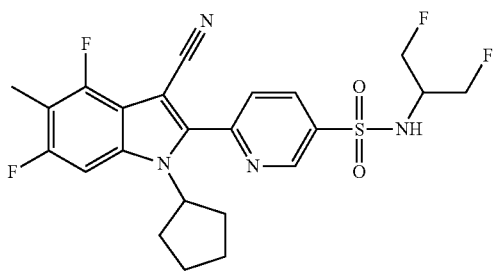
559
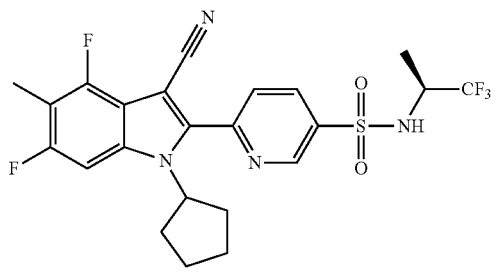
560
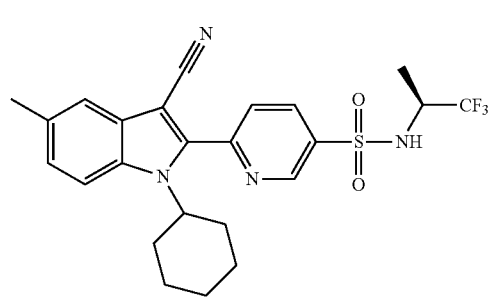

561
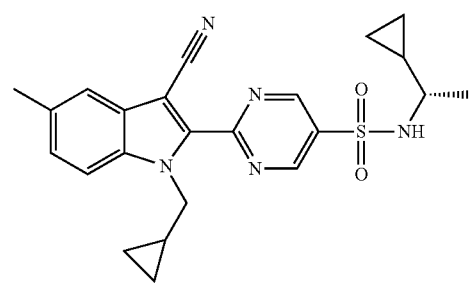
562
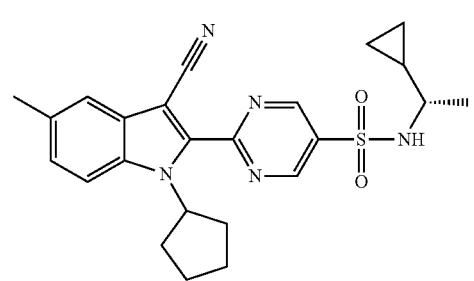
567
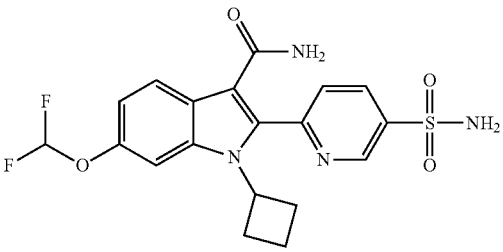
568
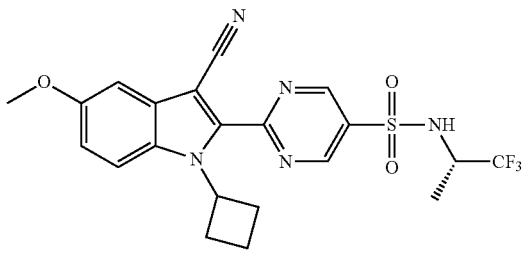
563
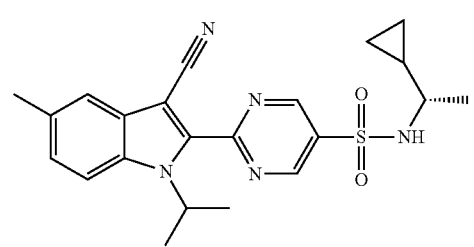
569
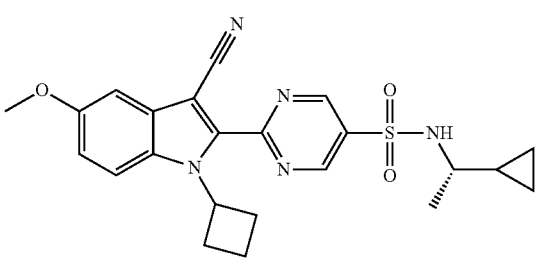
564
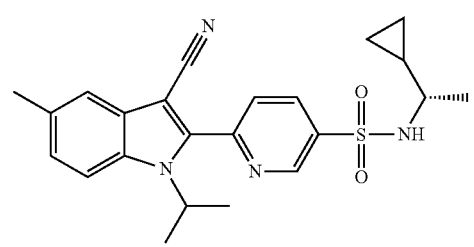
570
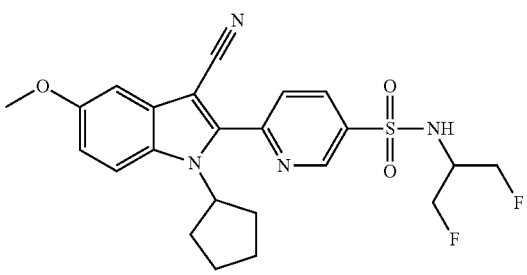
565
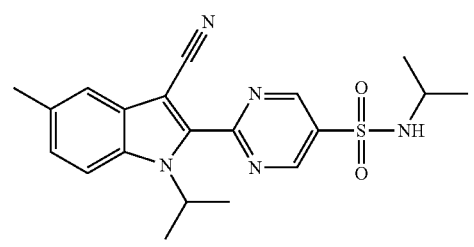
571
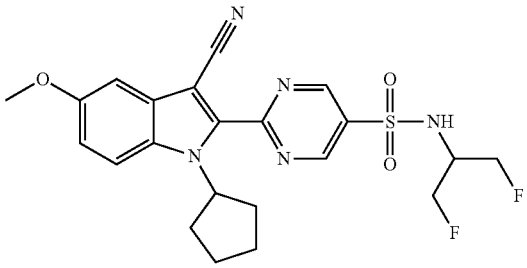
566
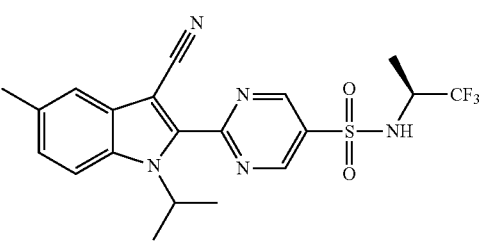
572

573 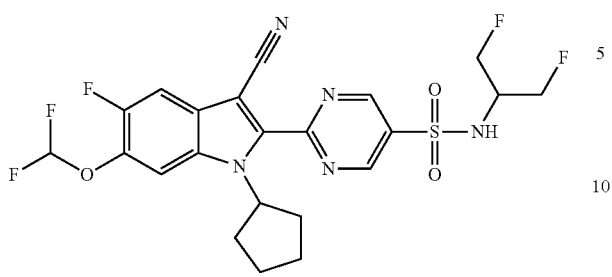
578 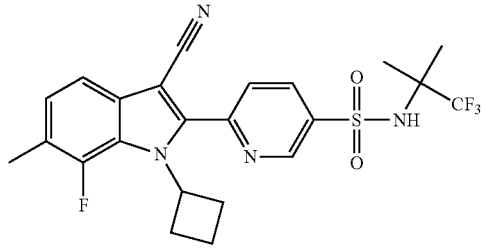
574 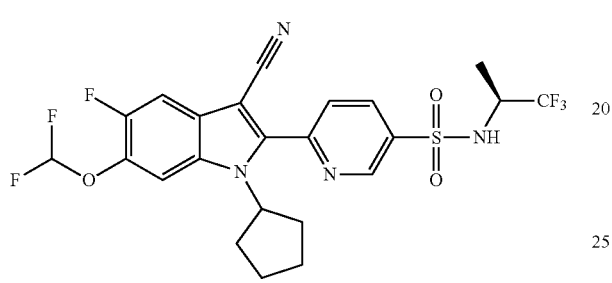
579 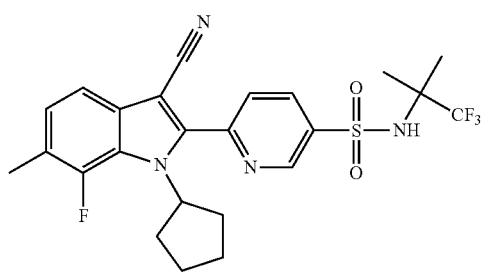
575 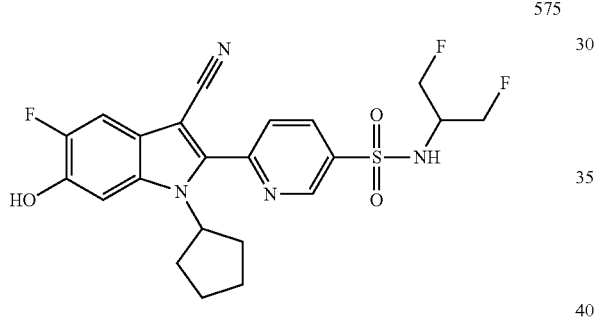
580 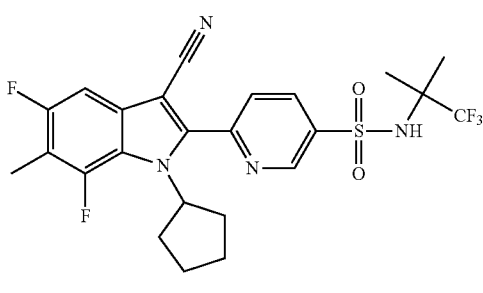
576 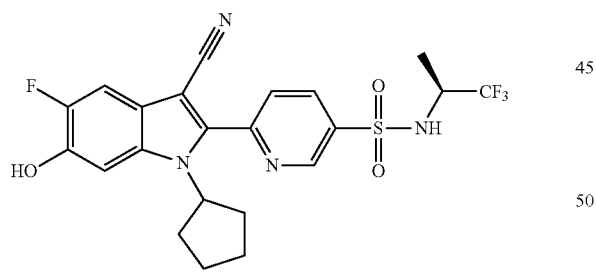
581 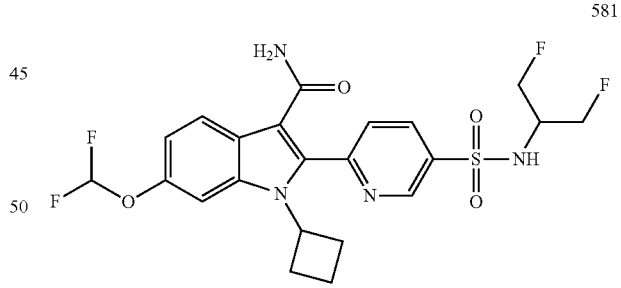
577 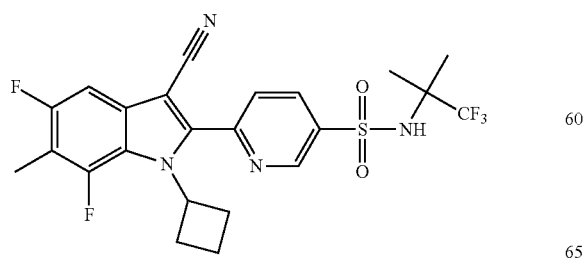
582 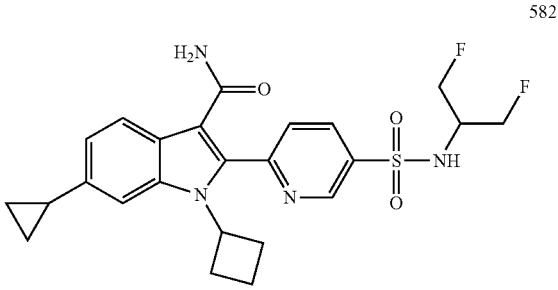

583
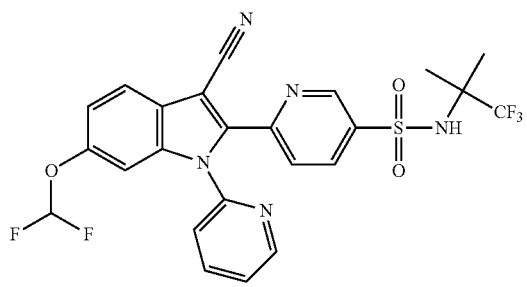
584
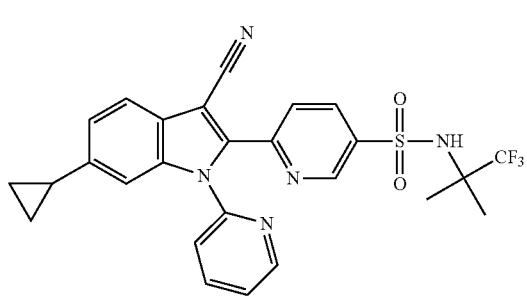
585
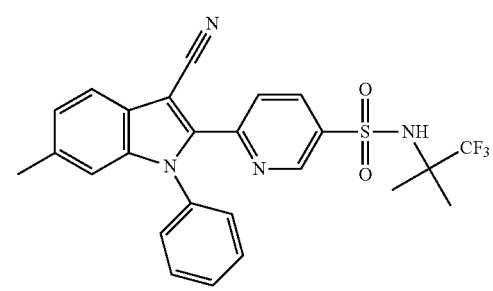
586
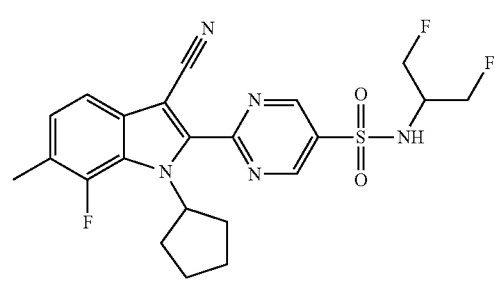
587
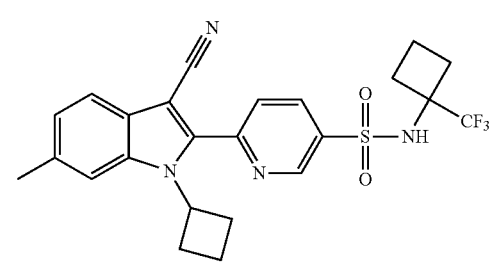
588
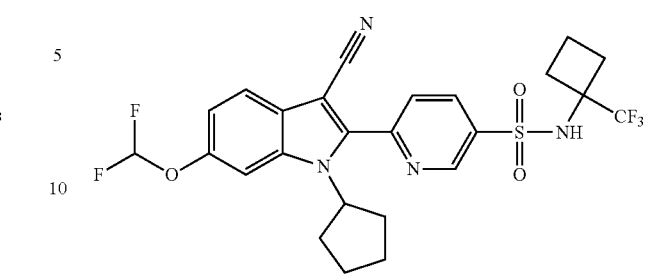
589
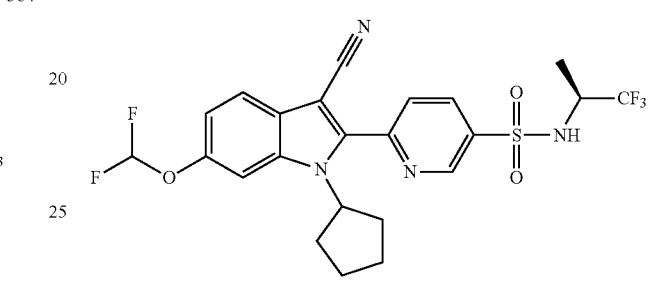
590
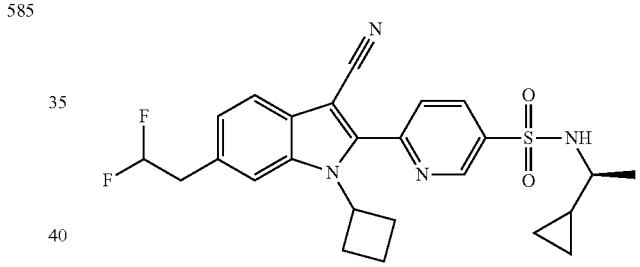
591
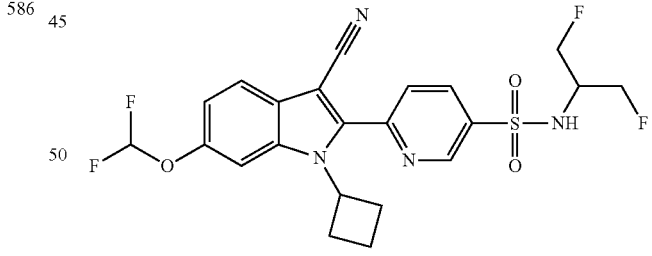
592
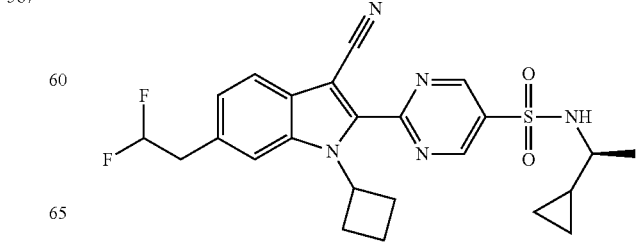

119
-continued
593
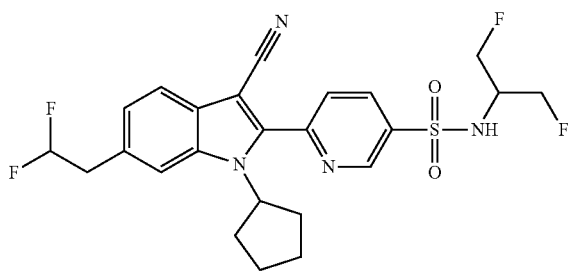
594
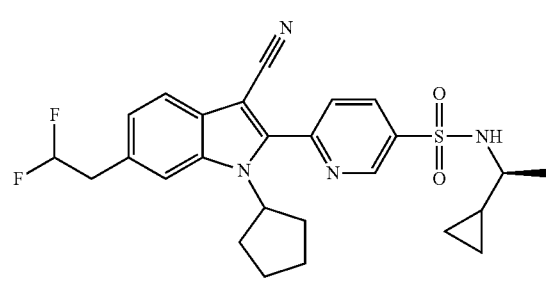
595
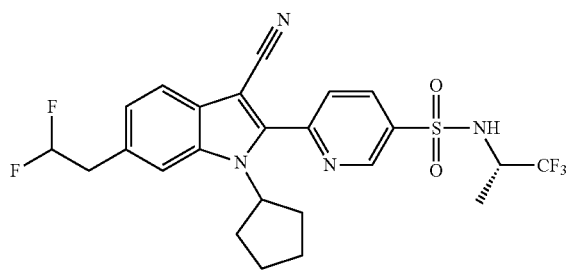
596
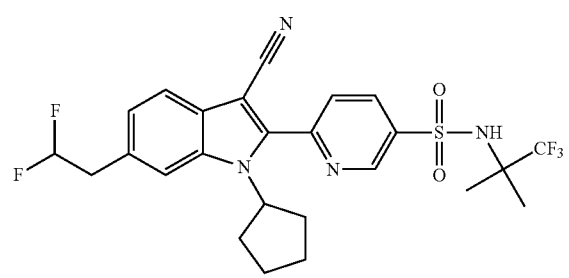
597
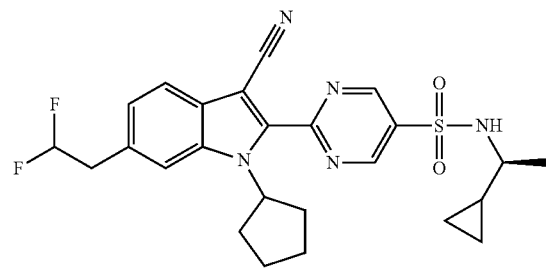
120
-continued
598
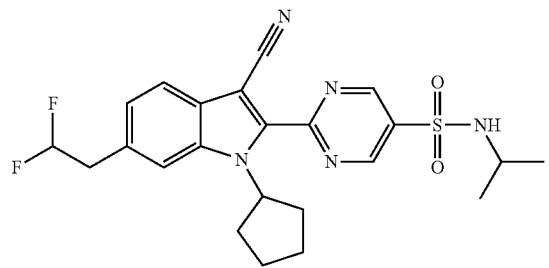
599
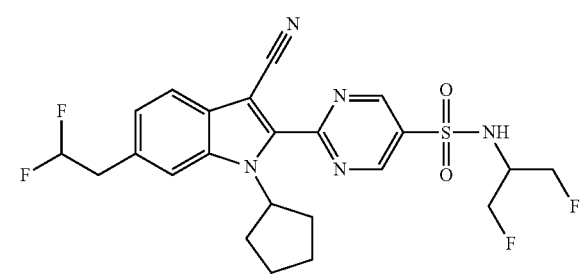
600
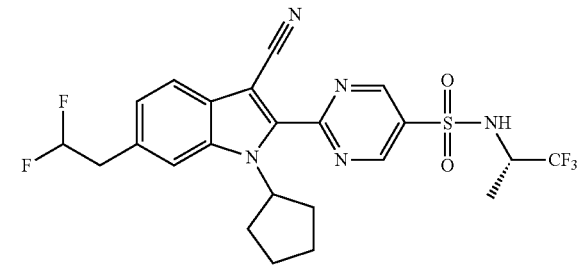
601
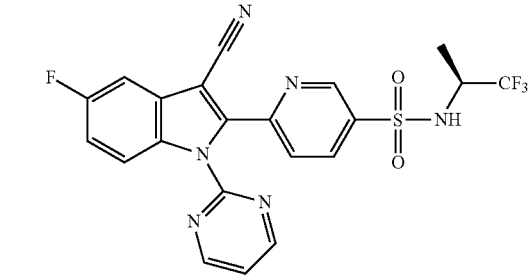
602
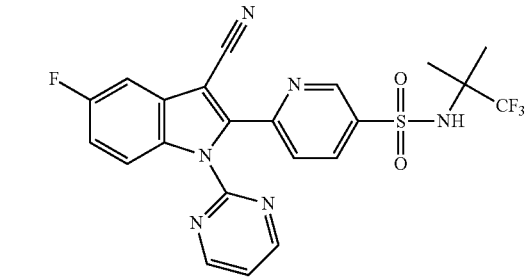

-continued
| 121 | 122 |
|---|---|
| 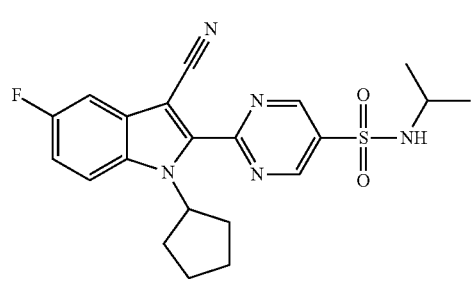 603 | 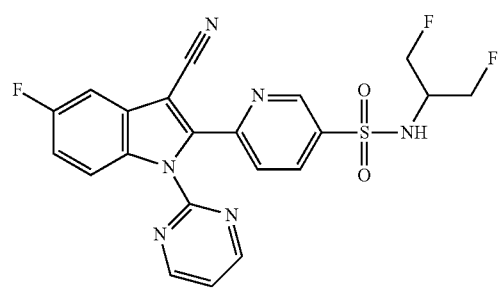 608 |
| 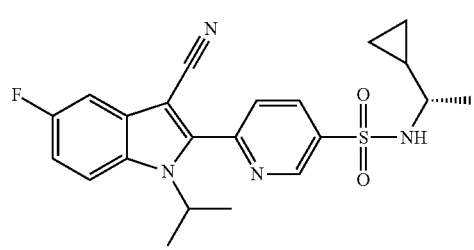 604 | 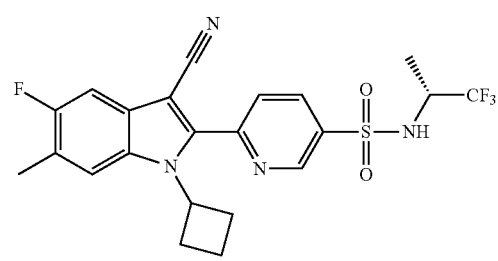 609 |
| 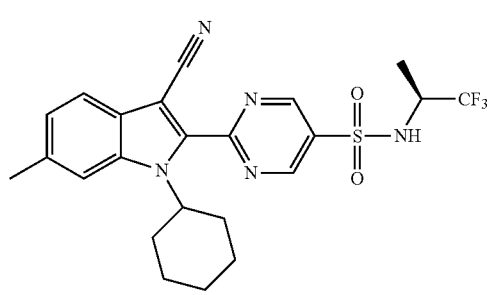 605 | 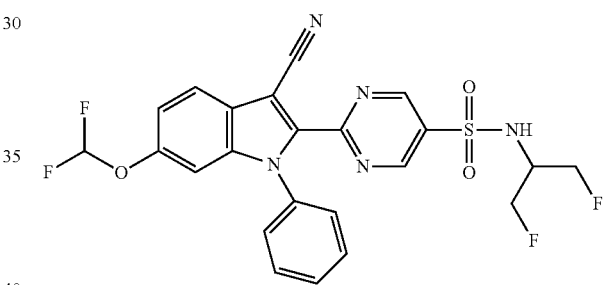 610 |
| 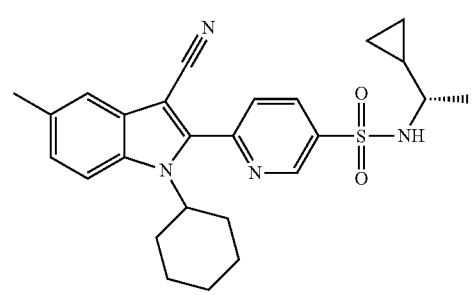 606 | 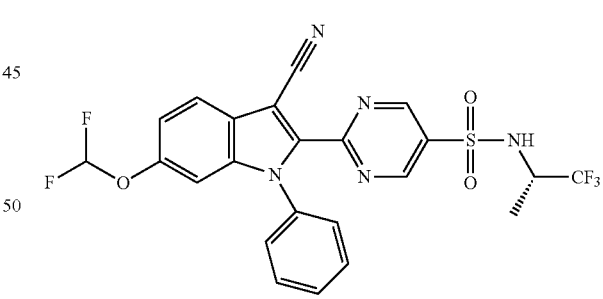 611 |
| 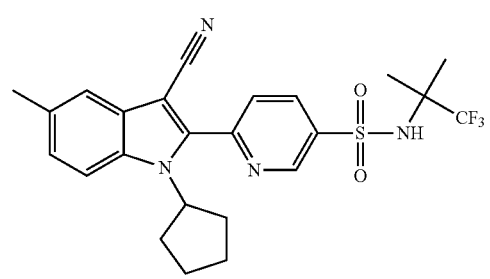 607 | 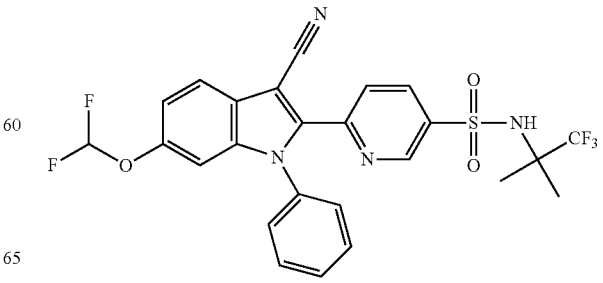 612 |

| 123 -continued | | 124 -continued | |
|---|---|---|---|
| 613 | 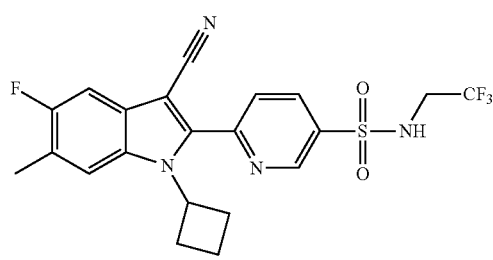 | 618 |  |
| 614 | 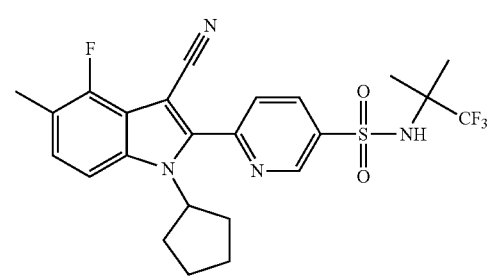 | 619 | 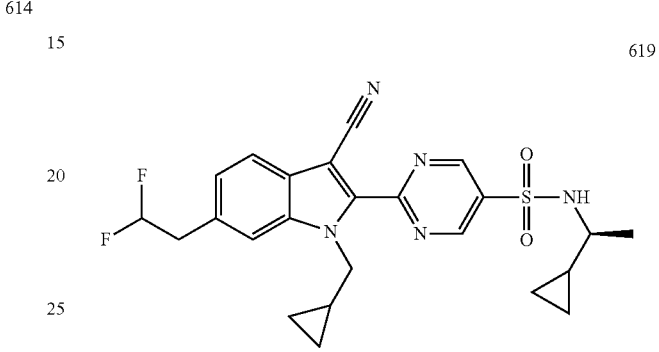 |
| 615 | 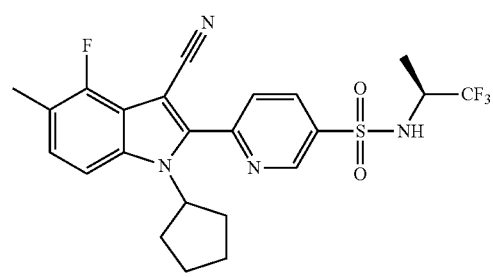 | 620 | 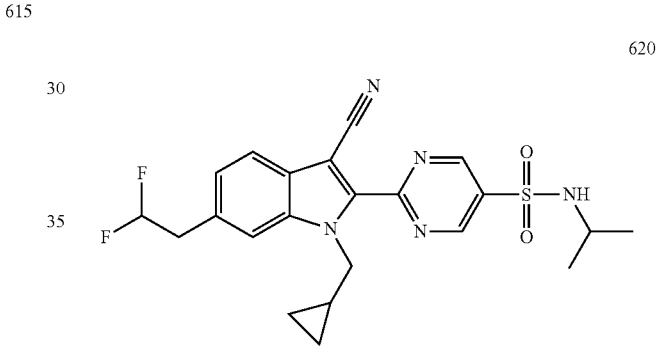 |
| 616 | 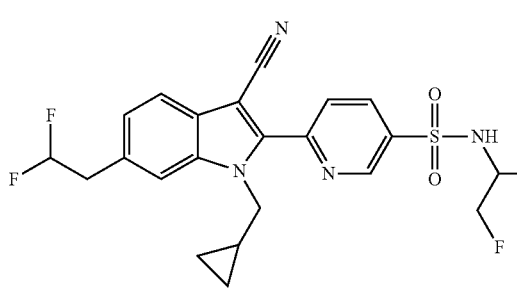 | 621 | 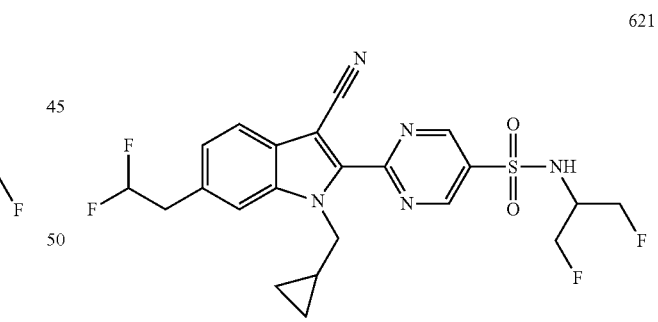 |
| 617 | 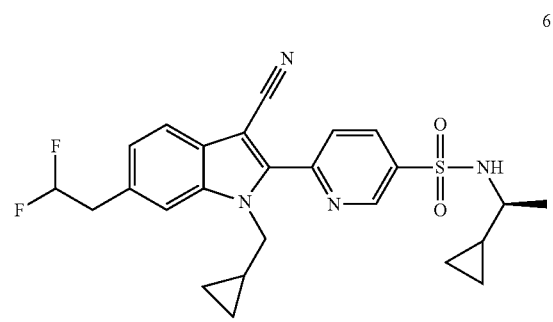 | 622 | 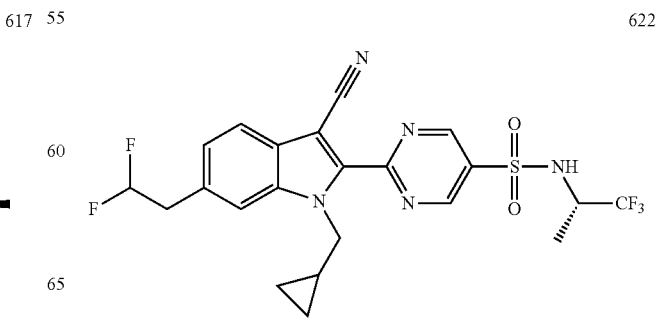 |

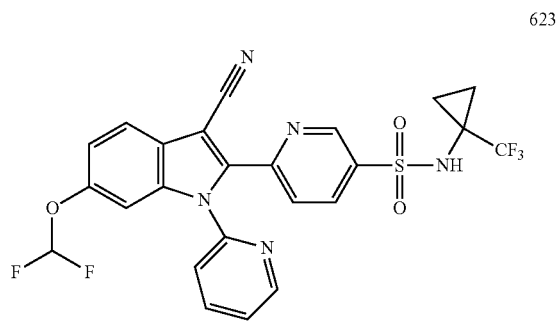
623
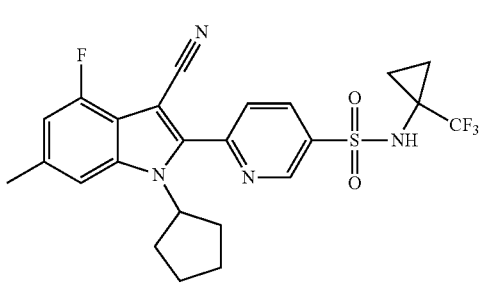
628
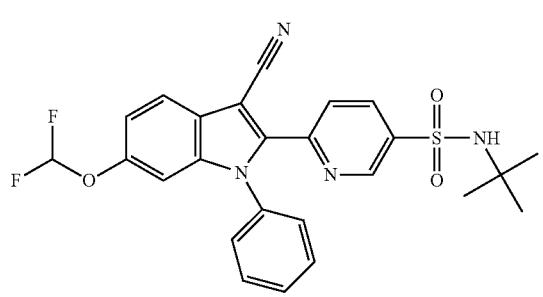
624
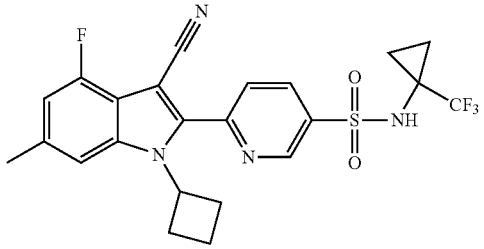
629
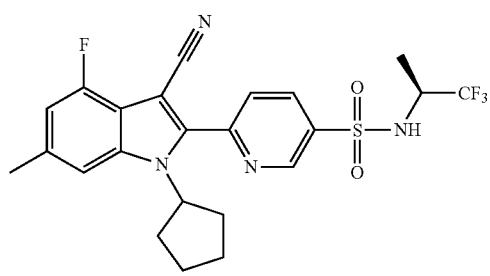
625
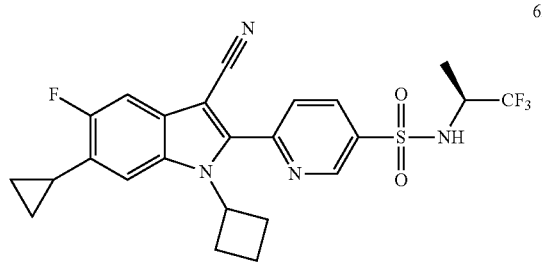
630
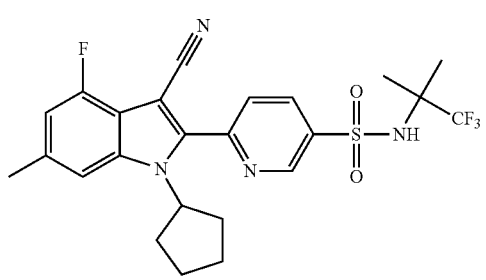
626
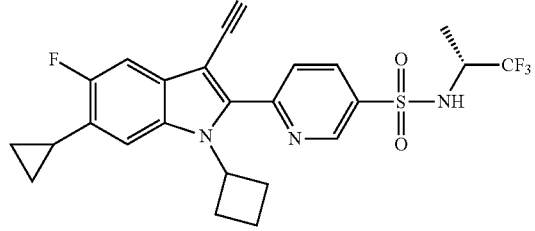
631
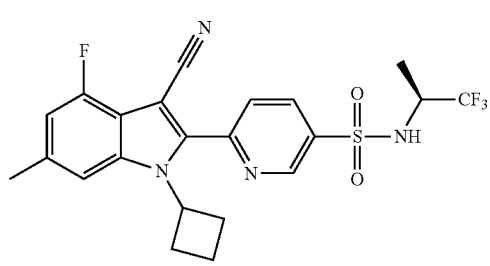
627
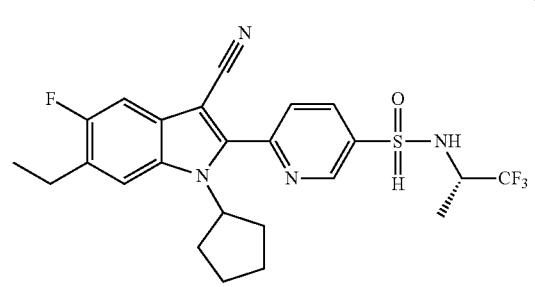
632
633

634 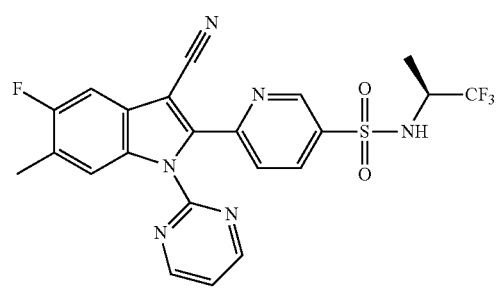
635 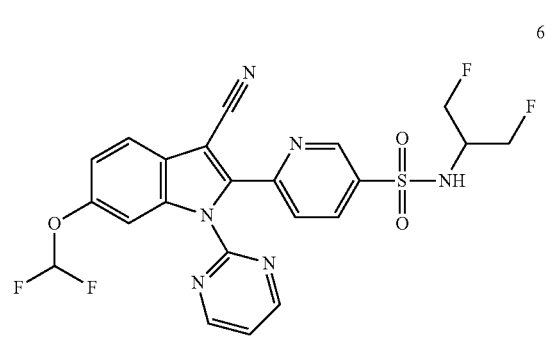
636 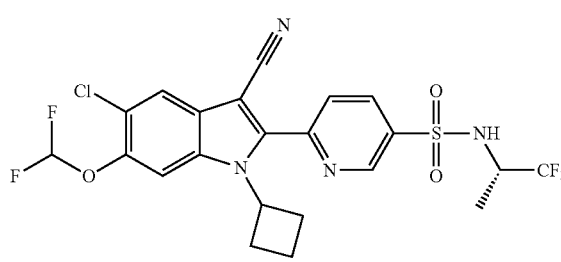
637 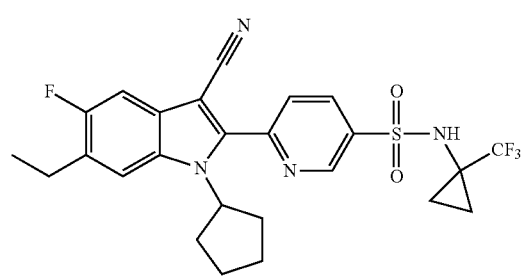
638 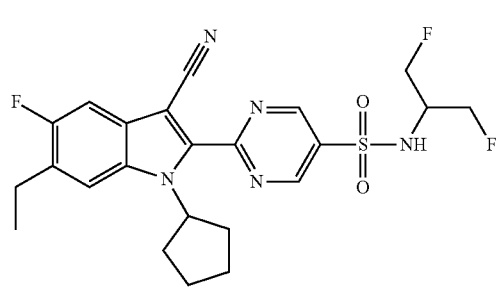
639 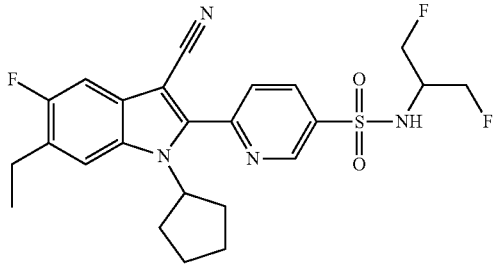
640 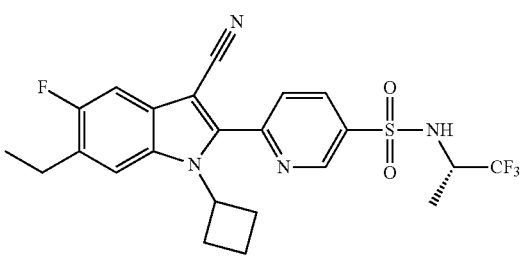
641 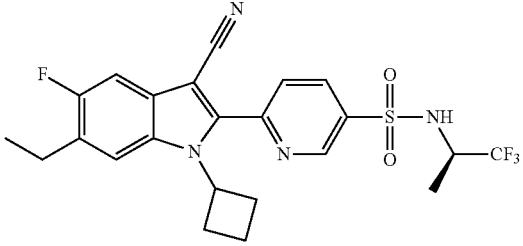
642 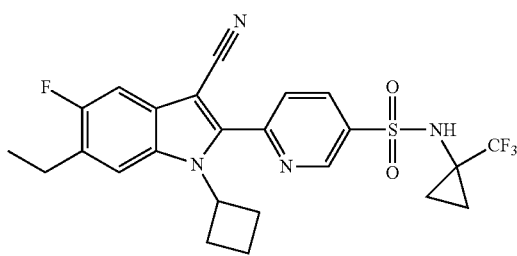
643 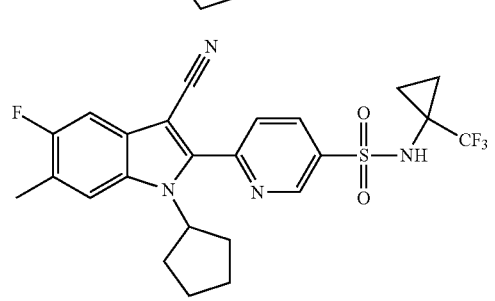
644

| 645 | 650 |
|---|---|
| 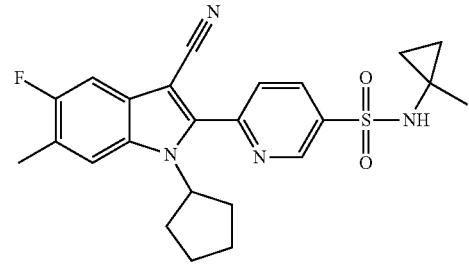 | 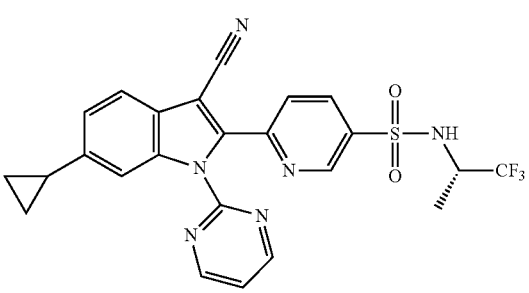 |
| 646 | 651 |
| 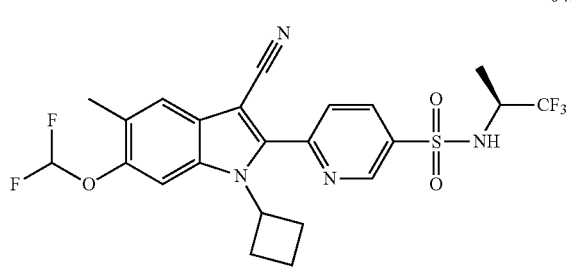 | 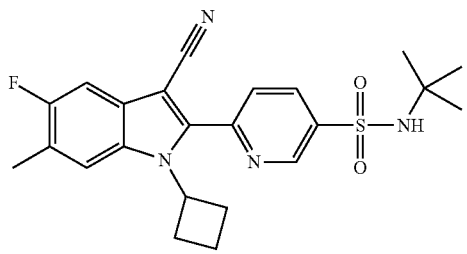 |
| 647 | 652 |
| 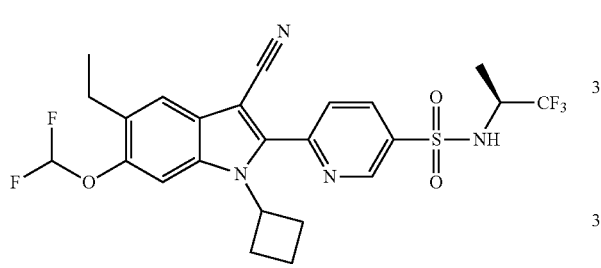 | 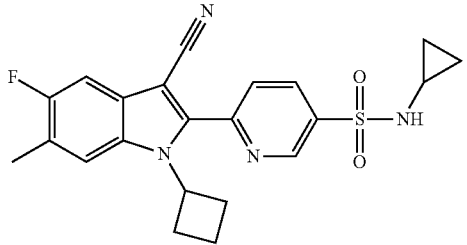 |
| 648 | 653 |
| 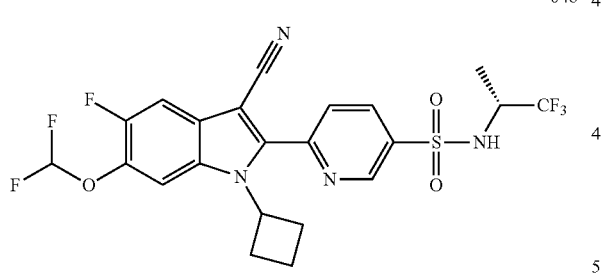 | 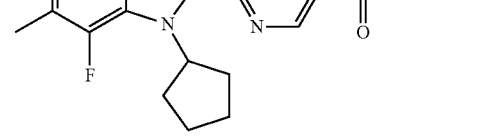 |
| 649 | 654 |
| 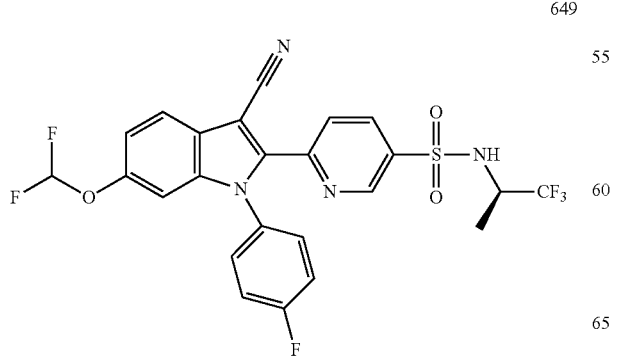 | 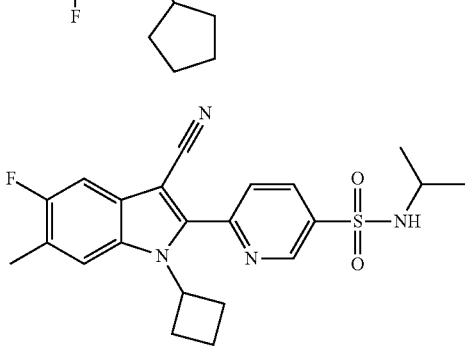 |
| | 655 |

656
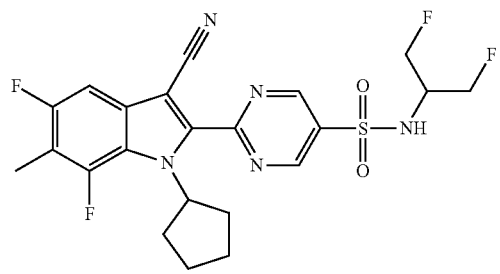
657
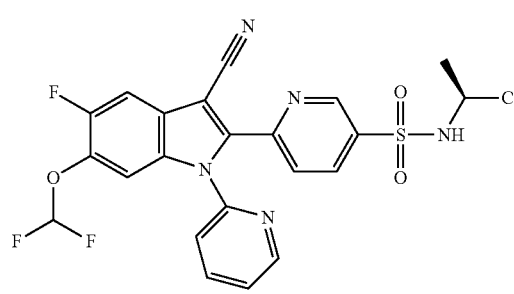
658
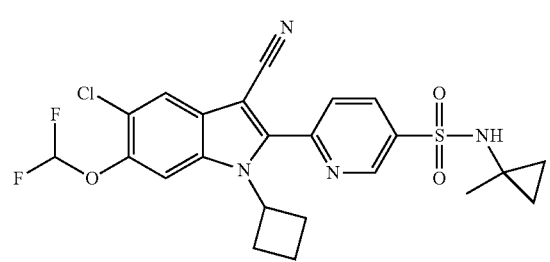
659
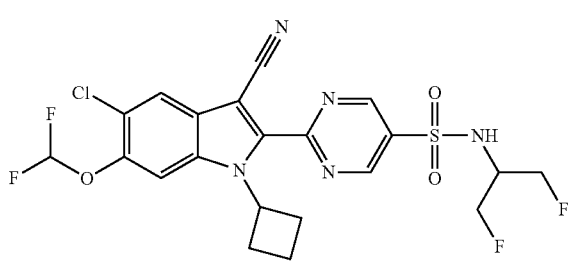
660
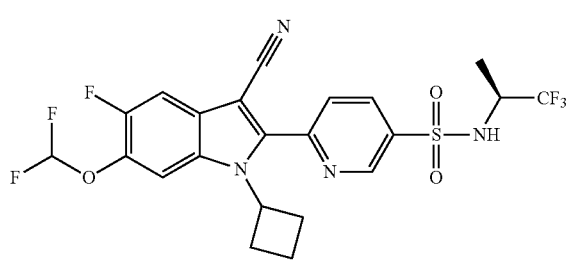
661
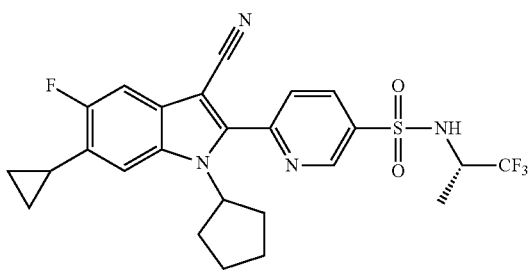
662
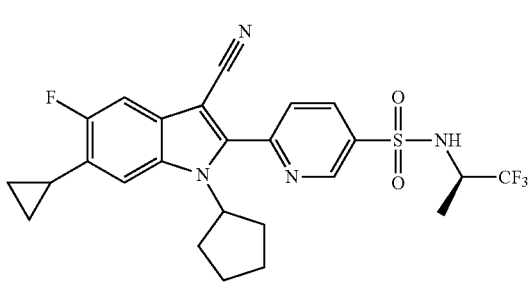
663
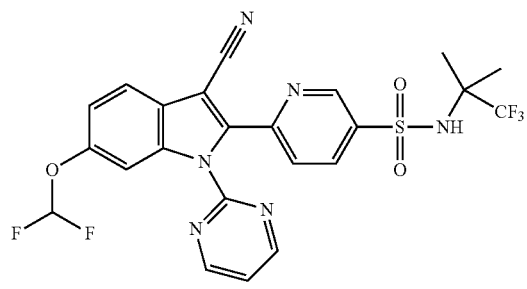
664
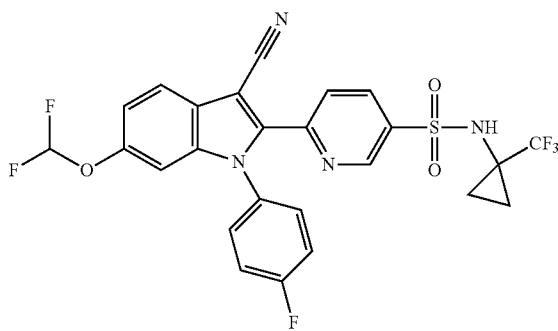
665
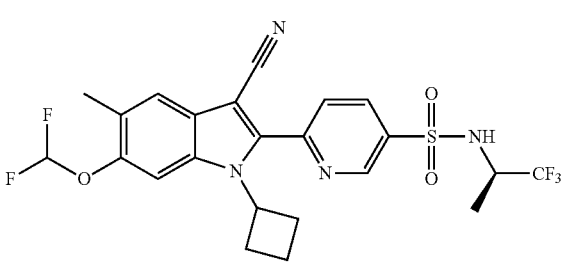

666 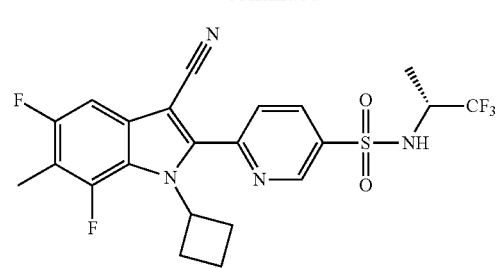
667 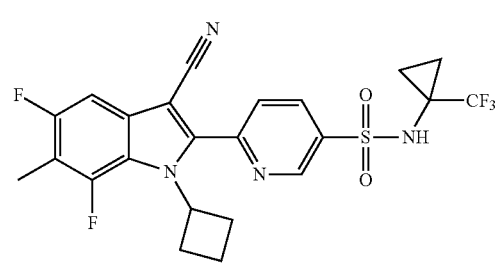
668 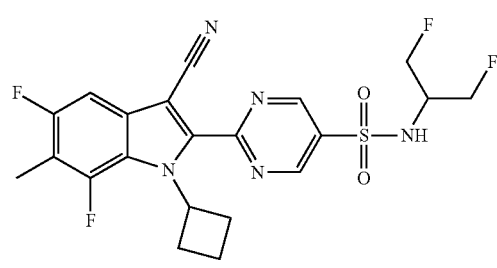
669 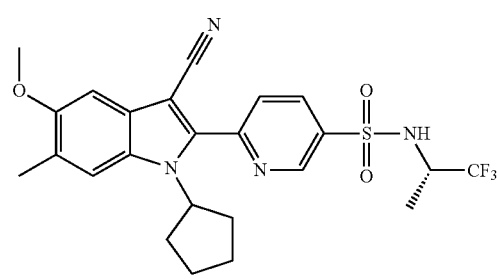
670 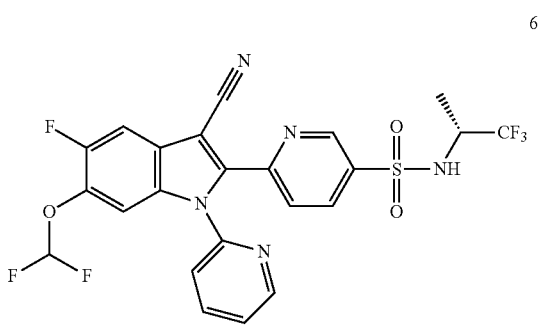
671 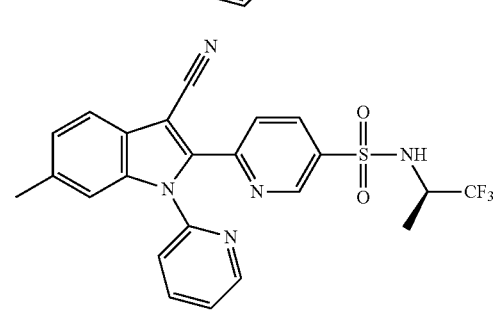
672 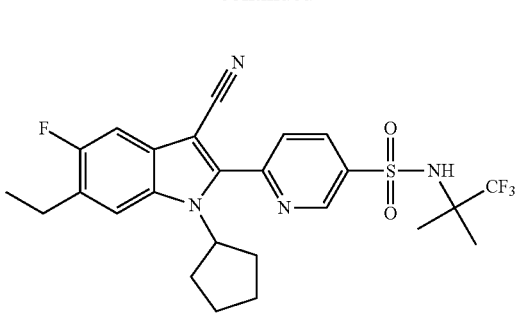
673 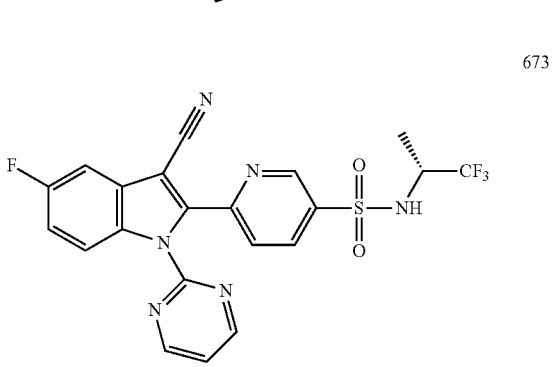
674 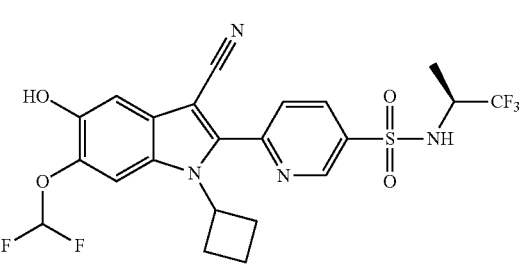
675 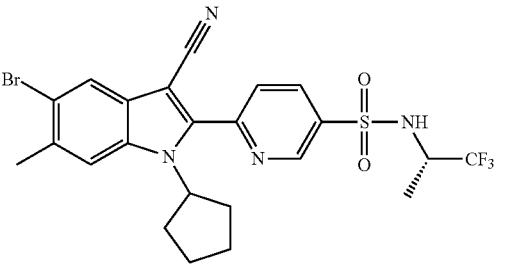
676 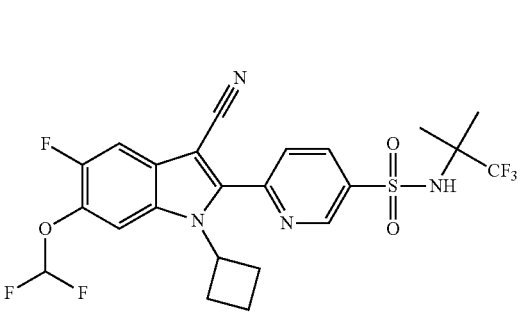

677
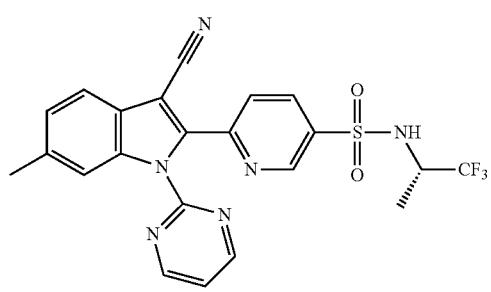
678
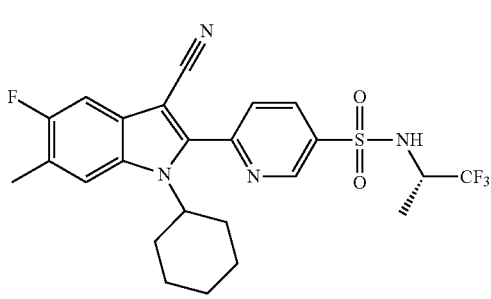
679
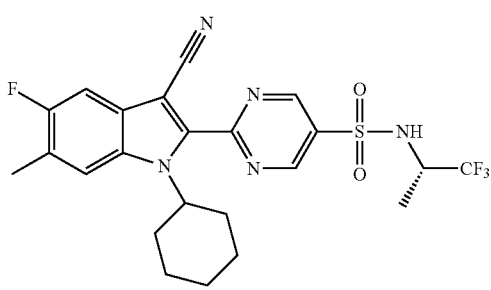
680
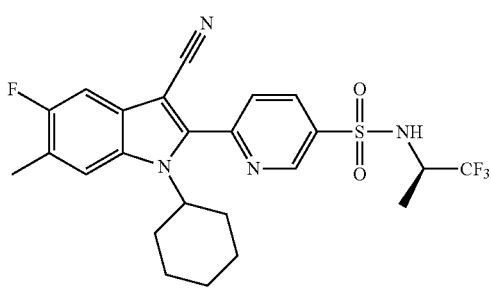
681
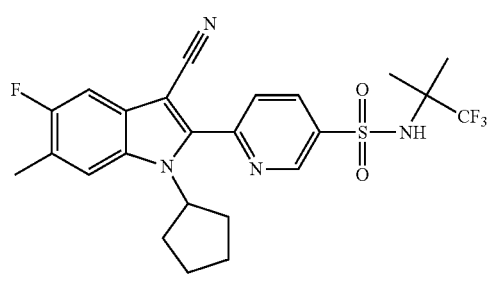
682
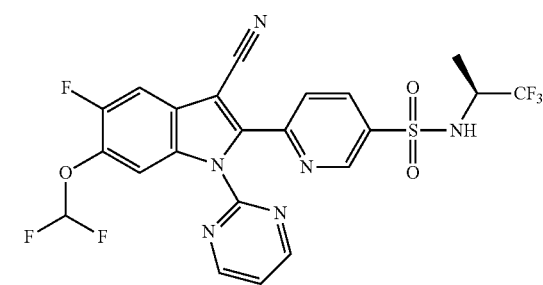
683
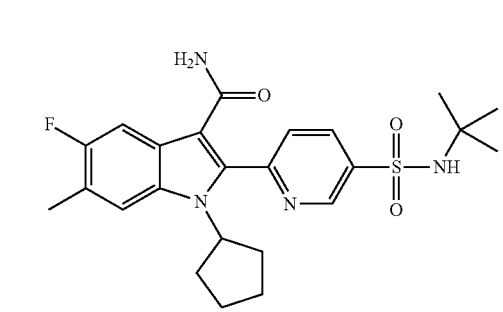
684
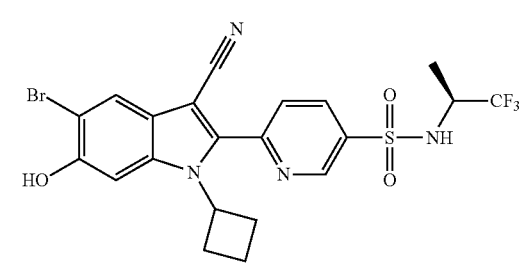
685
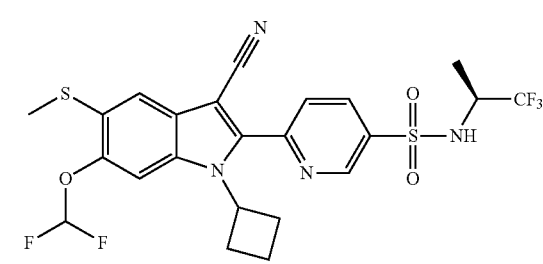
686
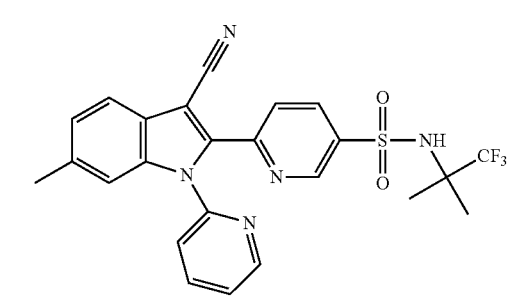

687 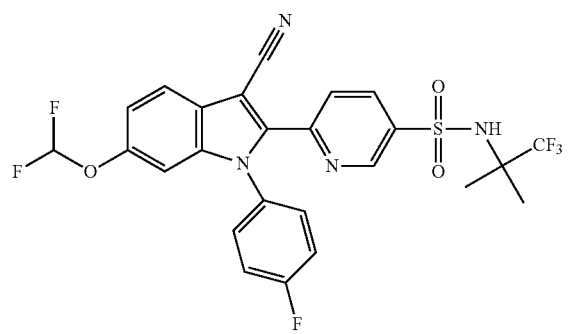
688 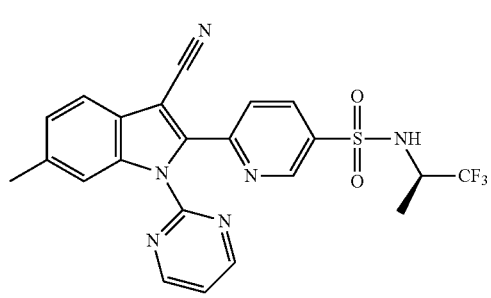
689 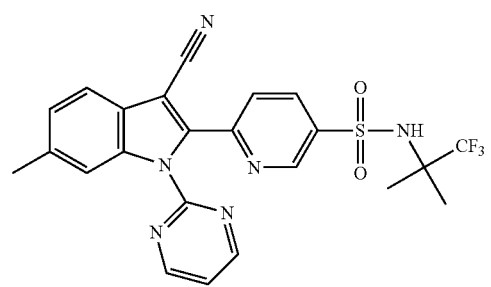
690 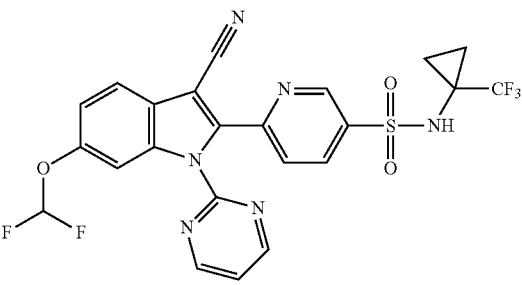
691 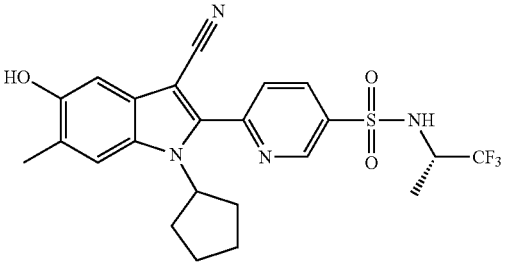
692 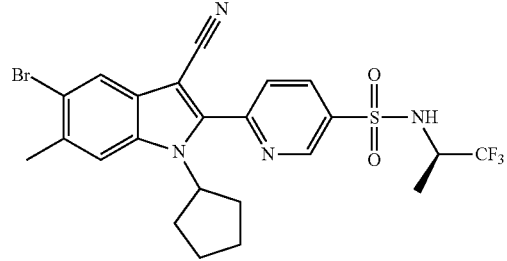
693 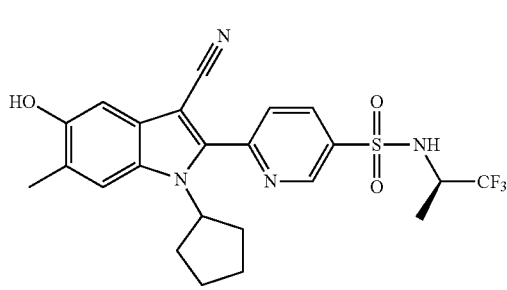
694 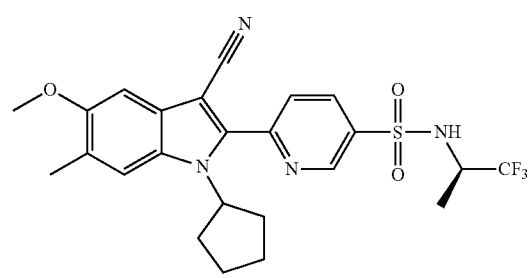
695 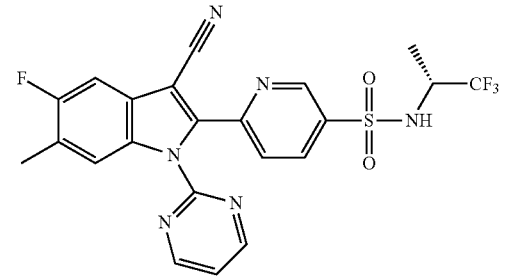
696 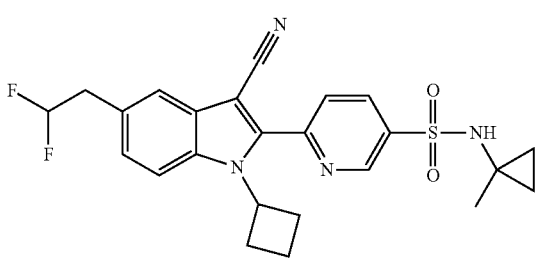

697 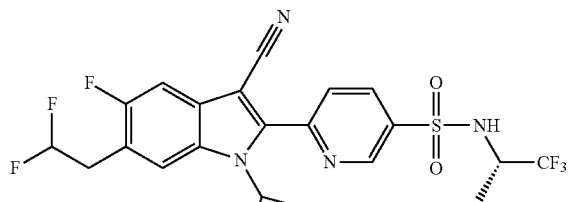
698 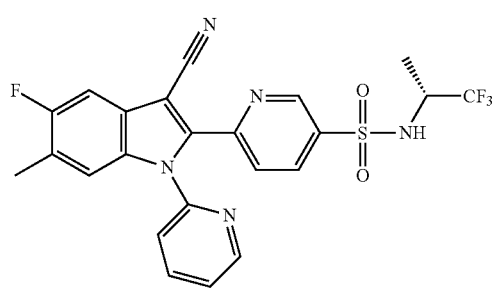
699 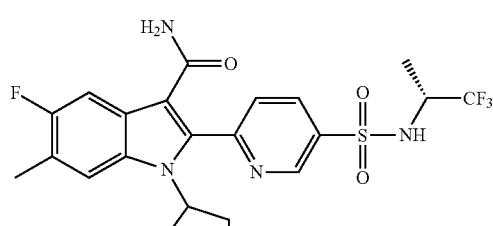
700 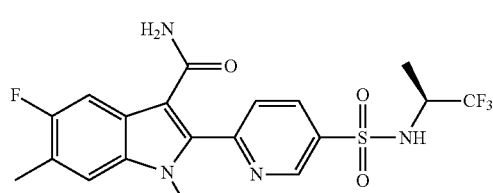
701 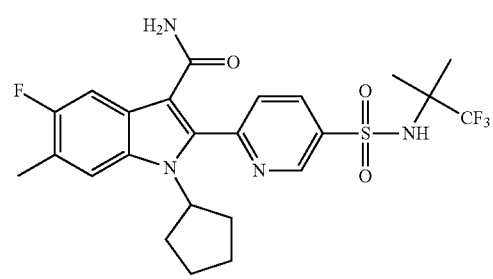
702 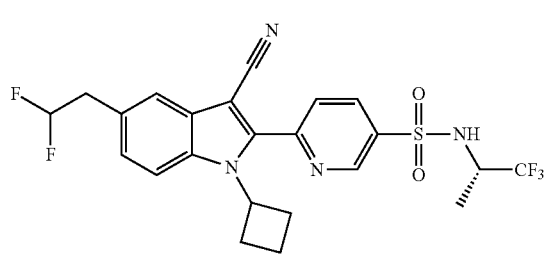
703 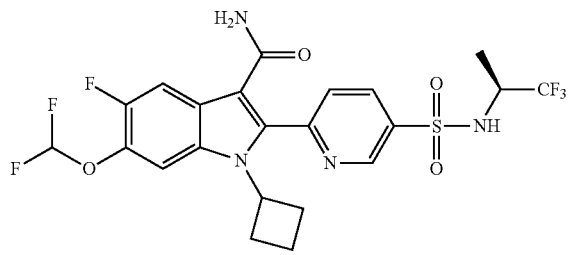
704 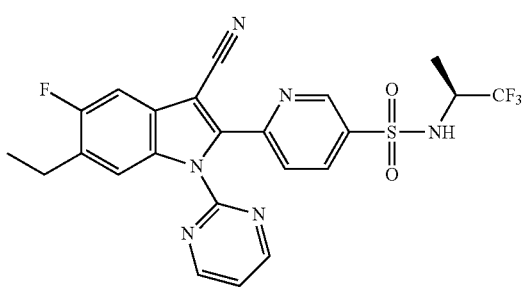
705 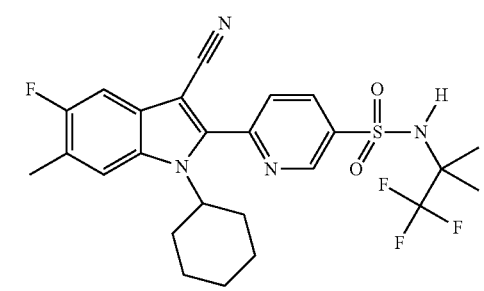
706 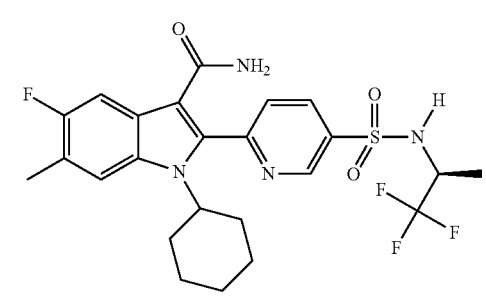
707 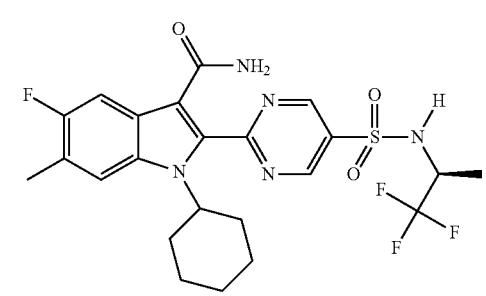

708 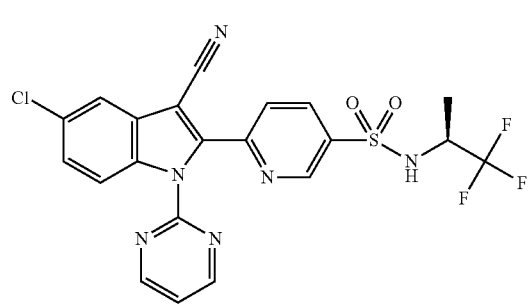
709 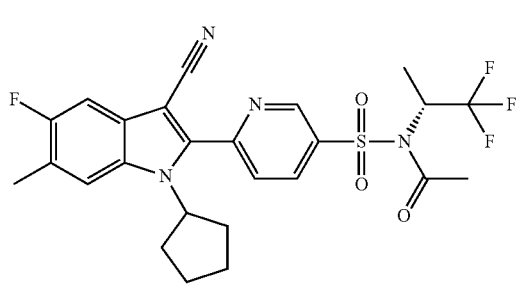
710 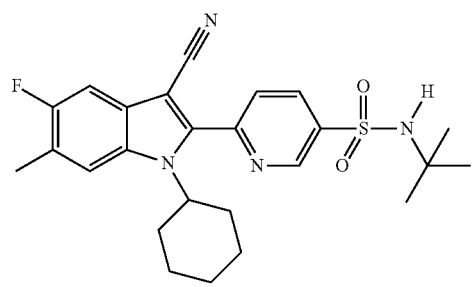
711 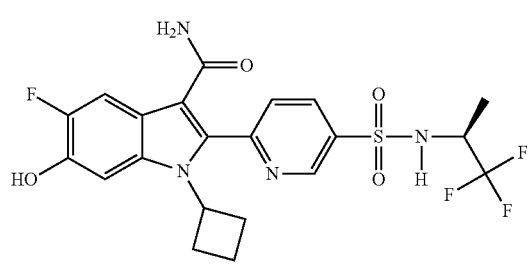
712 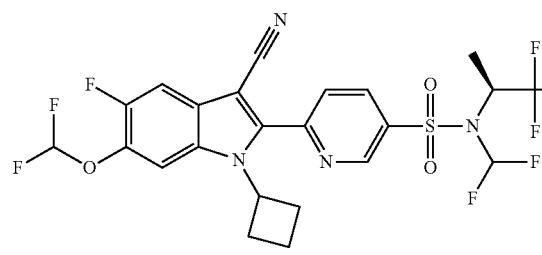
713 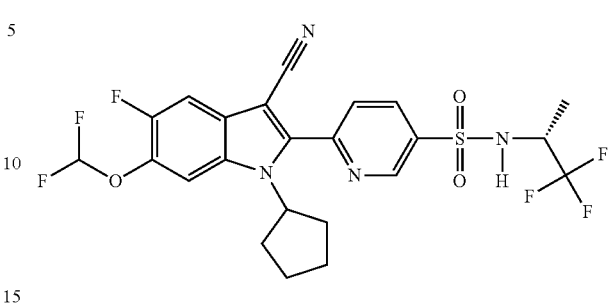
714 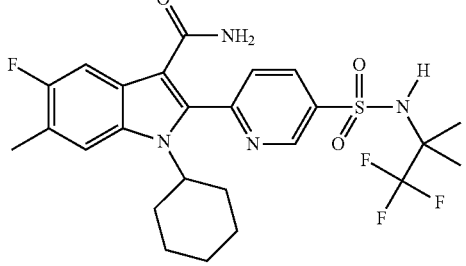
715 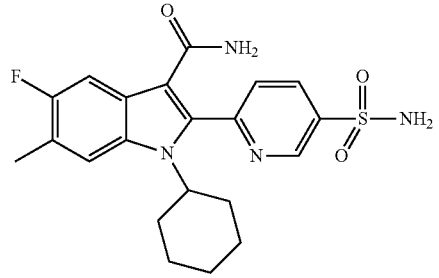
716 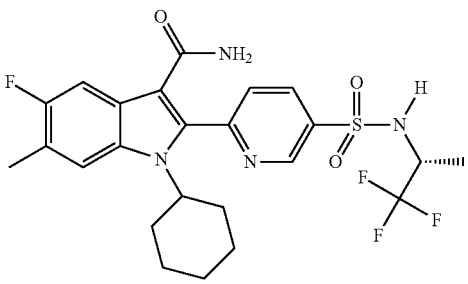
717 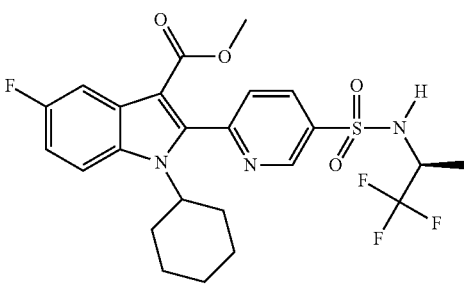

718 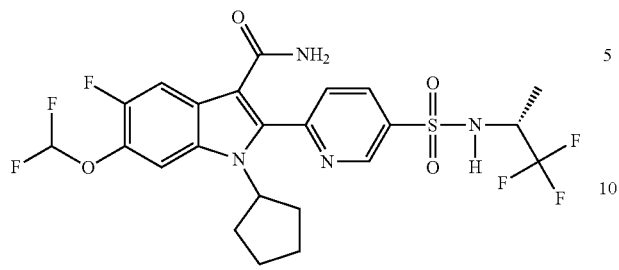
719 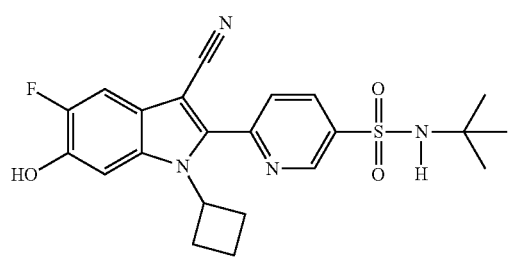
720 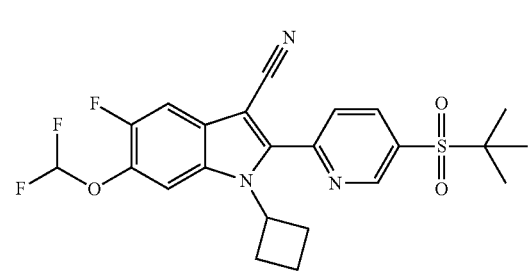
721 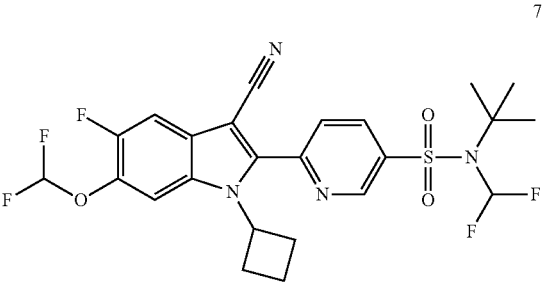
722 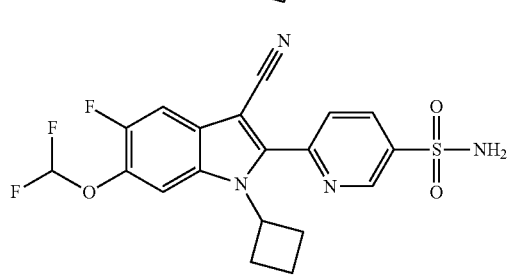
723 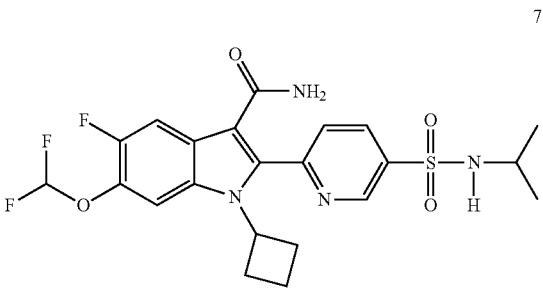
724 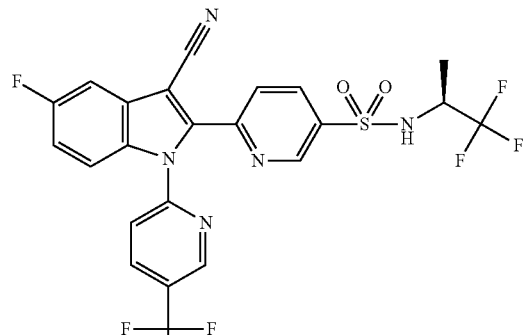
725 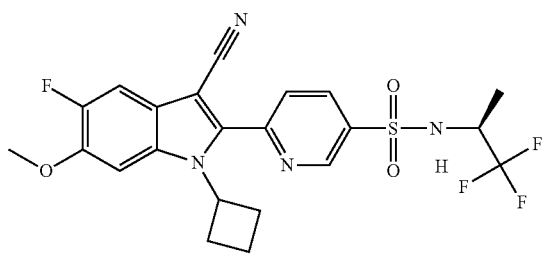
726 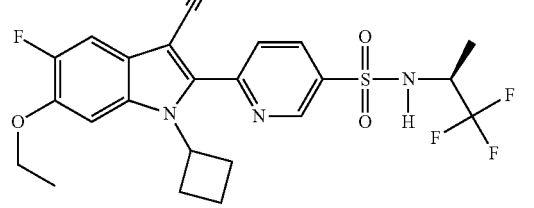
727 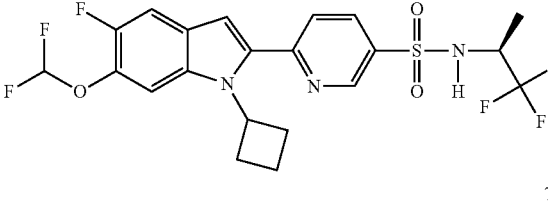
728 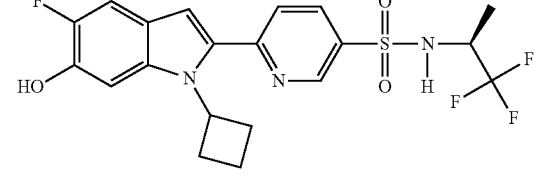
729 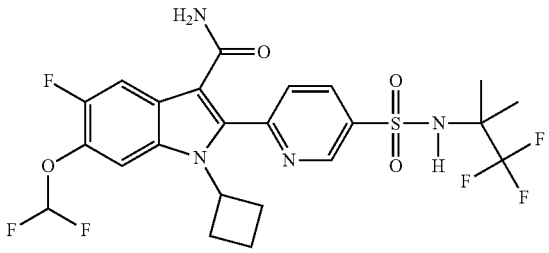

730
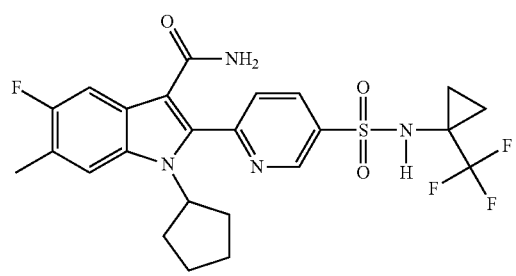
731
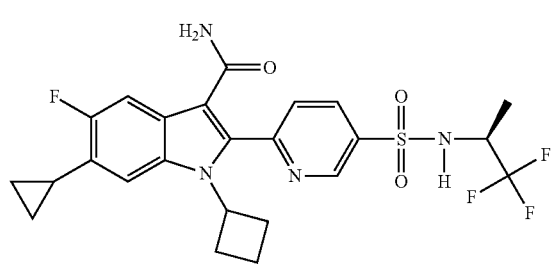
732
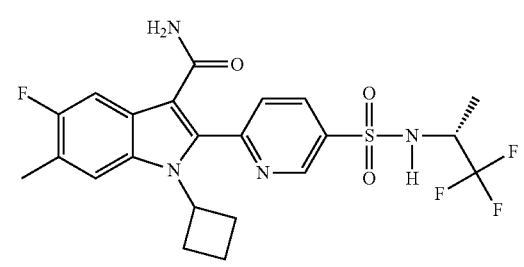
733
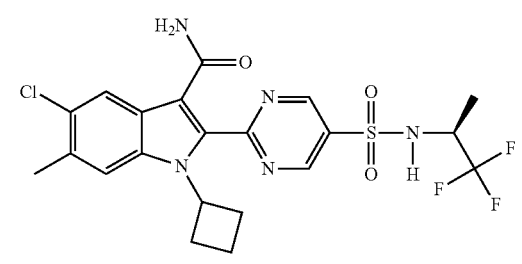
734
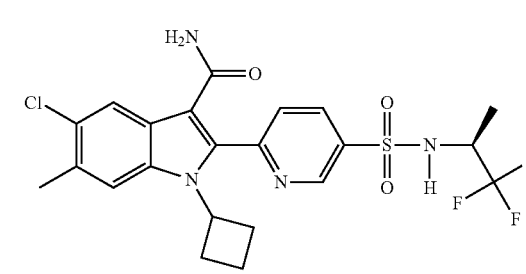
735
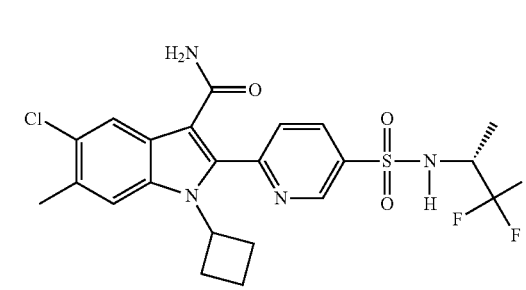
736
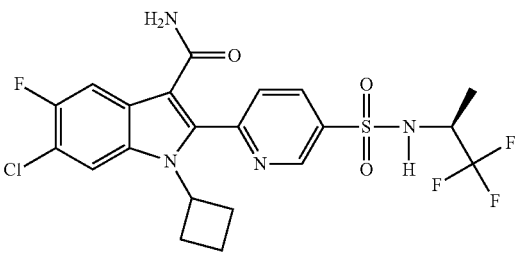
737
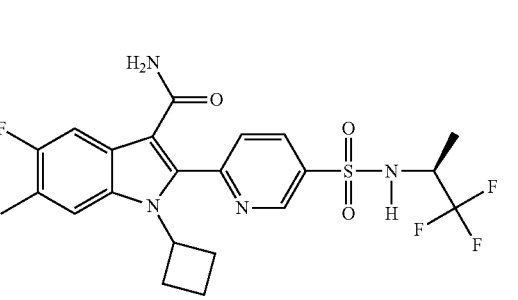
738
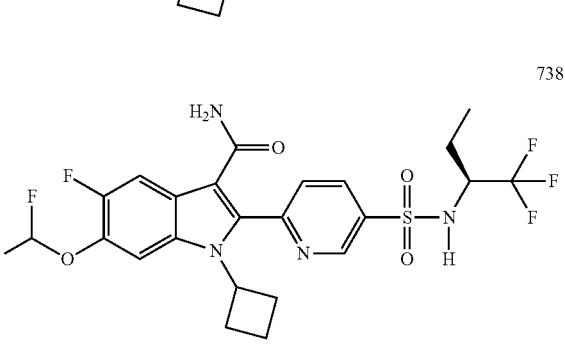
739
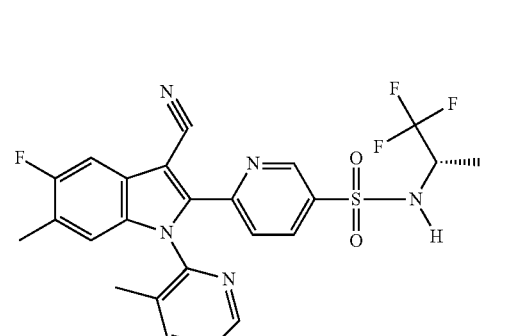
740
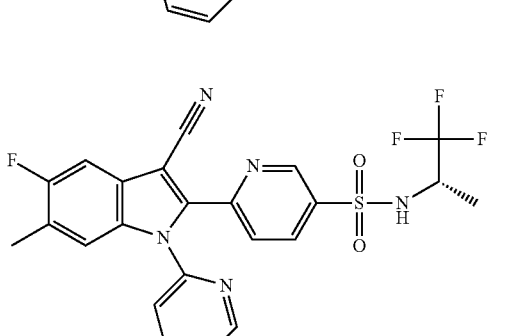

741
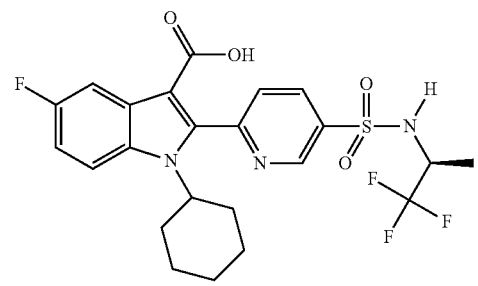
742
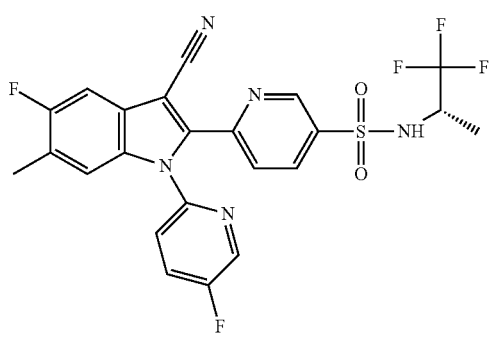
743
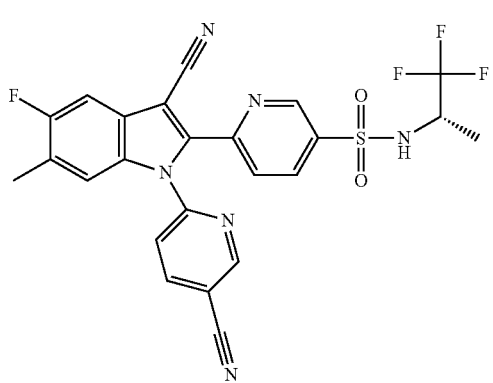
744
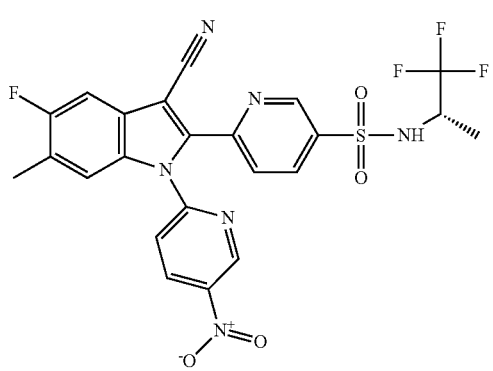
745
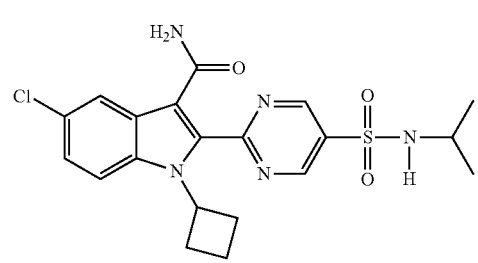
746
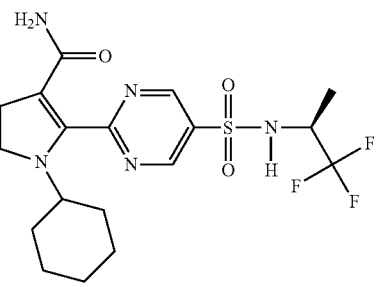
747
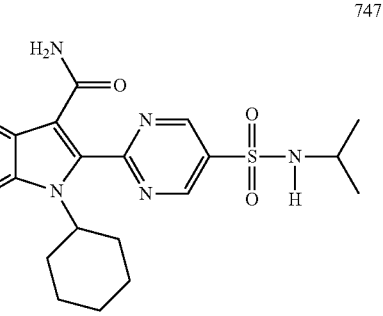
748
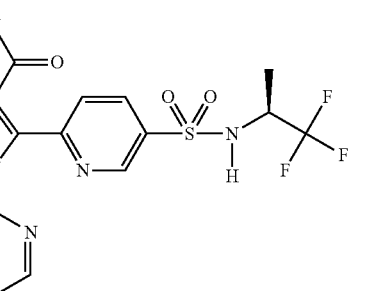
749
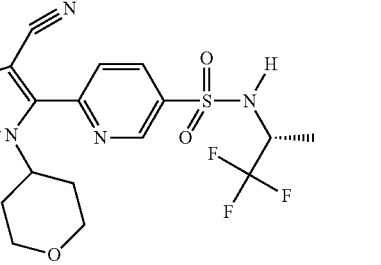
750
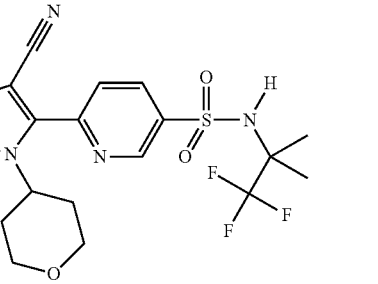

751
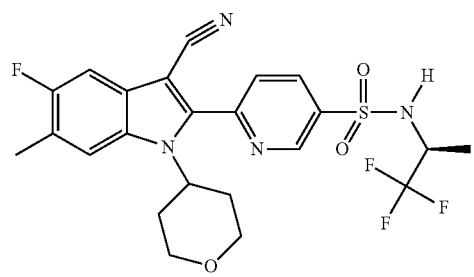
752
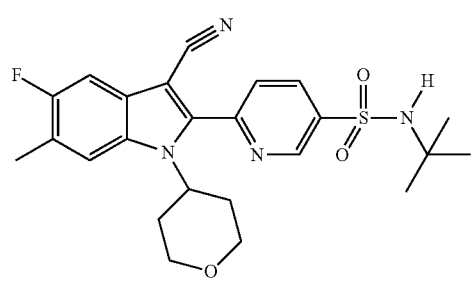
753
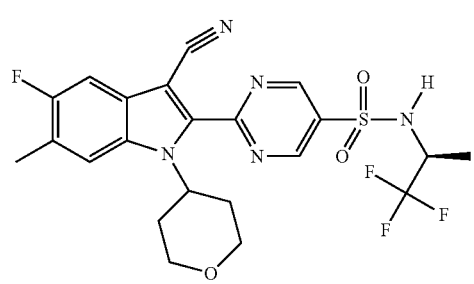
754
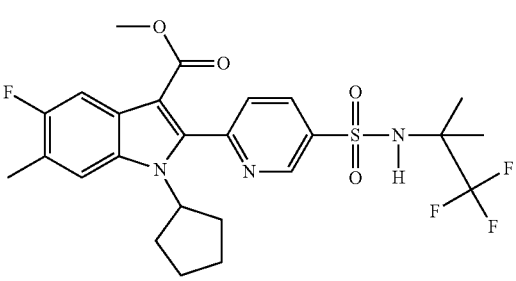
755
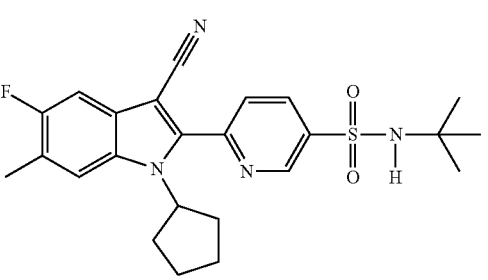
756
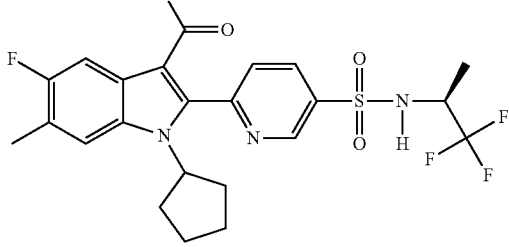
757
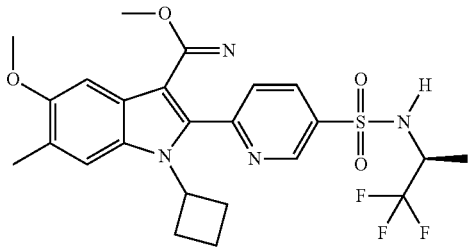
758
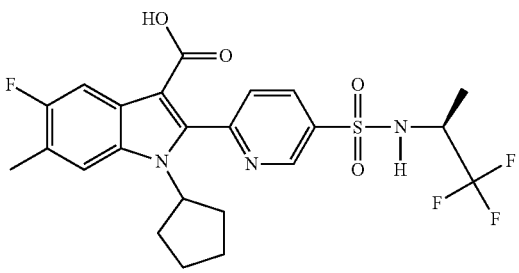
760
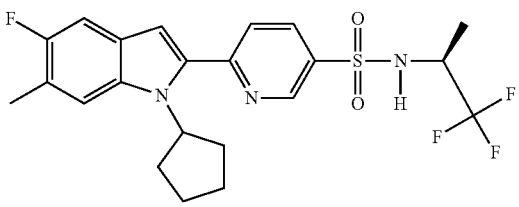
761
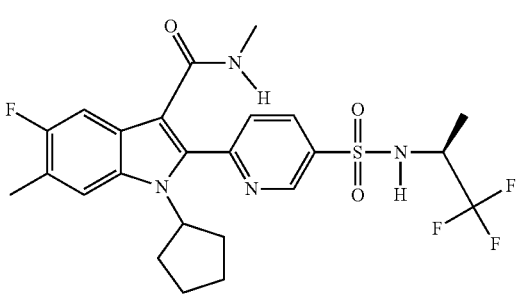

762
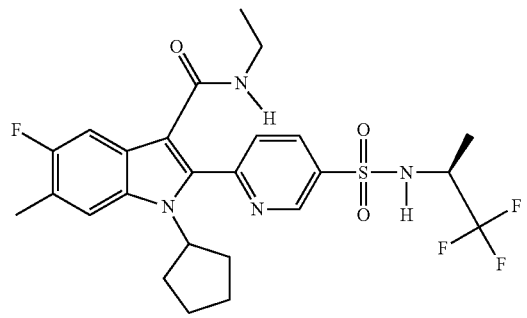
763
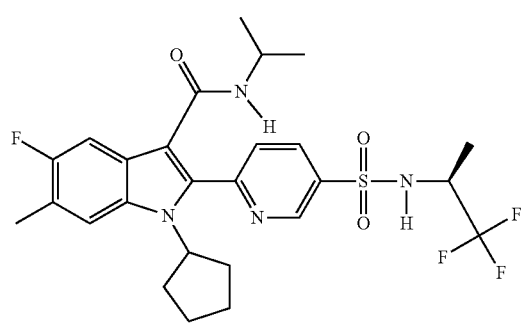
764
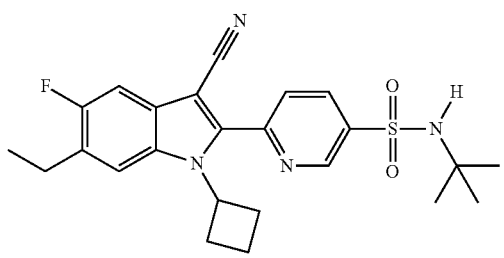
765
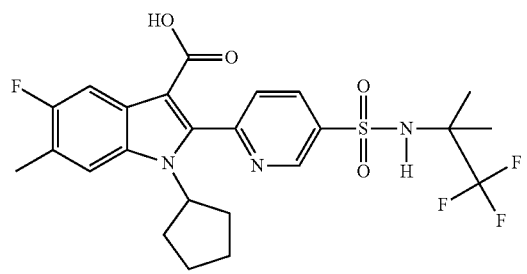
766
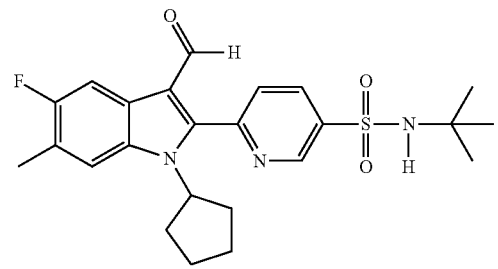
767
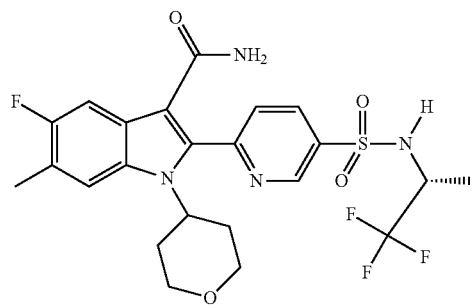
768
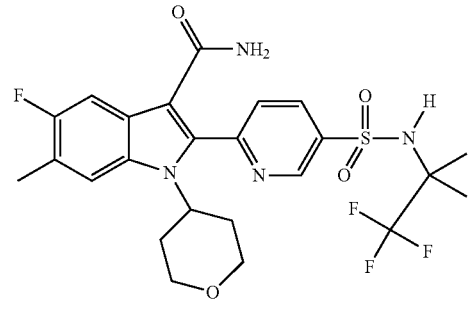
769
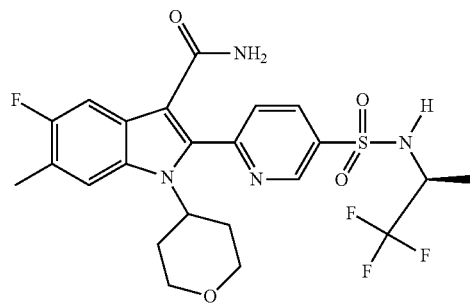
770
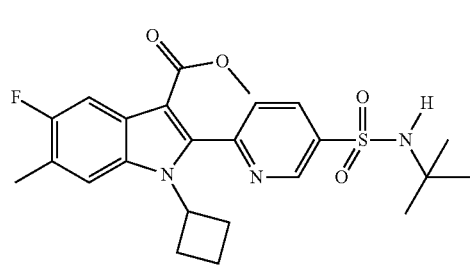
771
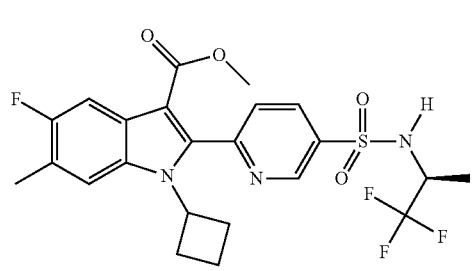

772 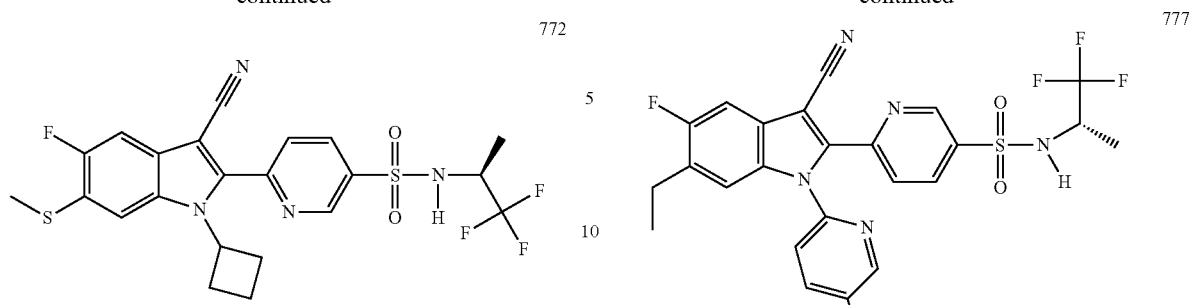
773 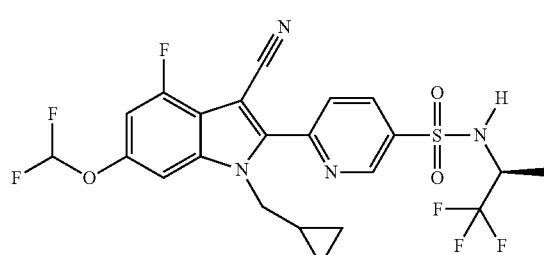
774 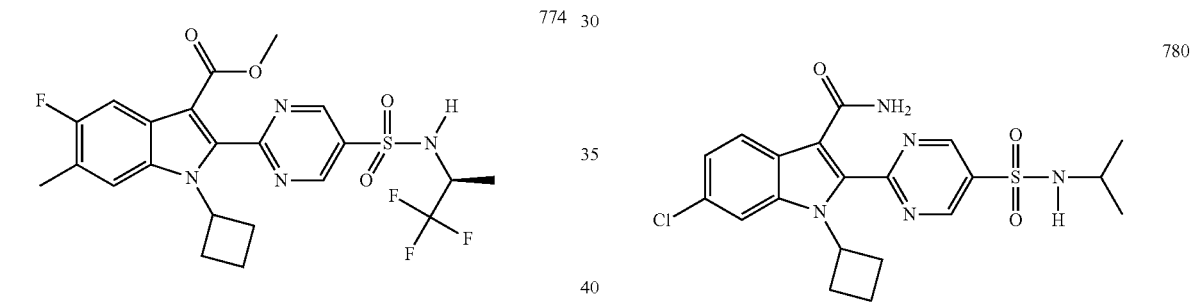
775 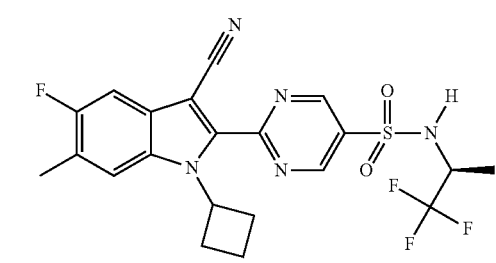
776 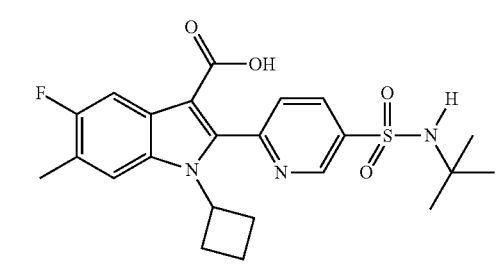
777 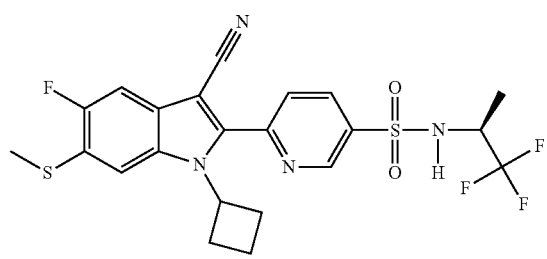
778 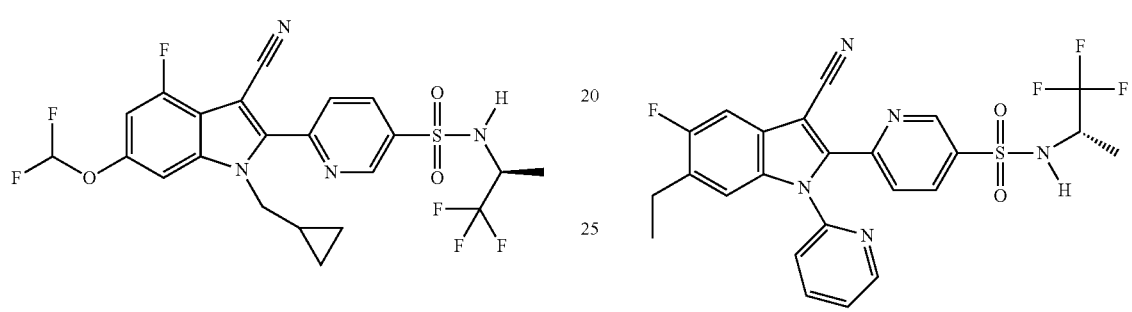
780 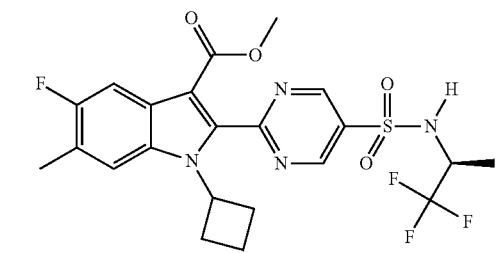
781 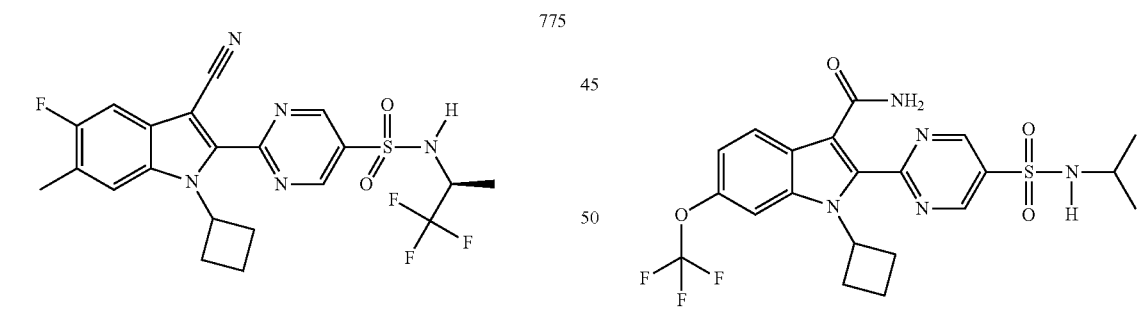
782 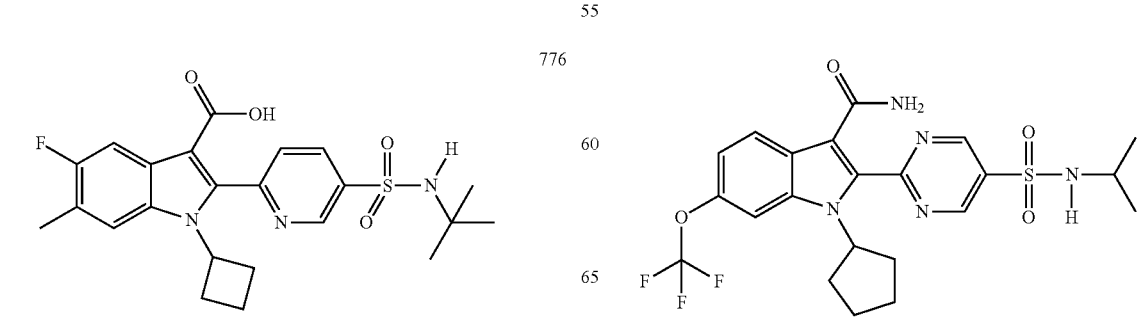

155
-continued
783
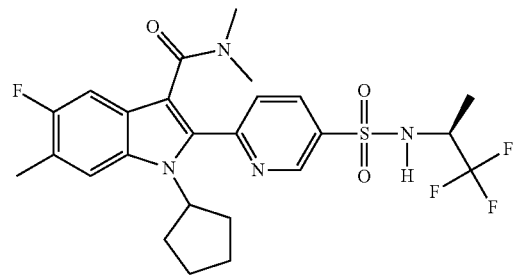
784
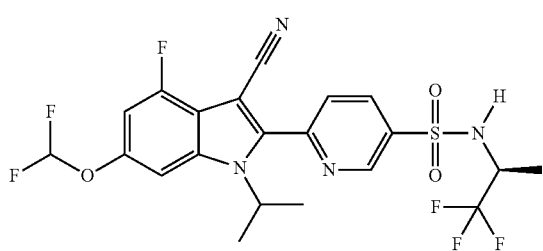
785
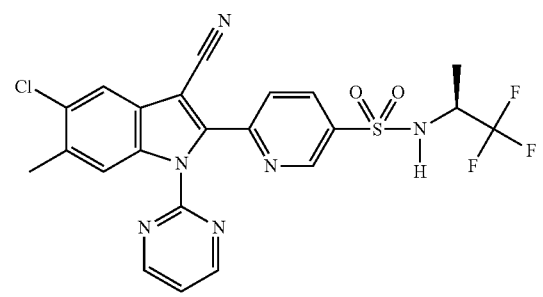
786
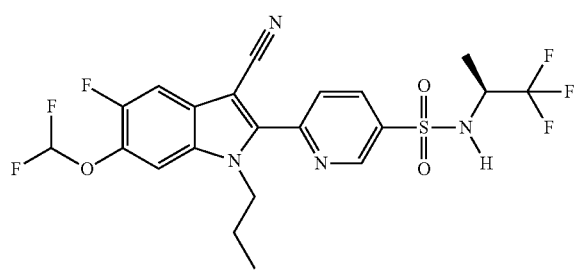
787
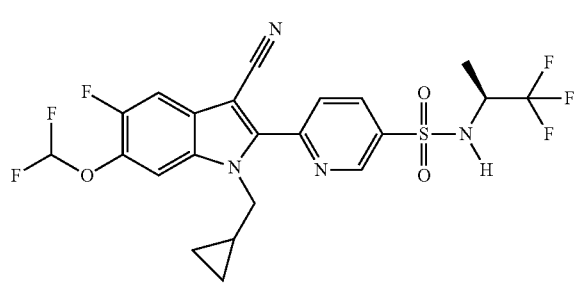
156
-continued
788
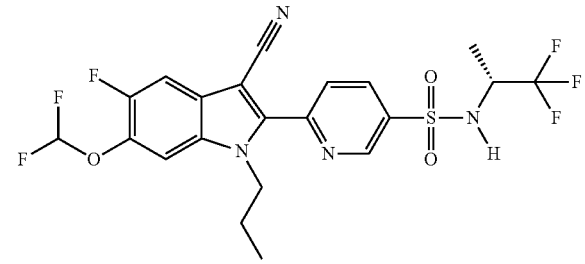
789
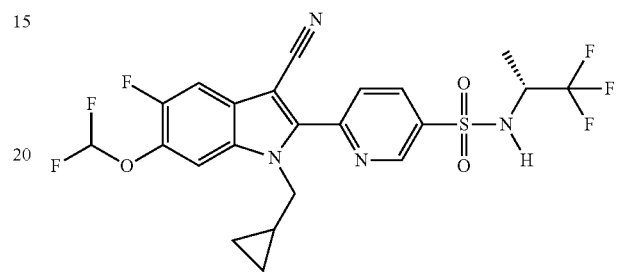
790
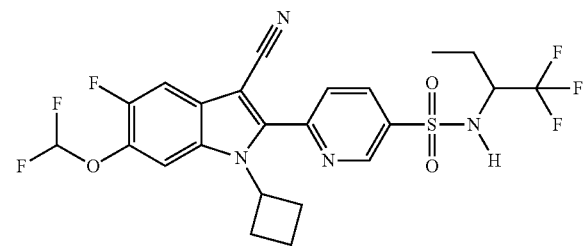
791
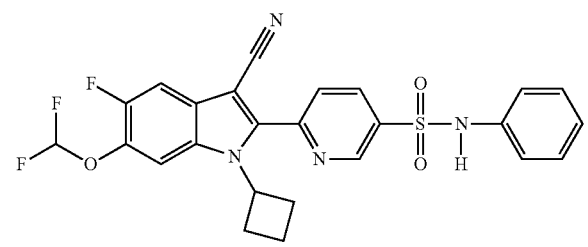
793
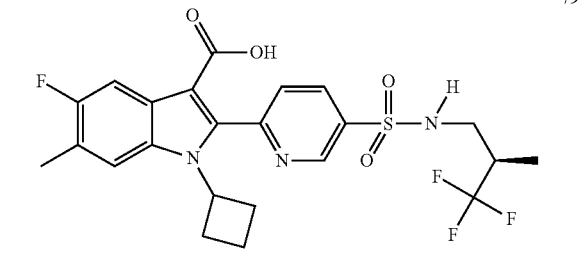
794
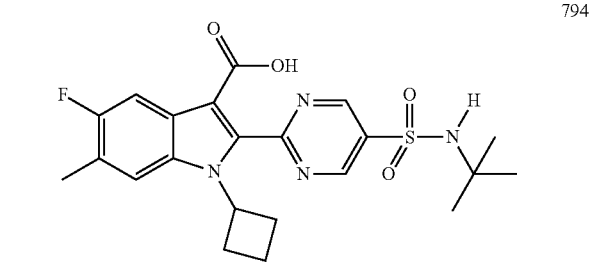

-continued
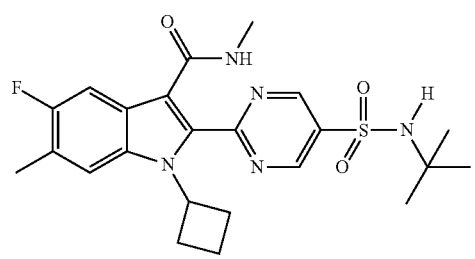 795
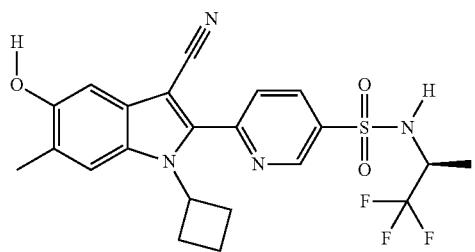 796
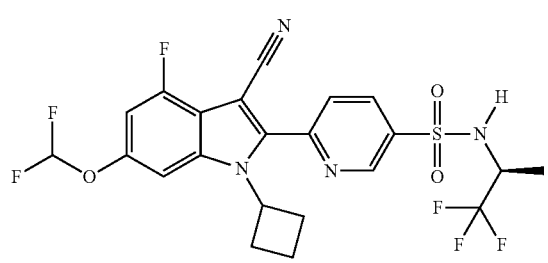 797
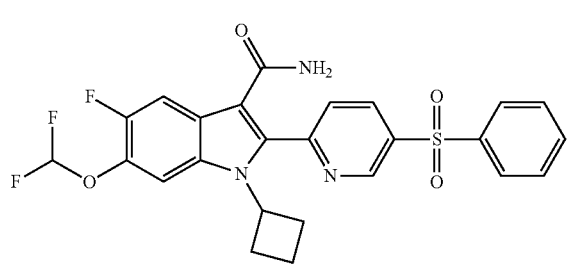 798
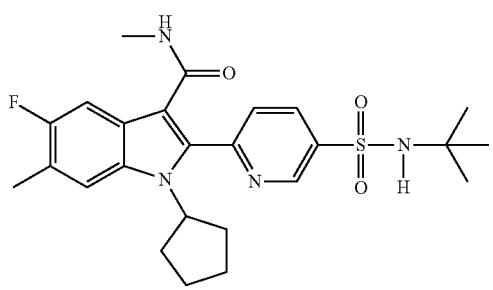 799
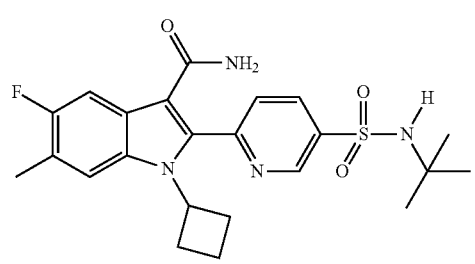 800
-continued
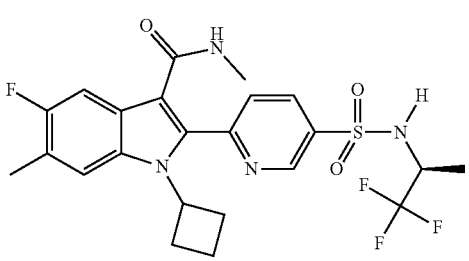 801
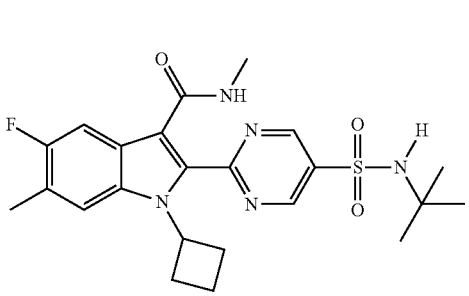 802
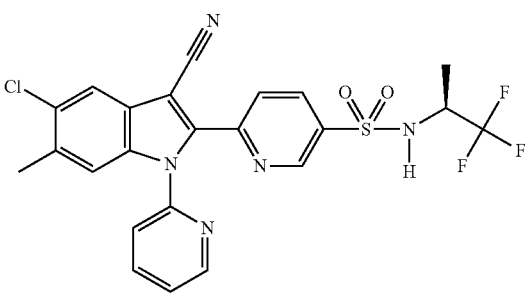 803
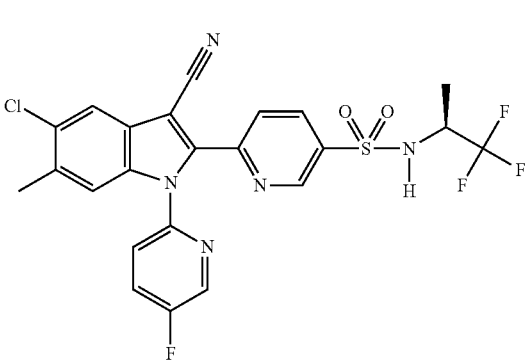 804
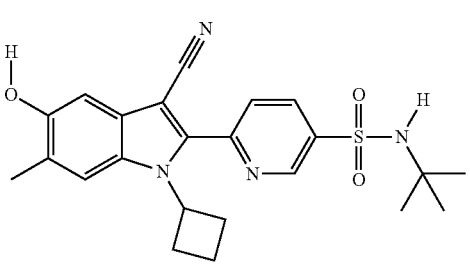 805

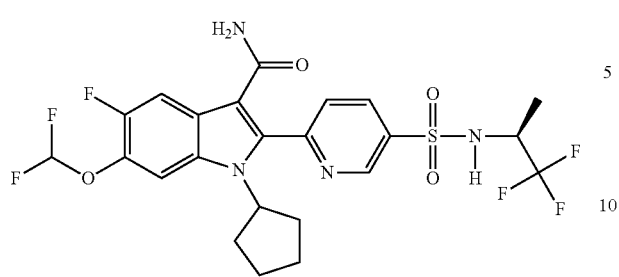
806
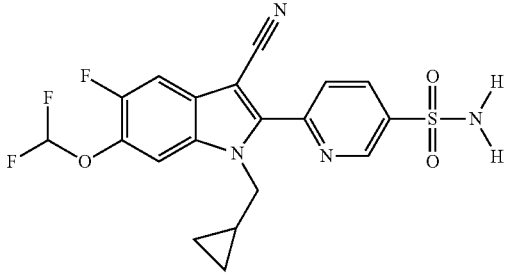
812
807
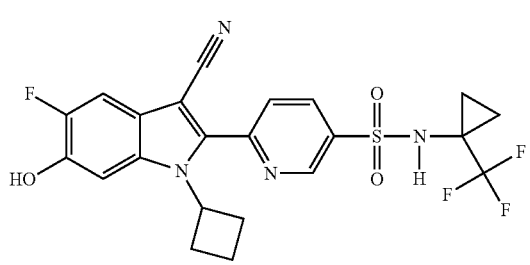
813
808
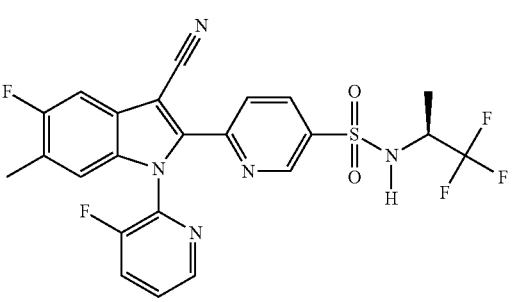
814
809
810
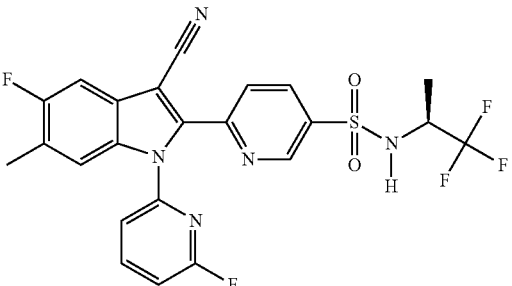
815
811
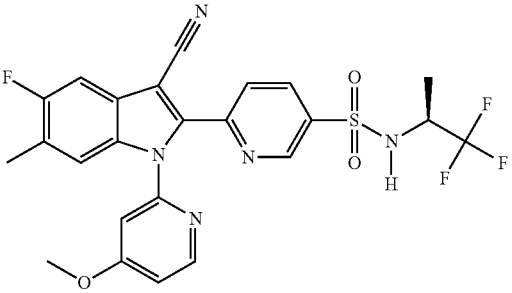
816

817
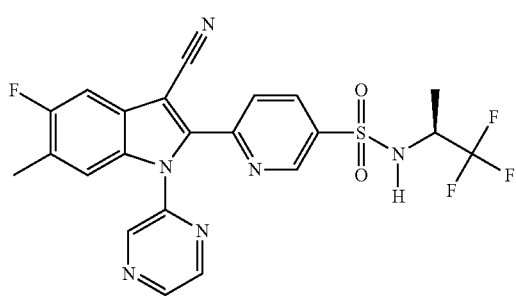
818
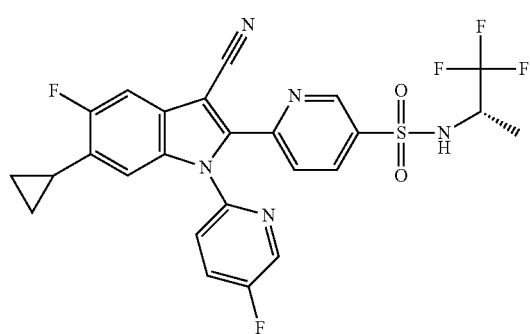
819
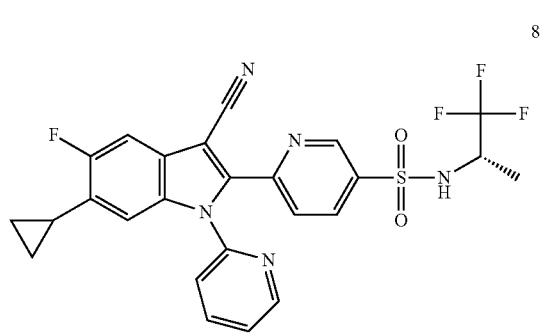
820
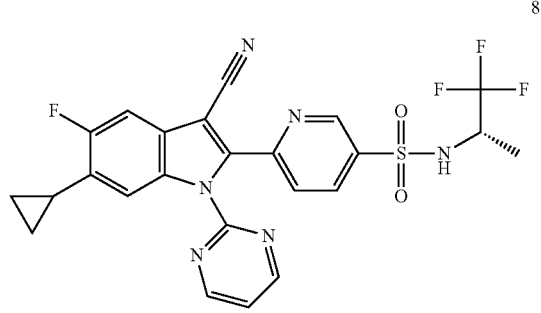
821
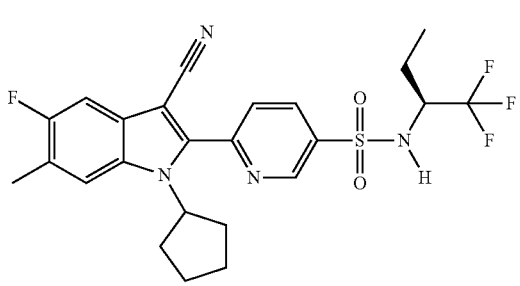
822
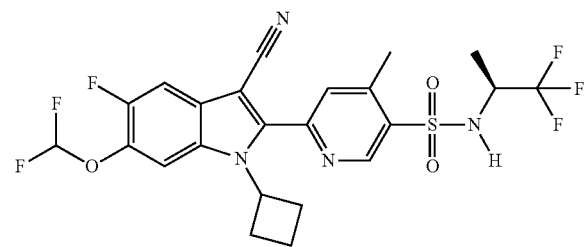
823
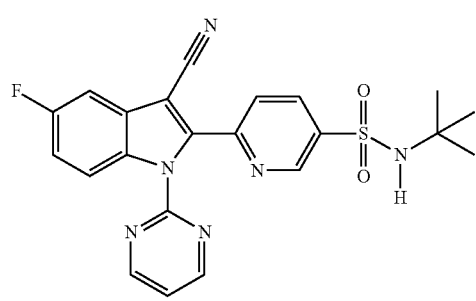
824
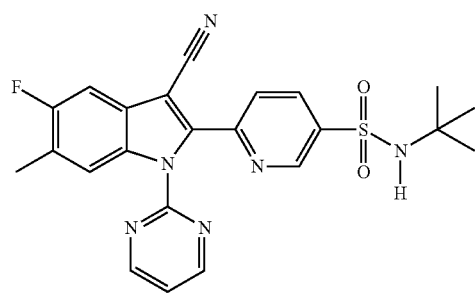
825
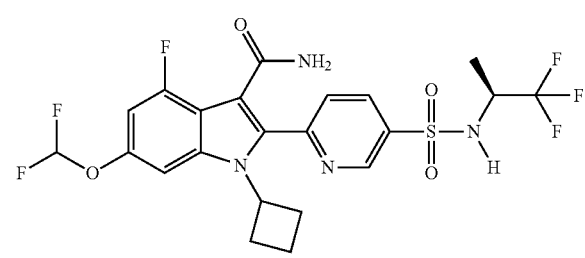
826
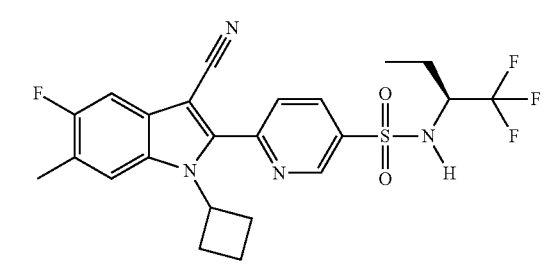

163
-continued
827
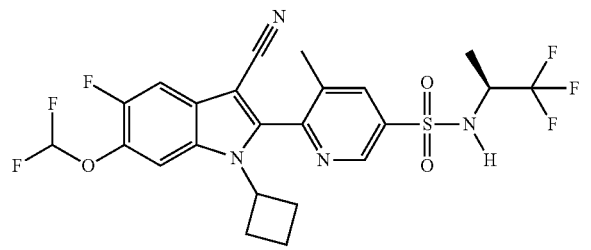
828
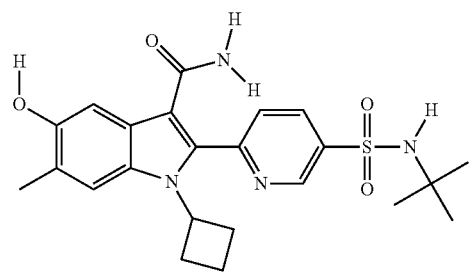
829
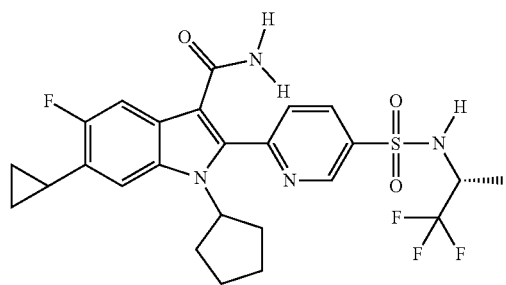
830
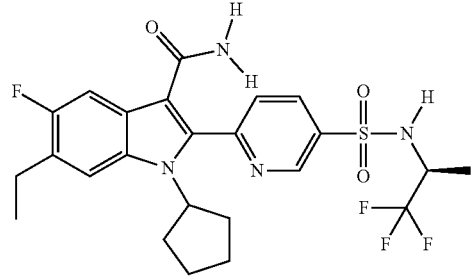
831
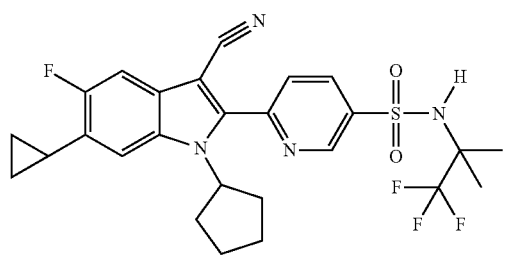
164
-continued
832
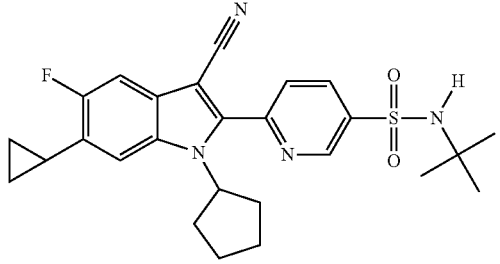
833
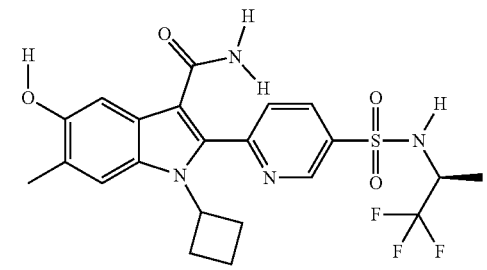
834
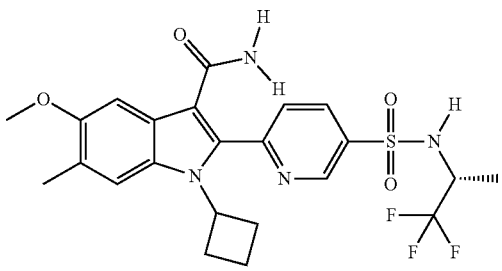
835
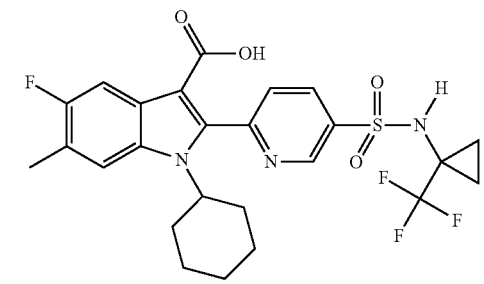
836
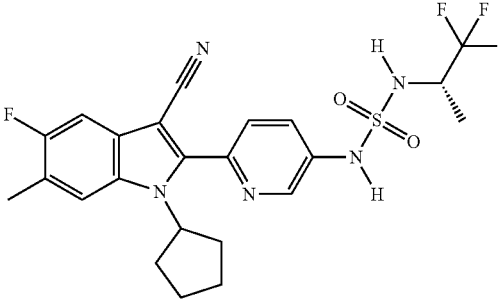

165
-continued
837
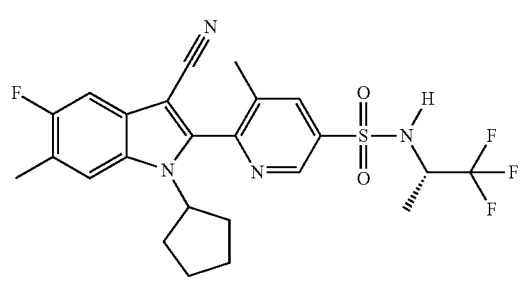
838
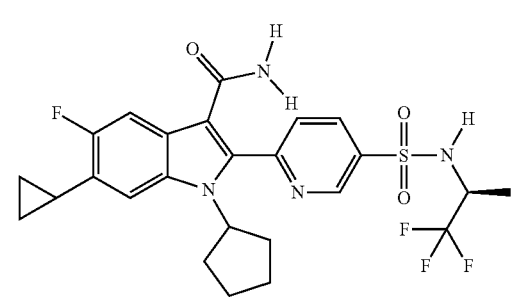
839
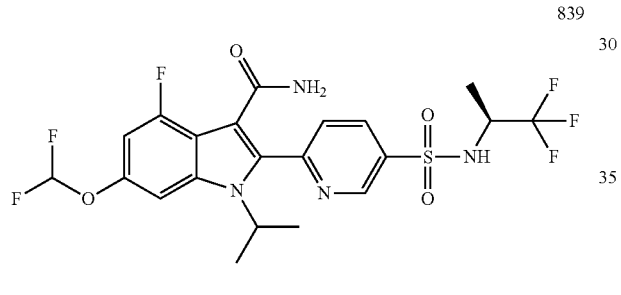
840
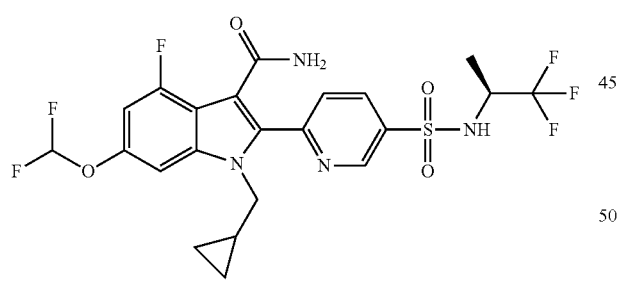
841
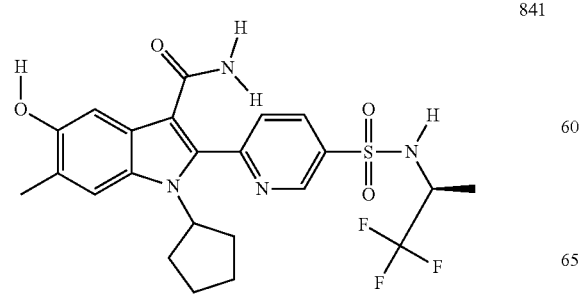
166
-continued
842
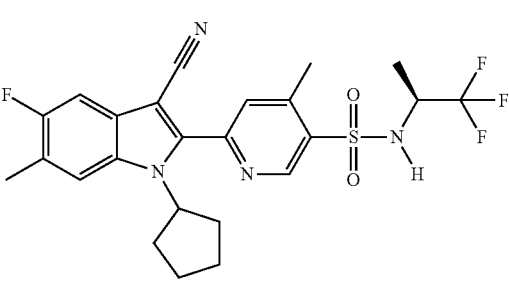
843
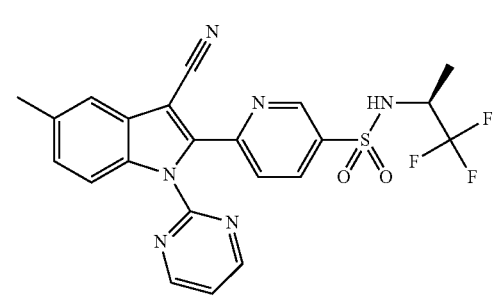
844
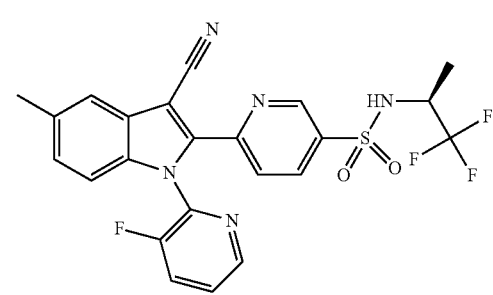
845
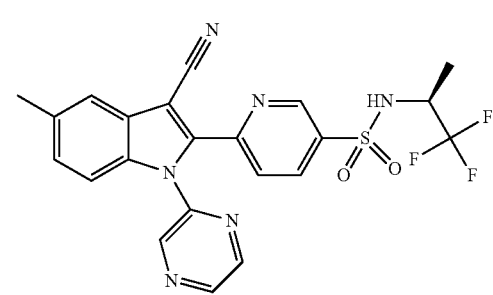
846
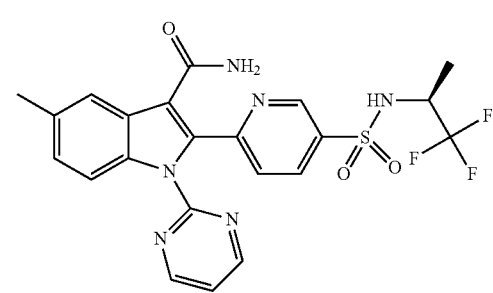

847
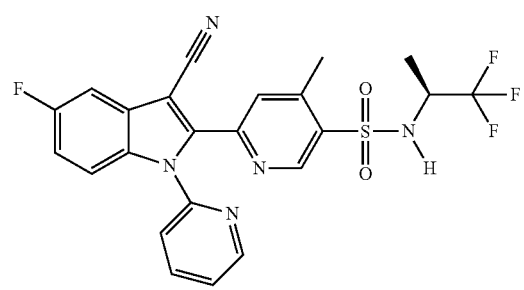
852
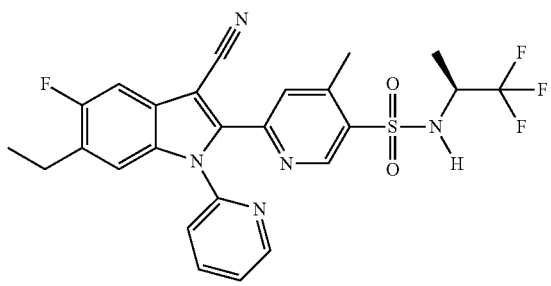
848
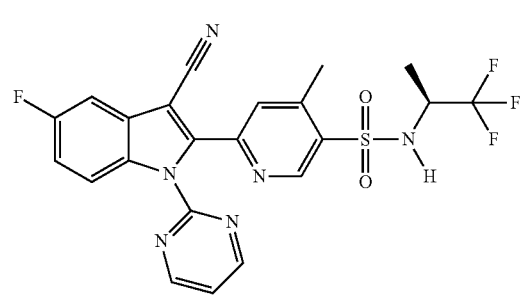
853
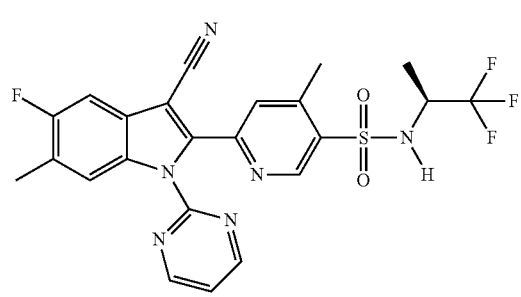
849
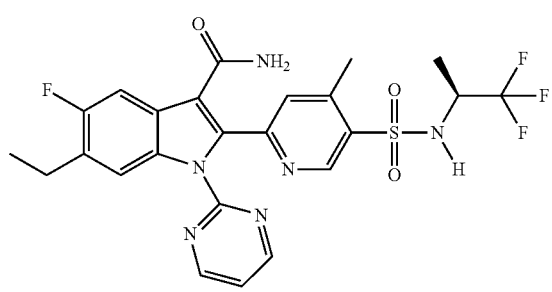
854
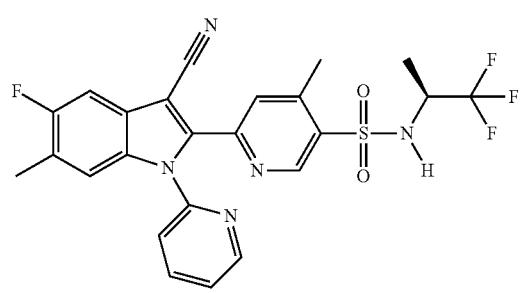
850
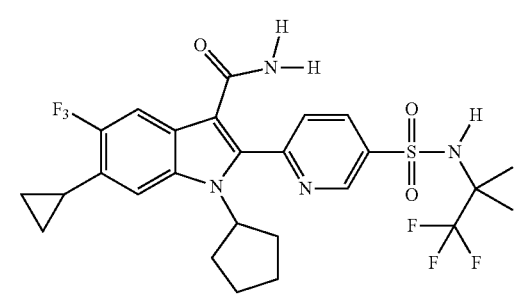
855
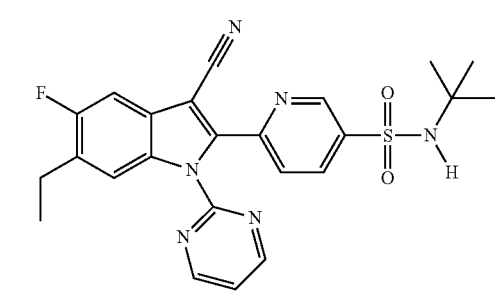
851
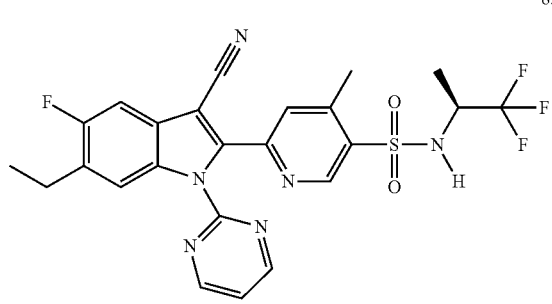
856
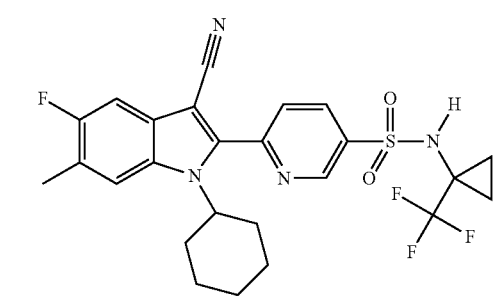

857
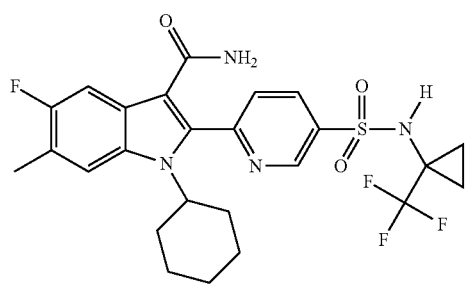
858
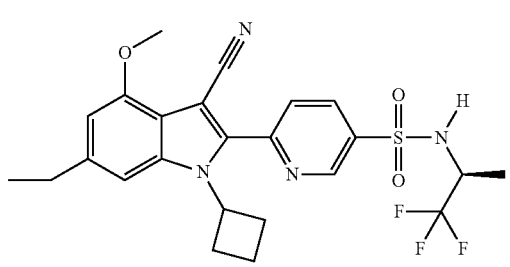
859
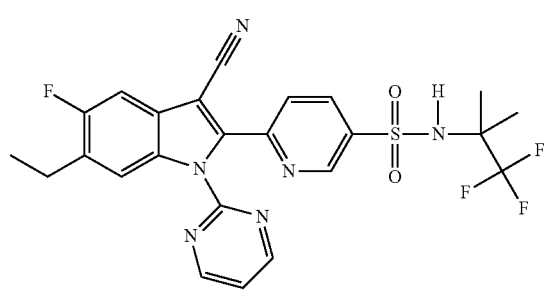
860
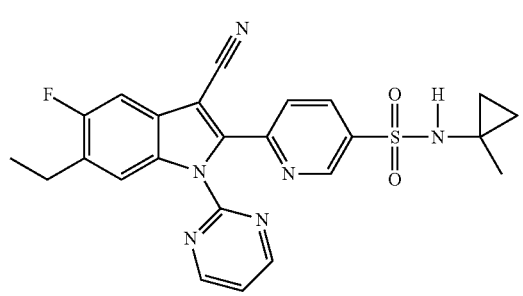
861
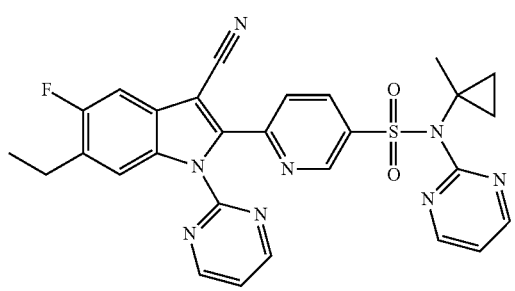
862
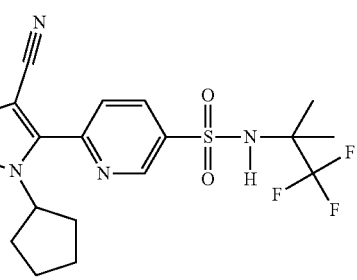
863
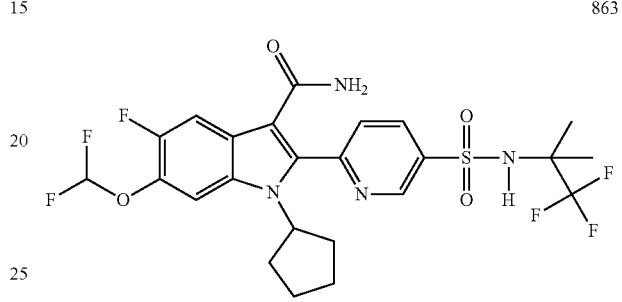
864
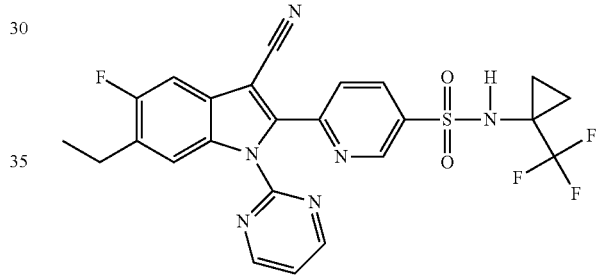
865
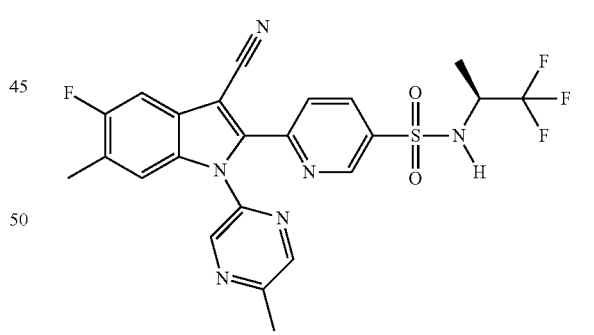
866
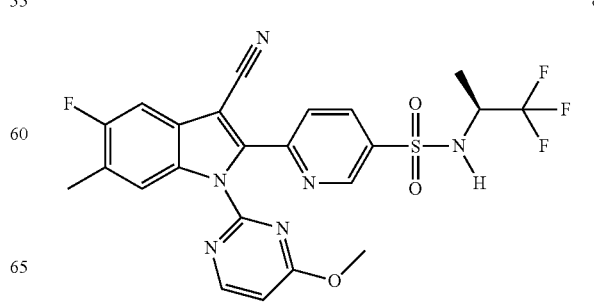

-continued
867
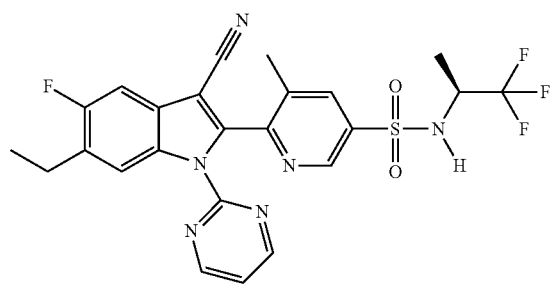
868
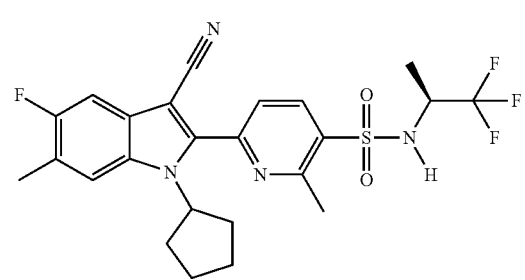
869
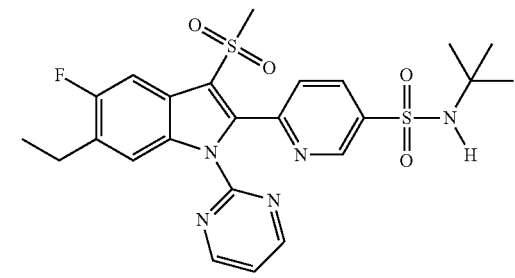
870
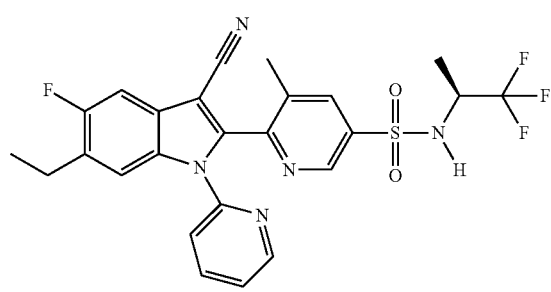
871
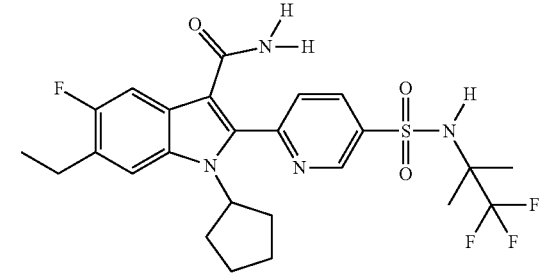
-continued
872
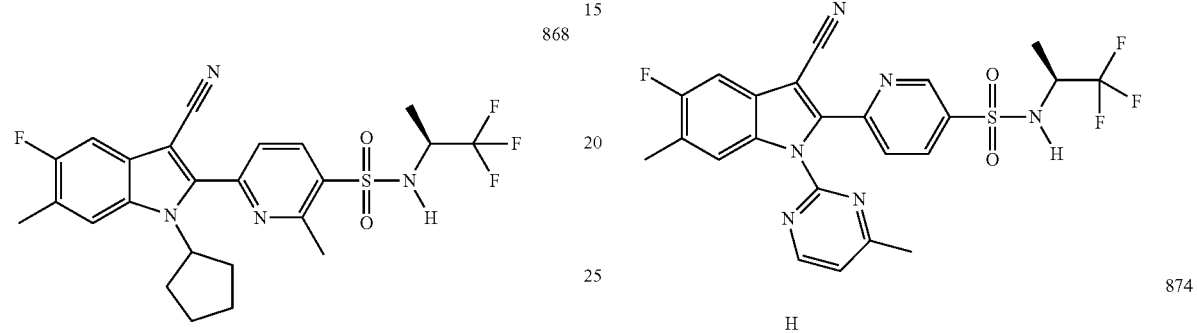
873
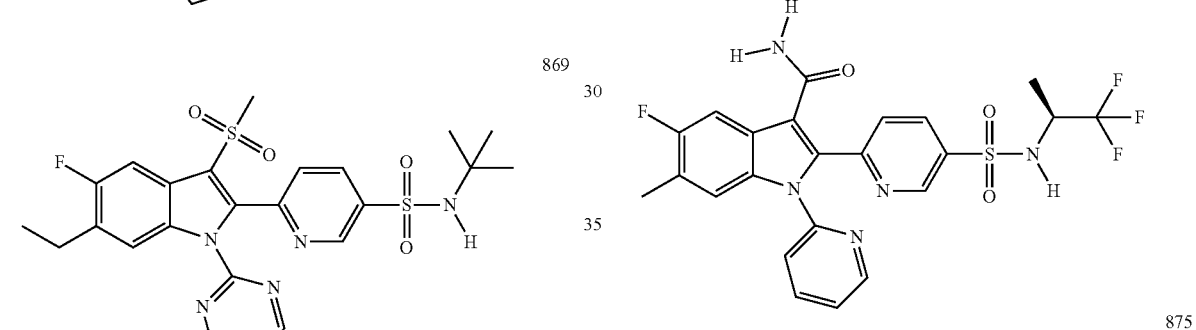
874
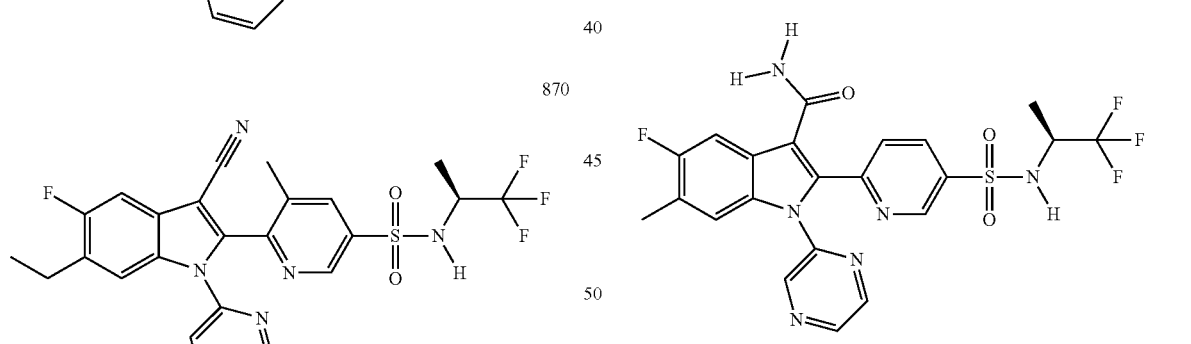
875
876
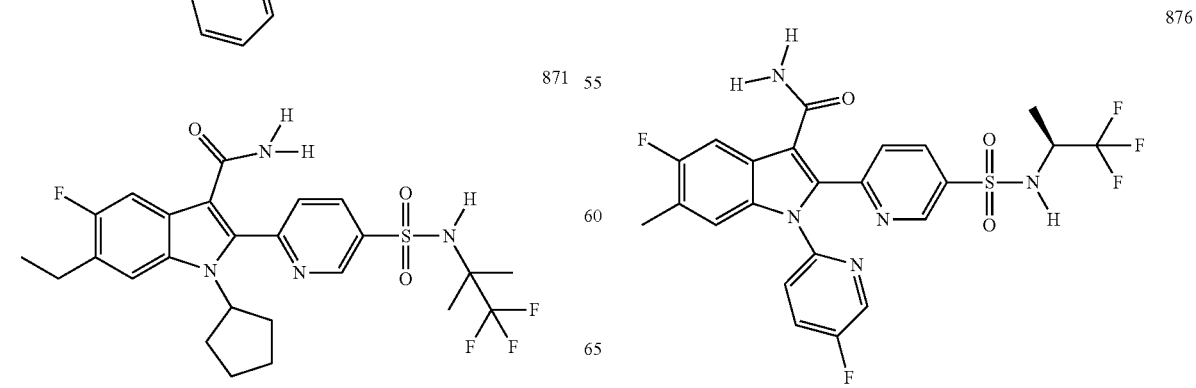

877 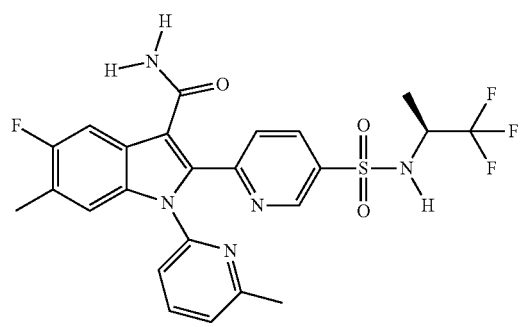
878 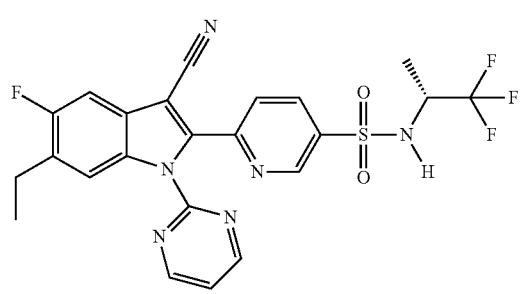
879 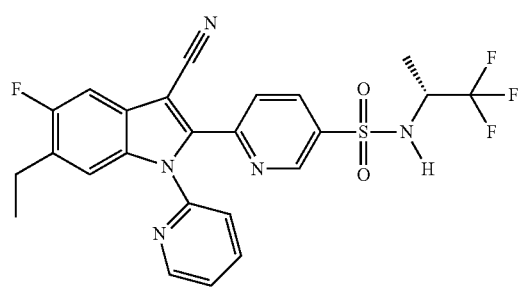
880 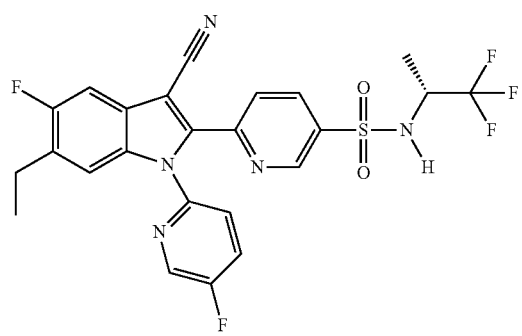
881 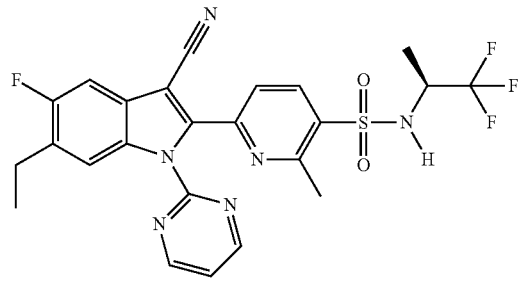
882 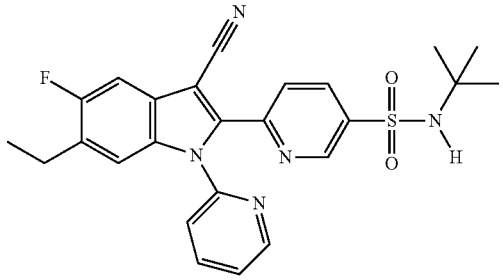
883 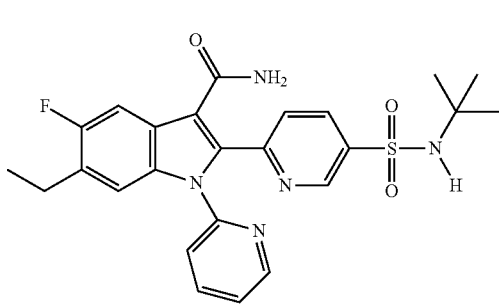
884 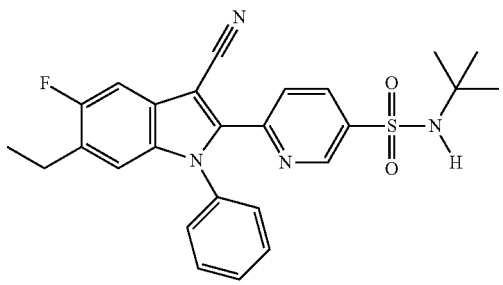
885 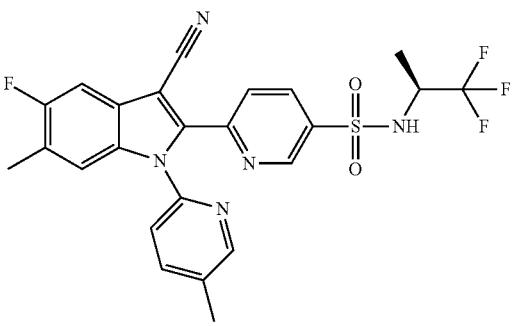
886 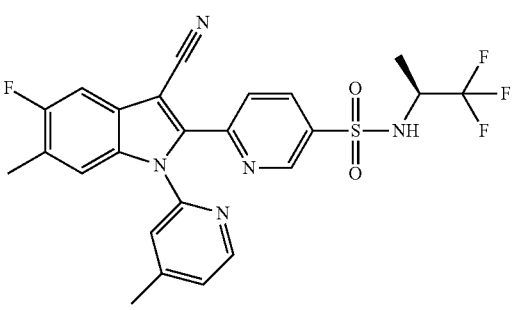

887
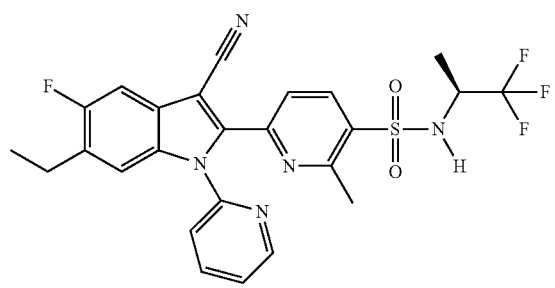
888
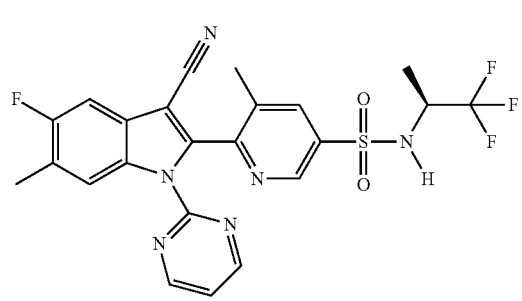
889
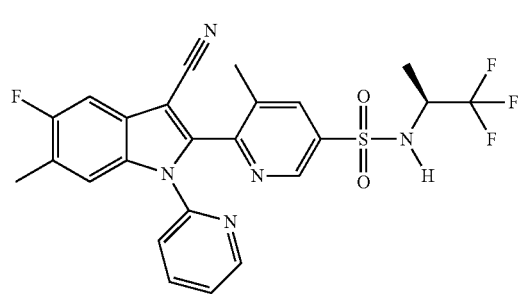
890
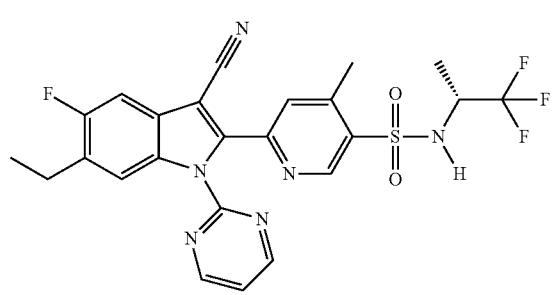
891
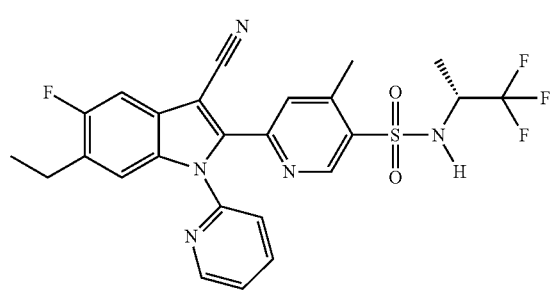
892
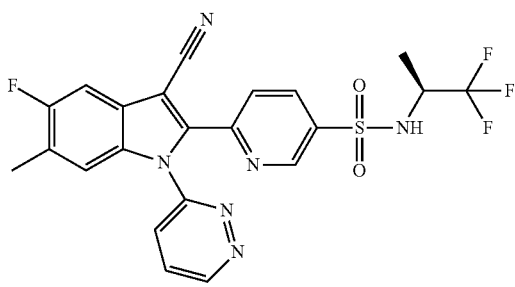
893
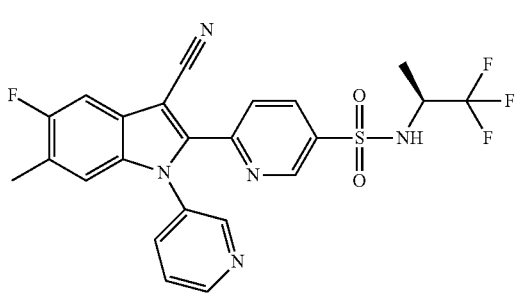
894
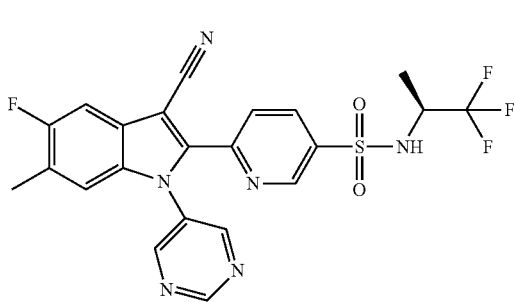
895
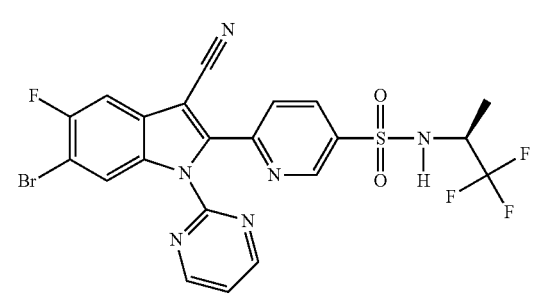
896
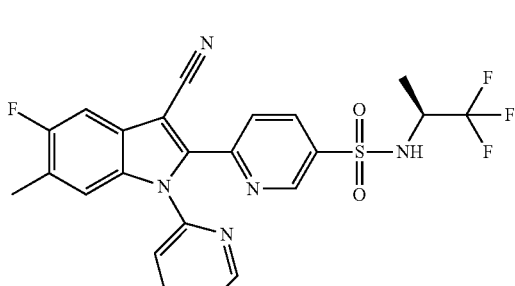

897 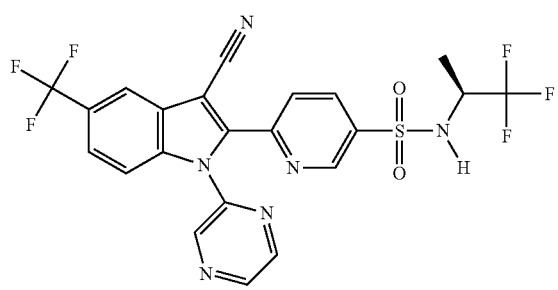
898 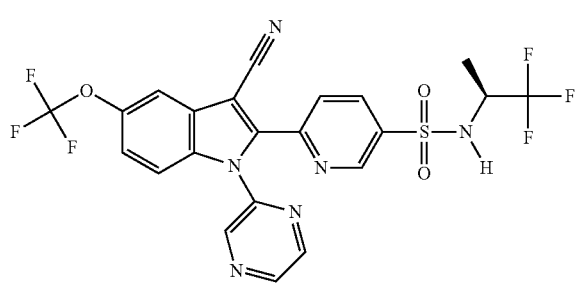
899 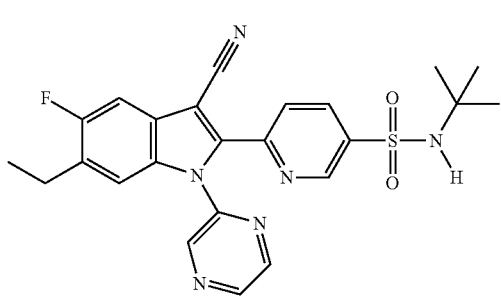
900 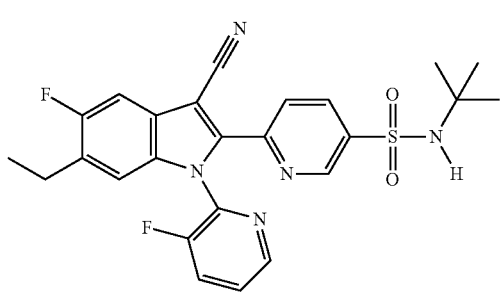
901 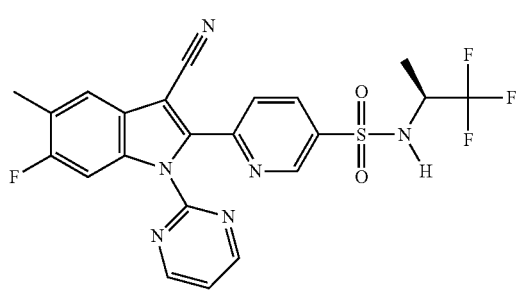
902 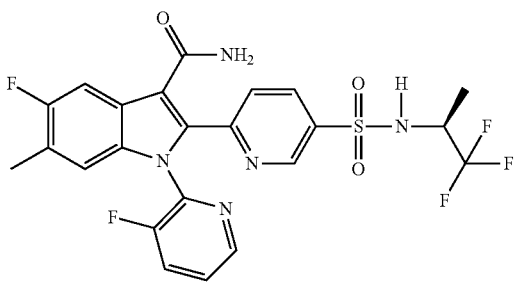
903 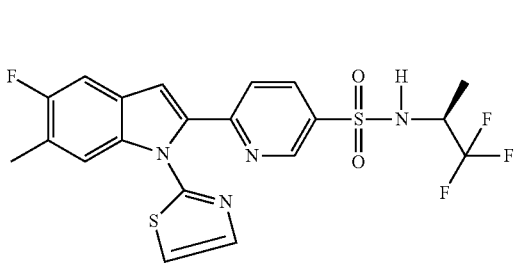
904 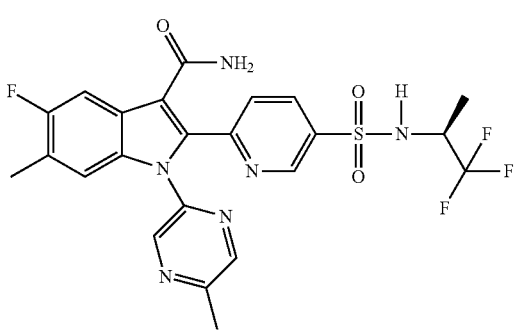
905 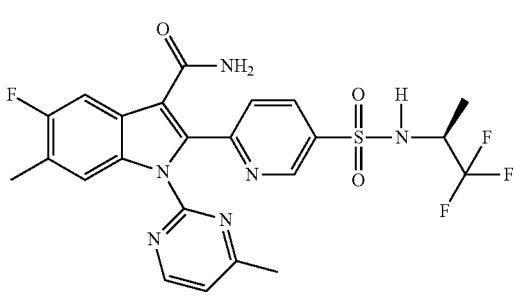
906 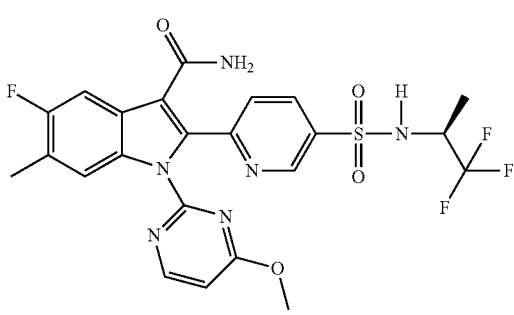

907
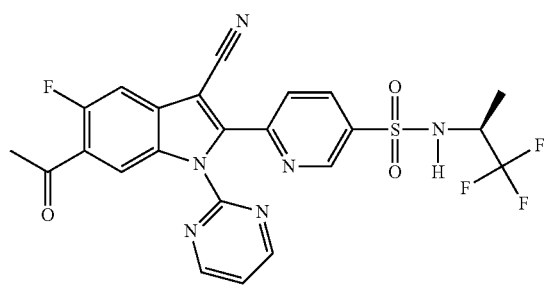
908
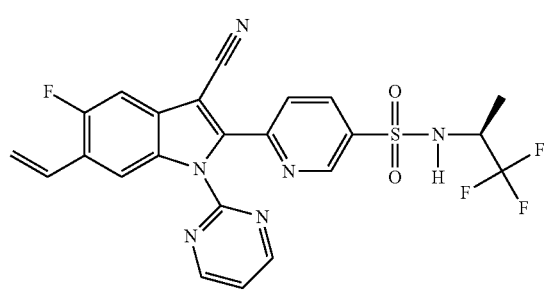
909
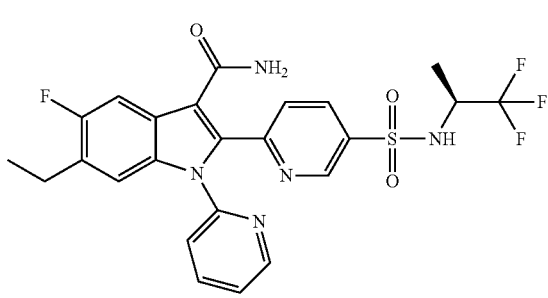
910
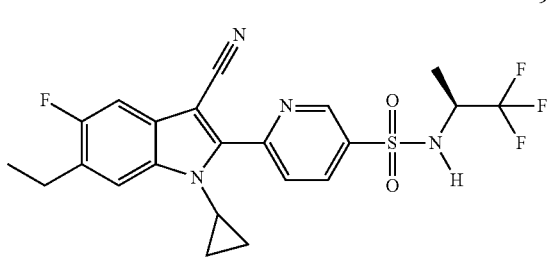
911
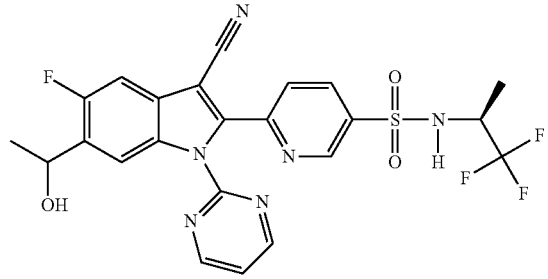
912
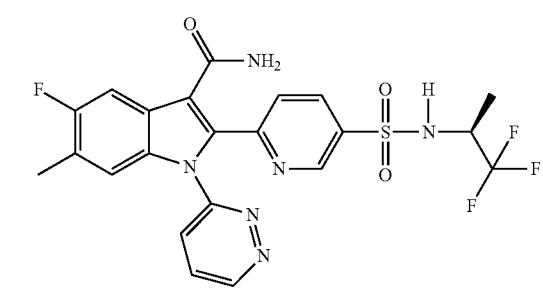
913
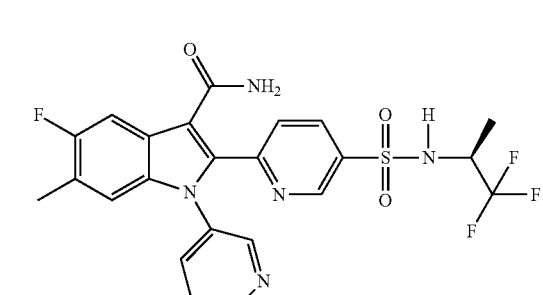
914
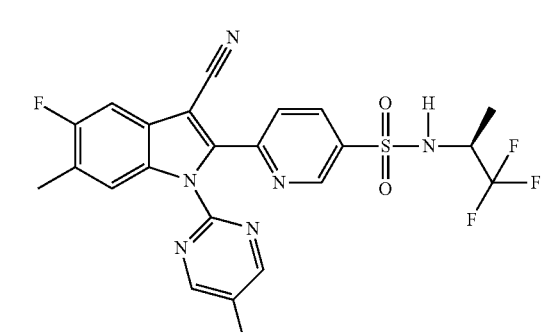
915
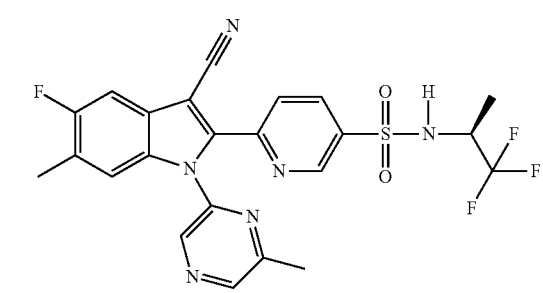
916
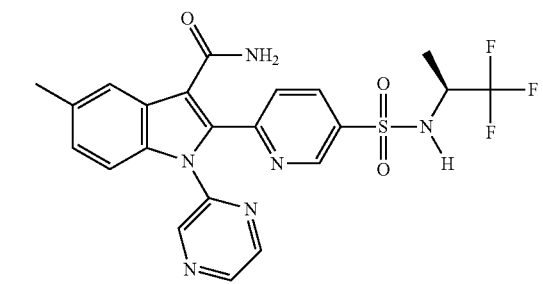

917
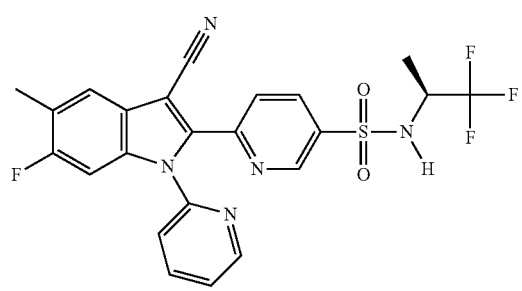
918
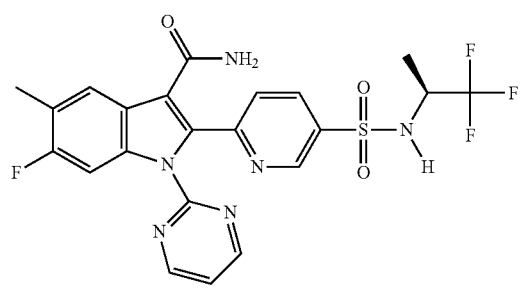
919
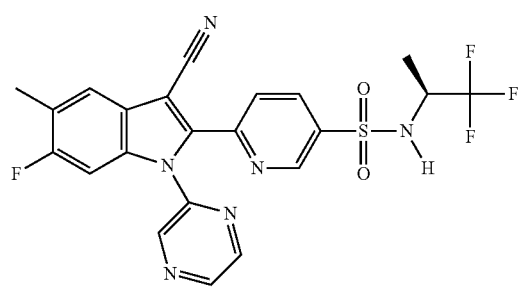
920
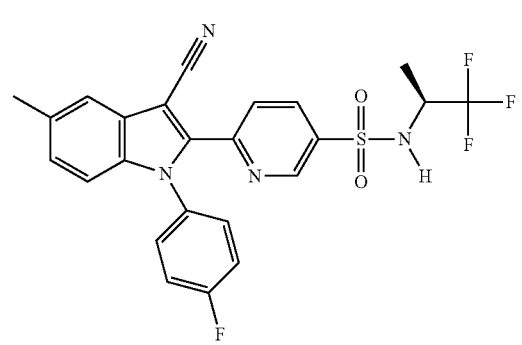
921
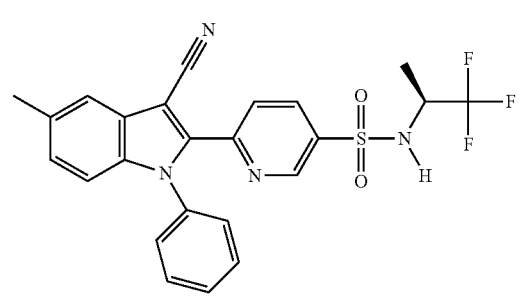
922
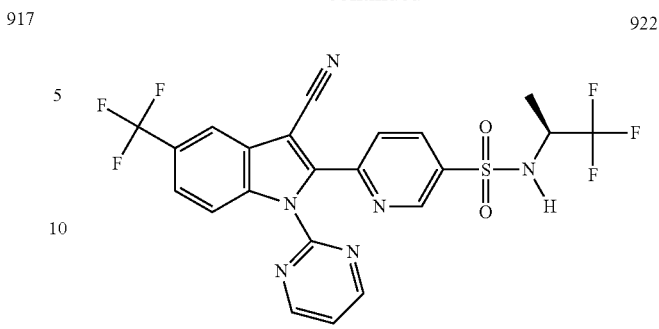
923
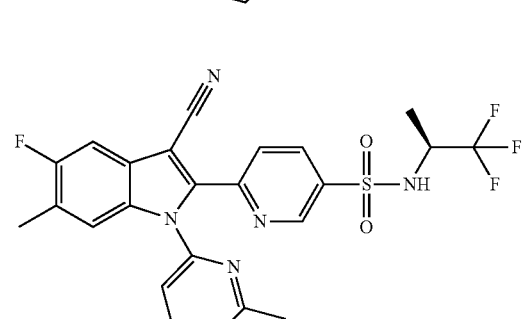
924
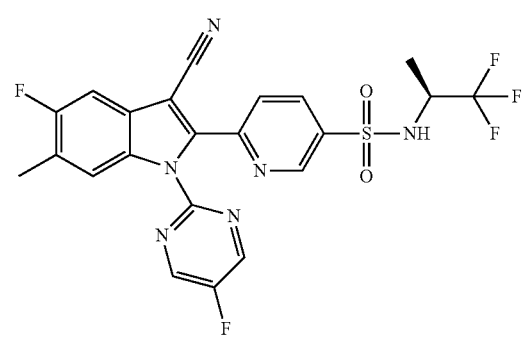
925
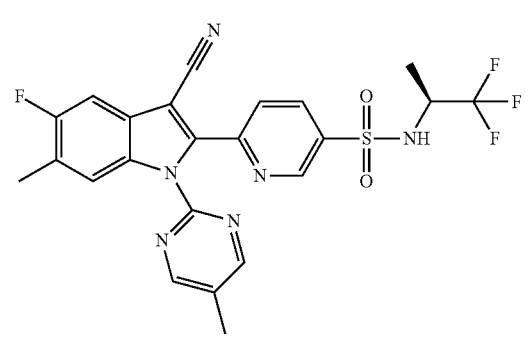
926
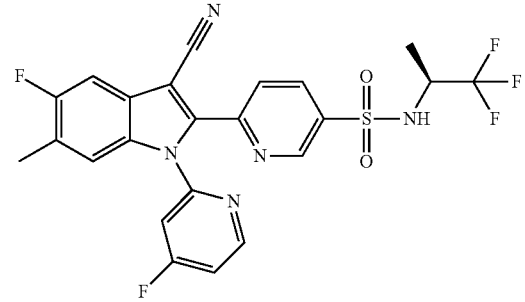

183
-continued
927
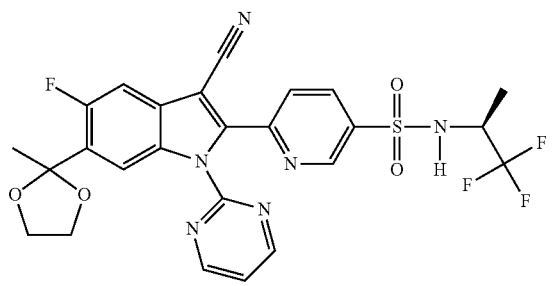
928
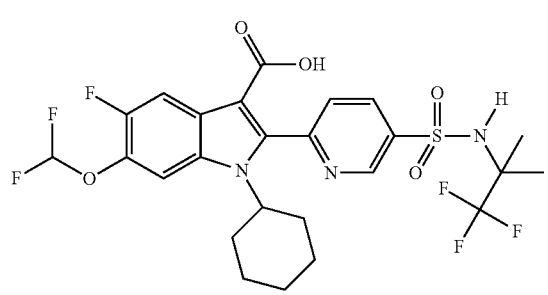
929
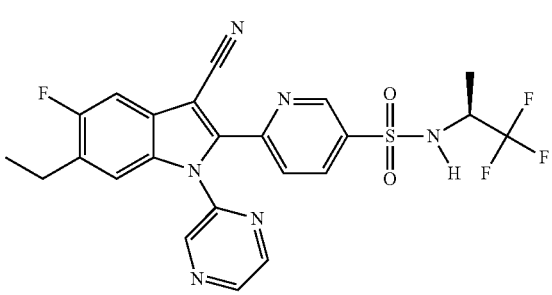
930
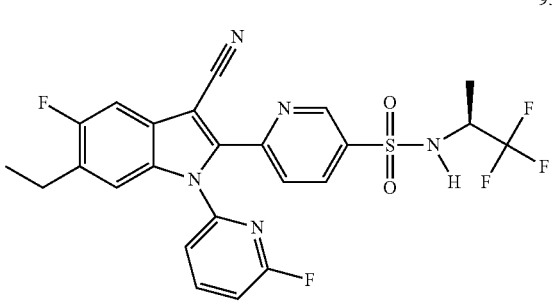
931
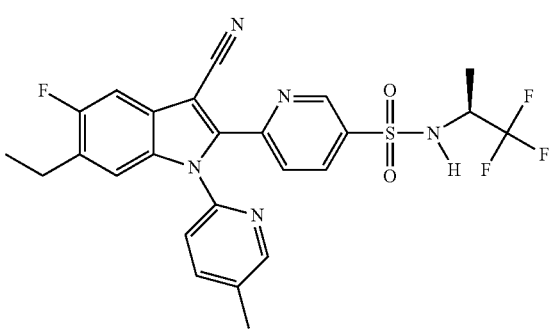
184
-continued
932
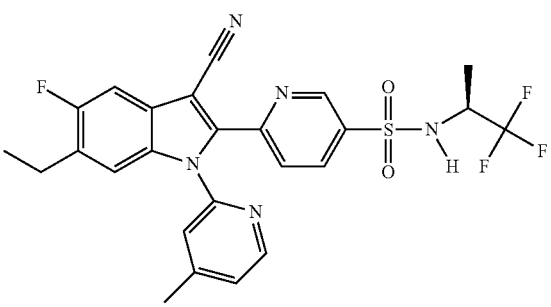
933
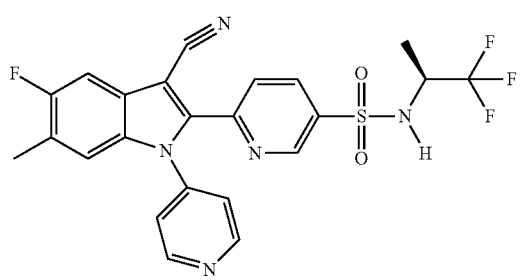
934
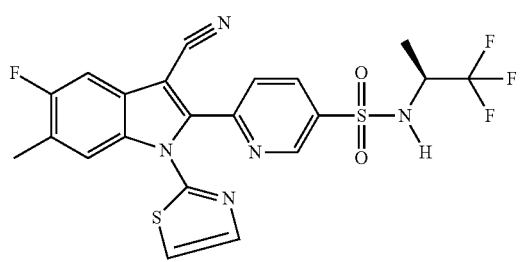
935
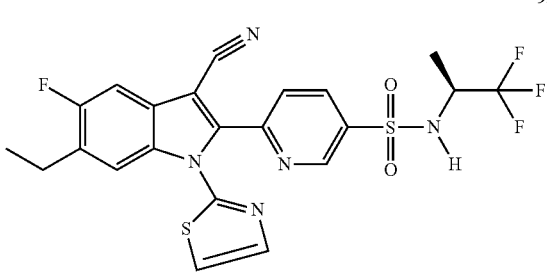
936
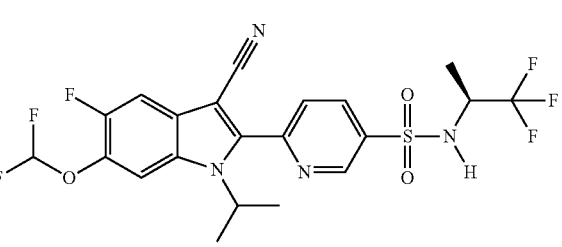

937
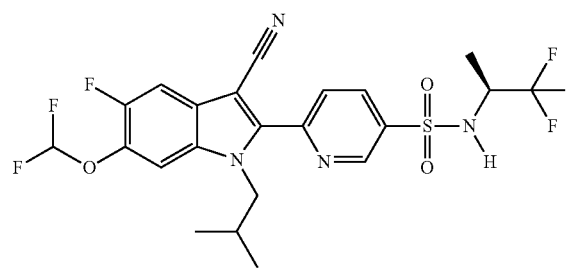
938
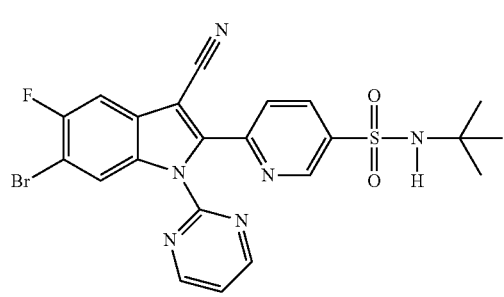
939
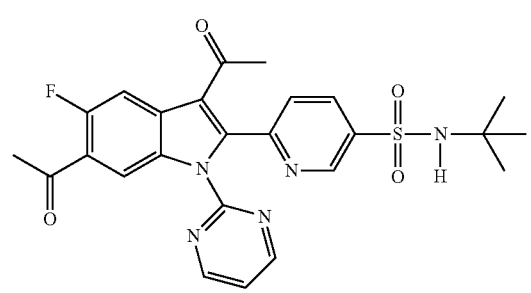
940
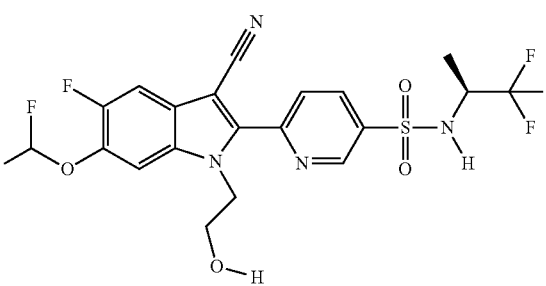
941
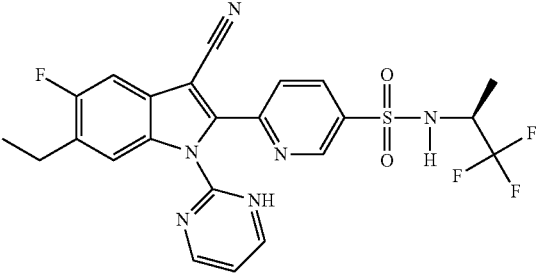
942
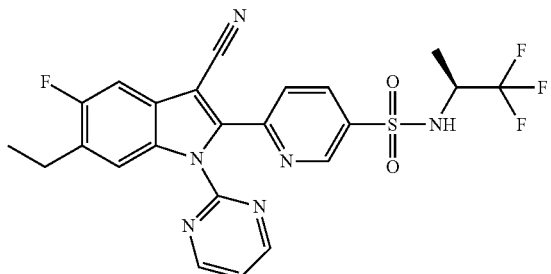
943
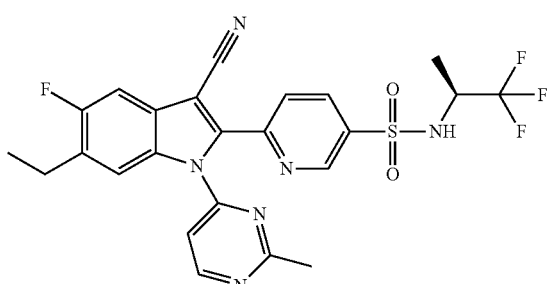
944
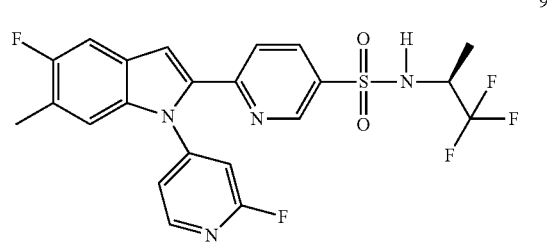
945
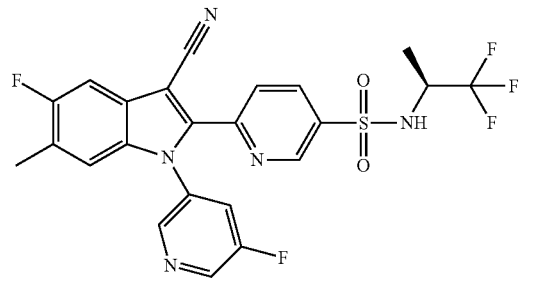
946
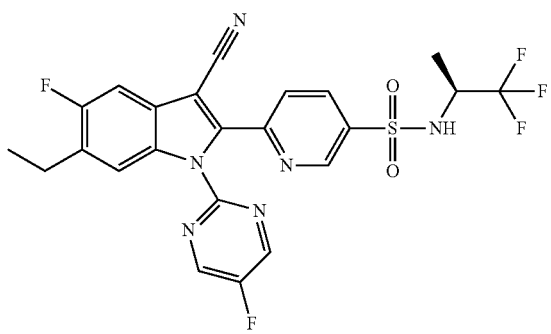

-continued
947
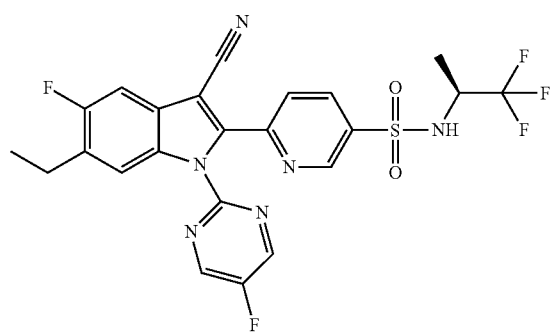
948
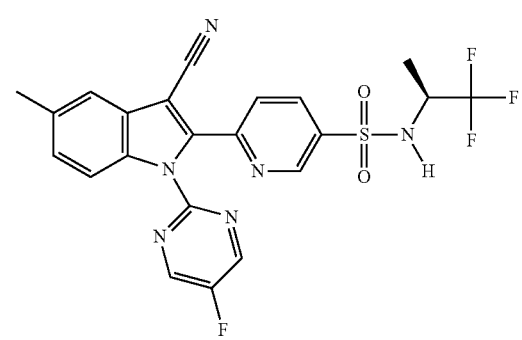
949
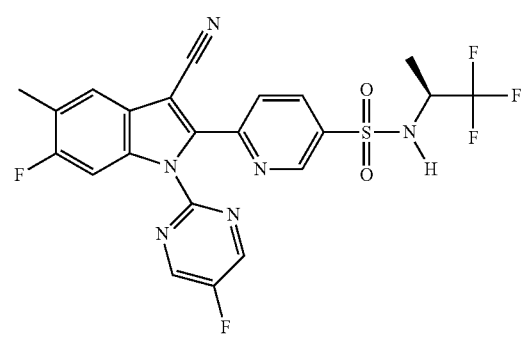
950
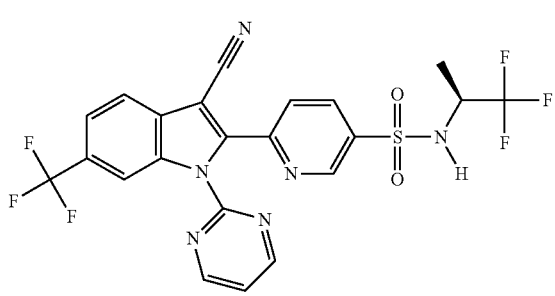
951
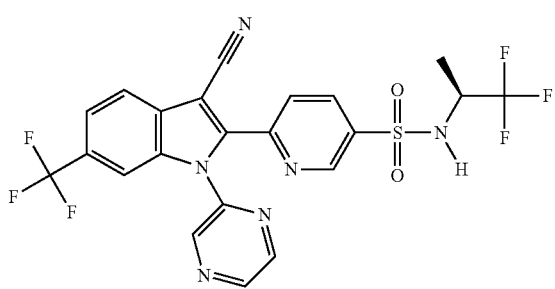
-continued
952
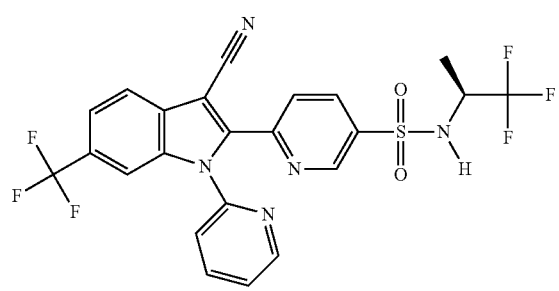
953
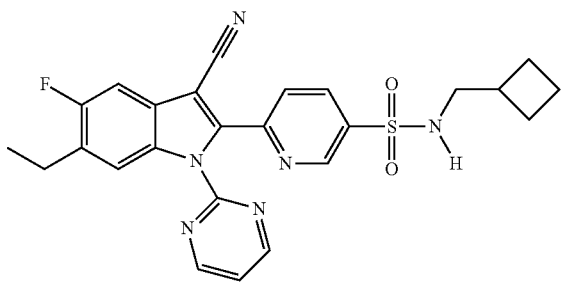
954
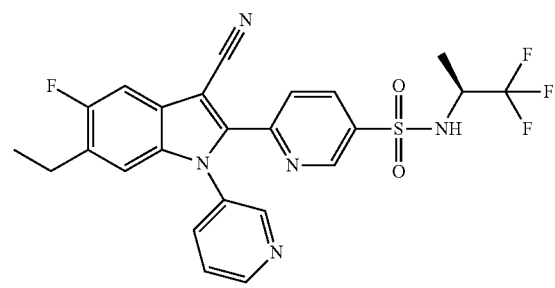
955
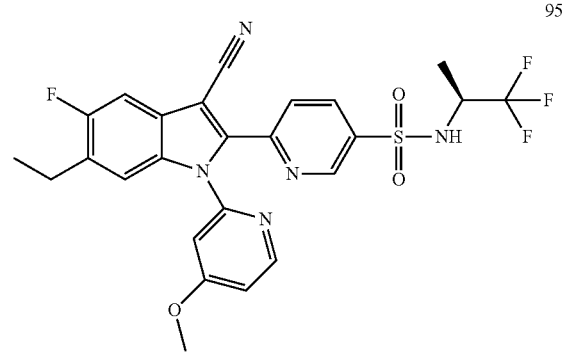
956
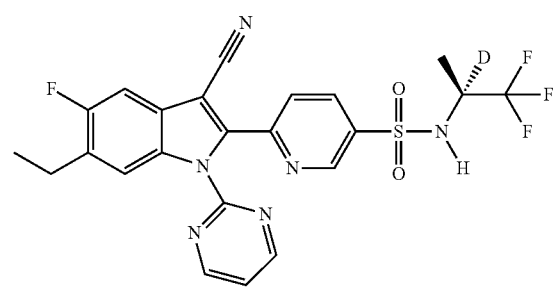

| 957 | 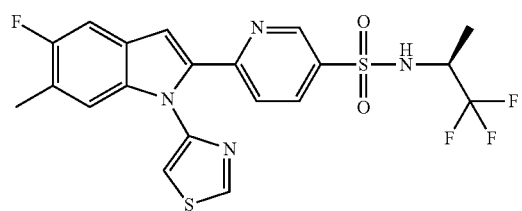 | 963 | 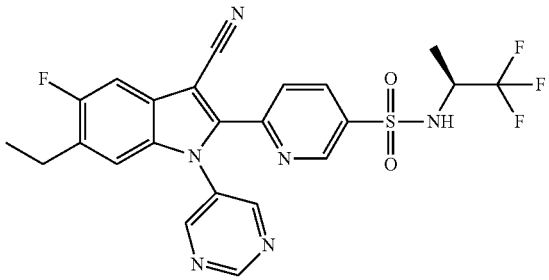 |
| 958 | 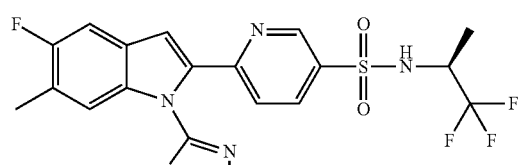 | 964 | 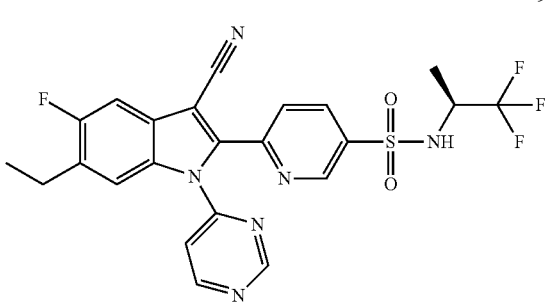 |
| 959 | 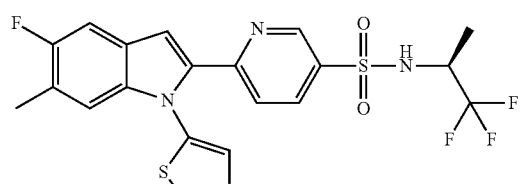 | 965 | 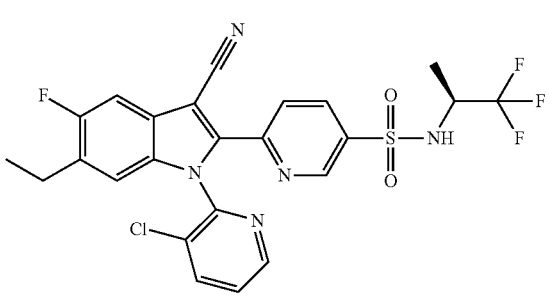 |
| 960 | 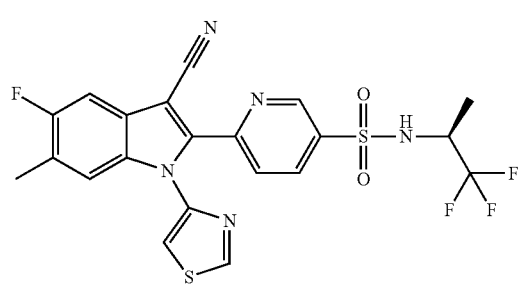 | 966 | 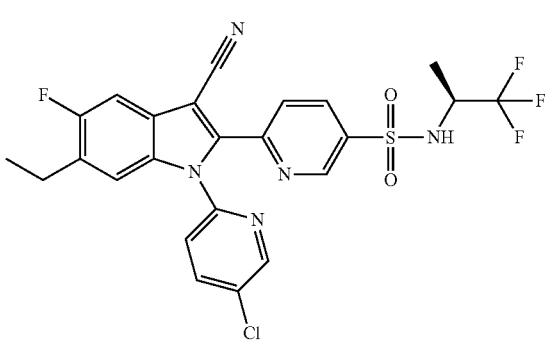 |
| 961 | 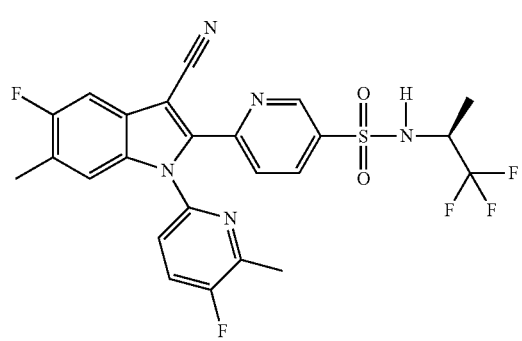 | 967 | 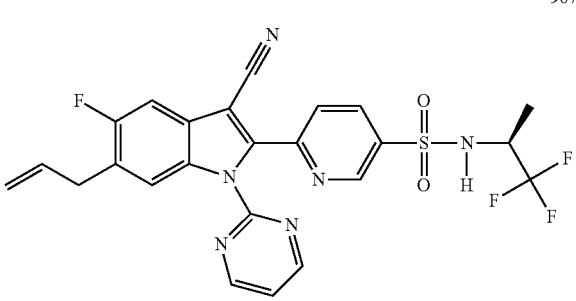 |
| 962 | 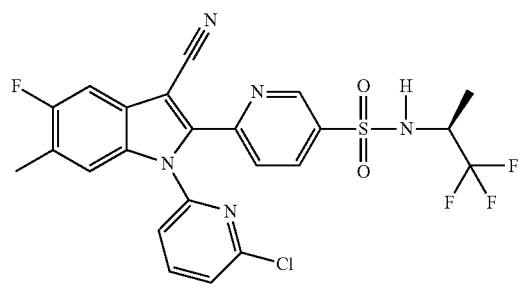 | | |

968
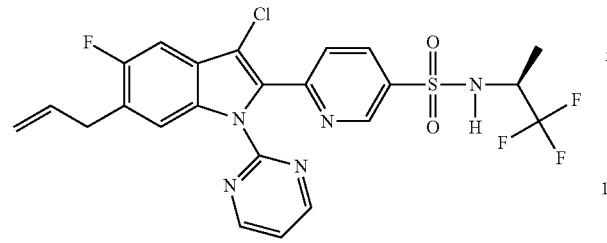
969
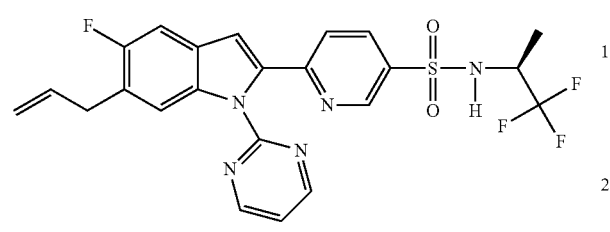
970
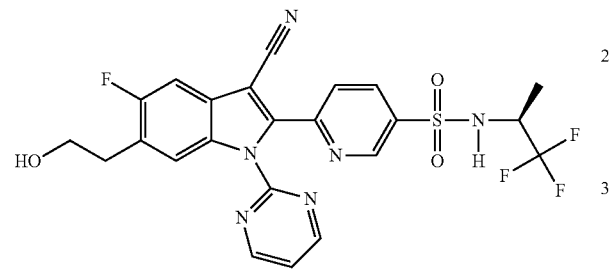
971
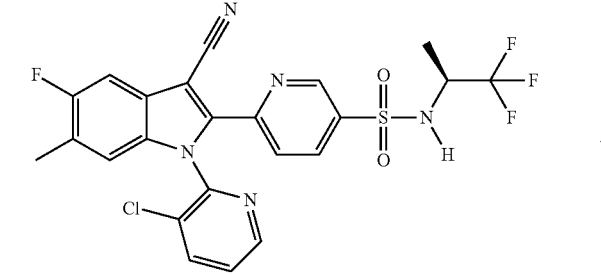
972
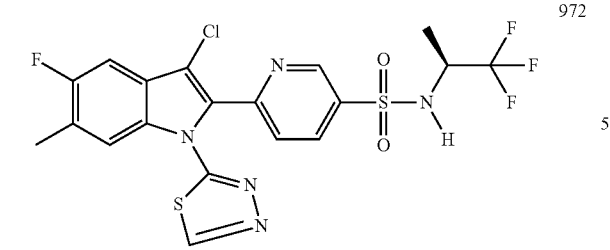
973
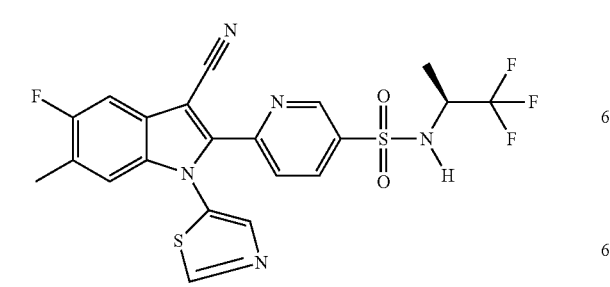
974
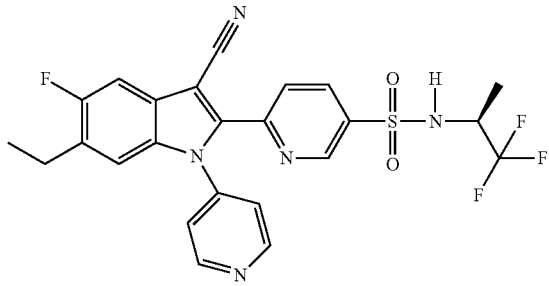
975
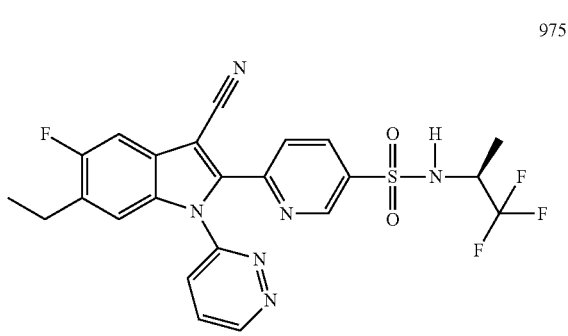
976
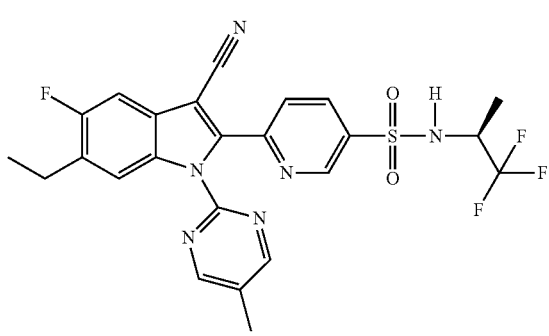
977
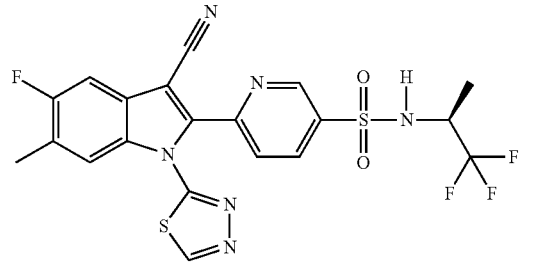
978
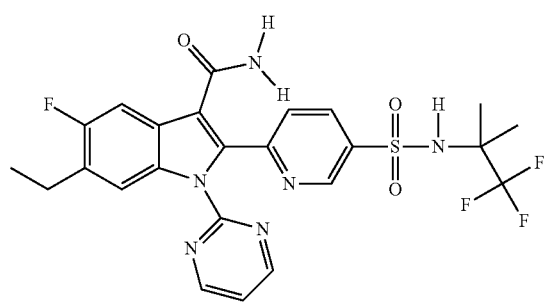

979 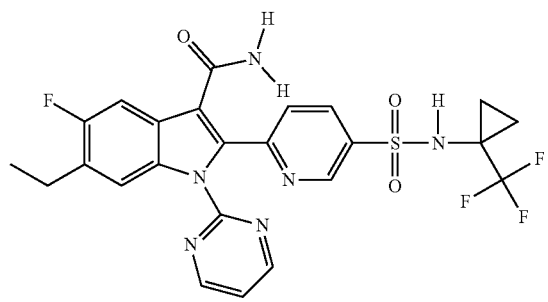
980 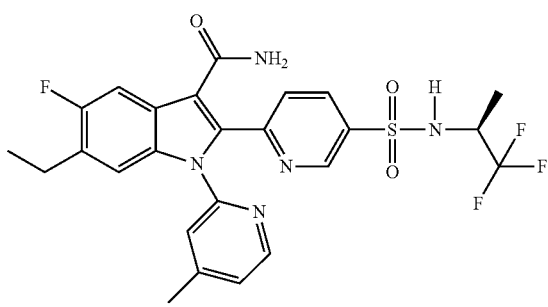
981 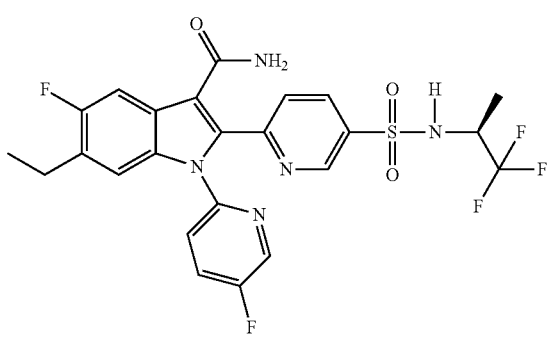
982 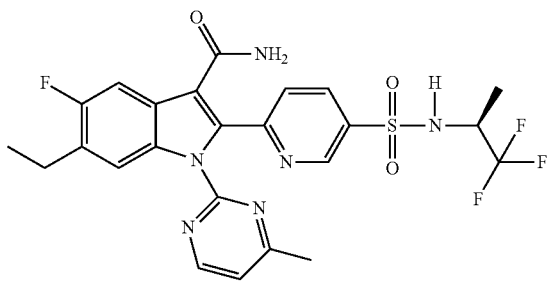
983 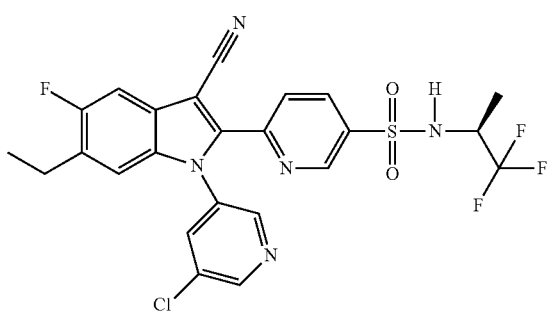
984 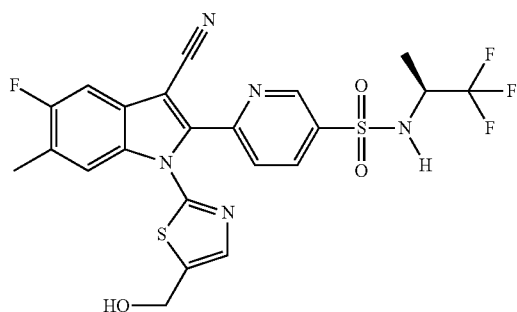
985 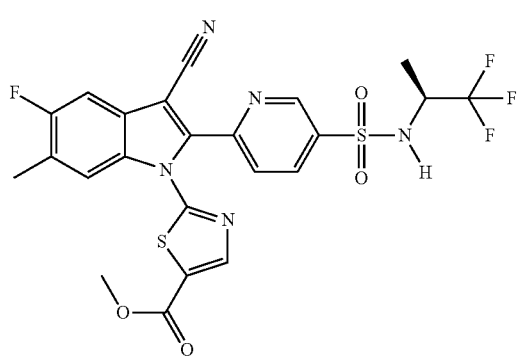
986 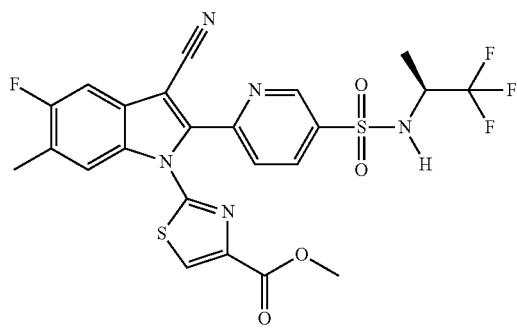
987 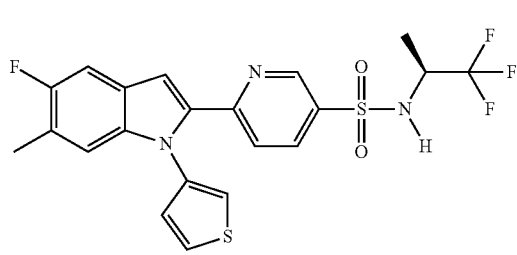
988 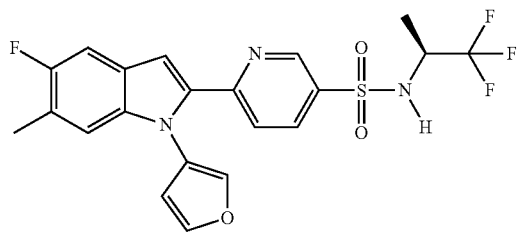

989 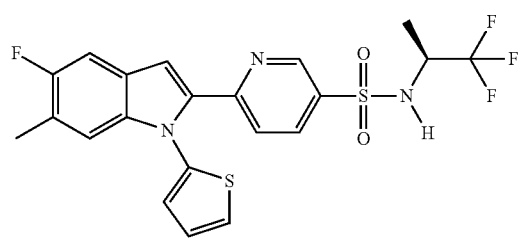
990 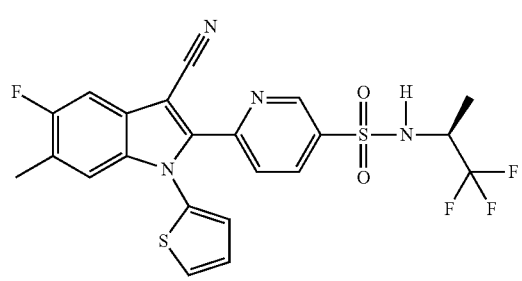
991 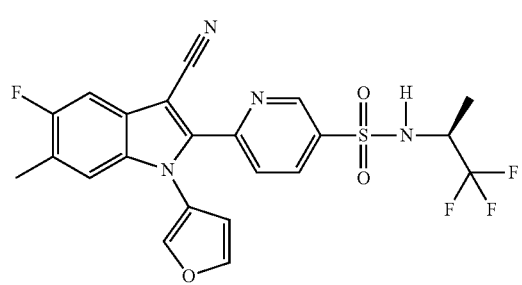
992 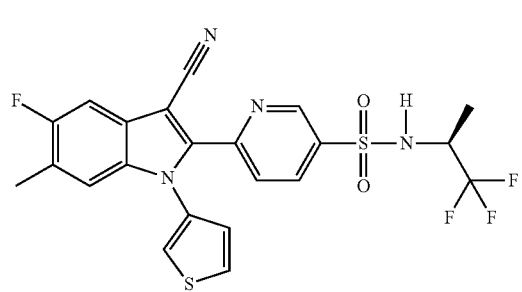
993 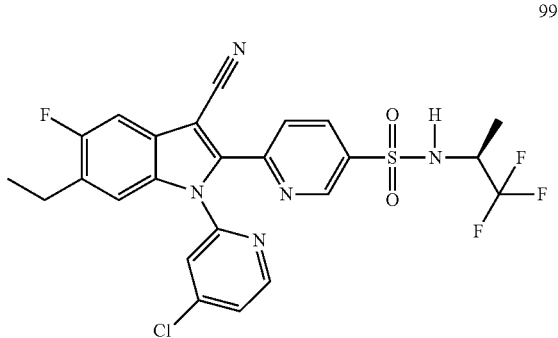
994 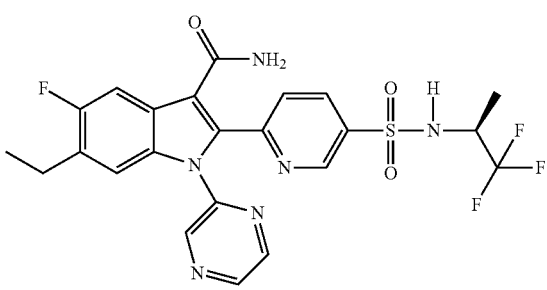
995 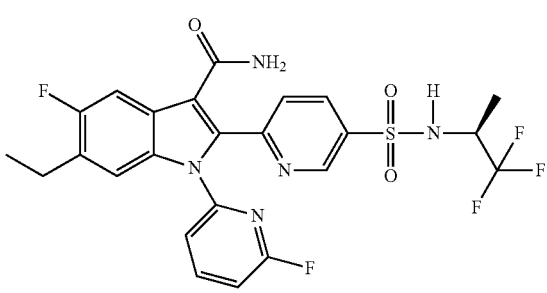
996 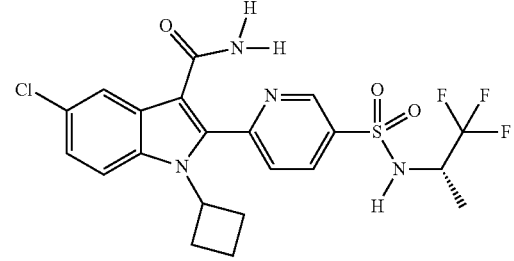
997 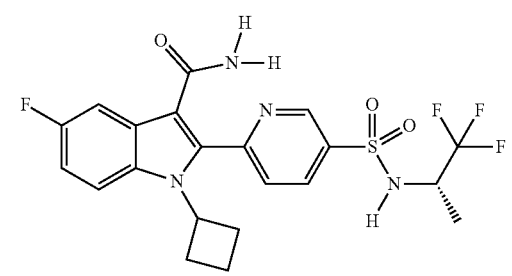
998 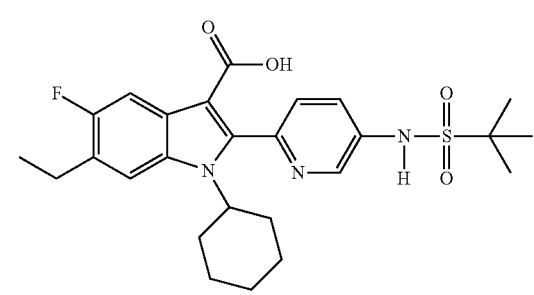

197
-continued
999
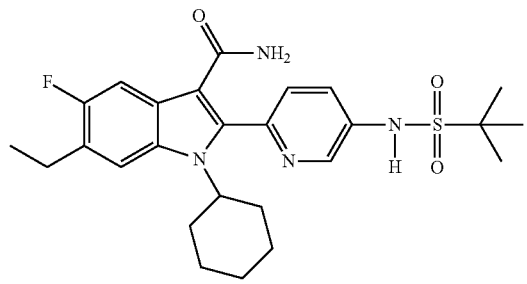
1000
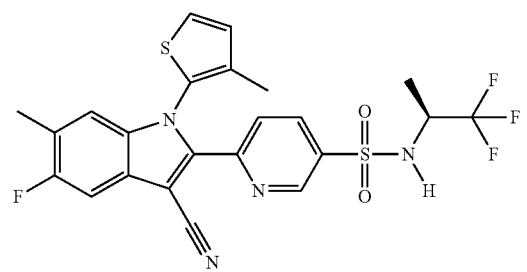
1001
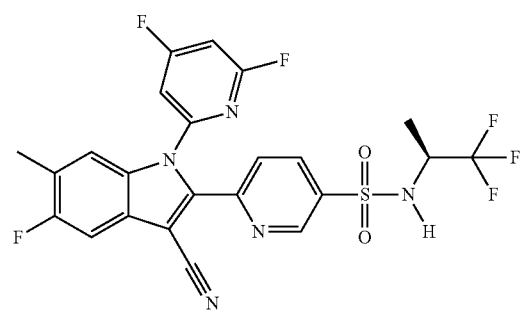
1002
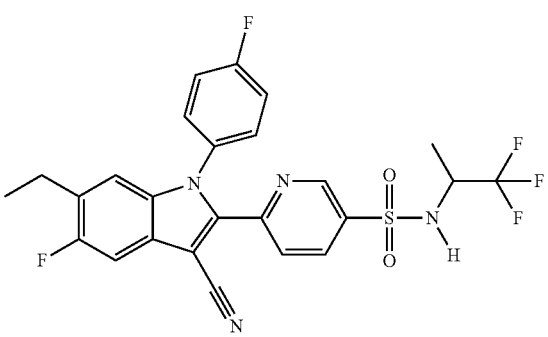
1003
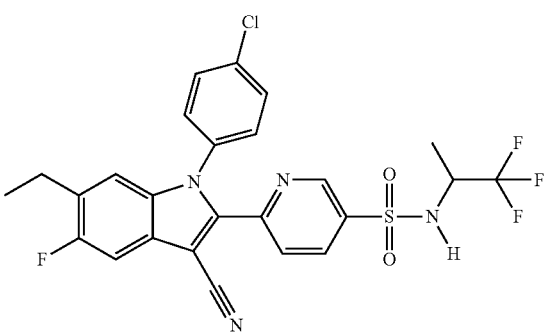
198
-continued
1004
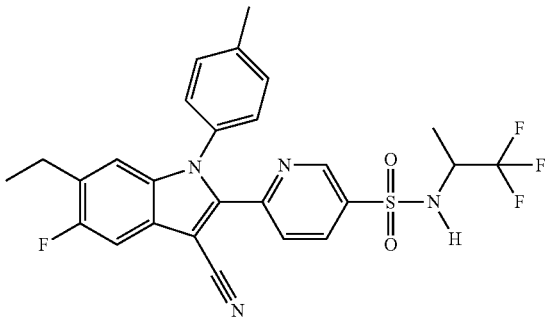
1005
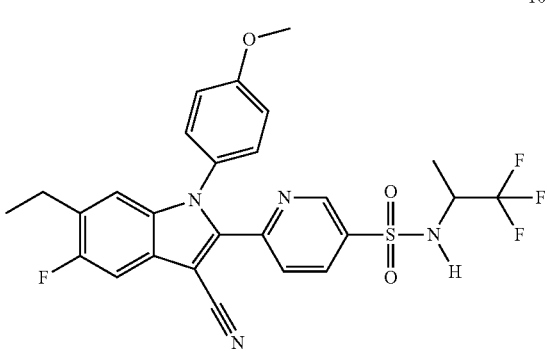
1006
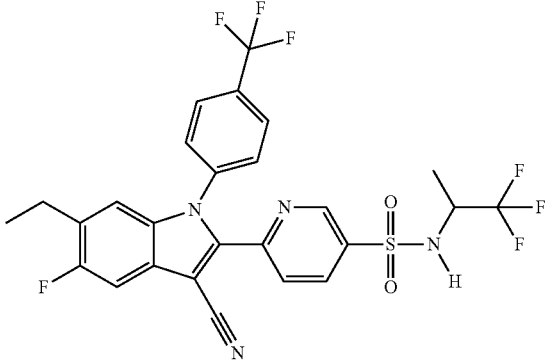
1007
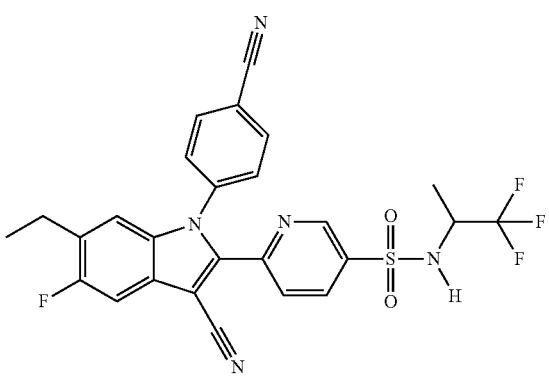

1008 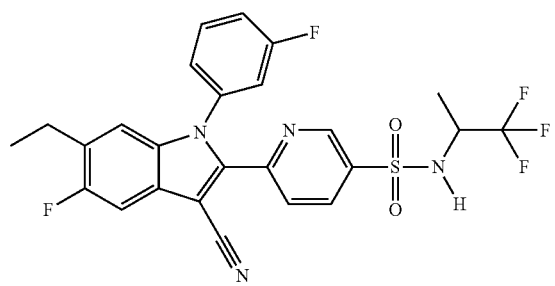
1013 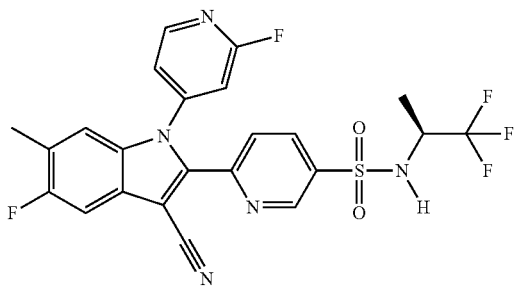
1009
1014 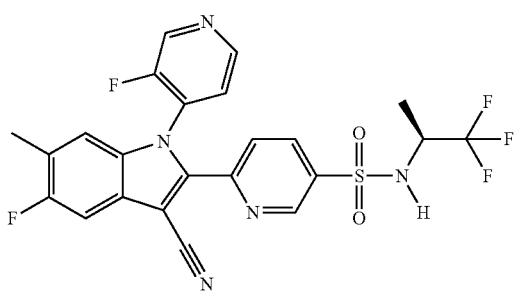
1010
1015 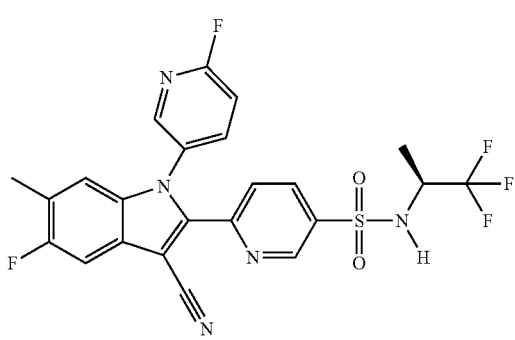
1011
1016 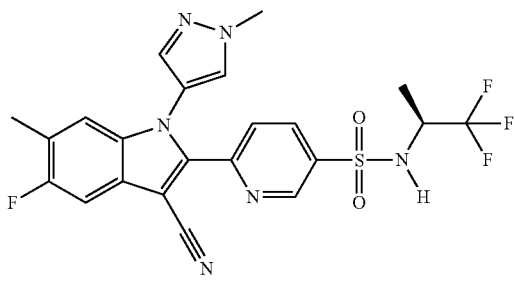
1012
1017 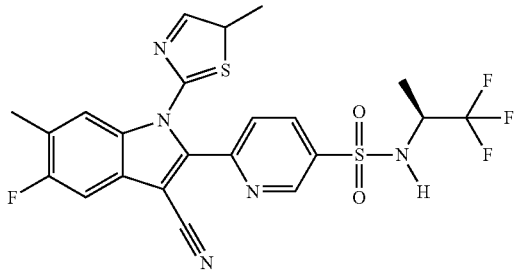

1018 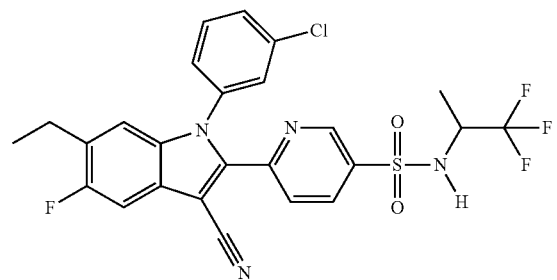
1019 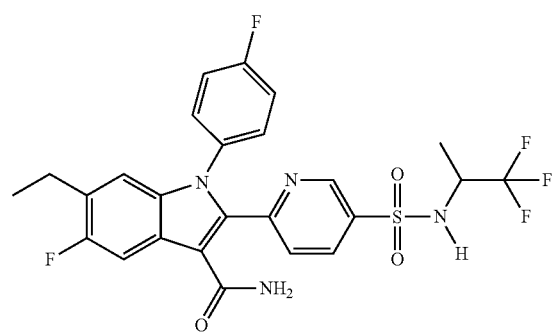
1020 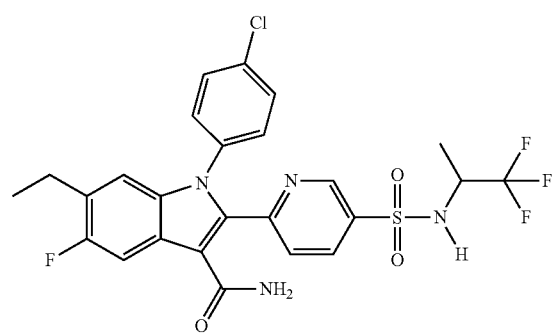
1021 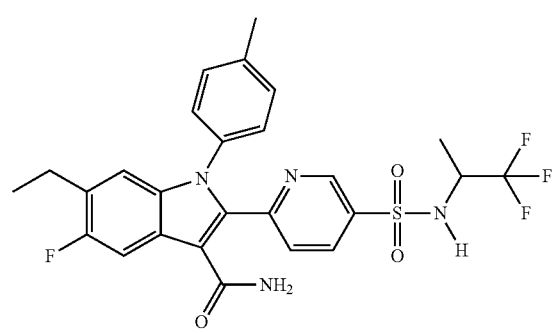
1022 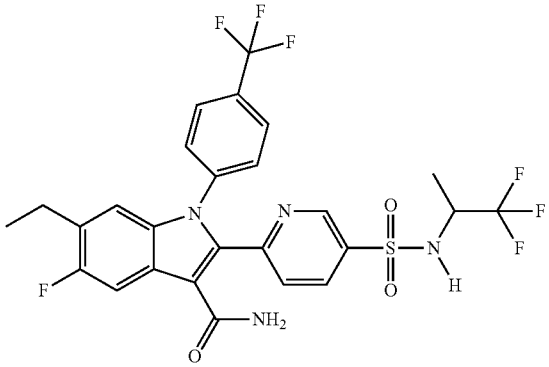
1023 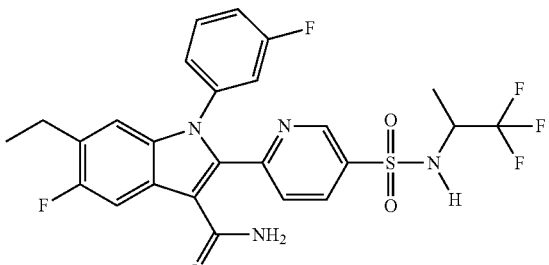
1024 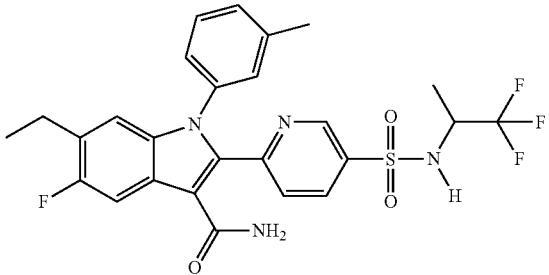
1025 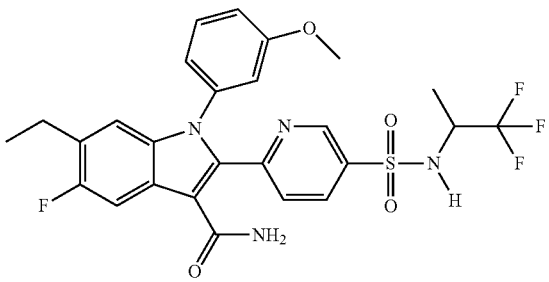
1026 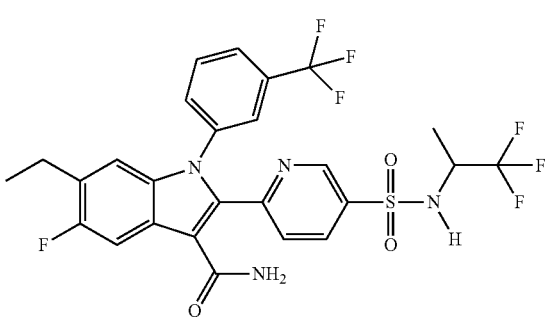

1027
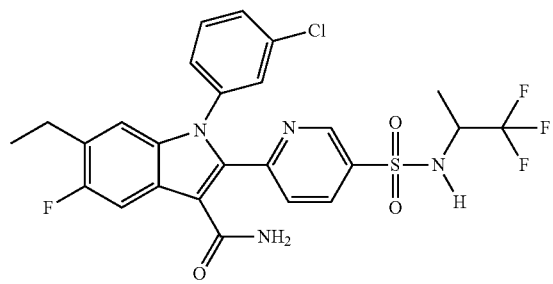
1028
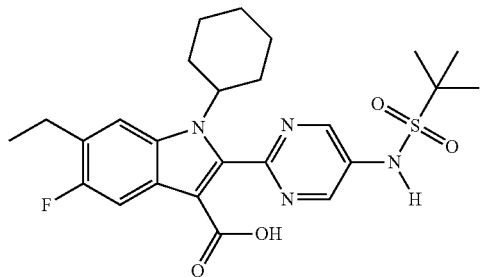
1029
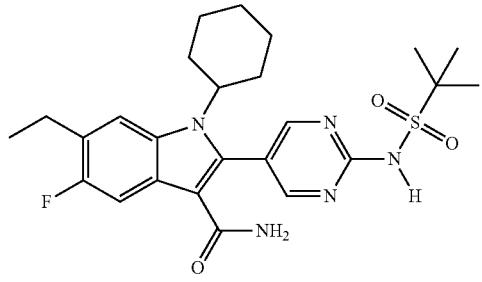
1030
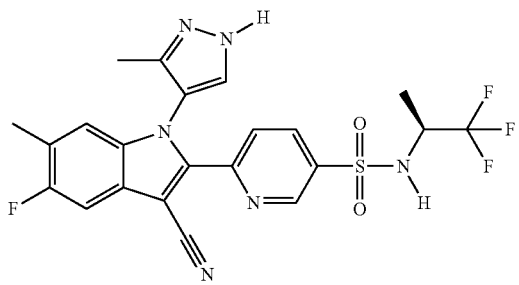
1031
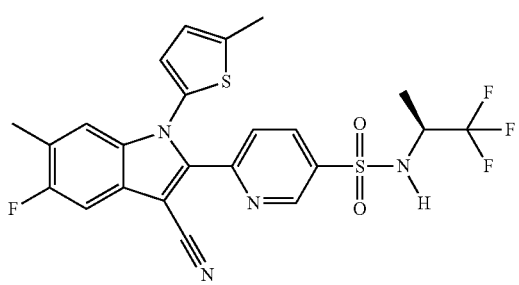
1032
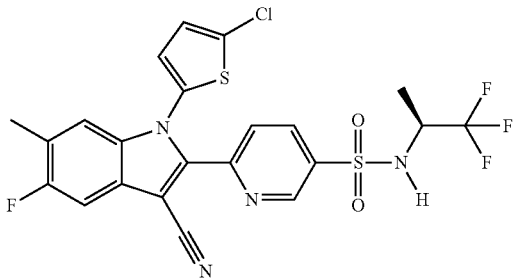
1033
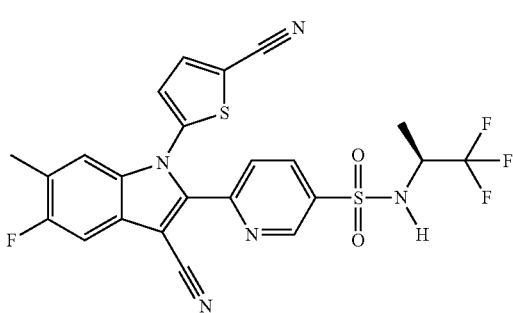
1034
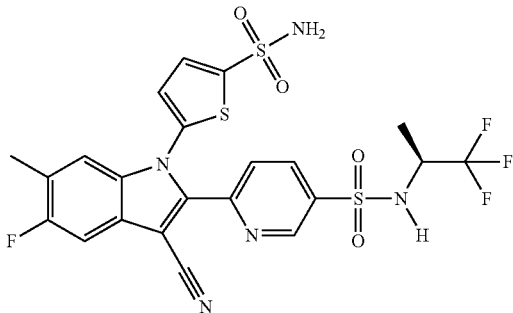
1035
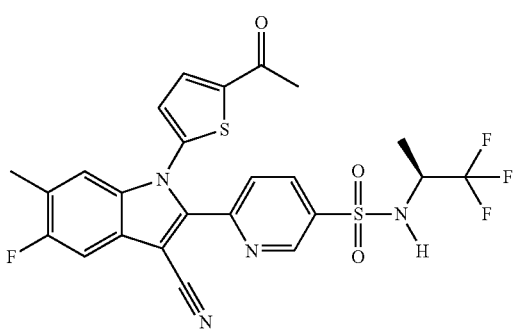
1036
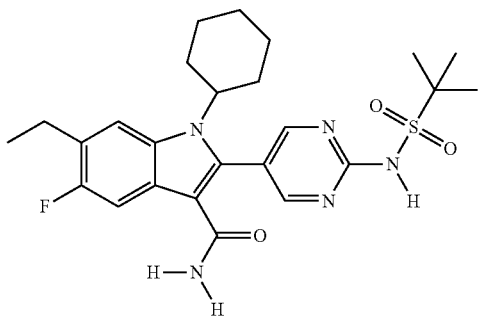

1037
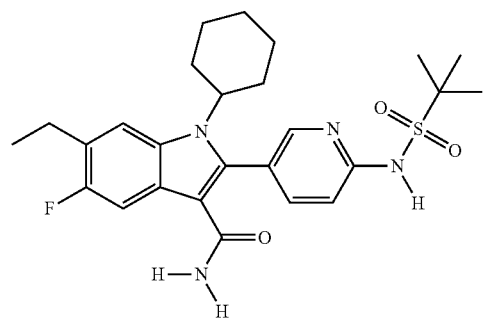
1038
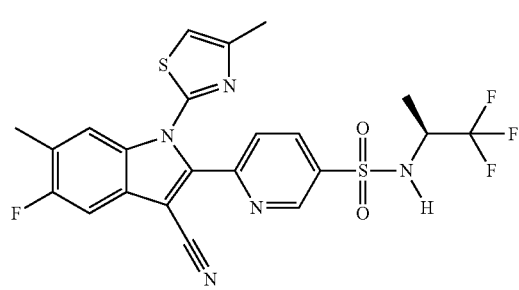
1039
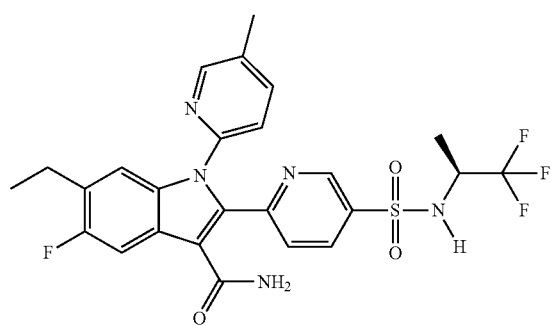
1040
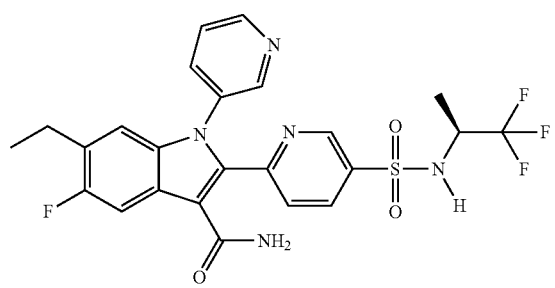
1041
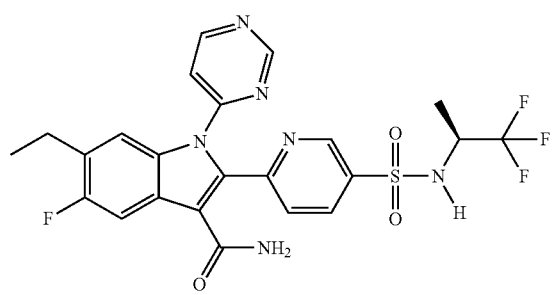
1042
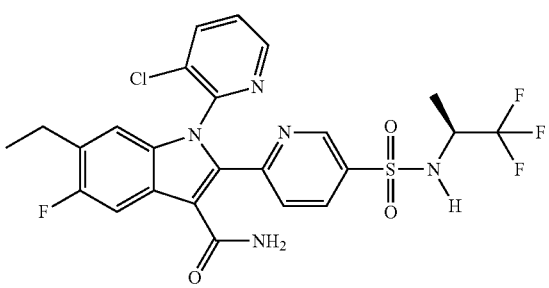
1043
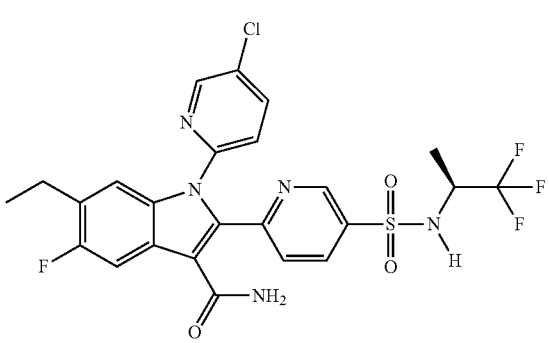
1044
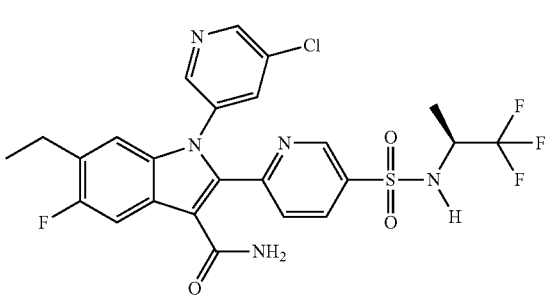
1045
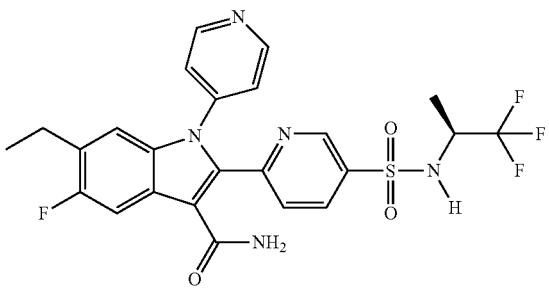
1046
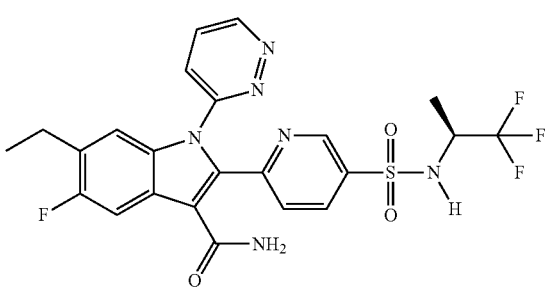

| 1047 | 1058 |
|---|---|
| 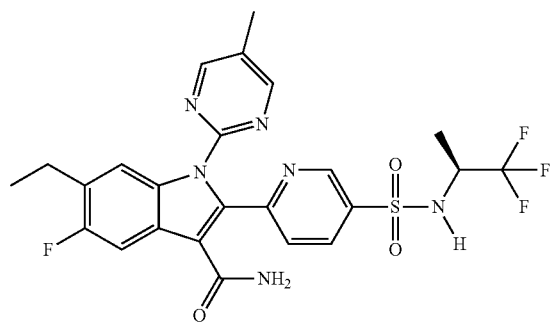 | 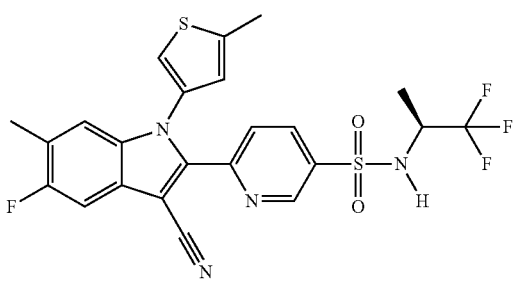 |
| 1048 | 1059 |
| 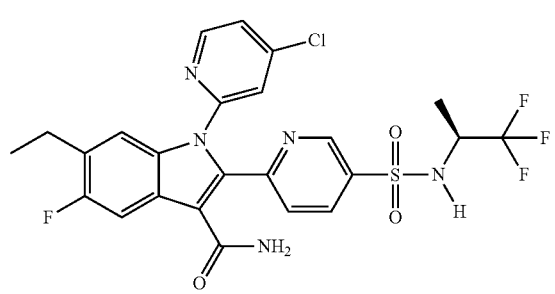 | 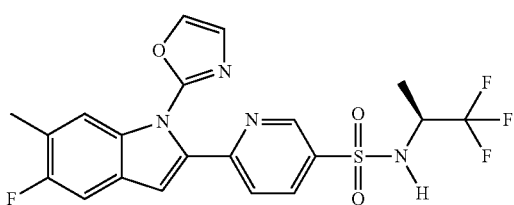 |
| 1055 | 1060 |
| 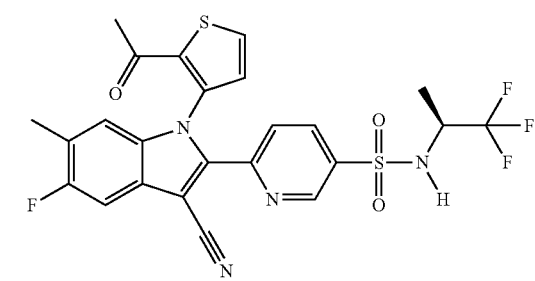 | 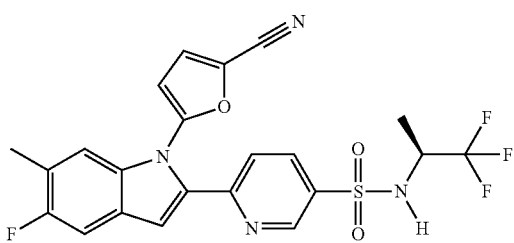 |
| 1056 | 1061 |
| 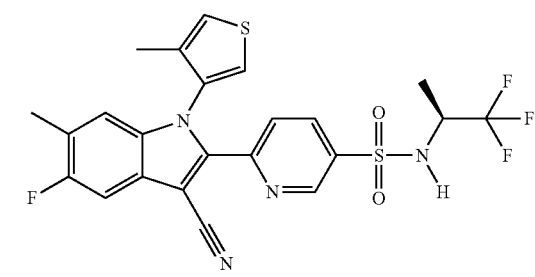 | 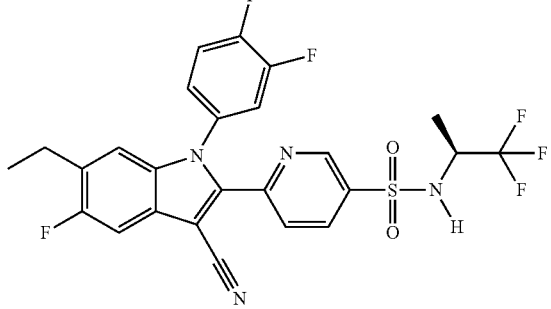 |
| 1057 | 1062 |
| 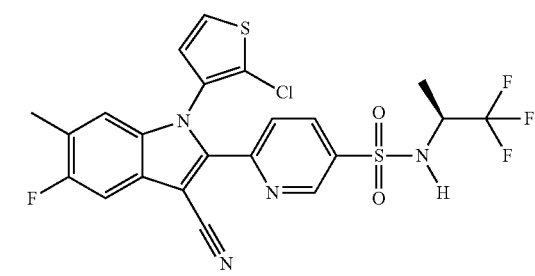 | 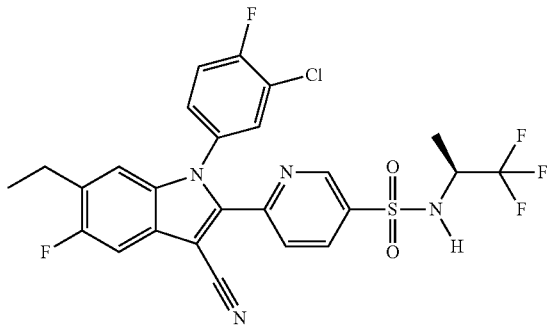 |

1063
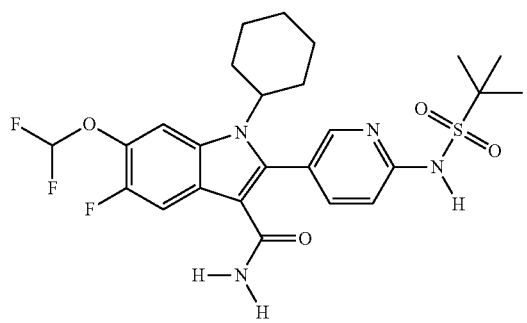
1064
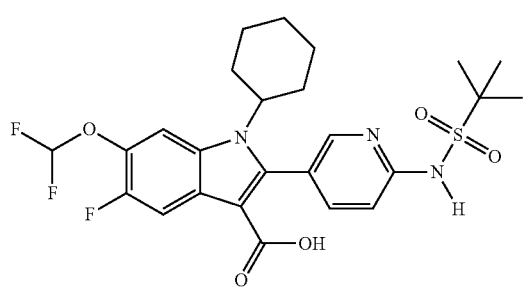
1065
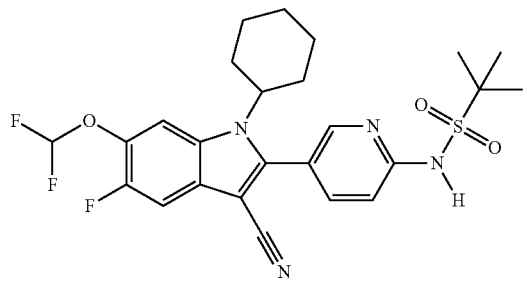
1072
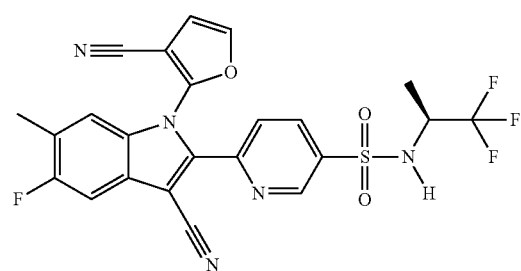
1073
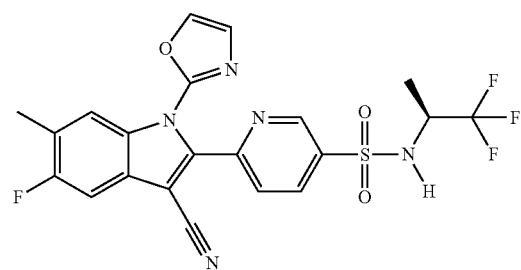
1074
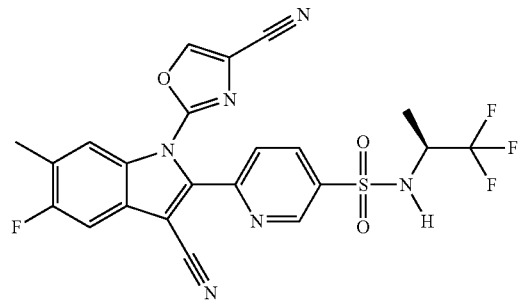
1075
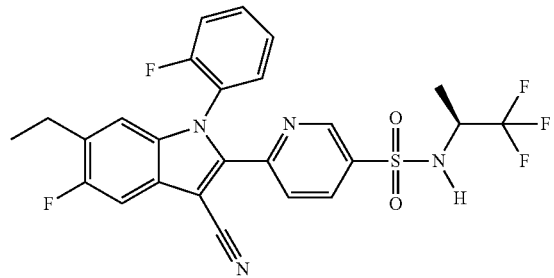
1078
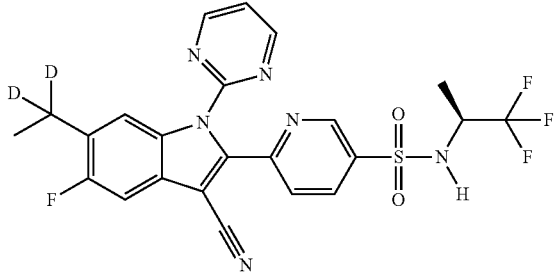
1079
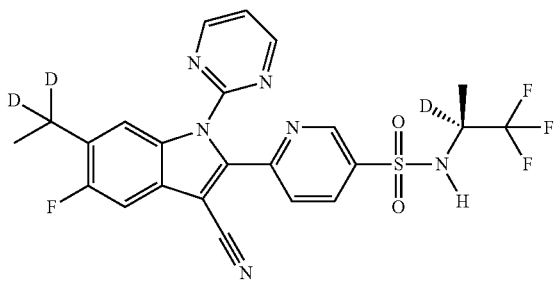
1080
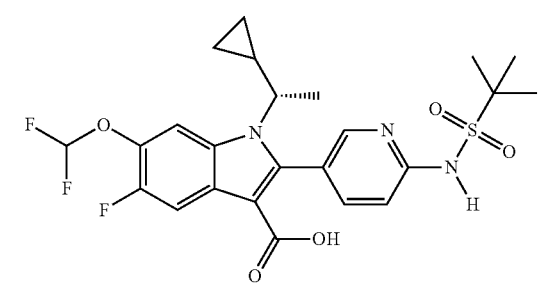

211
-continued
1081
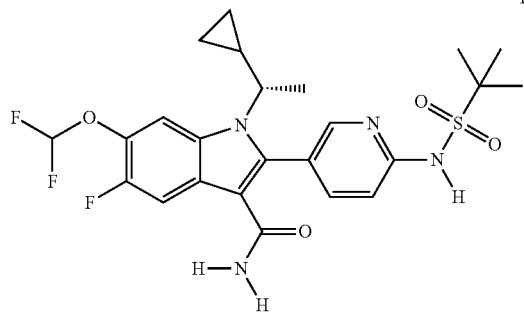
1082
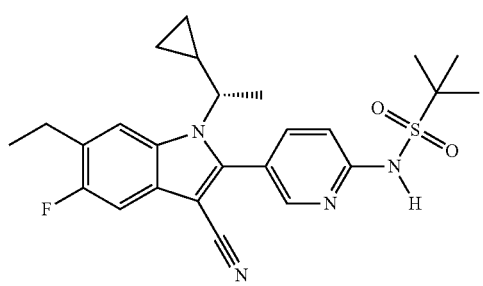
1083
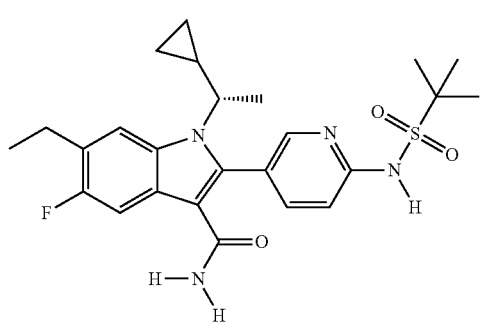
1084
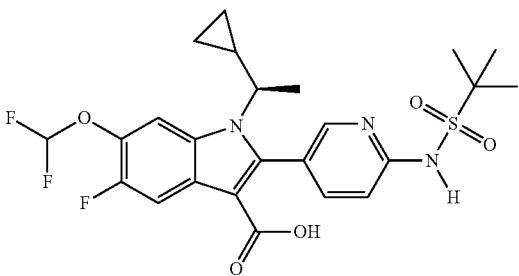
1085
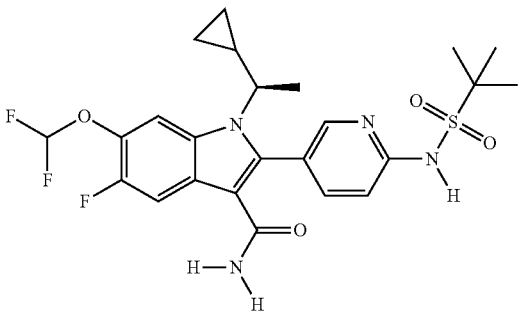
212
-continued
1086
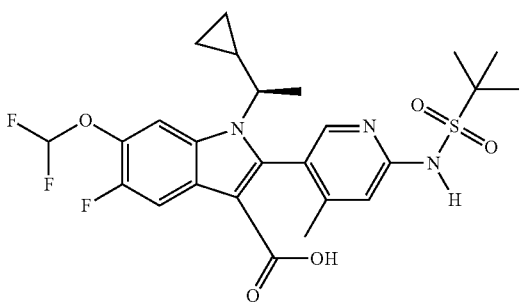
1087
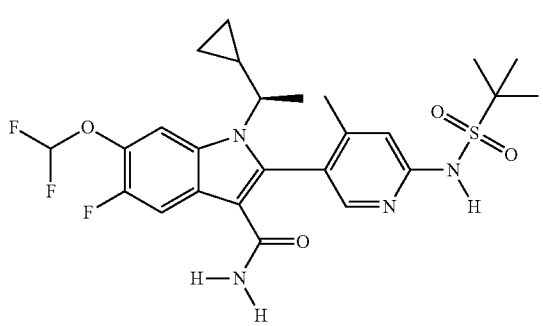
1088
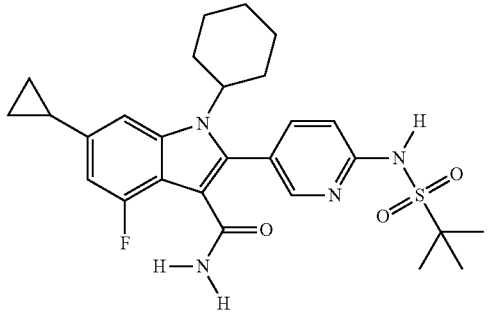
1092
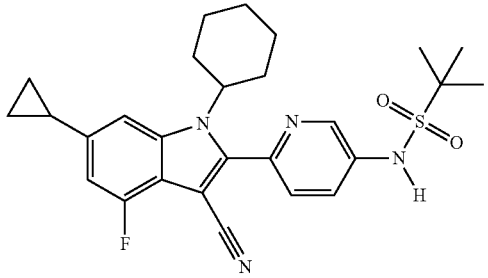
1093
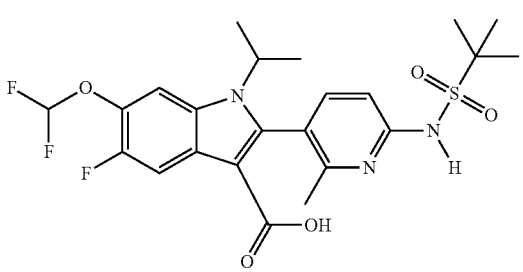

213
-continued
1094
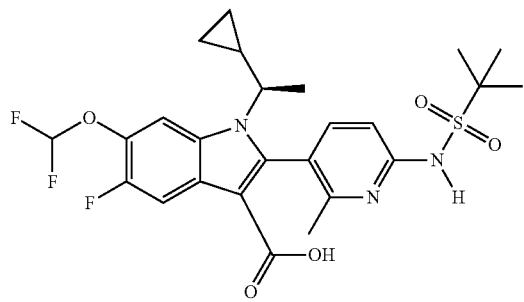
1095
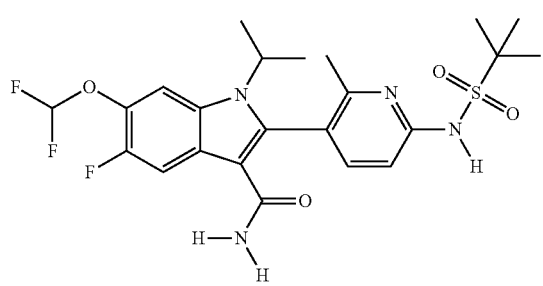
1096
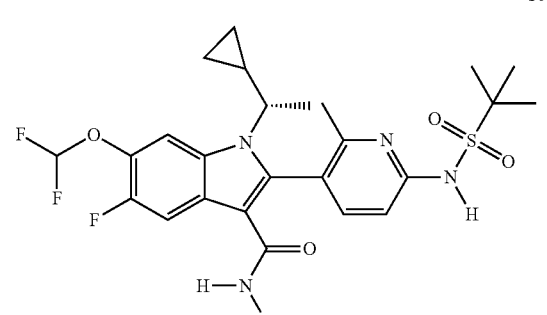
1097
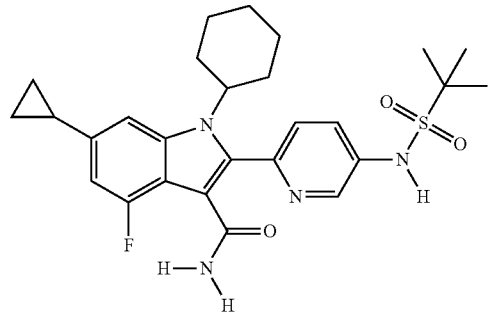
1098
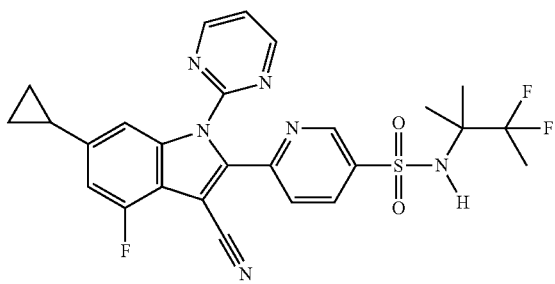
214
-continued
1099
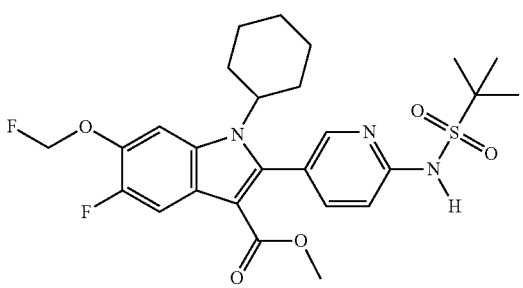
1100
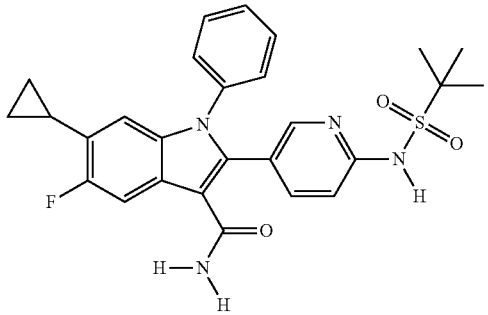
1101
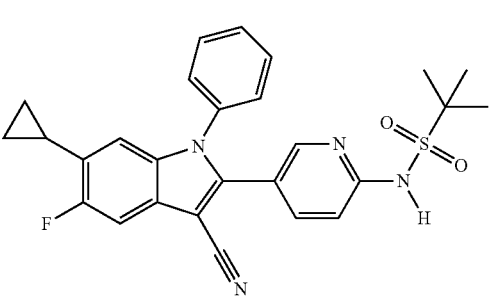
1102
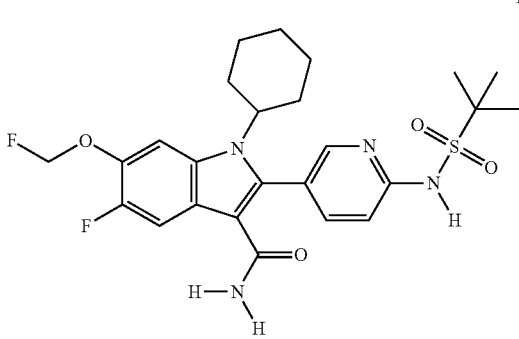
1103
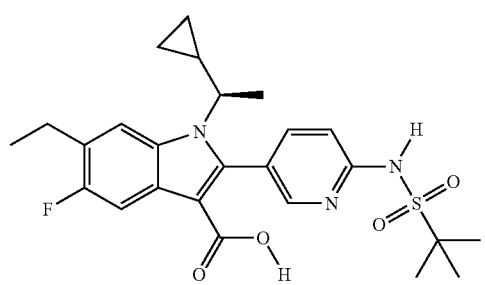

1104
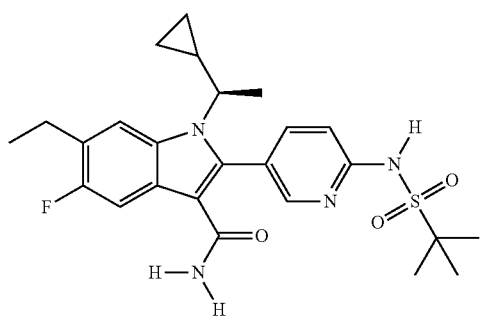
1105
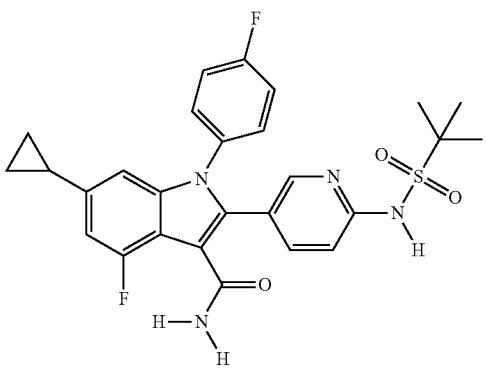
1106
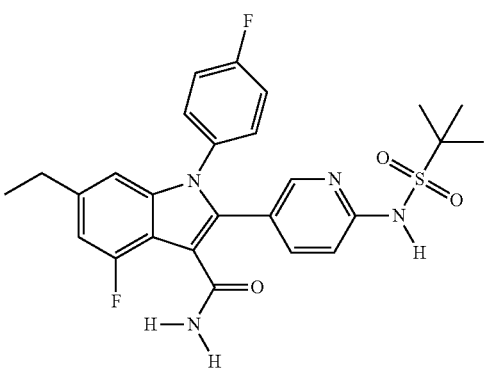
1107
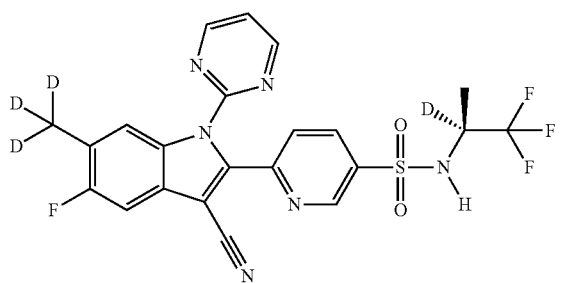
1108
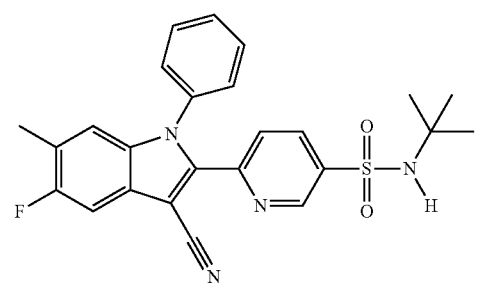
1109
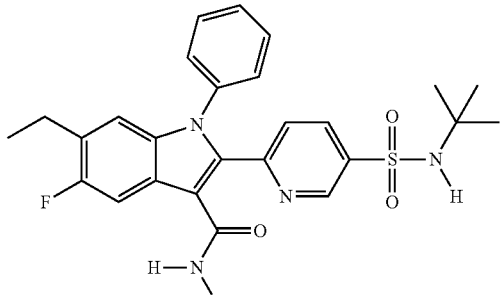
1110
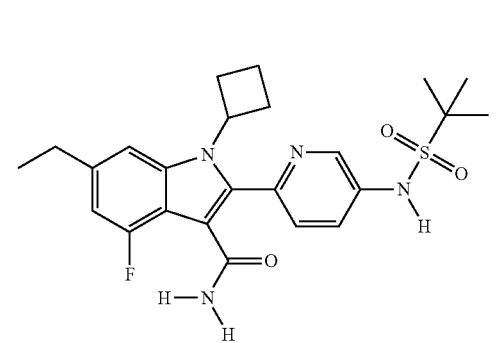
1111
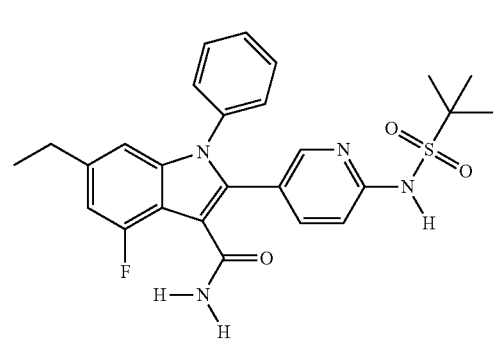
1112
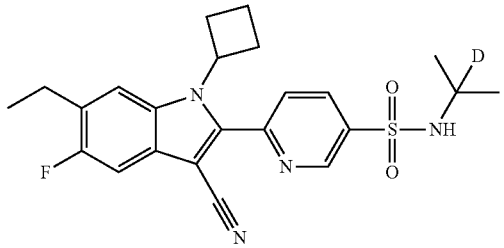
1113
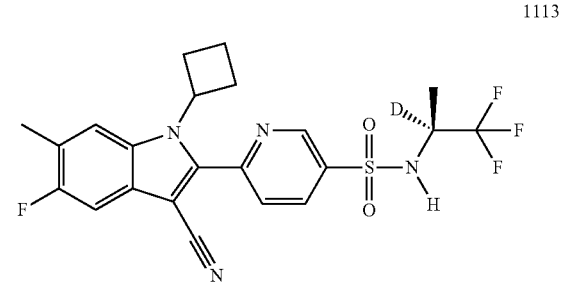

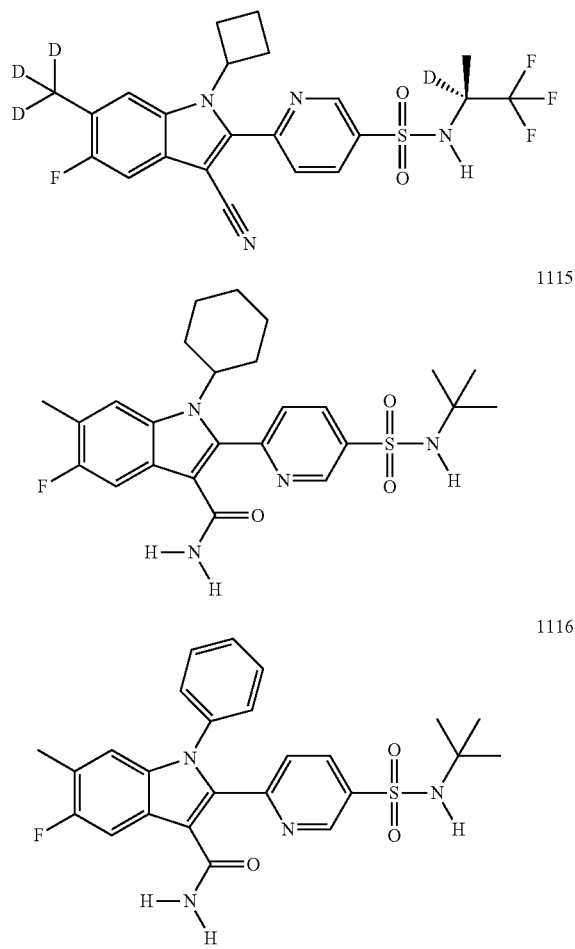

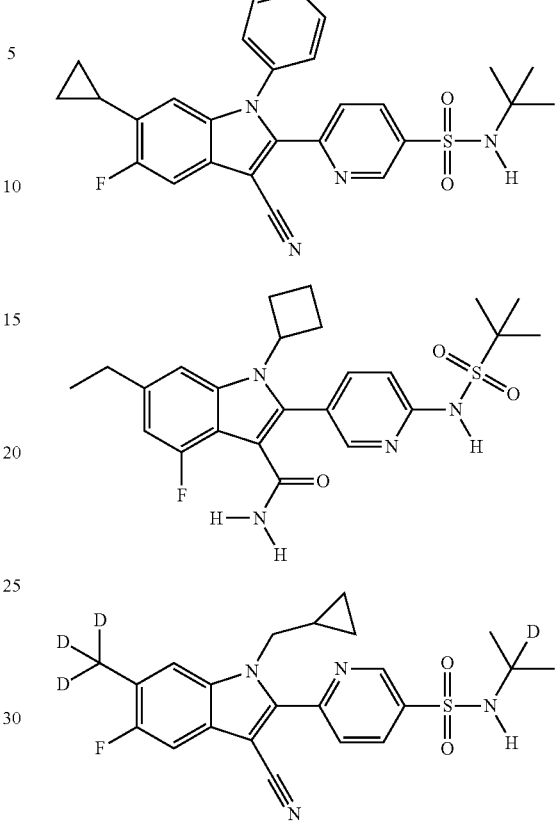

In another embodiment of the present invention, a compound of Formula (I) or a free acid, free base, salt, hydrate, solvate, clathrate, isotopologue, racemate, enantiomer, diastereomer, stereoisomer or polymorph form thereof is selected from:

| Cpd | Name |
|---|---|
| 1 | 6-[3-cyano-6-(difluoromethoxy)-1-(propan-2-yl)-1H-indol-2-yl]-N-(propan-2-yl)pyridine-3-sulfonamide, |
| 2 | 6-[3-cyano-6-(difluoromethoxy)-1-(propan-2-yl)-1H-indol-2-yl]-N-cyclobutylpyridine-3-sulfonamide, |
| 3 | 6-[3-cyano-6-(difluoromethoxy)-1-propyl-1H-indol-2-yl]-N-(propan-2-yl)pyridine-3-sulfonamide, |
| 4 | 5-[3-cyano-1-cyclobutyl-6-(cyclobutyloxy)-1H-indol-2-yl]-N-(propan-2-yl)pyridine-2-sulfonamide, |
| 5 | 6-(3-cyano-1-cyclobutyl-5-fluoro-1H-indol-2-yl)-N-(propan-2-yl)pyridine-3-sulfonamide, |
| 6 | 6-[3-cyano-1-(cyclopropylmethyl)-5-fluoro-1H-indol-2-yl]-N-(propan-2-yl)pyridine-3-sulfonamide, |
| 7 | 6-(3-cyano-1-cyclobutyl-6-cyclopropyl-1H-indol-2-yl)-N-(propan-2-yl)pyridine-3-sulfonamide, |
| 8 | 6-(3-cyano-1-cyclobutyl-5-cyclopropyl-1H-indol-2-yl)-N-(propan-2-yl)pyridine-3-sulfonamide, |
| 9 | N-tert-butyl-6-(3-cyano-1-cyclobutyl-5-fluoro-1H-indol-2-yl)pyridine-3-sulfonamide, |
| 10 | 6-[3-cyano-1-cyclobutyl-6-(trifluoromethoxy)-1H-indol-2-yl]-N-(propan-2-yl)pyridine-3-sulfonamide, |
| 11 | 6-[3-cyano-1-(cyclopropylmethyl)-6-(trifluoromethoxy)-1H-indol-2-yl]-N-(propan-2-yl)pyridine-3-sulfonamide, |
| 12 | 6-[3-cyano-1-(propan-2-yl)-6-(trifluoromethoxy)-1H-indol-2-yl]-N-(propan-2-yl)pyridine-3-sulfonamide, |
| 13 | 6-[3-cyano-1-(cyclopropylmethyl)-6-(difluoromethoxy)-1H-indol-2-yl]-N-(propan-2-yl)pyridine-3-sulfonamide, |

| Cpd | Name |
|---|---|
| 14 | 6-(5-chloro-3-cyano-1-cyclobutyl-1H-indol-2-yl)-N-(propan-2-yl)pyridine-3-sulfonamide, |
| 15 | N-tert-butyl-6-(5-chloro-3-cyano-1-cyclobutyl-1H-indol-2-yl)pyridine-3-sulfonamide, |
| 16 | 6-[3-cyano-1-cyclobutyl-6-(propan-2-ylsulfanyl)-1H-indol-2-yl]-N-(propan-2-yl)pyridine-3-sulfonamide, |
| 17 | 6-[3-cyano-1-cyclopentyl-6-(trifluoromethoxy)-1H-indol-2-yl]-N-(propan-2-yl)pyridine-3-sulfonamide, |
| 18 | N-tert-butyl-6-[3-cyano-1-cyclopentyl-6-(trifluoromethoxy)-1H-indol-2-yl]pyridine-3-sulfonamide, |
| 19 | 6-[3-cyano-1-cyclobutyl-5-(difluoromethoxy)-1H-indol-2-yl]-N-(propan-2-yl)pyridine-3-sulfonamide, |
| 20 | N-tert-butyl-6-[3-cyano-1-cyclobutyl-5-(difluoromethoxy)-1H-indol-2-yl]pyridine-3-sulfonamide, |
| 21 | 6-[3-cyano-1-cyclopentyl-5-(difluoromethoxy)-1H-indol-2-yl]-N-(propan-2-yl)pyridine-3-sulfonamide, |
| 22 | 1-cyclobutyl-2-[5-(piperidin-1-ylsulfonyl)pyridin-2-yl]-6-(propan-2-ylsulfanyl)-1H-indole-3-carbonitrile, |
| 23 | 6-[3-cyano-1-cyclobutyl-5-(trifluoromethoxy)-1H-indol-2-yl]-N-(propan-2-yl)pyridine-3-sulfonamide, |
| 24 | 6-[3-cyano-1-cyclobutyl-6-(trifluoromethoxy)-1H-indol-2-yl]-N-(1,3-difluoropropan-2-yl)pyridine-3-sulfonamide, |
| 25 | 6-[3-cyano-1-cyclobutyl-5-(trifluoromethoxy)-1H-indol-2-yl]-N-(1,3-difluoropropan-2-yl)pyridine-3-sulfonamide, |
| 26 | 5-[3-cyano-1-cyclobutyl-6-(trifluoromethoxy)-1H-indol-2-yl]-N-(propan-2-yl)pyridine-2-sulfonamide, |
| 27 | 5-(3-cyano-1-cyclobutyl-6-cyclopropyl-1H-indol-2-yl)-N-(propan-2-yl)pyridine-2-sulfonamide, |
| 28 | 5-(5-chloro-3-cyano-1-cyclobutyl-1H-indol-2-yl)-N-(propan-2-yl)pyridine-2-sulfonamide, |
| 29 | 6-(3-cyano-1-cyclobutyl-5-fluoro-1H-indol-2-yl)-N-(1,3-difluoropropan-2-yl)pyridine-3-sulfonamide, |
| 30 | 6-(5-chloro-3-cyano-1-cyclobutyl-1H-indol-2-yl)-N-(1,3-difluoropropan-2-yl)pyridine-3-sulfonamide, |
| 31 | 6-[3-cyano-1-cyclobutyl-6-(difluoromethoxy)-1H-indol-2-yl]-N-(1,3-difluoropropan-2-yl)pyridine-3-sulfonamide, |
| 32 | 6-[3-cyano-1-cyclobutyl-5-(difluoromethoxy)-1H-indol-2-yl]-N-(1,3-difluoropropan-2-yl)pyridine-3-sulfonamide, |
| 33 | 6-[3-cyano-1-cyclopentyl-5-(difluoromethoxy)-1H-indol-2-yl]-N-(1,3-difluoropropan-2-yl)pyridine-3-sulfonamide, |
| 34 | 6-[3-cyano-1-cyclopentyl-5-(trifluoromethoxy)-1H-indol-2-yl]-N-(1,3-difluoropropan-2-yl)pyridine-3-sulfonamide, |
| 35 | 6-(3-cyano-1-cyclobutyl-6-cyclopropyl-1H-indol-2-yl)-N-(1,3-difluoropropan-2-yl)pyridine-3-sulfonamide, |
| 36 | 6-[3-cyano-6-(difluoromethoxy)-1-(propan-2-yl)-1H-indol-2-yl]-N-(1,3-difluoropropan-2-yl)pyridine-3-sulfonamide, |
| 37 | 6-(6-chloro-3-cyano-1-cyclobutyl-1H-indol-2-yl)-N-(1,3-difluoropropan-2-yl)pyridine-3-sulfonamide, |
| 38 | 6-(3-cyano-1-cyclopentyl-5-fluoro-1H-indol-2-yl)-N-(1,3-difluoropropan-2-yl)pyridine-3-sulfonamide, |
| 39 | 5-[3-cyano-1-cyclopropyl-6-(difluoromethoxy)-1H-indol-2-yl]-N-(propan-2-yl)pyridine-2-sulfonamide, |
| 40 | 5-[3-cyano-1-(cyclopropylmethyl)-6-(difluoromethoxy)-1H-indol-2-yl]-N-(propan-2-yl)pyridine-2-sulfonamide, |
| 41 | 6-[3-cyano-1-(cyclopropylmethyl)-6-(difluoromethoxy)-1H-indol-2-yl]-N-(1,3-difluoropropan-2-yl)pyridine-3-sulfonamide, |
| 42 | 6-[3-cyano-1-cyclopropyl-6-(difluoromethoxy)-1H-indol-2-yl]-N-(1,3-difluoropropan-2-yl)pyridine-3-sulfonamide, |
| 43 | 6-[3-cyano-1-cyclobutyl-6-(propan-2-yl)-1H-indol-2-yl]-N-(1,3-difluoropropan-2-yl)pyridine-3-sulfonamide, |
| 44 | 6-(3-cyano-1-cyclopentyl-6-methyl-1H-indol-2-yl)-N-(1,3-difluoropropan-2-yl)pyridine-3-sulfonamide, |
| 45 | 6-[3-cyano-6-(difluoromethoxy)-1-propyl-1H-indol-2-yl]-N-(1,3-difluoropropan-2-yl)pyridine-3-sulfonamide, |
| 46 | 6-[3-cyano-5-fluoro-1-(tetrahydrofuran-3-yl)-1H-indol-2-yl]-N-(1,3-difluoropropan-2-yl)pyridine-3-sulfonamide, |
| 47 | 6-[3-cyano-5-fluoro-1-(tetrahydrofuran-3-yl)-1H-indol-2-yl]-N-(propan-2-yl)pyridine-3-sulfonamide, |
| 48 | 6-(3-cyano-1-cyclobutyl-6-ethyl-1H-indol-2-yl)-N-(1,3-difluoropropan-2-yl)pyridine-3-sulfonamide, |
| 49 | 6-[3-cyano-1-cyclopentyl-6-(difluoromethoxy)-1H-indol-2-yl]-N-(1,3-difluoropropan-2-yl)pyridine-3-sulfonamide, |
| 50 | 6-(6-chloro-3-cyano-1-cyclobutyl-5-fluoro-1H-indol-2-yl)-N-(1,3-difluoropropan-2-yl)pyridine-3-sulfonamide, |
| 51 | 6-[3-cyano-1-cyclobutyl-6-(difluoromethoxy)-1H-indol-2-yl]-N-(propan-2-yl)pyridine-3-sulfonamide, |
| 52 | 6-[3-cyano-1-cyclopentyl-6-(difluoromethoxy)-1H-indol-2-yl]-N-(propan-2-yl)pyridine-3-sulfonamide, |

-continued

| Cpd | Name |
|---|---|
| 53 | 6-[3-cyano-1-cyclopentyl-6-(difluoromethoxy)-1H-indol-2-yl]-N-(1,1,1-trifluoropropan-2-yl)pyridine-3-sulfonamide, |
| 54 | 6-{3-cyano-6-methyl-1-[(3R)-tetrahydrofuran-3-yl]-1H-indol-2-yl}-N-(1,3-difluoropropan-2-yl)pyridine-3-sulfonamide, |
| 55 | 6-{3-cyano-6-methyl-1-[(3R)-tetrahydrofuran-3-yl]-1H-indol-2-yl}-N-(propan-2-yl)pyridine-3-sulfonamide, |
| 56 | 6-(3-cyano-1-cyclobutyl-6-fluoro-1H-indol-2-yl)-N-(1,3-difluoropropan-2-yl)pyridine-3-sulfonamide, |
| 57 | 6-[3-cyano-1-(cyclopropylmethyl)-6-fluoro-1H-indol-2-yl]-N-(1,3-difluoropropan-2-yl)pyridine-3-sulfonamide, |
| 58 | 6-[3-cyano-1-(cyclopropylmethyl)-5-fluoro-1H-indol-2-yl]-N-(1,3-difluoropropan-2-yl)pyridine-3-sulfonamide, |
| 59 | 6-[3-cyano-1-cyclobutyl-6-(2,2-difluoroethoxy)-1H-indol-2-yl]-N-(propan-2-yl)pyridine-3-sulfonamide, |
| 60 | 6-[3-cyano-5-fluoro-1-(propan-2-yl)-1H-indol-2-yl]-N-(1,3-difluoropropan-2-yl)pyridine-3-sulfonamide, |
| 61 | 6-[3-cyano-6-fluoro-1-(propan-2-yl)-1H-indol-2-yl]-N-(1,3-difluoropropan-2-yl)pyridine-3-sulfonamide, |
| 62 | 6-[6-chloro-3-cyano-1-(cyclopropylmethyl)-1H-indol-2-yl]-N-(1,3-difluoropropan-2-yl)pyridine-3-sulfonamide, |
| 63 | 6-[6-chloro-3-cyano-1-(propan-2-yl)-1H-indol-2-yl]-N-(1,3-difluoropropan-2-yl)pyridine-3-sulfonamide, |
| 64 | 6-(6-chloro-3-cyano-1-cyclopentyl-1H-indol-2-yl)-N-(1,3-difluoropropan-2-yl)pyridine-3-sulfonamide, |
| 65 | 6-[5-chloro-3-cyano-1-(propan-2-yl)-1H-indol-2-yl]-N-(1,3-difluoropropan-2-yl)pyridine-3-sulfonamide, |
| 66 | 6-(3-cyano-1-cyclopentyl-7-fluoro-1H-indol-2-yl)-N-(propan-2-yl)pyridine-3-sulfonamide, |
| 67 | 6-[3-cyano-1-cyclopentyl-6-(difluoromethoxy)-1H-indol-2-yl]-N-(1-fluoro-2-methylpropan-2-yl)pyridine-3-sulfonamide, |
| 68 | 6-[3-cyano-1-(cyclopropylmethyl)-6-(trifluoromethoxy)-1H-indol-2-yl]-N-(1,3-difluoropropan-2-yl)pyridine-3-sulfonamide, |
| 69 | 6-[3-cyano-1-(propan-2-yl)-6-(trifluoromethoxy)-1H-indol-2-yl]-N-(1,3-difluoropropan-2-yl)pyridine-3-sulfonamide, |
| 70 | 6-[3-cyano-1-cyclopentyl-6-(trifluoromethoxy)-1H-indol-2-yl]-N-(1,3-difluoropropan-2-yl)pyridine-3-sulfonamide, |
| 71 | 2-(3-cyano-1-cyclobutyl-6-cyclopropyl-1H-indol-2-yl)-N-(propan-2-yl)pyrimidine-5-sulfonamide, |
| 72 | 6-(5-chloro-3-cyano-1-cyclopentyl-1H-indol-2-yl)-N-(1,3-difluoropropan-2-yl)pyridine-3-sulfonamide, |
| 73 | 6-[5-chloro-3-cyano-1-(cyclopropylmethyl)-1H-indol-2-yl]-N-(1,3-difluoropropan-2-yl)pyridine-3-sulfonamide, |
| 74 | 2-(3-cyano-1-cyclopentyl-6-methyl-1H-indol-2-yl)-N-(propan-2-yl)pyrimidine-5-sulfonamide, |
| 75 | 6-[3-cyano-6-ethyl-1-(propan-2-yl)-1H-indol-2-yl]-N-(propan-2-yl)pyridine-3-sulfonamide, |
| 77 | 6-[3-cyano-1-cyclobutyl-6-(difluoromethoxy)-1H-indol-2-yl]-N-(1-fluoro-2-methylpropan-2-yl)pyridine-3-sulfonamide, |
| 78 | 6-[3-cyano-1-cyclobutyl-6-(difluoromethoxy)-1H-indol-2-yl]-N-(1,1,1-trifluoropropan-2-yl)pyridine-3-sulfonamide, |
| 79 | 6-(5-chloro-3-cyano-1-cyclohexyl-1H-indol-2-yl)-N-(1,3-difluoropropan-2-yl)pyridine-3-sulfonamide, |
| 80 | 6-[3-cyano-6-methyl-1-(propan-2-yl)-1H-indol-2-yl]-N-(1,3-difluoropropan-2-yl)pyridine-3-sulfonamide, |
| 81 | 6-[3-cyano-1-(cyclopropylmethyl)-6-methyl-1H-indol-2-yl]-N-(1,3-difluoropropan-2-yl)pyridine-3-sulfonamide, |
| 82 | 6-(3-cyano-1-cyclobutyl-6-methyl-1H-indol-2-yl)-N-(1,3-difluoropropan-2-yl)pyridine-3-sulfonamide, |
| 83 | 6-[3-cyano-6-cyclopropyl-1-(propan-2-yl)-1H-indol-2-yl]-N-(1,3-difluoropropan-2-yl)pyridine-3-sulfonamide, |
| 84 | 6-[3-cyano-6-cyclopropyl-1-(cyclopropylmethyl)-1H-indol-2-yl]-N-(1,3-difluoropropan-2-yl)pyridine-3-sulfonamide, |
| 85 | 6-(3-cyano-1-cyclopentyl-6-cyclopropyl-1H-indol-2-yl)-N-(1,3-difluoropropan-2-yl)pyridine-3-sulfonamide, |
| 86 | 6-(3-cyano-1-cyclopentyl-6-cyclopropyl-1H-indol-2-yl)-N-(1,1,1-trifluoropropan-2-yl)pyridine-3-sulfonamide, |
| 87 | 6-(3-cyano-1-cyclopentyl-7-fluoro-1H-indol-2-yl)-N-(1,3-difluoropropan-2-yl)pyridine-3-sulfonamide, |
| 88 | 6-(7-chloro-3-cyano-1-cyclopentyl-1H-indol-2-yl)-N-(1,3-difluoropropan-2-yl)pyridine-3-sulfonamide, |
| 89 | 6-(6-chloro-3-cyano-1-cyclohexyl-1H-indol-2-yl)-N-(1,3-difluoropropan-2-yl)pyridine-3-sulfonamide, |
| 90 | 6-(3-cyano-1-cyclobutyl-6-cyclopropyl-1H-indol-2-yl)pyridine-3-sulfonamide, |
| 92 | 6-(3-cyano-1-cyclohexyl-6-cyclopropyl-1H-indol-2-yl)-N-(1,3-difluoropropan-2-yl)pyridine-3-sulfonamide, |
| 93 | 6-[3-cyano-1-cyclobutyl-6-(difluoromethoxy)-1H-indol-2-yl]-N-[1-(trifluoromethyl)cyclopropyl]pyridine-3-sulfonamide, |

| Cpd | Name |
|---|---|
| 94 | 6-[3-cyano-1-cyclopentyl-6-(difluoromethoxy)-1H-indol-2-yl]-N-[1-(trifluoromethyl)cyclopropyl]pyridine-3-sulfonamide, |
| 95 | 6-(3-cyano-6-cyclopropyl-1-phenyl-1H-indol-2-yl)-N-(1,3-difluoropropan-2-yl)pyridine-3-sulfonamide, |
| 96 | 6-[3-cyano-5-fluoro-1-(pyridin-2-yl)-1H-indol-2-yl]-N-(1,3-difluoropropan-2-yl)pyridine-3-sulfonamide, |
| 97 | 2-(5-chloro-3-cyano-1-cyclohexyl-1H-indol-2-yl)-N-(propan-2-yl)pyrimidine-5-sulfonamide, |
| 98 | 2-(3-cyano-1-cyclohexyl-6-methyl-1H-indol-2-yl)-N-(propan-2-yl)pyrimidine-5-sulfonamide, |
| 99 | 6-[3-cyano-1-cyclohexyl-6-(difluoromethoxy)-1H-indol-2-yl]-N-(propan-2-yl)pyridine-3-sulfonamide, |
| 100 | 6-[3-cyano-1-cyclohexyl-6-(difluoromethoxy)-1H-indol-2-yl]-N-(1,3-difluoropropan-2-yl)pyridine-3-sulfonamide, |
| 101 | 6-(3-cyano-1-cyclobutyl-5-fluoro-6-methoxy-1H-indol-2-yl)-N-(propan-2-yl)pyridine-3-sulfonamide, |
| 102 | 6-(3-cyano-1-cyclobutyl-5-fluoro-6-methoxy-1H-indol-2-yl)-N-(1,3-difluoropropan-2-yl)pyridine-3-sulfonamide, |
| 103 | 6-[3-cyano-1-cyclobutyl-6-(2,2-difluoroethenyl)-1H-indol-2-yl]-N-(1,3-difluoropropan-2-yl)pyridine-3-sulfonamide, |
| 104 | 6-(3-cyano-1-cyclohexyl-5-fluoro-1H-indol-2-yl)-N-(1,3-difluoropropan-2-yl)pyridine-3-sulfonamide, |
| 105 | 6-[3-cyano-1-cyclohexyl-6-(trifluoromethoxy)-1H-indol-2-yl]-N-(1,3-difluoropropan-2-yl)pyridine-3-sulfonamide, |
| 106 | 6-[3-cyano-1-cyclobutyl-6-(difluoromethoxy)-1H-indol-2-yl]-N-[1-(trifluoromethyl)cyclobutyl]pyridine-3-sulfonamide, |
| 107 | 6-(3-cyano-1-cyclobutyl-6-cyclopropyl-5-fluoro-1H-indol-2-yl)-N-(1,3-difluoropropan-2-yl)pyridine-3-sulfonamide, |
| 108 | 6-(3-cyano-1-cyclobutyl-5-fluoro-6-methyl-1H-indol-2-yl)-N-(1,3-difluoropropan-2-yl)pyridine-3-sulfonamide, |
| 109 | 6-(3-cyano-1,6-dicyclopropyl-1H-indol-2-yl)-N-(propan-2-yl)pyridine-3-sulfonamide, |
| 110 | 6-[6-chloro-3-cyano-1-(cyclopropylmethyl)-5-fluoro-1H-indol-2-yl]-N-(1,3-difluoropropan-2-yl)pyridine-3-sulfonamide, |
| 111 | 6-(3-cyano-6-methyl-1-phenyl-1H-indol-2-yl)-N-(1,3-difluoropropan-2-yl)pyridine-3-sulfonamide, |
| 112 | 6-(5-chloro-3-cyano-1-phenyl-1H-indol-2-yl)-N-(1,3-difluoropropan-2-yl)pyridine-3-sulfonamide, |
| 113 | 6-(3-cyano-5-fluoro-1-phenyl-1H-indol-2-yl)-N-(1,3-difluoropropan-2-yl)pyridine-3-sulfonamide, |
| 114 | 2-(5-chloro-3-cyano-1-cyclobutyl-1H-indol-2-yl)-N-(propan-2-yl)pyrimidine-5-sulfonamide, |
| 115 | 2-(6-chloro-3-cyano-1-cyclobutyl-1H-indol-2-yl)-N-(propan-2-yl)pyrimidine-5-sulfonamide, |
| 116 | 2-[3-cyano-1-cyclobutyl-6-(trifluoromethoxy)-1H-indol-2-yl]-N-(propan-2-yl)pyrimidine-5-sulfonamide, |
| 117 | 2-[3-cyano-1-cyclopentyl-6-(trifluoromethoxy)-1H-indol-2-yl]-N-(propan-2-yl)pyrimidine-5-sulfonamide, |
| 118 | 6-(5-chloro-3-cyano-1-cyclopentyl-1H-indol-2-yl)-N-[(1S)-1-cyclopropylethyl]pyridine-3-sulfonamide, |
| 119 | 6-(5-chloro-3-cyano-1-cyclobutyl-1H-indol-2-yl)-N-[(1S)-1-cyclopropylethyl]pyridine-3-sulfonamide, |
| 120 | 2-[5-chloro-3-cyano-1-(propan-2-yl)-1H-indol-2-yl]-N-(propan-2-yl)pyrimidine-5-sulfonamide, |
| 121 | 2-(3-cyano-1-cyclobutyl-5-methyl-1H-indol-2-yl)-N-(propan-2-yl)pyrimidine-5-sulfonamide, |
| 122 | 2-(3-cyano-1-cyclobutyl-5-methyl-1H-indol-2-yl)-N-(1,3-difluoropropan-2-yl)pyrimidine-5-sulfonamide, |
| 123 | 2-[3-cyano-5-fluoro-1-(propan-2-yl)-1H-indol-2-yl]-N-(propan-2-yl)pyrimidine-5-sulfonamide, |
| 124 | 2-[3-cyano-6-cyclopropyl-1-(cyclopropylmethyl)-1H-indol-2-yl]-N-(propan-2-yl)pyrimidine-5-sulfonamide, |
| 125 | 2-(3-cyano-1-cyclopentyl-6-cyclopropyl-1H-indol-2-yl)-N-(propan-2-yl)pyrimidine-5-sulfonamide, |
| 126 | 2-(3-cyano-1-cyclobutyl-6-cyclopropyl-1H-indol-2-yl)-N-(1,3-difluoropropan-2-yl)pyrimidine-5-sulfonamide, |
| 127 | 2-[3-cyano-1-cyclobutyl-6-(difluoromethoxy)-1H-indol-2-yl]-N-(propan-2-yl)pyrimidine-5-sulfonamide, |
| 128 | 2-[3-cyano-1-cyclobutyl-6-(difluoromethoxy)-1H-indol-2-yl]-N-(1,1,1-trifluoropropan-2-yl)pyrimidine-5-sulfonamide, |
| 129 | 2-[3-cyano-1-cyclobutyl-6-(difluoromethoxy)-1H-indol-2-yl]-N-(1,3-difluoropropan-2-yl)pyrimidine-5-sulfonamide, |
| 130 | 2-[3-cyano-1-cyclobutyl-6-(difluoromethoxy)-1H-indol-2-yl]-N-[(1S)-1-cyclopropylethyl]pyrimidine-5-sulfonamide, |
| 131 | 2-(3-cyano-1-cyclobutyl-6-cyclopropyl-1H-indol-2-yl)-N-[(1S)-1-cyclopropylethyl]pyrimidine-5-sulfonamide, |
| 132 | 2-(3-cyano-1-cyclobutyl-6-methyl-1H-indol-2-yl)-N-(1,3-difluoropropan-2-yl)pyrimidine-5-sulfonamide, |

-continued

| Cpd | Name |
|---|---|
| 133 | 2-[3-cyano-1-(cyclopropylmethyl)-6-methyl-1H-indol-2-yl]-N-(1,3-difluoropropan-2-yl)pyrimidine-5-sulfonamide, |
| 134 | 2-[3-cyano-6-methyl-1-(propan-2-yl)-1H-indol-2-yl]-N-(1,3-difluoropropan-2-yl)pyrimidine-5-sulfonamide, |
| 135 | 2-(3-cyano-1-cyclopentyl-6-methyl-1H-indol-2-yl)-N-(1,3-difluoropropan-2-yl)pyrimidine-5-sulfonamide, |
| 136 | 2-[3-cyano-1-(cyclopropylmethyl)-6-(difluoromethoxy)-1H-indol-2-yl]-N-(1,3-difluoropropan-2-yl)pyrimidine-5-sulfonamide, |
| 137 | 2-[3-cyano-6-(difluoromethoxy)-1-(propan-2-yl)-1H-indol-2-yl]-N-(1,3-difluoropropan-2-yl)pyrimidine-5-sulfonamide, |
| 138 | 2-(3-cyano-1-cyclobutyl-6-fluoro-1H-indol-2-yl)-N-(propan-2-yl)pyrimidine-5-sulfonamide, |
| 139 | 2-[3-cyano-1-(cyclopropylmethyl)-6-fluoro-1H-indol-2-yl]-N-(propan-2-yl)pyrimidine-5-sulfonamide, |
| 140 | 2-[3-cyano-6-fluoro-1-(propan-2-yl)-1H-indol-2-yl]-N-(propan-2-yl)pyrimidine-5-sulfonamide, |
| 141 | 2-(3-cyano-1-cyclopentyl-6-fluoro-1H-indol-2-yl)-N-(propan-2-yl)pyrimidine-5-sulfonamide, |
| 142 | 6-(3-cyano-1-cyclobutyl-5-fluoro-1H-indol-2-yl)-N-[(1S)-1-cyclopropylethyl]pyridine-3-sulfonamide, |
| 143 | 6-(3-cyano-1-cyclopentyl-5-fluoro-1H-indol-2-yl)-N-[(1S)-1-cyclopropylethyl]pyridine-3-sulfonamide, |
| 144 | 6-(3-cyano-1-cyclobutyl-6-fluoro-1H-indol-2-yl)-N-[(1S)-1-cyclopropylethyl]pyridine-3-sulfonamide, |
| 145 | 2-(3-cyano-1-cyclobutyl-6-cyclopropyl-5-fluoro-1H-indol-2-yl)-N-(1,3-difluoropropan-2-yl)pyrimidine-5-sulfonamide, |
| 146 | 2-(3-cyano-1-cyclobutyl-5-fluoro-6-methyl-1H-indol-2-yl)-N-(1,3-difluoropropan-2-yl)pyrimidine-5-sulfonamide, |
| 147 | 6-(3-cyano-1,6-dicyclopropyl-1H-indol-2-yl)-N-(1,3-difluoropropan-2-yl)pyridine-3-sulfonamide, |
| 148 | 2-(3-cyano-1,6-dicyclopropyl-1H-indol-2-yl)-N-(1,3-difluoropropan-2-yl)pyrimidine-5-sulfonamide, |
| 149 | 2-(6-chloro-3-cyano-1-cyclobutyl-5-fluoro-1H-indol-2-yl)-N-(1,3-difluoropropan-2-yl)pyrimidine-5-sulfonamide, |
| 150 | 2-(3-cyano-1-cyclobutyl-5-fluoro-6-methoxy-1H-indol-2-yl)-N-(1,3-difluoropropan-2-yl)pyrimidine-5-sulfonamide, |
| 151 | 6-[3-cyano-1-cyclobutyl-6-(difluoromethoxy)-1H-indol-2-yl]-N-[(1S)-1-cyclopropylethyl]pyridine-3-sulfonamide, |
| 152 | 6-[3-cyano-1-cyclobutyl-6-(trifluoromethoxy)-1H-indol-2-yl]-N-[(1S)-1-cyclopropylethyl]pyridine-3-sulfonamide, |
| 153 | 6-(3-cyano-1-cyclobutyl-6-cyclopropyl-1H-indol-2-yl)-N-[1-(trifluoromethyl)cyclopropyl]pyridine-3-sulfonamide, |
| 154 | 6-(6-chloro-3-cyano-1-cyclobutyl-1H-indol-2-yl)-N-[(1S)-1-cyclopropylethyl]pyridine-3-sulfonamide, |
| 155 | 6-(6-chloro-3-cyano-1-cyclopentyl-1H-indol-2-yl)-N-[(1S)-1-cyclopropylethyl]pyridine-3-sulfonamide, |
| 156 | 2-[6-chloro-3-cyano-1-(propan-2-yl)-1H-indol-2-yl]-N-(propan-2-yl)pyrimidine-5-sulfonamide, |
| 157 | 2-(6-chloro-3-cyano-1-cyclopentyl-1H-indol-2-yl)-N-(1,3-difluoropropan-2-yl)pyrimidine-5-sulfonamide, |
| 158 | 6-(3-cyano-1-cyclopentyl-5-methyl-1H-indol-2-yl)-N-(1,3-difluoropropan-2-yl)pyridine-3-sulfonamide, |
| 159 | 2-(3-cyano-1-cyclopentyl-5-methyl-1H-indol-2-yl)-N-(propan-2-yl)pyrimidine-5-sulfonamide, |
| 160 | 2-(3-cyano-1-cyclopentyl-5-methyl-1H-indol-2-yl)-N-(1,3-difluoropropan-2-yl)pyrimidine-5-sulfonamide, |
| 161 | 6-[3-cyano-1-cyclobutyl-6-(methylsulfanyl)-1H-indol-2-yl]-N-(1,3-difluoropropan-2-yl)pyridine-3-sulfonamide, |
| 162 | 2-[3-cyano-1-cyclobutyl-6-(methylsulfanyl)-1H-indol-2-yl]-N-(1,3-difluoropropan-2-yl)pyrimidine-5-sulfonamide, |
| 163 | 2-(3-cyano-1-cyclobutyl-6-fluoro-1H-indol-2-yl)-N-(1,3-difluoropropan-2-yl)pyrimidine-5-sulfonamide, |
| 164 | 2-[3-cyano-1-(cyclopropylmethyl)-6-fluoro-1H-indol-2-yl]-N-(1,3-difluoropropan-2-yl)pyrimidine-5-sulfonamide, |
| 165 | 2-[3-cyano-6-fluoro-1-(propan-2-yl)-1H-indol-2-yl]-N-(1,3-difluoropropan-2-yl)pyrimidine-5-sulfonamide, |
| 166 | 2-(3-cyano-1-cyclopentyl-6-fluoro-1H-indol-2-yl)-N-(1,3-difluoropropan-2-yl)pyrimidine-5-sulfonamide, |
| 167 | 2-[3-cyano-6-methyl-1-(propan-2-yl)-1H-indol-2-yl]-N-(propan-2-yl)pyrimidine-5-sulfonamide, |
| 168 | 2-[3-cyano-1-(cyclopropylmethyl)-6-methyl-1H-indol-2-yl]-N-(propan-2-yl)pyrimidine-5-sulfonamide, |
| 169 | 2-(3-cyano-1-cyclobutyl-6-methyl-1H-indol-2-yl)-N-(propan-2-yl)pyrimidine-5-sulfonamide, |
| 170 | 2-[3-cyano-1-(cyclopropylmethyl)-6-(difluoromethoxy)-1H-indol-2-yl]-N-(propan-2-yl)pyrimidine-5-sulfonamide, |
| 171 | 2-[3-cyano-6-(difluoromethoxy)-1-(propan-2-yl)-1H-indol-2-yl]-N-(propan-2-yl)pyrimidine-5-sulfonamide, |

| Cpd | Name |
|---|---|
| 172 | 2-(3-cyano-1-cyclobutyl-6-methoxy-1H-indol-2-yl)-N-(propan-2-yl)pyrimidine-5-sulfonamide, |
| 173 | 2-(3-cyano-1-cyclopentyl-6-cyclopropyl-1H-indol-2-yl)-N-(1,3-difluoropropan-2-yl)pyrimidine-5-sulfonamide, |
| 174 | 6-[3-cyano-1-cyclopentyl-6-(difluoromethoxy)-1H-indol-2-yl]-N-[(1S)-1-cyclopropylethyl]pyridine-3-sulfonamide, |
| 175 | 2-(5-chloro-3-cyano-1-cyclobutyl-1H-indol-2-yl)-N-(1,3-difluoropropan-2-yl)pyrimidine-5-sulfonamide, |
| 176 | 2-(6-chloro-3-cyano-1-cyclobutyl-1H-indol-2-yl)-N-(1,3-difluoropropan-2-yl)pyrimidine-5-sulfonamide, |
| 177 | 2-[3-cyano-1-cyclobutyl-6-(trifluoromethoxy)-1H-indol-2-yl]-N-(1,3-difluoropropan-2-yl)pyrimidine-5-sulfonamide, |
| 178 | 2-[3-cyano-1-cyclopentyl-6-(trifluoromethoxy)-1H-indol-2-yl]-N-(1,3-difluoropropan-2-yl)pyrimidine-5-sulfonamide, |
| 179 | 2-[3-cyano-1-cyclohexyl-6-(difluoromethoxy)-1H-indol-2-yl]-N-(1,3-difluoropropan-2-yl)pyrimidine-5-sulfonamide, |
| 180 | 2-(3-cyano-1-cyclobutyl-6-cyclopropyl-1H-indol-2-yl)-N-[(2R)-1,1,1-trifluoropropan-2-yl]pyrimidine-5-sulfonamide, |
| 181 | 2-(3-cyano-1-cyclobutyl-6-methyl-1H-indol-2-yl)-N-[(2R)-1,1,1-trifluoropropan-2-yl]pyrimidine-5-sulfonamide, |
| 182 | 2-(3-cyano-1-cyclopentyl-6-methyl-1H-indol-2-yl)-N-[(2R)-1,1,1-trifluoropropan-2-yl]pyrimidine-5-sulfonamide, |
| 183 | 2-(3-cyano-1-cyclobutyl-6-methoxy-1H-indol-2-yl)-N-[(2R)-1,1,1-trifluoropropan-2-yl]pyrimidine-5-sulfonamide, |
| 184 | 2-[3-cyano-1-cyclobutyl-6-(difluoromethoxy)-1H-indol-2-yl]-N-[(2R)-1,1,1-trifluoropropan-2-yl]pyrimidine-5-sulfonamide, |
| 185 | 2-[3-cyano-1-cyclobutyl-6-(propan-2-yl)-1H-indol-2-yl]-N-(propan-2-yl)pyrimidine-5-sulfonamide, |
| 186 | 2-[3-cyano-1-cyclobutyl-6-(propan-2-yl)-1H-indol-2-yl]-N-(1,3-difluoropropan-2-yl)pyrimidine-5-sulfonamide, |
| 187 | 2-[5-chloro-3-cyano-1-(propan-2-yl)-1H-indol-2-yl]-N-(1,3-difluoropropan-2-yl)pyrimidine-5-sulfonamide, |
| 188 | 2-(5-chloro-3-cyano-1-cyclopentyl-1H-indol-2-yl)-N-(1,3-difluoropropan-2-yl)pyrimidine-5-sulfonamide, |
| 189 | 2-(6-chloro-3-cyano-1-cyclopentyl-1H-indol-2-yl)-N-(propan-2-yl)pyrimidine-5-sulfonamide, |
| 190 | 6-(3-cyano-1-cyclopentyl-6-methyl-1H-indol-2-yl)-N-[1-(trifluoromethyl)cyclopropyl]pyridine-3-sulfonamide, |
| 191 | 6-[3-cyano-1-cyclobutyl-6-(trifluoromethoxy)-1H-indol-2-yl]-N-[(2R)-1,1,1-trifluoropropan-2-yl]pyridine-3-sulfonamide, |
| 192 | 6-(3-cyano-1-cyclobutyl-6-methyl-1H-indol-2-yl)-N-[(2R)-1,1,1-trifluoropropan-2-yl]pyridine-3-sulfonamide, |
| 193 | 2-(3-cyano-1-cyclohexyl-6-cyclopropyl-1H-indol-2-yl)-N-(1,3-difluoropropan-2-yl)pyrimidine-5-sulfonamide, |
| 194 | 6-[3-cyano-6-(difluoromethoxy)-1-(propan-2-yl)-1H-indol-2-yl]-N-[(2R)-1,1,1-trifluoropropan-2-yl]pyridine-3-sulfonamide, |
| 195 | 6-[3-cyano-1-cyclohexyl-6-(difluoromethoxy)-1H-indol-2-yl]-N-[(2R)-1,1,1-trifluoropropan-2-yl]pyridine-3-sulfonamide, |
| 196 | 6-[3-cyano-1-cyclobutyl-6-(difluoromethoxy)-1H-indol-2-yl]-N-[(2R)-1,1,1-trifluoropropan-2-yl]pyridine-3-sulfonamide, |
| 197 | 6-[3-cyano-1-(cyclopropylmethyl)-6-methyl-1H-indol-2-yl]-N-[(2R)-1,1,1-trifluoropropan-2-yl]pyridine-3-sulfonamide, |
| 198 | 2-(3-cyano-1-cyclohexyl-5-methyl-1H-indol-2-yl)-N-(1,3-difluoropropan-2-yl)pyrimidine-5-sulfonamide, |
| 199 | 6-(3-cyano-1-cyclohexyl-5-methyl-1H-indol-2-yl)-N-(1,3-difluoropropan-2-yl)pyridine-3-sulfonamide, |
| 200 | 2-(3-cyano-1-cyclohexyl-5-methyl-1H-indol-2-yl)-N-(propan-2-yl)pyrimidine-5-sulfonamide, |
| 201 | 6-(3-cyano-1-cyclobutyl-5-methyl-1H-indol-2-yl)-N-[(1S)-1-cyclopropylethyl]pyridine-3-sulfonamide, |
| 202 | 2-(3-cyano-1-cyclobutyl-6-methyl-1H-indol-2-yl)-N-[(1S)-1-cyclopropylethyl]pyrimidine-5-sulfonamide, |
| 203 | 2-[3-cyano-1-(cyclopropylmethyl)-6-methyl-1H-indol-2-yl]-N-[(1S)-1-cyclopropylethyl]pyrimidine-5-sulfonamide, |
| 204 | 2-(3-cyano-1-cyclopentyl-6-methyl-1H-indol-2-yl)-N-[(1S)-1-cyclopropylethyl]pyrimidine-5-sulfonamide, |
| 205 | 2-(3-cyano-1-cyclobutyl-6-methoxy-1H-indol-2-yl)-N-[(1S)-1-cyclopropylethyl]pyrimidine-5-sulfonamide, |
| 206 | 2-(3-cyano-1-cyclopentyl-6-methoxy-1H-indol-2-yl)-N-[(1S)-1-cyclopropylethyl]pyrimidine-5-sulfonamide, |
| 207 | 2-[3-cyano-6-(difluoromethoxy)-1-(propan-2-yl)-1H-indol-2-yl]-N-[(1S)-1-cyclopropylethyl]pyrimidine-5-sulfonamide, |
| 208 | 2-[3-cyano-6-(difluoromethoxy)-1-propyl-1H-indol-2-yl]-N-[(1S)-1-cyclopropylethyl]pyrimidine-5-sulfonamide, |
| 209 | 2-[3-cyano-1-cyclopentyl-6-(difluoromethoxy)-1H-indol-2-yl]-N-[(1S)-1-cyclopropylethyl]pyrimidine-5-sulfonamide, |
| 210 | 6-[3-cyano-6-methyl-1-(propan-2-yl)-1H-indol-2-yl]-N-[(2R)-1,1,1-trifluoropropan-2-yl]pyridine-3-sulfonamide, |

-continued

| Cpd | Name |
|---|---|
| 211 | 6-(3-cyano-1-cyclopentyl-6-cyclopropyl-1H-indol-2-yl)-N-[(2R)-1,1,1-trifluoropropan-2-yl]pyridine-3-sulfonamide, |
| 212 | 6-(3-cyano-1-cyclobutyl-6-cyclopropyl-1H-indol-2-yl)-N-[(2R)-1,1,1-trifluoropropan-2-yl]pyridine-3-sulfonamide, |
| 213 | 6-(3-cyano-1-cyclohexyl-6-methyl-1H-indol-2-yl)-N-[(2R)-1,1,1-trifluoropropan-2-yl]pyridine-3-sulfonamide, |
| 214 | 6-(3-cyano-1-cyclopentyl-6-methyl-1H-indol-2-yl)-N-[(2R)-1,1,1-trifluoropropan-2-yl]pyridine-3-sulfonamide, |
| 215 | 6-(3-cyano-1-cyclobutyl-6-fluoro-1H-indol-2-yl)-N-[(2R)-1,1,1-trifluoropropan-2-yl]pyridine-3-sulfonamide, |
| 216 | 6-[3-cyano-1-(cyclopropylmethyl)-6-fluoro-1H-indol-2-yl]-N-[(2R)-1,1,1-trifluoropropan-2-yl]pyridine-3-sulfonamide, |
| 217 | 6-(3-cyano-6-fluoro-1-propyl-1H-indol-2-yl)-N-[(2R)-1,1,1-trifluoropropan-2-yl]pyridine-3-sulfonamide, |
| 218 | 6-(3-cyano-1-cyclopentyl-6-fluoro-1H-indol-2-yl)-N-[(2R)-1,1,1-trifluoropropan-2-yl]pyridine-3-sulfonamide, |
| 219 | 6-(3-cyano-1-cyclobutyl-5-fluoro-1H-indol-2-yl)-N-[(2R)-1,1,1-trifluoropropan-2-yl]pyridine-3-sulfonamide, |
| 220 | 6-(3-cyano-1-cyclopentyl-5-fluoro-1H-indol-2-yl)-N-[(2R)-1,1,1-trifluoropropan-2-yl]pyridine-3-sulfonamide, |
| 221 | 2-[5-chloro-3-cyano-1-(cyclopropylmethyl)-1H-indol-2-yl]-N-(1,3-difluoropropan-2-yl)pyrimidine-5-sulfonamide, |
| 222 | 6-(6-chloro-3-cyano-1-cyclobutyl-1H-indol-2-yl)-N-[(2R)-1,1,1-trifluoropropan-2-yl]pyridine-3-sulfonamide, |
| 223 | 6-(6-chloro-3-cyano-1-cyclopentyl-1H-indol-2-yl)-N-[(2R)-1,1,1-trifluoropropan-2-yl]pyridine-3-sulfonamide, |
| 224 | 6-(5-chloro-3-cyano-1-cyclopentyl-1H-indol-2-yl)-N-[(2R)-1,1,1-trifluoropropan-2-yl]pyridine-3-sulfonamide, |
| 225 | 6-[3-cyano-1-(cyclopropylmethyl)-5-fluoro-6-methoxy-1H-indol-2-yl]-N-(1,3-difluoropropan-2-yl)pyridine-3-sulfonamide, |
| 226 | 6-[3-cyano-6-(difluoromethoxy)-1-phenyl-1H-indol-2-yl]-N-(1,3-difluoropropan-2-yl)pyridine-3-sulfonamide, |
| 227 | 6-[3-cyano-6-(difluoromethoxy)-1-(2-fluorophenyl)-1H-indol-2-yl]-N-(1,3-difluoropropan-2-yl)pyridine-3-sulfonamide, |
| 228 | 6-[3-cyano-6-(difluoromethoxy)-1-(4-fluorophenyl)-1H-indol-2-yl]-N-(1,3-difluoropropan-2-yl)pyridine-3-sulfonamide, |
| 229 | 6-(3-cyano-1-cyclobutyl-6-methoxy-1H-indol-2-yl)-N-(1,3-difluoropropan-2-yl)pyridine-3-sulfonamide, |
| 230 | 2-(3-cyano-1-cyclobutyl-6-methoxy-1H-indol-2-yl)-N-(1,3-difluoropropan-2-yl)pyrimidine-5-sulfonamide, |
| 231 | 2-(3-cyano-1-cyclopentyl-6-methoxy-1H-indol-2-yl)-N-(1,3-difluoropropan-2-yl)pyrimidine-5-sulfonamide, |
| 232 | 2-[3-cyano-6-(difluoromethoxy)-1-propyl-1H-indol-2-yl]-N-(1,3-difluoropropan-2-yl)pyrimidine-5-sulfonamide, |
| 233 | 2-[3-cyano-1-cyclopentyl-6-(difluoromethoxy)-1H-indol-2-yl]-N-(1,3-difluoropropan-2-yl)pyrimidine-5-sulfonamide, |
| 234 | 6-(3-cyano-1-cyclohexyl-6-fluoro-1H-indol-2-yl)-N-(1,3-difluoropropan-2-yl)pyridine-3-sulfonamide, |
| 235 | 2-(3-cyano-1-cyclohexyl-6-fluoro-1H-indol-2-yl)-N-(1,3-difluoropropan-2-yl)pyrimidine-5-sulfonamide, |
| 236 | 6-(3-cyano-1-cyclobutyl-6-cyclopropyl-1H-indol-2-yl)-N-[(1S)-1-cyclopropylethyl]pyridine-3-sulfonamide, |
| 237 | 6-[3-cyano-1-(cyclopropylmethyl)-6-methyl-1H-indol-2-yl]-N-[(1S)-1-cyclopropylethyl]pyridine-3-sulfonamide, |
| 238 | 6-(3-cyano-1-cyclobutyl-6-methyl-1H-indol-2-yl)-N-[(1S)-1-cyclopropylethyl]pyridine-3-sulfonamide, |
| 239 | 6-[3-cyano-1-cyclobutyl-6-(difluoromethoxy)-1H-indol-2-yl]-N-(1,3-dihydroxypropan-2-yl)pyridine-3-sulfonamide, |
| 240 | 2-(3-cyano-1-cyclopentyl-5-fluoro-1H-indol-2-yl)-N-(1,3-difluoropropan-2-yl)pyrimidine-5-sulfonamide, |
| 241 | 2-(3-cyano-1-cyclohexyl-6-methyl-1H-indol-2-yl)-N-(1,3-difluoropropan-2-yl)pyrimidine-5-sulfonamide, |
| 242 | 2-[3-cyano-5-(difluoromethoxy)-1-ethyl-1H-indol-2-yl]-N-(propan-2-yl)pyrimidine-5-sulfonamide, |
| 243 | 6-(5-chloro-3-cyano-1-cyclobutyl-1H-indol-2-yl)-N-(3,3-difluorocyclobutyl)pyridine-3-sulfonamide, |
| 244 | 6-(6-chloro-3-cyano-1-cyclobutyl-1H-indol-2-yl)-N-(3,3-difluorocyclobutyl)pyridine-3-sulfonamide, |
| 245 | 6-(3-cyano-1-cyclobutyl-6-methyl-1H-indol-2-yl)-N-(3,3-difluorocyclobutyl)pyridine-3-sulfonamide, |
| 246 | 6-(3-cyano-1-cyclopentyl-6-methoxy-1H-indol-2-yl)-N-(3,3-difluorocyclobutyl)pyridine-3-sulfonamide, |
| 247 | 6-(3-cyano-1-cyclobutyl-6-cyclopropyl-1H-indol-2-yl)-N-(3,3-difluorocyclobutyl)pyridine-3-sulfonamide, |
| 248 | 6-[3-cyano-6-methyl-1-(pyridin-2-yl)-1H-indol-2-yl]-N-(1,3-difluoropropan-2-yl)pyridine-3-sulfonamide, |
| 249 | 6-[3-cyano-6-(difluoromethoxy)-1-(pyridin-2-yl)-1H-indol-2-yl]-N-(1,3-difluoropropan-2-yl)pyridine-3-sulfonamide, |

-continued

| Cpd | Name |
|---|---|
| 250 | 6-(3-cyano-1-cyclohexyl-5-fluoro-1H-indol-2-yl)-N-[(1S)-1-cyclopropylethyl]pyridine-3-sulfonamide, |
| 251 | 2-(3-cyano-1-cyclohexyl-6-fluoro-1H-indol-2-yl)-N-(propan-2-yl)pyrimidine-5-sulfonamide, |
| 252 | 6-(3-cyano-1-cyclohexyl-6-fluoro-1H-indol-2-yl)-N-[(2R)-1,1,1-trifluoropropan-2-yl]pyridine-3-sulfonamide, |
| 253 | 6-(3-cyano-1-cyclopentyl-6-methyl-1H-indol-2-yl)-N-[1-(trifluoromethyl)cyclobutyl]pyridine-3-sulfonamide, |
| 254 | 2-(3-cyano-1-cyclopentyl-6-cyclopropyl-1H-indol-2-yl)-N-[(1S)-1-cyclopropylethyl]pyrimidine-5-sulfonamide, |
| 255 | 6-[3-cyano-1-(cyclopropylmethyl)-6-methyl-1H-indol-2-yl]-N-[1-(trifluoromethyl)cyclopropyl]pyridine-3-sulfonamide, |
| 256 | 6-(3-cyano-1-cyclobutyl-6-methyl-1H-indol-2-yl)-N-[1-(trifluoromethyl)cyclopropyl]pyridine-3-sulfonamide, |
| 257 | 2-[6-chloro-3-cyano-1-(propan-2-yl)-1H-indol-2-yl]-N-(1,3-difluoropropan-2-yl)pyrimidine-5-sulfonamide, |
| 258 | 6-(3-cyano-1-cyclobutyl-5-ethyl-1H-indol-2-yl)-N-(1,3-difluoropropan-2-yl)pyridine-3-sulfonamide, |
| 259 | 6-[3-cyano-5-fluoro-1-(pyridin-4-yl)-1H-indol-2-yl]-N-(1,3-difluoropropan-2-yl)pyridine-3-sulfonamide, |
| 260 | 2-(3-cyano-6-methyl-1-phenyl-1H-indol-2-yl)-N-(1,3-difluoropropan-2-yl)pyrimidine-5-sulfonamide, |
| 261 | 6-(3-cyano-1-cyclohexyl-5-fluoro-1H-indol-2-yl)-N-[(2R)-1,1,1-trifluoropropan-2-yl]pyridine-3-sulfonamide, |
| 262 | 6-(3-cyano-1-cyclohexyl-6-fluoro-1H-indol-2-yl)-N-[(1S)-1-cyclopropylethyl]pyridine-3-sulfonamide, |
| 263 | 6-(3-cyano-1,6-dicyclobutyl-1H-indol-2-yl)-N-[(1S)-1-cyclopropylethyl]pyridine-3-sulfonamide, |
| 264 | 2-(3-cyano-1,6-dicyclobutyl-1H-indol-2-yl)-N-(1,3-difluoropropan-2-yl)pyrimidine-5-sulfonamide, |
| 265 | 2-(3-cyano-1,6-dicyclobutyl-1H-indol-2-yl)-N-(propan-2-yl)pyrimidine-5-sulfonamide, |
| 266 | 6-(3-cyano-1,6-dicyclobutyl-1H-indol-2-yl)-N-(propan-2-yl)pyridine-3-sulfonamide, |
| 267 | 6-[3-cyano-1-cyclobutyl-6-(2,2-difluoroethyl)-1H-indol-2-yl]-N-(1,3-difluoropropan-2-yl)pyridine-3-sulfonamide, |
| 268 | N-{5-[3-cyano-1-cyclobutyl-6-(pyrimidin-2-yloxy)-1H-indol-2-yl]pyridin-2-yl}-2-methylpropane-2-sulfonamide, |
| 269 | N-{5-[3-cyano-1-(cyclopropylmethyl)-6-(difluoromethoxy)-1H-indol-2-yl]pyridin-2-yl}-2-methylpropane-2-sulfonamide, |
| 270 | N-{6-[3-cyano-1-(cyclopropylmethyl)-6-(difluoromethoxy)-1H-indol-2-yl]pyridin-3-yl}cyclopropanesulfonamide, |
| 271 | N-{6-[3-cyano-1-cyclobutyl-6-(pyrimidin-2-yloxy)-1H-indol-2-yl]pyridin-3-yl}propane-1-sulfonamide, |
| 272 | N-(6-{3-cyano-6-[(3-cyanopyridin-2-yl)oxy]-1-cyclobutyl-1H-indol-2-yl}pyridin-3-yl)propane-1-sulfonamide, |
| 273 | N-(6-{3-cyano-6-[(3-cyanopyrazin-2-yl)oxy]-1-cyclobutyl-1H-indol-2-yl}pyridin-3-yl)propane-1-sulfonamide, |
| 274 | N-{6-[3-cyano-1-cyclobutyl-6-(propan-2-yloxy)-1H-indol-2-yl]pyridazin-3-yl}cyclopropanesulfonamide, |
| 275 | N-{6-[3-cyano-1-cyclobutyl-6-(propan-2-yloxy)-1H-indol-2-yl]pyridazin-3-yl}methanesulfonamide, |
| 276 | N-{6-[3-cyano-1-cyclobutyl-6-(propan-2-yloxy)-1H-indol-2-yl]pyridazin-3-yl}ethanesulfonamide, |
| 277 | N-[6-(3-cyano-1-cyclobutyl-6-methoxy-1H-indol-2-yl)pyridazin-3-yl]ethanesulfonamide, |
| 278 | N-[6-(3-cyano-1-cyclobutyl-6-methoxy-1H-indol-2-yl)pyridazin-3-yl]-2-methylpropane-2-sulfonamide, |
| 279 | N-{6-[3-cyano-1-(cyclopropylmethyl)-6-(propan-2-yloxy)-1H-indol-2-yl]pyridin-3-yl}ethanesulfonamide, |
| 280 | N-{6-[3-cyano-1-(cyclopropylmethyl)-6-(propan-2-yloxy)-1H-indol-2-yl]pyridin-3-yl}cyclopropanesulfonamide, |
| 281 | N-{6-[3-cyano-1-(cyclopropylmethyl)-6-(propan-2-yloxy)-1H-indol-2-yl]pyridin-3-yl}propane-2-sulfonamide, |
| 282 | N-{6-[3-cyano-1-ethyl-6-(propan-2-yloxy)-1H-indol-2-yl]pyridin-3-yl}-N-(propan-2-yl)ethanesulfonamide, |
| 283 | N-{6-[3-cyano-1-(cyclopropylmethyl)-6-(2,2,2-trifluoroethoxy)-1H-indol-2-yl]pyridin-3-yl}propane-2-sulfonamide, |
| 284 | N-{6-[3-cyano-1-(cyclopropylmethyl)-6-(2,2,2-trifluoroethoxy)-1H-indol-2-yl]pyridin-3-yl}ethanesulfonamide, |
| 285 | N-{6-[3-cyano-1-ethyl-6-(propan-2-yloxy)-1H-indol-2-yl]pyridin-3-yl}cyclopropanesulfonamide, |
| 286 | N-{6-[3-cyano-1-ethyl-6-(propan-2-yloxy)-1H-indol-2-yl]pyridin-3-yl}propane-2-sulfonamide, |
| 287 | N-[5-(3-cyano-1-cyclobutyl-6-cyclopropyl-1H-indol-2-yl)pyridin-2-yl]methanesulfonamide, |
| 288 | N-[5-(3-cyano-1-cyclobutyl-6-cyclopropyl-1H-indol-2-yl)pyridin-2-yl]ethanesulfonamide, |

| Cpd | Name |
|---|---|
| 289 | N-[5-(3-cyano-1-cyclobutyl-6-cyclopropyl-1H-indol-2-yl)pyridin-2-yl]propane-2-sulfonamide, |
| 290 | N-{5-[3-cyano-1-(cyclopropylmethyl)-6-(2,2,2-trifluoroethoxy)-1H-indol-2-yl]pyridin-2-yl}ethanesulfonamide, |
| 291 | N-{5-[3-cyano-1-(cyclopropylmethyl)-6-(2,2,2-trifluoroethoxy)-1H-indol-2-yl]pyridin-2-yl}propane-2-sulfonamide, |
| 292 | N-{5-[3-cyano-1-ethyl-6-(propan-2-yloxy)-1H-indol-2-yl]pyridin-2-yl}-N-(2,2-difluoroethyl)cyclopropanesulfonamide, |
| 293 | N-{5-[3-cyano-1-ethyl-6-(propan-2-yloxy)-1H-indol-2-yl]pyridin-2-yl}-N-(2-hydroxyethyl)cyclopropanesulfonamide, |
| 294 | N-{5-[3-cyano-1-ethyl-6-(propan-2-yloxy)-1H-indol-2-yl]pyridin-2-yl}-N-(cyanomethyl)cyclopropanesulfonamide, |
| 295 | N-{5-[3-cyano-1-cyclobutyl-6-(difluoromethoxy)-1H-indol-2-yl]pyridin-2-yl}-2-methylpropane-2-sulfonamide, |
| 296 | N-[6-(3-cyano-1-cyclopentyl-6-methyl-1H-indol-2-yl)pyridin-3-yl]cyclopropanesulfonamide, |
| 297 | N-[6-(3-cyano-1-cyclobutyl-6-methyl-1H-indol-2-yl)pyridin-3-yl]cyclopropanesulfonamide, |
| 298 | N-[6-(5-chloro-3-cyano-1-cyclohexyl-1H-indol-2-yl)pyridin-3-yl]cyclopropanesulfonamide, |
| 299 | N-{5-[3-cyano-6-(difluoromethoxy)-1-(propan-2-yl)-1H-indol-2-yl]pyridin-2-yl}-2-methylpropane-2-sulfonamide, |
| 300 | 6-[3-cyano-1-cyclobutyl-6-(difluoromethoxy)-1H-indol-2-yl]-N-[(2S)-1,1,1-trifluoropropan-2-yl]pyridine-3-sulfonamide, |
| 301 | 6-[3-cyano-1-cyclobutyl-6-(difluoromethoxy)-1H-indol-2-yl]-N-(1-cyanoethyl)pyridine-3-sulfonamide, |
| 302 | 2-[3-cyano-1-(cyclopropylmethyl)-5-fluoro-1H-indol-2-yl]-N-(1,3-difluoropropan-2-yl)pyrimidine-5-sulfonamide, |
| 303 | 2-[3-cyano-1-(cyclopropylmethyl)-5-fluoro-1H-indol-2-yl]-N-(propan-2-yl)pyrimidine-5-sulfonamide, |
| 304 | 6-[3-cyano-1-cyclohexyl-6-(trifluoromethoxy)-1H-indol-2-yl]-N-[(2R)-1,1,1-trifluoropropan-2-yl]pyridine-3-sulfonamide, |
| 305 | 6-[3-cyano-1-cyclohexyl-6-(trifluoromethoxy)-1H-indol-2-yl]-N-[(1S)-1-cyclopropylethyl]pyridine-3-sulfonamide, |
| 306 | 2-[3-cyano-1-cyclohexyl-6-(trifluoromethoxy)-1H-indol-2-yl]-N-(1,3-difluoropropan-2-yl)pyrimidine-5-sulfonamide, |
| 307 | 6-(3-cyano-1-cyclopentyl-6-fluoro-1H-indol-2-yl)-N-(1,3-difluoropropan-2-yl)pyridine-3-sulfonamide, |
| 308 | 6-[3-cyano-1-(propan-2-yl)-6-(trifluoromethoxy)-1H-indol-2-yl]-N-[(1S)-1-cyclopropylethyl]pyridine-3-sulfonamide, |
| 309 | 6-[3-cyano-1-(cyclopropylmethyl)-6-(trifluoromethoxy)-1H-indol-2-yl]-N-[(1S)-1-cyclopropylethyl]pyridine-3-sulfonamide, |
| 310 | 6-(3-cyano-1-cyclopentyl-6-ethyl-1H-indol-2-yl)-N-(1,3-difluoropropan-2-yl)pyridine-3-sulfonamide, |
| 311 | 6-(3-cyano-1-cyclopentyl-6-ethyl-1H-indol-2-yl)-N-[(2R)-1,1,1-trifluoropropan-2-yl]pyridine-3-sulfonamide, |
| 312 | 6-(3-cyano-1-cyclopentyl-6-ethyl-1H-indol-2-yl)-N-[(1S)-1-cyclopropylethyl]pyridine-3-sulfonamide, |
| 313 | 6-(3-cyano-1-cyclopentyl-5-methyl-1H-indol-2-yl)-N-[1-(trifluoromethyl)cyclopropyl]pyridine-3-sulfonamide, |
| 314 | 2-(5-chloro-3-cyano-1-cyclopentyl-1H-indol-2-yl)-N-(propan-2-yl)pyrimidine-5-sulfonamide, |
| 315 | 2-[3-cyano-1-cyclobutyl-6-(fluoromethyl)-1H-indol-2-yl]-N-(propan-2-yl)pyrimidine-5-sulfonamide, |
| 316 | 6-(5-chloro-3-cyano-1-cyclobutyl-1H-indol-2-yl)-N-[(2R)-1,1,1-trifluoropropan-2-yl]pyridine-3-sulfonamide, |
| 317 | 6-[3-cyano-1-cyclobutyl-6-(fluoromethyl)-1H-indol-2-yl]-N-[(1S)-1-cyclopropylethyl]pyridine-3-sulfonamide, |
| 318 | 6-[3-cyano-1-cyclobutyl-6-(fluoromethyl)-1H-indol-2-yl]-N-(1,3-difluoropropan-2-yl)pyridine-3-sulfonamide, |
| 319 | 6-[3-cyano-1-cyclobutyl-6-(fluoromethyl)-1H-indol-2-yl]-N-[(2R)-1,1,1-trifluoropropan-2-yl]pyridine-3-sulfonamide, |
| 320 | 6-[3-cyano-1-cyclopentyl-6-(trifluoromethoxy)-1H-indol-2-yl]-N-[(1S)-1-cyclopropylethyl]pyridine-3-sulfonamide, |
| 321 | 2-[3-cyano-1-cyclobutyl-6-(morpholin-4-yl)-1H-indol-2-yl]-N-(1,3-difluoropropan-2-yl)pyrimidine-5-sulfonamide, |
| 322 | 6-[3-cyano-1-cyclobutyl-6-(morpholin-4-yl)-1H-indol-2-yl]-N-(1,3-difluoropropan-2-yl)pyridine-3-sulfonamide, |
| 323 | 2-[3-cyano-1-cyclobutyl-6-(difluoromethoxy)-1H-indol-2-yl]-N-[(2S)-1,1,1-trifluoropropan-2-yl]pyrimidine-5-sulfonamide, |
| 324 | 2-(3-cyano-1-cyclobutyl-6-cyclopropyl-1H-indol-2-yl)-N-[(2S)-1,1,1-trifluoropropan-2-yl]pyrimidine-5-sulfonamide, |
| 325 | 2-(3-cyano-1-cyclobutyl-6-methyl-1H-indol-2-yl)-N-[(2S)-1,1,1-trifluoropropan-2-yl]pyrimidine-5-sulfonamide, |
| 326 | 2-[3-cyano-1-cyclopentyl-6-(difluoromethoxy)-1H-indol-2-yl]-N-[(2S)-1,1,1-trifluoropropan-2-yl]pyrimidine-5-sulfonamide, |
| 327 | 6-(3-cyano-1-cyclopentyl-5-fluoro-1H-indol-2-yl)-N-[1-(trifluoromethyl)cyclopropyl]pyridine-3-sulfonamide, |

| Cpd | Name |
|---|---|
| 328 | 6-(3-cyano-1-cyclobutyl-5-methyl-1H-indol-2-yl)-N-[1-(trifluoromethyl)cyclopropyl]pyridine-3-sulfonamide, |
| 329 | 6-(3-cyano-1-cyclobutyl-5-fluoro-1H-indol-2-yl)-N-[1-(trifluoromethyl)cyclopropyl]pyridine-3-sulfonamide, |
| 330 | 2-[3-cyano-1-cyclobutyl-6-(difluoromethyl)-1H-indol-2-yl]-N-(1,3-difluoropropan-2-yl)pyrimidine-5-sulfonamide, |
| 331 | 6-[3-cyano-1-cyclobutyl-6-(difluoromethyl)-1H-indol-2-yl]-N-(1,3-difluoropropan-2-yl)pyridine-3-sulfonamide, |
| 332 | 2-[3-cyano-1-cyclobutyl-6-(difluoromethyl)-1H-indol-2-yl]-N-(propan-2-yl)pyrimidine-5-sulfonamide, |
| 333 | 6-[3-cyano-1-cyclobutyl-6-(difluoromethyl)-1H-indol-2-yl]-N-(propan-2-yl)pyridine-3-sulfonamide, |
| 334 | 6-[3-cyano-1-cyclobutyl-6-(difluoromethyl)-1H-indol-2-yl]-N-[(2R)-1,1,1-trifluoropropan-2-yl]pyridine-3-sulfonamide, |
| 335 | 6-[3-cyano-1-cyclobutyl-6-(difluoromethyl)-1H-indol-2-yl]-N-[(1S)-1-cyclopropylethyl]pyridine-3-sulfonamide, |
| 336 | 6-[3-cyano-5-fluoro-1-(4-methoxyphenyl)-1H-indol-2-yl]-N-(1,3-difluoropropan-2-yl)pyridine-3-sulfonamide, |
| 337 | 2-[3-cyano-5-fluoro-1-(4-methoxyphenyl)-1H-indol-2-yl]-N-(1,3-difluoropropan-2-yl)pyrimidine-5-sulfonamide, |
| 338 | 6-(3-cyano-1-cyclobutyl-6-ethyl-1H-indol-2-yl)-N-[(2S)-1,1,1-trifluoropropan-2-yl]pyridine-3-sulfonamide, |
| 339 | 6-(3-cyano-1-cyclobutyl-5-ethyl-1H-indol-2-yl)-N-[(2S)-1,1,1-trifluoropropan-2-yl]pyridine-3-sulfonamide, |
| 340 | 6-(3-cyano-1-cyclobutyl-5-fluoro-6-methyl-1H-indol-2-yl)-N-[(2S)-1,1,1-trifluoropropan-2-yl]pyridine-3-sulfonamide, |
| 341 | 6-[3-cyano-1-cyclohexyl-6-(difluoromethoxy)-1H-indol-2-yl]-N-[(2S)-1,1,1-trifluoropropan-2-yl]pyridine-3-sulfonamide, |
| 342 | 6-(3-cyano-1,6-dicyclobutyl-1H-indol-2-yl)-N-(1,3-difluoropropan-2-yl)pyridine-3-sulfonamide, |
| 343 | 6-(3-cyano-6-cyclobutyl-1-cyclopentyl-1H-indol-2-yl)-N-[(2R)-1,1,1-trifluoropropan-2-yl]pyridine-3-sulfonamide, |
| 344 | 2-[3-cyano-6-cyclopropyl-1-(cyclopropylmethyl)-1H-indol-2-yl]-N-(1,3-difluoropropan-2-yl)pyrimidine-5-sulfonamide, |
| 345 | 6-(3-cyano-1-cyclopentyl-5-methyl-1H-indol-2-yl)-N-[(2S)-1,1,1-trifluoropropan-2-yl]pyridine-3-sulfonamide, |
| 346 | 6-(3,5-dicyano-1-cyclopentyl-1H-indol-2-yl)-N-[(2S)-1,1,1-trifluoropropan-2-yl]pyridine-3-sulfonamide, |
| 347 | 6-[3,6-dicyano-1-(cyclopropylmethyl)-1H-indol-2-yl]-N-(1,3-difluoropropan-2-yl)pyridine-3-sulfonamide, |
| 348 | 6-[3,6-dicyano-1-(cyclopropylmethyl)-1H-indol-2-yl]-N-(propan-2-yl)pyridine-3-sulfonamide, |
| 349 | 6-[3,6-dicyano-1-(cyclopropylmethyl)-1H-indol-2-yl]-N-[(2S)-1,1,1-trifluoropropan-2-yl]pyridine-3-sulfonamide, |
| 350 | N-[(1S)-1-cyclopropylethyl]-6-[3,6-dicyano-1-(cyclopropylmethyl)-1H-indol-2-yl]pyridine-3-sulfonamide, |
| 351 | 6-(3-cyano-1-cyclobutyl-6-methyl-1H-indol-2-yl)-N-[(2S)-1,1,1-trifluoropropan-2-yl]pyridine-3-sulfonamide, |
| 352 | 6-(3-cyano-1-cyclopentyl-6-methyl-1H-indol-2-yl)-N-[(2S)-1,1,1-trifluoropropan-2-yl]pyridine-3-sulfonamide, |
| 353 | 6-[3-cyano-1-(cyclopropylmethyl)-6-methyl-1H-indol-2-yl]-N-[(2S)-1,1,1-trifluoropropan-2-yl]pyridine-3-sulfonamide, |
| 354 | 6-(3-cyano-1-cyclohexyl-6-methyl-1H-indol-2-yl)-N-[(2S)-1,1,1-trifluoropropan-2-yl]pyridine-3-sulfonamide, |
| 355 | 6-[3-cyano-6-methyl-1-(propan-2-yl)-1H-indol-2-yl]-N-[(2S)-1,1,1-trifluoropropan-2-yl]pyridine-3-sulfonamide, |
| 356 | 6-[3-cyano-5-fluoro-1-(4-methylphenyl)-1H-indol-2-yl]-N-(1,3-difluoropropan-2-yl)pyridine-3-sulfonamide, |
| 357 | 2-[3-cyano-5-fluoro-1-(4-methylphenyl)-1H-indol-2-yl]-N-(propan-2-yl)pyrimidine-5-sulfonamide, |
| 358 | 6-[3-cyano-1-cyclopentyl-6-(trifluoromethoxy)-1H-indol-2-yl]-N-[(2S)-1,1,1-trifluoropropan-2-yl]pyridine-3-sulfonamide, |
| 359 | 6-[3-cyano-6-(difluoromethoxy)-1-(propan-2-yl)-1H-indol-2-yl]-N-[(2S)-1,1,1-trifluoropropan-2-yl]pyridine-3-sulfonamide, |
| 360 | 6-(6-chloro-3-cyano-1-cyclobutyl-5-fluoro-1H-indol-2-yl)-N-[(2S)-1,1,1-trifluoropropan-2-yl]pyridine-3-sulfonamide, |
| 361 | 2-[3-cyano-1-cyclobutyl-6-(fluoromethyl)-1H-indol-2-yl]-N-(1,3-difluoropropan-2-yl)pyrimidine-5-sulfonamide, |
| 362 | 6-[3-cyano-1-cyclobutyl-6-(fluoromethyl)-1H-indol-2-yl]-N-[(2S)-1,1,1-trifluoropropan-2-yl]pyridine-3-sulfonamide, |
| 363 | 6-[3-cyano-1-cyclobutyl-6-(difluoromethyl)-1H-indol-2-yl]-N-[(2S)-1,1,1-trifluoropropan-2-yl]pyridine-3-sulfonamide, |
| 364 | 6-(6-chloro-3-cyano-1-cyclopentyl-1H-indol-2-yl)-N-[(2S)-1,1,1-trifluoropropan-2-yl]pyridine-3-sulfonamide, |
| 365 | 6-(5-chloro-3-cyano-1-cyclopentyl-1H-indol-2-yl)-N-[(2S)-1,1,1-trifluoropropan-2-yl]pyridine-3-sulfonamide, |
| 367 | N-[(1S)-1-cyclopropylethyl]-2-(3,5-dicyano-1-cyclopentyl-1H-indol-2-yl)pyrimidine-5-sulfonamide, |

| Cpd | Name |
|---|---|
| 368 | 6-[3-cyano-6-(difluoromethoxy)-1-(4-fluorophenyl)-1H-indol-2-yl]-N-[(2S)-1,1,1-trifluoropropan-2-yl]pyridine-3-sulfonamide, |
| 369 | 6-(3-cyano-1-cyclobutyl-6-cyclopropyl-1H-indol-2-yl)-N-[(2S)-1,1,1-trifluoropropan-2-yl]pyridine-3-sulfonamide, |
| 370 | 6-[3-cyano-1-cyclobutyl-6-(trifluoromethoxy)-1H-indol-2-yl]-N-[(2S)-1,1,1-trifluoropropan-2-yl]pyridine-3-sulfonamide, |
| 371 | 6-(3-cyano-1-cyclopentyl-6-methyl-1H-indol-2-yl)-N-(1,1,1-trifluoro-2-methylpropan-2-yl)pyridine-3-sulfonamide, |
| 372 | 6-[3-cyano-1-(cyclopropylmethyl)-5-methyl-1H-indol-2-yl]-N-[(2S)-1,1,1-trifluoropropan-2-yl]pyridine-3-sulfonamide, |
| 373 | 6-[3-cyano-1-(cyclopropylmethyl)-5-methyl-1H-indol-2-yl]-N-(1,3-difluoropropan-2-yl)pyridine-3-sulfonamide, |
| 374 | 6-(3-cyano-1-cyclopentyl-5-ethyl-1H-indol-2-yl)-N-[(2S)-1,1,1-trifluoropropan-2-yl]pyridine-3-sulfonamide, |
| 375 | 6-(6-chloro-3-cyano-1-cyclobutyl-1H-indol-2-yl)-N-[(2S)-1,1,1-trifluoropropan-2-yl]pyridine-3-sulfonamide, |
| 376 | 6-(5-chloro-3-cyano-1-cyclobutyl-1H-indol-2-yl)-N-[(2S)-1,1,1-trifluoropropan-2-yl]pyridine-3-sulfonamide, |
| 377 | 2-[3-cyano-1-cyclobutyl-5-(fluoromethyl)-1H-indol-2-yl]-N-(1,3-difluoropropan-2-yl)pyrimidine-5-sulfonamide, |
| 378 | 6-[3-cyano-1-cyclobutyl-5-(difluoromethyl)-1H-indol-2-yl]-N-(1,3-difluoropropan-2-yl)pyridine-3-sulfonamide, |
| 379 | 2-[3-cyano-1-cyclobutyl-5-(difluoromethyl)-1H-indol-2-yl]-N-(1,3-difluoropropan-2-yl)pyrimidine-5-sulfonamide, |
| 380 | 2-[3-cyano-1-cyclobutyl-5-(difluoromethyl)-1H-indol-2-yl]-N-[(2S)-1,1,1-trifluoropropan-2-yl]pyrimidine-5-sulfonamide, |
| 381 | 6-(3-cyano-1-cyclopentyl-5-ethyl-1H-indol-2-yl)-N-(1,3-difluoropropan-2-yl)pyridine-3-sulfonamide, |
| 382 | 6-[3-cyano-1-cyclopentyl-6-(difluoromethoxy)-1H-indol-2-yl]-N-(1,1,1-trifluoro-2-methylpropan-2-yl)pyridine-3-sulfonamide, |
| 383 | 6-(3-cyano-1-cyclopentyl-6-cyclopropyl-1H-indol-2-yl)-N-[(2S)-1,1,1-trifluoropropan-2-yl]pyridine-3-sulfonamide, |
| 384 | 6-[3-cyano-1-cyclobutyl-6-(2,2-difluoroethyl)-1H-indol-2-yl]-N-[(2S)-1,1,1-trifluoropropan-2-yl]pyridine-3-sulfonamide, |
| 385 | 2-[3-cyano-1-cyclobutyl-6-(2,2-difluoroethyl)-1H-indol-2-yl]-N-[(2S)-1,1,1-trifluoropropan-2-yl]pyrimidine-5-sulfonamide, |
| 386 | 6-[3-cyano-5-fluoro-1-(pyridin-2-yl)-1H-indol-2-yl]-N-[(2S)-1,1,1-trifluoropropan-2-yl]pyridine-3-sulfonamide, |
| 387 | 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, |
| 388 | 2-[3-cyano-1-(cyclopropylmethyl)-5-methyl-1H-indol-2-yl]-N-(propan-2-yl)pyrimidine-5-sulfonamide, |
| 389 | 2-[3-cyano-1-(cyclopropylmethyl)-5-methyl-1H-indol-2-yl]-N-[(2S)-1,1,1-trifluoropropan-2-yl]pyrimidine-5-sulfonamide, |
| 390 | 2-(3-cyano-1-cyclohexyl-5-methyl-1H-indol-2-yl)-N-[(2S)-1,1,1-trifluoropropan-2-yl]pyrimidine-5-sulfonamide, |
| 391 | 2-(3-cyano-1-cyclopentyl-5-methyl-1H-indol-2-yl)-N-[(2S)-1,1,1-trifluoropropan-2-yl]pyrimidine-5-sulfonamide, |
| 392 | 2-(3,5-dicyano-1-cyclopentyl-1H-indol-2-yl)-N-[(2S)-1,1,1-trifluoropropan-2-yl]pyrimidine-5-sulfonamide, |
| 393 | 2-(3-cyano-1-cyclohexyl-5-fluoro-1H-indol-2-yl)-N-[(2S)-1,1,1-trifluoropropan-2-yl]pyrimidine-5-sulfonamide, |
| 394 | 6-(3-cyano-1-cyclohexyl-6-fluoro-1H-indol-2-yl)-N-[(2S)-1,1,1-trifluoropropan-2-yl]pyridine-3-sulfonamide, |
| 395 | 6-(3-cyano-1-cyclobutyl-6-fluoro-1H-indol-2-yl)-N-[(2S)-1,1,1-trifluoropropan-2-yl]pyridine-3-sulfonamide, |
| 396 | 6-(3-cyano-1-cyclopentyl-6-fluoro-1H-indol-2-yl)-N-[(2S)-1,1,1-trifluoropropan-2-yl]pyridine-3-sulfonamide, |
| 397 | 6-[3-cyano-1-(cyclopropylmethyl)-6-fluoro-1H-indol-2-yl]-N-[(2S)-1,1,1-trifluoropropan-2-yl]pyridine-3-sulfonamide, |
| 398 | 2-[3-cyano-1-(cyclopropylmethyl)-6-(difluoromethoxy)-1H-indol-2-yl]-N-[(2S)-1,1,1-trifluoropropan-2-yl]pyrimidine-5-sulfonamide, |
| 399 | 2-[3-cyano-6-(difluoromethoxy)-1-(propan-2-yl)-1H-indol-2-yl]-N-[(2S)-1,1,1-trifluoropropan-2-yl]pyrimidine-5-sulfonamide, |
| 400 | 2-[3-cyano-6-(difluoromethoxy)-1-propyl-1H-indol-2-yl]-N-[(2S)-1,1,1-trifluoropropan-2-yl]pyrimidine-5-sulfonamide, |
| 401 | 2-(3-cyano-1-cyclopentyl-6-cyclopropyl-1H-indol-2-yl)-N-[(2S)-1,1,1-trifluoropropan-2-yl]pyrimidine-5-sulfonamide, |
| 402 | 2-[3-cyano-1-(cyclopropylmethyl)-6-methyl-1H-indol-2-yl]-N-[(2S)-1,1,1-trifluoropropan-2-yl]pyrimidine-5-sulfonamide, |
| 403 | 2-[3-cyano-6-methyl-1-(propan-2-yl)-1H-indol-2-yl]-N-[(2S)-1,1,1-trifluoropropan-2-yl]pyrimidine-5-sulfonamide, |
| 404 | 2-(3-cyano-1-cyclopentyl-6-methyl-1H-indol-2-yl)-N-[(2S)-1,1,1-trifluoropropan-2-yl]pyrimidine-5-sulfonamide, |
| 405 | 2-(3-cyano-1-cyclobutyl-6-methoxy-1H-indol-2-yl)-N-[(2S)-1,1,1-trifluoropropan-2-yl]pyrimidine-5-sulfonamide, |
| 406 | 2-(3-cyano-1-cyclopentyl-6-methoxy-1H-indol-2-yl)-N-[(2S)-1,1,1-trifluoropropan-2-yl]pyrimidine-5-sulfonamide, |

| Cpd | Name |
|---|---|
| 407 | 6-(3-cyano-1-cyclopentyl-5-fluoro-6-methyl-1H-indol-2-yl)-N-(1,3-difluoropropan-2-yl)pyridine-3-sulfonamide, |
| 408 | 6-(3-cyano-1-cyclopentyl-5-fluoro-6-methyl-1H-indol-2-yl)-N-[(2S)-1,1,1-trifluoropropan-2-yl]pyridine-3-sulfonamide, |
| 409 | 6-(3-cyano-1-cyclopentyl-5-fluoro-6-methyl-1H-indol-2-yl)-N-[(2R)-1,1,1-trifluoropropan-2-yl]pyridine-3-sulfonamide, |
| 410 | 6-(3-cyano-1-cyclohexyl-5-fluoro-1H-indol-2-yl)-N-[(2S)-1,1,1-trifluoropropan-2-yl]pyridine-3-sulfonamide, |
| 411 | 2-(3-cyano-1-cyclohexyl-6-fluoro-1H-indol-2-yl)-N-[(2S)-1,1,1-trifluoropropan-2-yl]pyrimidine-5-sulfonamide, |
| 412 | 6-[3-cyano-1-(cyclohex-2-en-1-yl)-5-fluoro-1H-indol-2-yl]-N-[(2R)-1,1,1-trifluoropropan-2-yl]pyridine-3-sulfonamide, |
| 413 | 6-[3-cyano-1-(cyclohex-2-en-1-yl)-5-fluoro-1H-indol-2-yl]-N-[(2S)-1,1,1-trifluoropropan-2-yl]pyridine-3-sulfonamide, |
| 414 | 2-(3-cyano-1-cyclobutyl-5-methyl-1H-indol-2-yl)-N-[(2S)-1,1,1-trifluoropropan-2-yl]pyrimidine-5-sulfonamide, |
| 415 | 2-[6-chloro-3-cyano-1-(cyclopropylmethyl)-1H-indol-2-yl]-N-[(2S)-1,1,1-trifluoropropan-2-yl]pyrimidine-5-sulfonamide, |
| 416 | 2-(3-cyano-1-cyclobutyl-5-fluoro-1H-indol-2-yl)-N-(propan-2-yl)pyrimidine-5-sulfonamide, |
| 417 | 2-(6-chloro-3-cyano-1-cyclopentyl-1H-indol-2-yl)-N-[(2S)-1,1,1-trifluoropropan-2-yl]pyrimidine-5-sulfonamide, |
| 418 | 2-[6-chloro-3-cyano-1-(propan-2-yl)-1H-indol-2-yl]-N-[(2S)-1,1,1-trifluoropropan-2-yl]pyrimidine-5-sulfonamide, |
| 419 | 2-(5-chloro-3-cyano-1-cyclopentyl-1H-indol-2-yl)-N-[(2S)-1,1,1-trifluoropropan-2-yl]pyrimidine-5-sulfonamide, |
| 420 | 2-[5-chloro-3-cyano-1-(propan-2-yl)-1H-indol-2-yl]-N-[(2S)-1,1,1-trifluoropropan-2-yl]pyrimidine-5-sulfonamide, |
| 421 | 6-(3-cyano-1-cyclobutyl-7-fluoro-6-methyl-1H-indol-2-yl)-N-[(2S)-1,1,1-trifluoropropan-2-yl]pyridine-3-sulfonamide, |
| 422 | 6-(3-cyano-1-cyclobutyl-7-fluoro-6-methyl-1H-indol-2-yl)-N-(1,3-difluoropropan-2-yl)pyridine-3-sulfonamide, |
| 423 | 6-(3-cyano-1-cyclopentyl-7-fluoro-6-methyl-1H-indol-2-yl)-N-(1,3-difluoropropan-2-yl)pyridine-3-sulfonamide, |
| 424 | 6-(3-cyano-1-cyclopentyl-7-fluoro-6-methyl-1H-indol-2-yl)-N-[(2S)-1,1,1-trifluoropropan-2-yl]pyridine-3-sulfonamide, |
| 425 | 6-[3-cyano-6-methyl-1-(propan-2-yl)-1H-indol-2-yl]-N-[(1S)-1-cyclopropylethyl]pyridine-3-sulfonamide, |
| 426 | 6-(3-cyano-1-cyclopentyl-6-methyl-1H-indol-2-yl)-N-[(1S)-1-cyclopropylethyl]pyridine-3-sulfonamide, |
| 427 | 6-(3-cyano-1-cyclobutyl-6-methoxy-1H-indol-2-yl)-N-[(2S)-1,1,1-trifluoropropan-2-yl]pyridine-3-sulfonamide, |
| 428 | 6-(3-cyano-1-cyclobutyl-6-methoxy-1H-indol-2-yl)-N-[(2R)-1,1,1-trifluoropropan-2-yl]pyridine-3-sulfonamide, |
| 429 | 6-(3-cyano-1-cyclobutyl-6-methoxy-1H-indol-2-yl)-N-[(1S)-1-cyclopropylethyl]pyridine-3-sulfonamide, |
| 430 | 6-(3-cyano-1-cyclopentyl-6-methoxy-1H-indol-2-yl)-N-[(2S)-1,1,1-trifluoropropan-2-yl]pyridine-3-sulfonamide, |
| 431 | 6-(3-cyano-1-cyclopentyl-6-methoxy-1H-indol-2-yl)-N-[(2R)-1,1,1-trifluoropropan-2-yl]pyridine-3-sulfonamide, |
| 432 | 6-(3-cyano-1-cyclopentyl-6-methoxy-1H-indol-2-yl)-N-[(1S)-1-cyclopropylethyl]pyridine-3-sulfonamide, |
| 433 | 6-(3-cyano-1-cyclopentyl-6-cyclopropyl-1H-indol-2-yl)-N-[(1S)-1-cyclopropylethyl]pyridine-3-sulfonamide, |
| 434 | 6-(3-cyano-1-cyclobutyl-5-fluoro-1H-indol-2-yl)-N-[(2S)-1,1,1-trifluoropropan-2-yl]pyridine-3-sulfonamide, |
| 435 | 6-(3-cyano-1-cyclopentyl-5-fluoro-1H-indol-2-yl)-N-[(2S)-1,1,1-trifluoropropan-2-yl]pyridine-3-sulfonamide, |
| 436 | 6-[3-cyano-1-(cyclopropylmethyl)-5-fluoro-1H-indol-2-yl]-N-[(2S)-1,1,1-trifluoropropan-2-yl]pyridine-3-sulfonamide, |
| 437 | 6-[6-chloro-3-cyano-1-(pyridin-2-yl)-1H-indol-2-yl]-N-[(2S)-1,1,1-trifluoropropan-2-yl]pyridine-3-sulfonamide, |
| 438 | 6-[6-chloro-3-cyano-1-(pyridin-2-yl)-1H-indol-2-yl]-N-(1,3-difluoropropan-2-yl)pyridine-3-sulfonamide, |
| 439 | 6-[3-cyano-5-fluoro-1-(pyridin-2-yl)-1H-indol-2-yl]-N-(propan-2-yl)pyridine-3-sulfonamide, |
| 440 | 6-(3-cyano-6-methyl-1-phenyl-1H-indol-2-yl)-N-[(2S)-1,1,1-trifluoropropan-2-yl]pyridine-3-sulfonamide, |
| 441 | 6-(5-chloro-3-cyano-1-phenyl-1H-indol-2-yl)-N-[(2S)-1,1,1-trifluoropropan-2-yl]pyridine-3-sulfonamide, |
| 442 | 6-[5-chloro-3-cyano-1-(pyridin-2-yl)-1H-indol-2-yl]-N-[(2S)-1,1,1-trifluoropropan-2-yl]pyridine-3-sulfonamide, |
| 443 | 6-[5-chloro-3-cyano-1-(pyridin-2-yl)-1H-indol-2-yl]-N-(1,3-difluoropropan-2-yl)pyridine-3-sulfonamide, |
| 444 | 6-(5-chloro-3-cyano-1-cyclobutyl-6-methyl-1H-indol-2-yl)-N-(1,3-difluoropropan-2-yl)pyridine-3-sulfonamide, |
| 445 | 6-(5-chloro-3-cyano-1-cyclobutyl-6-methyl-1H-indol-2-yl)-N-[(2R)-1,1,1-trifluoropropan-2-yl]pyridine-3-sulfonamide, |

| Cpd | Name |
|---|---|
| 446 | 6-(5-chloro-3-cyano-1-cyclobutyl-6-methyl-1H-indol-2-yl)-N-[(2S)-1,1,1-trifluoropropan-2-yl]pyridine-3-sulfonamide, |
| 447 | 2-(5-chloro-3-cyano-1-cyclobutyl-6-methyl-1H-indol-2-yl)-N-(1,3-difluoropropan-2-yl)pyrimidine-5-sulfonamide, |
| 448 | 2-(5-chloro-3-cyano-1-cyclobutyl-6-methyl-1H-indol-2-yl)-N-[(2S)-1,1,1-trifluoropropan-2-yl]pyrimidine-5-sulfonamide, |
| 449 | 2-[6-chloro-3-cyano-1-(pyridin-2-yl)-1H-indol-2-yl]-N-[(2S)-1,1,1-trifluoropropan-2-yl]pyrimidine-5-sulfonamide, |
| 450 | 2-[6-chloro-3-cyano-1-(pyridin-2-yl)-1H-indol-2-yl]-N-(1,3-difluoropropan-2-yl)pyrimidine-5-sulfonamide, |
| 451 | 2-(3-cyano-1-cyclobutyl-5-fluoro-1H-indol-2-yl)-N-[(2S)-1,1,1-trifluoropropan-2-yl]pyrimidine-5-sulfonamide, |
| 452 | 2-(3-cyano-1-cyclobutyl-5-fluoro-1H-indol-2-yl)-N-(1,3-difluoropropan-2-yl)pyrimidine-5-sulfonamide, |
| 453 | 6-(3-cyano-1-cyclobutyl-5-methoxy-1H-indol-2-yl)-N-[(2S)-1,1,1-trifluoropropan-2-yl]pyridine-3-sulfonamide, |
| 454 | 2-(5-chloro-3-cyano-1-cyclobutyl-1H-indol-2-yl)-N-[(2S)-1,1,1-trifluoropropan-2-yl]pyrimidine-5-sulfonamide, |
| 455 | 2-[3-cyano-1-cyclobutyl-6-(propan-2-yl)-1H-indol-2-yl]-N-[(2S)-1,1,1-trifluoropropan-2-yl]pyrimidine-5-sulfonamide, |
| 456 | 6-[3-cyano-1,6-di(propan-2-yl)-1H-indol-2-yl]-N-(1,3-difluoropropan-2-yl)pyridine-3-sulfonamide, |
| 457 | 6-[3-cyano-1-cyclopentyl-6-(propan-2-yl)-1H-indol-2-yl]-N-(1,3-difluoropropan-2-yl)pyridine-3-sulfonamide, |
| 458 | 6-[3-cyano-1-(cyclopropylmethyl)-5-methyl-1H-indol-2-yl]-N-[(2R)-1,1,1-trifluoropropan-2-yl]pyridine-3-sulfonamide, |
| 459 | 6-[3-cyano-1-cyclohexyl-6-(trifluoromethoxy)-1H-indol-2-yl]-N-[(2S)-1,1,1-trifluoropropan-2-yl]pyridine-3-sulfonamide, |
| 460 | 6-[3-cyano-1-(cyclopropylmethyl)-6-(propan-2-yl)-1H-indol-2-yl]-N-(1,3-difluoropropan-2-yl)pyridine-3-sulfonamide, |
| 461 | 6-(5-chloro-3-cyano-1-cyclohexyl-1H-indol-2-yl)-N-[(2R)-1,1,1-trifluoropropan-2-yl]pyridine-3-sulfonamide, |
| 462 | 6-(5-chloro-3-cyano-1-cyclohexyl-1H-indol-2-yl)-N-[(2S)-1,1,1-trifluoropropan-2-yl]pyridine-3-sulfonamide, |
| 463 | 2-(5-chloro-3-cyano-1-cyclohexyl-1H-indol-2-yl)-N-(1,3-difluoropropan-2-yl)pyrimidine-5-sulfonamide, |
| 464 | 2-(5-chloro-3-cyano-1-cyclohexyl-1H-indol-2-yl)-N-[(2S)-1,1,1-trifluoropropan-2-yl]pyrimidine-5-sulfonamide, |
| 465 | 6-(3,6-dicyano-1-cyclobutyl-1H-indol-2-yl)-N-(1,3-difluoropropan-2-yl)pyridine-3-sulfonamide, |
| 466 | 2-(3,6-dicyano-1-cyclobutyl-1H-indol-2-yl)-N-(1,3-difluoropropan-2-yl)pyrimidine-5-sulfonamide, |
| 467 | 6-(3,6-dicyano-1-cyclobutyl-1H-indol-2-yl)-N-[(2S)-1,1,1-trifluoropropan-2-yl]pyridine-3-sulfonamide, |
| 468 | 6-(3,6-dicyano-1-cyclopentyl-1H-indol-2-yl)-N-(1,3-difluoropropan-2-yl)pyridine-3-sulfonamide, |
| 469 | 2-(3,6-dicyano-1-cyclopentyl-1H-indol-2-yl)-N-(1,3-difluoropropan-2-yl)pyrimidine-5-sulfonamide, |
| 470 | 6-(3,6-dicyano-1-cyclopentyl-1H-indol-2-yl)-N-[(2S)-1,1,1-trifluoropropan-2-yl]pyridine-3-sulfonamide, |
| 471 | 2-[3-cyano-1-cyclohexyl-6-(difluoromethoxy)-1H-indol-2-yl]-N-[(1S)-1-cyclopropylethyl]pyrimidine-5-sulfonamide, |
| 472 | 2-[3-cyano-1-cyclohexyl-6-(difluoromethoxy)-1H-indol-2-yl]-N-[(2S)-1,1,1-trifluoropropan-2-yl]pyrimidine-5-sulfonamide, |
| 473 | 2-[3-cyano-1-cyclohexyl-6-(difluoromethoxy)-1H-indol-2-yl]-N-(propan-2-yl)pyrimidine-5-sulfonamide, |
| 474 | 2-[3-cyano-5-fluoro-1-(pyridin-2-yl)-1H-indol-2-yl]-N-[(2S)-1,1,1-trifluoropropan-2-yl]pyrimidine-5-sulfonamide, |
| 475 | 2-[3-cyano-6-methyl-1-(pyridin-2-yl)-1H-indol-2-yl]-N-[(2S)-1,1,1-trifluoropropan-2-yl]pyrimidine-5-sulfonamide, |
| 476 | 6-[3-cyano-6-methyl-1-(pyridin-2-yl)-1H-indol-2-yl]-N-[(2S)-1,1,1-trifluoropropan-2-yl]pyridine-3-sulfonamide, |
| 477 | 2-[3-cyano-6-(difluoromethoxy)-1-(4-fluorophenyl)-1H-indol-2-yl]-N-(1,3-difluoropropan-2-yl)pyrimidine-5-sulfonamide, |
| 478 | 6-(3-cyano-1-cyclobutyl-6-methyl-1H-indol-2-yl)-N-(1,1,1-trifluoro-2-methylpropan-2-yl)pyridine-3-sulfonamide, |
| 479 | 6-[3-cyano-1-cyclobutyl-6-(difluoromethoxy)-1H-indol-2-yl]-N-(1,1,1-trifluoro-2-methylpropan-2-yl)pyridine-3-sulfonamide, |
| 480 | 6-(3-cyano-1-cyclobutyl-5-methyl-1H-indol-2-yl)-N-(1,1,1-trifluoro-2-methylpropan-2-yl)pyridine-3-sulfonamide, |
| 481 | 6-(3-cyano-1-cyclobutyl-6-ethyl-1H-indol-2-yl)-N-(1,1,1-trifluoro-2-methylpropan-2-yl)pyridine-3-sulfonamide, |
| 482 | 6-(3-cyano-1-cyclopentyl-6-fluoro-5-methyl-1H-indol-2-yl)-N-(1,3-difluoropropan-2-yl)pyridine-3-sulfonamide, |
| 483 | 6-(3-cyano-1-cyclopentyl-6-fluoro-5-methyl-1H-indol-2-yl)-N-[(2S)-1,1,1-trifluoropropan-2-yl]pyridine-3-sulfonamide, |
| 484 | 6-(3-cyano-1-cyclobutyl-5-methyl-1H-indol-2-yl)-N-[(2R)-1,1,1-trifluoropropan-2-yl]pyridine-3-sulfonamide, |

-continued

| Cpd | Name |
|---|---|
| 485 | 6-[3-cyano-5-methyl-1-(propan-2-yl)-1H-indol-2-yl]-N-[(2R)-1,1,1-trifluoropropan-2-yl]pyridine-3-sulfonamide, |
| 486 | 6-(3-cyano-1-cyclopentyl-5-methyl-1H-indol-2-yl)-N-[(2R)-1,1,1-trifluoropropan-2-yl]pyridine-3-sulfonamide, |
| 487 | 6-(3-cyano-1-cyclohexyl-5-methyl-1H-indol-2-yl)-N-[(2R)-1,1,1-trifluoropropan-2-yl]pyridine-3-sulfonamide, |
| 488 | 6-[6-chloro-3-cyano-1-(pyridin-2-yl)-1H-indol-2-yl]-N-[(1S)-1-cyclopropylethyl]pyridine-3-sulfonamide, |
| 489 | 6-[6-chloro-3-cyano-1-(pyridin-2-yl)-1H-indol-2-yl]-N-[(2R)-1,1,1-trifluoropropan-2-yl]pyridine-3-sulfonamide, |
| 490 | 6-[5-chloro-3-cyano-1-(pyridin-2-yl)-1H-indol-2-yl]-N-[(1S)-1-cyclopropylethyl]pyridine-3-sulfonamide, |
| 491 | 6-[5-chloro-3-cyano-1-(pyridin-2-yl)-1H-indol-2-yl]-N-[(2R)-1,1,1-trifluoropropan-2-yl]pyridine-3-sulfonamide, |
| 492 | 6-(3-cyano-1-cyclobutyl-6-fluoro-5-methyl-1H-indol-2-yl)-N-[(2S)-1,1,1-trifluoropropan-2-yl]pyridine-3-sulfonamide, |
| 493 | 6-(3-cyano-1-cyclobutyl-6-fluoro-5-methyl-1H-indol-2-yl)-N-(1,3-difluoropropan-2-yl)pyridine-3-sulfonamide, |
| 494 | 2-(3-cyano-1-cyclobutyl-6-fluoro-1H-indol-2-yl)-N-[(2S)-1,1,1-trifluoropropan-2-yl]pyrimidine-5-sulfonamide, |
| 495 | 2-(3-cyano-1-cyclopentyl-6-fluoro-1H-indol-2-yl)-N-[(2S)-1,1,1-trifluoropropan-2-yl]pyrimidine-5-sulfonamide, |
| 496 | 2-(3-cyano-1-cyclobutyl-6-fluoro-1H-indol-2-yl)-N-[(1S)-1-cyclopropylethyl]pyrimidine-5-sulfonamide, |
| 497 | 2-(3-cyano-1-cyclopentyl-6-fluoro-1H-indol-2-yl)-N-[(1S)-1-cyclopropylethyl]pyrimidine-5-sulfonamide, |
| 498 | 2-[3-cyano-1-(cyclopropylmethyl)-6-fluoro-1H-indol-2-yl]-N-[(1S)-1-cyclopropylethyl]pyrimidine-5-sulfonamide, |
| 499 | 2-(3-cyano-1-cyclohexyl-6-fluoro-1H-indol-2-yl)-N-[(1S)-1-cyclopropylethyl]pyrimidine-5-sulfonamide, |
| 500 | 6-(3-cyano-1-cyclobutyl-5-methoxy-1H-indol-2-yl)-N-[(2R)-1,1,1-trifluoropropan-2-yl]pyridine-3-sulfonamide, |
| 501 | 6-[3-cyano-6-cyclopropyl-1-(pyridin-2-yl)-1H-indol-2-yl]-N-(1,3-difluoropropan-2-yl)pyridine-3-sulfonamide, |
| 502 | 6-[3-cyano-6-cyclopropyl-1-(pyridin-2-yl)-1H-indol-2-yl]-N-[(2S)-1,1,1-trifluoropropan-2-yl]pyridine-3-sulfonamide, |
| 503 | 6-[3-cyano-5-methyl-1-(pyridin-2-yl)-1H-indol-2-yl]-N-[(2S)-1,1,1-trifluoropropan-2-yl]pyridine-3-sulfonamide, |
| 504 | 6-[3-cyano-5-methyl-1-(pyridin-2-yl)-1H-indol-2-yl]-N-(1,3-difluoropropan-2-yl)pyridine-3-sulfonamide, |
| 505 | 6-(6-chloro-3-cyano-1-cyclobutyl-5-methyl-1H-indol-2-yl)-N-(1,3-difluoropropan-2-yl)pyridine-3-sulfonamide, |
| 506 | 6-(6-chloro-3-cyano-1-cyclobutyl-5-methyl-1H-indol-2-yl)-N-[(2S)-1,1,1-trifluoropropan-2-yl]pyridine-3-sulfonamide, |
| 507 | 2-(6-chloro-3-cyano-1-cyclobutyl-5-methyl-1H-indol-2-yl)-N-(propan-2-yl)pyrimidine-5-sulfonamide, |
| 508 | 6-(3-cyano-1-cyclopentyl-5,7-difluoro-6-methyl-1H-indol-2-yl)-N-[(2S)-1,1,1-trifluoropropan-2-yl]pyridine-3-sulfonamide, |
| 509 | 6-(3-cyano-1-cyclopentyl-5,7-difluoro-6-methyl-1H-indol-2-yl)-N-(1,3-difluoropropan-2-yl)pyridine-3-sulfonamide, |
| 510 | 6-(6-chloro-3-cyano-1-cyclobutyl-5-methyl-1H-indol-2-yl)-N-[(2R)-1,1,1-trifluoropropan-2-yl]pyridine-3-sulfonamide, |
| 511 | 6-(1-cyclobutyl-6-methyl-1H-indol-2-yl)-N-(1,3-difluoropropan-2-yl)pyridine-3-sulfonamide, |
| 512 | 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, |
| 513 | 6-(3-cyano-1-cyclohexyl-6-methyl-1H-indol-2-yl)-N-(1,3-difluoropropan-2-yl)pyridine-3-sulfonamide, |
| 514 | 6-(6-chloro-3-cyano-1-cyclohexyl-1H-indol-2-yl)-N-[(2R)-1,1,1-trifluoropropan-2-yl]pyridine-3-sulfonamide, |
| 515 | 6-(6-chloro-3-cyano-1-cyclohexyl-1H-indol-2-yl)-N-[(2S)-1,1,1-trifluoropropan-2-yl]pyridine-3-sulfonamide, |
| 516 | 2-(6-chloro-3-cyano-1-cyclohexyl-1H-indol-2-yl)-N-[(2S)-1,1,1-trifluoropropan-2-yl]pyrimidine-5-sulfonamide, |
| 517 | 2-(6-chloro-3-cyano-1-cyclohexyl-1H-indol-2-yl)-N-(1,3-difluoropropan-2-yl)pyrimidine-5-sulfonamide, |
| 518 | 6-(3-cyano-1-cyclohexyl-6-methoxy-1H-indol-2-yl)-N-[(2R)-1,1,1-trifluoropropan-2-yl]pyridine-3-sulfonamide, |
| 519 | 6-(3-cyano-1-cyclohexyl-6-methoxy-1H-indol-2-yl)-N-[(2S)-1,1,1-trifluoropropan-2-yl]pyridine-3-sulfonamide, |
| 520 | 2-(3-cyano-1-cyclohexyl-6-methoxy-1H-indol-2-yl)-N-(1,3-difluoropropan-2-yl)pyrimidine-5-sulfonamide, |
| 521 | 6-(6-chloro-3-cyano-1-cyclopentyl-5-methyl-1H-indol-2-yl)-N-(1,3-difluoropropan-2-yl)pyridine-3-sulfonamide, |
| 522 | 6-(6-chloro-3-cyano-1-cyclopentyl-5-methyl-1H-indol-2-yl)-N-[(2S)-1,1,1-trifluoropropan-2-yl]pyridine-3-sulfonamide, |
| 523 | 2-(6-chloro-3-cyano-1-cyclopentyl-5-methyl-1H-indol-2-yl)-N-(propan-2-yl)pyrimidine-5-sulfonamide, |

| Cpd | Name |
|---|---|
| 524 | 2-[3-cyano-1-(cyclopropylmethyl)-5-methyl-1H-indol-2-yl]-N-(1,3-difluoropropan-2-yl)pyrimidine-5-sulfonamide, |
| 525 | 6-[3-cyano-1-(cyclopropylmethyl)-5-methyl-1H-indol-2-yl]-N-[(1S)-1-cyclopropylethyl]pyridine-3-sulfonamide, |
| 526 | 2-(3-cyano-1-cyclohexyl-5-fluoro-1H-indol-2-yl)-N-(propan-2-yl)pyrimidine-5-sulfonamide, |
| 527 | 2-(3-cyano-1-cyclohexyl-5-fluoro-1H-indol-2-yl)-N-(1,3-difluoropropan-2-yl)pyrimidine-5-sulfonamide, |
| 528 | 2-(3-cyano-1-cyclohexyl-5-fluoro-1H-indol-2-yl)-N-[(1S)-1-cyclopropylethyl]pyrimidine-5-sulfonamide, |
| 529 | 2-[3-cyano-5-fluoro-1-(propan-2-yl)-1H-indol-2-yl]-N-[(1S)-1-cyclopropylethyl]pyrimidine-5-sulfonamide, |
| 530 | 2-(3-cyano-1-cyclopentyl-5-fluoro-1H-indol-2-yl)-N-[(1S)-1-cyclopropylethyl]pyrimidine-5-sulfonamide, |
| 531 | 2-[3-cyano-1-(cyclopropylmethyl)-5-fluoro-1H-indol-2-yl]-N-[(1S)-1-cyclopropylethyl]pyrimidine-5-sulfonamide, |
| 532 | 6-(3-cyano-1-cyclobutyl-5,7-difluoro-6-methyl-1H-indol-2-yl)-N-[(2S)-1,1,1-trifluoropropan-2-yl]pyridine-3-sulfonamide, |
| 533 | 6-(3-cyano-1-cyclobutyl-5,7-difluoro-6-methyl-1H-indol-2-yl)-N-(1,3-difluoropropan-2-yl)pyridine-3-sulfonamide, |
| 534 | 6-[3-cyano-6-(difluoromethoxy)-1-(pyridin-2-yl)-1H-indol-2-yl]-N-[(2R)-1,1,1-trifluoropropan-2-yl]pyridine-3-sulfonamide, |
| 535 | 6-[3-cyano-1-cyclopentyl-5-(difluoromethyl)-1H-indol-2-yl]-N-(1,3-difluoropropan-2-yl)pyridine-3-sulfonamide, |
| 536 | 2-[3-cyano-1-cyclopentyl-5-(difluoromethyl)-1H-indol-2-yl]-N-(1,3-difluoropropan-2-yl)pyrimidine-5-sulfonamide, |
| 537 | 6-[3-cyano-1-cyclopentyl-5-(difluoromethyl)-1H-indol-2-yl]-N-[(2S)-1,1,1-trifluoropropan-2-yl]pyridine-3-sulfonamide, |
| 538 | 6-[3-cyano-1-cyclopentyl-5-(difluoromethyl)-1H-indol-2-yl]-N-[(2R)-1,1,1-trifluoropropan-2-yl]pyridine-3-sulfonamide, |
| 539 | 6-(3-cyano-1-cyclobutyl-5-fluoro-6-methyl-1H-indol-2-yl)-N-(1,1,1-trifluoro-2-methylpropan-2-yl)pyridine-3-sulfonamide, |
| 540 | 6-[3-cyano-5-fluoro-6-methyl-1-(pyridin-2-yl)-1H-indol-2-yl]-N-(1,3-difluoropropan-2-yl)pyridine-3-sulfonamide, |
| 541 | 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, |
| 542 | 6-[3-cyano-1-cyclobutyl-6-(difluoromethoxy)-5-fluoro-1H-indol-2-yl]-N-(1,3-difluoropropan-2-yl)pyridine-3-sulfonamide, |
| 543 | N-tert-butyl-6-[3-cyano-1-cyclobutyl-6-(difluoromethoxy)-1H-indol-2-yl]pyridine-3-sulfonamide, |
| 544 | 2-(3-cyano-1-cyclobutyl-5-fluoro-1H-indol-2-yl)-N-[(1S)-1-cyclopropylethyl]pyrimidine-5-sulfonamide, |
| 545 | 2-(3-cyano-1-cyclobutyl-5-methyl-1H-indol-2-yl)-N-[(1S)-1-cyclopropylethyl]pyrimidine-5-sulfonamide, |
| 546 | 2-[3-cyano-5-fluoro-1-(propan-2-yl)-1H-indol-2-yl]-N-[(2S)-1,1,1-trifluoropropan-2-yl]pyrimidine-5-sulfonamide, |
| 547 | 2-(3-cyano-1-cyclopentyl-5-fluoro-1H-indol-2-yl)-N-[(2S)-1,1,1-trifluoropropan-2-yl]pyrimidine-5-sulfonamide, |
| 548 | 2-[3-cyano-1-(cyclopropylmethyl)-5-fluoro-1H-indol-2-yl]-N-[(2S)-1,1,1-trifluoropropan-2-yl]pyrimidine-5-sulfonamide, |
| 549 | 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, |
| 550 | 6-(3-cyano-1-cyclobutyl-5-methoxy-1H-indol-2-yl)-N-(1,3-difluoropropan-2-yl)pyridine-3-sulfonamide, |
| 551 | 2-(3-cyano-1-cyclobutyl-5-methoxy-1H-indol-2-yl)-N-(1,3-difluoropropan-2-yl)pyrimidine-5-sulfonamide, |
| 552 | 6-[3-cyano-1-cyclobutyl-6-(difluoromethoxy)-1H-indol-2-yl]pyridine-3-sulfonamide, |
| 553 | 6-[3-cyano-6-(difluoromethoxy)-1-phenyl-1H-indol-2-yl]-N-[(2S)-1,1,1-trifluoropropan-2-yl]pyridine-3-sulfonamide, |
| 554 | 6-[3-cyano-6-(difluoromethoxy)-1-phenyl-1H-indol-2-yl]-N-[(2R)-1,1,1-trifluoropropan-2-yl]pyridine-3-sulfonamide, |
| 555 | 6-(3-cyano-1-cyclobutyl-4,6-difluoro-5-methyl-1H-indol-2-yl)-N-[(2S)-1,1,1-trifluoropropan-2-yl]pyridine-3-sulfonamide, |
| 556 | 6-(3-cyano-1-cyclobutyl-4,6-difluoro-5-methyl-1H-indol-2-yl)-N-(1,3-difluoropropan-2-yl)pyridine-3-sulfonamide, |
| 557 | 2-(3-cyano-1-cyclobutyl-7-fluoro-6-methyl-1H-indol-2-yl)-N-(1,3-difluoropropan-2-yl)pyrimidine-5-sulfonamide, |
| 558 | 6-(3-cyano-1-cyclopentyl-4,6-difluoro-5-methyl-1H-indol-2-yl)-N-(1,3-difluoropropan-2-yl)pyridine-3-sulfonamide, |
| 559 | 6-(3-cyano-1-cyclopentyl-4,6-difluoro-5-methyl-1H-indol-2-yl)-N-[(2S)-1,1,1-trifluoropropan-2-yl]pyridine-3-sulfonamide, |
| 560 | 6-(3-cyano-1-cyclohexyl-5-methyl-1H-indol-2-yl)-N-[(2S)-1,1,1-trifluoropropan-2-yl]pyridine-3-sulfonamide, |
| 561 | 2-[3-cyano-1-(cyclopropylmethyl)-5-methyl-1H-indol-2-yl]-N-[(1S)-1-cyclopropylethyl]pyrimidine-5-sulfonamide, |
| 562 | 2-(3-cyano-1-cyclopentyl-5-methyl-1H-indol-2-yl)-N-[(1S)-1-cyclopropylethyl]pyrimidine-5-sulfonamide, |

-continued

| Cpd | Name |
|---|---|
| 563 | 2-[3-cyano-5-methyl-1-(propan-2-yl)-1H-indol-2-yl]-N-[(1S)-1-cyclopropylethyl]pyrimidine-5-sulfonamide, |
| 564 | 6-[3-cyano-5-methyl-1-(propan-2-yl)-1H-indol-2-yl]-N-[(1S)-1-cyclopropylethyl]pyridine-3-sulfonamide, |
| 565 | 2-[3-cyano-5-methyl-1-(propan-2-yl)-1H-indol-2-yl]-N-(propan-2-yl)pyrimidine-5-sulfonamide, |
| 566 | 2-[3-cyano-5-methyl-1-(propan-2-yl)-1H-indol-2-yl]-N-[(2S)-1,1,1-trifluoropropan-2-yl]pyrimidine-5-sulfonamide, |
| 567 | 2-[3-cyano-5-methyl-1-(propan-2-yl)-1H-indol-2-yl]-N-(1,3-difluoropropan-2-yl)pyrimidine-5-sulfonamide, |
| 568 | 1-cyclobutyl-6-(difluoromethoxy)-2-(5-sulfamoylpyridin-2-yl)-1H-indole-3-carboxamide, |
| 569 | 2-(3-cyano-1-cyclobutyl-5-methoxy-1H-indol-2-yl)-N-[(2S)-1,1,1-trifluoropropan-2-yl]pyrimidine-5-sulfonamide, |
| 570 | 2-(3-cyano-1-cyclobutyl-5-methoxy-1H-indol-2-yl)-N-[(1S)-1-cyclopropylethyl]pyrimidine-5-sulfonamide, |
| 571 | 6-(3-cyano-1-cyclopentyl-5-methoxy-1H-indol-2-yl)-N-(1,3-difluoropropan-2-yl)pyridine-3-sulfonamide, |
| 572 | 2-(3-cyano-1-cyclopentyl-5-methoxy-1H-indol-2-yl)-N-(1,3-difluoropropan-2-yl)pyrimidine-5-sulfonamide, |
| 573 | 6-[3-cyano-1-cyclopentyl-6-(difluoromethoxy)-5-fluoro-1H-indol-2-yl]-N-(1,3-difluoropropan-2-yl)pyridine-3-sulfonamide, |
| 574 | 6-[3-cyano-1-cyclopentyl-6-(difluoromethoxy)-5-fluoro-1H-indol-2-yl]-N-[(2S)-1,1,1-trifluoropropan-2-yl]pyridine-3-sulfonamide, |
| 575 | 6-(3-cyano-1-cyclopentyl-5-fluoro-6-hydroxy-1H-indol-2-yl)-N-(1,3-difluoropropan-2-yl)pyridine-3-sulfonamide, |
| 576 | 6-(3-cyano-1-cyclopentyl-5-fluoro-6-hydroxy-1H-indol-2-yl)-N-[(2S)-1,1,1-trifluoropropan-2-yl]pyridine-3-sulfonamide, |
| 577 | 6-(3-cyano-1-cyclobutyl-5,7-difluoro-6-methyl-1H-indol-2-yl)-N-(1,1,1-trifluoro-2-methylpropan-2-yl)pyridine-3-sulfonamide, |
| 578 | 6-(3-cyano-1-cyclobutyl-7-fluoro-6-methyl-1H-indol-2-yl)-N-(1,1,1-trifluoro-2-methylpropan-2-yl)pyridine-3-sulfonamide, |
| 579 | 6-(3-cyano-1-cyclopentyl-7-fluoro-6-methyl-1H-indol-2-yl)-N-(1,1,1-trifluoro-2-methylpropan-2-yl)pyridine-3-sulfonamide, |
| 580 | 6-(3-cyano-1-cyclopentyl-5,7-difluoro-6-methyl-1H-indol-2-yl)-N-(1,1,1-trifluoro-2-methylpropan-2-yl)pyridine-3-sulfonamide, |
| 581 | 1-cyclobutyl-6-(difluoromethoxy)-2-{5-[(1,3-difluoropropan-2-yl)sulfamoyl]pyridin-2-yl}-1H-indole-3-carboxamide, |
| 582 | 1-cyclobutyl-6-cyclopropyl-2-{5-[(1,3-difluoropropan-2-yl)sulfamoyl]pyridin-2-yl}-1H-indole-3-carboxamide, |
| 583 | 6-[3-cyano-6-(difluoromethoxy)-1-(pyridin-2-yl)-1H-indol-2-yl]-N-(1,1,1-trifluoro-2-methylpropan-2-yl)pyridine-3-sulfonamide, |
| 584 | 6-[3-cyano-6-cyclopropyl-1-(pyridin-2-yl)-1H-indol-2-yl]-N-(1,1,1-trifluoro-2-methylpropan-2-yl)pyridine-3-sulfonamide, |
| 585 | 6-(3-cyano-6-methyl-1-phenyl-1H-indol-2-yl)-N-(1,1,1-trifluoro-2-methylpropan-2-yl)pyridine-3-sulfonamide, |
| 586 | 2-(3-cyano-1-cyclopentyl-7-fluoro-6-methyl-1H-indol-2-yl)-N-(1,3-difluoropropan-2-yl)pyrimidine-5-sulfonamide, |
| 587 | 6-(3-cyano-1-cyclobutyl-6-methyl-1H-indol-2-yl)-N-[1-(trifluoromethyl)cyclobutyl]pyridine-3-sulfonamide, |
| 588 | 6-[3-cyano-1-cyclopentyl-6-(difluoromethoxy)-1H-indol-2-yl]-N-[1-(trifluoromethyl)cyclobutyl]pyridine-3-sulfonamide, |
| 589 | 6-[3-cyano-1-cyclopentyl-6-(difluoromethoxy)-1H-indol-2-yl]-N-[(2S)-1,1,1-trifluoropropan-2-yl]pyridine-3-sulfonamide, |
| 590 | 6-[3-cyano-1-cyclobutyl-6-(2,2-difluoroethyl)-1H-indol-2-yl]-N-[(1S)-1-cyclopropylethyl]pyridine-3-sulfonamide, |
| 591 | 2-[3-cyano-1-cyclobutyl-6-(2,2-difluoroethyl)-1H-indol-2-yl]-N-(1,3-difluoropropan-2-yl)pyrimidine-5-sulfonamide, |
| 592 | 2-[3-cyano-1-cyclobutyl-6-(2,2-difluoroethyl)-1H-indol-2-yl]-N-[(1S)-1-cyclopropylethyl]pyrimidine-5-sulfonamide, |
| 593 | 6-[3-cyano-1-cyclopentyl-6-(2,2-difluoroethyl)-1H-indol-2-yl]-N-(1,3-difluoropropan-2-yl)pyridine-3-sulfonamide, |
| 594 | 6-[3-cyano-1-cyclopentyl-6-(2,2-difluoroethyl)-1H-indol-2-yl]-N-[(1S)-1-cyclopropylethyl]pyridine-3-sulfonamide, |
| 595 | 6-[3-cyano-1-cyclopentyl-6-(2,2-difluoroethyl)-1H-indol-2-yl]-N-[(2S)-1,1,1-trifluoropropan-2-yl]pyridine-3-sulfonamide, |
| 596 | 6-[3-cyano-1-cyclopentyl-6-(2,2-difluoroethyl)-1H-indol-2-yl]-N-(1,1,1-trifluoro-2-methylpropan-2-yl)pyridine-3-sulfonamide, |
| 597 | 2-[3-cyano-1-cyclopentyl-6-(2,2-difluoroethyl)-1H-indol-2-yl]-N-[(1S)-1-cyclopropylethyl]pyrimidine-5-sulfonamide, |
| 598 | 2-[3-cyano-1-cyclopentyl-6-(2,2-difluoroethyl)-1H-indol-2-yl]-N-(propan-2-yl)pyrimidine-5-sulfonamide, |
| 599 | 2-[3-cyano-1-cyclopentyl-6-(2,2-difluoroethyl)-1H-indol-2-yl]-N-(1,3-difluoropropan-2-yl)pyrimidine-5-sulfonamide, |
| 600 | 2-[3-cyano-1-cyclopentyl-6-(2,2-difluoroethyl)-1H-indol-2-yl]-N-[(2S)-1,1,1-trifluoropropan-2-yl]pyrimidine-5-sulfonamide, |
| 601 | 6-[3-cyano-5-fluoro-1-(pyrimidin-2-yl)-1H-indol-2-yl]-N-[(2S)-1,1,1-trifluoropropan-2-yl]pyridine-3-sulfonamide, |

-continued

| Cpd | Name |
|---|---|
| 602 | 6-[3-cyano-5-fluoro-1-(pyrimidin-2-yl)-1H-indol-2-yl]-N-(1,1,1-trifluoro-2-methylpropan-2-yl)pyridine-3-sulfonamide, |
| 603 | 2-(3-cyano-1-cyclopentyl-5-fluoro-1H-indol-2-yl)-N-(propan-2-yl)pyrimidine-5-sulfonamide, |
| 604 | 6-[3-cyano-5-fluoro-1-(propan-2-yl)-1H-indol-2-yl]-N-[(1S)-1-cyclopropylethyl]pyridine-3-sulfonamide, |
| 605 | 2-(3-cyano-1-cyclohexyl-6-methyl-1H-indol-2-yl)-N-[(2S)-1,1,1-trifluoropropan-2-yl]pyrimidine-5-sulfonamide, |
| 606 | 6-(3-cyano-1-cyclohexyl-5-methyl-1H-indol-2-yl)-N-[(1S)-1-cyclopropylethyl]pyridine-3-sulfonamide, |
| 607 | 6-(3-cyano-1-cyclopentyl-5-methyl-1H-indol-2-yl)-N-(1,1,1-trifluoro-2-methylpropan-2-yl)pyridine-3-sulfonamide, |
| 608 | 6-[3-cyano-5-fluoro-1-(pyrimidin-2-yl)-1H-indol-2-yl]-N-(1,3-difluoropropan-2-yl)pyridine-3-sulfonamide, |
| 609 | 6-(3-cyano-1-cyclobutyl-5-fluoro-6-methyl-1H-indol-2-yl)-N-[(2R)-1,1,1-trifluoropropan-2-yl]pyridine-3-sulfonamide, |
| 610 | 2-[3-cyano-6-(difluoromethoxy)-1-phenyl-1H-indol-2-yl]-N-(1,3-difluoropropan-2-yl)pyrimidine-5-sulfonamide, |
| 611 | 2-[3-cyano-6-(difluoromethoxy)-1-phenyl-1H-indol-2-yl]-N-[(2S)-1,1,1-trifluoropropan-2-yl]pyrimidine-5-sulfonamide, |
| 612 | 6-[3-cyano-6-(difluoromethoxy)-1-phenyl-1H-indol-2-yl]-N-(1,1,1-trifluoro-2-methylpropan-2-yl)pyridine-3-sulfonamide, |
| 613 | 6-(3-cyano-1-cyclobutyl-5-fluoro-6-methyl-1H-indol-2-yl)-N-[1-(trifluoromethyl)cyclopropyl]pyridine-3-sulfonamide, |
| 614 | 6-(3-cyano-1-cyclopentyl-4-fluoro-5-methyl-1H-indol-2-yl)-N-(1,1,1-trifluoro-2-methylpropan-2-yl)pyridine-3-sulfonamide, |
| 615 | 6-(3-cyano-1-cyclopentyl-4-fluoro-5-methyl-1H-indol-2-yl)-N-[(2S)-1,1,1-trifluoropropan-2-yl]pyridine-3-sulfonamide, |
| 616 | 6-[3-cyano-1-(cyclopropylmethyl)-6-(2,2-difluoroethyl)-1H-indol-2-yl]-N-(1,3-difluoropropan-2-yl)pyridine-3-sulfonamide, |
| 617 | 6-[3-cyano-1-(cyclopropylmethyl)-6-(2,2-difluoroethyl)-1H-indol-2-yl]-N-[(1S)-1-cyclopropylethyl]pyridine-3-sulfonamide, |
| 618 | 6-[3-cyano-1-(cyclopropylmethyl)-6-(2,2-difluoroethyl)-1H-indol-2-yl]-N-[(2S)-1,1,1-trifluoropropan-2-yl]pyridine-3-sulfonamide, |
| 619 | 2-[3-cyano-1-(cyclopropylmethyl)-6-(2,2-difluoroethyl)-1H-indol-2-yl]-N-[(1S)-1-cyclopropylethyl]pyrimidine-5-sulfonamide, |
| 620 | 2-[3-cyano-1-(cyclopropylmethyl)-6-(2,2-difluoroethyl)-1H-indol-2-yl]-N-(propan-2-yl)pyrimidine-5-sulfonamide, |
| 621 | 2-[3-cyano-1-(cyclopropylmethyl)-6-(2,2-difluoroethyl)-1H-indol-2-yl]-N-(1,3-difluoropropan-2-yl)pyrimidine-5-sulfonamide, |
| 622 | 2-[3-cyano-1-(cyclopropylmethyl)-6-(2,2-difluoroethyl)-1H-indol-2-yl]-N-[(2S)-1,1,1-trifluoropropan-2-yl]pyrimidine-5-sulfonamide, |
| 623 | 6-[3-cyano-6-(difluoromethoxy)-1-(pyridin-2-yl)-1H-indol-2-yl]-N-[1-(trifluoromethyl)cyclopropyl]pyridine-3-sulfonamide, |
| 624 | N-tert-butyl-6-[3-cyano-6-(difluoromethoxy)-1-phenyl-1H-indol-2-yl]pyridine-3-sulfonamide, |
| 625 | 6-(3-cyano-1-cyclopentyl-4-fluoro-6-methyl-1H-indol-2-yl)-N-[(2S)-1,1,1-trifluoropropan-2-yl]pyridine-3-sulfonamide, |
| 626 | 6-(3-cyano-1-cyclopentyl-4-fluoro-6-methyl-1H-indol-2-yl)-N-(1,1,1-trifluoro-2-methylpropan-2-yl)pyridine-3-sulfonamide, |
| 627 | 6-(3-cyano-1-cyclobutyl-4-fluoro-6-methyl-1H-indol-2-yl)-N-[(2S)-1,1,1-trifluoropropan-2-yl]pyridine-3-sulfonamide, |
| 628 | 6-(3-cyano-1-cyclopentyl-4-fluoro-6-methyl-1H-indol-2-yl)-N-[1-(trifluoromethyl)cyclopropyl]pyridine-3-sulfonamide, |
| 629 | 6-(3-cyano-1-cyclobutyl-4-fluoro-6-methyl-1H-indol-2-yl)-N-[1-(trifluoromethyl)cyclopropyl]pyridine-3-sulfonamide, |
| 630 | 6-(3-cyano-1-cyclobutyl-6-cyclopropyl-5-fluoro-1H-indol-2-yl)-N-[(2S)-1,1,1-trifluoropropan-2-yl]pyridine-3-sulfonamide, |
| 631 | 6-(3-cyano-1-cyclobutyl-6-cyclopropyl-5-fluoro-1H-indol-2-yl)-N-[(2R)-1,1,1-trifluoropropan-2-yl]pyridine-3-sulfonamide, |
| 632 | 6-(3-cyano-1-cyclopentyl-6-ethyl-5-fluoro-1H-indol-2-yl)-N-[(2R)-1,1,1-trifluoropropan-2-yl]pyridine-3-sulfonamide, |
| 633 | 6-(3-cyano-1-cyclopentyl-6-ethyl-5-fluoro-1H-indol-2-yl)-N-[(2S)-1,1,1-trifluoropropan-2-yl]pyridine-3-sulfonamide, |
| 634 | 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, |
| 635 | 6-[3-cyano-6-(difluoromethoxy)-1-(pyrimidin-2-yl)-1H-indol-2-yl]-N-(1,3-difluoropropan-2-yl)pyridine-3-sulfonamide, |
| 636 | 6-[5-chloro-3-cyano-1-cyclobutyl-6-(difluoromethoxy)-1H-indol-2-yl]-N-[(2S)-1,1,1-trifluoropropan-2-yl]pyridine-3-sulfonamide, |
| 637 | 6-(3-cyano-1-cyclopentyl-6-ethyl-5-fluoro-1H-indol-2-yl)-N-[1-(trifluoromethyl)cyclopropyl]pyridine-3-sulfonamide, |
| 638 | 2-(3-cyano-1-cyclopentyl-6-ethyl-5-fluoro-1H-indol-2-yl)-N-(1,3-difluoropropan-2-yl)pyrimidine-5-sulfonamide, |
| 639 | 6-(3-cyano-1-cyclopentyl-6-ethyl-5-fluoro-1H-indol-2-yl)-N-(1,3-difluoropropan-2-yl)pyridine-3-sulfonamide, |
| 640 | 6-(3-cyano-1-cyclobutyl-6-ethyl-5-fluoro-1H-indol-2-yl)-N-[(2S)-1,1,1-trifluoropropan-2-yl]pyridine-3-sulfonamide, |

| Cpd | Name |
|---|---|
| 641 | 6-(3-cyano-1-cyclobutyl-6-ethyl-5-fluoro-1H-indol-2-yl)-N-[(2R)-1,1,1-trifluoropropan-2-yl]pyridine-3-sulfonamide, |
| 642 | 6-(3-cyano-1-cyclobutyl-6-ethyl-5-fluoro-1H-indol-2-yl)-N-[1-(trifluoromethyl)cyclopropyl]pyridine-3-sulfonamide, |
| 643 | N-tert-butyl-6-(3-cyano-1-cyclopentyl-5-fluoro-6-methyl-1H-indol-2-yl)pyridine-3-sulfonamide, |
| 644 | 6-(3-cyano-1-cyclopentyl-5-fluoro-6-methyl-1H-indol-2-yl)-N-[1-(trifluoromethyl)cyclopropyl]pyridine-3-sulfonamide, |
| 645 | 6-(3-cyano-1-cyclopentyl-5-fluoro-6-methyl-1H-indol-2-yl)-N-(1-methylcyclopropyl)pyridine-3-sulfonamide, |
| 646 | 6-[1-cyclobutyl-6-(difluoromethoxy)-5-methyl-1H-indol-2-yl]-N-[(2S)-1,1,1-trifluoropropan-2-yl]pyridine-3-sulfonamide, |
| 647 | 6-[3-cyano-1-cyclobutyl-6-(difluoromethoxy)-5-ethyl-1H-indol-2-yl]-N-[(2S)-1,1,1-trifluoropropan-2-yl]pyridine-3-sulfonamide, |
| 648 | 6-[3-cyano-1-cyclobutyl-6-(difluoromethoxy)-5-fluoro-1H-indol-2-yl]-N-[(2R)-1,1,1-trifluoropropan-2-yl]pyridine-3-sulfonamide, |
| 649 | 6-[3-cyano-6-(difluoromethoxy)-1-(4-fluorophenyl)-1H-indol-2-yl]-N-[(2R)-1,1,1-trifluoropropan-2-yl]pyridine-3-sulfonamide, |
| 650 | 6-[3-cyano-6-cyclopropyl-1-(pyrimidin-2-yl)-1H-indol-2-yl]-N-[(2S)-1,1,1-trifluoropropan-2-yl]pyridine-3-sulfonamide, |
| 651 | N-tert-butyl-6-(3-cyano-1-cyclobutyl-5-fluoro-6-methyl-1H-indol-2-yl)pyridine-3-sulfonamide, |
| 652 | 6-(3-cyano-1-cyclobutyl-5-fluoro-6-methyl-1H-indol-2-yl)-N-cyclopropylpyridine-3-sulfonamide, |
| 653 | 6-(3-cyano-1-cyclopentyl-5,7-difluoro-6-methyl-1H-indol-2-yl)-N-[(2R)-1,1,1-trifluoropropan-2-yl]pyridine-3-sulfonamide, |
| 654 | 6-(3-cyano-1-cyclopentyl-5,7-difluoro-6-methyl-1H-indol-2-yl)-N-[1-(trifluoromethyl)cyclopropyl]pyridine-3-sulfonamide, |
| 655 | 6-(3-cyano-1-cyclobutyl-5-fluoro-6-methyl-1H-indol-2-yl)-N-(propan-2-yl)pyridine-3-sulfonamide, |
| 656 | 2-(3-cyano-1-cyclopentyl-5,7-difluoro-6-methyl-1H-indol-2-yl)-N-(1,3-difluoropropan-2-yl)pyrimidine-5-sulfonamide, |
| 657 | 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, |
| 658 | 6-[5-chloro-3-cyano-1-cyclobutyl-6-(difluoromethoxy)-1H-indol-2-yl]-N-(1-methylcyclopropyl)pyridine-3-sulfonamide, |
| 659 | 2-[5-chloro-3-cyano-1-cyclobutyl-6-(difluoromethoxy)-1H-indol-2-yl]-N-(1,3-difluoropropan-2-yl)pyrimidine-5-sulfonamide, |
| 660 | 6-[3-cyano-1-cyclobutyl-6-(difluoromethoxy)-5-methyl-1H-indol-2-yl]-N-[(2S)-1,1,1-trifluoropropan-2-yl]pyridine-3-sulfonamide, |
| 661 | 6-(3-cyano-1-cyclopentyl-6-cyclopropyl-5-fluoro-1H-indol-2-yl)-N-[(2S)-1,1,1-trifluoropropan-2-yl]pyridine-3-sulfonamide, |
| 662 | 6-(3-cyano-1-cyclopentyl-6-cyclopropyl-5-fluoro-1H-indol-2-yl)-N-[(2R)-1,1,1-trifluoropropan-2-yl]pyridine-3-sulfonamide, |
| 663 | 6-[3-cyano-6-(difluoromethoxy)-1-(pyrimidin-2-yl)-1H-indol-2-yl]-N-(1,1,1-trifluoro-2-methylpropan-2-yl)pyridine-3-sulfonamide, |
| 664 | 6-[3-cyano-6-(difluoromethoxy)-1-(4-fluorophenyl)-1H-indol-2-yl]-N-[1-(trifluoromethyl)cyclopropyl]pyridine-3-sulfonamide, |
| 665 | 6-[3-cyano-1-cyclobutyl-6-(difluoromethoxy)-5-methyl-1H-indol-2-yl]-N-[(2R)-1,1,1-trifluoropropan-2-yl]pyridine-3-sulfonamide, |
| 666 | 6-(3-cyano-1-cyclobutyl-5,7-difluoro-6-methyl-1H-indol-2-yl)-N-[(2R)-1,1,1-trifluoropropan-2-yl]pyridine-3-sulfonamide, |
| 667 | 6-(3-cyano-1-cyclobutyl-5,7-difluoro-6-methyl-1H-indol-2-yl)-N-[1-(trifluoromethyl)cyclopropyl]pyridine-3-sulfonamide, |
| 668 | 2-(3-cyano-1-cyclobutyl-5,7-difluoro-6-methyl-1H-indol-2-yl)-N-(1,3-difluoropropan-2-yl)pyrimidine-5-sulfonamide, |
| 669 | 6-(3-cyano-1-cyclopentyl-5-methoxy-6-methyl-1H-indol-2-yl)-N-[(2S)-1,1,1-trifluoropropan-2-yl]pyridine-3-sulfonamide, |
| 670 | 6-[3-cyano-6-(difluoromethoxy)-5-fluoro-1-(pyridin-2-yl)-1H-indol-2-yl]-N-[(2R)-1,1,1-trifluoropropan-2-yl]pyridine-3-sulfonamide, |
| 671 | 6-[3-cyano-6-methyl-1-(pyridin-2-yl)-1H-indol-2-yl]-N-[(2R)-1,1,1-trifluoropropan-2-yl]pyridine-3-sulfonamide, |
| 672 | 6-(3-cyano-1-cyclopentyl-6-ethyl-5-fluoro-1H-indol-2-yl)-N-(1,1,1-trifluoro-2-methylpropan-2-yl)pyridine-3-sulfonamide, |
| 673 | 6-[3-cyano-5-fluoro-1-(pyrimidin-2-yl)-1H-indol-2-yl]-N-[(2R)-1,1,1-trifluoropropan-2-yl]pyridine-3-sulfonamide, |
| 674 | 6-[3-cyano-1-cyclobutyl-6-(difluoromethoxy)-5-hydroxy-1H-indol-2-yl]-N-[(2S)-1,1,1-trifluoropropan-2-yl]pyridine-3-sulfonamide, |
| 675 | 6-(5-bromo-3-cyano-1-cyclopentyl-6-methyl-1H-indol-2-yl)-N-[(2S)-1,1,1-trifluoropropan-2-yl]pyridine-3-sulfonamide, |
| 676 | 6-[3-cyano-1-cyclobutyl-6-(difluoromethoxy)-5-fluoro-1H-indol-2-yl]-N-(1,1,1-trifluoro-2-methylpropan-2-yl)pyridine-3-sulfonamide, |
| 677 | 6-[3-cyano-6-methyl-1-(pyrimidin-2-yl)-1H-indol-2-yl]-N-[(2S)-1,1,1-trifluoropropan-2-yl]pyridine-3-sulfonamide, |
| 678 | 6-(3-cyano-1-cyclohexyl-5-fluoro-6-methyl-1H-indol-2-yl)-N-[(2S)-1,1,1-trifluoropropan-2-yl]pyridine-3-sulfonamide, |
| 679 | 2-(3-cyano-1-cyclohexyl-5-fluoro-6-methyl-1H-indol-2-yl)-N-[(2S)-1,1,1-trifluoropropan-2-yl]pyrimidine-5-sulfonamide, |

-continued

| Cpd | Name |
|---|---|
| 680 | 6-(3-cyano-1-cyclohexyl-5-fluoro-6-methyl-1H-indol-2-yl)-N-[(2R)-1,1,1-trifluoropropan-2-yl]pyridine-3-sulfonamide, |
| 681 | 6-(3-cyano-1-cyclopentyl-5-fluoro-6-methyl-1H-indol-2-yl)-N-(1,1,1-trifluoro-2-methylpropan-2-yl)pyridine-3-sulfonamide, |
| 682 | 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, |
| 683 | 2-[5-(tert-butylsulfamoyl)pyridin-2-yl]-1-cyclopentyl-5-fluoro-6-methyl-1H-indole-3-carboxamide, |
| 684 | 6-(5-bromo-3-cyano-1-cyclobutyl-6-hydroxy-1H-indol-2-yl)-N-[(2S)-1,1,1-trifluoropropan-2-yl]pyridine-3-sulfonamide, |
| 685 | 6-[3-cyano-1-cyclopentyl-6-(difluoromethoxy)-5-(methylsulfanyl)-1H-indol-2-yl]-N-[(2S)-1,1,1-trifluoropropan-2-yl]pyridine-3-sulfonamide, |
| 686 | 6-[3-cyano-6-methyl-1-(pyridin-2-yl)-1H-indol-2-yl]-N-(1,1,1-trifluoro-2-methylpropan-2-yl)pyridine-3-sulfonamide, |
| 687 | 6-[3-cyano-6-(difluoromethoxy)-1-(4-fluorophenyl)-1H-indol-2-yl]-N-(1,1,1-trifluoro-2-methylpropan-2-yl)pyridine-3-sulfonamide, |
| 688 | 6-[3-cyano-6-methyl-1-(pyrimidin-2-yl)-1H-indol-2-yl]-N-[(2R)-1,1,1-trifluoropropan-2-yl]pyridine-3-sulfonamide, |
| 689 | 6-[3-cyano-6-methyl-1-(pyrimidin-2-yl)-1H-indol-2-yl]-N-(1,1,1-trifluoro-2-methylpropan-2-yl)pyridine-3-sulfonamide, |
| 690 | 6-[3-cyano-6-(difluoromethoxy)-1-(pyrimidin-2-yl)-1H-indol-2-yl]-N-[1-(trifluoromethyl)cyclopropyl]pyridine-3-sulfonamide, |
| 691 | 6-(3-cyano-1-cyclopentyl-5-hydroxy-6-methyl-1H-indol-2-yl)-N-[(2S)-1,1,1-trifluoropropan-2-yl]pyridine-3-sulfonamide, |
| 692 | 6-(5-bromo-3-cyano-1-cyclopentyl-6-methyl-1H-indol-2-yl)-N-[(2R)-1,1,1-trifluoropropan-2-yl]pyridine-3-sulfonamide, |
| 693 | 6-(3-cyano-1-cyclopentyl-5-hydroxy-6-methyl-1H-indol-2-yl)-N-[(2R)-1,1,1-trifluoropropan-2-yl]pyridine-3-sulfonamide, |
| 694 | 6-(3-cyano-1-cyclopentyl-5-methoxy-6-methyl-1H-indol-2-yl)-N-[(2R)-1,1,1-trifluoropropan-2-yl]pyridine-3-sulfonamide, |
| 695 | 6-[3-cyano-5-fluoro-6-methyl-1-(pyrimidin-2-yl)-1H-indol-2-yl]-N-[(2R)-1,1,1-trifluoropropan-2-yl]pyridine-3-sulfonamide, |
| 696 | 6-[3-cyano-1-cyclobutyl-5-(2,2-difluoroethyl)-1H-indol-2-yl]-N-(1-methylcyclopropyl)pyridine-3-sulfonamide, |
| 697 | 6-[3-cyano-1-cyclobutyl-6-(2,2-difluoroethyl)-5-fluoro-1H-indol-2-yl]-N-[(2S)-1,1,1-trifluoropropan-2-yl]pyridine-3-sulfonamide, |
| 698 | 6-[3-cyano-5-fluoro-6-methyl-1-(pyridin-2-yl)-1H-indol-2-yl]-N-[(2R)-1,1,1-trifluoropropan-2-yl]pyridine-3-sulfonamide, |
| 699 | 1-cyclopentyl-5-fluoro-6-methyl-2-(5-{[(2R)-1,1,1-trifluoropropan-2-yl]sulfamoyl}pyridin-2-yl)-1H-indole-3-carboxamide, |
| 700 | 1-cyclopentyl-5-fluoro-6-methyl-2-(5-{[(2S)-1,1,1-trifluoropropan-2-yl]sulfamoyl}pyridin-2-yl)-1H-indole-3-carboxamide, |
| 701 | 1-cyclopentyl-5-fluoro-6-methyl-2-{5-[(1,1,1-trifluoro-2-methylpropan-2-yl)sulfamoyl]pyridin-2-yl}-1H-indole-3-carboxamide, |
| 702 | 6-[3-cyano-1-cyclobutyl-5-(2,2-difluoroethyl)-1H-indol-2-yl]-N-[(2S)-1,1,1-trifluoropropan-2-yl]pyridine-3-sulfonamide, |
| 703 | 1-cyclobutyl-6-(difluoromethoxy)-5-fluoro-2-(5-{[(2S)-1,1,1-trifluoropropan-2-yl]sulfamoyl}pyridin-2-yl)-1H-indole-3-carboxamide, |
| 704 | 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, |
| 705 | 6-(3-cyano-1-cyclohexyl-5-fluoro-6-methyl-1H-indol-2-yl)-N-(1,1,1-trifluoro-2-methylpropan-2-yl)pyridine-3-sulfonamide, |
| 706 | 1-cyclohexyl-5-fluoro-6-methyl-2-(5-{[(2S)-1,1,1-trifluoropropan-2-yl]sulfamoyl}pyridin-2-yl)-1H-indole-3-carboxamide, |
| 707 | 1-cyclohexyl-5-fluoro-6-methyl-2-(5-{[(2S)-1,1,1-trifluoropropan-2-yl]sulfamoyl}pyrimidin-2-yl)-1H-indole-3-carboxamide, |
| 708 | 6-[5-chloro-3-cyano-1-(pyrimidin-2-yl)-1H-indol-2-yl]-N-[(2S)-1,1,1-trifluoropropan-2-yl]pyridine-3-sulfonamide, |
| 709 | N-{[6-(3-cyano-1-cyclopentyl-5-fluoro-6-methyl-1H-indol-2-yl)pyridin-3-yl]sulfonyl}-N-[(2R)-1,1,1-trifluoropropan-2-yl]acetamide, |
| 710 | N-tert-butyl-6-(3-cyano-1-cyclohexyl-5-fluoro-6-methyl-1H-indol-2-yl)pyridine-3-sulfonamide, |
| 711 | 6-(3-cyano-1-cyclobutyl-5-fluoro-6-hydroxy-1H-indol-2-yl)-N-[(2S)-1,1,1-trifluoropropan-2-yl]pyridine-3-sulfonamide, |
| 712 | 6-[3-cyano-1-cyclobutyl-6-(difluoromethoxy)-5-fluoro-1H-indol-2-yl]-N-(difluoromethyl)-N-[(2S)-1,1,1-trifluoropropan-2-yl]pyridine-3-sulfonamide, |
| 713 | 6-[3-cyano-1-cyclopentyl-6-(difluoromethoxy)-5-fluoro-1H-indol-2-yl]-N-[(2R)-1,1,1-trifluoropropan-2-yl]pyridine-3-sulfonamide, |
| 714 | 1-cyclohexyl-5-fluoro-6-methyl-2-{5-[(1,1,1-trifluoro-2-methylpropan-2-yl)sulfamoyl]pyridin-2-yl}-1H-indole-3-carboxamide, |
| 715 | 1-cyclohexyl-5-fluoro-6-methyl-2-(5-sulfamoylpyridin-2-yl)-1H-indole-3-carboxamide, |
| 716 | 1-cyclohexyl-5-fluoro-6-methyl-2-(5-{[(2R)-1,1,1-trifluoropropan-2-yl]sulfamoyl}pyridin-2-yl)-1H-indole-3-carboxamide, |
| 717 | methyl 1-cyclohexyl-5-fluoro-2-(5-{[(2S)-1,1,1-trifluoropropan-2-yl]sulfamoyl}pyridin-2-yl)-1H-indole-3-carboxylate, |

| Cpd | Name |
|---|---|
| 718 | 1-cyclopentyl-6-(difluoromethoxy)-5-fluoro-2-(5-{[(2R)-1,1,1-trifluoropropan-2-yl]sulfamoyl}pyridin-2-yl)-1H-indole-3-carboxamide, |
| 719 | N-tert-butyl-6-(3-cyano-1-cyclobutyl-5-fluoro-6-hydroxy-1H-indol-2-yl)pyridine-3-sulfonamide, |
| 720 | N-tert-butyl-6-[3-cyano-1-cyclobutyl-6-(difluoromethoxy)-5-fluoro-1H-indol-2-yl]pyridine-3-sulfonamide, |
| 721 | N-tert-butyl-6-[3-cyano-1-cyclobutyl-6-(difluoromethoxy)-5-fluoro-1H-indol-2-yl]-N-(difluoromethyl)pyridine-3-sulfonamide, |
| 722 | 6-[3-cyano-1-cyclobutyl-6-(difluoromethoxy)-5-fluoro-1H-indol-2-yl]pyridine-3-sulfonamide, |
| 723 | 2-[5-(tert-butylsulfamoyl)pyridin-2-yl]-1-cyclobutyl-6-(difluoromethoxy)-5-fluoro-1H-indole-3-carboxamide, |
| 724 | 6-{3-cyano-5-fluoro-1-[5-(trifluoromethyl)pyridin-2-yl]-1H-indol-2-yl}-N-[(2S)-1,1,1-trifluoropropan-2-yl]pyridine-3-sulfonamide, |
| 725 | 6-(3-cyano-1-cyclobutyl-5-fluoro-6-methoxy-1H-indol-2-yl)-N-[(2S)-1,1,1-trifluoropropan-2-yl]pyridine-3-sulfonamide, |
| 726 | 6-(3-cyano-1-cyclobutyl-6-ethoxy-5-fluoro-1H-indol-2-yl)-N-[(2S)-1,1,1-trifluoropropan-2-yl]pyridine-3-sulfonamide, |
| 727 | 6-[1-cyclobutyl-6-(difluoromethoxy)-5-fluoro-1H-indol-2-yl]-N-[(2S)-1,1,1-trifluoropropan-2-yl]pyridine-3-sulfonamide, |
| 728 | 6-(1-cyclobutyl-5-fluoro-6-hydroxy-1H-indol-2-yl)-N-[(2S)-1,1,1-trifluoropropan-2-yl]pyridine-3-sulfonamide, |
| 729 | 1-cyclobutyl-6-(difluoromethoxy)-5-fluoro-2-{5-[(1,1,1-trifluoro-2-methylpropan-2-yl)sulfamoyl]pyridin-2-yl}-1H-indole-3-carboxamide, |
| 730 | 1-cyclopentyl-5-fluoro-6-methyl-2-(5-{[1-(trifluoromethyl)cyclopropyl]sulfamoyl}pyridin-2-yl)-1H-indole-3-carboxamide, |
| 731 | 1-cyclobutyl-6-cyclopropyl-5-fluoro-2-(5-{[(2S)-1,1,1-trifluoropropan-2-yl]sulfamoyl}pyridin-2-yl)-1H-indole-3-carboxamide, |
| 732 | 1-cyclobutyl-5-fluoro-6-methyl-2-(5-{[(2R)-1,1,1-trifluoropropan-2-yl]sulfamoyl}pyridin-2-yl)-1H-indole-3-carboxamide, |
| 733 | 5-chloro-1-cyclobutyl-6-methyl-2-(5-{[(2S)-1,1,1-trifluoropropan-2-yl]sulfamoyl}pyrimidin-2-yl)-1H-indole-3-carboxamide, |
| 734 | 5-chloro-1-cyclobutyl-6-methyl-2-(5-{[(2S)-1,1,1-trifluoropropan-2-yl]sulfamoyl}pyridin-2-yl)-1H-indole-3-carboxamide, |
| 735 | 5-chloro-1-cyclobutyl-6-methyl-2-(5-{[(2R)-1,1,1-trifluoropropan-2-yl]sulfamoyl}pyridin-2-yl)-1H-indole-3-carboxamide, |
| 736 | 6-chloro-1-cyclobutyl-5-fluoro-2-(5-{[(2S)-1,1,1-trifluoropropan-2-yl]sulfamoyl}pyridin-2-yl)-1H-indole-3-carboxamide, |
| 737 | 1-cyclobutyl-5-fluoro-6-methyl-2-(5-{[(2S)-1,1,1-trifluoropropan-2-yl]sulfamoyl}pyridin-2-yl)-1H-indole-3-carboxamide, |
| 738 | 6-[3-cyano-1-cyclobutyl-6-(difluoromethoxy)-5-fluoro-1H-indol-2-yl]-N-[(2S)-1,1,1-trifluorobutan-2-yl]pyridine-3-sulfonamide, |
| 739 | 6-[3-cyano-5-fluoro-6-methyl-1-(3-methylpyridin-2-yl)-1H-indol-2-yl]-N-[(2S)-1,1,1-trifluoropropan-2-yl]pyridine-3-sulfonamide, |
| 740 | 6-{3-cyano-5-fluoro-6-methyl-1-[5-(trifluoromethyl)pyridin-2-yl]-1H-indol-2-yl}-N-[(2S)-1,1,1-trifluoropropan-2-yl]pyridine-3-sulfonamide, |
| 741 | 1-cyclohexyl-5-fluoro-2-(5-{[(2S)-1,1,1-trifluoropropan-2-yl]sulfamoyl}pyridin-2-yl)-1H-indole-3-carboxylic acid, |
| 742 | 6-[3-cyano-5-fluoro-1-(5-fluoropyridin-2-yl)-6-methyl-1H-indol-2-yl]-N-[(2S)-1,1,1-trifluoropropan-2-yl]pyridine-3-sulfonamide, |
| 743 | 6-[3-cyano-1-(5-cyanopyridin-2-yl)-5-fluoro-6-methyl-1H-indol-2-yl]-N-[(2S)-1,1,1-trifluoropropan-2-yl]pyridine-3-sulfonamide, |
| 744 | 6-[3-cyano-5-fluoro-6-methyl-1-(5-nitropyridin-2-yl)-1H-indol-2-yl]-N-[(2S)-1,1,1-trifluoropropan-2-yl]pyridine-3-sulfonamide, |
| 745 | 5-chloro-1-cyclobutyl-2-[5-(propan-2-ylsulfamoyl)pyrimidin-2-yl]-1H-indole-3-carboxamide, |
| 746 | 1-cyclohexyl-6-(difluoromethoxy)-2-(5-{[(2S)-1,1,1-trifluoropropan-2-yl]sulfamoyl}pyrimidin-2-yl)-1H-indole-3-carboxamide, |
| 747 | 1-cyclohexyl-6-(difluoromethoxy)-2-[5-(propan-2-ylsulfamoyl)pyrimidin-2-yl]-1H-indole-3-carboxamide, |
| 748 | 5-fluoro-1-(pyridin-2-yl)-2-(5-{[(2S)-1,1,1-trifluoropropan-2-yl]sulfamoyl}pyridin-2-yl)-1H-indole-3-carboxamide, |
| 749 | 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide, |
| 750 | 6-[3-cyano-5-fluoro-6-methyl-1-(tetrahydro-2H-pyran-4-yl)-1H-indol-2-yl]-N-(1,1,1-trifluoro-2-methylpropan-2-yl)pyridine-3-sulfonamide, |
| 751 | 6-[3-cyano-5-fluoro-6-methyl-1-(tetrahydro-2H-pyran-4-yl)-1H-indol-2-yl]-N-[(2S)-1,1,1-trifluoropropan-2-yl]pyridine-3-sulfonamide, |
| 752 | N-tert-butyl-6-[3-cyano-5-fluoro-6-methyl-1-(tetrahydro-2H-pyran-4-yl)-1H-indol-2-yl]pyridine-3-sulfonamide, |
| 753 | 2-[3-cyano-5-fluoro-6-methyl-1-(tetrahydro-2H-pyran-4-yl)-1H-indol-2-yl]-N-[(2S)-1,1,1-trifluoropropan-2-yl]pyrimidine-5-sulfonamide, |
| 754 | methyl 1-cyclopentyl-5-fluoro-6-methyl-2-{5-[(1,1,1-trifluoro-2-methylpropan-2-yl)sulfamoyl]pyridin-2-yl}-1H-indole-3-carboxylate, |
| 755 | methyl 2-[5-(tert-butylsulfamoyl)pyridin-2-yl]-1-cyclopentyl-5-fluoro-6-methyl-1H-indole-3-carboxylate, |

-continued

| Cpd | Name |
|---|---|
| 756 | methyl 1-cyclopentyl-5-fluoro-6-methyl-2-(5-{[(2S)-1,1,1-trifluoropropan-2-yl]sulfamoyl}pyridin-2-yl)-1H-indole-3-carboxylate, |
| 757 | 6-(3-cyano-1-cyclobutyl-5-methoxy-6-methyl-1H-indol-2-yl)-N-[(2S)-1,1,1-trifluoropropan-2-yl]pyridine-3-sulfonamide, |
| 758 | 1-cyclopentyl-5-fluoro-6-methyl-2-(5-{[(2S)-1,1,1-trifluoropropan-2-yl]sulfamoyl}pyridin-2-yl)-1H-indole-3-carboxylic acid, |
| 760 | 6-(1-cyclopentyl-5-fluoro-6-methyl-1H-indol-2-yl)-N-[(2S)-1,1,1-trifluoropropan-2-yl]pyridine-3-sulfonamide, |
| 761 | 1-cyclopentyl-5-fluoro-N,6-dimethyl-2-(5-{[(2S)-1,1,1-trifluoropropan-2-yl]sulfamoyl}pyridin-2-yl)-1H-indole-3-carboxamide, |
| 762 | 1-cyclopentyl-N-ethyl-5-fluoro-6-methyl-2-(5-{[(2S)-1,1,1-trifluoropropan-2-yl]sulfamoyl}pyridin-2-yl)-1H-indole-3-carboxamide, |
| 763 | 1-cyclopentyl-5-fluoro-6-methyl-N-(propan-2-yl)-2-(5-{[(2S)-1,1,1-trifluoropropan-2-yl]sulfamoyl}pyridin-2-yl)-1H-indole-3-carboxamide, |
| 764 | N-tert-butyl-6-(3-cyano-1-cyclobutyl-6-ethyl-5-fluoro-1H-indol-2-yl)pyridine-3-sulfonamide, |
| 765 | 1-cyclopentyl-5-fluoro-6-methyl-2-{5-[(1,1,1-trifluoro-2-methylpropan-2-yl)sulfamoyl]pyridin-2-yl}-1H-indole-3-carboxylic acid, |
| 766 | 2-[5-(tert-butylsulfamoyl)pyridin-2-yl]-1-cyclopentyl-5-fluoro-6-methyl-1H-indole-3-carboxylic acid, |
| 767 | 5-fluoro-6-methyl-1-(tetrahydro-2H-pyran-4-yl)-2-(5-{[(2R)-1,1,1-trifluoropropan-2-yl]sulfamoyl}pyridin-2-yl)-1H-indole-3-carboxamide, |
| 768 | 5-fluoro-6-methyl-1-(tetrahydro-2H-pyran-4-yl)-2-{5-[(1,1,1-trifluoro-2-methylpropan-2-yl)sulfamoyl]pyridin-2-yl}-1H-indole-3-carboxamide, |
| 769 | 5-fluoro-6-methyl-1-(tetrahydro-2H-pyran-4-yl)-2-(5-{[(2S)-1,1,1-trifluoropropan-2-yl]sulfamoyl}pyridin-2-yl)-1H-indole-3-carboxamide, |
| 770 | methyl 2-[5-(tert-butylsulfamoyl)pyridin-2-yl]-1-cyclobutyl-5-fluoro-6-methyl-1H-indole-3-carboxylate, |
| 771 | methyl 1-cyclobutyl-5-fluoro-6-methyl-2-(5-{[(2S)-1,1,1-trifluoropropa-2-yl]sulfamoyl}pyridin-2-yl)-1H-indole-3-carboxylate, |
| 772 | 6-[3-cyano-1-cyclobutyl-5-fluoro-6-(methylsulfanyl)-1H-indol-2-yl]-N-[(2S)-1,1,1-trifluoropropan-2-yl]pyridine-3-sulfonamide, |
| 773 | 6-[3-cyano-1-(cyclopropylmethyl)-6-(difluoromethoxy)-4-fluoro-1H-indol-2-yl]-N-[(2S)-1,1,1-trifluoropropan-2-yl]pyridine-3-sulfonamide, |
| 774 | methyl 1-cyclobutyl-5-fluoro-6-methyl-2-(5-{[(2S)-1,1,1-trifluoropropan-2-yl]sulfamoyl}pyrimidin-2-yl)-1H-indole-3-carboxylate, |
| 775 | 1-cyclobutyl-5-fluoro-6-methyl-2-(5-{[(2S)-1,1,1-trifluoropropan-2-yl]sulfamoyl}pyrimidin-2-yl)-1H-indole-3-carboxylic acid, |
| 776 | 2-[5-(tert-butylsulfamoyl)pyridin-2-yl]-1-cyclobutyl-5-fluoro-6-methyl-1H-indole-3-carboxylic acid, |
| 777 | 6-[3-cyano-6-ethyl-5-fluoro-1-(5-fluoropyridin-2-yl)-1H-indol-2-yl]-N-[(2S)-1,1,1-trifluoropropan-2-yl]pyridine-3-sulfonamide, |
| 778 | 6-[3-cyano-6-ethyl-5-fluoro-1-(pyridin-2-yl)-1H-indol-2-yl]-N-[(2S)-1,1,1-trifluoropropan-2-yl]pyridine-3-sulfonamide, |
| 780 | 6-chloro-1-cyclobutyl-2-[5-(propan-2-ylsulfamoyl)pyrimidin-2-yl]-1H-indole-3-carboxamide, |
| 781 | 1-cyclobutyl-2-[5-(propan-2-ylsulfamoyl)pyrimidin-2-yl]-6-(trifluoromethoxy)-1H-indole-3-carboxamide, |
| 782 | 1-cyclopentyl-2-[5-(propan-2-ylsulfamoyl)pyrimidin-2-yl]-6-(trifluoromethoxy)-1H-indole-3-carboxamide, |
| 783 | 1-cyclopentyl-5-fluoro-N,N,6-trimethyl-2-(5-{[(2S)-1,1,1-trifluoropropan-2-yl]sulfamoyl}pyridin-2-yl)-1H-indole-3-carboxamide, |
| 784 | 6-[3-cyano-6-(difluoromethoxy)-4-fluoro-1-(propan-2-yl)-1H-indol-2-yl]-N-[(2S)-1,1,1-trifluoropropan-2-yl]pyridine-3-sulfonamide, |
| 785 | 6-[5-chloro-3-cyano-6-methyl-1-(pyrimidin-2-yl)-1H-indol-2-yl]-N-[(2S)-1,1,1-trifluoropropan-2-yl]pyridine-3-sulfonamide, |
| 786 | 6-[3-cyano-6-(difluoromethoxy)-5-fluoro-1-propyl-1H-indol-2-yl]-N-[(2S)-1,1,1-trifluoropropan-2-yl]pyridine-3-sulfonamide, |
| 787 | 6-[3-cyano-1-(cyclopropylmethyl)-6-(difluoromethoxy)-5-fluoro-1H-indol-2-yl]-N-[(2S)-1,1,1-trifluoropropan-2-yl]pyridine-3-sulfonamide, |
| 788 | 6-[3-cyano-6-(difluoromethoxy)-5-fluoro-1-propyl-1H-indol-2-yl]-N-[(2R)-1,1,1-trifluoropropan-2-yl]pyridine-3-sulfonamide, |
| 789 | 6-[3-cyano-1-(cyclopropylmethyl)-6-(difluoromethoxy)-5-fluoro-1H-indol-2-yl]-N-[(2R)-1,1,1-trifluoropropan-2-yl]pyridine-3-sulfonamide, |
| 790 | 6-[3-cyano-1-cyclobutyl-6-(difluoromethoxy)-5-fluoro-1H-indol-2-yl]-N-(1,1,1-trifluorobutan-2-yl)pyridine-3-sulfonamide, |
| 791 | 6-[3-cyano-1-cyclobutyl-6-(difluoromethoxy)-5-fluoro-1H-indol-2-yl]-N-phenylpyridine-3-sulfonamide, |
| 793 | 1-cyclobutyl-5-fluoro-6-methyl-2-(5-{[(2S)-1,1,1-trifluoropropan-2-yl]sulfamoyl}pyridin-2-yl)-1H-indole-3-carboxylic acid, |
| 794 | 2-[5-(tert-butylsulfamoyl)pyrimidin-2-yl]-1-cyclobutyl-5-fluoro-6-methyl-1H-indole-3-carboxylic acid, |
| 795 | 2-[5-(tert-butylsulfamoyl)pyridin-2-yl]-1-cyclobutyl-5-fluoro-N,6-dimethyl-1H-indole-3-carboxamide, |
| 796 | 6-(3-cyano-1-cyclobutyl-5-hydroxy-6-methyl-1H-indol-2-yl)-N-[(2S)-1,1,1-trifluoropropan-2-yl]pyridine-3-sulfonamide, |
| 797 | 6-[3-cyano-1-cyclobutyl-6-(difluoromethoxy)-4-fluoro-1H-indol-2-yl]-N-[(2S)-1,1,1-trifluoropropan-2-yl]pyridine-3-sulfonamide, |

| Cpd | Name |
|---|---|
| 798 | 1-cyclobutyl-6-(difluoromethoxy)-5-fluoro-2-[5-(phenylsulfamoyl)pyridin-2-yl]-1H-indole-3-carboxamide, |
| 799 | 2-[5-(tert-butylsulfamoyl)pyridin-2-yl]-1-cyclopentyl-5-fluoro-N,6-dimethyl-1H-indole-3-carboxamide, |
| 800 | 2-[5-(tert-butylsulfamoyl)pyridin-2-yl]-1-cyclobutyl-5-fluoro-6-methyl-1H-indole-3-carboxamide, |
| 801 | 1-cyclobutyl-5-fluoro-N,6-dimethyl-2-(5-{[(2S)-1,1,1-trifluoropropan-2-yl]sulfamoyl}pyridin-2-yl)-1H-indole-3-carboxamide, |
| 802 | 2-[5-(tert-butylsulfamoyl)pyrimidin-2-yl]-1-cyclobutyl-5-fluoro-N,6-dimethyl-1H-indole-3-carboxamide, |
| 803 | 6-[5-chloro-3-cyano-6-methyl-1-(pyridin-2-yl)-1H-indol-2-yl]-N-[(2S)-1,1,1-trifluoropropan-2-yl]pyridine-3-sulfonamide, |
| 804 | 6-[5-chloro-3-cyano-1-(5-fluoropyridin-2-yl)-6-methyl-1H-indol-2-yl]-N-[(2S)-1,1,1-trifluoropropan-2-yl]pyridine-3-sulfonamide, |
| 805 | N-tert-butyl-6-(3-cyano-1-cyclobutyl-5-hydroxy-6-methyl-1H-indol-2-yl)pyridine-3-sulfonamide, |
| 806 | 1-cyclopentyl-6-(difluoromethoxy)-5-fluoro-2-(5-{[(2S)-1,1,1-trifluoropropan-2-yl]sulfamoyl}pyridin-2-yl)-1H-indole-3-carboxamide, |
| 807 | 6-(3-cyano-1-cyclobutyl-5-hydroxy-6-methyl-1H-indol-2-yl)-N-[(2R)-1,1,1-trifluoropropan-2-yl]pyridine-3-sulfonamide, |
| 808 | 6-[3-cyano-1-cyclobutyl-6-(difluoromethoxy)-5-fluoro-1H-indol-2-yl]-N-[1-(trifluoromethyl)cyclopropyl]pyridine-3-sulfonamide, |
| 809 | 1-cyclobutyl-6-(difluoromethoxy)-5-fluoro-2-(5-{[1-(trifluoromethyl)cyclopropyl]sulfamoyl}pyridin-2-yl)-1H-indole-3-carboxamide, |
| 810 | 6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide, |
| 811 | 6-[3-cyano-1-cyclobutyl-6-(difluoromethoxy)-5-fluoro-7-methyl-1H-indol-2-yl]-N-[(2S)-1,1,1-trifluoropropan-2-yl]pyridine-3-sulfonamide, |
| 812 | 6-[3-cyano-1-(cyclopropylmethyl)-6-(difluoromethoxy)-5-fluoro-1H-indol-2-yl]pyridine-3-sulfonamide, |
| 813 | 6-(3-cyano-1-cyclobutyl-5-fluoro-6-hydroxy-1H-indol-2-yl)-N-[1-(trifluoromethyl)cyclopropyl]pyridine-3-sulfonamide, |
| 814 | 6-[3-cyano-5-fluoro-1-(3-fluoropyridin-2-yl)-6-methyl-1H-indol-2-yl]-N-[(2S)-1,1,1-trifluoropropan-2-yl]pyridine-3-sulfonamide, |
| 815 | 6-[3-cyano-5-fluoro-1-(6-fluoropyridin-2-yl)-6-methyl-1H-indol-2-yl]-N-[(2S)-1,1,1-trifluoropropan-2-yl]pyridine-3-sulfonamide, |
| 816 | 6-[3-cyano-5-fluoro-1-(4-methoxypyridin-2-yl)-6-methyl-1H-indol-2-yl]-N-[(2S)-1,1,1-trifluoropropan-2-yl]pyridine-3-sulfonamide, |
| 817 | 6-[3-cyano-5-fluoro-6-methyl-1-(pyrazin-2-yl)-1H-indol-2-yl]-N-[(2S)-1,1,1-trifluoropropan-2-yl]pyridine-3-sulfonamide, |
| 818 | 6-[3-cyano-6-cyclopropyl-5-fluoro-1-(5-fluoropyridin-2-yl)-1H-indol-2-yl]-N-[(2S)-1,1,1-trifluoropropan-2-yl]pyridine-3-sulfonamide, |
| 819 | 6-[3-cyano-6-cyclopropyl-5-fluoro-1-(pyridin-2-yl)-1H-indol-2-yl]-N-[(2S)-1,1,1-trifluoropropan-2-yl]pyridine-3-sulfonamide, |
| 820 | 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 821 | 6-(3-cyano-1-cyclopentyl-5-fluoro-6-methyl-1H-indol-2-yl)-N-[(2S)-1,1,1-trifluorobutan-2-yl]pyridine-3-sulfonamide, |
| 822 | 6-[3-cyano-1-cyclobutyl-6-(difluoromethoxy)-5-fluoro-1H-indol-2-yl]-4-methyl-N-[(2S)-1,1,1-trifluoropropan-2-yl]pyridine-3-sulfonamide, |
| 823 | N-tert-butyl-6-[3-cyano-5-fluoro-1-(pyrimidin-2-yl)-1H-indol-2-yl]pyridine-3-sulfonamide, |
| 824 | N-tert-butyl-6-[3-cyano-5-fluoro-6-methyl-1-(pyrimidin-2-yl)-1H-indol-2-yl]pyridine-3-sulfonamide, |
| 825 | 1-cyclobutyl-6-(difluoromethoxy)-4-fluoro-2-(5-{[(2S)-1,1,1-trifluoropropan-2-yl]sulfamoyl}pyridin-2-yl)-1H-indole-3-carboxamide, |
| 826 | 6-(3-cyano-1-cyclobutyl-5-fluoro-6-methyl-1H-indol-2-yl)-N-[(2S)-1,1,1-trifluorobutan-2-yl]pyridine-3-sulfonamide, |
| 827 | 6-[3-cyano-1-cyclobutyl-6-(difluoromethoxy)-5-fluoro-1H-indol-2-yl]-5-methyl-N-[(2S)-1,1,1-trifluoropropan-2-yl]pyridine-3-sulfonamide, |
| 828 | 2-[5-(tert-butylsulfamoyl)pyridin-2-yl]-1-cyclobutyl-5-hydroxy-6-methyl-1H-indole-3-carboxamide, |
| 829 | 1-cyclopentyl-6-cyclopropyl-5-fluoro-2-(5-{[(2R)-1,1,1-trifluoropropan-2-yl]sulfamoyl}pyridin-2-yl)-1H-indole-3-carboxamide, |
| 830 | 1-cyclopentyl-6-ethyl-5-fluoro-2-(5-{[(2S)-1,1,1-trifluoropropan-2-yl]sulfamoyl}pyridin-2-yl)-1H-indole-3-carboxamide, |
| 831 | 6-(3-cyano-1-cyclopentyl-6-cyclopropyl-5-fluoro-1H-indol-2-yl)-N-(1,1,1-trifluoro-2-methylpropan-2-yl)pyridine-3-sulfonamide, |
| 832 | N-tert-butyl-6-(3-cyano-1-cyclopentyl-6-cyclopropyl-5-fluoro-1H-indol-2-yl)pyridine-3-sulfonamide, |
| 833 | 1-cyclobutyl-5-hydroxy-6-methyl-2-(5-{[(2S)-1,1,1-trifluoropropan-2-yl]sulfamoyl}pyridin-2-yl)-1H-indole-3-carboxamide, |
| 834 | 1-cyclopentyl-5-methoxy-6-methyl-2-(5-{[(2R)-1,1,1-trifluoropropan-2-yl]sulfamoyl}pyridin-2-yl)-1H-indole-3-carboxamide, |
| 835 | 1-cyclohexyl-5-fluoro-6-methyl-2-(5-{[1-(trifluoromethyl)cyclopropyl]sulfamoyl}pyridin-2-yl)-1H-indole-3-carboxylic acid, |

| Cpd | Name |
|---|---|
| 836 | N-[6-(3-cyano-1-cyclopentyl-5-fluoro-6-methyl-1H-indol-2-yl)pyridin-3-yl]-N'-[(2S)-1,1,1-trifluoropropan-2-yl]sulfuric diamide, |
| 837 | 6-(3-cyano-1-cyclopentyl-5-fluoro-6-methyl-1H-indol-2-yl)-5-methyl-N-[(2S)-1,1,1-trifluoropropan-2-yl]pyridine-3-sulfonamide, |
| 838 | 1-cyclopentyl-6-cyclopropyl-5-fluoro-2-(5-{[(2S)-1,1,1-trifluoropropan-2-yl]sulfamoyl}pyridin-2-yl)-1H-indole-3-carboxamide, |
| 839 | 6-(difluoromethoxy)-4-fluoro-1-(propan-2-yl)-2-(5-{[(2S)-1,1,1-trifluoropropan-2-yl]sulfamoyl}pyridin-2-yl)-1H-indole-3-carboxamide, |
| 840 | 1-(cyclopropylmethyl)-6-(difluoromethoxy)-4-fluoro-2-(5-{[(2S)-1,1,1-trifluoropropan-2-yl]sulfamoyl}pyridin-2-yl)-1H-indole-3-carboxamide, |
| 841 | 1-cyclopentyl-5-hydroxy-6-methyl-2-(5-{[(2S)-1,1,1-trifluoropropan-2-yl]sulfamoyl}pyridin-2-yl)-1H-indole-3-carboxamide, |
| 842 | 6-(3-cyano-1-cyclopentyl-5-fluoro-6-methyl-1H-indol-2-yl)-4-methyl-N-[(2S)-1,1,1-trifluoropropan-2-yl]pyridine-3-sulfonamide, |
| 843 | 6-[3-cyano-5-methyl-1-(pyrimidin-2-yl)-1H-indol-2-yl]-N-[(2S)-1,1,1-trifluoropropan-2-yl]pyridine-3-sulfonamide, |
| 844 | 6-[3-cyano-1-(3-fluoropyridin-2-yl)-5-methyl-1H-indol-2-yl]-N-[(2S)-1,1,1-trifluoropropan-2-yl]pyridine-3-sulfonamide, |
| 845 | 6-[3-cyano-5-methyl-1-(pyrazin-2-yl)-1H-indol-2-yl]-N-[(2S)-1,1,1-trifluoropropan-2-yl]pyridine-3-sulfonamide, |
| 846 | 5-methyl-1-(pyrimidin-2-yl)-2-(5-{[(2S)-1,1,1-trifluoropropan-2-yl]sulfamoyl}pyridin-2-yl)-1H-indole-3-carboxamide, |
| 847 | 6-[3-cyano-5-fluoro-1-(pyridin-2-yl)-1H-indol-2-yl]-4-methyl-N-[(2S)-1,1,1-trifluoropropan-2-yl]pyridine-3-sulfonamide, |
| 848 | 6-[3-cyano-5-fluoro-1-(pyrimidin-2-yl)-1H-indol-2-yl]-4-methyl-N-[(2S)-1,1,1-trifluoropropan-2-yl]pyridine-3-sulfonamide, |
| 849 | 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, |
| 850 | 1-cyclopentyl-6-cyclopropyl-5-fluoro-2-{5-[(1,1,1-trifluoro-2-methylpropan-2-yl)sulfamoyl]pyridin-2-yl}-1H-indole-3-carboxamide, |
| 851 | 6-[3-cyano-6-ethyl-5-fluoro-1-(pyrimidin-2-yl)-1H-indol-2-yl]-4-methyl-N-[(2S)-1,1,1-trifluoropropan-2-yl]pyridine-3-sulfonamide, |
| 852 | 6-[3-cyano-6-ethyl-5-fluoro-1-(pyridin-2-yl)-1H-indol-2-yl]-4-methyl-N-[(2S)-1,1,1-trifluoropropan-2-yl]pyridine-3-sulfonamide, |
| 853 | 6-[3-cyano-5-fluoro-6-methyl-1-(pyrimidin-2-yl)-1H-indol-2-yl]-4-methyl-N-[(2S)-1,1,1-trifluoropropan-2-yl]pyridine-3-sulfonamide, |
| 854 | 6-[3-cyano-5-fluoro-6-methyl-1-(pyridin-2-yl)-1H-indol-2-yl]-4-methyl-N-[(2S)-1,1,1-trifluoropropan-2-yl]pyridine-3-sulfonamide, |
| 855 | N-tert-butyl-6-[3-cyano-6-ethyl-5-fluoro-1-(pyrimidin-2-yl)-1H-indol-2-yl]pyridine-3-sulfonamide, |
| 856 | 6-(3-cyano-1-cyclohexyl-5-fluoro-6-methyl-1H-indol-2-yl)-N-[1-(trifluoromethyl)cyclopropyl]pyridine-3-sulfonamide, |
| 857 | 1-cyclohexyl-5-fluoro-6-methyl-2-(5-{[1-(trifluoromethyl)cyclopropyl]sulfamoyl}pyridin-2-yl)-1H-indole-3-carboxamide, |
| 858 | 6-(3-cyano-1-cyclobutyl-6-ethyl-4-methoxy-1H-indol-2-yl)-N-[(2S)-1,1,1-trifluoropropan-2-yl]pyridine-3-sulfonamide, |
| 859 | 6-[3-cyano-6-ethyl-5-fluoro-1-(pyrimidin-2-yl)-1H-indol-2-yl]-N-(1,1,1-trifluoro-2-methylpropan-2-yl)pyridine-3-sulfonamide, |
| 860 | 6-[3-cyano-6-ethyl-5-fluoro-1-(pyrimidin-2-yl)-1H-indol-2-yl]-N-(1-methylcyclopropyl)pyridine-3-sulfonamide, |
| 861 | 6-[3-cyano-6-ethyl-5-fluoro-1-(pyrimidin-2-yl)-1H-indol-2-yl]-N-(1-methylcyclopropyl)-N-(pyrimidin-2-yl)pyridine-3-sulfonamide, |
| 862 | 6-[3-cyano-1-cyclopentyl-6-(difluoromethoxy)-5-fluoro-1H-indol-2-yl]-N-(1,1,1-trifluoro-2-methylpropan-2-yl)pyridine-3-sulfonamide, |
| 863 | 1-cyclopentyl-6-(difluoromethoxy)-5-fluoro-2-{5-[(1,1,1-trifluoro-2-methylpropan-2-yl)sulfamoyl]pyridin-2-yl}-1H-indole-3-carboxamide, |
| 864 | 6-[3-cyano-6-ethyl-5-fluoro-1-(pyrimidin-2-yl)-1H-indol-2-yl]-N-[1-(trifluoromethyl)cyclopropyl]pyridine-3-sulfonamide, |
| 865 | 6-[3-cyano-5-fluoro-6-methyl-1-(5-methylpyrazin-2-yl)-1H-indol-2-yl]-N-[(2S)-1,1,1-trifluoropropan-2-yl]pyridine-3-sulfonamide, |
| 866 | 6-[3-cyano-5-fluoro-1-(4-methoxypyrimidin-2-yl)-6-methyl-1H-indol-2-yl]-N-[(2S)-1,1,1-trifluoropropan-2-yl]pyridine-3-sulfonamide, |
| 867 | 6-[3-cyano-6-ethyl-5-fluoro-1-(pyrimidin-2-yl)-1H-indol-2-yl]-5-methyl-N-[(2S)-1,1,1-trifluoropropan-2-yl]pyridine-3-sulfonamide, |
| 868 | 6-(3-cyano-1-cyclopentyl-5-fluoro-6-methyl-1H-indol-2-yl)-2-methyl-N-[(2S)-1,1,1-trifluoropropan-2-yl]pyridine-3-sulfonamide, |
| 869 | N-tert-butyl-6-[6-ethyl-5-fluoro-3-(methylsulfonyl)-1-(pyrimidin-2-yl)-1H-indol-2-yl]pyridine-3-sulfonamide, |
| 870 | 6-[3-cyano-6-ethyl-5-fluoro-1-(pyridin-2-yl)-1H-indol-2-yl]-5-methyl-N-[(2S)-1,1,1-trifluoropropan-2-yl]pyridine-3-sulfonamide, |
| 871 | 1-cyclopentyl-6-ethyl-5-fluoro-2-{5-[(1,1,1-trifluoro-2-methylpropan-2-yl)sulfamoyl]pyridin-2-yl}-1H-indole-3-carboxamide, |
| 872 | 1-cyclopentyl-6-ethyl-5-fluoro-2-(5-{[1-(trifluoromethyl)cyclopropyl]sulfamoyl}pyridin-2-yl)-1H-indole-3-carboxamide, |
| 873 | 6-[3-cyano-5-fluoro-6-methyl-1-(4-methylpyrimidin-2-yl)-1H-indol-2-yl]-N-[(2S)-1,1,1-trifluoropropan-2-yl]pyridine-3-sulfonamide, |

| Cpd | Name |
|---|---|
| 874 | 5-fluoro-6-methyl-1-(pyridin-2-yl)-2-(5-{[(2S)-1,1,1-trifluoropropan-2-yl]sulfamoyl}pyridin-2-yl)-1H-indole-3-carboxamide, |
| 875 | 5-fluoro-6-methyl-1-(pyrazin-2-yl)-2-(5-{[(2S)-1,1,1-trifluoropropan-2-yl]sulfamoyl}pyridin-2-yl)-1H-indole-3-carboxamide, |
| 876 | 5-fluoro-1-(5-fluoropyridin-2-yl)-6-methyl-2-(5-{[(2S)-1,1,1-trifluoropropan-2-yl]sulfamoyl}pyridin-2-yl)-1H-indole-3-carboxamide, |
| 877 | 5-fluoro-1-(6-fluoropyridin-2-yl)-6-methyl-2-(5-{[(2S)-1,1,1-trifluoropropan-2-yl]sulfamoyl}pyridin-2-yl)-1H-indole-3-carboxamide, |
| 878 | 6-[3-cyano-6-ethyl-5-fluoro-1-(pyrimidin-2-yl)-1H-indol-2-yl]-N-[(2R)-1,1,1-trifluoropropan-2-yl]pyridine-3-sulfonamide, |
| 879 | 6-[3-cyano-6-ethyl-5-fluoro-1-(pyridin-2-yl)-1H-indol-2-yl]-N-[(2R)-1,1,1-trifluoropropan-2-yl]pyridine-3-sulfonamide, |
| 880 | 6-[3-cyano-6-ethyl-5-fluoro-1-(5-fluoropyridin-2-yl)-1H-indol-2-yl]-N-[(2R)-1,1,1-trifluoropropan-2-yl]pyridine-3-sulfonamide, |
| 881 | 6-[3-cyano-6-ethyl-5-fluoro-1-(pyrimidin-2-yl)-1H-indol-2-yl]-2-methyl-N-[(2S)-1,1,1-trifluoropropan-2-yl]pyridine-3-sulfonamide, |
| 882 | N-tert-butyl-6-[3-cyano-6-ethyl-5-fluoro-1-(pyridin-2-yl)-1H-indol-2-yl]pyridine-3-sulfonamide, |
| 883 | 2-[5-(tert-butylsulfamoyl)pyridin-2-yl]-6-ethyl-5-fluoro-1-(pyridin-2-yl)-1H-indole-3-carboxamide, |
| 884 | N-tert-butyl-6-(3-cyano-6-ethyl-5-fluoro-1-phenyl-1H-indol-2-yl)pyridine-3-sulfonamide, |
| 885 | 6-[3-cyano-5-fluoro-6-methyl-1-(5-methylpyridin-2-yl)-1H-indol-2-yl]-N-[(2S)-1,1,1-trifluoropropan-2-yl]pyridine-3-sulfonamide, |
| 886 | 6-[3-cyano-5-fluoro-6-methyl-1-(4-methylpyridin-2-yl)-1H-indol-2-yl]-N-[(2S)-1,1,1-trifluoropropan-2-yl]pyridine-3-sulfonamide, |
| 887 | 6-[3-cyano-6-ethyl-5-fluoro-1-(pyridin-2-yl)-1H-indol-2-yl]-2-methyl-N-[(2S)-1,1,1-trifluoropropan-2-yl]pyridine-3-sulfonamide, |
| 888 | 6-[3-cyano-5-fluoro-6-methyl-1-(pyrimidin-2-yl)-1H-indol-2-yl]-5-methyl-N-[(2S)-1,1,1-trifluoropropan-2-yl]pyridine-3-sulfonamide, |
| 889 | 6-[3-cyano-5-fluoro-6-methyl-1-(pyridin-2-yl)-1H-indol-2-yl]-5-methyl-N-[(2S)-1,1,1-trifluoropropan-2-yl]pyridine-3-sulfonamide, |
| 890 | 6-[3-cyano-6-ethyl-5-fluoro-1-(pyrimidin-2-yl)-1H-indol-2-yl]-4-methyl-N-[(2R)-1,1,1-trifluoropropan-2-yl]pyridine-3-sulfonamide, |
| 891 | 6-[3-cyano-6-ethyl-5-fluoro-1-(pyridin-2-yl)-1H-indol-2-yl]-4-methyl-N-[(2R)-1,1,1-trifluoropropan-2-yl]pyridine-3-sulfonamide, |
| 892 | 6-[3-cyano-5-fluoro-6-methyl-1-(pyridazin-3-yl)-1H-indol-2-yl]-N-[(2S)-1,1,1-trifluoropropan-2-yl]pyridine-3-sulfonamide, |
| 893 | 6-[3-cyano-5-fluoro-6-methyl-1-(pyridin-3-yl)-1H-indol-2-yl]-N-[(2S)-1,1,1-trifluoropropan-2-yl]pyridine-3-sulfonamide, |
| 894 | 6-[3-cyano-5-fluoro-6-methyl-1-(pyrimidin-5-yl)-1H-indol-2-yl]-N-[(2S)-1,1,1-trifluoropropan-2-yl]pyridine-3-sulfonamide, |
| 895 | 6-[6-bromo-3-cyano-5-fluoro-1-(pyrimidin-2-yl)-1H-indol-2-yl]-N-[(2S)-1,1,1-trifluoropropan-2-yl]pyridine-3-sulfonamide, |
| 896 | 6-[3-cyano-5-fluoro-6-methyl-1-(pyrimidin-4-yl)-1H-indol-2-yl]-N-[(2S)-1,1,1-trifluoropropan-2-yl]pyridine-3-sulfonamide, |
| 897 | 6-[3-cyano-1-(pyrazin-2-yl)-5-(trifluoromethyl)-1H-indol-2-yl]-N-[(2S)-1,1,1-trifluoropropan-2-yl]pyridine-3-sulfonamide, |
| 898 | 6-[3-cyano-1-(pyrazin-2-yl)-5-(trifluoromethoxy)-1H-indol-2-yl]-N-[(2S)-1,1,1-trifluoropropan-2-yl]pyridine-3-sulfonamide, |
| 899 | N-tert-butyl-6-[3-cyano-6-ethyl-5-fluoro-1-(pyrazin-2-yl)-1H-indol-2-yl]pyridine-3-sulfonamide, |
| 900 | N-tert-butyl-6-[3-cyano-6-ethyl-5-fluoro-1-(3-fluoropyridin-2-yl)-1H-indol-2-yl]pyridine-3-sulfonamide, |
| 901 | 6-[3-cyano-6-fluoro-5-methyl-1-(pyrimidin-2-yl)-1H-indol-2-yl]-N-[(2S)-1,1,1-trifluoropropan-2-yl]pyridine-3-sulfonamide, |
| 902 | 5-fluoro-1-(3-fluoropyridin-2-yl)-6-methyl-2-(5-{[(2S)-1,1,1-trifluoropropan-2-yl]sulfamoyl}pyridin-2-yl)-1H-indole-3-carboxamide, |
| 903 | 6-[5-fluoro-6-methyl-1-(1,3-thiazol-2-yl)-1H-indol-2-yl]-N-[(2S)-1,1,1-trifluoropropan-2-yl]pyridine-3-sulfonamide, |
| 904 | 5-fluoro-6-methyl-1-(5-methylpyrazin-2-yl)-2-(5-{[(2S)-1,1,1-trifluoropropan-2-yl]sulfamoyl}pyridin-2-yl)-1H-indole-3-carboxamide, |
| 905 | 5-fluoro-6-methyl-1-(4-methylpyrimidin-2-yl)-2-(5-{[(2S)-1,1,1-trifluoropropan-2-yl]sulfamoyl}pyridin-2-yl)-1H-indole-3-carboxamide, |
| 906 | 5-fluoro-1-(4-methoxypyrimidin-2-yl)-6-methyl-2-(5-{[(2S)-1,1,1-trifluoropropan-2-yl]sulfamoyl}pyridin-2-yl)-1H-indole-3-carboxamide, |
| 907 | 6-[6-acetyl-3-cyano-5-fluoro-1-(pyrimidin-2-yl)-1H-indol-2-yl]-N-[(2S)-1,1,1-trifluoropropan-2-yl]pyridine-3-sulfonamide, |
| 908 | 6-[3-cyano-6-ethenyl-5-fluoro-1-(pyrimidin-2-yl)-1H-indol-2-yl]-N-[(2S)-1,1,1-trifluoropropan-2-yl]pyridine-3-sulfonamide, |
| 909 | 6-ethyl-5-fluoro-1-(pyridin-2-yl)-2-(5-{[(2S)-1,1,1-trifluoropropan-2-yl]sulfamoyl}pyridin-2-yl)-1H-indole-3-carboxamide, |
| 910 | 6-(3-cyano-1-cyclopropyl-6-ethyl-5-fluoro-1H-indol-2-yl)-N-[(2S)-1,1,1-trifluoropropan-2-yl]pyridine-3-sulfonamide, |
| 911 | 6-[3-cyano-5-fluoro-6-(1-hydroxyethyl)-1-(pyrimidin-2-yl)-1H-indol-2-yl]-N-[(2S)-1,1,1-trifluoropropan-2-yl]pyridine-3-sulfonamide, |
| 912 | 5-fluoro-6-methyl-1-(pyridazin-3-yl)-2-(5-{[(2S)-1,1,1-trifluoropropan-2-yl]sulfamoyl}pyridin-2-yl)-1H-indole-3-carboxamide, |

| Cpd | Name |
|---|---|
| 913 | 5-fluoro-6-methyl-1-(pyridin-3-yl)-2-(5-{[(2S)-1,1,1-trifluoropropan-2-yl]sulfamoyl}pyridin-2-yl)-1H-indole-3-carboxamide, |
| 914 | 6-[1-(5-chloropyrimidin-2-yl)-3-cyano-5-fluoro-6-methyl-1H-indol-2-yl]-N-[(2S)-1,1,1-trifluoropropan-2-yl]pyridine-3-sulfonamide, |
| 915 | 6-[3-cyano-5-fluoro-6-methyl-1-(6-methylpyrazin-2-yl)-1H-indol-2-yl]-N-[(2S)-1,1,1-trifluoropropan-2-yl]pyridine-3-sulfonamide, |
| 916 | 5-methyl-1-(pyrazin-2-yl)-2-(5-{[(2S)-1,1,1-trifluoropropan-2-yl]sulfamoyl}pyridin-2-yl)-1H-indole-3-carboxamide, |
| 917 | 6-[3-cyano-6-fluoro-5-methyl-1-(pyridin-2-yl)-1H-indol-2-yl]-N-[(2S)-1,1,1-trifluoropropan-2-yl]pyridine-3-sulfonamide, |
| 918 | 6-fluoro-5-methyl-1-(pyrimidin-2-yl)-2-(5-{[(2S)-1,1,1-trifluoropropan-2-yl]sulfamoyl}pyridin-2-yl)-1H-indole-3-carboxamide, |
| 919 | 6-[3-cyano-6-fluoro-5-methyl-1-(pyrazin-2-yl)-1H-indol-2-yl]-N-[(2S)-1,1,1-trifluoropropan-2-yl]pyridine-3-sulfonamide, |
| 920 | 6-[3-cyano-1-(4-fluorophenyl)-5-methyl-1H-indol-2-yl]-N-[(2S)-1,1,1-trifluoropropan-2-yl]pyridine-3-sulfonamide, |
| 921 | 6-(3-cyano-5-methyl-1-phenyl-1H-indol-2-yl)-N-[(2S)-1,1,1-trifluoropropan-2-yl]pyridine-3-sulfonamide, |
| 922 | 6-[3-cyano-1-(pyrimidin-2-yl)-5-(trifluoromethyl)-1H-indol-2-yl]-N-[(2S)-1,1,1-trifluoropropan-2-yl]pyridine-3-sulfonamide, |
| 923 | 6-[3-cyano-5-fluoro-6-methyl-1-(6-methylpyridin-2-yl)-1H-indol-2-yl]-N-[(2S)-1,1,1-trifluoropropan-2-yl]pyridine-3-sulfonamide, |
| 924 | 6-[3-cyano-5-fluoro-1-(5-fluoropyrimidin-2-yl)-6-methyl-1H-indol-2-yl]-N-[(2S)-1,1,1-trifluoropropan-2-yl]pyridine-3-sulfonamide, |
| 925 | 6-[3-cyano-5-fluoro-6-methyl-1-(5-methylpyrimidin-2-yl)-1H-indol-2-yl]-N-[(2S)-1,1,1-trifluoropropan-2-yl]pyridine-3-sulfonamide, |
| 926 | 6-[3-cyano-5-fluoro-1-(4-fluoropyridin-2-yl)-6-methyl-1H-indol-2-yl]-N-[(2S)-1,1,1-trifluoropropan-2-yl]pyridine-3-sulfonamide, |
| 927 | 6-[3-cyano-5-fluoro-6-(2-methyl-1,3-dioxolan-2-yl)-1-(pyrimidin-2-yl)-1H-indol-2-yl]-N-[(2S)-1,1,1-trifluoropropan-2-yl]pyridine-3-sulfonamide, |
| 928 | 1-cyclohexyl-6-(difluoromethoxy)-5-fluoro-2-{5-[(1,1,1-trifluoro-2-methylpropan-2-yl)sulfamoyl]pyridin-2-yl}-1H-indole-3-carboxylic acid, |
| 929 | 6-[3-cyano-6-ethyl-5-fluoro-1-(pyrazin-2-yl)-1H-indol-2-yl]-N-[(2S)-1,1,1-trifluoropropan-2-yl]pyridine-3-sulfonamide, |
| 930 | 6-[3-cyano-6-ethyl-5-fluoro-1-(6-fluoropyridin-2-yl)-1H-indol-2-yl]-N-[(2S)-1,1,1-trifluoropropan-2-yl]pyridine-3-sulfonamide, |
| 931 | 6-[3-cyano-6-ethyl-5-fluoro-1-(5-methylpyridin-2-yl)-1H-indol-2-yl]-N-[(2S)-1,1,1-trifluoropropan-2-yl]pyridine-3-sulfonamide, |
| 932 | 6-[3-cyano-6-ethyl-5-fluoro-1-(4-methylpyridin-2-yl)-1H-indol-2-yl]-N-[(2S)-1,1,1-trifluoropropan-2-yl]pyridine-3-sulfonamide, |
| 933 | 6-[3-cyano-5-fluoro-6-methyl-1-(pyridin-4-yl)-1H-indol-2-yl]-N-[(2S)-1,1,1-trifluoropropan-2-yl]pyridine-3-sulfonamide, |
| 934 | 6-[3-cyano-5-fluoro-6-methyl-1-(1,3-thiazol-2-yl)-1H-indol-2-yl]-N-[(2S)-1,1,1-trifluoropropan-2-yl]pyridine-3-sulfonamide, |
| 935 | 6-[3-cyano-6-ethyl-5-fluoro-1-(1,3-thiazol-2-yl)-1H-indol-2-yl]-N-[(2S)-1,1,1-trifluoropropan-2-yl]pyridine-3-sulfonamide, |
| 936 | 6-[3-cyano-6-(difluoromethoxy)-5-fluoro-1-(propan-2-yl)-1H-indol-2-yl]-N-[(2S)-1,1,1-trifluoropropan-2-yl]pyridine-3-sulfonamide, |
| 937 | 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide, |
| 938 | 6-[6-bromo-3-cyano-5-fluoro-1-(pyrimidin-2-yl)-1H-indol-2-yl]-N-tert-butylpyridine-3-sulfonamide, |
| 939 | N-tert-butyl-6-[3,6-diacetyl-5-fluoro-1-(pyrimidin-2-yl)-1H-indol-2-yl]pyridine-3-sulfonamide, |
| 940 | 6-[3-cyano-6-(difluoromethoxy)-5-fluoro-1-(2-hydroxyethyl)-1H-indol-2-yl]-N-[(2S)-1,1,1-trifluoropropan-2-yl]pyridine-3-sulfonamide, |
| 941 | 6-[3-cyano-1-(1,6-dihydropyrimidin-2-yl)-6-ethyl-5-fluoro-1H-indol-2-yl]-N-[(2S)-1,1,1-trifluoropropan-2-yl]pyridine-3-sulfonamide, |
| 942 | 6-[1-(5-chloropyrimidin-2-yl)-3-cyano-6-ethyl-5-fluoro-1H-indol-2-yl]-N-[(2S)-1,1,1-trifluoropropan-2-yl]pyridine-3-sulfonamide, |
| 943 | 6-[3-cyano-6-ethyl-5-fluoro-1-(2-methylpyrimidin-4-yl)-1H-indol-2-yl]-N-[(2S)-1,1,1-trifluoropropan-2-yl]pyridine-3-sulfonamide, |
| 944 | 6-[5-fluoro-1-(2-fluoropyridin-4-yl)-6-methyl-1H-indol-2-yl]-N-[(2S)-1,1,1-trifluoropropan-2-yl]pyridine-3-sulfonamide, |
| 945 | 6-[3-cyano-5-fluoro-1-(5-fluoropyridin-3-yl)-6-methyl-1H-indol-2-yl]-N-[(2S)-1,1,1-trifluoropropan-2-yl]pyridine-3-sulfonamide, |
| 946 | 6-[3-cyano-6-ethyl-5-fluoro-1-(5-fluoropyrimidin-2-yl)-1H-indol-2-yl]-N-[(2S)-1,1,1-trifluoropropan-2-yl]pyridine-3-sulfonamide, |
| 947 | 6-[3-chloro-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 948 | 6-[3-cyano-1-(5-fluoropyrimidin-2-yl)-5-methyl-1H-indol-2-yl]-N-[(2S)-1,1,1-trifluoropropan-2-yl]pyridine-3-sulfonamide, |
| 949 | 6-[3-cyano-6-fluoro-1-(5-fluoropyrimidin-2-yl)-5-methyl-1H-indol-2-yl]-N-[(2S)-1,1,1-trifluoropropan-2-yl]pyridine-3-sulfonamide, |
| 950 | 6-[3-cyano-1-(pyrimidin-2-yl)-6-(trifluoromethyl)-1H-indol-2-yl]-N-[(2S)-1,1,1-trifluoropropan-2-yl]pyridine-3-sulfonamide, |
| 951 | 6-[3-cyano-1-(pyrazin-2-yl)-6-(trifluoromethyl)-1H-indol-2-yl]-N-[(2S)-1,1,1-trifluoropropan-2-yl]pyridine-3-sulfonamide, |

| Cpd | Name |
|---|---|
| 952 | 6-[3-cyano-1-(pyridin-2-yl)-6-(trifluoromethyl)-1H-indol-2-yl]-N-[(2S)-1,1,1-trifluoropropan-2-yl]pyridine-3-sulfonamide, |
| 953 | 6-[3-cyano-6-ethyl-5-fluoro-1-(pyrimidin-2-yl)-1H-indol-2-yl]-N-(cyclobutylmethyl)pyridine-3-sulfonamide, |
| 954 | 6-[3-cyano-6-ethyl-5-fluoro-1-(pyridin-3-yl)-1H-indol-2-yl]-N-[(2S)-1,1,1-trifluoropropan-2-yl]pyridine-3-sulfonamide, |
| 955 | 6-[3-cyano-6-ethyl-5-fluoro-1-(4-methoxypyridin-2-yl)-1H-indol-2-yl]-N-[(2S)-1,1,1-trifluoropropan-2-yl]pyridine-3-sulfonamide, |
| 956 | 6-[3-cyano-6-ethyl-5-fluoro-1-(pyrimidin-2-yl)-1H-indol-2-yl]-N-[(2S)-1,1,1-trifluoro(2-deuterium)propan-2-yl]pyridine-3-sulfonamide, |
| 957 | 6-[5-fluoro-6-methyl-1-(1,3-thiazol-4-yl)-1H-indol-2-yl]-N-[(2S)-1,1,1-trifluoropropan-2-yl]pyridine-3-sulfonamide, |
| 958 | 6-[5-fluoro-6-methyl-1-(1,3,4-thiadiazol-2-yl)-1H-indol-2-yl]-N-[(2S)-1,1,1-trifluoropropan-2-yl]pyridine-3-sulfonamide, |
| 959 | 6-[5-fluoro-6-methyl-1-(1,3-thiazol-5-yl)-1H-indol-2-yl]-N-[(2S)-1,1,1-trifluoropropan-2-yl]pyridine-3-sulfonamide, |
| 960 | 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, |
| 961 | 6-[3-cyano-5-fluoro-1-(5-fluoro-6-methylpyridin-2-yl)-6-methyl-1H-indol-2-yl]-N-[(2S)-1,1,1-trifluoropropan-2-yl]pyridine-3-sulfonamide, |
| 962 | 6-[1-(6-chloropyridin-2-yl)-3-cyano-5-fluoro-6-methyl-1H-indol-2-yl]-N-[(2S)-1,1,1-trifluoropropan-2-yl]pyridine-3-sulfonamide, |
| 963 | 6-[3-cyano-6-ethyl-5-fluoro-1-(pyrimidin-5-yl)-1H-indol-2-yl]-N-[(2S)-1,1,1-trifluoropropan-2-yl]pyridine-3-sulfonamide, |
| 964 | 6-[3-cyano-6-ethyl-5-fluoro-1-(pyrimidin-4-yl)-1H-indol-2-yl]-N-[(2S)-1,1,1-trifluoropropan-2-yl]pyridine-3-sulfonamide, |
| 965 | 6-[1-(3-chloropyridin-2-yl)-3-cyano-6-ethyl-5-fluoro-1H-indol-2-yl]-N-[(2S)-1,1,1-trifluoropropan-2-yl]pyridine-3-sulfonamide, |
| 966 | 6-[1-(5-chloropyridin-2-yl)-3-cyano-6-ethyl-5-fluoro-1H-indol-2-yl]-N-[(2S)-1,1,1-trifluoropropan-2-yl]pyridine-3-sulfonamide, |
| 967 | 6-[3-cyano-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, |
| 968 | 6-[3-chloro-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, |
| 969 | 6-[5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, |
| 970 | 6-[3-cyano-5-fluoro-6-(2-hydroxyethyl)-1-(pyrimidin-2-yl)-1H-indol-2-yl]-N-[(2S)-1,1,1-trifluoropropan-2-yl]pyridine-3-sulfonamide, |
| 971 | 6-[1-(3-chloropyridin-2-yl)-3-cyano-5-fluoro-6-methyl-1H-indol-2-yl]-N-[(2S)-1,1,1-trifluoropropan-2-yl]pyridine-3-sulfonamide, |
| 972 | 6-[3-chloro-5-fluoro-6-methyl-1-(1,3,4-thiadiazol-2-yl)-1H-indol-2-yl]-N-[(2S)-1,1,1-trifluoropropan-2-yl]pyridine-3-sulfonamide, |
| 973 | 6-[3-cyano-5-fluoro-6-methyl-1-(1,3-thiazol-5-yl)-1H-indol-2-yl]-N-[(2S)-1,1,1-trifluoropropan-2-yl]pyridine-3-sulfonamide, |
| 974 | 6-[3-cyano-6-ethyl-5-fluoro-1-(pyridin-4-yl)-1H-indol-2-yl]-N-[(2S)-1,1,1-trifluoropropan-2-yl]pyridine-3-sulfonamide, |
| 975 | 6-[3-cyano-6-ethyl-5-fluoro-1-(pyridazin-3-yl)-1H-indol-2-yl]-N-[(2S)-1,1,1-trifluoropropan-2-yl]pyridine-3-sulfonamide, |
| 976 | 6-[3-cyano-6-ethyl-5-fluoro-1-(5-methylpyrimidin-2-yl)-1H-indol-2-yl]-N-[(2S)-1,1,1-trifluoropropan-2-yl]pyridine-3-sulfonamide, |
| 977 | 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide, |
| 978 | 6-ethyl-5-fluoro-1-(pyrimidin-2-yl)-2-{5-[(1,1,1-trifluoro-2-methylpropan-2-yl)sulfamoyl]pyridin-2-yl}-1H-indole-3-carboxamide, |
| 979 | 6-ethyl-5-fluoro-1-(pyrimidin-2-yl)-2-(5-{[1-(trifluoromethyl)cyclopropyl]sulfamoyl}pyridin-2-yl)-1H-indole-3-carboxamide, |
| 980 | 6-ethyl-5-fluoro-1-(4-methylpyridin-2-yl)-2-(5-{[(2S)-1,1,1-trifluoropropan-2-yl]sulfamoyl}pyridin-2-yl)-1H-indole-3-carboxamide, |
| 981 | 6-ethyl-5-fluoro-1-(5-fluoropyridin-2-yl)-2-(5-{[(2S)-1,1,1-trifluoropropan-2-yl]sulfamoyl}pyridin-2-yl)-1H-indole-3-carboxamide, |
| 982 | 6-ethyl-5-fluoro-1-(2-methylpyrimidin-4-yl)-2-(5-{[(2S)-1,1,1-trifluoropropan-2-yl]sulfamoyl}pyridin-2-yl)-1H-indole-3-carboxamide, |
| 983 | 6-[1-(5-chloropyridin-3-yl)-3-cyano-6-ethyl-5-fluoro-1H-indol-2-yl]-N-[(2S)-1,1,1-trifluoropropan-2-yl]pyridine-3-sulfonamide, |
| 984 | 6-{3-cyano-5-fluoro-1-[5-(hydroxymethyl)-1,3-thiazol-2-yl]-6-methyl-1H-indol-2-yl}-N-[(2S)-1,1,1-trifluoropropan-2-yl]pyridine-3-sulfonamide, |
| 985 | methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-5-carboxylate, |
| 986 | methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-4-carboxylate, |
| 987 | 6-[5-fluoro-6-methyl-1-(thiophen-3-yl)-1H-indol-2-yl]-N-[(2S)-1,1,1-trifluoropropan-2-yl]pyridine-3-sulfonamide, |
| 988 | 6-[5-fluoro-1-(furan-3-yl)-6-methyl-1H-indol-2-yl]-N-[(2S)-1,1,1-trifluoropropan-2-yl]pyridine-3-sulfonamide, |
| 989 | 6-[5-fluoro-6-methyl-1-(thiophen-2-yl)-1H-indol-2-yl]-N-[(2S)-1,1,1-trifluoropropan-2-yl]pyridine-3-sulfonamide, |

| Cpd | Name |
|---|---|
| 990 | 6-[3-cyano-5-fluoro-6-methyl-1-(thiophen-2-yl)-1H-indol-2-yl]-N-[(2S)-1,1,1-trifluoropropan-2-yl]pyridine-3-sulfonamide, |
| 991 | 6-[3-cyano-5-fluoro-1-(furan-3-yl)-6-methyl-1H-indol-2-yl]-N-[(2S)-1,1,1-trifluoropropan-2-yl]pyridine-3-sulfonamide, |
| 992 | 6-[3-cyano-5-fluoro-6-methyl-1-(thiophen-3-yl)-1H-indol-2-yl]-N-[(2S)-1,1,1-trifluoropropan-2-yl]pyridine-3-sulfonamide, |
| 993 | 6-[1-(4-chloropyridin-2-yl)-3-cyano-6-ethyl-5-fluoro-1H-indol-2-yl]-N-[(2S)-1,1,1-trifluoropropan-2-yl]pyridine-3-sulfonamide, |
| 994 | 6-ethyl-5-fluoro-1-(pyrazin-2-yl)-2-(5-{[(2S)-1,1,1-trifluoropropan-2-yl]sulfamoyl}pyridin-2-yl)-1H-indole-3-carboxamide |
| 995 | 6-ethyl-5-fluoro-1-(6-fluoropyridin-2-yl)-2-(5-{[(2S)-1,1,1-trifluoropropan-2-yl]sulfamoyl}pyridin-2-yl)-1H-indole-3-carboxamide, |
| 996 | 5-chloro-1-cyclobutyl-2-(5-{[(2S)-1,1,1-trifluoropropan-2-yl]sulfamoyl}pyridin-2-yl)-1H-indole-3-carboxamide, |
| 997 | 1-cyclobutyl-5-fluoro-2-(5-{[(2S)-1,1,1-trifluoropropan-2-yl]sulfamoyl}pyridin-2-yl)-1H-indole-3-carboxamide, |
| 998 | 2-{5-[(tert-butylsulfonyl)amino]pyridin-2-yl}-1-cyclohexyl-6-ethyl-5-fluoro-1H-indole-3-carboxylic, |
| 999 | 2-{5-[(tert-butylsulfonyl)amino]pyridin-2-yl}-1-cyclohexyl-6-ethyl-5-fluoro-1H-indole-3-carboxamide, |
| 1000 | 6-[3-cyano-5-fluoro-6-methyl-1-(3-methylthiophen-2-yl)-1H-indol-2-yl]-N-[(2S)-1,1,1-trifluoropropan-2-yl]pyridine-3-sulfonamide, |
| 1001 | 6-[3-cyano-1-(4,6-difluoropyridin-2-yl)-5-fluoro-6-methyl-1H-indol-2-yl]-N-[(2S)-1,1,1-trifluoropropan-2-yl]pyridine-3-sulfonamide, |
| 1002 | 6-[3-cyano-6-ethyl-5-fluoro-1-(4-fluorophenyl)-1H-indol-2-yl]-N-[(2S)-1,1,1-trifluoropropan-2-yl]pyridine-3-sulfonamide, |
| 1003 | 6-[1-(4-chlorophenyl)-3-cyano-6-ethyl-5-fluoro-1H-indol-2-yl]-N-[(2S)-1,1,1-trifluoropropan-2-yl]pyridine-3-sulfonamide, |
| 1004 | 6-[3-cyano-6-ethyl-5-fluoro-1-(4-methylphenyl)-1H-indol-2-yl]-N-[(2S)-1,1,1-trifluoropropan-2-yl]pyridine-3-sulfonamide, |
| 1005 | 6-[3-cyano-6-ethyl-5-fluoro-1-(4-methoxyphenyl)-1H-indol-2-yl]-N-[(2S)-1,1,1-trifluoropropan-2-yl]pyridine-3-sulfonamide, |
| 1006 | 6-{3-cyano-6-ethyl-5-fluoro-1-[4-(trifluoromethyl)phenyl]-1H-indol-2-yl}-N-[(2S)-1,1,1-trifluoropropan-2-yl]pyridine-3-sulfonamide, |
| 1007 | 6-[3-cyano-1-(4-cyanophenyl)-6-ethyl-5-fluoro-1H-indol-2-yl]-N-[(2S)-1,1,1-trifluoropropan-2-yl]pyridine-3-sulfonamide, |
| 1008 | 6-[3-cyano-6-ethyl-5-fluoro-1-(3-fluorophenyl)-1H-indol-2-yl]-N-[(2S)-1,1,1-trifluoropropan-2-yl]pyridine-3-sulfonamide, |
| 1009 | 6-[3-cyano-6-ethyl-5-fluoro-1-(3-methylphenyl)-1H-indol-2-yl]-N-[(2S)-1,1,1-trifluoropropan-2-yl]pyridine-3-sulfonamide, |
| 1010 | 6-[3-cyano-6-ethyl-5-fluoro-1-(3-methoxyphenyl)-1H-indol-2-yl]-N-[(2S)-1,1,1-trifluoropropan-2-yl]pyridine-3-sulfonamide, |
| 1011 | 6-{3-cyano-6-ethyl-5-fluoro-1-[3-(trifluoromethyl)phenyl]-1H-indol-2-yl}-N-[(2S)-1,1,1-trifluoropropan-2-yl]pyridine-3-sulfonamide, |
| 1012 | 6-[3-cyano-1-(3-cyanophenyl)-6-ethyl-5-fluoro-1H-indol-2-yl]-N-[(2S)-1,1,1-trifluoropropan-2-yl]pyridine-3-sulfonamide, |
| 1013 | 6-[3-cyano-5-fluoro-1-(2-fluoropyridin-4-yl)-6-methyl-1H-indol-2-yl]-N-[(2S)-1,1,1-trifluoropropan-2-yl]pyridine-3-sulfonamide, |
| 1014 | 6-[3-cyano-5-fluoro-1-(3-fluoropyridin-4-yl)-6-methyl-1H-indol-2-yl]-N-[(2S)-1,1,1-trifluoropropan-2-yl]pyridine-3-sulfonamide, |
| 1015 | 6-[3-cyano-5-fluoro-1-(6-fluoropyridin-3-yl)-6-methyl-1H-indol-2-yl]-N-[(2S)-1,1,1-trifluoropropan-2-yl]pyridine-3-sulfonamide, |
| 1016 | 6-[3-cyano-5-fluoro-6-methyl-1-(1-methyl-1H-pyrazol-4-yl)-1H-indol-2-yl]-N-[(2S)-1,1,1-trifluoropropan-2-yl]pyridine-3-sulfonamide, |
| 1017 | 6-[3-cyano-5-fluoro-6-methyl-1-(5-methyl-1,3-thiazol-2-yl)-1H-indol-2-yl]-N-[(2S)-1,1,1-trifluoropropan-2-yl]pyridine-3-sulfonamide, |
| 1018 | 6-[1-(3-chlorophenyl)-3-cyano-6-ethyl-5-fluoro-1H-indol-2-yl]-N-[(2S)-1,1,1-trifluoropropan-2-yl]pyridine-3-sulfonamide, |
| 1019 | 6-ethyl-5-fluoro-1-(4-fluorophenyl)-2-(5-{[(2S)-1,1,1-trifluoropropan-2-yl]sulfamoyl}pyridin-2-yl)-1H-indole-3-carboxamide, |
| 1020 | 1-(4-chlorophenyl)-6-ethyl-5-fluoro-2-(5-{[(2S)-1,1,1-trifluoropropan-2-yl]sulfamoyl}pyridin-2-yl)-1H-indole-3-carboxamide, |
| 1021 | 6-ethyl-5-fluoro-1-(4-methylphenyl)-2-(5-{[(2S)-1,1,1-trifluoropropan-2-yl]sulfamoyl}pyridin-2-yl)-1H-indole-3-carboxamide, |
| 1022 | 6-ethyl-5-fluoro-1-[4-(trifluoromethyl)phenyl]-2-(5-{[(2S)-1,1,1-trifluoropropan-2-yl]sulfamoyl}pyridin-2-yl)-1H-indole-3-carboxamide, |
| 1023 | 6-ethyl-5-fluoro-1-(3-fluorophenyl)-2-(5-{[(2S)-1,1,1-trifluoropropan-2-yl]sulfamoyl}pyridin-2-yl)-1H-indole-3-carboxamide, |
| 1024 | 6-ethyl-5-fluoro-1-(3-methylphenyl)-2-(5-{[(2S)-1,1,1-trifluoropropan-2-yl]sulfamoyl}pyridin-2-yl)-1H-indole-3-carboxamide, |
| 1025 | 6-ethyl-5-fluoro-1-(3-methoxyphenyl)-2-(5-{[(2S)-1,1,1-trifluoropropan-2-yl]sulfamoyl}pyridin-2-yl)-1H-indole-3-carboxamide, |
| 1026 | 6-ethyl-5-fluoro-1-[3-(trifluoromethyl)phenyl]-2-(5-{[(2S)-1,1,1-trifluoropropan-2-yl]sulfamoyl}pyridin-2-yl)-1H-indole-3-carboxamide, |
| 1027 | 1-(3-chlorophenyl)-6-ethyl-5-fluoro-2-(5-{[(2S)-1,1,1-trifluoropropan-2-yl]sulfamoyl}pyridin-2-yl)-1H-indole-3-carboxamide, |
| 1028 | 2-{5-[(tert-butylsulfonyl)amino]pyrimidin-2-yl}-1-cyclohexyl-6-ethyl-5-fluoro-1H-indole-3-carboxylic acid, |

-continued

| Cpd | Name |
|---|---|
| 1029 | 2-{2-[(tert-butylsulfonyl)amino]pyrimidin-5-yl}-1-cyclohexyl-6-ethyl-5-fluoro-1H-indole-3-carboxylic acid, |
| 1030 | 6-[3-cyano-5-fluoro-6-methyl-1-(3-methyl-1H-pyrazol-4-yl)-1H-indol-2-yl]-N-[(2S)-1,1,1-trifluoropropan-2-yl]pyridine-3-sulfonamide, |
| 1031 | 6-[3-cyano-5-fluoro-6-methyl-1-(5-methylthiophen-2-yl)-1H-indol-2-yl]-N-[(2S)-1,1,1-trifluoropropan-2-yl]pyridine-3-sulfonamide, |
| 1032 | 6-[1-(5-chlorothiophen-2-yl)-3-cyano-5-fluoro-6-methyl-1H-indol-2-yl]-N-[(2S)-1,1,1-trifluoropropan-2-yl]pyridine-3-sulfonamide, |
| 1033 | 6-[3-cyano-1-(5-cyanothiophen-2-yl)-5-fluoro-6-methyl-1H-indol-2-yl]-N-[(2S)-1,1,1-trifluoropropan-2-yl]pyridine-3-sulfonamide, |
| 1034 | 6-[3-cyano-5-fluoro-6-methyl-1-(5-sulfamoylthiophen-2-yl)-1H-indol-2-yl]-N-[(2S)-1,1,1-trifluoropropan-2-yl]pyridine-3-sulfonamide, |
| 1035 | 6-[1-(5-acetylthiophen-2-yl)-3-cyano-5-fluoro-6-methyl-1H-indol-2-yl]-N-[(2S)-1,1,1-trifluoropropan-2-yl]pyridine-3-sulfonamide, |
| 1036 | 2-{2-[(tert-butylsulfonyl)amino]pyrimidin-5-yl}-1-cyclohexyl-6-ethyl-5-fluoro-1H-indole-3-carboxamide, |
| 1037 | 2-{6-[(tert-butylsulfonyl)amino]pyridin-3-yl}-1-cyclohexyl-6-ethyl-5-fluoro-1H-indole-3-carboxamide, |
| 1038 | 6-[3-cyano-5-fluoro-6-methyl-1-(4-methyl-1,3-thiazol-2-yl)-1H-indol-2-yl]-N-[(2S)-1,1,1-trifluoropropan-2-yl]pyridine-3-sulfonamide, |
| 1039 | 6-ethyl-5-fluoro-1-(5-methylpyridin-2-yl)-2-(5-{[(2S)-1,1,1-trifluoropropan-2-yl]sulfamoyl}pyridin-2-yl)-1H-indole-3-carboxamide, |
| 1040 | 6-ethyl-5-fluoro-1-(pyridin-3-yl)-2-(5-{[(2S)-1,1,1-trifluoropropan-2-yl]sulfamoyl}pyridin-2-yl)-1H-indole-3-carboxamide, |
| 1041 | 6-ethyl-5-fluoro-1-(pyrimidin-4-yl)-2-(5-{[(2S)-1,1,1-trifluoropropan-2-yl]sulfamoyl}pyridin-2-yl)-1H-indole-3-carboxamide, |
| 1042 | 1-(3-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, |
| 1043 | 1-(5-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, |
| 1044 | 1-(5-chloropyridin-3-yl)-6-ethyl-5-fluoro-2-(5-{[(2S)-1,1,1-trifluoropropan-2-yl]sulfamoyl}pyridin-2-yl)-1H-indole-3-carboxamide, |
| 1045 | 6-ethyl-5-fluoro-1-(pyridin-4-yl)-2-(5-{[(2S)-1,1,1-trifluoropropan-2-yl]sulfamoyl}pyridin-2-yl)-1H-indole-3-carboxamide, |
| 1046 | 6-ethyl-5-fluoro-1-(pyridazin-3-yl)-2-(5-{[(2S)-1,1,1-trifluoropropan-2-yl]sulfamoyl}pyridin-2-yl)-1H-indole-3-carboxamide, |
| 1047 | 6-ethyl-5-fluoro-1-(5-methylpyrimidin-2-yl)-2-(5-{[(2S)-1,1,1-trifluoropropan-2-yl]sulfamoyl}pyridin-2-yl)-1H-indole-3-carboxamide, |
| 1048 | 1-(4-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, |
| 1055 | 6-[1-(2-acetylthiophen-3-yl)-3-cyano-5-fluoro-6-methyl-1H-indol-2-yl]-N-[(2S)-1,1,1-trifluoropropan-2-yl]pyridine-3-sulfonamide, |
| 1056 | 6-[3-cyano-5-fluoro-6-methyl-1-(4-methylthiophen-3-yl)-1H-indol-2-yl]-N-[(2S)-1,1,1-trifluoropropan-2-yl]pyridine-3-sulfonamide, |
| 1057 | 6-[1-(2-chlorothiophen-3-yl)-3-cyano-5-fluoro-6-methyl-1H-indol-2-yl]-N-[(2S)-1,1,1-trifluoropropan-2-yl]pyridine-3-sulfonamide, |
| 1058 | 6-[3-cyano-5-fluoro-6-methyl-1-(5-methylthiophen-3-yl)-1H-indol-2-yl]-N-[(2S)-1,1,1-trifluoropropan-2-yl]pyridine-3-sulfonamide, |
| 1059 | 6-[5-fluoro-6-methyl-1-(1,3-oxazol-2-yl)-1H-indol-2-yl]-N-[(2S)-1,1,1-trifluoropropan-2-yl]pyridine-3-sulfonamide, |
| 1060 | 6-[1-(5-cyanofuran-2-yl)-5-fluoro-6-methyl-1H-indol-2-yl]-N-[(2S)-1,1,1-trifluoropropan-2-yl]pyridine-3-sulfonamide, |
| 1061 | 6-[3-cyano-1-(3,4-difluorophenyl)-6-ethyl-5-fluoro-1H-indol-2-yl]-N-[(2S)-1,1,1-trifluoropropan-2-yl]pyridine-3-sulfonamide, |
| 1062 | 6-[1-(3-chloro-4-fluorophenyl)-3-cyano-6-ethyl-5-fluoro-1H-indol-2-yl]-N-[(2S)-1,1,1-trifluoropropan-2-yl]pyridine-3-sulfonamide, |
| 1063 | 2-{6-[(tert-butylsulfonyl)amino]pyridin-3-yl}-1-cyclohexyl-6-(difluoromethoxy)-5-fluoro-1H-indole-3-carboxamide, |
| 1064 | 2-{6-[(tert-butylsulfonyl)amino]pyridin-3-yl}-1-cyclohexyl-6-(difluoromethoxy)-5-fluoro-1H-indole-3-carboxylic acid, |
| 1065 | N-{5-[3-cyano-1-cyclohexyl-6-(difluoromethoxy)-5-fluoro-1H-indol-2-yl]pyridin-2-yl}-2-methylpropane-2-sulfonamide, |
| 1072 | 6-[3-cyano-1-(3-cyanofuran-2-yl)-5-fluoro-6-methyl-1H-indol-2-yl]-N-[(2S)-1,1,1-trifluoropropan-2-yl]pyridine-3-sulfonamide, |
| 1073 | 6-[3-cyano-5-fluoro-6-methyl-1-(1,3-oxazol-2-yl)-1H-indol-2-yl]-N-[(2S)-1,1,1-trifluoropropan-2-yl]pyridine-3-sulfonamide, |
| 1074 | 6-[3-cyano-1-(4-cyano-1,3-oxazol-2-yl)-5-fluoro-6-methyl-1H-indol-2-yl]-N-[(2S)-1,1,1-trifluoropropan-2-yl]pyridine-3-sulfonamide, |
| 1075 | 6-[3-cyano-6-ethyl-5-fluoro-1-(2-fluorophenyl)-1H-indol-2-yl]-N-[(2S)-1,1,1-trifluoropropan-2-yl]pyridine-3-sulfonamide, |
| 1078 | 6-{3-cyano-6-[(1,1-dideuterium)ethyl]-5-fluoro-1-(pyrimidin-2-yl)-1H-indol-2-yl}-N-[(2S)-1,1,1-trifluoropropan-2-yl]pyridine-3-sulfonamide, |
| 1079 | 6-{3-cyano-6-[(1,1-dideuterium)ethyl]-5-fluoro-1-(pyrimidin-2-yl)-1H-indol-2-yl}-N-[(2S)-1,1,1-trifluoro(2-deuterium)propan-2-yl]pyridine-3-sulfonamide, |
| 1080 | 2-{6-[(tert-butylsulfonyl)amino]pyridin-3-yl}-1-[(1S)-1-cyclopropylethyl]-6-(difluoromethoxy)-5-fluoro-1H-indole-3-carboxylic acid, |

-continued

| Cpd | Name |
|---|---|
| 1081 | 2-{6-[(tert-butylsulfonyl)amino]pyridin-3-yl}-1-[(1S)-1-cyclopropylethyl]-6-(difluoromethoxy)-5-fluoro-1H-indole-3-carboxamide, |
| 1082 | N-(5-{3-cyano-1-[(1S)-1-cyclopropylethyl]-6-ethyl-5-fluoro-1H-indol-2-yl}pyridin-2-yl)-2-methylpropane-2-sulfonamide, |
| 1083 | 2-{6-[(tert-butylsulfonyl)amino]pyridin-3-yl}-1-[(1S)-1-cyclopropylethyl]-6-ethyl-5-fluoro-1H-indole-3-carboxamide, |
| 1084 | 2-{6-[(tert-butylsulfonyl)amino]pyridin-3-yl}-1-[(1R)-1-cyclopropylethyl]-6-(difluoromethoxy)-5-fluoro-1H-indole-3-carboxylic acid, |
| 1085 | 2-{6-[(tert-butylsulfonyl)amino]pyridin-3-yl}-1-[(1R)-1-cyclopropylethyl]-6-(difluoromethoxy)-5-fluoro-1H-indole-3-carboxamide, |
| 1086 | 2-{6-[(tert-butylsulfonyl)amino]-4-methylpyridin-3-yl}-1-[(1R)-1-cyclopropylethyl]-6-(difluoromethoxy)-5-fluoro-1H-indole-3-carboxylic acid, |
| 1087 | 2-{6-[(tert-butylsulfonyl)amino]-4-methylpyridin-3-yl}-1-[(1R)-1-cyclopropylethyl]-6-(difluoromethoxy)-5-fluoro-1H-indole-3-carboxamide, |
| 1088 | 2-{6-[(tert-butylsulfonyl)amino]pyridin-3-yl}-1-cyclohexyl-6-cyclopropyl-4-fluoro-1H-indole-3-carboxamide, |
| 1092 | N-[6-(3-cyano-1-cyclohexyl-6-cyclopropyl-4-fluoro-1H-indol-2-yl)pyridin-3-yl]-2-methylpropane-2-sulfonamide, |
| 1093 | 2-{6-[(tert-butylsulfonyl)amino]-2-methylpyridin-3-yl}-6-(difluoromethoxy)-5-fluoro-1-(propan-2-yl)-1H-indole-3-carboxylic acid, |
| 1094 | 2-{6-[(tert-butylsulfonyl)amino]-2-methylpyridin-3-yl}-1-[(1R)-1-cyclopropylethyl]-6-(difluoromethoxy)-5-fluoro-1H-indole-3-carboxylic acid, |
| 1095 | 2-{6-[(tert-butylsulfonyl)amino]-2-methylpyridin-3-yl}-6-(difluoromethoxy)-5-fluoro-1-(propan-2-yl)-1H-indole-3-carboxamide, |
| 1096 | 2-{6-[(tert-butylsulfonyl)amino]-2-methylpyridin-3-yl}-1-[(1S)-1-cyclopropylethyl]-6-(difluoromethoxy)-5-fluoro-1H-indole-3-carboxamide, |
| 1097 | 2-{5-[(tert-butylsulfonyl)amino]pyridin-2-yl}-1-cyclohexyl-6-cyclopropyl-4-fluoro-1H-indole-3-carboxamide, |
| 1098 | 6-[3-cyano-6-cyclopropyl-4-fluoro-1-(pyrimidin-2-yl)-1H-indol-2-yl]-N-(1,1,1-trifluoro-2-methylpropan-2-yl)pyridine-3-sulfonamide, |
| 1099 | methyl 2-{6-[(tert-butylsulfonyl)amino]pyridin-3-yl}-1-cyclohexyl-5-fluoro-6-(fluoromethoxy)-1H-indole-3-carboxylate, |
| 1100 | 2-{6-[(tert-butylsulfonyl)amino]pyridin-3-yl}-6-cyclopropyl-5-fluoro-1-phenyl-1H-indole-3-carboxamide, |
| 1101 | N-[5-(3-cyano-6-cyclopropyl-5-fluoro-1-phenyl-1H-indol-2-yl)pyridin-2-yl]-2-methylpropane-2-sulfonamide, |
| 1102 | 2-{6-[(tert-butylsulfonyl)amino]pyridin-3-yl}-1-cyclohexyl-5-fluoro-6-(fluoromethoxy)-1H-indole-3-carboxamide, |
| 1103 | 2-{6-[(tert-butylsulfonyl)amino]pyridin-3-yl}-1-[(1R)-1-cyclopropylethyl]-6-ethyl-5-fluoro-1H-indole-3-carboxylic acid, |
| 1104 | 2-{6-[(tert-butylsulfonyl)amino]pyridin-3-yl}-1-[(1R)-1-cyclopropylethyl]-6-ethyl-5-fluoro-1H-indole-3-carboxamide, |
| 1105 | 2-{6-[(tert-butylsulfonyl)amino]pyridin-3-yl}-6-cyclopropyl-4-fluoro-1-(4-fluorophenyl)-1H-indole-3-carboxamide, |
| 1106 | 2-{6-[(tert-butylsulfonyl)amino]pyridin-3-yl}-6-ethyl-4-fluoro-1-(4-fluorophenyl)-1H-indole-3-carboxamide, |
| 1107 | 6-[3-cyano-5-fluoro-6-(1,1,1-trideuterium)methyl-1-(pyrimidin-2-yl)-1H-indol-2-yl]-N-[(2S)-1,1,1-trifluoro(2-deuterium)propan-2-yl]pyridine-3-sulfonamide, |
| 1108 | N-tert-butyl-6-(3-cyano-5-fluoro-6-methyl-1-phenyl-1H-indol-2-yl)pyridine-3-sulfonamide, |
| 1109 | 2-[5-(tert-butylsulfamoyl)pyridin-2-yl]-6-ethyl-5-fluoro-1-phenyl-1H-indole-3-carboxamide, |
| 1110 | 2-{5-[(tert-butylsulfonyl)amino]pyridin-2-yl}-1-cyclobutyl-6-ethyl-4-fluoro-1H-indole-3-carboxamide, |
| 1111 | 2-{6-[(tert-butylsulfonyl)amino]pyridin-3-yl}-6-ethyl-4-fluoro-1-phenyl-1H-indole-3-carboxamide, |
| 1112 | 6-(3-cyano-1-cyclobutyl-5-fluoro-6-methyl-1H-indol-2-yl)-N-[(2-deuterium)propan-2-yl]pyridine-3-sulfonamide, |
| 1113 | 6-(3-cyano-1-cyclobutyl-5-fluoro-6-methyl-1H-indol-2-yl)-N-[(2S)-1,1,1-trifluoro(2-deuterium)propan-2-yl]pyridine-3-sulfonamide, |
| 1114 | 6-[3-cyano-1-cyclobutyl-5-fluoro-6-(1,1,1-trideuterium)methyl-1H-indol-2-yl]-N-[(2S)-1,1,1-trifluoro(2-deuterium)propan-2-yl]pyridine-3-sulfonamide, |
| 1115 | 2-[5-(tert-butylsulfamoyl)pyridin-2-yl]-1-cyclohexyl-5-fluoro-6-methyl-1H-indole-3-carboxamide, |
| 1116 | 2-[5-(tert-butylsulfamoyl)pyridin-2-yl]-5-fluoro-6-methyl-1-phenyl-1H-indole-3-carboxamide, |
| 1117 | N-tert-butyl-6-(3-cyano-6-cyclopropyl-5-fluoro-1-phenyl-1H-indol-2-yl)pyridine-3-sulfonamide, |
| 1118 | 2-{6-[(tert-butylsulfonyl)amino]pyridin-3-yl}-1-cyclobutyl-6-ethyl-4-fluoro-1H-indole-3-carboxamide or |
| 1119 | 6-[3-cyano-1-(cyclopropylmethyl)-5-fluoro-6-(1,1,1-trideuterium)methyl-1H-indol-2-yl]-N-[(2-deuterium)propan-2-yl]pyridine-3-sulfonamide. |

In another embodiment of the present invention, a compound of Formula (I) or a free acid, free base, salt, hydrate, solvate, clathrate, isotopologue, racemate, enantiomer, diastereomer, stereoisomer or polymorph form thereof is selected from:

| Cpd | Name |
|---|---|
| 7 | 6-(3-cyano-1-cyclobutyl-6-cyclopropyl-1H-indol-2-yl)-N-(propan-2-yl)pyridine-3-sulfonamide, |
| 31 | 6-[3-cyano-1-cyclobutyl-6-(difluoromethoxy)-1H-indol-2-yl]-N-(1,3-difluoropropan-2-yl)pyridine-3-sulfonamide, |
| 35 | 6-(3-cyano-1-cyclobutyl-6-cyclopropyl-1H-indol-2-yl)-N-(1,3-difluoropropan-2-yl)pyridine-3-sulfonamide, |
| 44 | 6-(3-cyano-1-cyclopentyl-6-methyl-1H-indol-2-yl)-N-(1,3-difluoropropan-2-yl)pyridine-3-sulfonamide, |
| 51 | 6-[3-cyano-1-cyclobutyl-6-(difluoromethoxy)-1H-indol-2-yl]-N-(propan-2-yl)pyridine-3-sulfonamide, |
| 107 | 6-(3-cyano-1-cyclobutyl-6-cyclopropyl-5-fluoro-1H-indol-2-yl)-N-(1,3-difluoropropan-2-yl)pyridine-3-sulfonamide, |
| 108 | 6-(3-cyano-1-cyclobutyl-5-fluoro-6-methyl-1H-indol-2-yl)-N-(1,3-difluoropropan-2-yl)pyridine-3-sulfonamide, |
| 190 | 6-(3-cyano-1-cyclopentyl-6-methyl-1H-indol-2-yl)-N-[1-(trifluoromethyl)cyclopropyl]pyridine-3-sulfonamide, |
| 277 | N-[6-(3-cyano-1-cyclobutyl-6-methoxy-1H-indol-2-yl)pyridazin-3-yl]ethanesulfonamide, |
| 300 | 6-[3-cyano-1-cyclobutyl-6-(difluoromethoxy)-1H-indol-2-yl]-N-[(2S)-1,1,1-trifluoropropan-2-yl]pyridine-3-sulfonamide, |
| 371 | 6-(3-cyano-1-cyclopentyl-6-methyl-1H-indol-2-yl)-N-(1,1,1-trifluoro-2-methylpropan-2-yl)pyridine-3-sulfonamide, |
| 387 | 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, |
| 407 | 6-(3-cyano-1-cyclopentyl-5-fluoro-6-methyl-1H-indol-2-yl)-N-(1,3-difluoropropan-2-yl)pyridine-3-sulfonamide, |
| 408 | 6-(3-cyano-1-cyclopentyl-5-fluoro-6-methyl-1H-indol-2-yl)-N-[(2S)-1,1,1-trifluoropropan-2-yl]pyridine-3-sulfonamide, |
| 409 | 6-(3-cyano-1-cyclopentyl-5-fluoro-6-methyl-1H-indol-2-yl)-N-[(2R)-1,1,1-trifluoropropan-2-yl]pyridine-3-sulfonamide, |
| 421 | 6-(3-cyano-1-cyclobutyl-7-fluoro-6-methyl-1H-indol-2-yl)-N-[(2S)-1,1,1-trifluoropropan-2-yl]pyridine-3-sulfonamide, |
| 512 | 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, |
| 532 | 6-(3-cyano-1-cyclobutyl-5,7-difluoro-6-methyl-1H-indol-2-yl)-N-[(2S)-1,1,1-trifluoropropan-2-yl]pyridine-3-sulfonamide, |
| 541 | 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, |
| 549 | 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, |
| 601 | 6-[3-cyano-5-fluoro-1-(pyrimidin-2-yl)-1H-indol-2-yl]-N-[(2S)-1,1,1-trifluoropropan-2-yl]pyridine-3-sulfonamide, |
| 634 | 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, |
| 640 | 6-(3-cyano-1-cyclobutyl-6-ethyl-5-fluoro-1H-indol-2-yl)-N-[(2S)-1,1,1-trifluoropropan-2-yl]pyridine-3-sulfonamide, |
| 650 | 6-[3-cyano-6-cyclopropyl-1-(pyrimidin-2-yl)-1H-indol-2-yl]-N-[(2S)-1,1,1-trifluoropropan-2-yl]pyridine-3-sulfonamide, |
| 657 | 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, |
| 682 | 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, |
| 683 | 2-[5-(tert-butylsulfamoyl)pyridin-2-yl]-1-cyclopentyl-5-fluoro-6-methyl-1H-indole-3-carboxamide, |
| 704 | 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, |
| 716 | 1-cyclohexyl-5-fluoro-6-methyl-2-(5-{[(2R)-1,1,1-trifluoropropan-2-yl]sulfamoyl}pyridin-2-yl)-1H-indole-3-carboxamide, |
| 749 | 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide, |
| 810 | 6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide, |
| 820 | 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 821 | 6-(3-cyano-1-cyclopentyl-5-fluoro-6-methyl-1H-indol-2-yl)-N-[(2S)-1,1,1-trifluorobutan-2-yl]pyridine-3-sulfonamide, |
| 849 | 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, |
| 937 | 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide, |

-continued

| Cpd | Name |
|---|---|
| 960 | 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, |
| 977 | 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide, |
| 1037 | 2-{6-[(tert-butylsulfonyl)amino]pyridin-3-yl}-1-cyclohexyl-6-ethyl-5-fluoro-1H-indole-3-carboxamide, |
| 1064 | 2-{6-[(tert-butylsulfonyl)amino]pyridin-3-yl}-1-cyclohexyl-6-(difluoromethoxy)-5-fluoro-1H-indole-3-carboxylic acid, |
| 1065 | N-{5-[3-cyano-1-cyclohexyl-6-(difluoromethoxy)-5-fluoro-1H-indol-2-yl]pyridin-2-yl}-2-methylpropane-2-sulfonamide, |
| 1085 | 2-{6-[(tert-butylsulfonyl)amino]pyridin-3-yl}-1-[(1R)-1-cyclopropylethyl]-6-(difluoromethoxy)-5-fluoro-1H-indole-3-carboxamide, |
| 1088 | 2-{6-[(tert-butylsulfonyl)amino]pyridin-3-yl}-1-cyclohexyl-6-cyclopropyl-4-fluoro-1H-indole-3-carboxamide, |
| 1092 | N-[6-(3-cyano-1-cyclohexyl-6-cyclopropyl-4-fluoro-1H-indol-2-yl)pyridin-3-yl]-2-methylpropane-2-sulfonamide, |
| 1100 | 2-{6-[(tert-butylsulfonyl)amino]pyridin-3-yl}-6-cyclopropyl-5-fluoro-1-phenyl-1H-indole-3-carboxamide, |
| 1110 | 2-{5-[(tert-butylsulfonyl)amino]pyridin-2-yl}-1-cyclobutyl-6-ethyl-4-fluoro-1H-indole-3-carboxamide or |
| 1111 | 2-{6-[(tert-butylsulfonyl)amino]pyridin-3-yl}-6-ethyl-4-fluoro-1-phenyl-1H-indole-3-carboxamide. |

In another embodiment of the present invention, a compound of Formula (I) or a free acid, free base, salt, hydrate, solvate, clathrate, isotopologue, racemate, enantiomer, diastereomer, stereoisomer or polymorph form thereof is selected from:

| Cpd | Name |
|---|---|
| 300 | 6-[3-cyano-1-cyclobutyl-6-(difluoromethoxy)-1H-indol-2-yl]-N-[(2S)-1,1,1-trifluoropropan-2-yl]pyridine-3-sulfonamide, |
| 387 | 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, |
| 409 | 6-(3-cyano-1-cyclopentyl-5-fluoro-6-methyl-1H-indol-2-yl)-N-[(2R)-1,1,1-trifluoropropan-2-yl]pyridine-3-sulfonamide, |
| 512 | 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, |
| 541 | 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, |
| 549 | 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, |
| 601 | 6-[3-cyano-5-fluoro-1-(pyrimidin-2-yl)-1H-indol-2-yl]-N-[(2S)-1,1,1-trifluoropropan-2-yl]pyridine-3-sulfonamide, |
| 634 | 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, |
| 650 | 6-[3-cyano-6-cyclopropyl-1-(pyrimidin-2-yl)-1H-indol-2-yl]-N-[(2S)-1,1,1-trifluoropropan-2-yl]pyridine-3-sulfonamide, |
| 682 | 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, |
| 704 | 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, |
| 820 | 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, |
| 849 | 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, |
| 960 | 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, |
| 1037 | 2-{6-[(tert-butylsulfonyl)amino]pyridin-3-yl}-1-cyclohexyl-6-ethyl-5-fluoro-1H-indole-3-carboxamide, |
| 1064 | 2-{6-[(tert-butylsulfonyl)amino]pyridin-3-yl}-1-cyclohexyl-6-(difluoromethoxy)-5-fluoro-1H-indole-3-carboxylic acid, |
| 1065 | N-{5-[3-cyano-1-cyclohexyl-6-(difluoromethoxy)-5-fluoro-1H-indol-2-yl]pyridin-2-yl}-2-methylpropane-2-sulfonamide, |
| 1088 | 2-{6-[(tert-butylsulfonyl)amino]pyridin-3-yl}-1-cyclohexyl-6-cyclopropyl-4-fluoro-1H-indole-3-carboxamide or |
| 1100 | 2-{6-[(tert-butylsulfonyl)amino]pyridin-3-yl}-6-cyclopropyl-5-fluoro-1-phenyl-1H-indole-3-carboxamide. |

Chemical Definitions

The chemical terms used above and throughout the description of the invention, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including methyl, ethyl, n-propyl, isopropyl, n-butyl, isobutyl, sec-butyl, tert-butyl, n-pentyl, n-hexyl, n-heptyl, n-octyl and the like. In some embodiments, $C_{1-8}$alkyl includes $C_{1-6}$alkyl, $C_{1-4}$alkyl and the like. A $C_{1-8}$alkyl radical may be optionally substituted where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" generally refers to a saturated monocyclic, bicyclic or polycyclic hydrocarbon radical, including cyclopropyl, cyclobutyl, cyclopentyl, cyclohexyl, cycloheptyl, cyclooctyl, 1H-indanyl, indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "$C_{3-14}$cycloalkenyl" generally refers to a partially unsaturated monocyclic, bicyclic or polycyclic hydrocarbon radical having one or more chemically stable carbon-carbon double bonds therein, including cyclopropenyl, cyclobutenyl, cyclopentenyl, cyclohexenyl, cycloheptenyl, cyclooctenyl and the like. In some embodiments, $C_{3-14}$cycloalkenyl includes $C_{3-8}$cycloalkenyl, $C_{5-8}$cycloalkenyl, $C_{3-10}$cycloalkenyl and the like. A $C_{3-14}$cycloalkenyl radical may be optionally substituted where allowed by available valences.

As used herein, the term "aryl" generally refers to a monocyclic, bicyclic or polycyclic aromatic carbon atom ring structure radical, including phenyl, naphthyl, anthracenyl, fluorenyl, azulenyl, phenanthrenyl and the like. An aryl radical may be optionally substituted where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including furanyl, thienyl (or thiophenyl), 2H-pyrrolyl, 3H-pyrrolyl, pyrazolyl, imidazolyl, isoxazolyl, isothiazolyl, oxazolyl, thiazolyl, triazolyl, oxadiazolyl, thiadiazolyl, tetrazolyl, pyranyl, thiopyranyl, pyridinyl, pyrimidinyl, pyrazinyl, pyridazinyl, triazinyl, indole, indazolyl, isoindolyl, benzofuranyl, benzothienyl, benzimidazolyl, benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl and the like. A heteroaryl radical may be optionally substituted on a carbon or nitrogen atom ring member where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, dihydro-2H-pyranyl, tetrahydro-2H-pyranyl, tetrahydro-thiopyranyl, dihydro-pyridinyl, tetrahydro-pyridinyl, hexahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, dihydro-indole, tetrahydro-indole, dihydro-indazolyl, tetrahydro-indazolyl, dihydro-isoindolyl, tetrahydro-isoindolyl, dihydro-benzofuranyl, tetrahydro-benzofuranyl, dihydro-benzothienyl, tetrahydro-benzothienyl, dihydro-benzimidazolyl, tetrahydro-benzimidazolyl, dihydro-benzoxazolyl, tetrahydro-benzoxazolyl, benzo[1,3]dioxolyl, benzo[1,4]dioxanyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like. A heterocyclyl radical may be optionally substituted on a carbon or nitrogen atom ring member where allowed by available valences.

As used herein, the term "$C_{2-8}$alkenyl-$C_{1-8}$alkyl" refers to a radical of the formula: —$C_{1-8}$alkyl-$C_{2-8}$alkenyl.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino-$C_{1-8}$alkoxy" refers to a radical of the formula: —O—$C_{1-8}$alkyl-NH—$C_{1-8}$alkyl-O—$C_{1-8}$alkyl or —O—$C_{1-8}$alkyl-N($C_{1-8}$alkyl-O—$C_{1-8}$alkyl)$_2$.

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{1-8}$alkyl" refers to a radical of the formula: —$C_{1-8}$alkyl-C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkyl-amino" refers to a radical of the formula: —NH—$C_{1-8}$alkyl or —N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$alkyl or —$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl or —$C_{1-8}$alkyl-N($C_{1-8}$alkyl)$_2$.

As used herein, the term "$C_{1-8}$alkyl-amino-$C_{1-8}$alkyl-amino-$C_{1-8}$alkoxy" refers to a radical of the formula: —O—$C_{1-8}$alkyl-NH—$C_{1-8}$alkyl-NH—$C_{1-8}$alkyl or —O—$C_{1-8}$alkyl-N($C_{1-8}$alkyl-NH—$C_{1-8}$alkyl)$_2$.

As used herein, the term "$C_{1-8}$alkyl-amino-carbonyl" refers to a radical of the formula: —C(O)—NH—$C_{1-8}$alkyl or —C(O)—N($C_{1-8}$alkyl)$_2$.

As used herein, the term "$C_{1-8}$alkyl-amino-carbonyl-amino" refers to a radical of the formula: —NH—C(O)—NH—$C_{1-8}$alkyl or —NH—C(O)—N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyloxy" refers to a radical of the formula: —O—C(O)—$C_{1-8}$alkyl.

As used herein, the term "$C_{1-8}$alkyl-carbonyloxy-$C_{1-8}$alkoxy" refers to a radical of the formula: —O—$C_{1-8}$alkyl-O—C(O)—$C_{1-8}$alkyl.

As used herein, the term "$C_{1-8}$alkyl-carbonyloxy-$C_{1-8}$alkyl" refers to a radical of the formula: —$C_{1-8}$alkyl-O—C(O)—$C_{1-8}$alkyl.

As used herein, the term "$C_{1-8}$alkyl-sulfinyl" refers to a radical of the formula: —SO—$C_{1-8}$alkyl.

As used herein, the term "$C_{1-8}$alkyl-sulfonyl" refers to a radical of the formula: —SO$_2$—$C_{1-8}$alkyl.

As used herein, the term "amino-sulfonyl" refers to a radical of the formula: —SO$_2$—NH$_2$.

As used herein, the term "$C_{1-8}$alkyl-sulfonyl-amino" refers to a radical of the formula: —NH—SO$_2$—$C_{1-8}$alkyl.

As used herein, the term "$C_{1-8}$alkylthio" refers to a radical of the formula: —S—$C_{1-8}$alkyl.

As used herein, the term "$C_{2-8}$alkynyl-$C_{1-8}$alkyl" refers to a radical of the formula: —$C_{1-8}$alkyl-$C_{2-8}$alkynyl.

As used herein, the term "amino" refers to a radical of the formula: —NH$_2$.

As used herein, the term "amino-$C_{1-8}$alkoxy" refers to a radical of the formula: —O—$C_{1-8}$alkyl-NH$_2$.

As used herein, the term "amino-$C_{1-8}$alkyl" refers to a radical of the formula: —$C_{1-8}$alkyl-NH$_2$.

As used herein, the term "amino-$C_{1-8}$alkyl-amino-$C_{1-8}$alkoxy" refers to a radical of the formula: —O—$C_{1-8}$alkyl-NH—$C_{1-8}$alkyl-NH$_2$ or —O—$C_{1-8}$alkyl-N($C_{1-8}$alkyl-NH$_2$)$_2$.

As used herein, the term "amino-carbonyl" refers to a radical of the formula: —C(O)—NH$_2$.

As used herein, the term "amino-carbonyl-amino" refers to a radical of the formula: —NH—C(O)—NH$_2$.

As used herein, the term "aryl-$C_{1-8}$alkoxy" refers to a radical of the formula: —O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-carbonyl-amino" refers to a radical of the formula: —NH—C(O)-aryl.

As used herein, the term "aryloxy" refers to a radical of the formula: —O-aryl.

As used herein, the term "carboxyl" refers to a radical of the formula: —COOH, —C(O)OH or —CO$_2$H.

As used herein, the term "carboxyl-amino" refers to a radical of the formula: —NH—COOH, —NH—C(O)OH or —NH—CO$_2$H.

As used herein, the term "cyano-$C_{1-8}$alkyl" refers to a radical of the formula: —$C_{1-8}$alkyl-CN.

As used herein, the term "1-cyano-ethyl" refers to a radical of the formula: —CH(CN)—CH$_3$.

As used herein, the term "$C_{3-14}$cycloalkyl-$C_{1-8}$alkoxy" refers to a radical of the formula: —O—$C_{1-8}$alkyl-$C_{3-14}$cycloalkyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyloxy" refers to a radical of the formula: —O—$C_{3-14}$cycloalkyl.

As used herein, the term "1-cyclopropyl-ethyl" refers to a radical of the formula: —CH(cyclopropyl)-CH$_3$.

As used herein, the term "cyclopropyl-methyl" refers to a radical of the formula: —CH$_2$-cyclopropyl.

As used herein, the term "formyl" refers to a radical of the formula: —C(O)—H

As used herein, the term "halo" or "halogen" generally refers to a halogen atom radical, including fluoro, chloro, bromo and iodo.

As used herein, the term "halo-$C_{2-8}$alkenyl" refers to a radical of the formula: —$C_{2-8}$alkenyl-halo, wherein $C_{2-8}$alkenyl may be partially or completely substituted where allowed by available valences with one or more halogen atoms, including fluoroethenyl, difluoroethenyl or difluoroallyl and the like. In some embodiments, difluoroethenyl includes 2,2-difluorovinyl or 1,2-difluorovinyl and the like; difluoroallyl includes 1,1-difluoroallyl and the like. In some embodiments, halo-$C_{2-8}$alkenyl includes halo-$C_{2-8}$alkenyl, halo-$C_{2-4}$alkenyl and the like.

As used herein, the term "halo-$C_{1-8}$alkoxy" refers to a radical of the formula: —O—$C_{1-8}$alkyl-halo, wherein $C_{1-8}$alkyl may be partially or completely substituted where allowed by available valences with one or more halogen atoms, including fluoromethoxy, difluoromethoxy, trifluoromethoxy, fluoroethoxy, difluoroethoxy or trifluoroethoxy and the like. In some embodiments, difluoroethoxy includes 2,2-difluoroethoxy, 1,2-difluoroethoxy or 1,1-difluoroethoxy and the like. In some embodiments, halo-$C_{1-8}$alkoxy includes halo-$C_{1-6}$alkoxy, halo-$C_{1-4}$alkoxy and the like.

As used herein, the term "halo-$C_{1-8}$alkyl" refers to a radical of the formula: —$C_{1-8}$alkyl-halo, wherein $C_{1-8}$alkyl may be partially or completely substituted where allowed by available valences with one or more halogen atoms, including fluoromethyl, difluoromethyl, trifluoromethyl, fluoroethyl, difluoroethyl, trifluoroethyl, fluoroisopropyl, difluoroisopropyl, trifluoroisopropyl, fluoro-tert-butyl, difluoro-tert-butyl, trifluoro-tert-butyl and the like. In some embodiments, difluoroethyl includes 2,2-difluoroethyl, 1,2-difluoroethyl or 1,1-difluoroethyl and the like; difluoroisopropyl includes 1,3-difluoropropan-2-yl and the like; trifluoroisopropyl includes 1,1,1-trifluoropropan-2-yl and the like; trifluoro-tert-butyl includes 1,1,1-trifluoro-2-methylpropan-2-yl and the like. In some embodiments, halo-$C_{1-8}$alkyl includes halo-$C_{1-6}$alkyl, halo-$C_{1-4}$alkyl and the like.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$alkyl-heteroaryl.

As used herein, the term "heteroaryloxy" refers to a radical of the formula: —O-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "heterocyclyl-carbonyloxy" refers to a radical of the formula: —O—C(O)-heterocyclyl.

As used herein, the term "heterocyclyloxy" refers to a radical of the formula: —O-heterocyclyl.

As used herein, the term "hydroxy-$C_{1-8}$alkyl" refers to a radical of the formula: —$C_{1-8}$alkyl-OH, wherein $C_{1-8}$alkyl may be partially or completely substituted where allowed by available valences with one or more hydroxy radicals.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. It should also be noted that any carbon as well as heteroatom with valences that appear to be unsatisfied as described or shown herein is assumed to have a sufficient number of hydrogen atom(s) to satisfy the valences described or shown.

For the purposes of this invention, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I) or Formula (Ia), the pattern of substitution at each occurrence is independent of the pattern at any other occurrence. Further, the use of a generic substituent variable on any formula or structure for a compound of the present invention is understood to include the replacement of the generic substituent with species substituents that are included within the particular genus, e.g., aryl may be replaced with phenyl or naphthalenyl and the like, and that the resulting compound is to be included within the scope of the compounds representative of the present invention.

As used herein, the term "each instance of" when used in a phrase such as " . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " is intended to include optional, independent substitution on each of the aryl and heterocyclyl rings and on the aryl and heterocyclyl portions of aryl-$C_{1-8}$alkyl and heterocyclyl-$C_{1-8}$alkyl.

As used herein, the term "optionally substituted" means optional substitution with the specified substituent variables, groups, radicals or moieties.

As used herein, the terms "stable compound" or "stable structure" mean a compound that is sufficiently robust to survive isolation to a useful degree of purity from a reaction mixture and formulations thereof into an efficacious therapeutic agent.

Compound names used herein were obtained using ACD Labs Index Name software Version 10.0, provided by ACD Labs; and/or, were provided using the Autonom function of Chem Draw Ultra 10.0.4, provided by CambridgeSoft. When the compound name disclosed herein conflicts with the structure depicted, the structure shown will supercede the use of the name to define the compound intended.

Compound Forms

As used herein, the term "form" means a compound of Formula (I), or Formula (Ia) isolated for use selected from a free acid, free base, salt, hydrate, solvate, clathrate, isotopologue, racemate, enantiomer, diastereomer, stereoisomer, polymorph or tautomer form thereof.

As used herein, the term "isolated" means the physical state of a compound of Formula (I), or Formula (Ia) after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group in a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Prodrugs and solvates of the compounds of the invention are also contemplated herein.

As used herein, the term "prodrug" means a form of an instant compound (e.g., a drug precursor) that is transformed in vivo to yield an active compound of Formula (I) or a form thereof. The transformation may occur by various mechanisms (e.g., by metabolic and/or non-metabolic chemical processes), such as, for example, through hydrolysis and/or metabolism in blood, liver and/or other organs and tissues. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or carbonyloxy and the like. In another example, when a compound of Formula (I) or a form thereof contains an amine functional group, a prodrug can be formed by the replacement of one or more amine hydrogen atoms with a functional group such as alkyl or substituted carbonyl.

One or more compounds of the invention may exist in unsolvated as well as solvated forms with pharmaceutically acceptable solvents such as water, ethanol, and the like, and it is intended that the invention embrace both solvated and unsolvated forms.

As used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds of the invention may optionally be converted to a solvate. Preparation of solvates is generally known. The preparation of solvates of the antifungal fluconazole in ethyl acetate as well as from water has been described (see, M. Caira et al, *J. Pharmaceutical Sci.*, 93(3), 601-611 (2004)). Similar preparations of solvates, hemisolvate, hydrates and the like have also been described (see, E. C. van Tonder et al, *AAPS PharmSciTech.*, 5(1), article 12 (2004); and A. L. Bingham et al, *Chem. Commun.*, 603-604 (2001)). A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: carboxylic acid esters, sulfonate esters, amino acid esters phosphonate esters and mono-, di- or triphosphate esters.

Compounds of Formula I, and salts, solvates, esters and prodrugs thereof, may further exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention.

The compounds of the invention may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of the invention are (S) isomers and may exist as enantiomerically pure compositions substantially comprising only the (S) isomer. In another embodiment, the compounds of the invention are (R) isomers and may exist as enantiomerically pure compositions substantially comprising only the (R) isomer. As one of skill in the art will recognize, when more than one chiral center is present, the compounds of the invention may also exist as a (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the invention, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the invention, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present invention embraces all geometric and positional isomers. For example, if a compound of Formula (I) incorporates a double bond or a fused ring, both the cis- and trans-forms, as well as mixtures, are embraced within the scope of the invention. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures thereof, are embraced within the scope of the invention. Also, for example, all keto-enol and imine-enamine forms of the compounds are included in the invention. Individual stereoisomers of the compounds of the invention may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates, isotopologues or prodrugs of the instant compounds.

The term "isotopologue" refers to isotopically-enriched compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which are also within the scope of this invention.

Certain isotopically-enriched compounds of the present invention (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., $H^2$) may afford certain therapeutic advantages resulting from greater metabolic stability (e.g., increased in vivo half-life or reduced dosage requirements) and hence may be preferred in some circumstances. Isotopically-enriched compounds of Formula (I) can generally be prepared by following procedures analogous to those disclosed in the Schemes and/or in the Examples hereinbelow, by substituting an appropriate isotopically-enriched reagent for a non-isotopically-enriched reagent.

When the compounds are enriched with deuterium, the deuterium-to-hydrogen ratio in the deuterated areas of the molecules substantially exceeds the naturally occurring deuterium-to-hydrogen ratio. Wikipedia (http://en.wikipedia.org/wiki/Deuterium) suggests that deuterium has a natural abundance in the oceans of Earth of approximately one atom in 6500 of hydrogen (~154 PPM). Deuterium thus accounts for approximately 0.015% (on a weight basis, 0.030%) of all naturally occurring hydrogen in the oceans on Earth. However, other sources suggest a much higher abundance of e.g. $6 \cdot 10^{-4}$ (6 atoms in 10,000 or 0.06% atom basis).

Polymorphic crystalline and amorphous forms of the compounds of Formula (I), and of the salts, solvates, esters and prodrugs of the compounds of Formula (I), are further intended to be included in the present invention.

Use of the Invention

The present invention is directed to compounds useful for treating or ameliorating a viral infection by modulating viral replication. In accordance with the present invention, compounds that modulate HCV viral replication have been identified and methods of using these compounds for treating or ameliorating HCV infection or disorders or symptoms associated therewith are provided.

One embodiment of the present invention is directed to a method for treating a viral infection in a subject in need thereof comprising administering an effective amount of a compound of Formula (I) or a form thereof to the subject.

An embodiment of the present invention includes the use of a compound of Formula (I) or a form thereof in the manufacture of a medicament for treating a viral infection in a subject in need thereof comprising administering an effective amount of the medicament to the subject.

An embodiment of the present invention includes the use of a compound of Formula (I) or a form thereof in the preparation of a pharmaceutical kit comprising the compound of Formula (I) or a form thereof and instructions for administering the compound for treating a viral infection in a subject in need thereof.

For each of such embodiments for treating a viral infection in a subject in need thereof, the use of a compound of Formula (I) or a form thereof further includes a use of the compound of Formula (Ia) or a form thereof.

Another embodiment of the present invention is directed to the use of a compound of Formula (I) or Formula (Ia) or a form thereof for treating a viral infection by inhibiting viral replication.

An embodiment of the present invention includes the use of a compound of Formula (I) or Formula (Ia) or a form thereof for treating or ameliorating HCV infection or disorders or symptoms associated therewith by inhibiting Hepatitis C viral replication.

An embodiment of the present invention includes a method for treating or ameliorating HCV infection or disorders or symptoms associated therewith in a subject in need thereof comprising administering an effective amount of a compound of Formula (I) or a form thereof to the subject.

An embodiment of the present invention includes the use of a compound of Formula (I) or a form thereof in the manufacture of a medicament for treating or ameliorating HCV infection or disorders or symptoms associated therewith in a subject in need thereof comprising administering an effective amount of the medicament to the subject.

An embodiment of the present invention includes the use of a compound of Formula (I) or a form thereof in the preparation of a pharmaceutical kit comprising the compound of Formula (I) or a form thereof and instructions for administering the compound for treating or ameliorating HCV infection or disorders or symptoms associated therewith in a subject in need thereof.

For each of such embodiments for treating or ameliorating HCV infection or disorders or symptoms associated therewith in a subject in need thereof, the use of a compound of Formula (I) or a form thereof further includes a use of the compound of Formula (Ia) or a form thereof.

In one respect, for each of such embodiments, the subject is treatment naive. In another respect, for each of such embodiments, the subject is not treatment naive.

As used herein, the term "treating" refers to: (i) preventing a disease, disorder or condition from occurring in a subject that may be predisposed to the disease, disorder and/or condition but has not yet been diagnosed as having it; (ii) inhibiting a disease, disorder or condition, i.e., arresting its development; and/or (iii) relieving a disease, disorder or condition, i.e., causing regression of the disease, disorder and/or condition.

As used herein, the term "subject" refers to an animal or any living organism having sensation and the power of voluntary movement, and which requires for its existence oxygen and organic food. Nonlimiting examples include members of the human, equine, porcine, bovine, murine, canine and feline species. In some embodiments, the subject is a mammal or a warm-blooded vertebrate animal. In other embodiments, the subject is a human. As used herein, the term "patient" may be used interchangeably with "subject" and "human".

Another aspect of the invention relates to a method for treating a viral infection by a wild type virus or a virus that is resistant to a currently available antiviral agent, in a subject in need thereof, comprising administering to the subject an effective amount of a compound of Formula (I) or a form thereof.

Nonlimiting examples of viral infections intended to be included within the scope of the invention include viral infections resulting from viruses of the picornavirus genus (such as poliovirus, hepatitis A virus, coxsackievirus and rhinovirus), viruses of the coronaviridae genus (such as severe acute respiratory syndrome (SARS)), viruses of the arbovirus genus, viruses of the flavivirus genus (such as hepatitis C virus, yellow fever, dengue and West Nile virus), herpesviruses (such as herpes simplex virus and Kaposi's sarcoma-associated herpesvirus and other viruses with a similar mode of replication), a human immunodeficiency virus (HIV), or a human leukemia virus (HTLV).

As used herein, the terms "effective amount" or "therapeutically effective amount" mean an amount of compound of Formula (I) or a form, composition or medicament thereof effective in inhibiting the above-noted diseases and thus producing the desired therapeutic, ameliorative, inhibitory or preventative effect in a subject in need thereof.

In general, the effective amount will be in a range of from about 0.001 mg/Kg/day to about 500 mg/Kg/day, or about 0.01 mg/Kg/day to about 500 mg/Kg/day, or about 0.1 mg to about 500 mg/Kg/day, or about 1.0 mg/day to about 500 mg/Kg/day, in single, divided, or a continuous dose for a patient or subject having a weight in a range of between about 40 to about 200 Kg (which dose may be adjusted for patients or subjects above or below this range, particularly children under 40 Kg). The typical adult subject is expected to have a median weight in a range of between about 70 to about 100 Kg.

The dose administered to achieve an effective target plasma concentration may also be administered based upon the weight of the subject or patient. Doses administered on a weight basis may be in the range of about 0.01 mg/kg/day to about 50 mg/kg/day, or about 0.015 mg/kg/day to about 20 mg/kg/day, or about 0.02 mg/kg/day to about 10 mg/kg/day, or about 0.025 mg/kg/day to about 10 mg/kg/day, or about 0.03 mg/kg/day to about 10 mg/kg/day, wherein said amount is orally administered once (once in approximately a 24 hour period), twice (once in approximately a 12 hour period) or thrice (once in approximately an 8 hour period) daily according to subject weight.

In another embodiment, where daily doses are adjusted based upon the weight of the subject or patient, compounds of the invention may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 5.0, 10, 20 or 50 mg/kg/day. Daily doses adjusted based upon the weight of the subject or patient may be administered as a single, divided, or continuous dose. In embodiments where a dose of compound is given more than once per day, it may be administered twice, thrice, or more per day.

Within the scope of the present invention, the "effective amount" of a compound of Formula (I) or a form thereof for use in the manufacture of a medicament, the preparation of a pharmaceutical kit or in a method for treating or ameliorating HCV infection or disorders or symptoms associated therewith in a subject in need thereof, is intended to include an amount in a range of from about 1.0 mg to about 3500 mg administered once daily; 10.0 mg to about 600 mg administered once daily; 0.5 mg to about 2000 mg administered twice daily; or, an amount in a range of from about 5.0 mg to about 300 mg administered twice daily.

For example, the effective amount may be the amount required to treat a HCV infection, or the amount required to inhibit viral replication or infectivity, in a subject or, more specifically, in a human. In some instances, the desired effect can be determined by analyzing (1) the presence of HCV RNA; (2) the presence of anti-HCV antibodies; (3) the level of serum alanine amino transferase (ALT) and aspartate aminotransferase (AST) (ALT and AST are elevated in patients chronically infected with HCV); (4) hepatocellular damage resulting from HCV infection, including steatosis, fibrosis and cirrhosis; (5) hepatocellular carcinoma as a result of chronic HCV infection; and (6) extrahepatic sequelae (nonlimiting examples include pruritis, encephalopathies, mental disorders such as anxiety or depression) of infection with HCV or other viruses. The effective amount for a subject will depend upon various factors, including the subject's body weight, size and health. Effective amounts for a given patient can be determined by routine experimentation that is within the skill and judgment of the clinician.

For any compound, the effective amount can be estimated initially either in cell culture assays or in relevant animal models, such as a mouse, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. In some embodiments, the effective amount is such that a large therapeutic index is achieved. In further embodiments, the dosage is within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to a compound of Formula (I) or a form thereof indicate an trough target plasma concentration ranging from approximately 0.001 µg/mL to approximately 50 µg/mL, from approximately 0.01 µg/mL to approximately 20 µg/mL, from approximately 0.05 µg/mL to approximately 10 µg/mL, or from approximately 0.1 µg/mL to approximately 5 µg/mL. To achieve such plasma concentrations, the compounds of the invention may be administered at doses that vary from 0.1 µg to 100,000 mg, depending upon the route of administration in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject. Dosage and administration may be adjusted to provide sufficient levels of the active agent(s) or to maintain the desired effect. Factors which may be taken into account include the severity of the disease state, general health of the subject, ethinicity, age, weight, and gender of the subject, diet, time and frequency of administration, drug combination(s), reaction sensitivities, experience with other HCV therapies, and tolerance/response to therapy. Long-acting pharmaceutical compositions may be administered every 2, 3 or 4 days, once every week, or once every two weeks depending on half-life and clearance rate of the particular formulation.

The compounds and compositions of the present invention may be administered to the subject via any drug delivery route known in the art. Nonlimiting examples include oral, ocular, rectal, buccal, topical, nasal, ophthalmic, subcutaneous, intramuscular, intraveneous (bolus and infusion), intracerebral, transdermal, and pulmonary routes of administration.

Metabolites of the Compounds of the Invention

Also falling within the scope of the present invention are the in vivo metabolic products of the compounds described herein. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof.

Such products typically are identified by preparing a radiolabeled isotopologue (e.g. $C^{14}$ or $H^3$) of a compound of the invention, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. These products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

Pharmaceutical Compositions

Embodiments of the present invention include the use of a compound of Formula (I) or a form thereof in a pharmaceutical composition for the prevention or treatment of a viral infection comprising an effective amount of a compound of Formula (I) or a form thereof in admixture with a pharmaceutically acceptable excipient.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In some embodiments, the pharmaceutical composition is formulated to achieve a pH of from about pH 3 to about pH 7. In other embodiments, the pharmaceutical composition is formulated to achieve a pH of from about pH 5 to about pH 8.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions of the invention may be formulated as suspensions comprising a compound of Formula (I) or a form thereof in admixture with at least one pharmaceutically acceptable excipient suitable for the manufacture of a suspension. In yet other embodiments, pharmaceutical compositions of the invention may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds of the invention may be substantially insoluble in water and sparingly soluble in most pharmaceu tically acceptable protic solvents and vegetable oils, but generally soluble in medium-chain fatty acids (e.g., caprylic and capric acids) or triglycerides and in propylene glycol esters of medium-chain fatty acids. Thus, contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compound of the invention is formulated for oral administration in a lipid-based composition suitable for low solubility compounds. Lipid-based formulations can generally enhance the oral bioavailability of such compounds. As such, pharmaceutical compositions of the invention may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil.

In other embodiments, the bioavailability of low solubility compounds may be enhanced using particle size optimization techniques including the preparation of nanoparticles or nanosuspensions using techniques known to those skilled in art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the compound of the present invention in the composition.

PREPARATION OF COMPOUNDS OF THE INVENTION

General Synthetic Examples

Methods for preparing certain compounds useful for treating or ameliorating HCV infection or disorders or symptoms associated therewith are available via standard, well-known synthetic methodology and, furthermore, have been disclosed in U.S. patent application Ser. No. 11/653,450 (referenced above), U.S. patent application Ser. No. 11/653,448 (referenced above), U.S. patent application Ser. No. 11/331,180 (referenced above) and U.S. patent application Ser. No. 11/180,961 (referenced above), each of which are incorporated herein by reference in their entirety and for all purposes.

Similarly, as disclosed herein, methods for preparing the compounds of the invention are available via standard, well-known synthetic methodology. Many of the indole starting materials are commercially available or can be prepared using the routes described below using techniques known to those skilled in the art.

Scheme A
Compounds of Formula (I) can be prepared as described in Scheme A below.

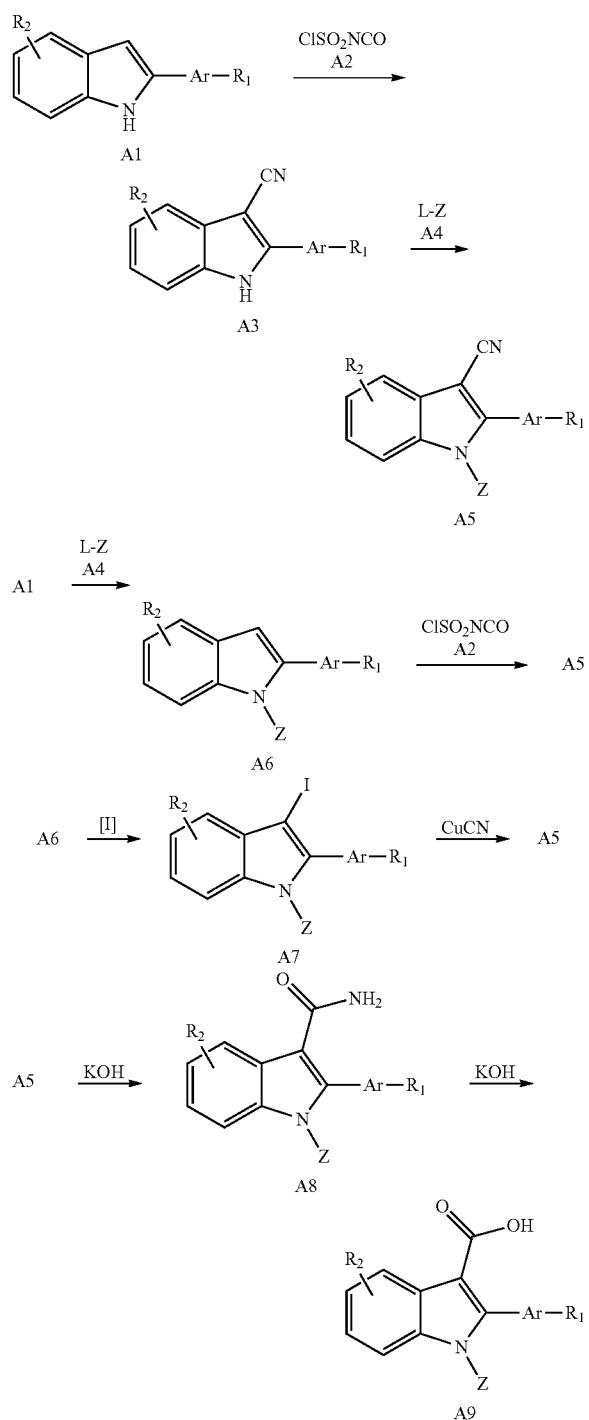

group and wherein Z is as previously defined) to afford a Compound A5, representative of a compound of Formula (I).

With respect to Compound A4, when the reactive functional group Z includes, but is not limited to, $C_{1-8}$alkyl and aryl-$C_{1-8}$alkyl and the L leaving group includes, but is not limited to, a halide (such as chloro, bromo or iodo) or an alkylsulfonate leaving group, the reaction can be carried out in a suitable solvent in the presence of an inorganic base (such as potassium carbonate or sodium hydride and the like) or an organic base (such as a trialkylamine and the like).

With respect to Compound A4, when the reactive functional group Z includes, but is not limited to, aryl or heteroaryl and the leaving group L includes, but is not limited to, a halide leaving group (such as chloro, bromo or iodo), the reaction can be carried out in a polar or nonpolar solvent at a temperature of from about ambient to about 200° C. in the presence of a copper catalyst (such as CuI and the like), and a base (such as $Cs_2CO_3$ or $K_3PO_4$ and the like), and optionally with an amine ligand (such as 1,2-bis(methylamino)ethane or 1,2-cyclohexanediamine and the like).

Alternatively, Compound A1 can be reacted with Compound A4 to give a Compound A6 that can then be reacted with Compound A2 as described above to obtain Compound A5.

Additionally, iodination of Compound A6 provides Compound A7. Subsequent reaction of Compound A7 with copper cyanide (CuCN) under appropriate conditions provides Compound A5.

Reaction of the cyano group of Compound A5 under base conditions (such as potassium hydroxide) affords Compound A8, the primary amide, and further reaction affords Compound A9, the carboxylic acid.

Scheme B
Compounds of Formula (I), wherein X is an aldehyde, can be prepared as described in Scheme B below.

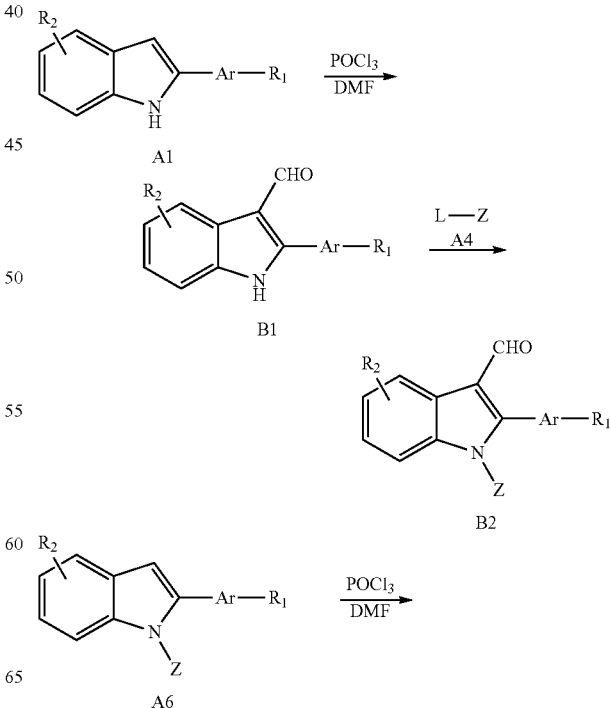

Substituted indole Compound A1 can be substituted on the 3-position with cyano using an appropriate cyanating agent Compound A2 (such as chlorosulfonyl isocyanate or a dialkyl phosphoryl isocyanate and the like) in a suitable solvent or solvent mixture (such as DMF, $CH_3CN$ or dioxane and the like) to afford a Compound A3. Compound A3 can then be reacted with a Compound A4 (wherein L represents a leaving -continued

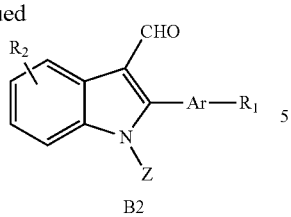

B2

Aldehyde substituted indole Compound B1 can be prepared by reacting Compound A1 with a formylating reagent (such as phosphorous oxychloride in the presence of DMF). Conversion of Compound B1 to Compound B2, representative of a compound of Formula (I), can be accomplished by treatment with Compound A4 as previously described in Scheme A.

Alternatively, Compound A6 may be reacted with a formylating reagent to directly provide Compound B2.

Scheme C
Intermediate compounds of Formula (I), wherein X is a formaldehyde oxime, can be prepared as described in Scheme C below.

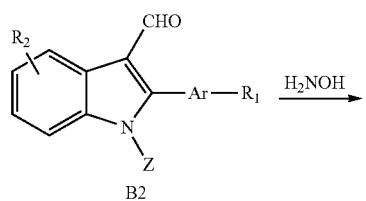

B2

$\xrightarrow{H_2NOH}$

C1

$\xrightarrow{-[H_2O]}$

A5

Aldehyde substituted indole Compound B2 can be converted to the oxime substituted indole Compound C1 via an aminating reagent (such as hydroxylamine). Conversion of Compound C1 via dehydration, by treatment with acetic anhydride and a base, or reaction with thionyl chloride affords Compound A5, representative of a compound of Formula (I).

Scheme D
Compounds of Formula (I), wherein X is nitro, can be prepared as described in Scheme D below.

A1

-continued

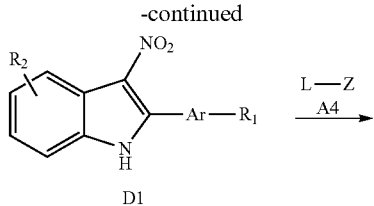

D1 $\xrightarrow{L-Z}{A4}$

D2

A6 →

D2

A nitroindole Compound D1 can be obtained by reacting Compound A1 with a nitrating agent (such as nitric acid or sodium nitrite and the like) in a solvent (such as acetic acid, acetic anhydride or sulfuric acid and the like or in a mixed solvent system further containing an organic solvent such as dichloromethane and the like). The reaction can be carried out a temperature of from about −30° C. to about 50° C.

Compound D1 may be reacted with Compound A4 to provide Compound D2, representative of a compound of Formula (I).

Alternatively, Compound A6 may be reacted in place of Compound A1 to directly provide Compound D2.

Scheme E
Compounds of Formula (I), wherein X is carboxyl, can be prepared as described in Scheme E below.

B2 $\xrightarrow{KMnO_4}{H_2O}$

E1 $\xrightarrow{SOCl_2}{NH-R_a}$

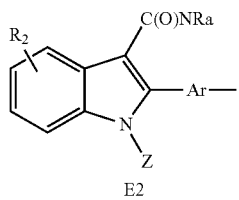

E2

Compound B2 may be reacted with a reagent (such as potassium permanganate and the like) under aqueous conditions to provide Compound E1, representative of a compound of Formula (I).

Further, Compound E1 may be reacted with thionyl chloride, followed by reaction with a substituted amine (wherein the nitrogen atom may be mono- or di-substituted with Ra, wherein Ra is $C_{1-8}$alkyl) to provide an amido substituted analog Compound E2, representative of a compound of Formula (I).

Scheme F
Compounds of Formula (I), wherein X is cyano, can be prepared as described in Scheme F below.

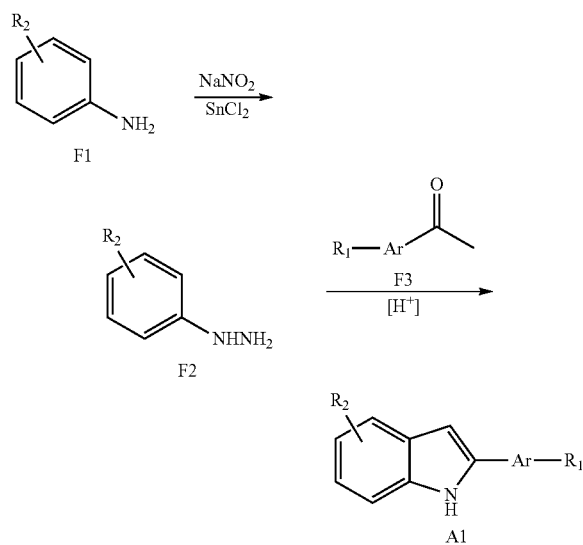

Substituted aniline Compound F1 can be diazotized and the resulting diazonium salt reduced to give a phenyl hydrazine Compound F2. Compound F2 is then reacted with ketone Compound F3 under acidic conditions to provide Compound A1, which may be carried forward as described in Scheme A to provide Compound A5, representative of a compound of Formula (I).

The conditions for the cyclization reaction between Compound F2 and Compound F3 can be carried out under typical conditions utilized by one skilled in the art. For example, acidic conditions may be provided using a Bronstead acid (such as acetic acid, hydrochloric acid or polyphosphoric acid and the like) or a Lewis acid (such as zinc chloride and the like). The reaction may be carried out in the presence of a co-solvent (such as $CH_2Cl_2$ or THF and the like), typically within a temperature range of from about 0° C. to about 120° C.

Scheme G
Compounds of Formula (I) can be prepared as described in Scheme G below.

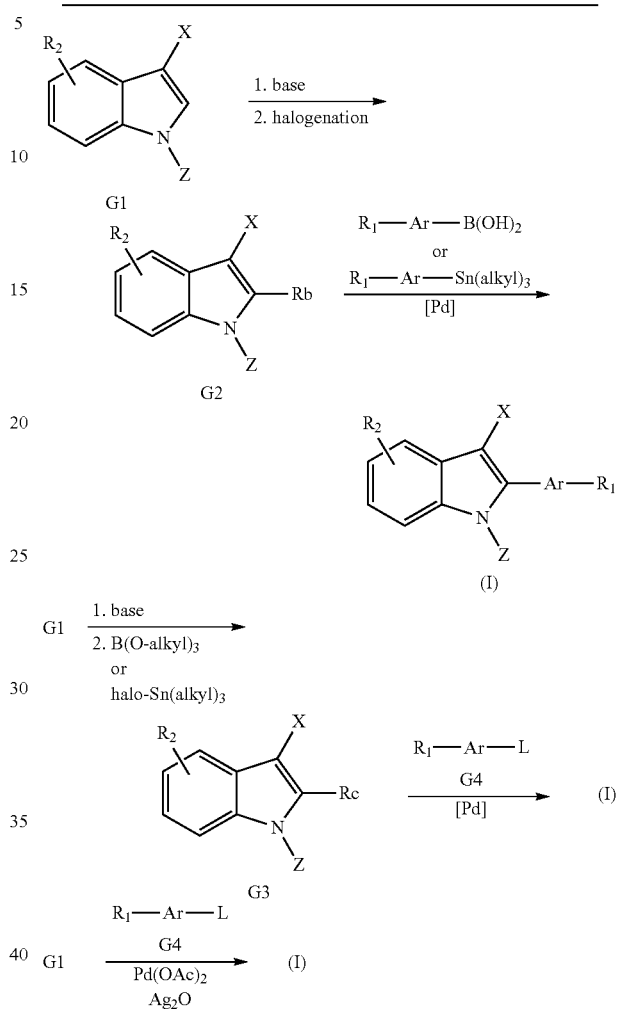

A Compound G1 can be converted to halogenated Compound G2 (wherein Rb represents a halogen atom such as iodo or bromo) by reaction with a strong base (such as n-butyllithium, s-butyllithium, lithium diisopropylamide, lithium or potassium hexamethyldisilazide and the like) in the presence of a suitable unreactive solvent (such as, ether or THF) or in solvent mixtures containing such an unreactive solvent to provide a 2-indolyl anion intermediate. The reaction is typically carried out in the range of from about −78° C. to about ambient temperature. Generation of the intermediate can be quenched with an electrophilic source of halogen (such as iodine, bromine or N-bromosuccinimide and the like) to afford Compound G2.

Compound G2 may then be reacted with a boronic acid in a Suzuki reaction or with trialkyl stannane in a Stille reaction in the presence of a palladium catalyst (such as tetrakis(triphenylphosphine)palladium(0), bis(triphenylphosphine)palladium(II) dichloride or palladium acetate) and an added phosphine ligand, to afford a compound of Formula (I).

The reaction is carried out in a suitable solvent (such as DMF, toluene, dimethoxy ethane or dioxane and the like) at a temperature of from about ambient to about 150° C. For Suzuki conditions, the reaction may be run with a base under aqueous conditions (such as aqueous sodium carbonate or sodium bicarbonate and the like) or under anhydrous conditions (such as with cesium or potassium fluoride and the like). For Stille conditions, the reaction may be run with a copper co-catalyst (such as copper iodide and the like).

Alternatively, Compound G1 can be converted to a Compound G3 derivative (wherein Rc represents boronic acid or trialkylstannane) by reacting the 2-indolyl anion intermediate described above with a trialkylborate or halo-trialkyl stannane derivative (wherein halo may be chloro, bromo or iodo), respectively. Compound G3 can then be reacted with a Compound G4 (wherein L represents a halide leaving group such as bromo or iodo), under either Suzuki or Stille conditions to provide a compound of Formula (I).

A further method is to react Compound G1 under Heck conditions (such as palladium acetate, silver (I) oxide, o-nitrobenzoic acid) in a suitable solvent (such as DMF) with G4 to afford a compound of Formula (I).

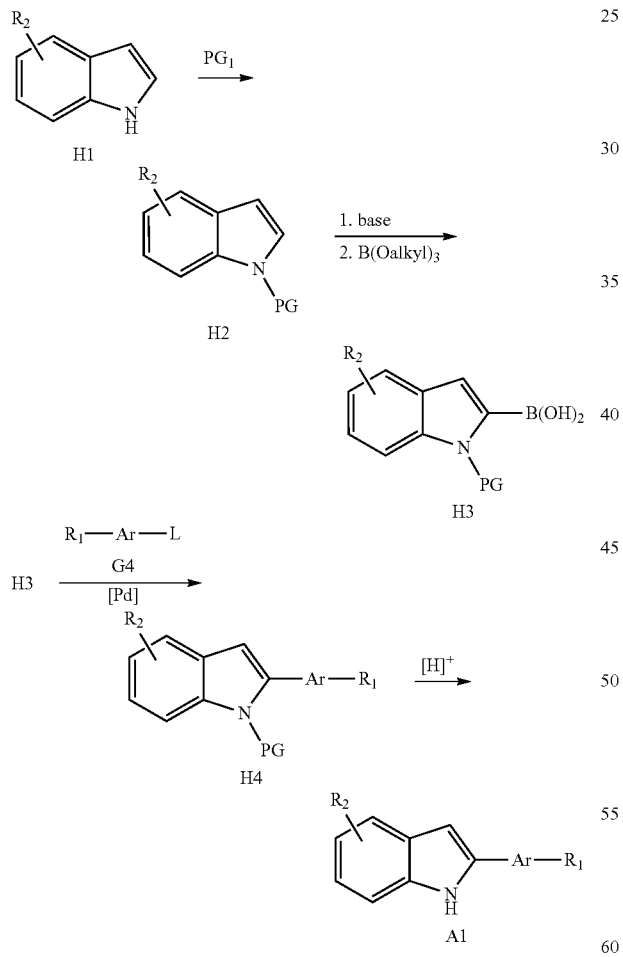

A Compound H1 may be protected by reaction with a protecting group (wherein $PG_1$ represents a reactive protecting group such as Boc anhydride and the like) to provide a Compound H2 (wherein PG represents a protecting group such as Boc, benzyl, alkyl, aryl-sulfonyl or trialkyl-silyl and the like). Treatment of Compound H2 with a strong base (such as lithium diisopropyl amide and the like) in an aprotic solvent (such as THF and the like), followed by quenching with a trialkylborate derivative obtains a Compound H3.

Reaction of Compound H3 with Compound G4 under reaction conditions described in Scheme G provides Compound H4 and removal of the protecting group affords Compound A1, which may be carried forward as described in Scheme A to provide Compound A5, representative of a compound of Formula (I).

Scheme I
Compounds of Formula (I) can be prepared as described in Scheme I below.

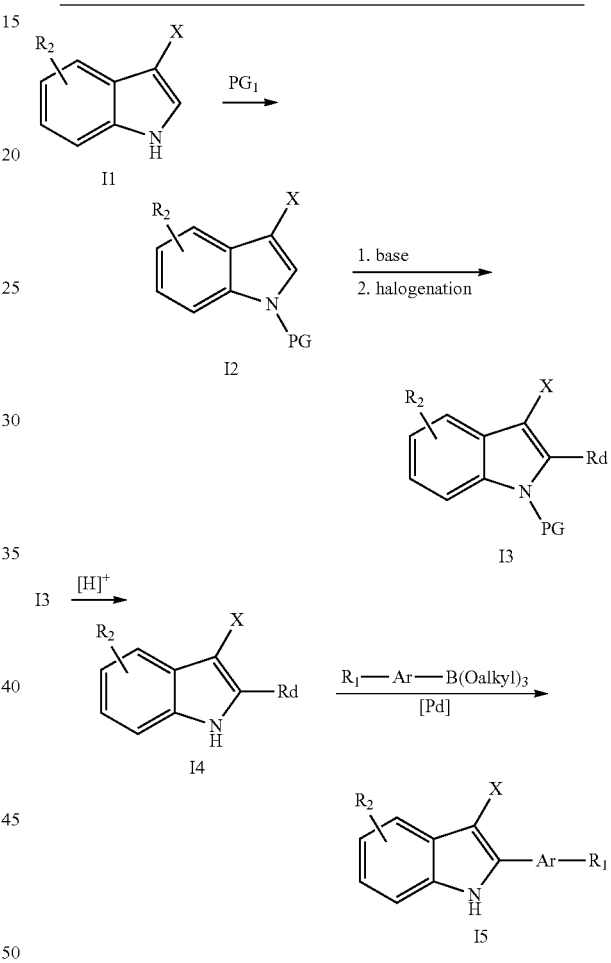

As described in Scheme H, Compound I1 can be used in place of Compound H1 to provide a protected Compound I2.

As described in Scheme G, Compound I2 can be used in place of Compound G1 to provide a halogenated Compound I3 (wherein Rd represents a halogen atom such as iodo or bromo).

As described in Scheme H, Compound I3 can be used in place of Compound H4 to provide a deprotected Compound I4.

As described in Scheme G, Compound I4 can be used in place of Compound G2 in a Suzuki reaction with a boronic acid or ester in the presence of a suitable palladium catalyst and an added phosphine ligand, to afford a Compound I5.

As described in Scheme A, Compound I5 can be used in place of Compound A1 to provide a compound of Formula (I).

Scheme J
Compounds of Formula (I) can be prepared as described in Scheme J below.

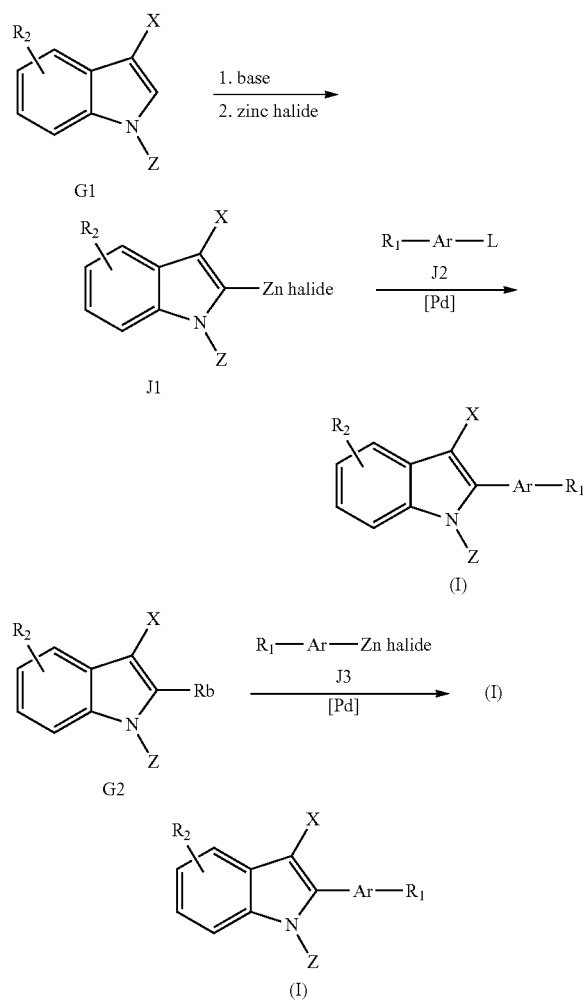

Scheme K
Compounds of Formula (I) can be prepared as described in Scheme I below.

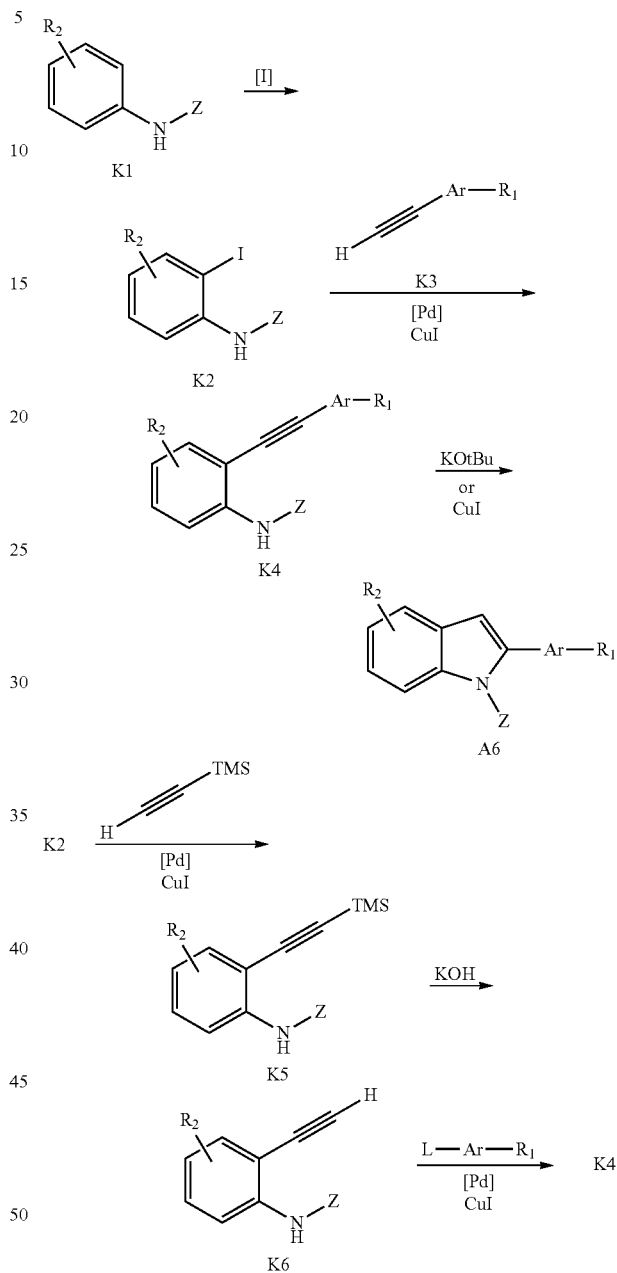

As described in Scheme G, Compound G1 is reacted to provide the 2-indolyl anion intermediate which can be quenched with a source of zinc halide, (such as zinc halide metal or solutions thereof) to give an organozinc compound Compound J1. Compound J1 can then be reacted with a Compound J2 (wherein L represents leaving group such as halogen or triflate and the like) in a Negishi reaction in the presence of a suitable palladium catalyst to afford a compound of Formula (I).

Alternatively, Compound G2 (wherein Rb is as described previously) can be reacted with a Compound J3 in the presence of a suitable palladium catalyst to provide a compound of Formula (I).

The conditions for the foregoing reactions include the presence of a palladium catalyst (such as tetrakis(triphenylphosphine)palladium(0) or bis(triphenylphosphine)palladium(II) dichloride) in a suitable solvent and a temperature in a range of from about ambient to about 150° C.

Compound J3 may be prepared by treatment of an aryl halide with activated zinc or by treatment of a lithium or magnesium substituted $R_1$—Ar compound with zinc halide.

Compound K1 is iodinated under suitable conditions (such as potassium iodide and potassium iodate or iodine monochloride) to provide Compound K2. Compound K2 can then be reacted with a Compound K3 in a Sonogashira reaction in the presence of a suitable palladium catalyst (such as bis(triphenylphosphine)palladium dichloride and the like) and copper co-catalyst (such as copper iodide and the like) to afford Compound K4. Compound K4 is reacted with either potassium tert-butoxide or a suitable copper catalyst (such as copper iodide and the like) to provide Compound A6, representative of a compound of Formula (I).

Alternatively, Compound K2 can be reacted with trimethylsilylacetylene under Sonogashira conditions to give a Compound K5. Removal of the trimethylsilyl group is accomplished employing potassium hydroxide to afford Compound K6. Reaction of Compound K6 with a compound L-Y (where L and Y has previously been defined) under Sonogashira conditions provides Compound K4 which can then be reacted as described above to obtain Compound A6, representative of a compound of Formula (I).

Scheme L
Compounds of Formula (I) can be prepared as described in Scheme L below.

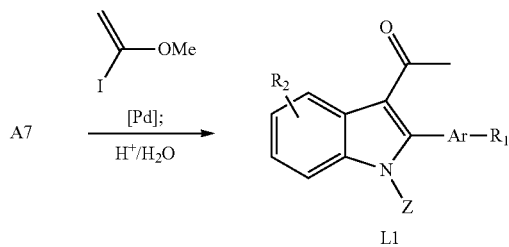

Reaction of Compound A7 with a vinyl iodide synthon with an appropriate catalyst (such as palladium(II)acetate, dppp) and subsequent treatment with aqueous acid affords Compound L1, representative of a compound of Formula (I).

Scheme M
Compounds of Formula (I) can be prepared as described in Scheme M below.

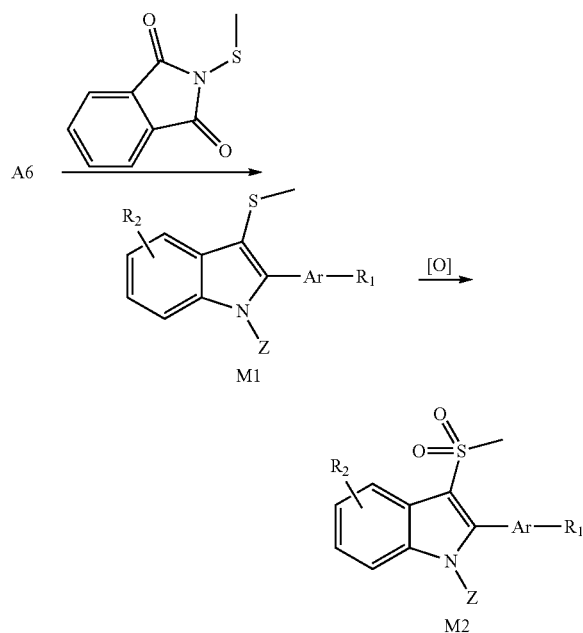

Compound A6 can be reacted with a thiomethylating agent (such as N-thiomethyl-phthalimide) in an appropriate solvent (such as dimethyl acetamide) to provide Compound M1. Subsequent oxidation of Compound M1 with an appropriate oxidant (such as mCPBA) and solvent (such as chloroform) affords Compound M2, representative of a compound of Formula (I).

Scheme O
Compounds of Formula (I) can be prepared as described in Scheme O below.

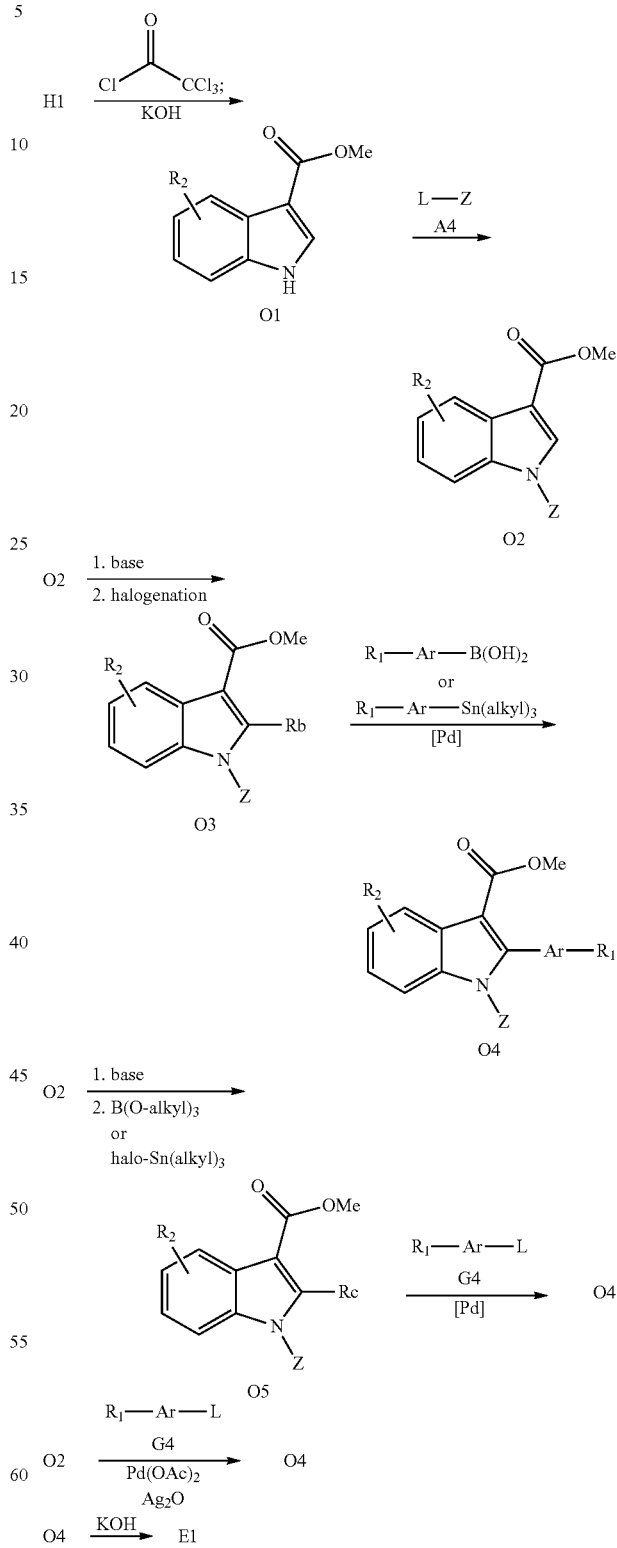

Compound H1 can be reacted with an acylating reagent (such as trichloroacetylchloride and then KOH) to provide Compound O1. Compound O1 may be reacted with Compound A4 to provide Compound O2. Compound O2 can be converted to halogenated Compound O3 (wherein Rb represents a halogen atom such as iodo or bromo) by reaction with a strong base (such as n-butyllithium, s-butyllithium, lithium diisopropylamide, lithium or potassium hexamethyldisilazide and the like) in the presence of a suitable unreactive solvent (such as, ether or THF) or in solvent mixtures containing such an unreactive solvent to provide a 2-indolyl anion intermediate. The reaction is typically carried out in the range of from about −78° C. to about ambient temperature. Generation of the intermediate can be quenched with an electrophilic source of halogen (such as iodine, bromine or N-bromosuccinimide and the like) to afford Compound O3.

Compound O3 may then be reacted with a boronic acid in a Suzuki reaction or with trialkyl stannane in a Stille reaction in the presence of a palladium catalyst (such as tetrakis(triphenylphosphine)palladium(0), bis(triphenylphosphine)palladium(II)dichloride or palladium acetate) and an added phosphine ligand, to afford a compound of Compound O4, representative of a compound of Formula (I).

The reaction is carried out in a suitable solvent (such as DMF, toluene, dimethoxy ethane or dioxane and the like) at a temperature of from about ambient to about 150° C. For Suzuki conditions, the reaction may be run with a base under aqueous conditions (such as aqueous sodium carbonate or sodium bicarbonate and the like) or under anhydrous conditions (such as with cesium or potassium fluoride and the like). For Stille conditions, the reaction may be run with a copper co-catalyst (such as copper iodide and the like).

Alternatively, Compound O2 can be converted to a Compound O5 derivative (wherein Rc represents boronic acid or trialkylstannane) by reacting the 2-indolyl anion intermediate described above with a trialkylborate or halo-trialkyl stannane derivative (wherein halo may be chloro, bromo or iodo), respectively. Compound O5 can then be reacted with a Compound G4 (wherein L represents a halide leaving group such as bromo or iodo), under either Suzuki or Stille conditions to provide a compound of Compound O4, representative of a compound of Formula (I).

A further method is to react Compound O2 under Heck conditions (such as palladium acetate, silver (I) oxide, o-nitrobenzoic acid) to afford a compound of Compound O4, representative of a compound of Formula (I).

Compound O4 can be reacted with KOH in a suitable solvent to provide Compound E1 which can be reacted as in Scheme E to provide E2, representative of a compound of Formula (I).

Specific Synthetic Examples

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

Other than in the working examples, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

Synthetic Examples

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

As used above, and throughout the description of the invention, the following abbreviations, unless otherwise indicated, shall be understood to have the following meanings:

| Abbreviation | Meaning |
|---|---|
| AcOH or HOAc | acetic acid |
| $^t$Bu or tBu | tert-butyl |
| CSI | chlorosulfonyl isocyanate |
| DCM | dichloromethane ($CH_2Cl_2$) |
| DIPA | diisopropylamine |
| DMF | dimethyl formamide |
| DME | dimethyl ether |
| DMSO | dimethylsulfoxide |
| HPLC | high performance liquid chromatography |
| iPR | isopropyl |
| KF | potassium fluoride |
| LDA | lithium diamine |
| MeOH | methanol |
| MS | mass spectroscopy |
| MTBE | methyl tert-butyl ether |
| NMR | nuclear magnetic resonance |
| Pd° | palladium |
| $Pd_2(dba)_3$ | tris(dibenzylideneacetone)dipalladium(0) |
| $PdCl_2$dppf | [1,1'-bis(diphenylphosphino)ferrocene]dichloropalladium(II) |
| $Pd(PPh_3)_4$ | tetrakis(triphenylphosphine)palladium |
| $PHBF_4$ | phosphonium tetrafluoroborate |
| RT | room temperature |
| $Bu_3SnI$ or $ISnBu_3$ | tributyltin iodide |
| TFA | trifluoroacetic acid |
| THF | tetrahydrofuran |
| TLC | thin layer chromatography |
| TMS | trimethylsilyl |
| Tos | tosyl |

Example 1

6-(3-cyano-1-cyclobutyl-6-cyclopropyl-1H-indol-2-yl)-N-(1,3-difluoropropan-2-yl)pyridine-3-sulfonamide (Cpd 35)

Step A. Preparation of 1,3-difluoro-2-propylamine hydrochloride

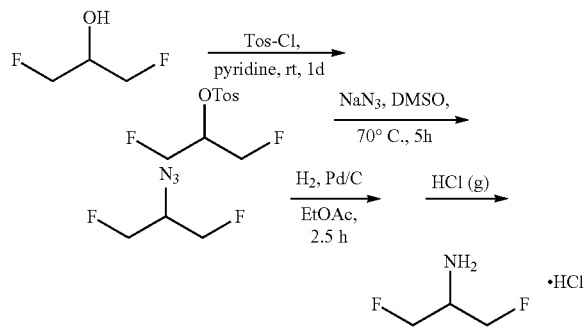

1,3-difluoro-2-propanol (60.75 g, 633 mmol) was dissolved in pyridine (375 mL) at 0° C. Tosyl chloride (134 g, 700 mmol) was added in portions and stirred overnight at room temperature. Pyridine was removed under reduced pressure and the residue was diluted with ethyl acetate. The mixture was washed sequentially with dilute aqueous HCl, water, sat. aq. NaHCO$_3$ and brine. The organic layer was dried over MgSO$_4$, filtered and concentrated. The residue was cooled to −78° C. until crystals began to form. The material was triturated with ice-cold hexane (2×200 mL) and filtered to provide O-Tosyl-1,3-difluoro-2-propanol as a white low-melting solid (143.9 g, 91%).

O-Tosyl-1,3-difluoro-2-propanol (30 g, 120 mmol), sodium azide (16 g, 246 mmol), and DMSO (60 mL) were combined and heated at 70° C. for 5 h. The reaction mixture was then diluted in 500 mL of water and extracted with ethyl acetate (4×40 mL). The organic layer was washed with 40 mL of water and brine. The mixture was dried over MgSO$_4$ and filtered into a 500 mL Parr bottle. Pd/C (10%, 1.5 g) was added and the mixture shaken on a Parr hydrogenator at 50 psi of H$_2$ for 30 minutes. The bottle was then quickly evacuated, charged again to 50 psi and shaken for another 30 minutes. This process was repeated three more times. The mixture was then filtered through celite and HCl (gas) was bubbled through until completely saturated with HCl (30 minutes). Ethyl acetate and HCl were evaporated to provide the title compound as a white solid (12.3 g, 78%). $^1$H NMR (DMSO-d$_6$, 500 MHz): δ 8.83 (3H, br s), 4.81 (1H, m), 4.72 (2H, m), 4.63 (1H, m), 3.78 (1H, m).

Part B. Preparation of 6-chloro-N-(1,3-difluoropropan-2-yl)pyridine-3-sulfonamide

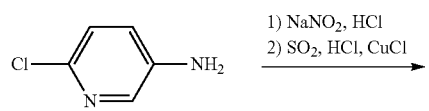

1) NaNO$_2$, HCl
2) SO$_2$, HCl, CuCl

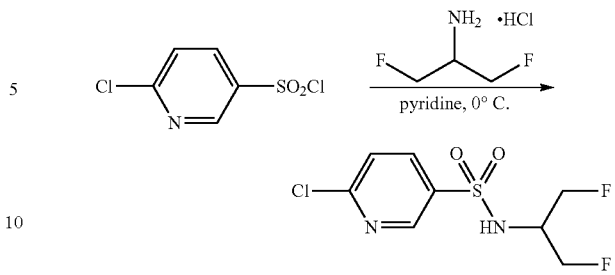

A solution of SO$_2$ was prepared by adding thionyl chloride (24.2 mL) into stirring water (144 mL) containing copper (I) chloride (87.0 mg). The solution was then stirred at room temperature overnight. 5-Amino-2-chloropyridine (10.0 g, 77.8 mmol) was added into stirring conc. aq. HCl (80 mL) portionwise. The mixture was stirred until all solid dissolved and was then cooled to −5° C. Into the mixture was added dropwise a solution of sodium nitrite (5.9 g, 85.6 mmol) dissolved in 24 mL of water while the temperature was kept between −5° C. and 0° C. The resulting mixture was stirred for 30 minutes after the completion of the addition and then added dropwise into the aqueous solution of SO$_2$. The temperature was kept below 0° C. during the addition. After the addition the mixture was stirred for 1 h below 0° C. and then filtered. The cake was washed with ice-cold water, dissolved in CH$_2$Cl$_2$, dried over Na$_2$SO$_4$ and concentrated to give 2-chloropyridine-5-sulfonyl chloride as a grey solid (13.6 g, 82%). $^1$H NMR (500 MHz, CDCl$_3$): δ 9.04 (1H, d, J=2.4 Hz), 8.27 (1H, dd, J=8.5 Hz, J=2.6 Hz), 7.62 (1H, dd, J=8.5 Hz, J=0.4 Hz).

2-Chloropyridine-5-sulfonyl chloride (18 g, 85 mmol) was added to a solution of 1,3-difluoro-2-propylamine hydrochloride (11.2 g, 58.1 mmol) in pyridine (25 mL) at 0° C. The reaction mixture was stirred at room temperature for 30 minutes, diluted with ethyl acetate (200 mL) and washed with 3N aq. HCl (3×100 mL). The organic layer was dried over Na$_2$SO$_4$, filtered and concentrated. The residue was triturated with hexane (2×50 mL) and filtered to provide the title compound as an off-white solid (15.7 g, 70%). $^1$H NMR (500 MHz, CDCl$_3$): δ 8.79 (1H, d, J=2.4 Hz), 8.17 (1H, dd, J=2.6 Hz, 2.5 Hz), 7.49 (1H, d, J=8.2 Hz), 5.25 (1H br s), 4.58 (2H, m), 4.47 (2H, m), 3.77 (1H, m).

Part C. Preparation of 3-cyano-1-cyclobutyl-6-cyclopropyl-1H-indol-2-ylboronic acid

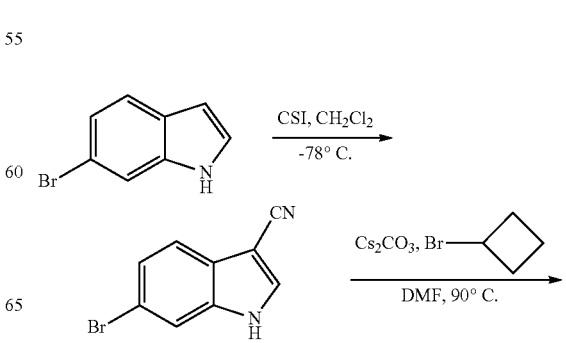

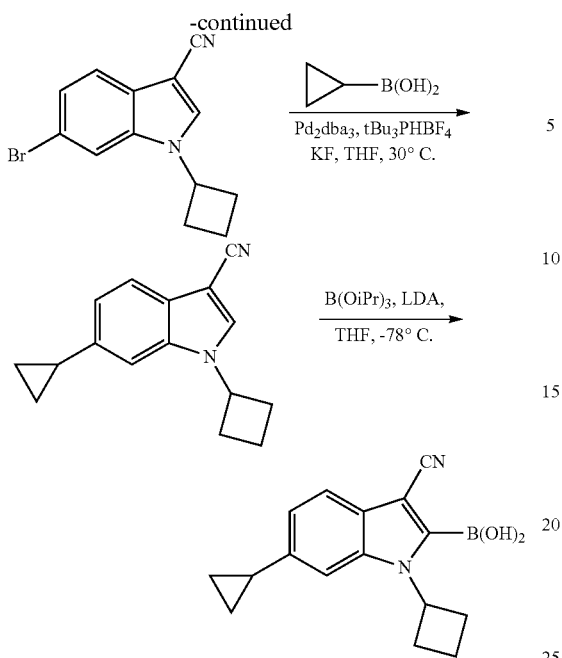

To 6-bromo-1H-indole (41.36 g, 211.0 mmol) in DMF (150 mL) at −78° C. was added chlorosulfonyl isocyanate (20 mL, 225 mmol). After complete addition, the mixture was allowed to warm to room temperature and stirred for 2 hrs. The reaction mixture was poured into ice (500 mL) and stirred for 30 minutes. The precipitate was collected on a filter and dried in a vacuum oven to give 6-bromo-1H-indole-3-carbonitrile as a light-beige solid (46.73 g, 100%).

To the 6-bromo-1H-indole-3-carbonitrile (20.28 g, 91.79 mmol) was added cesium carbonate (76 g, 233 mmol), DMF (20 mL), and then cyclobutylbromide (96%, 11 mL, 112 mmol). This mixture was stirred overnight at 100° C., cooled to room temperature and then poured into ice water (500 mL). The precipitate was collected on a filter and washed with ethyl ether (3×10 mL) and dried in a vacuum oven at 50° C. to give a first fraction of 6-bromo-1-cyclobutyl-1H-indole-3-carbonitrile as a light tan solid (19.70 g). The ethyl ether wash was collected, concentrated and triturated with ether to give a second fraction of 6-bromo-1-cyclobutyl-1H-indole-3-carbonitrile as a light orange solid (2.90 g) (89% combined yield).

To 6-bromo-1-cyclobutyl-1H-indole-3-carbonitrile (1.13 g, 4.11 mmol) in a nitrogen flushed flask was added cyclopropylboronic acid (0.62 g, 6.1 mmol), Pd$_2$(dba)$_3$ (0.19 g, 0.21 mmol), tri-tert-butylphosphonium tetrafluoroborate (0.14 g, 0.48 mmol), potassium fluoride (1.43 g, 24.6 mmol). The dry reagents were treated to three cycles of high vacuum/nitrogen backfill. Degassed THF (16 mL) was added and the mixture was stirred overnight at 30° C. THF was removed under a stream of nitrogen and then CH$_2$Cl$_2$ (30 mL) was added. The mixture was stirred for 2 hours, filtered through celite, concentrated and chromatographed on silica (0-10% ethyl acetate 1:1 in CH$_2$Cl$_2$/hexanes) to give 0.68 g of white solid containing ca. 1% 3-cyano-1-N-cyclobutylindole. The impurity was removed via a hot hexane wash; the solid was heated to 70° C. in hexane and then filtered (combined material, 11.2 g, gave 9.1 g of pure material) to provide 1-cyclobutyl-6-cyclopropyl-1H-indole-3-carbonitrile. $^1$H NMR (500 MHz, acetone-d$_6$): δ 8.15 (1H, s), 7.54 (1H, d, J=7.9 Hz), 7.35 (1H, s), 7.06 (1H, dd, J=8.2 Hz, J=1.4 Hz), 5.09 (1H, p, J=8.0 Hz), 2.72-2.61 (2H, m), 2.59-2.48 (2H, m), 2.12-2.05 (2H, m), 2.03-1.93 (3H, m), 1.00 (2H, ddd, J=8.4 Hz, J=6.4 Hz, J=4.4 Hz), 0.80-0.74 (2H, m).

Into a solution of 1-cyclobutyl-6-cyclopropyl-1H-indole-3-carbonitrile (2.0 g, 8.47 mmol) and triisopropyl borate (3.52 mL, 15.25 mmol) in THF (35 mL) at −78° C. was added LDA (1.5 M in cyclohexane, 7.3 mL, 11.01 mmol). The mixture was stirred at −78° C. for 30 min, quenched with ice water (60 mL) and stirred for 15 min without cooling. The mixture was extracted with ethyl acetate 1:1 in hexane (20 mL). The aqueous layer was acidified with 2 N aq. HCl to pH 5 and then extracted with CH$_2$Cl$_2$ (60 mL). The organic layer was dried over Na$_2$SO$_4$ and concentrated to give the title compound as a solid (2.5 g, 70% pure by LCMS) that was used in the next step without further purification.

Part D. Preparation of 6-(3-cyano-1-cyclobutyl-6-cyclopropyl-1H-indol-2-yl)-N-(1,3-difluoropropan-2-yl)pyridine-3-sulfonamide

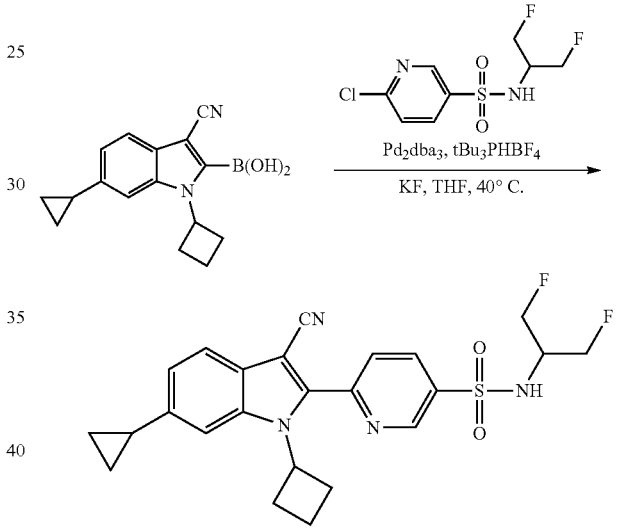

A mixture of 3-cyano-1-cyclobutyl-6-cyclopropyl-1H-indol-2-ylboronic acid (0.46 g, 1.15 mmol), 6-chloro-N-(1,3-difluoropropan-2-yl)pyridine-3-sulfonamide (0.17 g, 0.63 mmol), tri-tert-butylphosphonium tetrafluoroborate (20 mg, 0.069 mmol), Pd$_2$(dba)$_3$ (32 mg, 0.035 mmol) and potassium fluoride (0.4 g, 6.9 mmol) in THF (4.0 mL) was stirred at 40° C. overnight. The solvent was then evaporated and the residue purified by flash chromatography with 0-10% ethyl acetate in CH$_2$Cl$_2$ to provide the title Compound 35 (220 mg, 74%). Melting point: 175-178; MS m/z 471.1 M+H$^+$; $^1$H NMR (500 MHz, CDCl$_3$): δ 9.23 (1H, s), 8.33 (1H, dd, J=8.2 Hz, J=2.2 Hz), 8.01 (1H, d, J=8.2 Hz), 7.68 (1H, d, J=8.3 Hz), 7.45 (1H, s), 7.05 (1H, t, J=7.0 Hz), 5.36-5.31 (1H, m), 5.23 (1H, d, J=8.4 Hz), 4.63-4.44 (4H, m), 3.98-3.83 (1H, m), 2.69-2.60 (2H, m), 2.50-2.40 (2H, m), 2.14-2.08 (1H, m), 2.00-1.82 (2H, m), 1.12-1.05 (2H, m), 0.82-0.77 (2H, m).

Additional compounds representative of the present invention may be prepared according to the procedure of Example 1 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
|---|---|---|---|
| 5 | 6-(3-cyano-1-cyclobutyl-5-fluoro-1H-indol-2-yl)-N-(propan-2-yl)pyridine-3-sulfonamide | 203-205 | 413.2 |
| 6 | 6-[3-cyano-1-(cyclopropylmethyl)-5-fluoro-1H-indol-2-yl]-N-(propan-2-yl)pyridine-3-sulfonamide | 160-162 | 413.2 |
| 7 | 6-(3-cyano-1-cyclobutyl-6-cyclopropyl-1H-indol-2-yl)-N-(propan-2-yl)pyridine-3-sulfonamide | 174-176 | 435.3 |
| 8 | 6-(3-cyano-1-cyclobutyl-5-cyclopropyl-1H-indol-2-yl)-N-(propan-2-yl)pyridine-3-sulfonamide | 172-174 | 435.2 |
| 9 | N-tert-butyl-6-(3-cyano-1-cyclobutyl-5-fluoro-1H-indol-2-yl)pyridine-3-sulfonamide | 181-185 | 427.1 |
| 14 | 6-(5-chloro-3-cyano-1-cyclobutyl-1H-indol-2-yl)-N-(propan-2-yl)pyridine-3-sulfonamide | N/A | 429.3 |
| 15 | N-tert-butyl-6-(5-chloro-3-cyano-1-cyclobutyl-1H-indol-2-yl)pyridine-3-sulfonamide | 195-197 | 443.2 |
| 27 | 5-(3-cyano-1-cyclobutyl-6-cyclopropyl-1H-indol-2-yl)-N-(propan-2-yl)pyridine-2-sulfonamide | N/A | 435.3 |
| 28 | 5-(5-chloro-3-cyano-1-cyclobutyl-1H-indol-2-yl)-N-(propan-2-yl)pyridine-2-sulfonamide | N/A | 429.2 |
| 29 | 6-(3-cyano-1-cyclobutyl-5-fluoro-1H-indol-2-yl)-N-(1,3-difluoropropan-2-yl)pyridine-3-sulfonamide | 206-208 | 449.0 |
| 30 | 6-(5-chloro-3-cyano-1-cyclobutyl-1H-indol-2-yl)-N-(1,3-difluoropropan-2-yl)pyridine-3-sulfonamide | 182-186 | 465.0 |
| 37 | 6-(6-chloro-3-cyano-1-cyclobutyl-1H-indol-2-yl)-N-(1,3-difluoropropan-2-yl)pyridine-3-sulfonamide | 200-202 | 465.0 |
| 38 | 6-(3-cyano-1-cyclopentyl-5-fluoro-1H-indol-2-yl)-N-(1,3-difluoropropan-2-yl)pyridine-3-sulfonamide | 171-172 | 463.3 |
| 46 | 6-[3-cyano-5-fluoro-1-(tetrahydrofuran-3-yl)-1H-indol-2-yl]-N-(1,3-difluoropropan-2-yl)pyridine-3-sulfonamide | 194-197 | 465.1 |
| 47 | 6-[3-cyano-5-fluoro-1-(tetrahydrofuran-3-yl)-1H-indol-2-yl]-N-(propan-2-yl)pyridine-3-sulfonamide | 185-188 | 429.0 |
| 56 | 6-(3-cyano-1-cyclobutyl-6-fluoro-1H-indol-2-yl)-N-(1,3-difluoropropan-2-yl)pyridine-3-sulfonamide | 206-208 | 448.5 |
| 57 | 6-[3-cyano-1-(cyclopropylmethyl)-6-fluoro-1H-indol-2-yl]-N-(1,3-difluoropropan-2-yl)pyridine-3-sulfonamide | 188-190 | 449.0 |
| 58 | 6-[3-cyano-1-(cyclopropylmethyl)-5-fluoro-1H-indol-2-yl]-N-(1,3-difluoropropan-2-yl)pyridine-3-sulfonamide | 162-164 | 448.5 |
| 60 | 6-[3-cyano-5-fluoro-1-(propan-2-yl)-1H-indol-2-yl]-N-(1,3-difluoropropan-2-yl)pyridine-3-sulfonamide | 168-170 | 437.0 |
| 61 | 6-[3-cyano-6-fluoro-1-(propan-2-yl)-1H-indol-2-yl]-N-(1,3-difluoropropan-2-yl)pyridine-3-sulfonamide | 155-156 | 437.3 |
| 62 | 6-[6-chloro-3-cyano-1-(cyclopropylmethyl)-1H-indol-2-yl]-N-(1,3-difluoropropan-2-yl)pyridine-3-sulfonamide | 223-227 | 464.9 |
| 63 | 6-[6-chloro-3-cyano-1-(propan-2-yl)-1H-indol-2-yl]-N-(1,3-difluoropropan-2-yl)pyridine-3-sulfonamide | 200-202 | 453.0 |
| 64 | 6-(6-chloro-3-cyano-1-cyclopentyl-1H-indol-2-yl)-N-(1,3-difluoropropan-2-yl)pyridine-3-sulfonamide | 236-240 | 479.0 |
| 65 | 6-[5-chloro-3-cyano-1-(propan-2-yl)-1H-indol-2-yl]-N-(1,3-difluoropropan-2-yl)pyridine-3-sulfonamide | 212-215 | 452.8 |
| 66 | 6-(3-cyano-1-cyclopentyl-7-fluoro-1H-indol-2-yl)-N-(propan-2-yl)pyridine-3-sulfonamide | 152-153 | 427.0 |
| 71 | 2-(3-cyano-1-cyclobutyl-6-cyclopropyl-1H-indol-2-yl)-N-(propan-2-yl)pyrimidine-5-sulfonamide | 192-193 | 436.5 |
| 72 | 6-(5-chloro-3-cyano-1-cyclopentyl-1H-indol-2-yl)-N-(1,3-difluoropropan-2-yl)pyridine-3-sulfonamide | N/A | 479.0 |
| 73 | 6-[5-chloro-3-cyano-1-(cyclopropylmethyl)-1H-indol-2-yl]-N-(1,3-difluoropropan-2-yl)pyridine-3-sulfonamide | N/A | 464.9 |
| 79 | 6-(5-chloro-3-cyano-1-cyclohexyl-1H-indol-2-yl)-N-(1,3-difluoropropan-2-yl)pyridine-3-sulfonamide | N/A | 493.9 |
| 83 | 6-[3-cyano-6-cyclopropyl-1-(propan-2-yl)-1H-indol-2-yl]-N-(1,3-difluoropropan-2-yl)pyridine-3-sulfonamide | 184-190 | 459.1 |
| 84 | 6-[3-cyano-6-cyclopropyl-1-(cyclopropylmethyl)-1H-indol-2-yl]-N-(1,3-difluoropropan-2-yl)pyridine-3-sulfonamide | N/A | 471.0 |
| 85 | 6-(3-cyano-1-cyclopentyl-6-cyclopropyl-1H-indol-2-yl)-N-(1,3-difluoropropan-2-yl)pyridine-3-sulfonamide | 194-200 | 485.0 |
| 86 | 6-(3-cyano-1-cyclopentyl-6-cyclopropyl-1H-indol-2-yl)-N-(1,1,1-trifluoropropan-2-yl)pyridine-3-sulfonamide | 166-170 | 503.5 |
| 87 | 6-(3-cyano-1-cyclopentyl-7-fluoro-1H-indol-2-yl)-N-(1,3-difluoropropan-2-yl)pyridine-3-sulfonamide | 128-129 | 462.9 |
| 88 | 6-(7-chloro-3-cyano-1-cyclopentyl-1H-indol-2-yl)-N-(1,3-difluoropropan-2-yl)pyridine-3-sulfonamide | 149-150 | 410.8 |
| 89 | 6-(6-chloro-3-cyano-1-cyclohexyl-1H-indol-2-yl)-N-(1,3-difluoropropan-2-yl)pyridine-3-sulfonamide | 203-207 | 492.9 |
| 90 | 6-(3-cyano-1-cyclobutyl-6-cyclopropyl-1H-indol-2-yl)pyridine-3-sulfonamide | N/A | 393.0 |
| 92 | 6-(3-cyano-1-cyclohexyl-6-cyclopropyl-1H-indol-2-yl)-N-(1,3-difluoropropan-2-yl)pyridine-3-sulfonamide | 193-198 | 499.0 |

-continued

| Cpd | Name | m.p. | MS |
|---|---|---|---|
| 97 | 2-(5-chloro-3-cyano-1-cyclohexyl-1H-indol-2-yl)-N-(propan-2-yl)pyrimidine-5-sulfonamide | 210-215 | 458.0 |
| 104 | 6-(3-cyano-1-cyclohexyl-5-fluoro-1H-indol-2-yl)-N-(1,3-difluoropropan-2-yl)pyridine-3-sulfonamide | 138-141 | 477.0 |
| 109 | 6-(3-cyano-1,6-dicyclopropyl-1H-indol-2-yl)-N-(propan-2-yl)pyridine-3-sulfonamide | 209-208 | 421.4 |
| 114 | 2-(5-chloro-3-cyano-1-cyclobutyl-1H-indol-2-yl)-N-(propan-2-yl)pyrimidine-5-sulfonamide | >198.0 decomp. | 430.0 |
| 115 | 2-(6-chloro-3-cyano-1-cyclobutyl-1H-indol-2-yl)-N-(propan-2-yl)pyrimidine-5-sulfonamide | 228-229 | 430.0 |
| 120 | 2-[5-chloro-3-cyano-1-(propan-2-yl)-1H-indol-2-yl]-N-(propan-2-yl)pyrimidine-5-sulfonamide | 202-220 | 418.6 |
| 123 | 2-[3-cyano-5-fluoro-1-(propan-2-yl)-1H-indol-2-yl]-N-(propan-2-yl)pyrimidine-5-sulfonamide | 192-197 | 402.0 |
| 124 | 2-[3-cyano-6-cyclopropyl-1-(cyclopropylmethyl)-1H-indol-2-yl]-N-(propan-2-yl)pyrimidine-5-sulfonamide | 169-174 | 436.0 |
| 125 | 2-(3-cyano-1-cyclopentyl-6-cyclopropyl-1H-indol-2-yl)-N-(propan-2-yl)pyrimidine-5-sulfonamide | 211-212 | 450.0 |
| 126 | 2-(3-cyano-1-cyclobutyl-6-cyclopropyl-1H-indol-2-yl)-N-(1,3-difluoropropan-2-yl)pyrimidine-5-sulfonamide | 165-168 | 472.0 |
| 138 | 2-(3-cyano-1-cyclobutyl-6-fluoro-1H-indol-2-yl)-N-(propan-2-yl)pyrimidine-5-sulfonamide | 193-195 | 414.0 |
| 139 | 2-[3-cyano-1-(cyclopropylmethyl)-6-fluoro-1H-indol-2-yl]-N-(propan-2-yl)pyrimidine-5-sulfonamide | 218-219 | 414.6 |
| 140 | 2-[3-cyano-6-fluoro-1-(propan-2-yl)-1H-indol-2-yl]-N-(propan-2-yl)pyrimidine-5-sulfonamide | 158-160 | 402.6 |
| 141 | 2-(3-cyano-1-cyclopentyl-6-fluoro-1H-indol-2-yl)-N-(propan-2-yl)pyrimidine-5-sulfonamide | 216-217 | 428.1 |
| 147 | 6-(3-cyano-1,6-dicyclopropyl-1H-indol-2-yl)-N-(1,3-difluoropropan-2-yl)pyridine-3-sulfonamide | 226-228 | 457.7 |
| 148 | 2-(3-cyano-1,6-dicyclopropyl-1H-indol-2-yl)-N-(1,3-difluoropropan-2-yl)pyrimidine-5-sulfonamide | 259-260 | 422.7 |
| 153 | 6-(3-cyano-1-cyclobutyl-6-cyclopropyl-1H-indol-2-yl)-N-[1-(trifluoromethyl)cyclopropyl]pyridine-3-sulfonamide | 166-171 | 501.0 |
| 156 | 2-[6-chloro-3-cyano-1-(propan-2-yl)-1H-indol-2-yl]-N-(propan-2-yl)pyrimidine-5-sulfonamide | N/A | 418.0 |
| 157 | 2-(6-chloro-3-cyano-1-cyclopentyl-1H-indol-2-yl)-N-(1,3-difluoropropan-2-yl)pyrimidine-5-sulfonamide | 233-238 | 479.9 |
| 163 | 2-(3-cyano-1-cyclobutyl-6-fluoro-1H-indol-2-yl)-N-(1,3-difluoropropan-2-yl)pyrimidine-5-sulfonamide | 193-195 | 449.9 |
| 164 | 2-[3-cyano-1-(cyclopropylmethyl)-6-fluoro-1H-indol-2-yl]-N-(1,3-difluoropropan-2-yl)pyrimidine-5-sulfonamide | 176-178 | 449.9 |
| 165 | 2-[3-cyano-6-fluoro-1-(propan-2-yl)-1H-indol-2-yl]-N-(1,3-difluoropropan-2-yl)pyrimidine-5-sulfonamide | 149-150 | 438.1 |
| 166 | 2-(3-cyano-1-cyclopentyl-6-fluoro-1H-indol-2-yl)-N-(1,3-difluoropropan-2-yl)pyrimidine-5-sulfonamide | 167-169 | 464.0 |
| 173 | 2-(3-cyano-1-cyclopentyl-6-cyclopropyl-1H-indol-2-yl)-N-(1,3-difluoropropan-2-yl)pyrimidine-5-sulfonamide | 215-219 | 486.1 |
| 175 | 2-(5-chloro-3-cyano-1-cyclobutyl-1H-indol-2-yl)-N-(1,3-difluoropropan-2-yl)pyrimidine-5-sulfonamide | 210-212 | 465.9 |
| 176 | 2-(6-chloro-3-cyano-1-cyclobutyl-1H-indol-2-yl)-N-(1,3-difluoropropan-2-yl)pyrimidine-5-sulfonamide | 243-246 | 465.8 |
| 187 | 2-[5-chloro-3-cyano-1-(propan-2-yl)-1H-indol-2-yl]-N-(1,3-difluoropropan-2-yl)pyrimidine-5-sulfonamide | N/A | 453.9 |
| 188 | 2-(5-chloro-3-cyano-1-cyclopentyl-1H-indol-2-yl)-N-(1,3-difluoropropan-2-yl)pyrimidine-5-sulfonamide | N/A | 479.9 |
| 189 | 2-(6-chloro-3-cyano-1-cyclopentyl-1H-indol-2-yl)-N-(propan-2-yl)pyrimidine-5-sulfonamide | N/A | 443.9 |
| 193 | 2-(3-cyano-1-cyclohexyl-6-cyclopropyl-1H-indol-2-yl)-N-(1,3-difluoropropan-2-yl)pyrimidine-5-sulfonamide | >200 decomp. | 500.0 |
| 221 | 2-[5-chloro-3-cyano-1-(cyclopropylmethyl)-1H-indol-2-yl]-N-(1,3-difluoropropan-2-yl)pyrimidine-5-sulfonamide | 245-250 | 465.9 |
| 234 | 6-(3-cyano-1-cyclohexyl-6-fluoro-1H-indol-2-yl)-N-(1,3-difluoropropan-2-yl)pyridine-3-sulfonamide | 193-199 | 477.1 |
| 235 | 2-(3-cyano-1-cyclohexyl-6-fluoro-1H-indol-2-yl)-N-(1,3-difluoropropan-2-yl)pyrimidine-5-sulfonamide | 213-218 | 478.1 |
| 240 | 2-(3-cyano-1-cyclopentyl-5-fluoro-1H-indol-2-yl)-N-(1,3-difluoropropan-2-yl)pyrimidine-5-sulfonamide | 201-206 | 464.0 |
| 243 | 6-(5-chloro-3-cyano-1-cyclobutyl-1H-indol-2-yl)-N-(3,3-difluorocyclobutyl)pyridine-3-sulfonamide | N/A | 477.0 |
| 244 | 6-(6-chloro-3-cyano-1-cyclobutyl-1H-indol-2-yl)-N-(3,3-difluorocyclobutyl)pyridine-3-sulfonamide | 135-138 | 477.1 |
| 247 | 6-(3-cyano-1-cyclobutyl-6-cyclopropyl-1H-indol-2-yl)-N-(3,3-difluorocyclobutyl)pyridine-3-sulfonamide | 176-178 | 483.2 |
| 251 | 2-(3-cyano-1-cyclohexyl-6-fluoro-1H-indol-2-yl)-N-(propan-2-yl)pyrimidine-5-sulfonamide | 200-202 | 442.1 |
| 257 | 2-[6-chloro-3-cyano-1-(propan-2-yl)-1H-indol-2-yl]-N-(1,3-difluoropropan-2-yl)pyrimidine-5-sulfonamide | N/A | 454.1 |

-continued

| Cpd | Name | m.p. | MS |
|---|---|---|---|
| 264 | 2-(3-cyano-1,6-dicyclobutyl-1H-indol-2-yl)-N-(1,3-difluoropropan-2-yl)pyrimidine-5-sulfonamide | 184-188 | 486.0 |
| 265 | 2-(3-cyano-1,6-dicyclobutyl-1H-indol-2-yl)-N-(propan-2-yl)pyrimidine-5-sulfonamide | 192-194 | 450.0 |
| 266 | 6-(3-cyano-1,6-dicyclobutyl-1H-indol-2-yl)-N-(propan-2-yl)pyridine-3-sulfonamide | 178-180 | 449.0 |
| 287 | N-[5-(3-cyano-1-cyclobutyl-6-cyclopropyl-1H-indol-2-yl)pyridin-2-yl]methanesulfonamide | 239-241 | 407.1 |
| 288 | N-[5-(3-cyano-1-cyclobutyl-6-cyclopropyl-1H-indol-2-yl)pyridin-2-yl]ethanesulfonamide | 241-243 | 421.3 |
| 289 | N-[5-(3-cyano-1-cyclobutyl-6-cyclopropyl-1H-indol-2-yl)pyridin-2-yl]propane-2-sulfonamide | 226-228 | 435.3 |
| 298 | N-[6-(5-chloro-3-cyano-1-cyclohexyl-1H-indol-2-yl)pyridin-3-yl]cyclopropanesulfonamide | 230-235 | 455.3 |
| 302 | 2-[3-cyano-1-(cyclopropylmethyl)-5-fluoro-1H-indol-2-yl]-N-(1,3-difluoropropan-2-yl)pyrimidine-5-sulfonamide | 216-221 | 450.2 |
| 303 | 2-[3-cyano-1-(cyclopropylmethyl)-5-fluoro-1H-indol-2-yl]-N-(propan-2-yl)pyrimidine-5-sulfonamide | 215-220 | 414.3 |
| 306 | 2-[3-cyano-1-cyclohexyl-6-(trifluoromethoxy)-1H-indol-2-yl]-N-(1,3-difluoropropan-2-yl)pyrimidine-5-sulfonamide | 168-170 | 544.1 |
| 307 | 6-(3-cyano-1-cyclopentyl-6-fluoro-1H-indol-2-yl)-N-(1,3-difluoropropan-2-yl)pyridine-3-sulfonamide | 166-168 | 463.0 |
| 308 | 6-[3-cyano-1-(propan-2-yl)-6-(trifluoromethoxy)-1H-indol-2-yl]-N-[(1S)-1-cyclopropylethyl]pyridine-3-sulfonamide | 144-145 | 493.2 |
| 309 | 6-[3-cyano-1-(cyclopropylmethyl)-6-(trifluoromethoxy)-1H-indol-2-yl]-N-[(1S)-1-cyclopropylethyl]pyridine-3-sulfonamide | 115-117 | 505.2 |
| 310 | 6-(3-cyano-1-cyclopentyl-6-ethyl-1H-indol-2-yl)-N-(1,3-difluoropropan-2-yl)pyridine-3-sulfonamide | 204.5-205.0 | 473.1 |
| 311 | 6-(3-cyano-1-cyclopentyl-6-ethyl-1H-indol-2-yl)-N-[(2R)-1,1,1-trifluoropropan-2-yl]pyridine-3-sulfonamide | 185-186 | 491.2 |
| 312 | 6-(3-cyano-1-cyclopentyl-6-ethyl-1H-indol-2-yl)-N-[(1S)-1-cyclopropylethyl]pyridine-3-sulfonamide | 147.5-148.5 | 463.2 |
| 314 | 2-(5-chloro-3-cyano-1-cyclopentyl-1H-indol-2-yl)-N-(propan-2-yl)pyrimidine-5-sulfonamide | 239-245 | 444.0 |
| 315 | 2-[3-cyano-1-cyclobutyl-6-(fluoromethyl)-1H-indol-2-yl]-N-(propan-2-yl)pyrimidine-5-sulfonamide | N/A | 428.0 |
| 316 | 6-(5-chloro-3-cyano-1-cyclobutyl-1H-indol-2-yl)-N-[(2R)-1,1,1-trifluoropropan-2-yl]pyridine-3-sulfonamide | N/A | 482.9 |
| 317 | 6-[3-cyano-1-cyclobutyl-6-(fluoromethyl)-1H-indol-2-yl]-N-[(1S)-1-cyclopropylethyl]pyridine-3-sulfonamide | N/A | 453.0 |
| 318 | 6-[3-cyano-1-cyclobutyl-6-(fluoromethyl)-1H-indol-2-yl]-N-(1,3-difluoropropan-2-yl)pyridine-3-sulfonamide | N/A | 463.0 |
| 319 | 6-[3-cyano-1-cyclobutyl-6-(fluoromethyl)-1H-indol-2-yl]-N-[(2R)-1,1,1-trifluoropropan-2-yl]pyridine-3-sulfonamide | 200-213 | 480.9 |
| 320 | 6-[3-cyano-1-cyclopentyl-6-(trifluoromethoxy)-1H-indol-2-yl]-N-[(1S)-1-cyclopropylethyl]pyridine-3-sulfonamide | 133-134 | 519.0 |
| 321 | 2-[3-cyano-1-cyclobutyl-6-(morpholin-4-yl)-1H-indol-2-yl]-N-(1,3-difluoropropan-2-yl)pyrimidine-5-sulfonamide | 223-225 | 517.3 |
| 322 | 6-[3-cyano-1-cyclobutyl-6-(morpholin-4-yl)-1H-indol-2-yl]-N-(1,3-difluoropropan-2-yl)pyridine-3-sulfonamide | 241-242 | 516.3 |
| 324 | 2-(3-cyano-1-cyclobutyl-6-cyclopropyl-1H-indol-2-yl)-N-[(2S)-1,1,1-trifluoropropan-2-yl]pyrimidine-5-sulfonamide | 214-215 | 490.2 |
| 325 | 2-(3-cyano-1-cyclobutyl-6-methyl-1H-indol-2-yl)-N-[(2S)-1,1,1-trifluoropropan-2-yl]pyrimidine-5-sulfonamide | 242-243 | 464.2 |
| 330 | 2-[3-cyano-1-cyclobutyl-6-(difluoromethyl)-1H-indol-2-yl]-N-(1,3-difluoropropan-2-yl)pyrimidine-5-sulfonamide | N/A | 482.0 |
| 331 | 6-[3-cyano-1-cyclobutyl-6-(difluoromethyl)-1H-indol-2-yl]-N-(1,3-difluoropropan-2-yl)pyridine-3-sulfonamide | 217-222 | 481.0 |
| 332 | 2-[3-cyano-1-cyclobutyl-6-(difluoromethyl)-1H-indol-2-yl]-N-(propan-2-yl)pyrimidine-5-sulfonamide | 221-227 | 446.0 |
| 333 | 6-[3-cyano-1-cyclobutyl-6-(difluoromethyl)-1H-indol-2-yl]-N-(propan-2-yl)pyridine-3-sulfonamide | 212-220 | 445.1 |
| 334 | 6-[3-cyano-1-cyclobutyl-6-(difluoromethyl)-1H-indol-2-yl]-N-[(2R)-1,1,1-trifluoropropan-2-yl]pyridine-3-sulfonamide | 200-206 | 499.0 |
| 335 | 6-[3-cyano-1-cyclobutyl-6-(difluoromethyl)-1H-indol-2-yl]-N-[(1S)-1-cyclopropylethyl]pyridine-3-sulfonamide | 182-189 | 471.1 |
| 338 | 6-(3-cyano-1-cyclobutyl-6-ethyl-1H-indol-2-yl)-N-[(2S)-1,1,1-trifluoropropan-2-yl]pyridine-3-sulfonamide | 198-199 | 477.2 |
| 339 | 6-(3-cyano-1-cyclobutyl-5-ethyl-1H-indol-2-yl)-N-[(2S)-1,1,1-trifluoropropan-2-yl]pyridine-3-sulfonamide | 168-169 | 477.2 |
| 342 | 6-(3-cyano-1,6-dicyclobutyl-1H-indol-2-yl)-N-(1,3-difluoropropan-2-yl)pyridine-3-sulfonamide | Foam | 485.3 |
| 343 | 6-(3-cyano-6-cyclobutyl-1-cyclopentyl-1H-indol-2-yl)-N-[(2R)-1,1,1-trifluoropropan-2-yl]pyridine-3-sulfonamide | 176-178 | 517.3 |
| 344 | 2-[3-cyano-6-cyclopropyl-1-(cyclopropylmethyl)-1H-indol-2-yl]-N-(1,3-difluoropropan-2-yl)pyrimidine-5-sulfonamide | 205-210 | 472.2 |

-continued

| Cpd | Name | m.p. | MS |
|---|---|---|---|
| 345 | 6-(3-cyano-1-cyclopentyl-5-methyl-1H-indol-2-yl)-N-[(2S)-1,1,1-trifluoropropan-2-yl]pyridine-3-sulfonamide | 195-200 | 477.2 |
| 346 | 6-(3,5-dicyano-1-cyclopentyl-1H-indol-2-yl)-N-[(2S)-1,1,1-trifluoropropan-2-yl]pyridine-3-sulfonamide | 225-228 | 488.3 |
| 347 | 6-[3,6-dicyano-1-(cyclopropylmethyl)-1H-indol-2-yl]-N-(1,3-difluoropropan-2-yl)pyridine-3-sulfonamide | 199-201 | 456.1 |
| 348 | 6-[3,6-dicyano-1-(cyclopropylmethyl)-1H-indol-2-yl]-N-(propan-2-yl)pyridine-3-sulfonamide | 190-192 | 420.2 |
| 349 | 6-[3,6-dicyano-1-(cyclopropylmethyl)-1H-indol-2-yl]-N-[(2S)-1,1,1-trifluoropropan-2-yl]pyridine-3-sulfonamide | 187-188 | 474.2 |
| 350 | N-[(1S)-1-cyclopropylethyl]-6-[3,6-dicyano-1-(cyclopropylmethyl)-1H-indol-2-yl]pyridine-3-sulfonamide | 203-208 | 463.2 |
| 358 | 6-[3-cyano-1-cyclopentyl-6-(trifluoromethoxy)-1H-indol-2-yl]-N-[(2S)-1,1,1-trifluoropropan-2-yl]pyridine-3-sulfonamide | 168-170 | 546.9 |
| 360 | 6-(6-chloro-3-cyano-1-cyclobutyl-5-fluoro-1H-indol-2-yl)-N-[(2S)-1,1,1-trifluoropropan-2-yl]pyridine-3-sulfonamide | 203-206 | 501.0 |
| 361 | 2-[3-cyano-1-cyclobutyl-6-(fluoromethyl)-1H-indol-2-yl]-N-(1,3-difluoropropan-2-yl)pyrimidine-5-sulfonamide | 226-232 | 464.4 |
| 362 | 6-[3-cyano-1-cyclobutyl-6-(fluoromethyl)-1H-indol-2-yl]-N-[(2S)-1,1,1-trifluoropropan-2-yl]pyridine-3-sulfonamide | 205-209 | 481.3 |
| 363 | 6-[3-cyano-1-cyclobutyl-6-(difluoromethyl)-1H-indol-2-yl]-N-[(2S)-1,1,1-trifluoropropan-2-yl]pyridine-3-sulfonamide | 198-207 | 499.2 |
| 364 | 6-(6-chloro-3-cyano-1-cyclopentyl-1H-indol-2-yl)-N-[(2S)-1,1,1-trifluoropropan-2-yl]pyridine-3-sulfonamide | N/A | 497.2 |
| 365 | 6-(5-chloro-3-cyano-1-cyclopentyl-1H-indol-2-yl)-N-[(2S)-1,1,1-trifluoropropan-2-yl]pyridine-3-sulfonamide | 207-214 | 497.3 |
| 367 | N-[(1S)-1-cyclopropylethyl]-2-(3,5-dicyano-1-cyclopentyl-1H-indol-2-yl)pyrimidine-5-sulfonamide | 218-223 | 461.2 |
| 372 | 6-[3-cyano-1-(cyclopropylmethyl)-5-methyl-1H-indol-2-yl]-N-[(2S)-1,1,1-trifluoropropan-2-yl]pyridine-3-sulfonamide | 175-180 | 463.3 |
| 373 | 6-[3-cyano-1-(cyclopropylmethyl)-5-methyl-1H-indol-2-yl]-N-(1,3-difluoropropan-2-yl)pyridine-3-sulfonamide | 186-188 | 445.3 |
| 374 | 6-(3-cyano-1-cyclopentyl-5-ethyl-1H-indol-2-yl)-N-[(2S)-1,1,1-trifluoropropan-2-yl]pyridine-3-sulfonamide | 159.5-160.5 | 491.1 |
| 375 | 6-(6-chloro-3-cyano-1-cyclobutyl-1H-indol-2-yl)-N-[(2S)-1,1,1-trifluoropropan-2-yl]pyridine-3-sulfonamide | 198-204 | 482.9 |
| 376 | 6-(5-chloro-3-cyano-1-cyclobutyl-1H-indol-2-yl)-N-[(2S)-1,1,1-trifluoropropan-2-yl]pyridine-3-sulfonamide | 193-198 | 483.2 |
| 377 | 2-[3-cyano-1-cyclobutyl-5-(fluoromethyl)-1H-indol-2-yl]-N-(1,3-difluoropropan-2-yl)pyrimidine-5-sulfonamide | 131-134 | 464.0 |
| 378 | 6-[3-cyano-1-cyclobutyl-5-(difluoromethyl)-1H-indol-2-yl]-N-(1,3-difluoropropan-2-yl)pyridine-3-sulfonamide | N/A | 481.1 |
| 379 | 2-[3-cyano-1-cyclobutyl-5-(difluoromethyl)-1H-indol-2-yl]-N-(1,3-difluoropropan-2-yl)pyrimidine-5-sulfonamide | N/A | 482.1 |
| 380 | 2-[3-cyano-1-cyclobutyl-5-(difluoromethyl)-1H-indol-2-yl]-N-[(2S)-1,1,1-trifluoropropan-2-yl]pyrimidine-5-sulfonamide | 186-188 | 500.1 |
| 381 | 6-(3-cyano-1-cyclopentyl-5-ethyl-1H-indol-2-yl)-N-(1,3-difluoropropan-2-yl)pyridine-3-sulfonamide | 167-168 | 473.1 |
| 384 | 6-[3-cyano-1-cyclobutyl-6-(2,2-difluoroethyl)-1H-indol-2-yl]-N-[(2S)-1,1,1-trifluoropropan-2-yl]pyridine-3-sulfonamide | 172-174 | 513.0 |
| 385 | 2-[3-cyano-1-cyclobutyl-6-(2,2-difluoroethyl)-1H-indol-2-yl]-N-[(2S)-1,1,1-trifluoropropan-2-yl]pyrimidine-5-sulfonamide | 216-218 | 514.1 |
| 388 | 2-[3-cyano-1-(cyclopropylmethyl)-5-methyl-1H-indol-2-yl]-N-(propan-2-yl)pyrimidine-5-sulfonamide | 219-222 | 410.2 |
| 389 | 2-[3-cyano-1-(cyclopropylmethyl)-5-methyl-1H-indol-2-yl]-N-[(2S)-1,1,1-trifluoropropan-2-yl]pyrimidine-5-sulfonamide | 220-223 | 464.1 |
| 390 | 2-(3-cyano-1-cyclohexyl-5-methyl-1H-indol-2-yl)-N-[(2S)-1,1,1-trifluoropropan-2-yl]pyrimidine-5-sulfonamide | 218-223 | 492.2 |
| 391 | 2-(3-cyano-1-cyclopentyl-5-methyl-1H-indol-2-yl)-N-[(2S)-1,1,1-trifluoropropan-2-yl]pyrimidine-5-sulfonamide | 180-185 | 478.2 |
| 392 | 2-(3,5-dicyano-1-cyclopentyl-1H-indol-2-yl)-N-[(2S)-1,1,1-trifluoropropan-2-yl]pyrimidine-5-sulfonamide | 250-254 | 489.4 |
| 393 | 2-(3-cyano-1-cyclohexyl-5-fluoro-1H-indol-2-yl)-N-[(2S)-1,1,1-trifluoropropan-2-yl]pyrimidine-5-sulfonamide | 236-238 | 496.1 |
| 394 | 6-(3-cyano-1-cyclohexyl-6-fluoro-1H-indol-2-yl)-N-[(2S)-1,1,1-trifluoropropan-2-yl]pyridine-3-sulfonamide | 213-215 | 495.1 |
| 395 | 6-(3-cyano-1-cyclobutyl-6-fluoro-1H-indol-2-yl)-N-[(2S)-1,1,1-trifluoropropan-2-yl]pyridine-3-sulfonamide | 171-172 | 467.2 |
| 396 | 6-(3-cyano-1-cyclopentyl-6-fluoro-1H-indol-2-yl)-N-[(2S)-1,1,1-trifluoropropan-2-yl]pyridine-3-sulfonamide | 132-133 | 481.1 |
| 397 | 6-[3-cyano-1-(cyclopropylmethyl)-6-fluoro-1H-indol-2-yl]-N-[(2S)-1,1,1-trifluoropropan-2-yl]pyridine-3-sulfonamide | 174-175 | 467.1 |

-continued

| Cpd | Name | m.p. | MS |
|---|---|---|---|
| 401 | 2-(3-cyano-1-cyclopentyl-6-cyclopropyl-1H-indol-2-yl)-N-[(2S)-1,1,1-trifluoropropan-2-yl]pyrimidine-5-sulfonamide | 238-239 | 504.3 |
| 402 | 2-[3-cyano-1-(cyclopropylmethyl)-6-methyl-1H-indol-2-yl]-N-[(2S)-1,1,1-trifluoropropan-2-yl]pyrimidine-5-sulfonamide | 259-260 | 464.2 |
| 403 | 2-[3-cyano-6-methyl-1-(propan-2-yl)-1H-indol-2-yl]-N-[(2S)-1,1,1-trifluoropropan-2-yl]pyrimidine-5-sulfonamide | 235-236 | 452.3 |
| 404 | 2-(3-cyano-1-cyclopentyl-6-methyl-1H-indol-2-yl)-N-[(2S)-1,1,1-trifluoropropan-2-yl]pyrimidine-5-sulfonamide | 223-224 | 478.3 |
| 405 | 2-(3-cyano-1-cyclobutyl-6-methoxy-1H-indol-2-yl)-N-[(2S)-1,1,1-trifluoropropan-2-yl]pyrimidine-5-sulfonamide | 254-255 | 480.3 |
| 406 | 2-(3-cyano-1-cyclopentyl-6-methoxy-1H-indol-2-yl)-N-[(2S)-1,1,1-trifluoropropan-2-yl]pyrimidine-5-sulfonamide | 211-212 | 494.3 |
| 410 | 6-(3-cyano-1-cyclohexyl-5-fluoro-1H-indol-2-yl)-N-[(2S)-1,1,1-trifluoropropan-2-yl]pyridine-3-sulfonamide | 209-211 | 495.2 |
| 411 | 2-(3-cyano-1-cyclohexyl-6-fluoro-1H-indol-2-yl)-N-[(2S)-1,1,1-trifluoropropan-2-yl]pyrimidine-5-sulfonamide | 224-226 | 496.3 |
| 412 | 6-[3-cyano-1-(cyclohex-2-en-1-yl)-5-fluoro-1H-indol-2-yl]-N-[(2R)-1,1,1-trifluoropropan-2-yl]pyridine-3-sulfonamide | 187-188 | 493.1 |
| 413 | 6-[3-cyano-1-(cyclohex-2-en-1-yl)-5-fluoro-1H-indol-2-yl]-N-[(2S)-1,1,1-trifluoropropan-2-yl]pyridine-3-sulfonamide | 186-187 | 493.0 |
| 414 | 2-(3-cyano-1-cyclobutyl-5-methyl-1H-indol-2-yl)-N-[(2S)-1,1,1-trifluoropropan-2-yl]pyrimidine-5-sulfonamide | 190-195 | 464.3 |
| 415 | 2-[6-chloro-3-cyano-1-(cyclopropylmethyl)-1H-indol-2-yl]-N-[(2S)-1,1,1-trifluoropropan-2-yl]pyrimidine-5-sulfonamide | N/A | 483.9 |
| 416 | 2-(3-cyano-1-cyclobutyl-5-fluoro-1H-indol-2-yl)-N-(propan-2-yl)pyrimidine-5-sulfonamide | 195-200 | 414.2 |
| 417 | 2-(6-chloro-3-cyano-1-cyclopentyl-1H-indol-2-yl)-N-[(2S)-1,1,1-trifluoropropan-2-yl]pyrimidine-5-sulfonamide | 220-224 | 497.8 |
| 418 | 2-[6-chloro-3-cyano-1-(propan-2-yl)-1H-indol-2-yl]-N-[(2S)-1,1,1-trifluoropropan-2-yl]pyrimidine-5-sulfonamide | 241-248 | 471.9 |
| 419 | 2-(5-chloro-3-cyano-1-cyclopentyl-1H-indol-2-yl)-N-[(2S)-1,1,1-trifluoropropan-2-yl]pyrimidine-5-sulfonamide | 243-249 | 497.8 |
| 420 | 2-[5-chloro-3-cyano-1-(propan-2-yl)-1H-indol-2-yl]-N-[(2S)-1,1,1-trifluoropropan-2-yl]pyrimidine-5-sulfonamide | N/A | 471.8 |
| 425 | 6-[3-cyano-6-methyl-1-(propan-2-yl)-1H-indol-2-yl]-N-[(1S)-1-cyclopropylethyl]pyridine-3-sulfonamide | N/A | 422.9 |
| 426 | 6-(3-cyano-1-cyclopentyl-6-methyl-1H-indol-2-yl)-N-[(1S)-1-cyclopropylethyl]pyridine-3-sulfonamide | N/A | 449.0 |
| 427 | 6-(3-cyano-1-cyclobutyl-6-methoxy-1H-indol-2-yl)-N-[(2S)-1,1,1-trifluoropropan-2-yl]pyridine-3-sulfonamide | 206-212 | 478.9 |
| 428 | 6-(3-cyano-1-cyclobutyl-6-methoxy-1H-indol-2-yl)-N-[(2R)-1,1,1-trifluoropropan-2-yl]pyridine-3-sulfonamide | 206-212 | 478.9 |
| 429 | 6-(3-cyano-1-cyclobutyl-6-methoxy-1H-indol-2-yl)-N-[(1S)-1-cyclopropylethyl]pyridine-3-sulfonamide | 193-199 | 450.9 |
| 430 | 6-(3-cyano-1-cyclopentyl-6-methoxy-1H-indol-2-yl)-N-[(2S)-1,1,1-trifluoropropan-2-yl]pyridine-3-sulfonamide | 209-216 | 492.9 |
| 431 | 6-(3-cyano-1-cyclopentyl-6-methoxy-1H-indol-2-yl)-N-[(2R)-1,1,1-trifluoropropan-2-yl]pyridine-3-sulfonamide | 209-216 | 492.9 |
| 432 | 6-(3-cyano-1-cyclopentyl-6-methoxy-1H-indol-2-yl)-N-[(1S)-1-cyclopropylethyl]pyridine-3-sulfonamide | 199-209 | 465.0 |
| 433 | 6-(3-cyano-1-cyclopentyl-6-cyclopropyl-1H-indol-2-yl)-N-[(1S)-1-cyclopropylethyl]pyridine-3-sulfonamide | N/A | 475.0 |
| 434 | 6-(3-cyano-1-cyclobutyl-5-fluoro-1H-indol-2-yl)-N-[(2S)-1,1,1-trifluoropropan-2-yl]pyridine-3-sulfonamide | N/A | 466.8 |
| 435 | 6-(3-cyano-1-cyclopentyl-5-fluoro-1H-indol-2-yl)-N-[(2S)-1,1,1-trifluoropropan-2-yl]pyridine-3-sulfonamide | N/A | 481.3 |
| 436 | 6-[3-cyano-1-(cyclopropylmethyl)-5-fluoro-1H-indol-2-yl]-N-[(2S)-1,1,1-trifluoropropan-2-yl]pyridine-3-sulfonamide | 165-167 | 467.2 |
| 444 | 6-(5-chloro-3-cyano-1-cyclobutyl-6-methyl-1H-indol-2-yl)-N-(1,3-difluoropropan-2-yl)pyridine-3-sulfonamide | 189-193 | 478.9 |
| 445 | 6-(5-chloro-3-cyano-1-cyclobutyl-6-methyl-1H-indol-2-yl)-N-[(2R)-1,1,1-trifluoropropan-2-yl]pyridine-3-sulfonamide | 213-215 | 497.4 |
| 446 | 6-(5-chloro-3-cyano-1-cyclobutyl-6-methyl-1H-indol-2-yl)-N-[(2S)-1,1,1-trifluoropropan-2-yl]pyridine-3-sulfonamide | 209-210 | 496.8 |
| 447 | 2-(5-chloro-3-cyano-1-cyclobutyl-6-methyl-1H-indol-2-yl)-N-(1,3-difluoropropan-2-yl)pyrimidine-5-sulfonamide | 275-279 | 480.3 |
| 448 | 2-(5-chloro-3-cyano-1-cyclobutyl-6-methyl-1H-indol-2-yl)-N-[(2S)-1,1,1-trifluoropropan-2-yl]pyrimidine-5-sulfonamide | >300 | 498.2 |
| 451 | 2-(3-cyano-1-cyclobutyl-5-fluoro-1H-indol-2-yl)-N-[(2S)-1,1,1-trifluoropropan-2-yl]pyrimidine-5-sulfonamide | 198-203 | 468.3 |
| 452 | 2-(3-cyano-1-cyclobutyl-5-fluoro-1H-indol-2-yl)-N-(1,3-difluoropropan-2-yl)pyrimidine-5-sulfonamide | 175-180 | 450.4 |

-continued

| Cpd | Name | m.p. | MS |
|---|---|---|---|
| 453 | 6-(3-cyano-1-cyclobutyl-5-methoxy-1H-indol-2-yl)-N-[(2S)-1,1,1-trifluoropropan-2-yl]pyridine-3-sulfonamide | 181-183 | 479.4 |
| 454 | 2-(5-chloro-3-cyano-1-cyclobutyl-1H-indol-2-yl)-N-[(2S)-1,1,1-trifluoropropan-2-yl]pyrimidine-5-sulfonamide | 232-234 | 483.9 |
| 455 | 2-[3-cyano-1-cyclobutyl-6-(propan-2-yl)-1H-indol-2-yl]-N-[(2S)-1,1,1-trifluoropropan-2-yl]pyrimidine-5-sulfonamide | 217-222 | 492.0 |
| 456 | 6-[3-cyano-1,6-di(propan-2-yl)-1H-indol-2-yl]-N-(1,3-difluoropropan-2-yl)pyridine-3-sulfonamide | 165-173 | 461.0 |
| 457 | 6-[3-cyano-1-cyclopentyl-6-(propan-2-yl)-1H-indol-2-yl]-N-(1,3-difluoropropan-2-yl)pyridine-3-sulfonamide | 163-172 | 487.0 |
| 458 | 6-[3-cyano-1-(cyclopropylmethyl)-5-methyl-1H-indol-2-yl]-N-[(2R)-1,1,1-trifluoropropan-2-yl]pyridine-3-sulfonamide | 166-172 | 463.0 |
| 459 | 6-[3-cyano-1-cyclohexyl-6-(trifluoromethoxy)-1H-indol-2-yl]-N-[(2S)-1,1,1-trifluoropropan-2-yl]pyridine-3-sulfonamide | N/A | 561.2 |
| 460 | 6-[3-cyano-1-(cyclopropylmethyl)-6-(propan-2-yl)-1H-indol-2-yl]-N-(1,3-difluoropropan-2-yl)pyridine-3-sulfonamide | 132-134 | 473.4 |
| 461 | 6-(5-chloro-3-cyano-1-cyclohexyl-1H-indol-2-yl)-N-[(2R)-1,1,1-trifluoropropan-2-yl]pyridine-3-sulfonamide | 226-227 | 511.2 |
| 462 | 6-(5-chloro-3-cyano-1-cyclohexyl-1H-indol-2-yl)-N-[(2S)-1,1,1-trifluoropropan-2-yl]pyridine-3-sulfonamide | 220-222 | 511.3 |
| 463 | 2-(5-chloro-3-cyano-1-cyclohexyl-1H-indol-2-yl)-N-(1,3-difluoropropan-2-yl)pyrimidine-5-sulfonamide | 251-253 | 494.2 |
| 464 | 2-(5-chloro-3-cyano-1-cyclohexyl-1H-indol-2-yl)-N-[(2S)-1,1,1-trifluoropropan-2-yl]pyrimidine-5-sulfonamide | 253-255 | 512.2 |
| 465 | 6-(3,6-dicyano-1-cyclobutyl-1H-indol-2-yl)-N-(1,3-difluoropropan-2-yl)pyridine-3-sulfonamide | 203-204 | 455.9 |
| 466 | 2-(3,6-dicyano-1-cyclobutyl-1H-indol-2-yl)-N-(1,3-difluoropropan-2-yl)pyrimidine-5-sulfonamide | 240-241 | 456.9 |
| 467 | 6-(3,6-dicyano-1-cyclobutyl-1H-indol-2-yl)-N-[(2S)-1,1,1-trifluoropropan-2-yl]pyridine-3-sulfonamide | 223-225 | 474.0 |
| 468 | 6-(3,6-dicyano-1-cyclopentyl-1H-indol-2-yl)-N-(1,3-difluoropropan-2-yl)pyridine-3-sulfonamide | 219-221 | 470.0 |
| 469 | 2-(3,6-dicyano-1-cyclopentyl-1H-indol-2-yl)-N-(1,3-difluoropropan-2-yl)pyrimidine-5-sulfonamide | 246-247 | 471.0 |
| 470 | 6-(3,6-dicyano-1-cyclopentyl-1H-indol-2-yl)-N-[(2S)-1,1,1-trifluoropropan-2-yl]pyridine-3-sulfonamide | 203-205 | 488.0 |
| 478 | 6-(3-cyano-1-cyclobutyl-6-methyl-1H-indol-2-yl)-N-(1,1,1-trifluoro-2-methylpropan-2-yl)pyridine-3-sulfonamide | 222-227 | 477.4 |
| 479 | 6-[3-cyano-1-cyclobutyl-6-(difluoromethoxy)-1H-indol-2-yl]-N-(1,1,1-trifluoro-2-methylpropan-2-yl)pyridine-3-sulfonamide | 165-171 | 529.2 |
| 480 | 6-(3-cyano-1-cyclobutyl-5-methyl-1H-indol-2-yl)-N-(1,1,1-trifluoro-2-methylpropan-2-yl)pyridine-3-sulfonamide | 182-187 | 477.0 |
| 484 | 6-(3-cyano-1-cyclobutyl-5-methyl-1H-indol-2-yl)-N-[(2R)-1,1,1-trifluoropropan-2-yl]pyridine-3-sulfonamide | 134-142 | 463.0 |
| 485 | 6-[3-cyano-5-methyl-1-(propan-2-yl)-1H-indol-2-yl]-N-[(2R)-1,1,1-trifluoropropan-2-yl]pyridine-3-sulfonamide | 167-173 | 451.0 |
| 486 | 6-(3-cyano-1-cyclopentyl-5-methyl-1H-indol-2-yl)-N-[(2R)-1,1,1-trifluoropropan-2-yl]pyridine-3-sulfonamide | N/A | 477.0 |
| 487 | 6-(3-cyano-1-cyclohexyl-5-methyl-1H-indol-2-yl)-N-[(2R)-1,1,1-trifluoropropan-2-yl]pyridine-3-sulfonamide | 180-189 | 491.0 |
| 494 | 2-(3-cyano-1-cyclobutyl-6-fluoro-1H-indol-2-yl)-N-[(2S)-1,1,1-trifluoropropan-2-yl]pyrimidine-5-sulfonamide | 223-225 | 468.3 |
| 495 | 2-(3-cyano-1-cyclopentyl-6-fluoro-1H-indol-2-yl)-N-[(2S)-1,1,1-trifluoropropan-2-yl]pyrimidine-5-sulfonamide | 217-219 | 482.4 |
| 496 | 2-(3-cyano-1-cyclobutyl-6-fluoro-1H-indol-2-yl)-N-[(1S)-1-cyclopropylethyl]pyrimidine-5-sulfonamide | 207-208 | 440.2 |
| 497 | 2-(3-cyano-1-cyclopentyl-6-fluoro-1H-indol-2-yl)-N-[(1S)-1-cyclopropylethyl]pyrimidine-5-sulfonamide | N/A | 454.3 |
| 498 | 2-[3-cyano-1-(cyclopropylmethyl)-6-fluoro-1H-indol-2-yl]-N-[(1S)-1-cyclopropylethyl]pyrimidine-5-sulfonamide | 198-199 | 440.2 |
| 499 | 2-(3-cyano-1-cyclohexyl-6-fluoro-1H-indol-2-yl)-N-[(1S)-1-cyclopropylethyl]pyrimidine-5-sulfonamide | 169-170 | 468.3 |
| 500 | 6-(3-cyano-1-cyclobutyl-5-methoxy-1H-indol-2-yl)-N-[(2R)-1,1,1-trifluoropropan-2-yl]pyridine-3-sulfonamide | 181-186 | 479.3 |
| 505 | 6-(6-chloro-3-cyano-1-cyclobutyl-5-methyl-1H-indol-2-yl)-N-(1,3-difluoropropan-2-yl)pyridine-3-sulfonamide | 195-196 | 479.2 |
| 506 | 6-(6-chloro-3-cyano-1-cyclobutyl-5-methyl-1H-indol-2-yl)-N-[(2S)-1,1,1-trifluoropropan-2-yl]pyridine-3-sulfonamide | 198-198.5 | 479.2 |
| 507 | 2-(6-chloro-3-cyano-1-cyclobutyl-5-methyl-1H-indol-2-yl)-N-(propan-2-yl)pyrimidine-5-sulfonamide | 217-218 | 444.1 |

-continued

| Cpd | Name | m.p. | MS |
|---|---|---|---|
| 510 | 6-(6-chloro-3-cyano-1-cyclobutyl-5-methyl-1H-indol-2-yl)-N-[(2R)-1,1,1-trifluoropropan-2-yl]pyridine-3-sulfonamide | 200-200.5 | 497.2 |
| 511 | 6-(1-cyclobutyl-6-methyl-1H-indol-2-yl)-N-(1,3-difluoropropan-2-yl)pyridine-3-sulfonamide | 137-139 | 420.2 |
| 513 | 6-(3-cyano-1-cyclohexyl-6-methyl-1H-indol-2-yl)-N-(1,3-difluoropropan-2-yl)pyridine-3-sulfonamide | 195-203 | 473.3 |
| 514 | 6-(6-chloro-3-cyano-1-cyclohexyl-1H-indol-2-yl)-N-[(2R)-1,1,1-trifluoropropan-2-yl]pyridine-3-sulfonamide | 218-223 | 511.2 |
| 515 | 6-(6-chloro-3-cyano-1-cyclohexyl-1H-indol-2-yl)-N-[(2S)-1,1,1-trifluoropropan-2-yl]pyridine-3-sulfonamide | 217-224 | 511.2 |
| 516 | 2-(6-chloro-3-cyano-1-cyclohexyl-1H-indol-2-yl)-N-[(2S)-1,1,1-trifluoropropan-2-yl]pyrimidine-5-sulfonamide | 215-220 | 512.2 |
| 517 | 2-(6-chloro-3-cyano-1-cyclohexyl-1H-indol-2-yl)-N-(1,3-difluoropropan-2-yl)pyrimidine-5-sulfonamide | 228-234 | 494.2 |
| 518 | 6-(3-cyano-1-cyclohexyl-6-methoxy-1H-indol-2-yl)-N-[(2R)-1,1,1-trifluoropropan-2-yl]-pyridine-3-sulfonamide | 198-204 | 507.2 |
| 519 | 6-(3-cyano-1-cyclohexyl-6-methoxy-1H-indol-2-yl)-N-[(2S)-1,1,1-trifluoropropan-2-yl]pyridine-3-sulfonamide | 197-204 | 507.2 |
| 520 | 2-(3-cyano-1-cyclohexyl-6-methoxy-1H-indol-2-yl)-N-(1,3-difluoropropan-2-yl)pyrimidine-5-sulfonamide | 209-215 | 490.2 |
| 521 | 6-(6-chloro-3-cyano-1-cyclopentyl-5-methyl-1H-indol-2-yl)-N-(1,3-difluoropropan-2-yl)pyridine-3-sulfonamide | 217.5-218 | 493.3 |
| 522 | 6-(6-chloro-3-cyano-1-cyclopentyl-5-methyl-1H-indol-2-yl)-N-[(2S)-1,1,1-trifluoropropan-2-yl]pyridine-3-sulfonamide | 186-187 | 511.0 |
| 523 | 2-(6-chloro-3-cyano-1-cyclopentyl-5-methyl-1H-indol-2-yl)-N-(propan-2-yl)pyrimidine-5-sulfonamide | 216.0-216.5 | 458.2 |
| 524 | 2-[3-cyano-1-(cyclopropylmethyl)-5-methyl-1H-indol-2-yl]-N-(1,3-difluoropropan-2-yl)pyrimidine-5-sulfonamide | 151-155 | 446.4 |
| 525 | 6-[3-cyano-1-(cyclopropylmethyl)-5-methyl-1H-indol-2-yl]-N-[(1S)-1-cyclopropylethyl]pyridine-3-sulfonamide | 181-185 | 435.3 |
| 526 | 2-(3-cyano-1-cyclohexyl-5-fluoro-1H-indol-2-yl)-N-(propan-2-yl)pyrimidine-5-sulfonamide | 223-225 | 442.4 |
| 527 | 2-(3-cyano-1-cyclohexyl-5-fluoro-1H-indol-2-yl)-N-(1,3-difluoropropan-2-yl)pyrimidine-5-sulfonamide | 250-253 | 478.2 |
| 528 | 2-(3-cyano-1-cyclohexyl-5-fluoro-1H-indol-2-yl)-N-[(1S)-1-cyclopropylethyl]pyrimidine-5-sulfonamide | 219-221 | 468.3 |
| 529 | 2-[3-cyano-5-fluoro-1-(propan-2-yl)-1H-indol-2-yl]-N-[(1S)-1-cyclopropylethyl]pyrimidine-5-sulfonamide | 176-179 | 428.3 |
| 530 | 2-(3-cyano-1-cyclopentyl-5-fluoro-1H-indol-2-yl)-N-[(1S)-1-cyclopropylethyl]pyrimidine-5-sulfonamide | 184-186 | 454.2 |
| 531 | 2-[3-cyano-1-(cyclopropylmethyl)-5-fluoro-1H-indol-2-yl]-N-[(1S)-1-cyclopropylethyl]pyrimidine-5-sulfonamide | 184-188 | 440.2 |
| 535 | 6-[3-cyano-1-cyclopentyl-5-(difluoromethyl)-1H-indol-2-yl]-N-(1,3-difluoropropan-2-yl)pyridine-3-sulfonamide | N/A | 495.3 |
| 536 | 2-[3-cyano-1-cyclopentyl-5-(difluoromethyl)-1H-indol-2-yl]-N-(1,3-difluoropropan-2-yl)pyrimidine-5-sulfonamide | 176-177 | 496.3 |
| 537 | 6-[3-cyano-1-cyclopentyl-5-(difluoromethyl)-1H-indol-2-yl]-N-[(2S)-1,1,1-trifluoropropan-2-yl]pyridine-3-sulfonamide | 187-188 | 513.2 |
| 538 | 6-[3-cyano-1-cyclopentyl-5-(difluoromethyl)-1H-indol-2-yl]-N-[(2R)-1,1,1-trifluoropropan-2-yl]pyridine-3-sulfonamide | 186-188 | 513.3 |
| 544 | 2-(3-cyano-1-cyclobutyl-5-fluoro-1H-indol-2-yl)-N-[(1S)-1-cyclopropylethyl]pyrimidine-5-sulfonamide | 178-181 | 440.3 |
| 545 | 2-(3-cyano-1-cyclobutyl-5-methyl-1H-indol-2-yl)-N-[(1S)-1-cyclopropylethyl]pyrimidine-5-sulfonamide | 168-171 | 436.3 |
| 546 | 2-[3-cyano-5-fluoro-1-(propan-2-yl)-1H-indol-2-yl]-N-[(2S)-1,1,1-trifluoropropan-2-yl]pyrimidine-5-sulfonamide | 172-176 | 456.3 |
| 547 | 2-(3-cyano-1-cyclopentyl-5-fluoro-1H-indol-2-yl)-N-[(2S)-1,1,1-trifluoropropan-2-yl]pyrimidine-5-sulfonamide | 214-218 | 482.2 |
| 548 | 2-[3-cyano-1-(cyclopropylmethyl)-5-fluoro-1H-indol-2-yl]-N-[(2S)-1,1,1-trifluoropropan-2-yl]pyrimidine-5-sulfonamide | 175-180 | 468.3 |
| 550 | 6-(3-cyano-1-cyclobutyl-5-methoxy-1H-indol-2-yl)-N-(1,3-difluoropropan-2-yl)pyridine-3-sulfonamide | 149-150 | 461.2 |
| 551 | 2-(3-cyano-1-cyclobutyl-5-methoxy-1H-indol-2-yl)-N-(1,3-difluoropropan-2-yl)pyrimidine-5-sulfonamide | 217-219 | 462.3 |
| 560 | 6-(3-cyano-1-cyclohexyl-5-methyl-1H-indol-2-yl)-N-[(2S)-1,1,1-trifluoropropan-2-yl]pyridine-3-sulfonamide | 175-180 | 491.2 |
| 561 | 2-[3-cyano-1-(cyclopropylmethyl)-5-methyl-1H-indol-2-yl]-N-[(1S)-1-cyclopropylethyl]pyrimidine-5-sulfonamide | 174-178 | 436.3 |
| 562 | 2-(3-cyano-1-cyclopentyl-5-methyl-1H-indol-2-yl)-N-[(1S)-1-cyclopropylethyl]pyrimidine-5-sulfonamide | 168-171 | 450.3 |
| 563 | 2-[3-cyano-5-methyl-1-(propan-2-yl)-1H-indol-2-yl]-N-[(1S)-1-cyclopropylethyl]pyrimidine-5-sulfonamide | 171-174 | 424.2 |

-continued

| Cpd | Name | m.p. | MS |
|---|---|---|---|
| 564 | 6-[3-cyano-5-methyl-1-(propan-2-yl)-1H-indol-2-yl]-N-[(1S)-1-cyclopropylethyl]pyridine-3-sulfonamide | 170-173 | 423.2 |
| 565 | 2-[3-cyano-5-methyl-1-(propan-2-yl)-1H-indol-2-yl]-N-(propan-2-yl)pyrimidine-5-sulfonamide | 175-177 | 398.4 |
| 566 | 2-[3-cyano-5-methyl-1-(propan-2-yl)-1H-indol-2-yl]-N-[(2S)-1,1,1-trifluoropropan-2-yl]pyrimidine-5-sulfonamide | 195-198 | 452.4 |
| 567 | 2-[3-cyano-5-methyl-1-(propan-2-yl)-1H-indol-2-yl]-N-(1,3-difluoropropan-2-yl)pyrimidine-5-sulfonamide | 160-163 | 434.3 |
| 569 | 2-(3-cyano-1-cyclobutyl-5-methoxy-1H-indol-2-yl)-N-[(2S)-1,1,1-trifluoropropan-2-yl]pyrimidine-5-sulfonamide | 203-205 | 480.3 |
| 570 | 2-(3-cyano-1-cyclobutyl-5-methoxy-1H-indol-2-yl)-N-[(1S)-1-cyclopropylethyl]pyrimidine-5-sulfonamide | 182-183 | 452.3 |
| 571 | 6-(3-cyano-1-cyclopentyl-5-methoxy-1H-indol-2-yl)-N-(1,3-difluoropropan-2-yl)pyridine-3-sulfonamide | 167-169 | 475.5 |
| 572 | 2-(3-cyano-1-cyclopentyl-5-methoxy-1H-indol-2-yl)-N-(1,3-difluoropropan-2-yl)pyrimidine-5-sulfonamide | 200-202 | 476.2 |
| 590 | 6-[3-cyano-1-cyclobutyl-6-(2,2-difluoroethyl)-1H-indol-2-yl]-N-[(1S)-1-cyclopropylethyl]pyridine-3-sulfonamide | 146-155 | 485.1 |
| 591 | 2-[3-cyano-1-cyclobutyl-6-(2,2-difluoroethyl)-1H-indol-2-yl]-N-(1,3-difluoropropan-2-yl)pyrimidine-5-sulfonamide | N/A | 496.1 |
| 592 | 2-[3-cyano-1-cyclobutyl-6-(2,2-difluoroethyl)-1H-indol-2-yl]-N-[(1S)-1-cyclopropylethyl]pyrimidine-5-sulfonamide | 168-175 | 486.1 |
| 593 | 6-[3-cyano-1-cyclopentyl-6-(2,2-difluoroethyl)-1H-indol-2-yl]-N-(1,3-difluoropropan-2-yl)pyridine-3-sulfonamide | 178-184 | 509.1 |
| 594 | 6-[3-cyano-1-cyclopentyl-6-(2,2-difluoroethyl)-1H-indol-2-yl]-N-[(1S)-1-cyclopropylethyl]pyridine-3-sulfonamide | N/A | 499.1 |
| 595 | 6-[3-cyano-1-cyclopentyl-6-(2,2-difluoroethyl)-1H-indol-2-yl]-N-[(2S)-1,1,1-trifluoropropan-2-yl]pyridine-3-sulfonamide | 181-189 | 527.1 |
| 596 | 6-[3-cyano-1-cyclopentyl-6-(2,2-difluoroethyl)-1H-indol-2-yl]-N-(1,1,1-trifluoro-2-methylpropan-2-yl)pyridine-3-sulfonamide | 194-199 | 541.1 |
| 597 | 2-[3-cyano-1-cyclopentyl-6-(2,2-difluoroethyl)-1H-indol-2-yl]-N-[(1S)-1-cyclopropylethyl]pyrimidine-5-sulfonamide | 181-189 | 500.2 |
| 598 | 2-[3-cyano-1-cyclopentyl-6-(2,2-difluoroethyl)-1H-indol-2-yl]-N-(propan-2-yl)pyrimidine-5-sulfonamide | 204-218 | 474.1 |
| 599 | 2-[3-cyano-1-cyclopentyl-6-(2,2-difluoroethyl)-1H-indol-2-yl]-N-(1,3-difluoropropan-2-yl)pyrimidine-5-sulfonamide | 174-210 | 510.1 |
| 600 | 2-[3-cyano-1-cyclopentyl-6-(2,2-difluoroethyl)-1H-indol-2-yl]-N-[(2S)-1,1,1-trifluoropropan-2-yl]pyrimidine-5-sulfonamide | 240-246 | 528.1 |
| 603 | 2-(3-cyano-1-cyclopentyl-5-fluoro-1H-indol-2-yl)-N-(propan-2-yl)pyrimidine-5-sulfonamide | 217-222 | 428.3 |
| 604 | 6-[3-cyano-5-fluoro-1-(propan-2-yl)-1H-indol-2-yl]-N-[(1S)-1-cyclopropylethyl]pyridine-3-sulfonamide | 138-143 | 427.3 |
| 605 | 2-(3-cyano-1-cyclohexyl-6-methyl-1H-indol-2-yl)-N-[(2S)-1,1,1-trifluoropropan-2-yl]pyrimidine-5-sulfonamide | 257-260 | 492.3 |
| 606 | 6-(3-cyano-1-cyclohexyl-5-methyl-1H-indol-2-yl)-N-[(1S)-1-cyclopropylethyl]pyridine-3-sulfonamide | 169-174 | 463.2 |
| 607 | 6-(3-cyano-1-cyclopentyl-5-methyl-1H-indol-2-yl)-N-(1,1,1-trifluoro-2-methylpropan-2-yl)pyridine-3-sulfonamide | 176-181 | 491.3 |
| 616 | 6-[3-cyano-1-(cyclopropylmethyl)-6-(2,2-difluoroethyl)-1H-indol-2-yl]-N-(1,3-difluoropropan-2-yl)pyridine-3-sulfonamide | N/A | 495.2 |
| 617 | 6-[3-cyano-1-(cyclopropylmethyl)-6-(2,2-difluoroethyl)-1H-indol-2-yl]-N-[(1S)-1-cyclopropylethyl]pyridine-3-sulfonamide | N/A | 485.2 |
| 618 | 6-[3-cyano-1-(cyclopropylmethyl)-6-(2,2-difluoroethyl)-1H-indol-2-yl]-N-[(2S)-1,1,1-trifluoropropan-2-yl]pyridine-3-sulfonamide | N/A | 513.1 |
| 619 | 2-[3-cyano-1-(cyclopropylmethyl)-6-(2,2-difluoroethyl)-1H-indol-2-yl]-N-[(1S)-1-cyclopropylethyl]pyrimidine-5-sulfonamide | 144-150 | 486.2 |
| 620 | 2-[3-cyano-1-(cyclopropylmethyl)-6-(2,2-difluoroethyl)-1H-indol-2-yl]-N-(propan-2-yl)pyrimidine-5-sulfonamide | 152-161 | 485.1 |
| 621 | 2-[3-cyano-1-(cyclopropylmethyl)-6-(2,2-difluoroethyl)-1H-indol-2-yl]-N-(1,3-difluoropropan-2-yl)pyrimidine-5-sulfonamide | 180-188 | 496.2 |
| 622 | 2-[3-cyano-1-(cyclopropylmethyl)-6-(2,2-difluoroethyl)-1H-indol-2-yl]-N-[(2S)-1,1,1-trifluoropropan-2-yl]pyrimidine-5-sulfonamide | 195-205 | 514.2 |
| 696 | 6-[3-cyano-1-cyclobutyl-5-(2,2-difluoroethyl)-1H-indol-2-yl]-N-(1-methylcyclopropyl)pyridine-3-sulfonamide | N/A | 471.2 |

| Cpd | Name | m.p. | MS |
|---|---|---|---|
| 702 | 6-[3-cyano-1-cyclobutyl-5-(2,2-difluoroethyl)-1H-indol-2-yl]-N-[(2S)-1,1,1-trifluoropropan-2-yl]pyridine-3-sulfonamide | 143-147 | 513.3 |

Example 2

6-[3-cyano-1-cyclobutyl-6-(difluoromethoxy)-1H-indol-2-yl]-N-(1,3-difluoropropan-2-yl)pyridine-3-sulfonamide (Cpd 31)

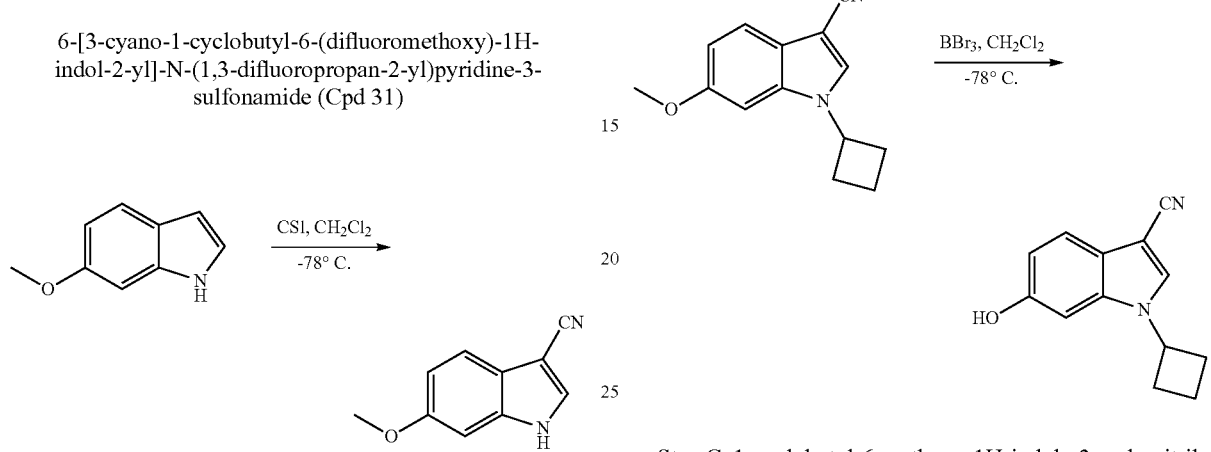

Step A: A solution of 6-methoxy-1H-indole (100.0 g, 679.0 mmol) in DMF (560 mL) was cooled to −78° C. and treated with chlorosulfonyl isocyanate (71 mL, 815 mmol). After the addition the reaction mixture was stirred for 1 hour. The dark solution was poured into ice water (2 L) and the light brown solid was collected by filtration, washed with additional water and dried to afford 6-methoxy-1H-indole-3-carbonitrile as a light brown solid (104.8 g, 90%).

Step C: 1-cyclobutyl-6-methoxy-1H-indole-3-carbonitrile (100 g, 442 mmol) was dissolved in $CH_2Cl_2$ (700 mL) and cooled to −20° C. Boron tribromide (300 g, 1.2 mol) was added dropwise over 2.5 hours to the cooled solution. The reaction was poured into ice water (2 L), neutralized to pH 7 with 5 N aq. sodium hydroxide and stirred overnight at room temperature. The remaining organic solvent was evaporated and the resulting suspension was filtered. The solid was washed with water (2×200 mL), 1/1 hexane/ethyl ether (2×125 mL) and dried in a stream of nitrogen to give 1-cyclobutyl-6-hydroxy-1H-indole-3-carbonitrile as a beige powder (90.0 g, 96%).

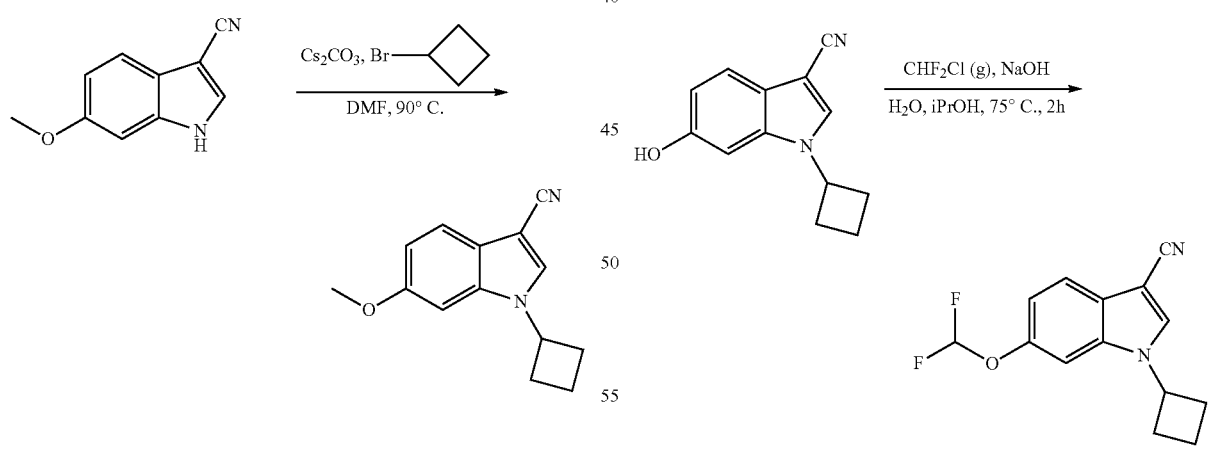

Step B: To 6-methoxy-1H-indole-3-carbonitrile (98.2 g, 0.57 mol) was added cesium carbonate (430 g, 1.32 mol), DMF (165 mL) and cyclobutylbromide (96%, 67.5 mL, 0.69 mol). The mixture was heated to 90° C. and stirred overnight. The mixture was cooled to 37° C. and poured into ice water (500 mL), washing in with water. After stirring for 1 hour the precipitate was collected on a filter and dried under a stream of nitrogen to give 1-cyclobutyl-6-methoxy-1H-indole-3-carbonitrile as a tan solid (124.1 g, 96%).

Step D: 1-cyclobutyl-6-hydroxy-1H-indole-3-carbonitrile (31.7 g, 149.5 mmol) was dissolved in 160 mL of isopropanol at 75° C. and $CClF_2H$ (gas) was bubbled into the reaction mixture via a needle. To this mixture was added 20% aq. NaOH (40 mL) via an addition funnel. Three additional portions of 20% aq. NaOH (40 mL) were added every 30 minute. After 2 hours of total reaction time the mixture was cooled to room temperature and the organic layer was separated and concentrated. The aqueous layer was extracted into ethyl acetate and the combined organic phases were washed with brine and then dried over MgSO$_4$, filtered and concentrated. The residue was dissolved in 4/1 hexane/CH$_2$Cl$_2$ (800 mL) and stirred with basic alumina (80 g, pH 9.5), and then filtered and concentrated to yield a first crude fraction (28 g). The alumina was washed with CH$_2$Cl$_2$ to provide a second crude fraction (8.7 g) which was purified in the same manner to provide a third crude fraction (4.0 g). The combined crude fractions were again purified in the same manner to yield 1-cyclobutyl-6-(difluoromethoxy)-1H-indole-3-carbonitrile as a white solid (28.3 g, 72%). $^1$H NMR (CDCl$_3$, 500 MHz): δ 7.76 (1H, s), 7.72 (1H, d, J=8.5 Hz), 7.18 (1H, d, J=2 Hz), 7.12 (1H, dd, J=8.5 Hz, 2.0 Hz), 6.55 (1H, t, J=75 Hz), 4.82 (1H, p, J=8 Hz), 2.66 (2H, m), 2.47 (2H, m), 2.01 (2H, m).

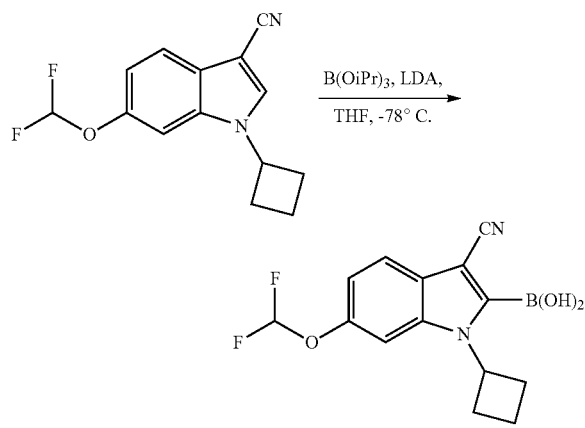

Step E: Into a solution of 1-cyclobutyl-6-(difluoromethoxy)-1H-indole-3-carbonitrile (1.5 g, 5.7 mmol) and triisopropyl borate (2.4 mL, 10.3 mmol) in THF (25 mL) at −78° C. was added LDA (1.5 M in cyclohexane, 5.0 mL, 7.5 mmol). The mixture was stirred at −78° C. for 30 min and then quenched with ice water (60 mL) and stirred for 15 min without cooling. The mixture was extracted with ethyl acetate 1:1 in hexane (20 mL). The aqueous layer was acidified with 2 N aq. HCl to pH 5 and extracted with CH$_2$Cl$_2$ (60 mL). The organic layer was dried over Na$_2$SO$_4$ and concentrated to give 3-cyano-1-cyclobutyl-6-(difluoromethoxy)-1H-indol-2-ylboronic acid as a solid (1.8 g, 60% pure by LCMS) that was used in the next step without further purification.

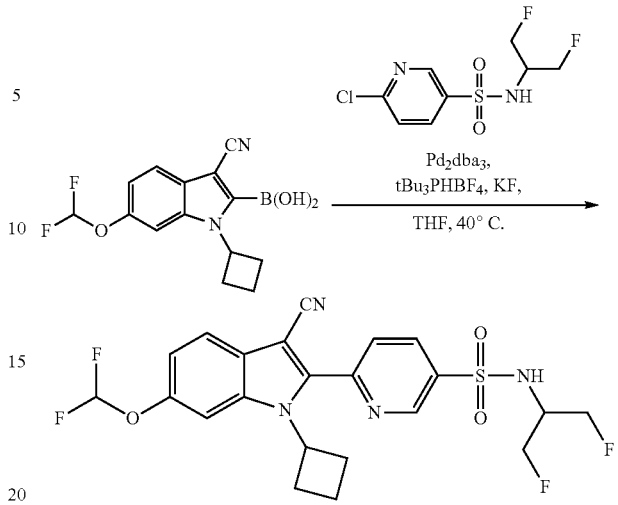

Step F: A mixture of 3-cyano-1-cyclobutyl-6-(difluoromethoxy)-1H-indol-2-ylboronic acid (0.68 g, 1.33 mmol), 6-chloro-N-(1,3-difluoropropan-2-yl)pyridine-3-sulfonamide (0.25 g, 0.93 mmol), tri-tert-butylphosphonium tetrafluoroborate (22 mg, 0.076 mmol) and Pd$_2$(dba)$_3$ (34 mg, 0.037 mmol) and potassium fluoride (0.17 g, 2.93 mmol) in THF (8.0 mL) was stirred at 35° C. overnight. The solvent was then evaporated and the residue was purified by flash chromatography with 0-10% ethyl acetate in CH$_2$Cl$_2$ to provide the title Compound 31 as a solid (210 mg, 46%). Melting point: 159-161; MS m/z 497.0 M+H$^+$; $^1$H NMR (500 MHz, CDCl$_3$): δ 9.25 (1H, dd, J=2.2 Hz, J=0.6 Hz), 8.37 (1H, dd, J=8.2 Hz, J=2.3 Hz), 8.03 (1H, dd, J=8.3 Hz, J=0.8 Hz), 7.80 (1H, d, J=8.7 Hz), 7.50 (1H, d, J=1.9 Hz), 7.18 (1H, dd, J=8.6 Hz, J=1.9 Hz), 6.60 (1H, t, J=3.7 Hz), 5.37-5.33 (1H, m), 5.20 (1H, d, J=9.2 Hz), 4.64-4.46 (4H, m), 3.96-3.90 (1H, m), 2.62-2.55 (2H, m), 2.46-2.40 (2H, m), 1.95-1.88 (2H, m).

Additional compounds representative of the present invention may be prepared according to the procedure of Example 2 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
|---|---|---|---|
| 1 | 6-[3-cyano-6-(difluoromethoxy)-1-(propan-2-yl)-1H-indol-2-yl]-N-(propan-2-yl)pyridine-3-sulfonamide | 157-159 | 449.1 |
| 2 | 6-[3-cyano-6-(difluoromethoxy)-1-(propan-2-yl)-1H-indol-2-yl]-N-cyclobutylpyridine-3-sulfonamide | 130-132 | 461.4 |
| 3 | 6-[3-cyano-6-(difluoromethoxy)-1-propyl-1H-indol-2-yl]-N-(propan-2-yl)pyridine-3-sulfonamide | 166-170 | 449.3 |
| 4 | 5-[3-cyano-1-cyclobutyl-6-(cyclobutyloxy)-1H-indol-2-yl]-N-(propan-2-yl)pyridine-2-sulfonamide | 178-180 | 465.3 |
| 10 | 6-[3-cyano-1-cyclobutyl-6-(trifluoromethoxy)-1H-indol-2-yl]-N-(propan-2-yl)pyridine-3-sulfonamide | 191-193 | 479.1 |
| 11 | 6-[3-cyano-1-(cyclopropylmethyl)-6-(trifluoromethoxy)-1H-indol-2-yl]-N-(propan-2-yl)pyridine-3-sulfonamide | 203-205 | 479.3 |
| 12 | 6-[3-cyano-1-(propan-2-yl)-6-(trifluoromethoxy)-1H-indol-2-yl]-N-(propan-2-yl)pyridine-3-sulfonamide | 160-162 | 467.3 |
| 13 | 6-[3-cyano-1-(cyclopropylmethyl)-6-(difluoromethoxy)-1H-indol-2-yl]-N-(propan-2-yl)pyridine-3-sulfonamide | 154-156 | 461.3 |
| 16 | 6-[3-cyano-1-cyclobutyl-6-(propan-2-ylsulfanyl)-1H-indol-2-yl]-N-(propan-2-yl)pyridine-3-sulfonamide | 129-131 | 469.2 |

-continued

| Cpd | Name | m.p. | MS |
|---|---|---|---|
| 17 | 6-[3-cyano-1-cyclopentyl-6-(trifluoromethoxy)-1H-indol-2-yl]-N-(propan-2-yl)pyridine-3-sulfonamide | N/A | 493.1 |
| 18 | N-tert-butyl-6-[3-cyano-1-cyclopentyl-6-(trifluoromethoxy)-1H-indol-2-yl]pyridine-3-sulfonamide | 182-184 | 507.1 |
| 19 | 6-[3-cyano-1-cyclobutyl-5-(difluoromethoxy)-1H-indol-2-yl]-N-(propan-2-yl)pyridine-3-sulfonamide | 148-153 | 461.3 |
| 20 | N-tert-butyl-6-[3-cyano-1-cyclobutyl-5-(difluoromethoxy)-1H-indol-2-yl]pyridine-3-sulfonamide | 167-170 | 475.3 |
| 21 | 6-[3-cyano-1-cyclopentyl-5-(difluoromethoxy)-1H-indol-2-yl]-N-(propan-2-yl)pyridine-3-sulfonamide | 177-179 | 475.2 |
| 22 | 1-cyclobutyl-2-[5-(piperidin-1-ylsulfonyl)pyridin-2-yl]-6-(propan-2-ylsulfanyl)-1H-indole-3-carbonitrile | 169-171 | 495.2 |
| 23 | 6-[3-cyano-1-cyclobutyl-5-(trifluoromethoxy)-1H-indol-2-yl]-N-(propan-2-yl)pyridine-3-sulfonamide | 174-176 | 479.3 |
| 24 | 6-[3-cyano-1-cyclobutyl-6-(trifluoromethoxy)-1H-indol-2-yl]-N-(1,3-difluoropropan-2-yl)pyridine-3-sulfonamide | 158-160 | 515.2 |
| 25 | 6-[3-cyano-1-cyclobutyl-5-(trifluoromethoxy)-1H-indol-2-yl]-N-(1,3-difluoropropan-2-yl)pyridine-3-sulfonamide | 179-182 | 515.3 |
| 26 | 5-[3-cyano-1-cyclobutyl-6-(trifluoromethoxy)-1H-indol-2-yl]-N-(propan-2-yl)pyridine-2-sulfonamide | N/A | 479.2 |
| 32 | 6-[3-cyano-1-cyclobutyl-5-(difluoromethoxy)-1H-indol-2-yl]-N-(1,3-difluoropropan-2-yl)pyridine-3-sulfonamide | 166-172 | 497.1 |
| 33 | 6-[3-cyano-1-cyclopentyl-5-(difluoromethoxy)-1H-indol-2-yl]-N-(1,3-difluoropropan-2-yl)pyridine-3-sulfonamide | 172-175 | 511.1 |
| 34 | 6-[3-cyano-1-cyclopentyl-5-(trifluoromethoxy)-1H-indol-2-yl]-N-(1,3-difluoropropan-2-yl)pyridine-3-sulfonamide | 159-160 | 529.3 |
| 36 | 6-[3-cyano-6-(difluoromethoxy)-1-(propan-2-yl)-1H-indol-2-yl]-N-(1,3-difluoropropan-2-yl)pyridine-3-sulfonamide | 142-145 | 485.1 |
| 39 | 5-[3-cyano-1-cyclopropyl-6-(difluoromethoxy)-1H-indol-2-yl]-N-(propan-2-yl)pyridine-2-sulfonamide | 209-210 | 447.7 |
| 40 | 5-[3-cyano-1-(cyclopropylmethyl)-6-(difluoromethoxy)-1H-indol-2-yl]-N-(propan-2-yl)pyridine-2-sulfonamide | 186-188 | 461.2 |
| 41 | 6-[3-cyano-1-(cyclopropylmethyl)-6-(difluoromethoxy)-1H-indol-2-yl]-N-(1,3-difluoropropan-2-yl)pyridine-3-sulfonamide | 150-151 | 497.2 |
| 42 | 6-[3-cyano-1-cyclopropyl-6-(difluoromethoxy)-1H-indol-2-yl]-N-(1,3-difluoropropan-2-yl)pyridine-3-sulfonamide | 219-220 | 483.0 |
| 43 | 6-[3-cyano-1-cyclobutyl-6-(propan-2-yl)-1H-indol-2-yl]-N-(1,3-difluoropropan-2-yl)pyridine-3-sulfonamide | 135-140 | 473.3 |
| 44 | 6-(3-cyano-1-cyclopentyl-6-methyl-1H-indol-2-yl)-N-(1,3-difluoropropan-2-yl)pyridine-3-sulfonamide | 144-145 | 457.2 (M − H) |
| 45 | 6-[3-cyano-6-(difluoromethoxy)-1-propyl-1H-indol-2-yl]-N-(1,3-difluoropropan-2-yl)pyridine-3-sulfonamide | 156-158 | 485.2 |
| 48 | 6-(3-cyano-1-cyclobutyl-6-ethyl-1H-indol-2-yl)-N-(1,3-difluoropropan-2-yl)pyridine-3-sulfonamide | 201-202 | 459.0 |
| 49 | 6-[3-cyano-1-cyclopentyl-6-(difluoromethoxy)-1H-indol-2-yl]-N-(1,3-difluoropropan-2-yl)pyridine-3-sulfonamide | 177-178 | 511.3 |
| 51 | 6-[3-cyano-1-cyclobutyl-6-(difluoromethoxy)-1H-indol-2-yl]-N-(propan-2-yl)pyridine-3-sulfonamide | 158-159 | 461.1 |
| 52 | 6-[3-cyano-1-cyclopentyl-6-(difluoromethoxy)-1H-indol-2-yl]-N-(propan-2-yl)pyridine-3-sulfonamide | 157-158 | 475.2 |
| 53 | 6-[3-cyano-1-cyclopentyl-6-(difluoromethoxy)-1H-indol-2-yl]-N-(1,1,1-trifluoropropan-2-yl)pyridine-3-sulfonamide | 189-195 | 529.1 |
| 54 | 6-{3-cyano-6-methyl-1-[(3R)-tetrahydrofuran-3-yl]-1H-indol-2-yl}-N-(1,3-difluoropropan-2-yl)pyridine-3-sulfonamide | 152-153 | 461.2 |
| 55 | 6-{3-cyano-6-methyl-1-[(3R)-tetrahydrofuran-3-yl]-1H-indol-2-yl}-N-(propan-2-yl)pyridine-3-sulfonamide | 164-167 | 425.2 |
| 59 | 6-[3-cyano-1-cyclobutyl-6-(2,2-difluoroethoxy)-1H-indol-2-yl]-N-(propan-2-yl)pyridine-3-sulfonamide | 171-173 | 475.1 |
| 67 | 6-[3-cyano-1-cyclopentyl-6-(difluoromethoxy)-1H-indol-2-yl]-N-(1-fluoro-2-methylpropan-2-yl)pyridine-3-sulfonamide | 224-229 | 507.4 |
| 68 | 6-[3-cyano-1-(cyclopropylmethyl)-6-(trifluoromethoxy)-1H-indol-2-yl]-N-(1,3-difluoropropan-2-yl)pyridine-3-sulfonamide | 132-133 | 515.0 |
| 69 | 6-[3-cyano-1-(propan-2-yl)-6-(trifluoromethoxy)-1H-indol-2-yl]-N-(1,3-difluoropropan-2-yl)pyridine-3-sulfonamide | 116-117 | 503.3 |
| 70 | 6-[3-cyano-1-cyclopentyl-6-(trifluoromethoxy)-1H-indol-2-yl]-N-(1,3-difluoropropan-2-yl)pyridine-3-sulfonamide | 141-143 | 529.3 |
| 74 | 2-(3-cyano-1-cyclopentyl-6-methyl-1H-indol-2-yl)-N-(propan-2-yl)pyrimidine-5-sulfonamide | 213-214 | 424.4 |
| 75 | 6-[3-cyano-6-ethyl-1-(propan-2-yl)-1H-indol-2-yl]-N-(propan-2-yl)pyridine-3-sulfonamide | 185-186 | 411.0 |

-continued

| Cpd | Name | m.p. | MS |
|---|---|---|---|
| 77 | 6-[3-cyano-1-cyclobutyl-6-(difluoromethoxy)-1H-indol-2-yl]-N-(1-fluoro-2-methylpropan-2-yl)pyridine-3-sulfonamide | 171-178 | 493.4 |
| 78 | 6-[3-cyano-1-cyclobutyl-6-(difluoromethoxy)-1H-indol-2-yl]-N-(1,1,1-trifluoropropan-2-yl)pyridine-3-sulfonamide | 159-165 | 515.0 |
| 80 | 6-[3-cyano-6-methyl-1-(propan-2-yl)-1H-indol-2-yl]-N-(1,3-difluoropropan-2-yl)pyridine-3-sulfonamide | 188-195 | 433.0 |
| 81 | 6-[3-cyano-1-(cyclopropylmethyl)-6-methyl-1H-indol-2-yl]-N-(1,3-difluoropropan-2-yl)pyridine-3-sulfonamide | 175-182 | 445.0 |
| 82 | 6-(3-cyano-1-cyclobutyl-6-methyl-1H-indol-2-yl)-N-(1,3-difluoropropan-2-yl)pyridine-3-sulfonamide | N/A | 445.0 |
| 93 | 6-[3-cyano-1-cyclobutyl-6-(difluoromethoxy)-1H-indol-2-yl]-N-[1-(trifluoromethyl)cyclopropyl]pyridine-3-sulfonamide | 182-187 | 527.0 |
| 94 | 6-[3-cyano-1-cyclopentyl-6-(difluoromethoxy)-1H-indol-2-yl]-N-[1-(trifluoromethyl)cyclopropyl]pyridine-3-sulfonamide | 186-193 | 541.0 |
| 98 | 2-(3-cyano-1-cyclohexyl-6-methyl-1H-indol-2-yl)-N-(propan-2-yl)pyrimidine-5-sulfonamide | 196-201 | 438.0 |
| 99 | 6-[3-cyano-1-cyclohexyl-6-(difluoromethoxy)-1H-indol-2-yl]-N-(propan-2-yl)pyridine-3-sulfonamide | 187-190 | 489.0 |
| 100 | 6-[3-cyano-1-cyclohexyl-6-(difluoromethoxy)-1H-indol-2-yl]-N-(1,3-difluoropropan-2-yl)pyridine-3-sulfonamide | 175-178 | 525.0 |
| 103 | 6-[3-cyano-1-cyclobutyl-6-(2,2-difluoroethenyl)-1H-indol-2-yl]-N-(1,3-difluoropropan-2-yl)pyridine-3-sulfonamide | N/A | 492.9 |
| 105 | 6-[3-cyano-1-cyclohexyl-6-(trifluoromethoxy)-1H-indol-2-yl]-N-(1,3-difluoropropan-2-yl)pyridine-3-sulfonamide | 146-148 | 542.8 |
| 106 | 6-[3-cyano-1-cyclobutyl-6-(difluoromethoxy)-1H-indol-2-yl]-N-[1-(trifluoromethyl)cyclobutyl]pyridine-3-sulfonamide | 162-168 | 541.0 |
| 116 | 2-[3-cyano-1-cyclobutyl-6-(trifluoromethoxy)-1H-indol-2-yl]-N-(propan-2-yl)pyrimidine-5-sulfonamide | 200-203 | 480.7 |
| 117 | 2-[3-cyano-1-cyclopentyl-6-(trifluoromethoxy)-1H-indol-2-yl]-N-(propan-2-yl)pyrimidine-5-sulfonamide | 216-218 | 494.0 |
| 121 | 2-(3-cyano-1-cyclobutyl-5-methyl-1H-indol-2-yl)-N-(propan-2-yl)pyrimidine-5-sulfonamide | 134-138 | 410.2 |
| 122 | 2-(3-cyano-1-cyclobutyl-5-methyl-1H-indol-2-yl)-N-(1,3-difluoropropan-2-yl)pyrimidine-5-sulfonamide | 140-145 | 446.0 |
| 127 | 2-[3-cyano-1-cyclobutyl-6-(difluoromethoxy)-1H-indol-2-yl]-N-(propan-2-yl)pyrimidine-5-sulfonamide | 192-194 | 462.0 |
| 128 | 2-[3-cyano-1-cyclobutyl-6-(difluoromethoxy)-1H-indol-2-yl]-N-(1,1,1-trifluoropropan-2-yl)pyrimidine-5-sulfonamide | 227-229 | 515.9 |
| 129 | 2-[3-cyano-1-cyclobutyl-6-(difluoromethoxy)-1H-indol-2-yl]-N-(1,3-difluoropropan-2-yl)pyrimidine-5-sulfonamide | 205-207 | 497.9 |
| 132 | 2-(3-cyano-1-cyclobutyl-6-methyl-1H-indol-2-yl)-N-(1,3-difluoropropan-2-yl)pyrimidine-5-sulfonamide | 236-238 | 446.0 |
| 133 | 2-[3-cyano-1-(cyclopropylmethyl)-6-methyl-1H-indol-2-yl]-N-(1,3-difluoropropan-2-yl)pyrimidine-5-sulfonamide | 261-262 | 446.0 |
| 134 | 2-[3-cyano-6-methyl-1-(propan-2-yl)-1H-indol-2-yl]-N-(1,3-difluoropropan-2-yl)pyrimidine-5-sulfonamide | 213-215 | 433.9 |
| 135 | 2-(3-cyano-1-cyclopentyl-6-methyl-1H-indol-2-yl)-N-(1,3-difluoropropan-2-yl)pyrimidine-5-sulfonamide | 229-231 | 460.0 |
| 136 | 2-[3-cyano-1-(cyclopropylmethyl)-6-(difluoromethoxy)-1H-indol-2-yl]-N-(1,3-difluoropropan-2-yl)pyrimidine-5-sulfonamide | 207-209 | 497.9 |
| 137 | 2-[3-cyano-6-(difluoromethoxy)-1-(propan-2-yl)-1H-indol-2-yl]-N-(1,3-difluoropropan-2-yl)pyrimidine-5-sulfonamide | 219-221 | 485.9 |
| 158 | 6-(3-cyano-1-cyclopentyl-5-methyl-1H-indol-2-yl)-N-(1,3-difluoropropan-2-yl)pyridine-3-sulfonamide | 168-173 | 459.2 |
| 159 | 2-(3-cyano-1-cyclopentyl-5-methyl-1H-indol-2-yl)-N-(propan-2-yl)pyrimidine-5-sulfonamide | 193-198 | 424.2 |
| 160 | 2-(3-cyano-1-cyclopentyl-5-methyl-1H-indol-2-yl)-N-(1,3-difluoropropan-2-yl)pyrimidine-5-sulfonamide | 202-207 | 460.0 |
| 161 | 6-[3-cyano-1-cyclobutyl-6-(methylsulfanyl)-1H-indol-2-yl]-N-(1,3-difluoropropan-2-yl)pyridine-3-sulfonamide | 182-186 | 488.9 |
| 162 | 2-[3-cyano-1-cyclobutyl-6-(methylsulfanyl)-1H-indol-2-yl]-N-(1,3-difluoropropan-2-yl)pyrimidine-5-sulfonamide | 199-201 | 478.1 |
| 167 | 2-[3-cyano-6-methyl-1-(propan-2-yl)-1H-indol-2-yl]-N-(propan-2-yl)pyrimidine-5-sulfonamide | 205-206 | 398.1 |
| 168 | 2-[3-cyano-1-(cyclopropylmethyl)-6-methyl-1H-indol-2-yl]-N-(propan-2-yl)pyrimidine-5-sulfonamide | 245-247 | 410.1 |
| 169 | 2-(3-cyano-1-cyclobutyl-6-methyl-1H-indol-2-yl)-N-(propan-2-yl)pyrimidine-5-sulfonamide | 217-219 | 410.0 |
| 170 | 2-[3-cyano-1-(cyclopropylmethyl)-6-(difluoromethoxy)-1H-indol-2-yl]-N-(propan-2-yl)pyrimidine-5-sulfonamide | 182-184 | 462.0 |

| Cpd | Name | m.p. | MS |
|---|---|---|---|
| 171 | 2-[3-cyano-6-(difluoromethoxy)-1-(propan-2-yl)-1H-indol-2-yl]-N-(propan-2-yl)pyrimidine-5-sulfonamide | 193-196 | 450.1 |
| 172 | 2-(3-cyano-1-cyclobutyl-6-methoxy-1H-indol-2-yl)-N-(propan-2-yl)pyrimidine-5-sulfonamide | 200-202 | 426.0 |
| 177 | 2-[3-cyano-1-cyclobutyl-6-(trifluoromethoxy)-1H-indol-2-yl]-N-(1,3-difluoropropan-2-yl)pyrimidine-5-sulfonamide | 202-204 | 515.9 |
| 178 | 2-[3-cyano-1-cyclopentyl-6-(trifluoromethoxy)-1H-indol-2-yl]-N-(1,3-difluoropropan-2-yl)pyrimidine-5-sulfonamide | 181-187 | 529.9 |
| 179 | 2-[3-cyano-1-cyclohexyl-6-(difluoromethoxy)-1H-indol-2-yl]-N-(1,3-difluoropropan-2-yl)pyrimidine-5-sulfonamide | 174-176 | 526.0 |
| 185 | 2-[3-cyano-1-cyclobutyl-6-(propan-2-yl)-1H-indol-2-yl]-N-(propan-2-yl)pyrimidine-5-sulfonamide | 220-222 | 438.2 |
| 186 | 2-[3-cyano-1-cyclobutyl-6-(propan-2-yl)-1H-indol-2-yl]-N-(1,3-difluoropropan-2-yl)pyrimidine-5-sulfonamide | 214-222 | 474.2 |
| 190 | 6-(3-cyano-1-cyclopentyl-6-methyl-1H-indol-2-yl)-N-[1-(trifluoromethyl)cyclopropyl]pyridine-3-sulfonamide | 199-210 | 489.1 |
| 198 | 2-(3-cyano-1-cyclohexyl-5-methyl-1H-indol-2-yl)-N-(1,3-difluoropropan-2-yl)pyrimidine-5-sulfonamide | 211-215 | 474.1 |
| 199 | 6-(3-cyano-1-cyclohexyl-5-methyl-1H-indol-2-yl)-N-(1,3-difluoropropan-2-yl)pyridine-3-sulfonamide | 210-215 | 473.5 |
| 200 | 2-(3-cyano-1-cyclohexyl-5-methyl-1H-indol-2-yl)-N-(propan-2-yl)pyrimidine-5-sulfonamide | 183-188 | 438.1 |
| 229 | 6-(3-cyano-1-cyclobutyl-6-methoxy-1H-indol-2-yl)-N-(1,3-difluoropropan-2-yl)pyridine-3-sulfonamide | 174-177 | 461.2 |
| 230 | 2-(3-cyano-1-cyclobutyl-6-methoxy-1H-indol-2-yl)-N-(1,3-difluoropropan-2-yl)pyrimidine-5-sulfonamide | 217-219 | 462.1 |
| 231 | 2-(3-cyano-1-cyclopentyl-6-methoxy-1H-indol-2-yl)-N-(1,3-difluoropropan-2-yl)pyrimidine-5-sulfonamide | 232-234 | 476.1 |
| 232 | 2-[3-cyano-6-(difluoromethoxy)-1-propyl-1H-indol-2-yl]-N-(1,3-difluoropropan-2-yl)pyrimidine-5-sulfonamide | 177-179 | 486.0 |
| 233 | 2-[3-cyano-1-cyclopentyl-6-(difluoromethoxy)-1H-indol-2-yl]-N-(1,3-difluoropropan-2-yl)pyrimidine-5-sulfonamide | 199-201 | 512.0 |
| 239 | 6-[3-cyano-1-cyclobutyl-6-(difluoromethoxy)-1H-indol-2-yl]-N-(1,3-dihydroxypropan-2-yl)pyridine-3-sulfonamide | 132-135 | 493.1 |
| 241 | 2-(3-cyano-1-cyclohexyl-6-methyl-1H-indol-2-yl)-N-(1,3-difluoropropan-2-yl)pyrimidine-5-sulfonamide | 225-230 | 474.0 |
| 242 | 2-[3-cyano-5-(difluoromethoxy)-1-ethyl-1H-indol-2-yl]-N-(propan-2-yl)pyrimidine-5-sulfonamide | 180-185 | 436.2 |
| 245 | 6-(3-cyano-1-cyclobutyl-6-methyl-1H-indol-2-yl)-N-(3,3-difluorocyclobutyl)pyridine-3-sulfonamide | 165-166 | 457.1 |
| 246 | 6-(3-cyano-1-cyclopentyl-6-methoxy-1H-indol-2-yl)-N-(3,3-difluorocyclobutyl)pyridine-3-sulfonamide | N/A | 487.0 |
| 253 | 6-(3-cyano-1-cyclopentyl-6-methyl-1H-indol-2-yl)-N-[1-(trifluoromethyl)cyclobutyl]pyridine-3-sulfonamide | 214-218 | 503.1 |
| 255 | 6-[3-cyano-1-(cyclopropylmethyl)-6-methyl-1H-indol-2-yl]-N-[1-(trifluoromethyl)cyclopropyl]pyridine-3-sulfonamide | 191-195 | 475.0 |
| 256 | 6-(3-cyano-1-cyclobutyl-6-methyl-1H-indol-2-yl)-N-[1-(trifluoromethyl)cyclopropyl]pyridine-3-sulfonamide | 189-194 | 475.1 |
| 258 | 6-(3-cyano-1-cyclobutyl-5-ethyl-1H-indol-2-yl)-N-(1,3-difluoropropan-2-yl)pyridine-3-sulfonamide | 163-164 | 459.2 |
| 267 | 6-[3-cyano-1-cyclobutyl-6-(2,2-difluoroethyl)-1H-indol-2-yl]-N-(1,3-difluoropropan-2-yl)pyridine-3-sulfonamide | 166-168 | 495.0 |
| 268 | N-{5-[3-cyano-1-cyclobutyl-6-(pyrimidin-2-yloxy)-1H-indol-2-yl]pyridin-2-yl}-2-methylpropane-2-sulfonamide | 275-277 | 503.3 |
| 269 | N-{5-[3-cyano-1-(cyclopropylmethyl)-6-(difluoromethoxy)-1H-indol-2-yl]pyridin-2-yl}-2-methylpropane-2-sulfonamide | 214-215 | 475.3 |
| 270 | N-{6-[3-cyano-1-(cyclopropylmethyl)-6-(difluoromethoxy)-1H-indol-2-yl]pyridin-3-yl}cyclopropanesulfonamide | 156-158 | 459.3 |
| 271 | N-{6-[3-cyano-1-cyclobutyl-6-(pyrimidin-2-yloxy)-1H-indol-2-yl]pyridin-3-yl}propane-1-sulfonamide | 206-208 | 489.2 |
| 272 | N-(6-{3-cyano-6-[(3-cyanopyridin-2-yl)oxy]-1-cyclobutyl-1H-indol-2-yl}pyridin-3-yl)propane-1-sulfonamide | 199-201 | 513.3 |
| 273 | N-(6-{3-cyano-6-[(3-cyanopyrazin-2-yl)oxy]-1-cyclobutyl-1H-indol-2-yl}pyridin-3-yl)propane-1-sulfonamide | 252-254 | 514.2 |
| 274 | N-{6-[3-cyano-1-cyclobutyl-6-(propan-2-yloxy)-1H-indol-2-yl]pyridazin-3-yl}cyclopropanesulfonamide | 175-177 | 452.3 |
| 275 | N-{6-[3-cyano-1-cyclobutyl-6-(propan-2-yloxy)-1H-indol-2-yl]pyridazin-3-yl}methanesulfonamide | 225-227 | 426.3 |
| 276 | N-{6-[3-cyano-1-cyclobutyl-6-(propan-2-yloxy)-1H-indol-2-yl]pyridazin-3-yl}ethanesulfonamide | 181-183 | 440.4 |
| 277 | N-[6-(3-cyano-1-cyclobutyl-6-methoxy-1H-indol-2-yl)pyridazin-3-yl]ethanesulfonamide | 212-214 | 412.3 |

-continued

| Cpd | Name | m.p. | MS |
|---|---|---|---|
| 278 | N-[6-(3-cyano-1-cyclobutyl-6-methoxy-1H-indol-2-yl)pyridazin-3-yl]-2-methylpropane-2-sulfonamide | 218-220 | 440.3 |
| 279 | N-{6-[3-cyano-1-(cyclopropylmethyl)-6-(propan-2-yloxy)-1H-indol-2-yl]pyridin-3-yl}ethanesulfonamide | 149-154 | 439.9 |
| 280 | N-{6-[3-cyano-1-(cyclopropylmethyl)-6-(propan-2-yloxy)-1H-indol-2-yl]pyridin-3-yl}cyclopropanesulfonamide | 150-155 | 451.1 |
| 281 | N-{6-[3-cyano-1-(cyclopropylmethyl)-6-(propan-2-yloxy)-1H-indol-2-yl]pyridin-3-yl}propane-2-sulfonamide | 168-172 | 453.5 |
| 282 | N-{6-[3-cyano-1-ethyl-6-(propan-2-yloxy)-1H-indol-2-yl]pyridin-3-yl}-N-(propan-2-yl)ethanesulfonamide | 170-175 | 455.2 |
| 283 | N-{6-[3-cyano-1-(cyclopropylmethyl)-6-(2,2,2-trifluoroethoxy)-1H-indol-2-yl]pyridin-3-yl}propane-2-sulfonamide | 188-193 | 493.3 |
| 284 | N-{6-[3-cyano-1-(cyclopropylmethyl)-6-(2,2,2-trifluoroethoxy)-1H-indol-2-yl]pyridin-3-yl}ethanesulfonamide | 190-195 | 479.3 |
| 285 | N-{6-[3-cyano-1-ethyl-6-(propan-2-yloxy)-1H-indol-2-yl]pyridin-3-yl}cyclopropanesulfonamide | 180-185 | 425.3 |
| 286 | N-{6-[3-cyano-1-ethyl-6-(propan-2-yloxy)-1H-indol-2-yl]pyridin-3-yl}propane-2-sulfonamide | 180-185 | 427.2 |
| 290 | N-{5-[3-cyano-1-(cyclopropylmethyl)-6-(2,2,2-trifluoroethoxy)-1H-indol-2-yl]pyridin-2-yl}ethanesulfonamide | N/A | 479.3 |
| 291 | N-{5-[3-cyano-1-(cyclopropylmethyl)-6-(2,2,2-trifluoroethoxy)-1H-indol-2-yl]pyridin-2-yl}propane-2-sulfonamide | N/A | 493.3 |
| 292 | N-{5-[3-cyano-1-ethyl-6-(propan-2-yloxy)-1H-indol-2-yl]pyridin-2-yl}-N-(2,2-difluoroethyl)cyclopropanesulfonamide | 232-235 | 489.1 |
| 293 | N-{5-[3-cyano-1-ethyl-6-(propan-2-yloxy)-1H-indol-2-yl]pyridin-2-yl}-N-(2-hydroxyethyl)cyclopropanesulfonamide | 212-214 | 469.3 |
| 294 | N-{5-[3-cyano-1-ethyl-6-(propan-2-yloxy)-1H-indol-2-yl]pyridin-2-yl}-N-(cyanomethyl)cyclopropanesulfonamide | 236-238 | 464.1 |
| 295 | N-{5-[3-cyano-1-cyclobutyl-6-(difluoromethoxy)-1H-indol-2-yl]pyridin-2-yl}-2-methylpropane-2-sulfonamide | 239-240 | 475.3 |
| 296 | N-[6-(3-cyano-1-cyclopentyl-6-methyl-1H-indol-2-yl)pyridin-3-yl]cyclopropanesulfonamide | 241-245 | 421.2 |
| 297 | N-[6-(3-cyano-1-cyclobutyl-6-methyl-1H-indol-2-yl)pyridin-3-yl]cyclopropanesulfonamide | 200-205 | 407.1 |
| 299 | N-{5-[3-cyano-6-(difluoromethoxy)-1-(propan-2-yl)-1H-indol-2-yl]pyridin-2-yl}-2-methylpropane-2-sulfonamide | 263-264 | 462.5 |
| 301 | 6-[3-cyano-1-cyclobutyl-6-(difluoromethoxy)-1H-indol-2-yl]-N-(1-cyanoethyl)pyridine-3-sulfonamide | 188-190 | 472.1 |
| 304 | 6-[3-cyano-1-cyclohexyl-6-(trifluoromethoxy)-1H-indol-2-yl]-N-[(2R)-1,1,1-trifluoropropan-2-yl]pyridine-3-sulfonamide | 181-183 | 561.0 |
| 305 | 6-[3-cyano-1-cyclohexyl-6-(trifluoromethoxy)-1H-indol-2-yl]-N-[(1S)-1-cyclopropylethyl]pyridine-3-sulfonamide | 195-197 | 533.2 |
| 323 | 2-[3-cyano-1-cyclobutyl-6-(difluoromethoxy)-1H-indol-2-yl]-N-[(2S)-1,1,1-trifluoropropan-2-yl]pyrimidine-5-sulfonamide | 221-223 | 516.2 |
| 326 | 2-[3-cyano-1-cyclopentyl-6-(difluoromethoxy)-1H-indol-2-yl]-N-[(2S)-1,1,1-trifluoropropan-2-yl]pyrimidine-5-sulfonamide | 231-232 | 530.2 |
| 341 | 6-[3-cyano-1-cyclohexyl-6-(difluoromethoxy)-1H-indol-2-yl]-N-[(2S)-1,1,1-trifluoropropan-2-yl]pyridine-3-sulfonamide | 149-151 | 543.0 |
| 359 | 6-[3-cyano-6-(difluoromethoxy)-1-(propan-2-yl)-1H-indol-2-yl]-N-[(2S)-1,1,1-trifluoropropan-2-yl]pyridine-3-sulfonamide | 163-166 | 503.1 |
| 398 | 2-[3-cyano-1-(cyclopropylmethyl)-6-(difluoromethoxy)-1H-indol-2-yl]-N-[(2S)-1,1,1-trifluoropropan-2-yl]pyrimidine-5-sulfonamide | 211-212 | 516.2 |
| 399 | 2-[3-cyano-6-(difluoromethoxy)-1-(propan-2-yl)-1H-indol-2-yl]-N-[(2S)-1,1,1-trifluoropropan-2-yl]pyrimidine-5-sulfonamide | 219-221 | 504.3 |
| 400 | 2-[3-cyano-6-(difluoromethoxy)-1-propyl-1H-indol-2-yl]-N-[(2S)-1,1,1-trifluoropropan-2-yl]pyrimidine-5-sulfonamide | 207-208 | 504.2 |
| 471 | 2-[3-cyano-1-cyclohexyl-6-(difluoromethoxy)-1H-indol-2-yl]-N-[(1S)-1-cyclopropylethyl]pyrimidine-5-sulfonamide | 150-152 | 516.0 |
| 472 | 2-[3-cyano-1-cyclohexyl-6-(difluoromethoxy)-1H-indol-2-yl]-N-[(2S)-1,1,1-trifluoropropan-2-yl]pyrimidine-5-sulfonamide | 187-189 | 544.0 |

-continued

| Cpd | Name | m.p. | MS |
|---|---|---|---|
| 473 | 2-[3-cyano-1-cyclohexyl-6-(difluoromethoxy)-1H-indol-2-yl]-N-(propan-2-yl)pyrimidine-5-sulfonamide | 176-179 | 490.0 |
| 543 | N-tert-butyl-6-[3-cyano-1-cyclobutyl-6-(difluoromethoxy)-1H-indol-2-yl]pyridine-3-sulfonamide | 178-180 | 475.3 |

Example 3

6-(3-cyano-1-cyclobutyl-5-fluoro-6-methyl-1H-indol-2-yl)-N-(1,3-difluoropropan-2-yl)pyridine-3-sulfonamide (Cpd 108)

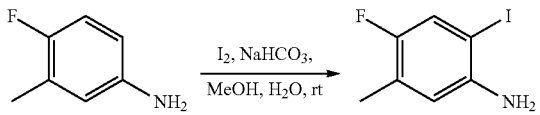

Step A: Into a solution of 4-fluoro-3-methylaniline (8.75 g, 70 mmol) in methanol (65 mL) and water (65 mL) was added sodium bicarbonate (5.88 g, 70 mmol) followed by portionwise addition of powdered $I_2$ (17.78 g, 70 mmol). The mixture was stirred at room temperature overnight then treated with water (300 mL). The aqueous mixture was extracted with $CH_2Cl_2$ (3×200 mL). The organics were combined and washed with sat. aq. sodium thiosulfate, water, and brine. The mixture was dried over $Na_2SO_4$ and concentrated. The residue was purified by flash chromatography with 30-100% $CH_2Cl_2$/hexane to give 4-fluoro-2-iodo-5-methylaniline (12.1 g, 69%), which contained ~10% of the undesired isomer (4-fluoro-2-iodo-3-methylaniline).

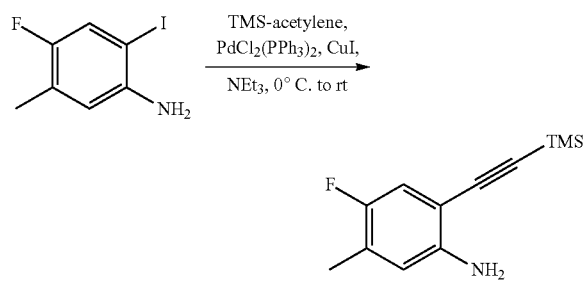

Step B: Into a mixture of 4-fluoro-2-iodo-5-methylaniline (12.0 g, 47.8 mmol, plus ca. 10% of the undesired isomer), $PdCl_2(PPh_3)_2$ (1.68 g, 2.39 mmol) and copper(I) iodide (0.455 g, 2.39 mmol) in triethylamine (125 mL) at 0° C. was added trimethylsilylacetylene (5.15 g, 52.6 mmol) dropwise. The mixture was warmed to room temperature and stirred overnight. The solvent was evaporated and the residue was dissolved in ethyl ether and filtered. The filtrate was evaporated and purified via flash chromatography with 5-35% ethyl acetate in hexane to give 4-fluoro-5-methyl-2-((trimethylsilyl)ethynyl)aniline (10.3 g, 97%), which contained ~10% of the undesired isomer (4-fluoro-3-methyl-2-((trimethylsilyl)ethynyl)aniline).

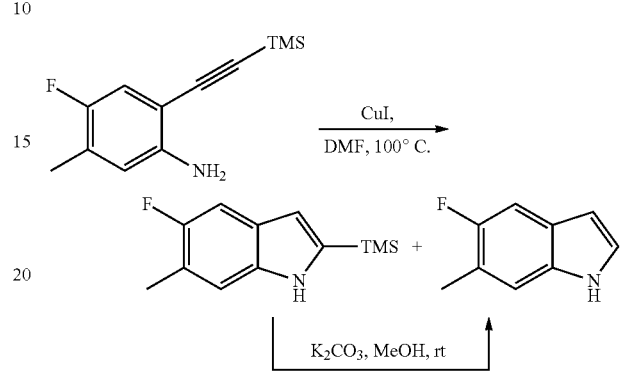

Step C: A mixture of 4-fluoro-5-methyl-2-((trimethylsilyl)ethynyl)aniline (plus ca. 10% of the undesired isomer) (10.3 g, 46.6 mmol) and copper(I) iodide (17.75 g, 93.2 mmol) in DMF (200 mL) was stirred at 100° C. for 4 hours. The mixture was then treated with ethyl ether (300 mL) and filtered. The filtrate was washed with water (200 mL) and extracted with ether. The organics were combined and washed with water, brine, and dried over $Na_2SO_4$ and concentrated. The residue was purified by flash chromatography with 5-35% ethyl acetate in hexane to give 1.9 g 5-fluoro-6-methyl-2-(trimethylsilyl)-1H-indole containing ~10% of the undesired isomer, 5-fluoro-4-methyl-2-(trimethylsilyl)-1H-indole plus desilylated product, 5-fluoro-6-methyl-1H-indole (2.8 g) with ~10% of the undesired isomer, 5-fluoro-4-methyl-1H-indole. Silylated material, 5-fluoro-6-methyl-2-(trimethylsilyl)-1H-indole containing ~10% of the undesired isomer, was re-dissolved in methanol (20 mL) and stirred with potassium carbonate overnight, filtered and concentrated. All desilylated material was combined (3.7 g) and recrystallized from $CH_2Cl_2$ and hexane to provide 5-fluoro-6-methyl-1H-indole (1.9 g).

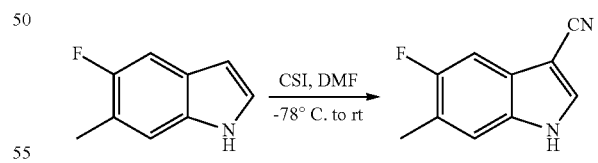

Step D: Into a solution of 5-fluoro-6-methyl-1H-indole (1.9 g, 12.8 mmol) in DMF (13 mL) at −78° C. was added chlorosulfonyl isocyanate (1.33 mL, 15.3 mmol). After addition the cooling bath was removed and the mixture was allowed to warm to room temperature. The mixture was then poured into ice water, filtered and washed with water and brine. The cake was then dissolved in acetonitrile and concentrated to give 5-fluoro-6-methyl-1H-indole-3-carbonitrile (2.2 g, 100%).

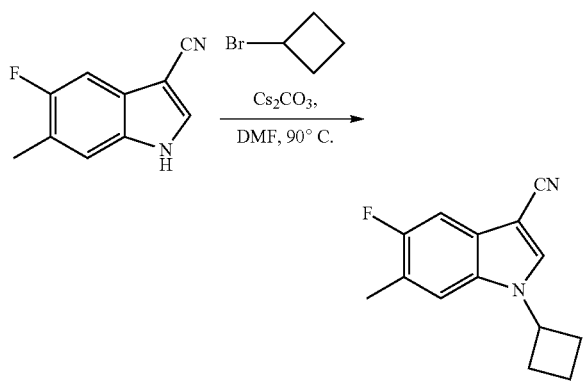

Step E: A mixture of 5-fluoro-6-methyl-1H-indole-3-carbonitrile (1.0 g, 5.8 mmol), cyclobutylbromide (0.81 mL, 8.6 mmol) and cesium carbonate (3.9 g, 12.1 mmol) in DMF (10 mL) was stirred at 90° C. overnight. The mixture was then poured into ice water and extracted with ethyl acetate. The organics were combined and washed with water, brine and dried over Na$_2$SO$_4$ and evaporated. The residue was purified by flash chromatography with 5-35% ethyl acetate in hexane to give 1-cyclobutyl-5-fluoro-6-methyl-1H-indole-3-carbonitrile (1.2 g, 92%). $^1$H NMR (500 MHz, CDCl$_3$): 7.68 (1H, s), 7.35 (1H, d, J=9.6 Hz), 7.17 (1H, d, J=6.1 Hz), 4.83-4.79 (1H, m), 2.68-2.60 (2H, m), 2.48-2.37 (5H, m), 2.05-1.96 (2H, m).

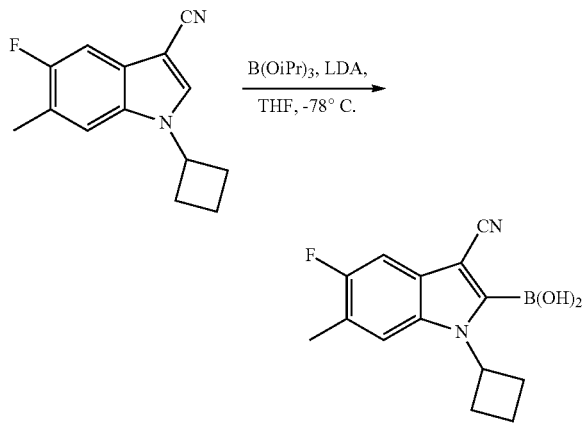

Step F: Into a solution of 1-cyclobutyl-5-fluoro-6-methyl-1H-indole-3-carbonitrile (1.2 g, 5.3 mmol) and triisopropyl borate (2.18 mL, 9.47 mmol) in THF (20 mL) at −78° C. was added LDA (1.5 M in cyclohexane, 4.6 mL, 6.84 mmol). The mixture was stirred at −78° C. for 30 min and quenched with ice water (60 mL) and stirred for 15 min without cooling. The mixture was extracted with ethyl acetate 1:1 in hexane (20 mL). The aqueous layer was acidified with 2 N aq. HCl to pH 5 and then extracted with CH$_2$Cl$_2$ (60 mL). The organic layer was dried over Na$_2$SO$_4$ and concentrated to give 3-cyano-1-cyclobutyl-5-fluoro-6-methyl-1H-indol-2-ylboronic acid as a solid (1.44 g, 98% pure by LCMS) that was used in the next step without further purification.

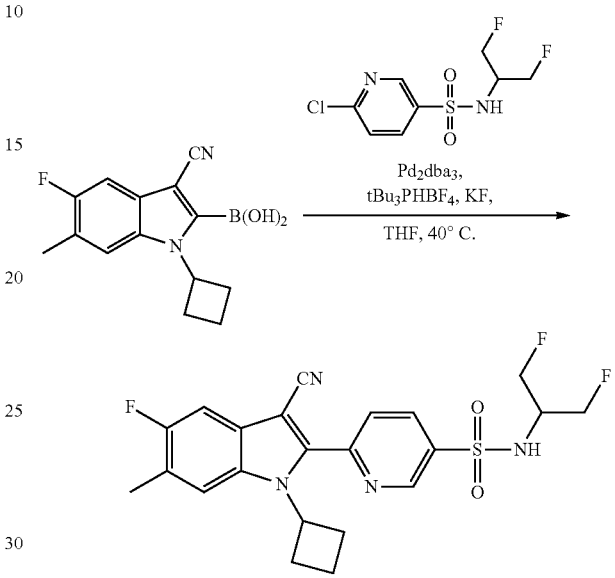

Step G: A mixture of 3-cyano-1-cyclobutyl-5-fluoro-6-methyl-1H-indol-2-ylboronic acid (0.45 g, 1.5 mmol), 6-chloro-N-(1,3-difluoropropan-2-yl)pyridine-3-sulfonamide (0.27 g, 1.0 mmol), tri-tert-butylphosphonium tetrafluoroborate (29 mg, 0.1 mmol) and Pd$_2$(dba)$_3$ (46 mg, 0.05 mmol) and potassium fluoride (0.23 g, 4.0 mmol) in THF (5.0 mL) was stirred at 40° C. overnight. The solvent was then evaporated and the residue was purified by flash chromatography with 0-10% ethyl acetate in CH$_2$Cl$_2$ to provide the title Compound 108 (220 mg, 48%). Melting point: 186-188; MS m/z 463.0 M+H$^+$; $^1$H NMR (500 MHz, CDCl$_3$): δ 9.24 (1H, d, J=1.7 Hz), 8.35 (1H, dd, J=8.3 Hz, J=2.3 Hz), 8.02 (1H, d, J=8.2 Hz), 7.51 (1H, d, J=6.0 Hz), 7.42 (1H, dd, J=9.2 Hz), 5.35-5.20 (1H, m), 5.19 (1H, d, J=9.0 Hz), 4.63-4.45 (4H, m), 3.94-3.90 (1H, m), 2.65-2.59 (2H, m), 2.59 (3H, s), 2.48-2.40 (2H, m), 1.95-1.87 (2H, m).

Additional compounds representative of the present invention may be prepared according to the procedure of Example 3 by substituting the appropriate starting materials, reagents and reaction conditions and include compounds selected from (wherein MS represents mass spec as MH$^+$, unless otherwise indicated, and m.p. represents melting point in ° C.):

| Cpd | Name | m.p. | MS |
|---|---|---|---|
| 50 | 6-(6-chloro-3-cyano-1-cyclobutyl-5-fluoro-1H-indol-2-yl)-N-(1,3-difluoropropan-2-yl)pyridine-3-sulfonamide | 211-213 | 482.8 |
| 101 | 6-(3-cyano-1-cyclobutyl-5-fluoro-6-methoxy-1H-indol-2-yl)-N-(propan-2-yl)pyridine-3-sulfonamide | 234-237 | 443.0 |
| 102 | 6-(3-cyano-1-cyclobutyl-5-fluoro-6-methoxy-1H-indol-2-yl)-N-(1,3-difluoropropan-2-yl)pyridine-3-sulfonamide | 217-219 | 478.9 |
| 107 | 6-(3-cyano-1-cyclobutyl-6-cyclopropyl-5-fluoro-1H-indol-2-yl)-N-(1,3-difluoropropan-2-yl)pyridine-3-sulfonamide | 182-186 | 488.9 |

-continued

| Cpd | Name | m.p. | MS |
|---|---|---|---|
| 110 | 6-[6-chloro-3-cyano-1-(cyclopropylmethyl)-5-fluoro-1H-indol-2-yl]-N-(1,3-difluoropropan-2-yl)pyridine-3-sulfonamide | 202-204 | 483.0 |
| 145 | 2-(3-cyano-1-cyclobutyl-6-cyclopropyl-5-fluoro-1H-indol-2-yl)-N-(1,3-difluoropropan-2-yl)pyrimidine-5-sulfonamide | 237-238 | 477.0 |
| 146 | 2-(3-cyano-1-cyclobutyl-5-fluoro-6-methyl-1H-indol-2-yl)-N-(1,3-difluoropropan-2-yl)pyrimidine-5-sulfonamide | 243-249 | 464.1 |
| 149 | 2-(6-chloro-3-cyano-1-cyclobutyl-5-fluoro-1H-indol-2-yl)-N-(1,3-difluoropropan-2-yl)pyrimidine-5-sulfonamide | >245 decomp. | 483.9 |
| 150 | 2-(3-cyano-1-cyclobutyl-5-fluoro-6-methoxy-1H-indol-2-yl)-N-(1,3-difluoropropan-2-yl)pyrimidine-5-sulfonamide | 245-247 | 480.0 |
| 225 | 6-[3-cyano-1-(cyclopropylmethyl)-5-fluoro-6-methoxy-1H-indol-2-yl]-N-(1,3-difluoropropan-2-yl)pyridine-3-sulfonamide | 196-199 | 479.0 |

Example 4

6-[3-cyano-1-cyclobutyl-6-(difluoromethoxy)-1H-indol-2-yl]-N-[(2S)-1,1,1-trifluoropropan-2-yl]pyridine-3-sulfonamide (Cpd 300)

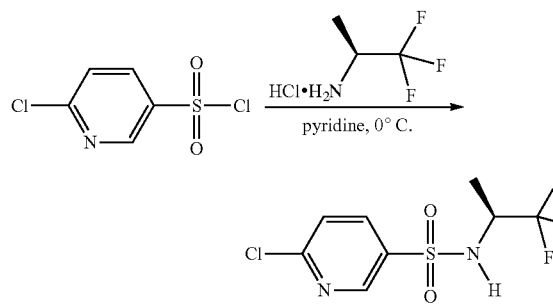

Step A: 2-chloropyridine-5-sulfonyl chloride (12 g, 56.6 mmol) was added to a solution of (S)-1,1,1-trifluoropropan-2-amine hydrochloride (7.8 g, 51.2 mmol) in pyridine (15 mL) at 0° C. The mixture was stirred at room temperature for 10 minutes and diluted with ethyl acetate (200 ml) and washed with 3 N aq. HCl (2×100 mL). The organic layer was dried over $Na_2SO_4$, filtered, and concentrated. The solid was triturated with hexane (2×40 mL) and filtered to provide (S)-6-chloro-pyridine-3-sulfonic acid (2,2,2-trifluoro-1-methyl-ethyl)-amide as an off-white solid (11.84 g, 75%). $^1$H NMR (500 MHz, $CDCl_3$): δ0.81 (1H, d, J=2.4 Hz), 8.18 (1H, dd, J=2.5 Hz, 2.6 Hz), 7.51 (1H, d, J=8.8 Hz), 4.92 (1H, br s), 4.08 (1H, m), 1.45 (3H, d, J=7.0 Hz).

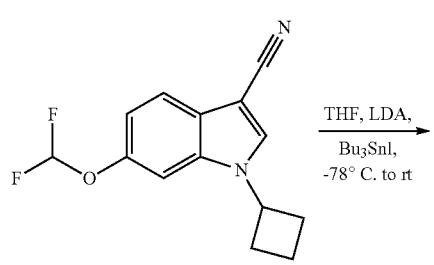

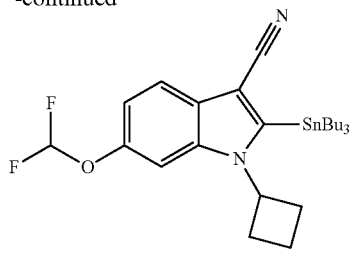

Step B: To 1-cyclobutyl-6-difluoromethoxy-1H-indole-3-carbonitrile (830 mg, 3.17 mmol) in THF (10 mL) was added tributyltin iodide (1.13 mL, 4.04 mmol) and the solution cooled to −78° C. A solution of LDA (1.5M in cyclohexane, 3.4 mL, 5.1 mmol) was added dropwise. After complete addition the bath was removed and the mixture stirred at room temperature for 1 hour. THF was then removed under vacuum and the residue filtered through silica gel using $CH_2Cl_2$ as an eluant and the mixture concentrated. The residue was purified by flash chromatography using 30-50% $CH_2Cl_2$/hexanes to provide 1-cyclobutyl-6-difluoromethoxy-2-tributylstannanyl-1H-indole-3-carbonitrile as a clear, colorless oil (1.23 g, 70%).

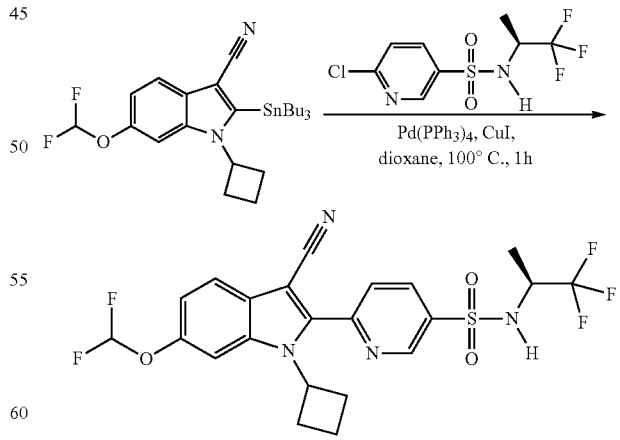

Step C: 1-cyclobutyl-6-difluoromethoxy-2-tributylstannanyl-1H-indole-3-carbonitrile (650 mg, 1.17 mmol) was combined with (S)-6-chloro-pyridine-3-sulfonic acid (2,2,2-trifluoro-1-methyl-ethyl)-amide (338 mg, 1.17 mmol, >98% ee), cuprous iodide (68 mg, 0.36 mmol), and tetrakis(triphenylphosphine)palladium (105 mg, 0.091 mmol) under nitrogen. Dioxane (2.6 mL) was added and the mixture stirred at 100° C. for 1 hour. The mixture was diluted in ethyl acetate (50 mL) and filtered. The filtrate was concentrated under vacuum and purified by two successive silica gel chromatographic separations (5% ethyl acetate in $CH_2Cl_2$; then 20% ethyl acetate in hexanes). Triturating with 1/1 hexanes/ethyl ether yielded the title Compound 300 as a white solid (260 mg, 43%). Melting point: 159-162; MS m/z 515.4 M+H+; $^1$H NMR (CDCl$_3$, 500 MHz): δ 9.23 (1H, d, J=2 Hz), 8.34 (1H, dd, J=8.0 Hz, 2.5 Hz), 8.03 (1H, d, J=8.0 Hz), 7.80 (1H, d, J=8.5 Hz), 7.49 (1H, d, J=1.5 Hz), 7.17 (1H, dd, J=8.5 Hz, 2 Hz), 6.59 (1H, t, J=75 Hz), 5.35 (1H, p, J=8.5 Hz), 4.98 (1H, br s), 4.17

Additional compounds representative of the present invention may be prepared according to the procedure of Example 4 by substituting the appropriate starting materials, reagents and reaction conditions and include compounds selected from (wherein MS represents mass spec as MH+, unless otherwise indicated, m.p. represents melting point in ° C., and N/A indicates that the data was not obtained):

| Cpd | Name | m.p. | MS |
|---|---|---|---|
| 118 | 6-(5-chloro-3-cyano-1-cyclopentyl-1H-indol-2-yl)-N-[(1S)-1-cyclopropylethyl]pyridine-3-sulfonamide | N/A | 469.5 |
| 119 | 6-(5-chloro-3-cyano-1-cyclobutyl-1H-indol-2-yl)-N-[(1S)-1-cyclopropylethyl]pyridine-3-sulfonamide | 154-155 | 455.0 |
| 130 | 2-[3-cyano-1-cyclobutyl-6-(difluoromethoxy)-1H-indol-2-yl]-N-[(1S)-1-cyclopropylethyl]pyrimidine-5-sulfonamide | 172-174 | 488.0 |
| 131 | 2-(3-cyano-1-cyclobutyl-6-cyclopropyl-1H-indol-2-yl)-N-[(1S)-1-cyclopropylethyl]pyrimidine-5-sulfonamide | 165-167 | 462.0 |
| 142 | 6-(3-cyano-1-cyclobutyl-5-fluoro-1H-indol-2-yl)-N-[(1S)-1-cyclopropylethyl]pyridine-3-sulfonamide | 128-130 | 439.0 |
| 143 | 6-(3-cyano-1-cyclopentyl-5-fluoro-1H-indol-2-yl)-N-[(1S)-1-cyclopropylethyl]pyridine-3-sulfonamide | 159-160 | 453.0 |
| 144 | 6-(3-cyano-1-cyclobutyl-6-fluoro-1H-indol-2-yl)-N-[(1S)-1-cyclopropylethyl]pyridine-3-sulfonamide | 136-138 | 439.0 |
| 151 | 6-[3-cyano-1-cyclobutyl-6-(difluoromethoxy)-1H-indol-2-yl]-N-[(1S)-1-cyclopropylethyl]pyridine-3-sulfonamide | 163-168 | 487.1 |
| 152 | 6-[3-cyano-1-cyclobutyl-6-(trifluoromethoxy)-1H-indol-2-yl]-N-[(1S)-1-cyclopropylethyl]pyridine-3-sulfonamide | N/A | 505.0 |
| 154 | 6-(6-chloro-3-cyano-1-cyclobutyl-1H-indol-2-yl)-N-[(1S)-1-cyclopropylethyl]pyridine-3-sulfonamide | N/A | 454.9 |
| 155 | 6-(6-chloro-3-cyano-1-cyclopentyl-1H-indol-2-yl)-N-[(1S)-1-cyclopropylethyl]pyridine-3-sulfonamide | N/A | 469.0 |
| 174 | 6-[3-cyano-1-cyclopentyl-6-(difluoromethoxy)-1H-indol-2-yl]-N-[(1S)-1-cyclopropylethyl]pyridine-3-sulfonamide | 176-182 | 501.3 |
| 180 | 2-(3-cyano-1-cyclobutyl-6-cyclopropyl-1H-indol-2-yl)-N-[(2R)-1,1,1-trifluoropropan-2-yl]pyrimidine-5-sulfonamide | 211-212 | 490.1 |
| 181 | 2-(3-cyano-1-cyclobutyl-6-methyl-1H-indol-2-yl)-N-[(2R)-1,1,1-trifluoropropan-2-yl]pyrimidine-5-sulfonamide | 143-145 | 464.0 |
| 182 | 2-(3-cyano-1-cyclopentyl-6-methyl-1H-indol-2-yl)-N-[(2R)-1,1,1-trifluoropropan-2-yl]pyrimidine-5-sulfonamide | 116-118 | 478.0 |
| 183 | 2-(3-cyano-1-cyclobutyl-6-methoxy-1H-indol-2-yl)-N-[(2R)-1,1,1-trifluoropropan-2-yl]pyrimidine-5-sulfonamide | 147-149 | 480.0 |
| 184 | 2-[3-cyano-1-cyclobutyl-6-(difluoromethoxy)-1H-indol-2-yl]-N-[(2R)-1,1,1-trifluoropropan-2-yl]pyrimidine-5-sulfonamide | 112-114 | 516.1 |
| 191 | 6-[3-cyano-1-cyclobutyl-6-(trifluoromethoxy)-1H-indol-2-yl]-N-[(2R)-1,1,1-trifluoropropan-2-yl]pyridine-3-sulfonamide | 171-177 | 533.1 |
| 192 | 6-(3-cyano-1-cyclobutyl-6-methyl-1H-indol-2-yl)-N-[(2R)-1,1,1-trifluoropropan-2-yl]pyridine-3-sulfonamide | 204-208 | 463.0 |
| 194 | 6-[3-cyano-6-(difluoromethoxy)-1-(propan-2-yl)-1H-indol-2-yl]-N-[(2R)-1,1,1-trifluoropropan-2-yl]pyridine-3-sulfonamide | 166-168 | 503.0 |
| 195 | 6-[3-cyano-1-cyclohexyl-6-(difluoromethoxy)-1H-indol-2-yl]-N-[(2R)-1,1,1-trifluoropropan-2-yl]pyridine-3-sulfonamide | 170-172 | 543.0 |
| 196 | 6-[3-cyano-1-cyclobutyl-6-(difluoromethoxy)-1H-indol-2-yl]-N-[(2R)-1,1,1-trifluoropropan-2-yl]pyridine-3-sulfonamide | 159-164 | 515.0 |
| 197 | 6-[3-cyano-1-(cyclopropylmethyl)-6-methyl-1H-indol-2-yl]-N-[(2R)-1,1,1-trifluoropropan-2-yl]pyridine-3-sulfonamide | 165-169 | 463.0 |
| 201 | 6-(3-cyano-1-cyclobutyl-5-methyl-1H-indol-2-yl)-N-[(1S)-1-cyclopropylethyl]pyridine-3-sulfonamide | 173-178 | 435.1 |
| 202 | 2-(3-cyano-1-cyclobutyl-6-methyl-1H-indol-2-yl)-N-[(1S)-1-cyclopropylethyl]pyrimidine-5-sulfonamide | 129-131 | 136.1 |
| 203 | 2-[3-cyano-1-(cyclopropylmethyl)-6-methyl-1H-indol-2-yl]-N-[(1S)-1-cyclopropylethyl]pyrimidine-5-sulfonamide | 205-207 | 436.0 |
| 204 | 2-(3-cyano-1-cyclopentyl-6-methyl-1H-indol-2-yl)-N-[(1S)-1-cyclopropylethyl]pyrimidine-5-sulfonamide | 180-182 | 450.1 |

-continued

| Cpd | Name | m.p. | MS |
|---|---|---|---|
| 205 | 2-(3-cyano-1-cyclobutyl-6-methoxy-1H-indol-2-yl)-N-[(1S)-1-cyclopropylethyl]pyrimidine-5-sulfonamide | 204-206 | 452.0 |
| 206 | 2-(3-cyano-1-cyclopentyl-6-methoxy-1H-indol-2-yl)-N-[(1S)-1-cyclopropylethyl]pyrimidine-5-sulfonamide | 192-194 | 466.0 |
| 207 | 2-[3-cyano-6-(difluoromethoxy)-1-(propan-2-yl)-1H-indol-2-yl]-N-[(1S)-1-cyclopropylethyl]pyrimidine-5-sulfonamide | 169-170 | 476.0 |
| 208 | 2-[3-cyano-6-(difluoromethoxy)-1-propyl-1H-indol-2-yl]-N-[(1S)-1-cyclopropylethyl]pyrimidine-5-sulfonamide | 152-154 | 476.1 |
| 209 | 2-[3-cyano-1-cyclopentyl-6-(difluoromethoxy)-1H-indol-2-yl]-N-[(1S)-1-cyclopropylethyl]pyrimidine-5-sulfonamide | 183-185 | 502.0 |
| 210 | 6-[3-cyano-6-methyl-1-(propan-2-yl)-1H-indol-2-yl]-N-[(2R)-1,1,1-trifluoropropan-2-yl]pyridine-3-sulfonamide | 211-216 | 450.8 |
| 211 | 6-(3-cyano-1-cyclopentyl-6-cyclopropyl-1H-indol-2-yl)-N-[(2R)-1,1,1-trifluoropropan-2-yl]pyridine-3-sulfonamide | 178-181 | 503.0 |
| 212 | 6-(3-cyano-1-cyclobutyl-6-cyclopropyl-1H-indol-2-yl)-N-[(2R)-1,1,1-trifluoropropan-2-yl]pyridine-3-sulfonamide | 192-196 | 489.0 |
| 213 | 6-(3-cyano-1-cyclohexyl-6-methyl-1H-indol-2-yl)-N-[(2R)-1,1,1-trifluoropropan-2-yl]pyridine-3-sulfonamide | 208-212 | 491.1 |
| 214 | 6-(3-cyano-1-cyclopentyl-6-methyl-1H-indol-2-yl)-N-[(2R)-1,1,1-trifluoropropan-2-yl]pyridine-3-sulfonamide | 176-182 | 477.0 |
| 215 | 6-(3-cyano-1-cyclobutyl-6-fluoro-1H-indol-2-yl)-N-[(2R)-1,1,1-trifluoropropan-2-yl]pyridine-3-sulfonamide | 178-180 | 467.0 |
| 216 | 6-[3-cyano-1-(cyclopropylmethyl)-6-fluoro-1H-indol-2-yl]-N-[(2R)-1,1,1-trifluoropropan-2-yl]pyridine-3-sulfonamide | 173-175 | 466.9 |
| 217 | 6-(3-cyano-6-fluoro-1-propyl-1H-indol-2-yl)-N-[(2R)-1,1,1-trifluoropropan-2-yl]pyridine-3-sulfonamide | 195-197 | 455.0 |
| 218 | 6-(3-cyano-1-cyclopentyl-6-fluoro-1H-indol-2-yl)-N-[(2R)-1,1,1-trifluoropropan-2-yl]pyridine-3-sulfonamide | 141-144 | 481.2 |
| 219 | 6-(3-cyano-1-cyclobutyl-5-fluoro-1H-indol-2-yl)-N-[(2R)-1,1,1-trifluoropropan-2-yl]pyridine-3-sulfonamide | 109-110 | 467.2 |
| 220 | 6-(3-cyano-1-cyclopentyl-5-fluoro-1H-indol-2-yl)-N-[(2R)-1,1,1-trifluoropropan-2-yl]pyridine-3-sulfonamide | 158-160 | 481.0 |
| 222 | 6-(6-chloro-3-cyano-1-cyclobutyl-1H-indol-2-yl)-N-[(2R)-1,1,1-trifluoropropan-2-yl]pyridine-3-sulfonamide | 202-206 | 483.0 |
| 223 | 6-(6-chloro-3-cyano-1-cyclopentyl-1H-indol-2-yl)-N-[(2R)-1,1,1-trifluoropropan-2-yl]pyridine-3-sulfonamide | N/A | 497.0 |
| 224 | 6-(5-chloro-3-cyano-1-cyclopentyl-1H-indol-2-yl)-N-[(2R)-1,1,1-trifluoropropan-2-yl]pyridine-3-sulfonamide | N/A | 497.0 |
| 236 | 6-(3-cyano-1-cyclobutyl-6-cyclopropyl-1H-indol-2-yl)-N-[(1S)-1-cyclopropylethyl]pyridine-3-sulfonamide | 170-176 | 461.1 |
| 237 | 6-[3-cyano-1-(cyclopropylmethyl)-6-methyl-1H-indol-2-yl]-N-[(1S)-1-cyclopropylethyl]pyridine-3-sulfonamide | N/A | 435.1 |
| 238 | 6-(3-cyano-1-cyclobutyl-6-methyl-1H-indol-2-yl)-N-[(1S)-1-cyclopropylethyl]pyridine-3-sulfonamide | 181-187 | 435.1 |
| 250 | 6-(3-cyano-1-cyclohexyl-5-fluoro-1H-indol-2-yl)-N-[(1S)-1-cyclopropylethyl]pyridine-3-sulfonamide | 161-163 | 467.0 |
| 252 | 6-(3-cyano-1-cyclohexyl-6-fluoro-1H-indol-2-yl)-N-[(2R)-1,1,1-trifluoropropan-2-yl]pyridine-3-sulfonamide | 188-189 | 465.0 |
| 254 | 2-(3-cyano-1-cyclopentyl-6-cyclopropyl-1H-indol-2-yl)-N-[(1S)-1-cyclopropylethyl]pyrimidine-5-sulfonamide | 185-189 | 476.1 |
| 261 | 6-(3-cyano-1-cyclohexyl-5-fluoro-1H-indol-2-yl)-N-[(2R)-1,1,1-trifluoropropan-2-yl]pyridine-3-sulfonamide | 208-210 | 494.9 |
| 262 | 6-(3-cyano-1-cyclohexyl-6-fluoro-1H-indol-2-yl)-N-[(1S)-1-cyclopropylethyl]pyridine-3-sulfonamide | 161-162 | 467.0 |
| 263 | 6-(3-cyano-1,6-dicyclobutyl-1H-indol-2-yl)-N-[(1S)-1-cyclopropylethyl]pyridine-3-sulfonamide | 124-126 | 475.0 |
| 313 | 6-(3-cyano-1-cyclopentyl-5-methyl-1H-indol-2-yl)-N-[1-(trifluoromethyl)cyclopropyl]pyridine-3-sulfonamide | 209-214 | 489.2 |
| 327 | 6-(3-cyano-1-cyclopentyl-5-fluoro-1H-indol-2-yl)-N-[1-(trifluoromethyl)cyclopropyl]pyridine-3-sulfonamide | 202-206 | 493.2 |
| 328 | 6-(3-cyano-1-cyclobutyl-5-methyl-1H-indol-2-yl)-N-[1-(trifluoromethyl)cyclopropyl]pyridine-3-sulfonamide | 193-199 | 475.0 |
| 329 | 6-(3-cyano-1-cyclobutyl-5-fluoro-1H-indol-2-yl)-N-[1-(trifluoromethyl)cyclopropyl]pyridine-3-sulfonamide | 176-183 | 479.3 |
| 351 | 6-(3-cyano-1-cyclobutyl-6-methyl-1H-indol-2-yl)-N-[(2S)-1,1,1-trifluoropropan-2-yl]pyridine-3-sulfonamide | 203-208 | 463.2 |
| 352 | 6-(3-cyano-1-cyclopentyl-6-methyl-1H-indol-2-yl)-N-[(2S)-1,1,1-trifluoropropan-2-yl]pyridine-3-sulfonamide | 176-180 | 477.0 |
| 353 | 6-[3-cyano-1-(cyclopropylmethyl)-6-methyl-1H-indol-2-yl]-N-[(2S)-1,1,1-trifluoropropan-2-yl]pyridine-3-sulfonamide | 165-168 | 463.2 |
| 354 | 6-(3-cyano-1-cyclohexyl-6-methyl-1H-indol-2-yl)-N-[(2S)-1,1,1-trifluoropropan-2-yl]pyridine-3-sulfonamide | 207-212 | 491.2 |

-continued

| Cpd | Name | m.p. | MS |
|---|---|---|---|
| 355 | 6-[3-cyano-6-methyl-1-(propan-2-yl)-1H-indol-2-yl]-N-[(2S)-1,1,1-trifluoropropan-2-yl]pyridine-3-sulfonamide | 211-216 | 450.9 |
| 369 | 6-(3-cyano-1-cyclobutyl-6-cyclopropyl-1H-indol-2-yl)-N-[(2S)-1,1,1-trifluoropropan-2-yl]pyridine-3-sulfonamide | 191-197 | 489.1 |
| 370 | 6-[3-cyano-1-cyclobutyl-6-(trifluoromethoxy)-1H-indol-2-yl]-N-[(2S)-1,1,1-trifluoropropan-2-yl]pyridine-3-sulfonamide | 165-175 | 533.0 |
| 371 | 6-(3-cyano-1-cyclopentyl-6-methyl-1H-indol-2-yl)-N-(1,1,1-trifluoro-2-methylpropan-2-yl)pyridine-3-sulfonamide | 202-211 | 491.1 |
| 382 | 6-[3-cyano-1-cyclopentyl-6-(difluoromethoxy)-1H-indol-2-yl]-N-(1,1,1-trifluoro-2-methylpropan-2-yl)pyridine-3-sulfonamide | 170-174 | 543.1 |
| 383 | 6-(3-cyano-1-cyclopentyl-6-cyclopropyl-1H-indol-2-yl)-N-[(2S)-1,1,1-trifluoropropan-2-yl]pyridine-3-sulfonamide | 178-181 | 503.2 |
| 421 | 6-(3-cyano-1-cyclobutyl-7-fluoro-6-methyl-1H-indol-2-yl)-N-[(2S)-1,1,1-trifluoropropan-2-yl]pyridine-3-sulfonamide | 210-220 | 481.2 |
| 422 | 6-(3-cyano-1-cyclobutyl-7-fluoro-6-methyl-1H-indol-2-yl)-N-(1,3-difluoropropan-2-yl)pyridine-3-sulfonamide | 186-201 | 463.2 |
| 423 | 6-(3-cyano-1-cyclopentyl-7-fluoro-6-methyl-1H-indol-2-yl)-N-(1,3-difluoropropan-2-yl)pyridine-3-sulfonamide | 211-216 | 477.3 |
| 424 | 6-(3-cyano-1-cyclopentyl-7-fluoro-6-methyl-1H-indol-2-yl)-N-[(2S)-1,1,1-trifluoropropan-2-yl]pyridine-3-sulfonamide | 191-195 | 495.3 |
| 481 | 6-(3-cyano-1-cyclobutyl-6-ethyl-1H-indol-2-yl)-N-(1,1,1-trifluoro-2-methylpropan-2-yl)pyridine-3-sulfonamide | 160-165 | 491.0 |
| 482 | 6-(3-cyano-1-cyclopentyl-6-fluoro-5-methyl-1H-indol-2-yl)-N-(1,3-difluoropropan-2-yl)pyridine-3-sulfonamide | 207-211 | 477.0 |
| 483 | 6-(3-cyano-1-cyclopentyl-6-fluoro-5-methyl-1H-indol-2-yl)-N-[(2S)-1,1,1-trifluoropropan-2-yl]pyridine-3-sulfonamide | 219-223 | 495.3 |
| 492 | 6-(3-cyano-1-cyclobutyl-6-fluoro-5-methyl-1H-indol-2-yl)-N-[(2S)-1,1,1-trifluoropropan-2-yl]pyridine-3-sulfonamide | 185-190 | 481.2 |
| 493 | 6-(3-cyano-1-cyclobutyl-6-fluoro-5-methyl-1H-indol-2-yl)-N-(1,3-difluoropropan-2-yl)pyridine-3-sulfonamide | 209-213 | 463.2 |
| 508 | 6-(3-cyano-1-cyclopentyl-5,7-difluoro-6-methyl-1H-indol-2-yl)-N-[(2S)-1,1,1-trifluoropropan-2-yl]pyridine-3-sulfonamide | 215-219 | 513.2 |
| 509 | 6-(3-cyano-1-cyclopentyl-5,7-difluoro-6-methyl-1H-indol-2-yl)-N-(1,3-difluoropropan-2-yl)pyridine-3-sulfonamide | 199-203 | 495.2 |
| 532 | 6-(3-cyano-1-cyclobutyl-5,7-difluoro-6-methyl-1H-indol-2-yl)-N-[(2S)-1,1,1-trifluoropropan-2-yl]pyridine-3-sulfonamide | 186-191 | 499.2 |
| 533 | 6-(3-cyano-1-cyclobutyl-5,7-difluoro-6-methyl-1H-indol-2-yl)-N-(1,3-difluoropropan-2-yl)pyridine-3-sulfonamide | 158-170 | 481.2 |
| 555 | 6-(3-cyano-1-cyclobutyl-4,6-difluoro-5-methyl-1H-indol-2-yl)-N-[(2S)-1,1,1-trifluoropropan-2-yl]pyridine-3-sulfonamide | 181-186 | 499.2 |
| 556 | 6-(3-cyano-1-cyclobutyl-4,6-difluoro-5-methyl-1H-indol-2-yl)-N-(1,3-difluoropropan-2-yl)pyridine-3-sulfonamide | 207-212 | 481.2 |
| 557 | 2-(3-cyano-1-cyclobutyl-7-fluoro-6-methyl-1H-indol-2-yl)-N-(1,3-difluoropropan-2-yl)pyrimidine-5-sulfonamide | 191-198 | 464.0 |
| 558 | 6-(3-cyano-1-cyclopentyl-4,6-difluoro-5-methyl-1H-indol-2-yl)-N-(1,3-difluoropropan-2-yl)pyridine-3-sulfonamide | 214-219 | 495.2 |
| 559 | 6-(3-cyano-1-cyclopentyl-4,6-difluoro-5-methyl-1H-indol-2-yl)-N-[(2S)-1,1,1-trifluoropropan-2-yl]pyridine-3-sulfonamide | 218-224 | 513.1 |
| 577 | 6-(3-cyano-1-cyclobutyl-5,7-difluoro-6-methyl-1H-indol-2-yl)-N-(1,1,1-trifluoro-2-methylpropan-2-yl)pyridine-3-sulfonamide | 180-187 | 513.4 |
| 578 | 6-(3-cyano-1-cyclobutyl-7-fluoro-6-methyl-1H-indol-2-yl)-N-(1,1,1-trifluoro-2-methylpropan-2-yl)pyridine-3-sulfonamide | 168-175 | 495.1 |
| 579 | 6-(3-cyano-1-cyclopentyl-7-fluoro-6-methyl-1H-indol-2-yl)-N-(1,1,1-trifluoro-2-methylpropan-2-yl)pyridine-3-sulfonamide | 203-205 | 509.1 |
| 580 | 6-(3-cyano-1-cyclopentyl-5,7-difluoro-6-methyl-1H-indol-2-yl)-N-(1,1,1-trifluoro-2-methylpropan-2-yl)pyridine-3-sulfonamide | 226-232 | 527.3 |
| 586 | 2-(3-cyano-1-cyclopentyl-7-fluoro-6-methyl-1H-indol-2-yl)-N-(1,3-difluoropropan-2-yl)pyrimidine-5-sulfonamide | 226-232 | 478.2 |
| 587 | 6-(3-cyano-1-cyclobutyl-6-methyl-1H-indol-2-yl)-N-[1-(trifluoromethyl)cyclobutyl]pyridine-3-sulfonamide | 228-232 | 489.1 |

-continued

| Cpd | Name | m.p. | MS |
|---|---|---|---|
| 588 | 6-[3-cyano-1-cyclopentyl-6-(difluoromethoxy)-1H-indol-2-yl]-N-[1-(trifluoromethyl)cyclobutyl]pyridine-3-sulfonamide | 172-176 | 555.3 |
| 589 | 6-[3-cyano-1-cyclopentyl-6-(difluoromethoxy)-1H-indol-2-yl]-N-[(2S)-1,1,1-trifluoropropan-2-yl]pyridine-3-sulfonamide | 188-194 | 529.3 |
| 613 | 6-(3-cyano-1-cyclobutyl-5-fluoro-6-methyl-1H-indol-2-yl)-N-[1-(trifluoromethyl)cyclopropyl]pyridine-3-sulfonamide | 223-232 | 493.2 |
| 614 | 6-(3-cyano-1-cyclopentyl-4-fluoro-5-methyl-1H-indol-2-yl)-N-(1,1,1-trifluoro-2-methylpropan-2-yl)pyridine-3-sulfonamide | 200-205 | 509.2 |
| 615 | 6-(3-cyano-1-cyclopentyl-4-fluoro-5-methyl-1H-indol-2-yl)-N-[(2S)-1,1,1-trifluoropropan-2-yl]pyridine-3-sulfonamide | 186-197 | 495.1 |
| 625 | 6-(3-cyano-1-cyclopentyl-4-fluoro-6-methyl-1H-indol-2-yl)-N-[(2S)-1,1,1-trifluoropropan-2-yl]pyridine-3-sulfonamide | 207-211 | 495.4 |
| 626 | 6-(3-cyano-1-cyclopentyl-4-fluoro-6-methyl-1H-indol-2-yl)-N-(1,1,1-trifluoro-2-methylpropan-2-yl)pyridine-3-sulfonamide | 218-223 | 509.3 |
| 627 | 6-(3-cyano-1-cyclobutyl-4-fluoro-6-methyl-1H-indol-2-yl)-N-[(2S)-1,1,1-trifluoropropan-2-yl]pyridine-3-sulfonamide | 205-210 | 481.4 |
| 628 | 6-(3-cyano-1-cyclopentyl-4-fluoro-6-methyl-1H-indol-2-yl)-N-[1-(trifluoromethyl)cyclopropyl]pyridine-3-sulfonamide | 242-246 | 507.1 |
| 629 | 6-(3-cyano-1-cyclobutyl-4-fluoro-6-methyl-1H-indol-2-yl)-N-[1-(trifluoromethyl)cyclopropyl]pyridine-3-sulfonamide | 241-246 | 493.1 |
| 653 | 6-(3-cyano-1-cyclopentyl-5,7-difluoro-6-methyl-1H-indol-2-yl)-N-[(2R)-1,1,1-trifluoropropan-2-yl]pyridine-3-sulfonamide | 212-217 | 513.2 |
| 654 | 6-(3-cyano-1-cyclopentyl-5,7-difluoro-6-methyl-1H-indol-2-yl)-N-[1-(trifluoromethyl)cyclopropyl]pyridine-3-sulfonamide | 241-246 | 525.2 |
| 655 | 6-(3-cyano-1-cyclobutyl-5-fluoro-6-methyl-1H-indol-2-yl)-N-(propan-2-yl)pyridine-3-sulfonamide | 222-226 | 427.2 |
| 656 | 2-(3-cyano-1-cyclopentyl-5,7-difluoro-6-methyl-1H-indol-2-yl)-N-(1,3-difluoropropan-2-yl)pyrimidine-5-sulfonamide | 230-234 | 496.0 |
| 666 | 6-(3-cyano-1-cyclobutyl-5,7-difluoro-6-methyl-1H-indol-2-yl)-N-[(2R)-1,1,1-trifluoropropan-2-yl]pyridine-3-sulfonamide | 185-190 | 499.0 |
| 667 | 6-(3-cyano-1-cyclobutyl-5,7-difluoro-6-methyl-1H-indol-2-yl)-N-[1-(trifluoromethyl)cyclopropyl]pyridine-3-sulfonamide | 235-241 | 510.8 |
| 668 | 2-(3-cyano-1-cyclobutyl-5,7-difluoro-6-methyl-1H-indol-2-yl)-N-(1,3-difluoropropan-2-yl)pyrimidine-5-sulfonamide | N/A | 481.9 |

Example 5

6-[3-cyano-5-fluoro-1-(pyridin-2-yl)-1H-indol-2-yl]-N-(1,3-difluoropropan-2-yl)pyridine-3-sulfonamide (Cpd 96)

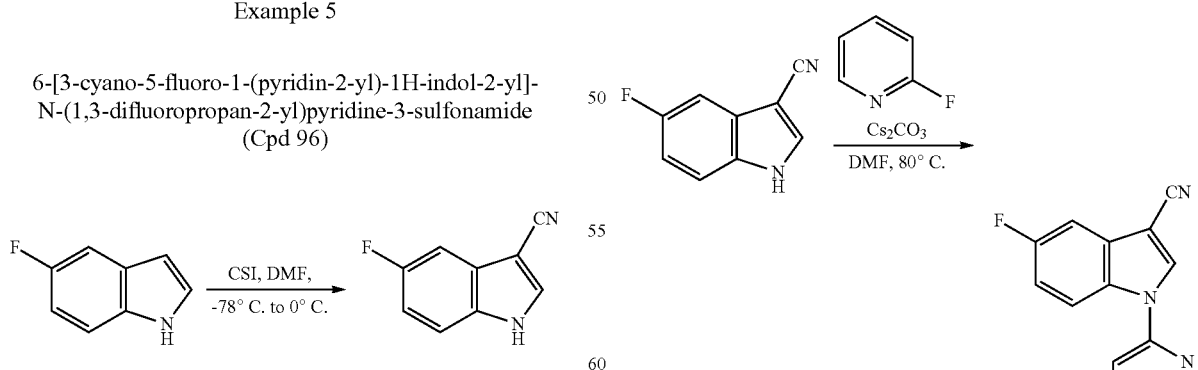

Step A: A solution of 5-fluoroindole (4.03 g, 29.82 mmol) in DMF (30 ml) was cooled to −30° C. and treated with chlorosulfonyl isocyanate (6.33 g, 44.73 mmol). After the addition the reaction mixture was stirred at 0° C. for 3 h. The reaction mixture was poured into ice water (350 mL) and solid was collected by filtration, washed with water and dried to afford a light-yellow solid (4.58 g, 96% yield).

Step B: To a solution of 5-fluoro-1H-indole-3-carbonitrile (500 mg, 3.1 mmol) in DMF (10 mL) was added 2-fluoropyridine (390 mg, 4.1 mmol) and cesium carbonate (2.1 g, 6.2 mmol). The mixture was heated at 90° C. for 16 hours, cooled to room temperature and poured into water (200 mL). After stirring for 1 hour a precipitate was collected and washed with water (200 mL) and hexane (200 mL). The solid was dried under vacuum to provide a light yellow powder (650 mg, 88%). $^1$H NMR (CDCl$_3$, 500 MHz): δ 8.65 (1H, m), 8.24 (1H, s), 8.15 (1H, m), 7.95 (1H, m), 7.50 (2H, m), 7.36 (1H, m), 7.17 (1H, m).

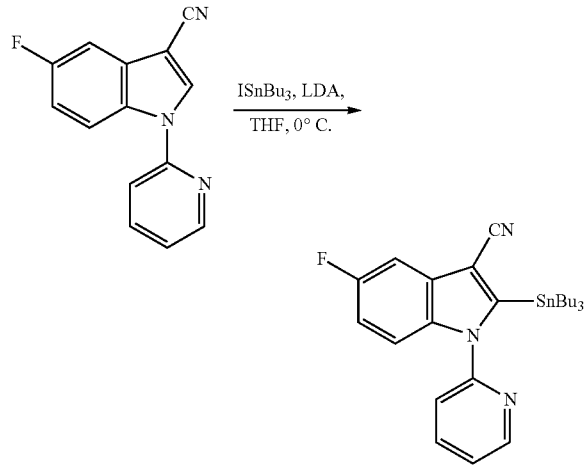

Step C: To a solution of 5-fluoro-1-(pyridin-2-yl)-1H-indole-3-carbonitrile (490 mg, 2.1 mmol) in THF (10 mL) at 0° C. was added tributyltin iodide (1.56 g, 3.7 mmol) followed by LDA (2.1 mL, 3.1 mmol). The mixture was stirred at 0° C. for 30 minutes, quenched with sat. aq. ammonium chloride (10 mL) and extracted with ethyl acetate (100 mL). The organic layer was filtered through a short layer of silica gel and celite and concentrated to provide a light-yellow oil (0.8 g, 75%).

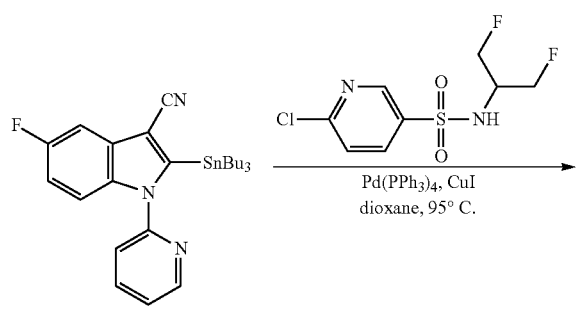

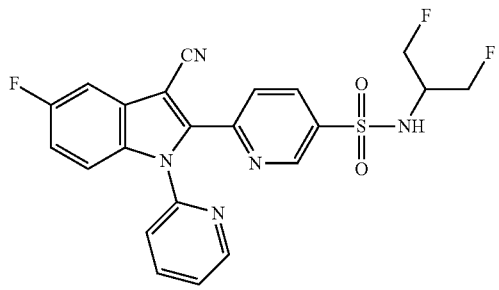

Step D: To a solution of 5-fluoro-1-(pyridin-2-yl)-2-(tributylstannyl)-1H-indole-3-carbonitrile (200 mg, 0.37 mmol) in dioxane (0.6 mL) was added 6-chloro-N-(1,3-difluoropropan-2-yl)pyridine-3-sulfonamide (65 mg, 0.24 mmol), palladium tetrakis-triphenylphosphine (29 mg, 0.024 mmol), and copper (I) iodide (4 mg, 0.048 mmol). The mixture was purged with argon, heated to 95° C. and stirred for 16 hours. The mixture was cooled to room temperature, filtered through a layer of celite, then condensed and purified by flash chromatography to provide the title Compound 96 as a light yellow powder (49 mg, 42%) was obtained. Melting point: 170-172; MS m/z 472.0 M+H$^+$; $^1$H NMR (CDCl$_3$, 500 MHz): δ 8.75 (1H, d, J=1.9 Hz), 8.43 (1H, dd, J=1.3 Hz, 4.9 Hz), 8.17 (1H, dd, J=2.4 Hz, 8.4 Hz), 7.97 (1H, d, J=8.4 Hz), 7.83 (1H, m), 7.40 (1H, m), 7.34 (3H, m), 7.08 (1H, m), 5.06 (1H, d, J=9.0 Hz), 4.38 (4H, m), 3.78 (1H, m).

Additional compounds representative of the present invention may be prepared according to the procedure of Example 5 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
|---|---|---|---|
| 95 | 6-(3-cyano-6-cyclopropyl-1-phenyl-1H-indol-2-yl)-N-(1,3-difluoropropan-2-yl)pyridine-3-sulfonamide | 171-175 | 493.0 |
| 111 | 6-(3-cyano-6-methyl-1-phenyl-1H-indol-2-yl)-N-(1,3-difluoropropan-2-yl)pyridine-3-sulfonamide | 181-185 | 466.9 |
| 112 | 6-(5-chloro-3-cyano-1-phenyl-1H-indol-2-yl)-N-(1,3-difluoropropan-2-yl)pyridine-3-sulfonamide | 192-196 | 486.9 |
| 113 | 6-(3-cyano-5-fluoro-1-phenyl-1H-indol-2-yl)-N-(1,3-difluoropropan-2-yl)pyridine-3-sulfonamide | 165-168 | 471.1 |
| 226 | 6-[3-cyano-6-(difluoromethoxy)-1-phenyl-1H-indol-2-yl]-N-(1,3-difluoropropan-2-yl)pyridine-3-sulfonamide | 200-202 | 519.0 |
| 227 | 6-[3-cyano-6-(difluoromethoxy)-1-(2-fluorophenyl)-1H-indol-2-yl]-N-(1,3-difluoropropan-2-yl)pyridine-3-sulfonamide | 188-191 | 537.0 |
| 228 | 6-[3-cyano-6-(difluoromethoxy)-1-(4-fluorophenyl)-1H-indol-2-yl]-N-(1,3-difluoropropan-2-yl)pyridine-3-sulfonamide | 192-198 | 537.1 |
| 248 | 6-[3-cyano-6-methyl-1-(pyridin-2-yl)-1H-indol-2-yl]-N-(1,3-difluoropropan-2-yl)pyridine-3-sulfonamide | 159-162 | 468.0 |

-continued

| Cpd | Name | m.p. | MS |
|---|---|---|---|
| 249 | 6-[3-cyano-6-(difluoromethoxy)-1-(pyridin-2-yl)-1H-indol-2-yl]-N-(1,3-difluoropropan-2-yl)pyridine-3-sulfonamide | 186-190 | 519.8 |
| 259 | 6-[3-cyano-5-fluoro-1-(pyridin-4-yl)-1H-indol-2-yl]-N-(1,3-difluoropropan-2-yl)pyridine-3-sulfonamide | 199-203 | 472.0 |
| 260 | 2-(3-cyano-6-methyl-1-phenyl-1H-indol-2-yl)-N-(1,3-difluoropropan-2-yl)pyrimidine-5-sulfonamide | 169-171 | 468.1 |
| 336 | 6-[3-cyano-5-fluoro-1-(4-methoxyphenyl)-1H-indol-2-yl]-N-(1,3-difluoropropan-2-yl)pyridine-3-sulfonamide | 198-200 | 501.0 |
| 337 | 2-[3-cyano-5-fluoro-1-(4-methoxyphenyl)-1H-indol-2-yl]-N-(1,3-difluoropropan-2-yl)pyrimidine-5-sulfonamide | 209-211 | 502.2 |
| 356 | 6-[3-cyano-5-fluoro-1-(4-methylphenyl)-1H-indol-2-yl]-N-(1,3-difluoropropan-2-yl)pyridine-3-sulfonamide | 208-210 | 485.8 |
| 357 | 2-[3-cyano-5-fluoro-1-(4-methylphenyl)-1H-indol-2-yl]-N-(propan-2-yl)pyrimidine-5-sulfonamide | 200-202 | 450.1 |
| 368 | 6-[3-cyano-6-(difluoromethoxy)-1-(4-fluorophenyl)-1H-indol-2-yl]-N-[(2S)-1,1,1-trifluoropropan-2-yl]pyridine-3-sulfonamide | 195-198 | 550.0 |
| 386 | 6-[3-cyano-5-fluoro-1-(pyridin-2-yl)-1H-indol-2-yl]-N-[(2S)-1,1,1-trifluoropropan-2-yl]pyridine-3-sulfonamide | 210-212 | 490.0 |
| 387 | 6-[3-cyano-6-(difluoromethoxy)-1-(pyridin-2-yl)-1H-indol-2-yl]-N-[(2S)-1,1,1-trifluoropropan-2-yl]pyridine-3-sulfonamide | 199-203 | 538.0 |
| 437 | 6-[6-chloro-3-cyano-1-(pyridin-2-yl)-1H-indol-2-yl]-N-[(2S)-1,1,1-trifluoropropan-2-yl]pyridine-3-sulfonamide | 177-178 | 506.1 |
| 438 | 6-[6-chloro-3-cyano-1-(pyridin-2-yl)-1H-indol-2-yl]-N-(1,3-difluoropropan-2-yl)pyridine-3-sulfonamide | 219-221 | 488.1 |
| 439 | 6-[3-cyano-5-fluoro-1-(pyridin-2-yl)-1H-indol-2-yl]-N-(propan-2-yl)pyridine-3-sulfonamide | 208-210 | 437.0 |
| 440 | 6-(3-cyano-6-methyl-1-phenyl-1H-indol-2-yl)-N-[(2S)-1,1,1-trifluoropropan-2-yl]pyridine-3-sulfonamide | 196-198 | 465.2 |
| 441 | 6-(5-chloro-3-cyano-1-phenyl-1H-indol-2-yl)-N-[(2S)-1,1,1-trifluoropropan-2-yl]pyridine-3-sulfonamide | 210-212 | 505.3 |
| 442 | 6-[5-chloro-3-cyano-1-(pyridin-2-yl)-1H-indol-2-yl]-N-[(2S)-1,1,1-trifluoropropan-2-yl]pyridine-3-sulfonamide | 186-188 | 506.2 |
| 443 | 6-[5-chloro-3-cyano-1-(pyridin-2-yl)-1H-indol-2-yl]-N-(1,3-difluoropropan-2-yl)pyridine-3-sulfonamide | 187-188 | 487.8 |
| 449 | 2-[6-chloro-3-cyano-1-(pyridin-2-yl)-1H-indol-2-yl]-N-[(2S)-1,1,1-trifluoropropan-2-yl]pyrimidine-5-sulfonamide | 163-166 | 507.1 |
| 450 | 2-[6-chloro-3-cyano-1-(pyridin-2-yl)-1H-indol-2-yl]-N-(1,3-difluoropropan-2-yl)pyrimidine-5-sulfonamide | 234-235 | 490.9 |
| 474 | 2-[3-cyano-5-fluoro-1-(pyridin-2-yl)-1H-indol-2-yl]-N-[(2S)-1,1,1-trifluoropropan-2-yl]pyrimidine-5-sulfonamide | 209-210 | 491.3 |
| 475 | 2-[3-cyano-6-methyl-1-(pyridin-2-yl)-1H-indol-2-yl]-N-[(2S)-1,1,1-trifluoropropan-2-yl]pyrimidine-5-sulfonamide | 210-212 | 487.2 |
| 476 | 6-[3-cyano-6-methyl-1-(pyridin-2-yl)-1H-indol-2-yl]-N-[(2S)-1,1,1-trifluoropropan-2-yl]pyridine-3-sulfonamide | 199-203 | 486.2 |
| 477 | 2-[3-cyano-6-(difluoromethoxy)-1-(4-fluorophenyl)-1H-indol-2-yl]-N-(1,3-difluoropropan-2-yl)pyrimidine-5-sulfonamide | 213-216 | 538.2 |
| 488 | 6-[6-chloro-3-cyano-1-(pyridin-2-yl)-1H-indol-2-yl]-N-[(1S)-1-cyclopropylethyl]pyridine-3-sulfonamide | 199-201 | 477.9 |
| 489 | 6-[6-chloro-3-cyano-1-(pyridin-2-yl)-1H-indol-2-yl]-N-[(2R)-1,1,1-trifluoropropan-2-yl]pyridine-3-sulfonamide | 198-199 | 506.2 |
| 490 | 6-[5-chloro-3-cyano-1-(pyridin-2-yl)-1H-indol-2-yl]-N-[(1S)-1-cyclopropylethyl]pyridine-3-sulfonamide | 136-139 | 477.9 |
| 491 | 6-[5-chloro-3-cyano-1-(pyridin-2-yl)-1H-indol-2-yl]-N-[(2R)-1,1,1-trifluoropropan-2-yl]pyridine-3-sulfonamide | 150-154 | 506.3 |
| 501 | 6-[3-cyano-6-cyclopropyl-1-(pyridin-2-yl)-1H-indol-2-yl]-N-(1,3-difluoropropan-2-yl)pyridine-3-sulfonamide | 210-213 | 494.3 |
| 502 | 6-[3-cyano-6-cyclopropyl-1-(pyridin-2-yl)-1H-indol-2-yl]-N-[(2S)-1,1,1-trifluoropropan-2-yl]pyridine-3-sulfonamide | 185-189 | 512.3 |
| 503 | 6-[3-cyano-5-methyl-1-(pyridin-2-yl)-1H-indol-2-yl]-N-[(2S)-1,1,1-trifluoropropan-2-yl]pyridine-3-sulfonamide | 165-167 | 486.3 |
| 504 | 6-[3-cyano-5-methyl-1-(pyridin-2-yl)-1H-indol-2-yl]-N-(1,3-difluoropropan-2-yl)pyridine-3-sulfonamide | 177-179 | 468.2 |
| 512 | 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide | 186-189 | 539.3 |
| 534 | 6-[3-cyano-6-(difluoromethoxy)-1-(pyridin-2-yl)-1H-indol-2-yl]-N-[(2R)-1,1,1-trifluoropropan-2-yl]pyridine-3-sulfonamide | 159-161 | 538.2 |
| 540 | 6-[3-cyano-5-fluoro-6-methyl-1-(pyridin-2-yl)-1H-indol-2-yl]-N-(1,3-difluoropropan-2-yl)pyridine-3-sulfonamide | 233-236 | 486.2 |
| 553 | 6-[3-cyano-6-(difluoromethoxy)-1-phenyl-1H-indol-2-yl]-N-[(2S)-1,1,1-trifluoropropan-2-yl]pyridine-3-sulfonamide | 209-211 | 537.1 |
| 554 | 6-[3-cyano-6-(difluoromethoxy)-1-phenyl-1H-indol-2-yl]-N-[(2R)-1,1,1-trifluoropropan-2-yl]pyridine-3-sulfonamide | 212-213 | 537.2 |

-continued

| Cpd | Name | m.p. | MS |
|---|---|---|---|
| 583 | 6-[3-cyano-6-(difluoromethoxy)-1-(pyridin-2-yl)-1H-indol-2-yl]-N-(1,1,1-trifluoro-2-methylpropan-2-yl)pyridine-3-sulfonamide | 170-173 | 553.2 |
| 584 | 6-[3-cyano-6-cyclopropyl-1-(pyridin-2-yl)-1H-indol-2-yl]-N-(1,1,1-trifluoro-2-methylpropan-2-yl)pyridine-3-sulfonamide | N/A | 526.3 |
| 585 | 6-(3-cyano-6-methyl-1-phenyl-1H-indol-2-yl)-N-(1,1,1-trifluoro-2-methylpropan-2-yl)pyridine-3-sulfonamide | 210-212 | 499.2 |
| 602 | 6-[3-cyano-5-fluoro-1-(pyrimidin-2-yl)-1H-indol-2-yl]-N-(1,1,1-trifluoro-2-methylpropan-2-yl)pyridine-3-sulfonamide | 231-234 | 505.1 |
| 608 | 6-[3-cyano-5-fluoro-1-(pyrimidin-2-yl)-1H-indol-2-yl]-N-(1,3-difluoropropan-2-yl)pyridine-3-sulfonamide | N/A | 473.0 |
| 610 | 2-[3-cyano-6-(difluoromethoxy)-1-phenyl-1H-indol-2-yl]-N-(1,3-difluoropropan-2-yl)pyrimidine-5-sulfonamide | 206-208 | 520.2 |
| 611 | 2-[3-cyano-6-(difluoromethoxy)-1-phenyl-1H-indol-2-yl]-N-[(2S)-1,1,1-trifluoropropan-2-yl]pyrimidine-5-sulfonamide | 216-218 | 538.2 |
| 612 | 6-[3-cyano-6-(difluoromethoxy)-1-phenyl-1H-indol-2-yl]-N-(1,1,1-trifluoro-2-methylpropan-2-yl)pyridine-3-sulfonamide | 218-220 | 551.3 |
| 623 | 6-[3-cyano-6-(difluoromethoxy)-1-(pyridin-2-yl)-1H-indol-2-yl]-N-[1-(trifluoromethyl)cyclopropyl]pyridine-3-sulfonamide | N/A | 550.8 |
| 624 | N-tert-butyl-6-[3-cyano-6-(difluoromethoxy)-1-phenyl-1H-indol-2-yl]pyridine-3-sulfonamide | 216-218 | 497.2 |
| 635 | 6-[3-cyano-6-(difluoromethoxy)-1-(pyrimidin-2-yl)-1H-indol-2-yl]-N-(1,3-difluoropropan-2-yl)pyridine-3-sulfonamide | 173-176 | 521.8 |
| 649 | 6-[3-cyano-6-(difluoromethoxy)-1-(4-fluorophenyl)-1H-indol-2-yl]-N-[(2R)-1,1,1-trifluoropropan-2-yl]pyridine-3-sulfonamide | 199-203 | 555.0 |
| 657 | 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide | 161-163 | 556.0 |
| 663 | 6-[3-cyano-6-(difluoromethoxy)-1-(pyrimidin-2-yl)-1H-indol-2-yl]-N-(1,1,1-trifluoro-2-methylpropan-2-yl)pyridine-3-sulfonamide | 179-180 | 552.9 |
| 664 | 6-[3-cyano-6-(difluoromethoxy)-1-(4-fluorophenyl)-1H-indol-2-yl]-N-[1-(trifluoromethyl)cyclopropyl]pyridine-3-sulfonamide | 195-198 | 567.2 |
| 670 | 6-[3-cyano-6-(difluoromethoxy)-5-fluoro-1-(pyridin-2-yl)-1H-indol-2-yl]-N-[(2R)-1,1,1-trifluoropropan-2-yl]pyridine-3-sulfonamide | 179-180 | 552.9 |
| 671 | 6-[3-cyano-6-methyl-1-(pyridin-2-yl)-1H-indol-2-yl]-N-[(2R)-1,1,1-trifluoropropan-2-yl]pyridine-3-sulfonamide | 195-198 | 567.2 |
| 672 | 6-(3-cyano-1-cyclopentyl-6-ethyl-5-fluoro-1H-indol-2-yl)-N-(1,1,1-trifluoro-2-methylpropan-2-yl)pyridine-3-sulfonamide | 142-143 | 523.2 |
| 673 | 6-[3-cyano-5-fluoro-1-(pyrimidin-2-yl)-1H-indol-2-yl]-N-[(2R)-1,1,1-trifluoropropan-2-yl]pyridine-3-sulfonamide | 202-205 | 490.8 |
| 677 | 6-[3-cyano-6-methyl-1-(pyrimidin-2-yl)-1H-indol-2-yl]-N-[(2S)-1,1,1-trifluoropropan-2-yl]pyridine-3-sulfonamide | 195-198 | 487.2 |
| 686 | 6-[3-cyano-6-methyl-1-(pyridin-2-yl)-1H-indol-2-yl]-N-(1,1,1-trifluoro-2-methylpropan-2-yl)pyridine-3-sulfonamide | 208-209 | 499.9 |
| 687 | 6-[3-cyano-6-(difluoromethoxy)-1-(4-fluorophenyl)-1H-indol-2-yl]-N-(1,1,1-trifluoro-2-methylpropan-2-yl)pyridine-3-sulfonamide | 215-216 | 569.2 |
| 688 | 6-[3-cyano-6-methyl-1-(pyrimidin-2-yl)-1H-indol-2-yl]-N-[(2R)-1,1,1-trifluoropropan-2-yl]pyridine-3-sulfonamide | 196-198 | 487.0 |
| 689 | 6-[3-cyano-6-methyl-1-(pyrimidin-2-yl)-1H-indol-2-yl]-N-(1,1,1-trifluoro-2-methylpropan-2-yl)pyridine-3-sulfonamide | 202-205 | 501.2 |
| 690 | 6-[3-cyano-6-(difluoromethoxy)-1-(pyrimidin-2-yl)-1H-indol-2-yl]-N-[1-(trifluoromethyl)cyclopropyl]pyridine-3-sulfonamide | 170-174 | 550.8 |
| 695 | 6-[3-cyano-5-fluoro-6-methyl-1-(pyrimidin-2-yl)-1H-indol-2-yl]-N-[(2R)-1,1,1-trifluoropropan-2-yl]pyridine-3-sulfonamide | N/A | 505.2 |
| 698 | 6-[3-cyano-5-fluoro-6-methyl-1-(pyridin-2-yl)-1H-indol-2-yl]-N-[(2R)-1,1,1-trifluoropropan-2-yl]pyridine-3-sulfonamide | 170-174 | 504.1 |

Example 6

6-(3-cyano-1-cyclopentyl-5-fluoro-6-methyl-1H-indol-2-yl)-N-[(2R)-1,1,1-trifluoropropan-2-yl]pyridine-3-sulfonamide (Cpd 409)

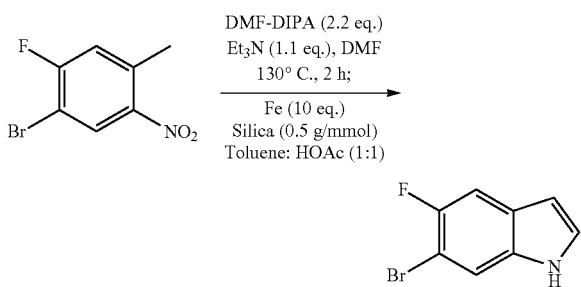

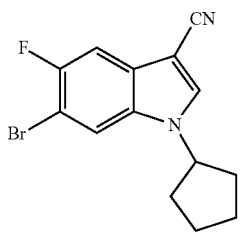

Step A: A 2 L dry round bottom flask was charged with 1-bromo-2-fluoro-4-methyl-5-nitrobenzene (24.5 g, 0.1 mol, 97%), DMF-DIPA (39 g, 0.22 mol), Et₃N (16 mL, 0.11 mol) and dry DMF (100 mL). The mixture was stirred at 130° C. for 2 h. After removal of the volatiles the residue was dissolved in a mixture of toluene (650 mL) and acetic acid (390 mL) followed by addition of iron powder (55 g) and silica gel (50 g). The dark red mixture was heated to 100° C. with vigorous stirring. The dark color disappeared after refluxing for 20 min indicating completion of reaction. The mixture was then cooled to 25° C., diluted with EtOAc and filtered. The cake was washed thoroughly with EtOAc. The combined filtrates were washed with sat. aq. Na₂S₂O₅, sat. aq. NaHCO₃, and brine, dried over Na₂SO₄ and concentrated. The residue was purified on a silica gel column eluting with 5/1 hexanes/CH₂Cl₂ to provide 6-bromo-5-fluoro-1H-indole as a white crystalline solid (16.2 g, 76%).

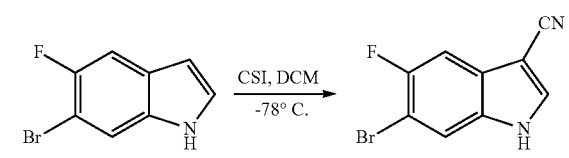 [SMILES: Fc1cc2cc[nH]c2cc1Br ; N#Cc1c[nH]c2cc(Br)c(F)cc12]

Step B: To 6-bromo-5-fluoro-1H-indole (9.4 g, 43.9 mmol) in DMF (50 mL) at −78° C. was added chlorosulfonyl isocyanate (4.6 mL, 53 mmol). After complete addition the mixture was allowed to warm to room temperature and stir for 2 hrs. The reaction mixture was poured into ice water and stirred for 30 minutes. The precipitate was collected on a filter, washed with ice water and dried in a vacuum oven to give 6-bromo-5-fluoro-1H-indole-3-carbonitrile as a light-beige solid (10.5 g, 100%).

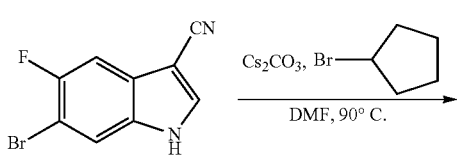

Step C: To the 6-bromo-5-fluoro-1H-indole-3-carbonitrile (10.5 g, 43.9 mmol) was added cesium carbonate (30 g, 92.2 mmol), DMF (80 mL), and then cyclopentylbromide (6.2 mL, 65.8 mmol). This mixture was stirred at 88° C. for 40 h, cooled to room temperature and then poured into ice water. The precipitate was collected, washed with water and dried to give 6-bromo-1-cyclopentyl-5-fluoro-1H-indole-3-carbonitrite as a light grey solid (12.6 g, 93%).

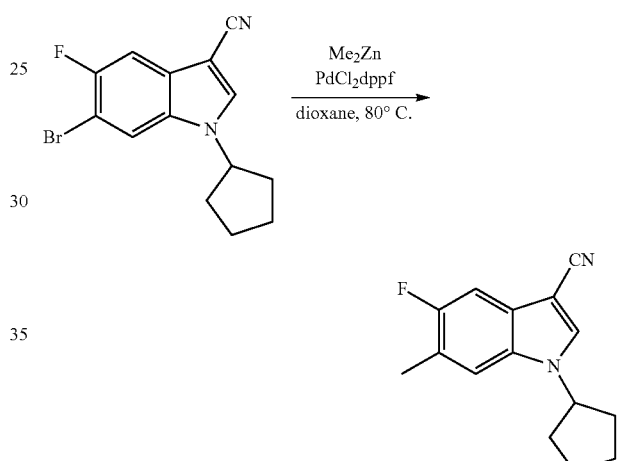

Step D: Into a solution of 6-bromo-1-cyclopentyl-5-fluoro-1H-indole-3-carbonitrile (6.6 g, 21.5 mmol) and PdCl₂dppf (0.31 g, 0.43 mmol) in dioxane (45 mL) was added a solution of dimethylzinc in toluene (1.2 M, 35.8 mL, 43 mmol). The atmosphere was replaced with nitrogen. The mixture was stirred at 90° C. for 90 min and then cooled to room temperature. The reaction was quenched by careful addition of methanol. Ethyl acetate (200 mL) was added and the mixture washed with aq. 2 N HCl, water and brine, dried over Na₂SO₄ and concentrated. The residue was purified on silica gel eluting with a gradient of 5 to 35% ethyl acetate in hexane to provide 1-cyclopentyl-5-fluoro-6-methyl-1H-indole-3-carbonitrile (4.4 g, 85%)

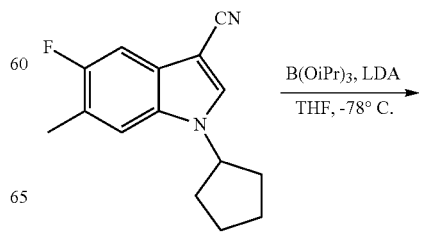

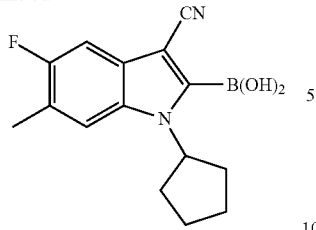

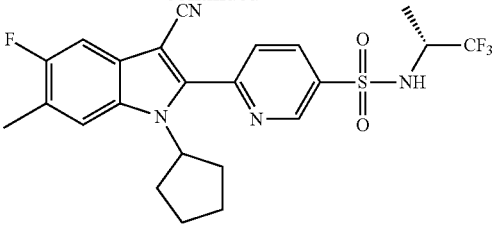

Step E: Into a solution of 1-cyclopentyl-5-fluoro-6-methyl-1H-indole-3-carbonitrile (4.4 g, 18.2 mmol) and triisopropyl borate (7.6 mL, 33 mmol) in THF (75 mL) at −78° C. was added LDA (1.5 M in cyclohexane, 15.8 mL, 23.7 mmol). The mixture was stirred at −78° C. for 30 min, quenched with ice water (200 mL) and stirred for 15 min without cooling. The mixture was extracted with ethyl acetate 1:1 in hexane (20 mL). The aqueous layer was acidified with aq. 2 N HCl to pH 5 and then extracted with $CH_2Cl_2$ (100 mL). The organic layer was dried over $Na_2SO_4$ and concentrated to give 3-cyano-1-cyclobutyl-6-cyclopropyl-1H-indol-2-ylboronic acid as a solid (6.2 g, 90% pure by LCMS) which was used in the next step without further purification.

Step F: A mixture of 3-cyano-1-cyclobutyl-6-cyclopropyl-1H-indol-2-ylboronic acid prepared as above (6.0 g, 18.8 mmol, 90%), (R)-6-chloro-N-(1,1,1-trifluoropropan-2-yl)pyridine-3-sulfonamide (3.63 g, 12.5 mmol) (similarly prepared as described in Example 4, Step A), tri-tert-butylphosphonium tetrafluoroborate (0.36 g, 1.2 mmol), $Pd_2(dba)_3$ (0.57 g, 0.62 mmol) and potassium fluoride (7.25 g, 125 mmol) in THF (80 mL) was stirred at 40° C. overnight. The solvent was then evaporated and the residue purified on silica gel eluting with a gradient of 0 to 10% ethyl acetate in $CH_2Cl_2$ to provide (R)-6-(3-cyano-1-cyclopentyl-5-fluoro-6-methyl-1H-indol-2-yl)-N-(1,1,1-trifluoropropan-2-yl)pyridine-3-sulfonamide (5.83 g, 94%). Melting point: 191-193° C.; MS m/z 495.0 M+H$^+$; $^1$H NMR (500 MHz, CDCl$_3$): δ 9.24 (1H, t, J=1.1 Hz), 8.34 (1H, dd, J=8.3 Hz, J=2.4 Hz), 8.05 (1H, dd, J=8.3, 0.7 Hz), 7.43 (1H, d, J=9.2 Hz), 7.37 (1H, d, J=6.0 Hz), 5.26-5.19 (2H, m), 4.20-4.12 (1H, m), 2.46 (3H, d, J=1.9 Hz), 2.31-2.26 (2H, m), 2.20-2.16 (2H, m), 2.07-2.04 (2H, m), 1.80-1.76 (2H, m), 1.45 (3H, d, J=7.0 Hz).

Additional compounds representative of the present invention may be prepared according to the procedure of Example 6 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

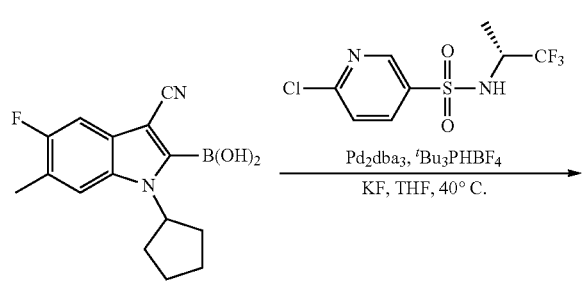

| Cpd | Name | m.p. | MS |
|---|---|---|---|
| 340 | 6-(3-cyano-1-cyclobutyl-5-fluoro-6-methyl-1H-indol-2-yl)-N-[(2S)-1,1,1-trifluoropropan-2-yl]pyridine-3-sulfonamide | 218-219 | 481.0 |
| 407 | 6-(3-cyano-1-cyclopentyl-5-fluoro-6-methyl-1H-indol-2-yl)-N-(1,3-difluoropropan-2-yl)pyridine-3-sulfonamide | 211-213 | 477.1 |
| 408 | 6-(3-cyano-1-cyclopentyl-5-fluoro-6-methyl-1H-indol-2-yl)-N-[(2S)-1,1,1-trifluoropropan-2-yl]pyridine-3-sulfonamide | 168-171 | 495.0 |
| 539 | 6-(3-cyano-1-cyclobutyl-5-fluoro-6-methyl-1H-indol-2-yl)-N-(1,1,1-trifluoro-2-methylpropan-2-yl)pyridine-3-sulfonamide | 238-243 | 495.3 |
| 609 | 6-(3-cyano-1-cyclobutyl-5-fluoro-6-methyl-1H-indol-2-yl)-N-[(2R)-1,1,1-trifluoropropan-2-yl]pyridine-3-sulfonamide | 211-214 | 481.3 |
| 630 | 6-(3-cyano-1-cyclobutyl-6-cyclopropyl-5-fluoro-1H-indol-2-yl)-N-[(2S)-1,1,1-trifluoropropan-2-yl]pyridine-3-sulfonamide | 201-203 | 507.1 |
| 631 | 6-(3-cyano-1-cyclobutyl-6-cyclopropyl-5-fluoro-1H-indol-2-yl)-N-[(2R)-1,1,1-trifluoropropan-2-yl]pyridine-3-sulfonamide | 190-194 | 507.1 |
| 632 | 6-(3-cyano-1-cyclopentyl-6-ethyl-5-fluoro-1H-indol-2-yl)-N-[(2R)-1,1,1-trifluoropropan-2-yl]pyridine-3-sulfonamide | 205.5-206 | 509.2 |
| 633 | 6-(3-cyano-1-cyclopentyl-6-ethyl-5-fluoro-1H-indol-2-yl)-N-[(2S)-1,1,1-trifluoropropan-2-yl]pyridine-3-sulfonamide | 201-202 | 509.2 |
| 637 | 6-(3-cyano-1-cyclopentyl-6-ethyl-5-fluoro-1H-indol-2-yl)-N-[1-(trifluoromethyl)cyclopropyl]pyridine-3-sulfonamide | 198-199 | 521.2 |
| 638 | 2-(3-cyano-1-cyclopentyl-6-ethyl-5-fluoro-1H-indol-2-yl)-N-(1,3-difluoropropan-2-yl)pyrimidine-5-sulfonamide | 184-185 | 492.2 |

-continued

| Cpd | Name | m.p. | MS |
|---|---|---|---|
| 639 | 6-(3-cyano-1-cyclopentyl-6-ethyl-5-fluoro-1H-indol-2-yl)-N-(1,3-difluoropropan-2-yl)pyridine-3-sulfonamide | 179.5-180.0 | 491.2 |
| 640 | 6-(3-cyano-1-cyclobutyl-6-ethyl-5-fluoro-1H-indol-2-yl)-N-[(2S)-1,1,1-trifluoropropan-2-yl]pyridine-3-sulfonamide | 205-206 | 495.2 |
| 641 | 6-(3-cyano-1-cyclobutyl-6-ethyl-5-fluoro-1H-indol-2-yl)-N-[(2R)-1,1,1-trifluoropropan-2-yl]pyridine-3-sulfonamide | 199-199.5 | 495.2 |
| 642 | 6-(3-cyano-1-cyclobutyl-6-ethyl-5-fluoro-1H-indol-2-yl)-N-[1-(trifluoromethyl)cyclopropyl]pyridine-3-sulfonamide | 203-203.5 | 507.2 |
| 643 | N-tert-butyl-6-(3-cyano-1-cyclopentyl-5-fluoro-6-methyl-1H-indol-2-yl)pyridine-3-sulfonamide | 208-209 | 455.2 |
| 644 | 6-(3-cyano-1-cyclopentyl-5-fluoro-6-methyl-1H-indol-2-yl)-N-[1-(trifluoromethyl)cyclopropyl]pyridine-3-sulfonamide | N/A | 507.7 |
| 645 | 6-(3-cyano-1-cyclopentyl-5-fluoro-6-methyl-1H-indol-2-yl)-N-(1-methylcyclopropyl)pyridine-3-sulfonamide | 208-209 | 453.2 |
| 651 | N-tert-butyl-6-(3-cyano-1-cyclobutyl-5-fluoro-6-methyl-1H-indol-2-yl)pyridine-3-sulfonamide | 223-228 | 441.2 |
| 652 | 6-(3-cyano-1-cyclobutyl-5-fluoro-6-methyl-1H-indol-2-yl)-N-cyclopropylpyridine-3-sulfonamide | N/A | 425.2 |
| 661 | 6-(3-cyano-1-cyclopentyl-6-cyclopropyl-5-fluoro-1H-indol-2-yl)-N-[(2S)-1,1,1-trifluoropropan-2-yl]pyridine-3-sulfonamide | 189-190 | 521.3 |
| 662 | 6-(3-cyano-1-cyclopentyl-6-cyclopropyl-5-fluoro-1H-indol-2-yl)-N-[(2R)-1,1,1-trifluoropropan-2-yl]pyridine-3-sulfonamide | 180-181 | 521.2 |
| 665 | 6-[3-cyano-1-cyclobutyl-6-(difluoromethoxy)-5-methyl-1H-indol-2-yl]-N-[(2R)-1,1,1-trifluoropropan-2-yl]pyridine-3-sulfonamide | N/A | 529.2 |
| 678 | 6-(3-cyano-1-cyclohexyl-5-fluoro-6-methyl-1H-indol-2-yl)-N-[(2S)-1,1,1-trifluoropropan-2-yl]pyridine-3-sulfonamide | 224-229 | 509.2 |
| 679 | 2-(3-cyano-1-cyclohexyl-5-fluoro-6-methyl-1H-indol-2-yl)-N-[(2S)-1,1,1-trifluoropropan-2-yl]pyrimidine-5-sulfonamide | N/A | 510.2 |
| 680 | 6-(3-cyano-1-cyclohexyl-5-fluoro-6-methyl-1H-indol-2-yl)-N-[(2R)-1,1,1-trifluoropropan-2-yl]pyridine-3-sulfonamide | 224-229 | 509.3 |
| 681 | 6-(3-cyano-1-cyclopentyl-5-fluoro-6-methyl-1H-indol-2-yl)-N-(1,1,1-trifluoro-2-methylpropan-2-yl)pyridine-3-sulfonamide | 223-225 | 509.2 |
| 697 | 6-[3-cyano-1-cyclobutyl-6-(2,2-difluoroethyl)-5-fluoro-1H-indol-2-yl]-N-[(2S)-1,1,1-trifluoropropan-2-yl]pyridine-3-sulfonamide | N/A | 531.2 |
| 705 | 6-(3-cyano-1-cyclohexyl-5-fluoro-6-methyl-1H-indol-2-yl)-N-(1,1,1-trifluoro-2-methylpropan-2-yl)pyridine-3-sulfonamide | 248-254 | 523.3 |
| 709 | N-{[6-(3-cyano-1-cyclopentyl-5-fluoro-6-methyl-1H-indol-2-yl)pyridin-3-yl]sulfonyl}-N-[(2R)-1,1,1-trifluoropropan-2-yl]acetamide | 162-163 | 536.9 |
| 710 | N-tert-butyl-6-(3-cyano-1-cyclohexyl-5-fluoro-6-methyl-1H-indol-2-yl)pyridine-3-sulfonamide | 244-245 | 470.0 |
| 749 | 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide | N/A | 511.2 |
| 750 | 6-[3-cyano-5-fluoro-6-methyl-1-(tetrahydro-2H-pyran-4-yl)-1H-indol-2-yl]-N-(1,1,1-trifluoro-2-methylpropan-2-yl)pyridine-3-sulfonamide | N/A | 525.2 |
| 751 | 6-[3-cyano-5-fluoro-6-methyl-1-(tetrahydro-2H-pyran-4-yl)-1H-indol-2-yl]-N-[(2S)-1,1,1-trifluoropropan-2-yl]pyridine-3-sulfonamide | N/A | 511.1 |
| 752 | N-tert-butyl-6-[3-cyano-5-fluoro-6-methyl-1-(tetrahydro-2H-pyran-4-yl)-1H-indol-2-yl]pyridine-3-sulfonamide | N/A | 471.2 |
| 753 | 2-[3-cyano-5-fluoro-6-methyl-1-(tetrahydro-2H-pyran-4-yl)-1H-indol-2-yl]-N-[(2S)-1,1,1-trifluoropropan-2-yl]pyrimidine-5-sulfonamide | N/A | 512.2 |
| 764 | N-tert-butyl-6-(3-cyano-1-cyclobutyl-6-ethyl-5-fluoro-1H-indol-2-yl)pyridine-3-sulfonamide | 186-188 | 453.1 |
| 772 | 6-[3-cyano-1-cyclobutyl-5-fluoro-6-(methylsulfanyl)-1H-indol-2-yl]-N-[(2S)-1,1,1-trifluoropropan-2-yl]pyridine-3-sulfonamide | 201-203 | 513.2 |
| 821 | 6-(3-cyano-1-cyclopentyl-5-fluoro-6-methyl-1H-indol-2-yl)-N-[(2S)-1,1,1-trifluorobutan-2-yl]pyridine-3-sulfonamide | 201-207 | 509.1 |
| 826 | 6-(3-cyano-1-cyclobutyl-5-fluoro-6-methyl-1H-indol-2-yl)-N-[(2S)-1,1,1-trifluorobutan-2-yl]pyridine-3-sulfonamide | 212-217 | 495.5 |

| Cpd | Name | m.p. | MS |
|---|---|---|---|
| 831 | 6-(3-cyano-1-cyclopentyl-6-cyclopropyl-5-fluoro-1H-indol-2-yl)-N-(1,1,1-trifluoro-2-methylpropan-2-yl)pyridine-3-sulfonamide | 183-185 | 533.2 |
| 832 | N-tert-butyl-6-(3-cyano-1-cyclopentyl-6-cyclopropyl-5-fluoro-1H-indol-2-yl)pyridine-3-sulfonamide | 186-188 | 479.2 |
| 836 | N-[6-(3-cyano-1-cyclopentyl-5-fluoro-6-methyl-1H-indol-2-yl)pyridin-3-yl]-N'-[(2S)-1,1,1-trifluoropropan-2-yl]sulfuric diamide | 206-208 | 510.6 |
| 837 | 6-(3-cyano-1-cyclopentyl-5-fluoro-6-methyl-1H-indol-2-yl)-5-methyl-N-[(2S)-1,1,1-trifluoropropan-2-yl]pyridine-3-sulfonamide | 237-242 | 509.3 |
| 842 | 1-cyclopentyl-6-cyclopropyl-5-fluoro-2-(5-{[(2S)-1,1,1-trifluoropropan-2-yl]sulfamoyl}pyridin-2-yl)-1H-indole-3-carboxamide | 255-257 | 537.5 |
| 856 | 6-(3-cyano-1-cyclohexyl-5-fluoro-6-methyl-1H-indol-2-yl)-N-[1-(trifluoromethyl)cyclopropyl]pyridine-3-sulfonamide | N/A | 521.2 |
| 858 | 6-(3-cyano-1-cyclobutyl-6-ethyl-4-methoxy-1H-indol-2-yl)-N-[(2S)-1,1,1-trifluoropropan-2-yl]pyridine-3-sulfonamide | 187-188 | 505.1 |
| 868 | 6-(3-cyano-1-cyclopentyl-5-fluoro-6-methyl-1H-indol-2-yl)-2-methyl-N-[(2S)-1,1,1-trifluoropropan-2-yl]pyridine-3-sulfonamide | 206-211 | 509.3 |
| 910 | 6-(3-cyano-1-cyclopropyl-6-ethyl-5-fluoro-1H-indol-2-yl)-N-[(2S)-1,1,1-trifluoropropan-2-yl]pyridine-3-sulfonamide | N/A | 481.1 |

Example 7

6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide (Cpd 549)

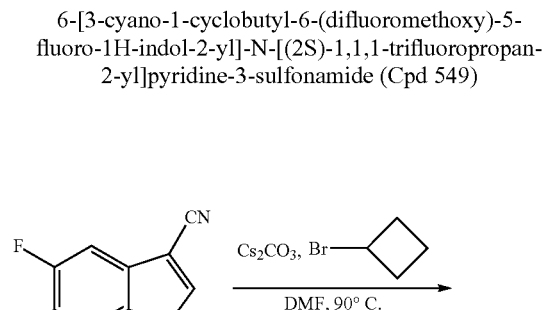

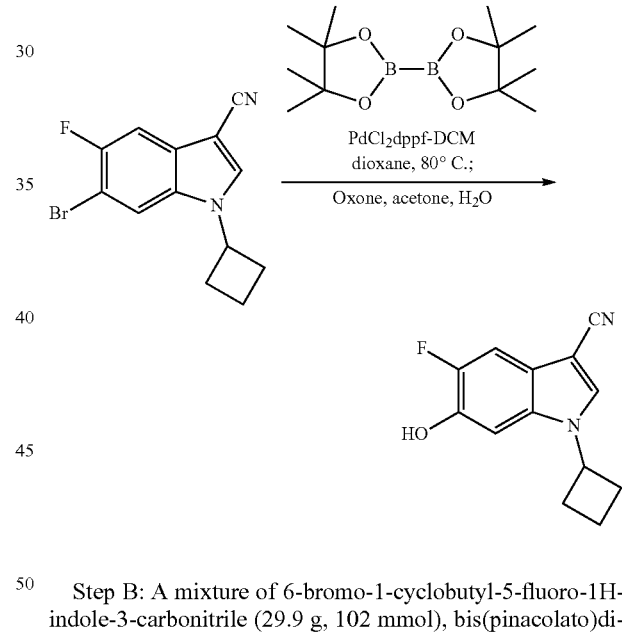

Step A: To 6-bromo-5-fluoro-1H-indole-3-carbonitrile (49.2 g, 206 mmol) [prepared as in Example 6, Step B] was added cesium carbonate (133 g, 408 mmol), DMF (200 mL), and cyclobutylbromide (30 mL, 311 mmol). This mixture was stirred at 90° C. for three days, cooled to room temperature and poured into ice water. The precipitate was collected, washed with water and dried to give 6-bromo-1-cyclobutyl-5-fluoro-1H-indole-3-carbonitrile as a light grey solid (55 g, 90%).

Step B: A mixture of 6-bromo-1-cyclobutyl-5-fluoro-1H-indole-3-carbonitrile (29.9 g, 102 mmol), bis(pinacolato)diboron (33.7 g, 133 mmol), $PdCl_2$dppf-$CH_2Cl_2$ complex (4.16 g, 5.1 mmol) and potassium acetate (30 g, 306 mmol) in dioxane (300 mL) was stirred at 80° C. overnight. The mixture was then cooled to room temperature, treated with ethyl acetate (200 mL) and filtered through a silica-celite pad. The filtrate was concentrated, dissolved in acetone (300 mL) and cooled to 0° C. Into this solution was added a slurry of Oxone (125.5 g, 204 mmol) in water (300 mL). The mixture was stirred at room temperature for 15 min, diluted with ethyl acetate and separated. The aqueous layer was extracted with ethyl acetate. The organic extractions were combined and washed with sat. aq. $NaHSO_3$, and brine, dried over $Na_2SO_4$ and concentrated. The residue was purified on silica gel to provide 1-cyclobutyl-5-fluoro-6-hydroxy-1H-indole-3-carbonitrile as a light grey solid (19.2 g, 82%).

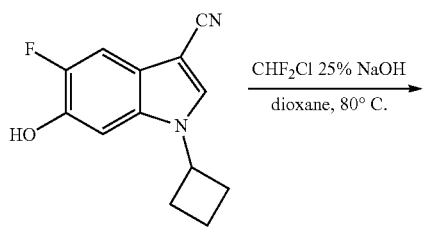

mL, 3.85 mmol). The mixture was stirred at −78° C. for 45 min then quenched with 1 N HCl (3.85 mL, 3.85 mmol). Organic volatiles were evaporated and the mixture was treated with dichloromethane (30 mL) and water (15 mL) which was acidified to pH ~5. The organic layer was dried over Na₂SO₄ and evaporated to give a residue (0.94 g, ~50% desired boronic acid by LC/MS), which was used in the next step without further purification.

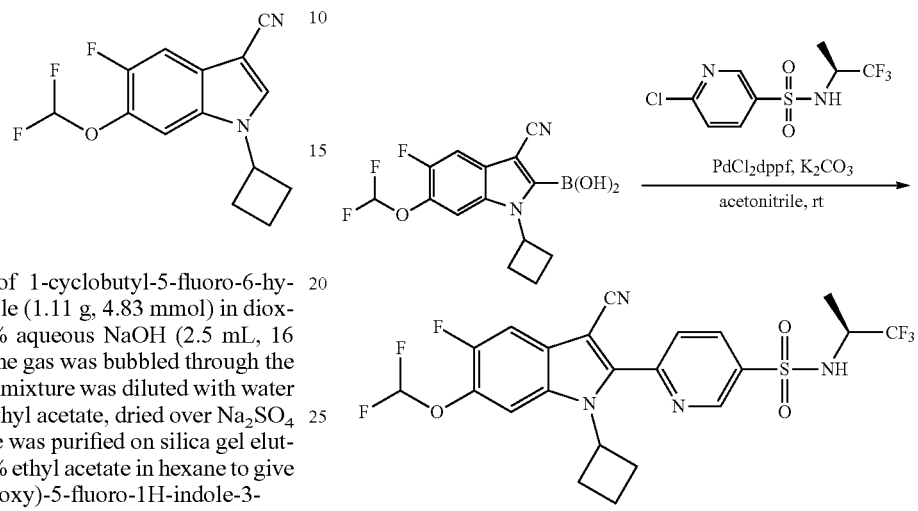

Step C: Into a solution of 1-cyclobutyl-5-fluoro-6-hydroxy-1H-indole-3-carbonitrile (1.11 g, 4.83 mmol) in dioxane (10 mL) was added 25% aqueous NaOH (2.5 mL, 16 mmol). Chlorodifluoromethane gas was bubbled through the mixture at 80° C. for 3 h. The mixture was diluted with water (20 mL) and extracted with ethyl acetate, dried over Na₂SO₄ and concentrated. The residue was purified on silica gel eluting with a gradient of 5 to 35% ethyl acetate in hexane to give 1-cyclobutyl-6-(difluoromethoxy)-5-fluoro-1H-indole-3-carbonitrile (1.1 g, 82%).

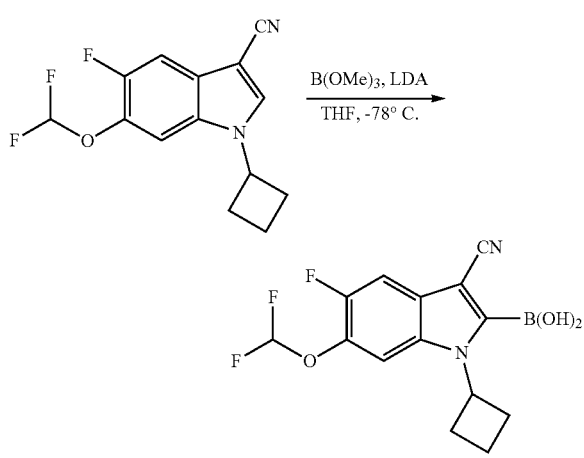

Step D: Into a solution of 1-cyclobutyl-6-(difluoromethoxy)-5-fluoro-1H-indole-3-carbonitrile (0.83 g, 2.96 mmol) and trimethyl borate (0.5 mL, 4.44 mmol) in THF (12 mL) at −78° C. was added LDA (1.5 M in cyclohexane, 2.6

Step E: Into a mixture of the crude boronic acid from step D (0.30 g, ~40% purity, 0.37 mmol), (S)-6-chloro-N-(1,1,1-trifluoropropan-2-yl)pyridine-3-sulfonamide (0.076 g, 0.26 mmol) and PdCl₂dppf (0.02 g, 0.027 mmol) in acetonitrile (2.0 mL) was added an aqueous solution of K₂CO₃ (2.0 M, 0.55 mL, 1.1 mmol). The mixture was stirred at room temperature over a period of three days. Aqueous workup followed by flash chromatography with dichloromethane and ethylacetate (0 to 10%) provided the title compound (0.063 g, 45%). Melting point: 172-175° C.; MS m/z 533.2 M+H⁺; ¹H NMR (500 MHz, CDCl₃): δ 9.23 (1H, d, J=2.0 Hz), 8.35 (1H, dd, J=8.5 Hz, J=2.5 Hz), 8.02 (1H, d, J=8.5 Hz), 7.60 (1H, d, J=2.0 Hz), 7.58 (1H, d, J=6.0 Hz), 6.64 (1H, t, J=73.5 Hz), 5.37-5.30 (1H, m), 4.99 (1H, d, J=9.5 Hz), 4.19-4.13 (1H, m), 2.54-2.40 (4H, m), 1.94-1.86 (2H, m), 1.47 (3H, d, J=7.0 Hz).

Additional compounds representative of the present invention may be prepared according to the procedure of Example 7 by substituting the appropriate starting materials, reagents and reaction conditions and include compounds selected from (wherein MS represents mass spec as MH⁺, unless otherwise indicated, m.p. represents melting point in ° C., and N/A indicates that the data was not obtained):

| Cpd | Name | m. p. | MS |
|---|---|---|---|
| 542 | 6-[3-cyano-1-cyclobutyl-6-(difluoromethoxy)-5-fluoro-1H-indol-2-yl]-N-(1,3-difluoropropan-2-yl)pyridine-3-sulfonamide | 160-164 | 515.2 |
| 573 | 6-[3-cyano-1-cyclopentyl-6-(difluoromethoxy)-5-fluoro-1H-indol-2-yl]-N-(1,3-difluoropropan-2-yl)pyridine-3-sulfonamide | 190-194 | 529.2 |
| 574 | 6-[3-cyano-1-cyclopentyl-6-(difluoromethoxy)-5-fluoro-1H-indol-2-yl]-N-[(2S)-1,1,1-trifluoropropan-2-yl]pyridine-3-sulfonamide | 181-184 | 547.4 |
| 575 | 6-(3-cyano-1-cyclopentyl-5-fluoro-6-hydroxy-1H-indol-2-yl)-N-(1,3-difluoropropan-2-yl)pyridine-3-sulfonamide | N/A | 479.1 |

-continued

| Cpd | Name | m. p. | MS |
|---|---|---|---|
| 576 | 6-(3-cyano-1-cyclopentyl-5-fluoro-6-hydroxy-1H-indol-2-yl)-N-[(2S)-1,1,1-trifluoropropan-2-yl]pyridine-3-sulfonamide | 214-216 | 497.2 |
| 648 | 6-[3-cyano-1-cyclobutyl-6-(difluoromethoxy)-5-fluoro-1H-indol-2-yl]-N-[(2R)-1,1,1-trifluoropropan-2-yl]pyridine-3-sulfonamide | 173-175 | 533.2 |
| 676 | 6-[3-cyano-1-cyclobutyl-6-(difluoromethoxy)-5-fluoro-1H-indol-2-yl]-N-(1,1,1-trifluoro-2-methylpropan-2-yl)pyridine-3-sulfonamide | 162-165 | 546.9 |
| 691 | 6-(3-cyano-1-cyclopentyl-5-hydroxy-6-methyl-1H-indol-2-yl)-N-[(2S)-1,1,1-trifluoropropan-2-yl]pyridine-3-sulfonamide | 232-233 | 493.1 |
| 711 | 6-(3-cyano-1-cyclobutyl-5-fluoro-6-hydroxy-1H-indol-2-yl)-N-[(2S)-1,1,1-trifluoropropan-2-yl]pyridine-3-sulfonamide | 194-196 | 483.9 |
| 712 | 6-[3-cyano-1-cyclobutyl-6-(difluoromethoxy)-5-fluoro-1H-indol-2-yl]-N-(difluoromethyl)-N-[(2S)-1,1,1-trifluoropropan-2-yl]pyridine-3-sulfonamide | N/A | 583.4 |
| 713 | 6-[3-cyano-1-cyclopentyl-6-(difluoromethoxy)-5-fluoro-1H-indol-2-yl]-N-[(2R)-1,1,1-trifluoropropan-2-yl]pyridine-3-sulfonamide | 197-200 | 547.3 |
| 719 | N-tert-butyl-6-(3-cyano-1-cyclobutyl-5-fluoro-6-hydroxy-1H-indol-2-yl)pyridine-3-sulfonamide | 242-245 | 443.2 |
| 720 | N-tert-butyl-6-[3-cyano-1-cyclobutyl-6-(difluoromethoxy)-5-fluoro-1H-indol-2-yl]pyridine-3-sulfonamide | N/A | 493.3 |
| 721 | N-tert-butyl-6-[3-cyano-1-cyclobutyl-6-(difluoromethoxy)-5-fluoro-1H-indol-2-yl]-N-(difluoromethyl)pyridine-3-sulfonamide | N/A | 543.2 |
| 722 | 6-[3-cyano-1-cyclobutyl-6-(difluoromethoxy)-5-fluoro-1H-indol-2-yl]pyridine-3-sulfonamide | 172-175 | 437.2 |
| 725 | 6-(3-cyano-1-cyclobutyl-5-fluoro-6-methoxy-1H-indol-2-yl)-N-[(2S)-1,1,1-trifluoropropan-2-yl]pyridine-3-sulfonamide | N/A | 497.3 |
| 726 | 6-(3-cyano-1-cyclobutyl-6-ethoxy-5-fluoro-1H-indol-2-yl)-N-[(2S)-1,1,1-trifluoropropan-2-yl]pyridine-3-sulfonamide | 193-196 | 511.2 |
| 738 | 6-[3-cyano-1-cyclobutyl-6-(difluoromethoxy)-5-fluoro-1H-indol-2-yl]-N-[(2S)-1,1,1-trifluorobutan-2-yl]pyridine-3-sulfonamide | 166-173 | N/A |
| 733 | 5-chloro-1-cyclobutyl-6-methyl-2-(5-{[(2S)-1,1,1-trifluoropropan-2-yl]sulfamoyl}pyrimidin-2-yl)-1H-indole-3-carboxamide | 171-173 | 516.2 |
| 780 | 6-chloro-1-cyclobutyl-2-[5-(propan-2-ylsulfamoyl)pyrimidin-2-yl]-1H-indole-3-carboxamide | 251-253 | 448.1 |
| 781 | 1-cyclobutyl-2-[5-(propan-2-ylsulfamoyl)pyrimidin-2-yl]-6-(trifluoromethoxy)-1H-indole-3-carboxamide | 222-223 | 498.1 |
| 782 | 1-cyclopentyl-2-[5-(propan-2-ylsulfamoyl)pyrimidin-2-yl]-6-(trifluoromethoxy)-1H-indole-3-carboxamide | 238-241 | 512.2 |
| 784 | 6-[3-cyano-6-(difluoromethoxy)-4-fluoro-1-(propan-2-yl)-1H-indol-2-yl]-N-[(2S)-1,1,1-trifluoropropan-2-yl]pyridine-3-sulfonamide | 193-194 | 519.2 |
| 786 | 6-[3-cyano-6-(difluoromethoxy)-5-fluoro-1-propyl-1H-indol-2-yl]-N-[(2S)-1,1,1-trifluoropropan-2-yl]pyridine-3-sulfonamide | 162-168 | 521.2 |
| 787 | 6-[3-cyano-1-(cyclopropylmethyl)-6-(difluoromethoxy)-5-fluoro-1H-indol-2-yl]-N-[(2S)-1,1,1-trifluoropropan-2-yl]pyridine-3-sulfonamide | 149-153 | 533.2 |
| 788 | 6-[3-cyano-6-(difluoromethoxy)-5-fluoro-1-propyl-1H-indol-2-yl]-N-[(2R)-1,1,1-trifluoropropan-2-yl]pyridine-3-sulfonamide | 160-166 | 521.2 |
| 789 | 6-[3-cyano-1-(cyclopropylmethyl)-6-(difluoromethoxy)-5-fluoro-1H-indol-2-yl]-N-[(2R)-1,1,1-trifluoropropan-2-yl]pyridine-3-sulfonamide | 148-153 | 533.2 |
| 790 | 6-[3-cyano-1-cyclobutyl-6-(difluoromethoxy)-5-fluoro-1H-indol-2-yl]-N-(1,1,1-trifluorobutan-2-yl)pyridine-3-sulfonamide | N/A | 546.5 |
| 791 | 6-[3-cyano-1-cyclobutyl-6-(difluoromethoxy)-5-fluoro-1H-indol-2-yl]-N-phenylpyridine-3-sulfonamide | 178-179 | 513.2 |
| 797 | 6-[3-cyano-1-cyclobutyl-6-(difluoromethoxy)-4-fluoro-1H-indol-2-yl]-N-[(2S)-1,1,1-trifluoropropan-2-yl]pyridine-3-sulfonamide | 210-212 | 531.1 |
| 808 | 6-[3-cyano-1-cyclobutyl-6-(difluoromethoxy)-5-fluoro-1H-indol-2-yl]-N-[1-(trifluoromethyl)cyclopropyl]pyridine-3-sulfonamide | 169-171 | 545.2 |
| 812 | 6-[3-cyano-1-(cyclopropylmethyl)-6-(difluoromethoxy)-5-fluoro-1H-indol-2-yl]pyridine-3-sulfonamide | 173-178 | 437.2 |
| 813 | 6-(3-cyano-1-cyclobutyl-5-fluoro-6-hydroxy-1H-indol-2-yl)-N-[1-(trifluoromethyl)cyclopropyl]pyridine-3-sulfonamide | N/A | 495.1 |
| 822 | 6-[3-cyano-1-cyclobutyl-6-(difluoromethoxy)-5-fluoro-1H-indol-2-yl]-4-methyl-N-[(2S)-1,1,1-trifluoropropan-2-yl]pyridine-3-sulfonamide | 204-210 | 547.1 |

-continued

| Cpd | Name | m. p. | MS |
|---|---|---|---|
| 827 | 6-[3-cyano-1-cyclobutyl-6-(difluoromethoxy)-5-fluoro-1H-indol-2-yl]-5-methyl-N-[(2S)-1,1,1-trifluoropropan-2-yl]pyridine-3-sulfonamide | 150-155 | 547.1 |
| 862 | 6-[3-cyano-1-cyclopentyl-6-(difluoromethoxy)-5-fluoro-1H-indol-2-yl]-N-(1,1,1-trifluoro-2-methylpropan-2-yl)pyridine-3-sulfonamide | 185-186 | 461.3 |
| 936 | 6-[3-cyano-6-(difluoromethoxy)-5-fluoro-1-(propan-2-yl)-1H-indol-2-yl]-N-[(2S)-1,1,1-trifluoropropan-2-yl]pyridine-3-sulfonamide | 184-188 | 521.0 |
| 937 | 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide | 130-134 | 535.3 |
| 940 | 6-[3-cyano-6-(difluoromethoxy)-5-fluoro-1-(2-hydroxyethyl)-1H-indol-2-yl]-N-[(2S)-1,1,1-trifluoropropan-2-yl]pyridine-3-sulfonamide | 203-208 | 523.1 |
| 1065 | N-{5-[3-cyano-1-cyclohexyl-6-(difluoromethoxy)-5-fluoro-1H-indol-2-yl]pyridin-2-yl}-2-methylpropane-2-sulfonamide | 278-280 | 521.6 |
| 1082 | N-(5-{3-cyano-1-[(1S)-1-cyclopropylethyl]-6-ethyl-5-fluoro-1H-indol-2-yl}pyridin-2-yl)-2-methylpropane-2-sulfonamide | 215.5-217.0 | 496.6 |
| 1092 | N-[6-(3-cyano-1-cyclohexyl-6-cyclopropyl-4-fluoro-1H-indol-2-yl)pyridin-3-yl]-2-methylpropane-2-sulfonamide | 252-255 | 495.5 |
| 1118 | 2-{6-[(tert-butylsulfonyl)amino]pyridin-3-yl}-1-cyclobutyl-6-ethyl-4-fluoro-1H-indole-3-carboxamide | 263-268 | 473.3 |

Example 8

6-[3-cyano-6-cyclopropyl-1-(pyrimidin-2-yl)-1H-indol-2-yl]-N-[(2S)-1,1,1-trifluoropropan-2-yl]pyridine-3-sulfonamide (Cpd 650)

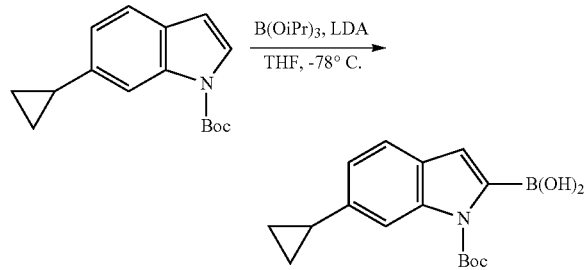

Step A: To a solution of tert-butyl 6-cyclopropyl-1H-indole-1-carboxylate (1.93 g, 7.51 mmol) and triisopropylborate (2.58 mL, 11.26 mmol) in THF was added LDA (1.5 M in cyclohexane, 7.0 mL, 10.5 mmol) at −78° C. The mixture was stirred at −78° C. for 30 min, quenched with ice water (60 mL) and stirred for 15 min without cooling. The mixture was extracted with ethyl acetate 1:1 in hexane (20 mL). The aqueous layer was acidified with aq. 2 N HCl to pH 5 and then extracted with CH$_2$Cl$_2$ (60 mL). The organic layer was dried over Na$_2$SO$_4$ and concentrated to give 1-(tert-butoxycarbonyl)-6-cyclopropyl-1H-indol-2-ylboronic acid as a solid (2.0 g, 88% yield) that was used in the next step without further purification.

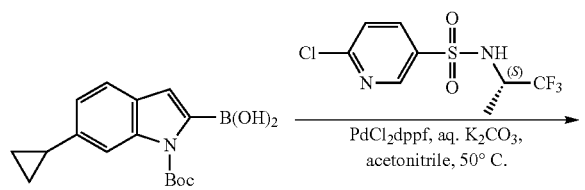

-continued

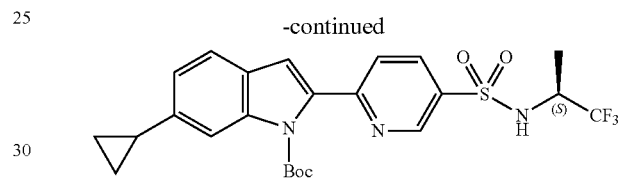

Step B: A mixture of 1-(tert-butoxycarbonyl)-6-cyclopropyl-1H-indol-2-ylboronic acid (1.10 g, 3.64 mmol), (S)-6-chloro-N-(1,1,1-trifluoropropan-2-yl)pyridine-3-sulfonamide (1.05 g, 3.64 mmol), PdCl$_2$(dppf) (178 mg, 0.22 mmol), aq. K$_2$CO$_3$ (2 M, 5.46 mL, 10.9 mmol) in acetonitrile (8 mL) was stirred at 50° C. overnight. The solvent was then evaporated and the residue purified on silica gel eluting with 0 to 10% ethyl acetate in CH$_2$Cl$_2$ to provide (S)-tert-butyl 6-cyclopropyl-2-(5-(N-(1,1,1-trifluoropropan-2-yl)sulfamoyl)pyridin-2-yl)-1H-indole-1-carboxylate (1.51 g, 81% yield). MS m/z 510.3 M+H$^+$; $^1$H NMR (500 MHz, CDCl$_3$): δ 9.65 (1H, s), 8.50 (1H, m), 8.01 (1H, d, J=8.2 Hz), 7.85 (1H, s), 7.52-7.49 (2H, m), 6.98 (1H, d, J=8.2 Hz), 4.98 (1H, d, J=8.4 Hz), 4.02 (1H, m), 2.02-1.98 (1H, m), 1.34 (3H, d, J=7.5 Hz), 0.98-0.96 (2H, m), 0.76-0.72 (2H, m).

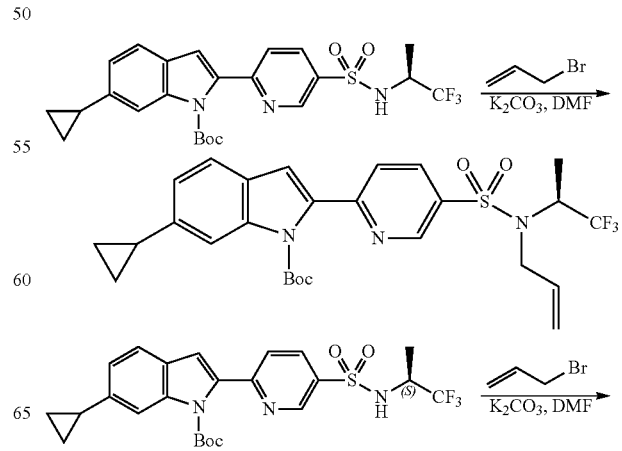

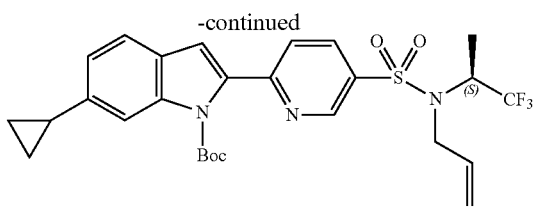

Step C: To a solution of (S)-tert-butyl 6-cyclopropyl-2-(5-(N-(1,1,1-trifluoropropan-2-yl)sulfamoyl)pyridin-2-yl)-1H-indole-1-carboxylate (503 mg, 0.99 mmol) and K$_2$CO$_3$ (276 mg, 2 mmol) in DMF (5 mL) was added allyl bromide (0.11 mL, 1.30 mmol). The mixture was stirred at room temperature for 2 hrs, and quenched with water (60 mL). The mixture was extracted with CH$_2$Cl$_2$ (3×20 mL). The solvent was then evaporated and (S)-tert-butyl 2-(5-(N-allyl-N-(1,1,1-trifluoropropan-2-yl)sulfamoyl)pyridin-2-yl)-6-cyclopropyl-1H-indole-1-carboxylate was obtained as a light yellow oil (500 mg, 92% yield). MS m/z 550.3 M+H$^+$. This material was used in the next step without further purification.

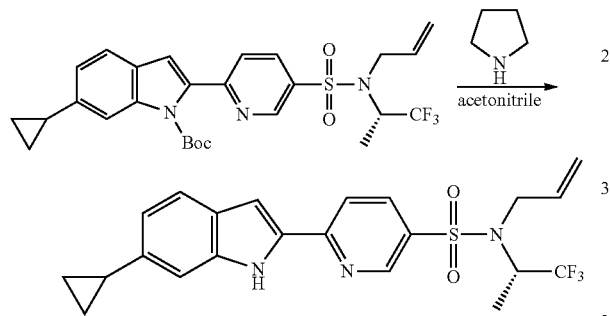

Step D: To a solution of (S)-tert-butyl 2-(5-(N-allyl-N-(1,1,1-trifluoropropan-2-yl)sulfamoyl)pyridin-2-yl)-6-cyclopropyl-1H-indole-1-carboxylate (500 mg, 0.91 mmol) in acetonitrile was added pyrrolidine (0.35 mL, 4.55 mmol). The mixture was stirred at room temperature for 5 hrs and the solvent was evaporated. The residue was purified on silica gel eluting with 0 to 10% ethyl acetate in CH$_2$Cl$_2$ to provide (S)-N-allyl-6-(6-cyclopropyl-1H-indol-2-yl)-N-(1,1,1-trifluoropropan-2-yl)pyridine-3-sulfonamide (370 mg, 91% yield). MS m/z 450.2 M+H$^+$; $^1$H NMR (500 MHz, CDCl$_3$): δ 9.28 (1H, s), 8.85 (1H, s), 7.96 (1H, d, J=5.5 Hz), 7.74 (1H, d, J=9.5 Hz), 7.49 (1H, d, J=5.5 Hz), 7.09 (1H, s), 7.01 (1H, s), 6.82-6.80 (1H, m), 5.75 (1H, m), 5.16-5.10 (2H, m), 4.64-4.62 (1H, m), 3.89 (2H, d, J=5.0 Hz), 2.00-1.96 (1H, m), 1.35 (3H, d, J=6.0 Hz), 0.98-0.96 (2H, m), 0.75-0.72 (2H, m).

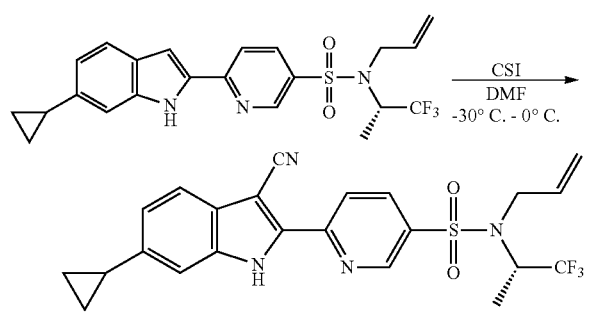

Step E: To a solution of (S)-N-allyl-6-(6-cyclopropyl-1H-indol-2-yl)-N-(1,1,1-trifluoropropan-2-yl)pyridine-3-sulfonamide sulfonamide (370 mg, 0.82 mmol) in DMF (5 mL) was added chlorosulfonyl isocyanate (0.14 mL, 1.6 mmol) at −30° C. The mixture was then warmed to 0° C. and stirred for 2 hrs. The mixture was then quenched with water (60 mL), extracted with CH$_2$Cl$_2$ (3×20 mL) and washed with brine (3×30 mL). The organic layer was collected, dried over Na$_2$SO$_4$, concentrated and the purified on silica gel eluting with 0 to 10% ethyl acetate in CH$_2$Cl$_2$ to provide (S)-N-allyl-6-(3-cyano-6-cyclopropyl-1H-indol-2-yl)-N-(1,1,1-trifluoropropan-2-yl)pyridine-3-sulfonamide (186 mg, 50% yield). MS m/z 475.2 M+H$^+$; $^1$H NMR (500 MHz, CDCl$_3$): δ 9.80 (1H, s), 9.02 (1H, s), 8.44 (1H, dd, J=1.0, 9.0 Hz), 8.11 (1H, dd, J=2.5, 8.5 Hz), 7.59 (1H, d, J=8.5 Hz), 7.20 (1H, s), 7.00 (1H, d, J=2.5, 8.5 Hz), 5.52 (1H, m), 5.28-5.20 (2H, m), 4.50 (1H, m), 3.98 (1H, bs), 2.02-1.96 (1H, m), 1.43 (3H, d, J=7.0 Hz), 0.98-0.96 (2H, m), 0.75-0.72 (2H, m).

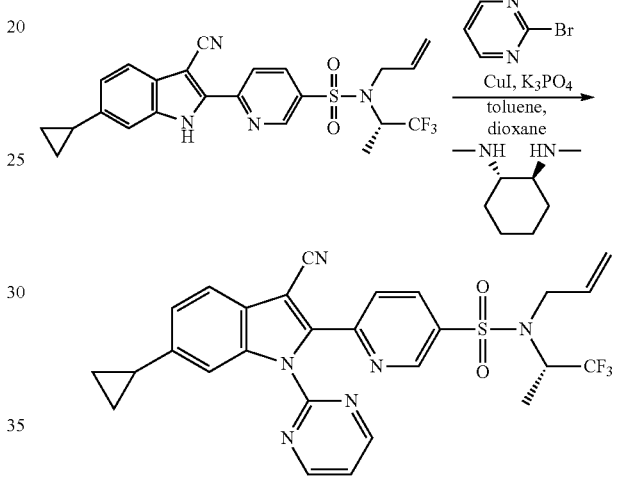

Step F: A mixture of (S)-N-allyl-6-(3-cyano-6-cyclopropyl-1H-indol-2-yl)-N-(1,1,1-trifluoropropan-2-yl)pyridine-3-sulfonamide (140 mg, 0.30 mmol), 2-bromo-pyrimidine (98 mg, 0.59 mmol), copper (I) iodide (11 mg, 0.06 mmol), (1R,2R)-N1,N2-dimethylcyclohexane-1,2-diamine (0.02 mL, 0.12 mmol), and K$_3$PO$_4$ (134 mg, 0.60 mmol) in toluene was stirred at 100° C. for 16 hrs. The mixture was then filtered through celite and the solvent evaporated. The residue was purified on silica gel eluting with 0 to 10% ethyl acetate in CH$_2$Cl$_2$ to provide (S)-N-allyl-6-(3-cyano-6-cyclopropyl-1-(pyrimidin-2-yl)-1H-indol-2-yl)-N-(1,1,1-trifluoropropan-2-yl)pyridine-3-sulfonamide (140 mg, 86%). MS m/z 553.3 M+H$^+$; $^1$H NMR (500 MHz, CDCl$_3$): δ 8.65 (1H, d, J=3.0 Hz), 8.62 (2H, d, J=4.0 Hz), 8.14 (1H, dd, J=4.0, 8.0 Hz), 8.01 (1H, d, J=9.0 Hz), 7.75 (1H, s), 7.64 (1H, d, J=7.5 Hz), 7.21-7.19 (1H, m), 7.04 (1H, d, J=9.0 Hz), 5.60 (1H, m), 5.28-5.25 (2H, m), 4.50 (1H, m), 3.86 (1H, d, J=6.5 Hz), 2.02-1.96 (1H, m), 1.32 (3H, d, J=8.5 Hz), 0.98-0.96 (2H, m), 0.75-0.72 (2H, m).

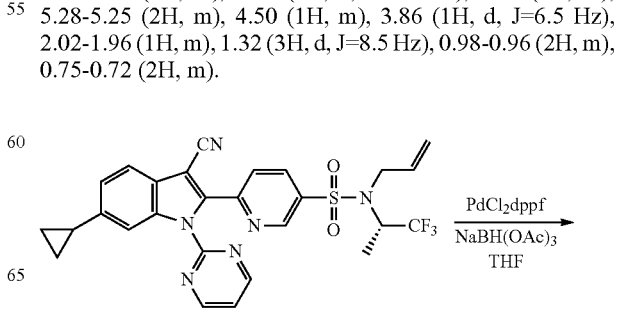

377
-continued

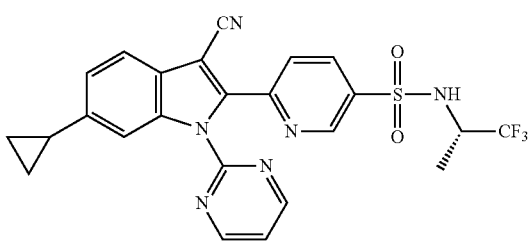

Step G: To a solution of (S)-N-allyl-6-(3-cyano-6-cyclopropyl-1-(pyrimidin-2-yl)-1H-indol-2-yl)-N-(1,1,1-trifluoropropan-2-yl)pyridine-3-sulfonamide (70 mg, 0.13 mmol) and PdCl$_2$(dppf) (10 mg, 0.013 mmol) in THF (1 mL) was added NaBH(AcO)$_3$ (40 mg, 0.19 mmol). The mixture was stirred at room temperature for 16 hrs and CH$_2$Cl$_2$ (20 mL) was added. The mixture was washed with sat. aq. NH$_4$Cl (20 mL), concentrated and purified on silica gel eluting with 0 to 10% ethyl acetate in CH$_2$Cl$_2$ to provide (S)-6-(3-cyano-6-cyclopropyl-1-(pyrimidin-2-yl)-1H-indol-2-yl)-N-(1,1,1-trifluoropropan-2-yl)pyridine-3-sulfonamide (54 mg, 83%). Melting point: 181-184° C.; MS m/z 513.2 M+H$^+$; $^1$H NMR (500 MHz, CDCl$_3$): δ8.28 (1H, s), 8.72 (1H, d, J=2.0 Hz), 8.60 (2H, d, J=9.0 Hz), 8.19 (1H, d, J=2.5 Hz), 8.18 (1H, d, J=2.0 Hz), 8.02 (1H, d, J=9.0 Hz), 7.76 (1H, s), 7.65 (1H, d, J=8.0 Hz), 7.21-7.20 (1H, m), 7.05 (1H, d, J=9.0 Hz), 5.50 (1H, s), 4.02-3.98 (1H, m), 2.02-1.96 (1H, m), 1.31 (3H, d, J=6.0 Hz), 0.98-0.96 (2H, m), 0.75-0.72 (2H, m).

Additional compounds representative of the present invention may be prepared according to the procedure of Example 8 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
| --- | --- | --- | --- |
| 541 | 6-[3-cyano-5-fluoro-6-methyl-1-(pyridin-2-yl)-1H-indol-2-yl]-N-[(2S)-1,1,1-trifluoropropan-2-yl]pyridine-3-sulfonamide | 160-164 | 504.8 |
| 601 | 6-[3-cyano-5-fluoro-1-(pyrimidin-2-yl)-1H-indol-2-yl]-N-[(2S)-1,1,1-trifluoropropan-2-yl]pyridine-3-sulfonamide | 201-203 | 491.2 |
| 634 | 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide | N/A | 505.1 |
| 682 | 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide | N/A | 556.9 |
| 704 | 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide | 195-198 | 519.1 |

378

Example 9

2-[5-(tert-butylsulfamoyl)pyridin-2-yl]-1-cyclopentyl-5-fluoro-6-methyl-1H-indole-3-carboxamide
(Cpd 683)

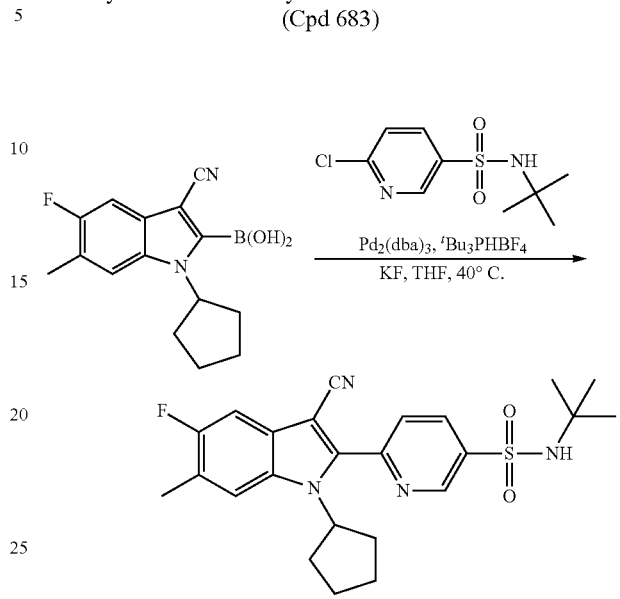

Step A: A mixture of 3-cyano-1-cyclopentyl-5-fluoro-6-methyl-1H-indol-2-ylboronic acid (125 mg, 0.42 mmol, 90%)[prepared as in Example 6, Step E], N-tert-butyl-6-chloropyridine-3-sulfonamide (69 mg, 0.28 mmol), tri-tert-butylphosphonium tetrafluoroborate (10 mg, 0.034 mmol), Pd$_2$(dba)$_3$ (16 mg, 0.017 mmol) and potassium fluoride (150 mg, 2.58 mmol) in THF (2.0 mL) was stirred at 40° C. overnight. The solvent was then evaporated and the residue purified on silica gel eluting with 0 to 10% ethyl acetate in CH$_2$Cl$_2$ to provide N-tert-butyl-6-(3-cyano-1-cyclopentyl-5-fluoro-6-methyl-1H-indol-2-yl)pyridine-3-sulfonamide (99 mg, 78%).

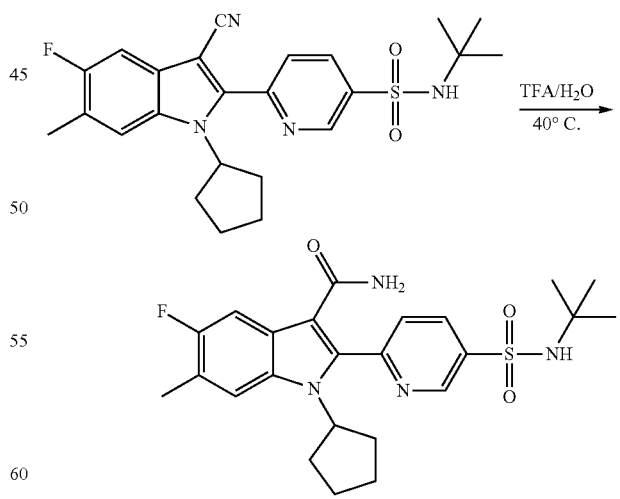

Step B: Into a solution of N-tert-butyl-6-(3-cyano-1-cyclopentyl-5-fluoro-6-methyl-1H-indol-2-yl)pyridine-3-sulfonamide (90 mg, 0.2 mmol) in TFA (2.0 mL) was added 2 drops of water. The mixture was stirred at 40° C. for 30 min and then evaporated. The residue was purified on silica gel eluting with 5 to 30% ethyl acetate in CH₂Cl₂ to provide the title compound (19 mg, 20%). MS m/z 473.3 M+H⁺; ¹H NMR (500 MHz, DMSO-d₆): δ 9.10 (1H, dd, J=2.0, 1.0 Hz), 8.29 (1H, dd, J=10.5, 2.5 Hz), 7.89 (1H, s), 7.81 (1H, dd, J=8.5, 1.0 Hz), 7.59 (1H, d, J=10.5 Hz), 7.49 (1H, d, J=6.5 Hz), 7.02 (2H, br s), 4.63-4.56 (1H, m), 2.46 (3H, s), 2.16-2.08 (2H, m), 1.96-1.85 (4H, m), 1.60-1.56 (2H, m), 1.17 (9H, s).

Additional compounds representative of the present invention may be prepared according to the procedure of Example 9 by substituting the appropriate starting materials, reagents and reaction conditions and include compounds selected from (wherein MS represents mass spec as MH⁺, unless otherwise indicated, m.p. represents melting point in ° C., and N/A indicates that the data was not obtained):

| Cpd | Name | m.p. | MS |
| --- | --- | --- | --- |
| 552 | 6-[3-cyano-1-cyclobutyl-6-(difluoromethoxy)-1H-indol-2-yl]pyridine-3-sulfonamide | 204-205 | 419.2 |
| 568 | 1-cyclobutyl-6-(difluoromethoxy)-2-(5-sulfamoylpyridin-2-yl)-1H-indole-3-carboxamide | 230-231 | 437.2 |
| 581 | 1-cyclobutyl-6-(difluoromethoxy)-2-{5-[(1,3-difluoropropan-2-yl)sulfamoyl]pyridin-2-yl}-1H-indole-3-carboxamide | 211-213 | 515.3 |
| 582 | 1-cyclobutyl-6-cyclopropyl-2-{5-[(1,3-difluoropropan-2-yl)sulfamoyl]pyridin-2-yl}-1H-indole-3-carboxamide | N/A | 489.3 |
| 699 | 1-cyclopentyl-5-fluoro-6-methyl-2-(5-{[(2R)-1,1,1-trifluoropropan-2-yl]sulfamoyl}pyridin-2-yl)-1H-indole-3-carboxamide | 243-245 | 513.3 |
| 700 | 1-cyclopentyl-5-fluoro-6-methyl-2-(5-{[(2S)-1,1,1-trifluoropropan-2-yl]sulfamoyl}pyridin-2-yl)-1H-indole-3-carboxamide | 244-246 | 512.8 |
| 701 | 1-cyclopentyl-5-fluoro-6-methyl-2-{5-[(1,1,1-trifluoro-2-methylpropan-2-yl)sulfamoyl]pyridin-2-yl}-1H-indole-3-carboxamide | 211-214 | 527.3 |
| 703 | 1-cyclobutyl-6-(difluoromethoxy)-5-fluoro-2-(5-{[(2S)-1,1,1-trifluoropropan-2-yl]sulfamoyl}pyridin-2-yl)-1H-indole-3-carboxamide | 184-186 | 550.8 |
| 706 | 1-cyclohexyl-5-fluoro-6-methyl-2-(5-{[(2S)-1,1,1-trifluoropropan-2-yl]sulfamoyl}pyridin-2-yl)-1H-indole-3-carboxamide | 273-279 | 527.3 |
| 707 | 1-cyclohexyl-5-fluoro-6-methyl-2-(5-{[(2S)-1,1,1-trifluoropropan-2-yl]sulfamoyl}pyrimidin-2-yl)-1H-indole-3-carboxamide | N/A | 528.3 |
| 714 | 1-cyclohexyl-5-fluoro-6-methyl-2-{5-[(1,1,1-trifluoro-2-methylpropan-2-yl)sulfamoyl]pyridin-2-yl}-1H-indole-3-carboxamide | 245-250 | 542.1 |
| 715 | 1-cyclohexyl-5-fluoro-6-methyl-2-(5-sulfamoylpyridin-2-yl)-1H-indole-3-carboxamide | 254-257 | 432.0 |
| 716 | 1-cyclohexyl-5-fluoro-6-methyl-2-(5-{[(2R)-1,1,1-trifluoropropan-2-yl]sulfamoyl}pyridin-2-yl)-1H-indole-3-carboxamide | 272-276 | 528.0 |
| 718 | 1-cyclopentyl-6-(difluoromethoxy)-5-fluoro-2-(5-{[(2R)-1,1,1-trifluoropropan-2-yl]sulfamoyl}pyridin-2-yl)-1H-indole-3-carboxamide | 218-220 | 565.4 |
| 723 | 2-[5-(tert-butylsulfamoyl)pyridin-2-yl]-1-cyclobutyl-6-(difluoromethoxy)-5-fluoro-1H-indole-3-carboxamide | 158-160 | 511.3 |
| 729 | 1-cyclobutyl-6-(difluoromethoxy)-5-fluoro-2-{5-[(1,1,1-trifluoro-2-methylpropan-2-yl)sulfamoyl]pyridin-2-yl}-1H-indole-3-carboxamide | 207-209 | 565.1 |
| 730 | 1-cyclopentyl-5-fluoro-6-methyl-2-(5-{[1-(trifluoromethyl)cyclopropyl]sulfamoyl}pyridin-2-yl)-1H-indole-3-carboxamide | 220-221 | 525.3 |
| 731 | 1-cyclobutyl-6-cyclopropyl-5-fluoro-2-(5-{[(2S)-1,1,1-trifluoropropan-2-yl]sulfamoyl}pyridin-2-yl)-1H-indole-3-carboxamide | 225-227 | 525.2 |
| 732 | 1-cyclobutyl-5-fluoro-6-methyl-2-(5-{[(2R)-1,1,1-trifluoropropan-2-yl]sulfamoyl}pyridin-2-yl)-1H-indole-3-carboxamide | 195-197 | 499.2 |
| 733 | 5-chloro-1-cyclobutyl-6-methyl-2-(5-{[(2S)-1,1,1-trifluoropropan-2-yl]sulfamoyl}pyrimidin-2-yl)-1H-indole-3-carboxamide | 171-173 | 516.2 |
| 734 | 5-chloro-1-cyclobutyl-6-methyl-2-(5-{[(2S)-1,1,1-trifluoropropan-2-yl]sulfamoyl}pyridin-2-yl)-1H-indole-3-carboxamide | 207-209 | 516.2 |
| 735 | 5-chloro-1-cyclobutyl-6-methyl-2-(5-{[(2R)-1,1,1-trifluoropropan-2-yl]sulfamoyl}pyridin-2-yl)-1H-indole-3-carboxamide | 208-210 | 515.2 |
| 736 | 6-chloro-1-cyclobutyl-5-fluoro-2-(5-{[(2S)-1,1,1-trifluoropropan-2-yl]sulfamoyl}pyridin-2-yl)-1H-indole-3-carboxamide | 241-243 | 519.2 |
| 737 | 1-cyclobutyl-5-fluoro-6-methyl-2-(5-{[(2S)-1,1,1-trifluoropropan-2-yl]sulfamoyl}pyridin-2-yl)-1H-indole-3-carboxamide | 190-194 | 499.2 |

-continued

| Cpd | Name | m.p. | MS |
|---|---|---|---|
| 745 | 5-chloro-1-cyclobutyl-2-[5-(propan-2-ylsulfamoyl)pyrimidin-2-yl]-1H-indole-3-carboxamide | 245-247 | 448.2 |
| 746 | 1-cyclohexyl-6-(difluoromethoxy)-2-(5-{[(2S)-1,1,1-trifluoropropan-2-yl]sulfamoyl}pyrimidin-2-yl)-1H-indole-3-carboxamide | 217-219 | 562.3 |
| 747 | 1-cyclohexyl-6-(difluoromethoxy)-2-[5-(propan-2-ylsulfamoyl)pyrimidin-2-yl]-1H-indole-3-carboxamide | 216-218 | 508.3 |
| 748 | 5-fluoro-1-(pyridin-2-yl)-2-(5-{[(2S)-1,1,1-trifluoropropan-2-yl]sulfamoyl}pyridin-2-yl)-1H-indole-3-carboxamide | N/A | 507.8 |
| 767 | 5-fluoro-6-methyl-1-(tetrahydro-2H-pyran-4-yl)-2-(5-{[(2R)-1,1,1-trifluoropropan-2-yl]sulfamoyl}pyridin-2-yl)-1H-indole-3-carboxamide | 258-262 | 529.2 |
| 768 | 5-fluoro-6-methyl-1-(tetrahydro-2H-pyran-4-yl)-2-{5-[(1,1,1-trifluoro-2-methylpropan-2-yl)sulfamoyl]pyridin-2-yl}-1H-indole-3-carboxamide | 200-206 | 543.2 |
| 769 | 5-fluoro-6-methyl-1-(tetrahydro-2H-pyran-4-yl)-2-(5-{[(2S)-1,1,1-trifluoropropan-2-yl]sulfamoyl}pyridin-2-yl)-1H-indole-3-carboxamide | 261-264 | 529.3 |
| 798 | 1-cyclobutyl-6-(difluoromethoxy)-5-fluoro-2-[5-(phenylsulfamoyl)pyridin-2-yl]-1H-indole-3-carboxamide | 204-206 | 531.2 |
| 806 | 1-cyclopentyl-6-(difluoromethoxy)-5-fluoro-2-(5-{[(2S)-1,1,1-trifluoropropan-2-yl]sulfamoyl}pyridin-2-yl)-1H-indole-3-carboxamide | 220-222 | 565.1 |
| 809 | 1-cyclobutyl-6-(difluoromethoxy)-5-fluoro-2-(5-{[1-(trifluoromethyl)cyclopropyl]sulfamoyl}pyridin-2-yl)-1H-indole-3-carboxamide | 197-200 | 563.1 |
| 825 | 1-cyclobutyl-6-(difluoromethoxy)-4-fluoro-2-(5-{[(2S)-1,1,1-trifluoropropan-2-yl]sulfamoyl}pyridin-2-yl)-1H-indole-3-carboxamide | 254-256 | 549.1 |
| 828 | 2-[5-(tert-butylsulfamoyl)pyridin-2-yl]-1-cyclobutyl-5-hydroxy-6-methyl-1H-indole-3-carboxamide | 292-293 | 455.1 |
| 829 | 1-cyclopentyl-6-cyclopropyl-5-fluoro-2-(5-{[(2R)-1,1,1-trifluoropropan-2-yl]sulfamoyl}pyridin-2-yl)-1H-indole-3-carboxamide | 233-234 | 537.1 |
| 830 | 1-cyclopentyl-6-ethyl-5-fluoro-2-(5-{[(2S)-1,1,1-trifluoropropan-2-yl]sulfamoyl}pyridin-2-yl)-1H-indole-3-carboxamide | 237-238 | 525.1 |
| 833 | 1-cyclobutyl-5-hydroxy-6-methyl-2-(5-{[(2S)-1,1,1-trifluoropropan-2-yl]sulfamoyl}pyridin-2-yl)-1H-indole-3-carboxamide | 256-258 | 495.1 |
| 834 | 1-cyclopentyl-5-methoxy-6-methyl-2-(5-{[(2R)-1,1,1-trifluoropropan-2-yl]sulfamoyl}pyridin-2-yl)-1H-indole-3-carboxamide | 273-275 | 523.1 |
| 838 | 1-cyclopentyl-6-cyclopropyl-5-fluoro-2-(5-{[(2S)-1,1,1-trifluoropropan-2-yl]sulfamoyl}pyridin-2-yl)-1H-indole-3-carboxamide | 255-257 | 537.5 |
| 839 | 6-(difluoromethoxy)-4-fluoro-1-(propan-2-yl)-2-(5-{[(2S)-1,1,1-trifluoropropan-2-yl]sulfamoyl}pyridin-2-yl)-1H-indole-3-carboxamide | 197-198 | 537.1 |
| 840 | 1-(cyclopropylmethyl)-6-(difluoromethoxy)-4-fluoro-2-(5-{[(2S)-1,1,1-trifluoropropan-2-yl]sulfamoyl}pyridin-2-yl)-1H-indole-3-carboxamide | 211-212 | 549.1 |
| 841 | 1-cyclopentyl-5-hydroxy-6-methyl-2-(5-{[(2S)-1,1,1-trifluoropropan-2-yl]sulfamoyl}pyridin-2-yl)-1H-indole-3-carboxamide | 272-274 | 509.1 |
| 849 | 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide | 235-236 | 537.3 |
| 850 | 1-cyclopentyl-6-cyclopropyl-5-fluoro-2-{5-[(1,1,1-trifluoro-2-methylpropan-2-yl)sulfamoyl]pyridin-2-yl}-1H-indole-3-carboxamide | 236-237 | 551.2 |
| 857 | 1-cyclohexyl-5-fluoro-6-methyl-2-(5-{[1-(trifluoromethyl)cyclopropyl]sulfamoyl}pyridin-2-yl)-1H-indole-3-carboxamide | 273-274 | 539.1 |
| 863 | 1-cyclopentyl-6-(difluoromethoxy)-5-fluoro-2-{5-[(1,1,1-trifluoro-2-methylpropan-2-yl)sulfamoyl]pyridin-2-yl}-1H-indole-3-carboxamide | 215-217 | 579.2 |
| 871 | 1-cyclopentyl-6-ethyl-5-fluoro-2-{5-[(1,1,1-trifluoro-2-methylpropan-2-yl)sulfamoyl]pyridin-2-yl}-1H-indole-3-carboxamide | 185-188 | 539.2 |
| 872 | 1-cyclopentyl-6-ethyl-5-fluoro-2-(5-{[1-(trifluoromethyl)cyclopropyl]sulfamoyl}pyridin-2-yl)-1H-indole-3-carboxamide | 196-197 | 537.2 |
| 874 | 5-fluoro-6-methyl-1-(pyridin-2-yl)-2-(5-{[(2S)-1,1,1-trifluoropropan-2-yl]sulfamoyl}pyridin-2-yl)-1H-indole-3-carboxamide | 142-148 | 521.5 |

-continued

| Cpd | Name | m.p. | MS |
|---|---|---|---|
| 875 | 5-fluoro-6-methyl-1-(pyrazin-2-yl)-2-(5-{[(2S)-1,1,1-trifluoropropan-2-yl]sulfamoyl}pyridin-2-yl)-1H-indole-3-carboxamide | 162-169 | 522.5 |
| 876 | 5-fluoro-1-(5-fluoropyridin-2-yl)-6-methyl-2-(5-{[(2S)-1,1,1-trifluoropropan-2-yl]sulfamoyl}pyridin-2-yl)-1H-indole-3-carboxamide | 224-228 | 539.5 |
| 877 | 5-fluoro-1-(6-fluoropyridin-2-yl)-6-methyl-2-(5-{[(2S)-1,1,1-trifluoropropan-2-yl]sulfamoyl}pyridin-2-yl)-1H-indole-3-carboxamide | 210-214 | 539.5 |
| 902 | 5-fluoro-1-(3-fluoropyridin-2-yl)-6-methyl-2-(5-{[(2S)-1,1,1-trifluoropropan-2-yl]sulfamoyl}pyridin-2-yl)-1H-indole-3-carboxamide | 130-138 | 539.5 |
| 904 | 5-fluoro-6-methyl-1-(5-methylpyrazin-2-yl)-2-(5-{[(2S)-1,1,1-trifluoropropan-2-yl]sulfamoyl}pyridin-2-yl)-1H-indole-3-carboxamide | 202-208 | 536.5 |
| 905 | 5-fluoro-6-methyl-1-(4-methylpyrimidin-2-yl)-2-(5-{[(2S)-1,1,1-trifluoropropan-2-yl]sulfamoyl}pyridin-2-yl)-1H-indole-3-carboxamide | 205-210 | 536.5 |
| 906 | 5-fluoro-1-(4-methoxypyrimidin-2-yl)-6-methyl-2-(5-{[(2S)-1,1,1-trifluoropropan-2-yl]sulfamoyl}pyridin-2-yl)-1H-indole-3-carboxamide | 167-174 | 552.5 |
| 909 | 6-ethyl-5-fluoro-1-(pyridin-2-yl)-2-(5-{[(2S)-1,1,1-trifluoropropan-2-yl]sulfamoyl}pyridin-2-yl)-1H-indole-3-carboxamide | N/A | 536.2 |
| 912 | 5-fluoro-6-methyl-1-(pyridazin-3-yl)-2-(5-{[(2S)-1,1,1-trifluoropropan-2-yl]sulfamoyl}pyridin-2-yl)-1H-indole-3-carboxamide | 176-181 | 522.5 |
| 913 | 5-fluoro-6-methyl-1-(pyridin-3-yl)-2-(5-{[(2S)-1,1,1-trifluoropropan-2-yl]sulfamoyl}pyridin-2-yl)-1H-indole-3-carboxamide | 223-227 | 521.5 |
| 980 | 6-ethyl-5-fluoro-1-(4-methylpyridin-2-yl)-2-(5-{[(2S)-1,1,1-trifluoropropan-2-yl]sulfamoyl}pyridin-2-yl)-1H-indole-3-carboxamide | 137-145 | 550.3 |
| 981 | 6-ethyl-5-fluoro-1-(5-fluoropyridin-2-yl)-2-(5-{[(2S)-1,1,1-trifluoropropan-2-yl]sulfamoyl}pyridin-2-yl)-1H-indole-3-carboxamide | 200-204 | 554.3 |
| 982 | 6-ethyl-5-fluoro-1-(2-methylpyrimidin-4-yl)-2-(5-{[(2S)-1,1,1-trifluoropropan-2-yl]sulfamoyl}pyridin-2-yl)-1H-indole-3-carboxamide | 115-120 | 551.3 |
| 994 | 6-ethyl-5-fluoro-1-(pyrazin-2-yl)-2-(5-{[(2S)-1,1,1-trifluoropropan-2-yl]sulfamoyl}pyridin-2-yl)-1H-indole-3-carboxamide | 120-127 | 537.3 |
| 995 | 6-ethyl-5-fluoro-1-(6-fluoropyridin-2-yl)-2-(5-{[(2S)-1,1,1-trifluoropropan-2-yl]sulfamoyl}pyridin-2-yl)-1H-indole-3-carboxamide | 230-233 | 554.3 |
| 996 | 5-chloro-1-cyclobutyl-2-(5-{[(2S)-1,1,1-trifluoropropan-2-yl]sulfamoyl}pyridin-2-yl)-1H-indole-3-carboxamide | 244-245 | 501.1 |
| 997 | 1-cyclobutyl-5-fluoro-2-(5-{[(2S)-1,1,1-trifluoropropan-2-yl]sulfamoyl}pyridin-2-yl)-1H-indole-3-carboxamide | 224-227 | 485.1 |
| 1019 | 6-ethyl-5-fluoro-1-(4-fluorophenyl)-2-(5-{[(2S)-1,1,1-trifluoropropan-2-yl]sulfamoyl}pyridin-2-yl)-1H-indole-3-carboxamide | 210-217 | 553.3 |
| 1020 | 1-(4-chlorophenyl)-6-ethyl-5-fluoro-2-(5-{[(2S)-1,1,1-trifluoropropan-2-yl]sulfamoyl}pyridin-2-yl)-1H-indole-3-carboxamide | 240-247 | 569.2-571.2 |
| 1021 | 6-ethyl-5-fluoro-1-(4-methylphenyl)-2-(5-{[(2S)-1,1,1-trifluoropropan-2-yl]sulfamoyl}pyridin-2-yl)-1H-indole-3-carboxamide | 228-233 | 549.3 |
| 1022 | 6-ethyl-5-fluoro-1-[4-(trifluoromethyl)phenyl]-2-(5-{[(2S)-1,1,1-trifluoropropan-2-yl]sulfamoyl}pyridin-2-yl)-1H-indole-3-carboxamide | 253-259 | 603.3 |
| 1023 | 6-ethyl-5-fluoro-1-(3-fluorophenyl)-2-(5-{[(2S)-1,1,1-trifluoropropan-2-yl]sulfamoyl}pyridin-2-yl)-1H-indole-3-carboxamide | 233-238 | 554.0 |
| 1024 | 6-ethyl-5-fluoro-1-(3-methylphenyl)-2-(5-{[(2S)-1,1,1-trifluoropropan-2-yl]sulfamoyl}pyridin-2-yl)-1H-indole-3-carboxamide | 179-189 | 550.1 |
| 1025 | 6-ethyl-5-fluoro-1-(3-methoxyphenyl)-2-(5-{[(2S)-1,1,1-trifluoropropan-2-yl]sulfamoyl}pyridin-2-yl)-1H-indole-3-carboxamide | N/A | 566.1 |
| 1026 | 6-ethyl-5-fluoro-1-[3-(trifluoromethyl)phenyl]-2-(5-{[(2S)-1,1,1-trifluoropropan-2-yl]sulfamoyl}pyridin-2-yl)-1H-indole-3-carboxamide | N/A | 604.0 |
| 1027 | 1-(3-chlorophenyl)-6-ethyl-5-fluoro-2-(5-{[(2S)-1,1,1-trifluoropropan-2-yl]sulfamoyl}pyridin-2-yl)-1H-indole-3-carboxamide | 200-205 | 569.2-571.2 |

-continued

| Cpd | Name | m.p. | MS |
|---|---|---|---|
| 1039 | 6-ethyl-5-fluoro-1-(5-methylpyridin-2-yl)-2-(5-{[(2S)-1,1,1-trifluoropropan-2-yl]sulfamoyl}pyridin-2-yl)-1H-indole-3-carboxamide | N/A | 550.5 |
| 1040 | 6-ethyl-5-fluoro-1-(pyridin-3-yl)-2-(5-{[(2S)-1,1,1-trifluoropropan-2-yl]sulfamoyl}pyridin-2-yl)-1H-indole-3-carboxamide | N/A | 537.3 |
| 1041 | 6-ethyl-5-fluoro-1-(pyrimidin-4-yl)-2-(5-{[(2S)-1,1,1-trifluoropropan-2-yl]sulfamoyl}pyridin-2-yl)-1H-indole-3-carboxamide | N/A | 537.2 |
| 1042 | 1-(3-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide | N/A | 570.5 572.5 |
| 1043 | 1-(5-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide | 256-254 | 570.5 572.5 |
| 1044 | 1-(5-chloropyridin-3-yl)-6-ethyl-5-fluoro-2-(5-{[(2S)-1,1,1-trifluoropropan-2-yl]sulfamoyl}pyridin-2-yl)-1H-indole-3-carboxamide | N/A | 570.2 572.2 |
| 1045 | 6-ethyl-5-fluoro-1-(pyridin-4-yl)-2-(5-{[(2S)-1,1,1-trifluoropropan-2-yl]sulfamoyl}pyridin-2-yl)-1H-indole-3-carboxamide | 219-224 | 536.3 |
| 1046 | 6-ethyl-5-fluoro-1-(pyridazin-3-yl)-2-(5-{[(2S)-1,1,1-trifluoropropan-2-yl]sulfamoyl}pyridin-2-yl)-1H-indole-3-carboxamide | 206-212 | 537.3 |
| 1047 | 6-ethyl-5-fluoro-1-(5-methylpyrimidin-2-yl)-2-(5-{[(2S)-1,1,1-trifluoropropan-2-yl]sulfamoyl}pyridin-2-yl)-1H-indole-3-carboxamide | 257-261 | 551.5 |
| 1048 | 1-(4-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide | 200-204 | 570.5 572.5 |

Example 10

6-(3-cyano-1-cyclopentyl-5-hydroxy-6-methyl-1H-indol-2-yl)-N-[(2R)-1,1,1-trifluoropropan-2-yl]pyridine-3-sulfonamide (Cpd 693)

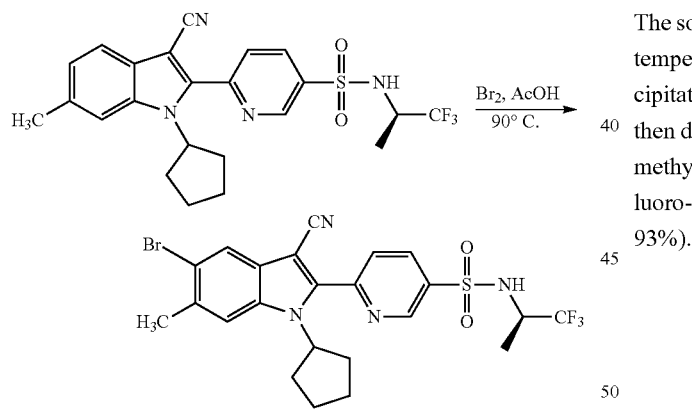

Step A: To a solution of (R)-6-(3-cyano-1-cyclopentyl-6-methyl-1H-indol-2-yl)-pyridine-3-sulfonic acid (2,2,2-trifluoro-1-methyl-ethyl)-amide (0.48 g, 1.05 mmol) in acidic acid (3 mL) was added bromine (0.35 g, 2.1 mmol) dropwise. The solution was stirred at 90° C. for 30 min, cooled to room temperature and then diluted with water (20 mL). The precipitate was collected and washed thoroughly with water, then dried to give (R)-6-(5-bromo-3-cyano-1-cyclopentyl-6-methyl-1H-indol-2-yl)-pyridine-3-sulfonic acid (2,2,2-trifluoro-1-methyl-ethyl)-amide as a light yellow solid (0.54 g, 93%).

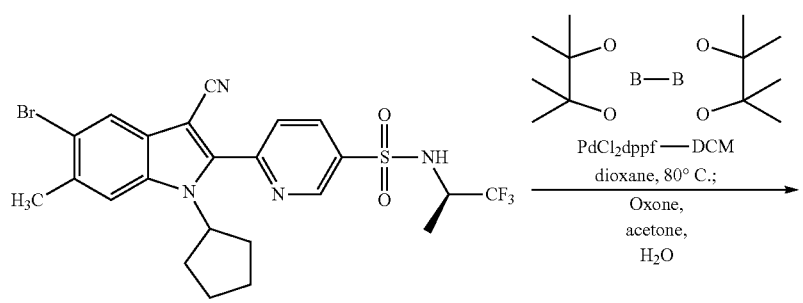

-continued

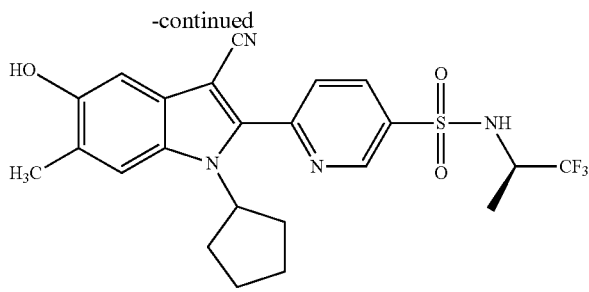

Step B: A mixture of (R)-6-(5-bromo-3-cyano-1-cyclopentyl-6-methyl-1H-indol-2-yl)-pyridine-3-sulfonic acid (2,2,2-trifluoro-1-methyl-ethyl)-amide (0.54 g, 0.97 mmol), bis(pinacolato)diboron (0.5 g, 2.0 mmol), PdCl₂dppf-CH₂Cl₂ complex (16 mg, 0.02 mmol) and potassium acetate (0.40 g, 4.0 mmol) in dioxane (5 mL) was stirred at 80° C. overnight. The mixture was then cooled to room temperature, diluted with ethyl acetate and filtered through a silica-celite pad. The filtrate was concentrated, dissolved in acetone (10 mL) and cooled to 0° C. Into this solution was added an aqueous solution of Oxone (10 mL, 1.0 M). The mixture was stirred at room temperature for 15 min and diluted with ethyl acetate and water. The aqueous layer was extracted with ethyl acetate. The organic extractions were combined and washed with aq. NaHSO₃ and brine, dried over Na₂SO₄, and concentrated. Purification on silica gel eluting with 40% ethyl acetate in hexane gave (R)-6-(3-cyano-1-cyclopentyl-5-hydroxy-6-methyl-1H-indol-2-yl)-pyridine-3-sulfonic acid (2,2,2-trifluoro-1-methyl-ethyl)-amide as a yellow solid (0.40 g, 84%); Melting point: 239-240° C.; MS m/z 493.2 M+H⁺; ¹H NMR (500 MHz, CD₃COCD₃) δ 9.24 (dd, J=2.30, 0.65 Hz, 1H), 8.50 (dd, J=8.25, 2.35 Hz, 1H), 8.42 (s, 1H), 8.10 (dd, J=8.25, 0.85 Hz, 1H), 7.47 (bs, 1H), 7.54 (s, 1H), 7.15 (s, 1H), 5.30-5.26 (m, 1H), 4.40-4.35 (m, 1H), 2.40 (s, 3H), 2.34-2.31 (m, 2H), 2.16-2.14 (m, 2H), 2.10-2.07 (m, 2H), 1.74-1.72 (m, 2H), 1.21 (d, J=2.25 Hz, 3H).

Additional compounds representative of the present invention may be prepared according to the procedure of Example 10 by substituting the appropriate starting materials, reagents and reaction conditions and include compounds selected from (wherein MS represents mass spec as MH⁺, unless otherwise indicated, m.p. represents melting point in ° C., and N/A indicates that the data was not obtained):

| Cpd | Name | m.p. | MS |
|---|---|---|---|
| 636 | 6-[5-chloro-3-cyano-1-cyclobutyl-6-(difluoromethoxy)-1H-indol-2-yl]-N-[(2S)-1,1,1-trifluoropropan-2-yl]pyridine-3-sulfonamide | N/A | 549.0 |
| 646 | 6-[1-cyclobutyl-6-(difluoromethoxy)-5-methyl-1H-indol-2-yl]-N-[(2S)-1,1,1-trifluoropropan-2-yl]pyridine-3-sulfonamide | 151-153 | 503.9 |
| 647 | 6-[3-cyano-1-cyclobutyl-6-(difluoromethoxy)-5-ethyl-1H-indol-2-yl]-N-[(2S)-1,1,1-trifluoropropan-2-yl]pyridine-3-sulfonamide | 160-162 | 543.0 |
| 658 | 6-[5-chloro-3-cyano-1-cyclobutyl-6-(difluoromethoxy)-1H-indol-2-yl]-N-(1-methylcyclopropyl)pyridine-3-sulfonamide | 218-226 | 507.1 |
| 659 | 2-[5-chloro-3-cyano-1-cyclobutyl-6-(difluoromethoxy)-1H-indol-2-yl]-N-(1,3-difluoropropan-2-yl)pyrimidine-5-sulfonamide | 228-232 | 532.1 |
| 660 | 6-[3-cyano-1-cyclobutyl-6-(difluoromethoxy)-5-methyl-1H-indol-2-yl]-N-[(2S)-1,1,1-trifluoropropan-2-yl]pyridine-3-sulfonamide | 168-170 | 529.2 |
| 669 | 6-(3-cyano-1-cyclopentyl-5-methoxy-6-methyl-1H-indol-2-yl)-N-[(2S)-1,1,1-trifluoropropan-2-yl]pyridine-3-sulfonamide | 211-211.5 | 506.9 |
| 674 | 6-[3-cyano-1-cyclobutyl-6-(difluoromethoxy)-5-hydroxy-1H-indol-2-yl]-N-[(2S)-1,1,1-trifluoropropan-2-yl]pyridine-3-sulfonamide | 174-177 | 530.9 |
| 675 | 6-(5-bromo-3-cyano-1-cyclopentyl-6-methyl-1H-indol-2-yl)-N-[(2S)-1,1,1-trifluoropropan-2-yl]pyridine-3-sulfonamide | 204-204.5 | 555.2 |
| 684 | 6-(5-bromo-3-cyano-1-cyclobutyl-6-hydroxy-1H-indol-2-yl)-N-[(2S)-1,1,1-trifluoropropan-2-yl]pyridine-3-sulfonamide | 223-224 | 545.1 |
| 685 | 6-[3-cyano-1-cyclobutyl-6-(difluoromethoxy)-5-(methylsulfanyl)-1H-indol-2-yl]-N-[(2S)-1,1,1-trifluoropropan-2-yl]pyridine-3-sulfonamide | N/A | 561.2 |
| 692 | 6-(5-bromo-3-cyano-1-cyclopentyl-6-methyl-1H-indol-2-yl)-N-[(2R)-1,1,1-trifluoropropan-2-yl]pyridine-3-sulfonamide, | 226.5-227 | 555.2 |
| 694 | 6-(3-cyano-1-cyclopentyl-5-methoxy-6-methyl-1H-indol-2-yl)-N-[(2R)-1,1,1-trifluoropropan-2-yl]pyridine-3-sulfonamide | 210.5-211 | 507.3 |

-continued

| Cpd | Name | m.p. | MS |
|---|---|---|---|
| 728 | 6-(1-cyclobutyl-5-fluoro-6-hydroxy-1H-indol-2-yl)-N-[(2S)-1,1,1-trifluoropropan-2-yl]pyridine-3-sulfonamide | 193-195 | 458.2 |
| 757 | 6-(3-cyano-1-cyclobutyl-5-methoxy-6-methyl-1H-indol-2-yl)-N-[(2S)-1,1,1-trifluoropropan-2-yl]pyridine-3-sulfonamide | 222-223 | 491.2 |
| 796 | 6-(3-cyano-1-cyclobutyl-5-hydroxy-6-methyl-1H-indol-2-yl)-N-[(2S)-1,1,1-trifluoropropan-2-yl]pyridine-3-sulfonamide | 193-195 | 477.0 |
| 805 | N-tert-butyl-6-(3-cyano-1-cyclobutyl-5-hydroxy-6-methyl-1H-indol-2-yl)pyridine-3-sulfonamide | 211-213 | 437.1 |
| 807 | 6-(3-cyano-1-cyclobutyl-5-hydroxy-6-methyl-1H-indol-2-yl)-N-[(2R)-1,1,1-trifluoropropan-2-yl]pyridine-3-sulfonamide | 209-210 | 477.0 |

Example 11

N-tert-butyl-6-(6-ethyl-5-fluoro-3-(methylsulfonyl)-1-(pyrimidin-2-yl)-1H-indol-2-yl)pyridine-3-sulfonamide (Cmp 869)

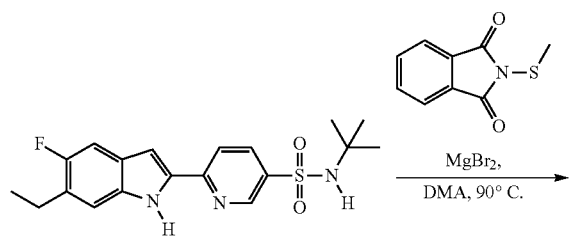

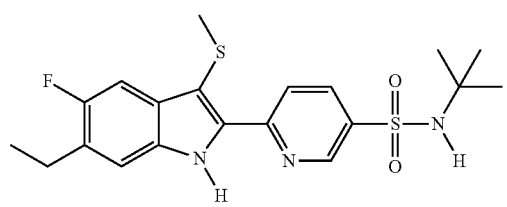

Step A: A mixture of N-tert-butyl-6-(6-ethyl-5-fluoro-3-1H-indol-2-yl)pyridine-3-sulfonamide (300 mg, 0.80 mmol), 2-(methylthio)isoindoline-1,3-dione (198 mg, 1.04 mmol), MgBr₂ (60 mg, 0.32 mmol), and DMA (1.5 mL) was heated at 90° C. for 15 hours. The reaction mixture was diluted in water and was extracted into ethyl acetate. The organic layer was washed with water and brine. The organic layer was dried over MgSO₄, filtered, and concentrated under reduced pressure. Purification by silica gel chromatography (4:1 hexanes:ethyl acetate) yielded N-tert-butyl-6-(6-ethyl-5-fluoro-3-(methylthio)-1H-indol-2-yl)pyridine-3-sulfonamide (328 mg, 97%) as a yellow solid.

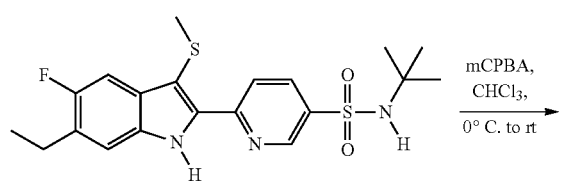

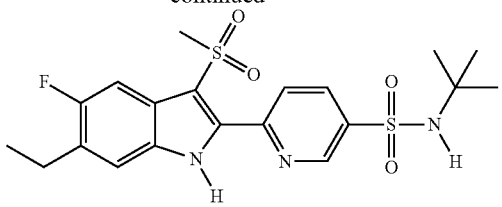

Step B: A suspension of N-tert-butyl-6-(6-ethyl-5-fluoro-3-(methylthio)-1H-indol-2-yl)pyridine-3-sulfonamide (250 mg, 0.60 mmol) in CHCl₃ (4 mL) was cooled to 0° C. m-CPBA (425 mg, 2.46 mmol) was added in one portion and stirred at room temperature for 1 hour. The reaction mixture was diluted in CH₂Cl₂, and washed with aq. NaHCO₃. The organic layer was dried over MgSO₄, filtered, and concentrated under reduced pressure. Purification by silica gel chromatography (30-40% ethyl acetate in hexanes), followed by ether trituration, yielded N-tert-butyl-6-(6-ethyl-5-fluoro-3-(methylsulfonyl)-1H-indol-2-yl)pyridine-3-sulfonamide (124 mg, 45%) as a white solid.

Step C: A mixture of N-tert-butyl-6-(6-ethyl-5-fluoro-3-(methylsulfonyl)-1H-indol-2-yl)pyridine-3-sulfonamide (115 mg, 0.25 mmol), 2-bromopyrimidine (88 mg, 0.55 mmol), CuI (28 mg, 0.15 mmol), K₂CO₃ (160 mg, 1.15 mmol), and DMF (0.5 mL) was heated at 110° C. for 15 hours. The reaction mixture was diluted in water and extracted into ethyl acetate. The organic layer was washed with water and then with brine. The organic layer was dried over MgSO₄, filtered, and concentrated under reduced pressure. Purification by silica gel chromatography (40% ethyl acetate in hexanes) yielded N-tert-butyl-6-(6-ethyl-5-fluoro-3-(methylsulfonyl)-1-(pyrimidin-2-yl)-1H-indol-2-yl)pyridine-3-sulfonamide (121 mg, 91%) as a white solid. Melting point: 244-248° C.; MS m/z 532.2 M+H$^+$; $^1$H NMR (DMSO-d$^6$, 500 MHz): δ 8.82 (d, 1H, J=2 Hz), 8.73 (d, 2H, 5.0 Hz), 8.23 (dd, 1H, J=8.0 Hz, 2 Hz), 8.05 (d, 1H, J=6.5 Hz), 7.96 (d, 1H, J=8 Hz), 7.87 (s, 1H), 7.76 (d, 1H, 10.5 Hz), 7.51 (t, 1H, J=5 Hz), 3.38 (s, 3H), 2.78 (q, 2H, J=7.5 Hz), 1.23 (t, 3H, 3.75 Hz), 1.13 (s, 9H).

Example 12

(S)-methyl 1-cyclopentyl-5-fluoro-6-methyl-2-(5-(N-(1,1,1-trifluoropropan-2-yl)sulfamoyl)pyridin-2-yl)-1H-indole-3-carboxylate (Cmp 756)

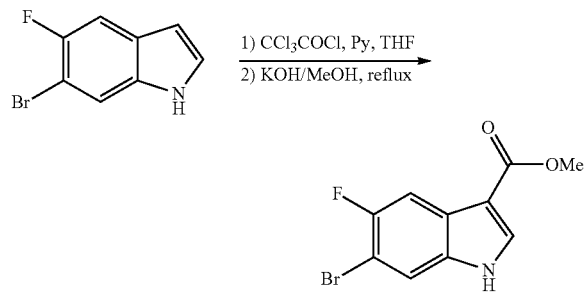

Step A: Into a solution of 6-bromo-5-fluoro-1H-indole (14.9 g, 70 mmol) in THF (160 mL) at 0° C. was added trichloroacetylchloride (7.4 mL, 90 mmol) dropwise. The mixture was stirred at room temperature over the weekend, and then partitioned between ethyl acetate and water. The ethyl acetate was washed with HCl (1 N), dried and evaporated. The residue was dissolved in methanol (500 mL), into which was added 50% KOH (5 mL) and the mixture was refluxed for 6 hr. The mixture was then evaporated until crystals started to come out and then filtered. The solid was washed with methanol and collected to give the title compound (10.6 g). The filtrate was concentrated and triturated with CH$_2$Cl$_2$ and hexane to give the second crop (3.8 g). The mother liquor was purified by flash chromatography with CH$_2$Cl$_2$ and ethyl acetate (0 to 20%) to give methyl 6-bromo-5-fluoro-1H-indole-3-carboxylate (0.75 g). The total yield was about 80%.

Step B: A mixture of methyl 6-bromo-5-fluoro-1H-indole-3-carboxylate (9.0 g, 33 mmol), bromocyclopentane (5.3 mL, 49.6 mmol) and Cs$_2$CO$_3$ (21.5 g, 66 mmol) in DMF (40 mL) was stirred at 80° C. overnight. The mixture was then poured into ice water, filtered and washed with water. The solid was collected and dried to give methyl 6-bromo-1-cyclopentyl-5-fluoro-1H-indole-3-carboxylate (10.3 g, yield 91%), which was used in the next step without further purification.

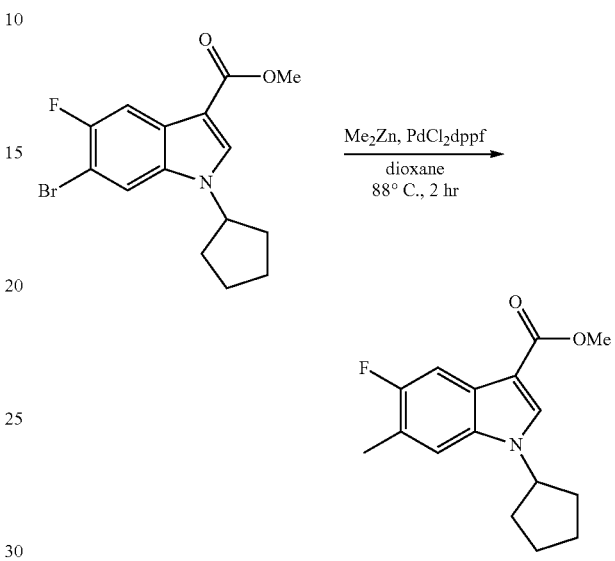

Step C: A mixture of methyl 6-bromo-1-cyclopentyl-5-fluoro-1H-indole-3-carboxylate (3.4 g, 10 mmol), dimethylzinc (1.2 M, 16.7 mL, 20 mmol) and PdCl$_2$dppf (163 mg, 0.2 mmol) in dioxane (20 mL) was stirred at 88° C. for 2 hr under nitrogen atmosphere. The mixture was then cooled and methanol was added in slowly followed by 2 N HCl. The mixture was treated with ethyl acetate, washed with water and brine, dried and evaporated. The residue was purified by flash chromatography with dichloromethane and hexane (1:1) to give methyl 1-cyclopentyl-5-fluoro-6-methyl-1H-indole-3-carboxylate (2.66 g, yield 97%).

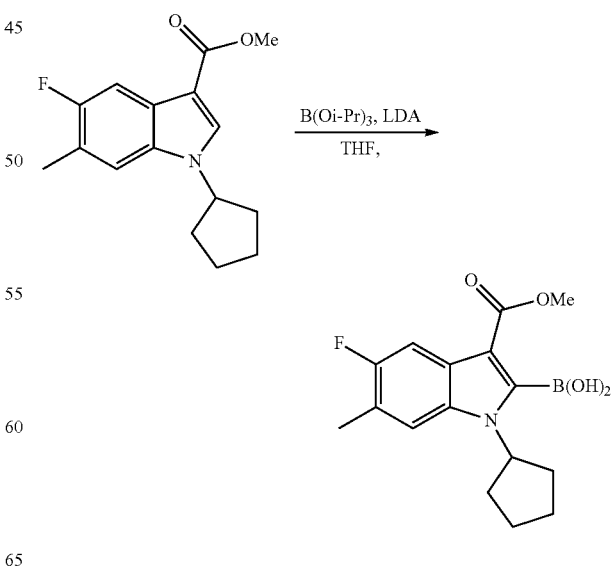

Step D: Into a solution of methyl 1-cyclopentyl-5-fluoro-6-methyl-1H-indole-3-carboxylate (2.64 g, 9.6 mmol) and triisopropylborate (4.0 mL, 17.28 mmol) in THF (40 mL) at −78° C. was added LDA (1.5 M, 8.3 mL, 12.48 mmol) dropwise. The mixture was stirred for 45 min, and then treated with ice water and extracted with dichloromethane. The organic layer was dried over sodium sulfate and evaporated to give 1-cyclopentyl-5-fluoro-3-(methoxycarbonyl)-6-methyl-1H-indol-2-ylboronic acid as a semi-solid (3.1 g, ~50% pure), which was used in next step without further purification.

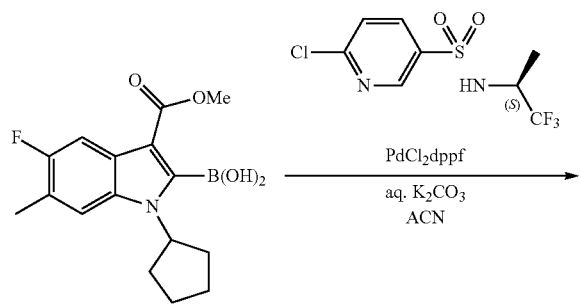

Step E: A mixture of 1-cyclopentyl-5-fluoro-3-(methoxycarbonyl)-6-methyl-1H-indol-2-ylboronic acid (2.2 mmol), (S)-6-chloro-N-(1,1,1-trifluoropropan-2-yl)pyridine-3-sulfonamide (0.53 g, 1.83 mmol), PdCl$_2$dppf (0.15 g, 0.183 mmol), aq. K$_2$CO$_3$ (2.0 M, 3.6 mL, 7.2 mmol) in acetonitrile (10 mL) was stirred at room temperature over the weekend. The mixture was treated with ethyl acetate and washed with water and brine and then concentrated. The residue was purified by flash chromatography with 0-15% ethyl acetate in CH$_2$Cl$_2$ to provide (S)-methyl 1-cyclopentyl-5-fluoro-6-methyl-2-(5-(N-(1,1,1-trifluoropropan-2-yl)sulfamoyl)pyridin-2-yl)-1H-indole-3-carboxylate (0.52 g, 54%). MS m/z 528.2 M+H$^+$; $^1$H NMR (500 MHz, CDCl$_3$): δ 9.21 (1H, d, J=1.8 Hz), 8.25 (1H, dd, J=8.2 Hz, J=2.2 Hz), 7.87 (1H, d, J=10.6 Hz), 7.73 (1H, d, J=8.2 Hz), 7.27 (1H, d, J=5.2 Hz), 5.09 (1H, d, J=9.6 Hz), 4.39-4.31 (1H, m), 4.17-4.10 (1H, m), 3.70 (3H, s), 2.44 (3H, d, J=1.8 Hz), 2.41-2.36 (2H, m), 2.20-1.96 (4H, m), 1.67-1.63 (2H, m), 1.45 (3H, d, J=7.0 Hz).

Additional compounds representative of the present invention may be prepared according to the procedure of Example 12 by substituting the appropriate starting materials, reagents and reaction conditions and include compounds selected from (wherein MS represents mass spec as MH$^+$ (unless otherwise indicated), m.p. represents melting point in ° C. and N/A indicates that the data was not obtained):

| Cpd | Name | m.p. | MS |
|---|---|---|---|
| 717 | methyl 1-cyclohexyl-5-fluoro-2-(5-{[(2S)-1,1,1-trifluoropropan-2-yl]sulfamoyl}pyridin-2-yl)-1H-indole-3-carboxylate | 232-240 | 528.2 |
| 754 | methyl 1-cyclopentyl-5-fluoro-6-methyl-2-{5-[(1,1,1-trifluoro-2-methylpropan-2-yl)sulfamoyl]pyridin-2-yl}-1H-indole-3-carboxylate | N/A | 542.2 |
| 755 | methyl 2-[5-(tert-butylsulfamoyl)pyridin-2-yl]-1-cyclopentyl-5-fluoro-6-methyl-1H-indole-3-carboxylate | N/A | 488.3 |
| 770 | methyl 2-[5-(tert-butylsulfamoyl)pyridin-2-yl]-1-cyclobutyl-5-fluoro-6-methyl-1H-indole-3-carboxylate | N/A | 474.3 |
| 771 | methyl 1-cyclobutyl-5-fluoro-6-methyl-2-(5-{[(2S)-1,1,1-trifluoropropan-2-yl]sulfamoyl}pyridin-2-yl)-1H-indole-3-carboxylate | N/A | 514.2 |
| 774 | methyl 1-cyclobutyl-5-fluoro-6-methyl-2-(5-{[(2S)-1,1,1-trifluoropropan-2-yl]sulfamoyl}pyrimidin-2-yl)-1H-indole-3-carboxylate | N/A | 515.2 |
| 1099 | methyl 2-{6-[(tert-butylsulfonyl)amino]pyridin-3-yl}-1-cyclohexyl-5-fluoro-6-(fluoromethoxy)-1H-indole-3-carboxylate | 166-167 | 356.0 |

Example 13

(S)-1-cyclopentyl-5-fluoro-6-methyl-2-(5-(N-(1,1,1-trifluoropropan-2-yl)sulfamoyl)pyridin-2-yl)-1H-indole-3-carboxylic acid (Cmp 758)

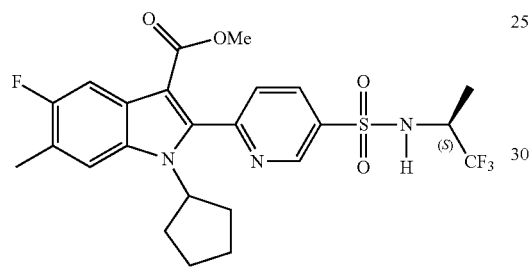

A mixture of (S)-methyl 1-cyclopentyl-5-fluoro-6-methyl-2-(5-(N-(1,1,1-trifluoropropan-2-yl)sulfamoyl)pyridin-2-yl)-1H-indole-3-carboxylate (0.45 g, 0.85 mmol), 25% aq. NaOH (2.0 mL) in ethanol (4.0 mL) was stirred at 80° C. overnight. The mixture was then treated with water and extracted with ether. The aqueous layer was acidified with 1N HCl to pH 4 and extracted with ethyl acetate. The organic layers were washed with brine, dried over Na₂SO₄ and evaporated to give (S)-1-cyclopentyl-5-fluoro-6-methyl-2-(5-(N-(1,1,1-trifluoropropan-2-yl)sulfamoyl)pyridin-2-yl)-1H-indole-3-carboxylic acid (0.36 g, 82%). MS m/z 514.2 M+H⁺; ¹H NMR (500 MHz, acetone-d₆): δ 10.55 (1H, br s), 9.17 (1H, d, J=2.2 Hz), 8.38 (1H, dd, J=8.2 Hz, J=2.2 Hz), 7.96 (1H, dd, J=8.2, 0.8 Hz), 7.89 (1H, d, J=10.7 Hz), 7.70 (br s, 1H), 7.57 (1H, d, J=6.4 Hz), 4.63-4.56 (1H, m), 4.34-4.29 (1H, m), 2.44 (3H, d, J=1.8 Hz), 2.29-2.25 (2H, m), 2.10-1.90 (4H, m), 1.67-1.56 (2H, m), 1.25 (3H, d, J=7.0 Hz).

Additional compounds representative of the present invention may be prepared according to the procedure of Example 13 by substituting the appropriate starting materials, reagents and reaction conditions and include compounds selected from (wherein MS represents mass spec as MH⁺ (unless otherwise indicated), m.p. represents melting point in °C. and N/A indicates that the data was not obtained):

| Cpd | Name | m.p. | MS |
|---|---|---|---|
| 741 | 1-cyclohexyl-5-fluoro-2-(5-{[(2S)-1,1,1-trifluoropropan-2-yl]sulfamoyl}pyridin-2-yl)-1H-indole-3-carboxylic acid | 216-220 | 514.2 |
| 765 | 1-cyclopentyl-5-fluoro-6-methyl-2-{5-[(1,1,1-trifluoro-2-methylpropan-2-yl)sulfamoyl]pyridin-2-yl}-1H-indole-3-carboxylic acid | 233-234 | 528.2 |
| 766 | 2-[5-(tert-butylsulfamoyl)pyridin-2-yl]-1-cyclopentyl-5-fluoro-6-methyl-1H-indole-3-carboxylic acid | 238-240 | 474.2 |
| 775 | 1-cyclobutyl-5-fluoro-6-methyl-2-(5-{[(2S)-1,1,1-trifluoropropan-2-yl]sulfamoyl}pyrimidin-2-yl)-1H-indole-3-carboxylic acid | N/A | 500.7 |
| 776 | 2-[5-(tert-butylsulfamoyl)pyridin-2-yl]-1-cyclobutyl-5-fluoro-6-methyl-1H-indole-3-carboxylic acid | N/A | 459.7 |
| 793 | 1-cyclobutyl-5-fluoro-6-methyl-2-(5-{[(2S)-1,1,1-trifluoropropan-2-yl]sulfamoyl}pyridin-2-yl)-1H-indole-3-carboxylic acid | 234-240 | 500.6 |
| 794 | 2-[5-(tert-butylsulfamoyl)pyrimidin-2-yl]-1-cyclobutyl-5-fluoro-6-methyl-1H-indole-3-carboxylic acid | 194-201 | 461.2 |
| 835 | 1-cyclohexyl-5-fluoro-6-methyl-2-(5-{[1-(trifluoromethyl)cyclopropyl]sulfamoyl}pyridin-2-yl)-1H-indole-3-carboxylic acid | 205-213 | 540.7 |
| 928 | 1-cyclohexyl-6-(difluoromethoxy)-5-fluoro-2-{5-[(1,1,1-trifluoro-2-methylpropan-2-yl)sulfamoyl]pyridin-2-yl}-1H-indole-3-carboxylic acid | N/A | 594.3 |
| 998 | 2-{5-[(tert-butylsulfonyl)amino]pyridin-2-yl}-1-cyclohexyl-6-ethyl-5-fluoro-1H-indole-3-carboxylic acid | 224-226 | 502.3 |
| 1028 | 2-{5-[(tert-butylsulfonyl)amino]pyrimidin-2-yl}-1-cyclohexyl-6-ethyl-5-fluoro-1H-indole-3-carboxylic acid | 236-237 | 503.6 |
| 1029 | 2-{2-[(tert-butylsulfonyl)amino]pyrimidin-5-yl}-1-cyclohexyl-6-ethyl-5-fluoro-1H-indole-3-carboxylic acid | N/A | 503.6 |
| 1036 | 2-{2-[(tert-butylsulfonyl)amino]pyrimidin-5-yl}-1-cyclohexyl-6-ethyl-5-fluoro-1H-indole-3-carboxamide | >300 | 502.6 |
| 1037 | 2-{6-[(tert-butylsulfonyl)amino]pyridin-3-yl}-1-cyclohexyl-6-ethyl-5-fluoro-1H-indole-3-carboxamide | 297-299 | 501.7 |
| 1064 | 2-{6-[(tert-butylsulfonyl)amino]pyridin-3-yl}-1-cyclohexyl-6-(difluoromethoxy)-5-fluoro-1H-indole-3-carboxylic acid | N/A | 540.6 |
| 1080 | 2-{6-[(tert-butylsulfonyl)amino]pyridin-3-yl}-1-[(1S)-1-cyclopropylethyl]-6-(difluoromethoxy)-5-fluoro-1H-indole-3-carboxylic acid | N/A | 526.3 |
| 1084 | 2-{6-[(tert-butylsulfonyl)amino]pyridin-3-yl}-1-[(1R)-1-cyclopropylethyl]-6-(difluoromethoxy)-5-fluoro-1H-indole-3-carboxylic acid | N/A | 526.1 |
| 1086 | 2-{6-[(tert-butylsulfonyl)amino]-4-methylpyridin-3-yl}-1-[(1R)-1-cyclopropylethyl]-6-(difluoromethoxy)-5-fluoro-1H-indole-3-carboxylic acid | N/A | 540.7 |
| 1093 | 2-{6-[(tert-butylsulfonyl)amino]-2-methylpyridin-3-yl}-6-(difluoromethoxy)-5-fluoro-1-(propan-2-yl)-1H-indole-3-carboxylic acid | N/A | 514.8 |
| 1094 | 2-{6-[(tert-butylsulfonyl)amino]-2-methylpyridin-3-yl}-1-[(1R)-1-cyclopropylethyl]-6-(difluoromethoxy)-5-fluoro-1H-indole-3-carboxylic acid | N/A | 540.2 |
| 1103 | 2-{6-[(tert-butylsulfonyl)amino]pyridin-3-yl}-1-[(1R)-1-cyclopropylethyl]-6-ethyl-5-fluoro-1H-indole-3-carboxylic acid | 165-decomp. | 488.5 |

Example 14

(S)-1-cyclopentyl-5-fluoro-N,6-dimethyl-2-(5-(N-(1,1,1-trifluoropropan-2-yl)sulfamoyl)pyridin-2-yl)-1H-indole-3-carboxamide (Cmp 761)

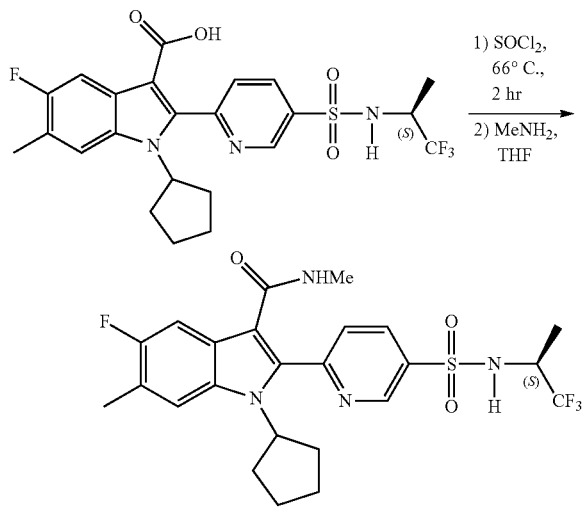

A mixture of (S)-1-cyclopentyl-5-fluoro-6-methyl-2-(5-(N-(1,1,1-trifluoropropan-2-yl)sulfamoyl)pyridin-2-yl)-1H-indole-3-carboxylic acid (300 mg, 0.58 mmol) in $SOCl_2$ (4 mL) was stirred at 66° C. for 2 h. Volatiles were removed by a stream of nitrogen followed by vacuum to give (S)-1-cyclopentyl-5-fluoro-6-methyl-2-(5-(N-(1,1,1-trifluoropropan-2-yl)sulfamoyl)pyridin-2-yl)-1H-indole-3-carbonyl chloride as a solid. The above prepared (S)-1-cyclopentyl-5-fluoro-6-methyl-2-(5-(N-(1,1,1-trifluoropropan-2-yl)sulfamoyl)pyridin-2-yl)-1H-indole-3-carbonyl chloride (100 mg, 0.188 mmol) was treated with a solution of methylamine in THF (2.0 M, 5 mL, 10 mmol) and stirred at room temperature for 5 min. The mixture was then treated with ethyl acetate, washed with water and brine, dried over $Na_2SO_4$ and evaporated to give (S)-1-cyclopentyl-5-fluoro-N,6-dimethyl-2-(5-(N-(1,1,1-trifluoropropan-2-yl)sulfamoyl)pyridin-2-yl)-1H-indole-3-carboxamide (66 mg, 67%). MS m/z 527.3 M+H$^+$; $^1$H NMR (500 MHz, CDCl$_3$): δ 9.18 (1H, br s), 8.30 (1H, dd, J=8.0 Hz, J=2.0 Hz), 7.73 (1H, d, J=8.5 Hz), 7.66 (1H, d, J=10.5 Hz), 7.28 (1H, br s), 6.26 (1H, br s), 5.91 (1H, d, J=9.5 Hz), 4.51-4.40 (1H, m), 4.15-4.10 (1H, m), 2.84 (3H, s), 2.43 (3H, d, J=1.5 Hz), 2.30-2.23 (2H, m), 2.10-1.90 (4H, m), 1.68-1.62 (2H, m), 1.42 (3H, d, J=8.5 Hz).

Additional compounds representative of the present invention may be prepared according to the procedure of Example 14 by substituting the appropriate starting materials, reagents and reaction conditions and include compounds selected from (wherein MS represents mass spec as MH$^+$ (unless otherwise indicated), m.p. represents melting point in ° C. and N/A indicates that the data was not obtained):

| Cpd | Name | m.p. | MS |
| --- | --- | --- | --- |
| 762 | 1-cyclopentyl-N-ethyl-5-fluoro-6-methyl-2-(5-{[(2S)-1,1,1-trifluoropropan-2-yl]sulfamoyl}pyridin-2-yl)-1H-indole-3-carboxamide | 160-162 | 541.3 |
| 763 | 1-cyclopentyl-5-fluoro-6-methyl-N-(propan-2-yl)-2-(5-{[(2S)-1,1,1-trifluoropropan-2-yl]sulfamoyl}pyridin-2-yl)-1H-indole-3-carboxamide | 234-236 | 555.3 |
| 783 | 1-cyclopentyl-5-fluoro-N,N,6-trimethyl-2-(5-{[(2S)-1,1,1-trifluoropropan-2-yl]sulfamoyl}pyridin-2-yl)-1H-indole-3-carboxamide | 278-280 | 541.2 |
| 795 | 2-[5-(tert-butylsulfamoyl)pyridin-2-yl]-1-cyclobutyl-5-fluoro-N,6-dimethyl-1H-indole-3-carboxamide | 215-218 | 473.2 |
| 799 | 2-[5-(tert-butylsulfamoyl)pyridin-2-yl]-1-cyclopentyl-5-fluoro-N,6-dimethyl-1H-indole-3-carboxamide | 248-250 | 487.3 |
| 800 | 2-[5-(tert-butylsulfamoyl)pyridin-2-yl]-1-cyclobutyl-5-fluoro-6-methyl-1H-indole-3-carboxamide | 189-193 | 459.3 |
| 801 | 1-cyclobutyl-5-fluoro-N,6-dimethyl-2-(5-{[(2S)-1,1,1-trifluoropropan-2-yl]sulfamoyl}pyridin-2-yl)-1H-indole-3-carboxamide | N/A | 513.2 |
| 802 | 2-[5-(tert-butylsulfamoyl)pyrimidin-2-yl]-1-cyclobutyl-5-fluoro-N,6-dimethyl-1H-indole-3-carboxamide | 211-213 | 474.2 |
| 999 | 2-{5-[(tert-butylsulfonyl)amino]pyridin-2-yl}-1-cyclohexyl-6-ethyl-5-fluoro-1H-indole-3-carboxamide | 264-265 | 501.4 |
| 1063 | 2-{6-[(tert-butylsulfonyl)amino]pyridin-3-yl}-1-cyclohexyl-6-(difluoromethoxy)-5-fluoro-1H-indole-3-carboxamide | 296-297 | 539.6 |
| 1081 | 2-{6-[(tert-butylsulfonyl)amino]pyridin-3-yl}-1-[(1S)-1-cyclopropylethyl]-6-(difluoromethoxy)-5-fluoro-1H-indole-3-carboxamide | 239-241 | 525.4 |
| 1085 | 2-{6-[(tert-butylsulfonyl)amino]pyridin-3-yl}-1-[(1R)-1-cyclopropylethyl]-6-(difluoromethoxy)-5-fluoro-1H-indole-3-carboxamide | 228-230 | 525.1 |
| 1087 | 2-{6-[(tert-butylsulfonyl)amino]-4-methylpyridin-3-yl}-1-[(1R)-1-cyclopropylethyl]-6-(difluoromethoxy)-5-fluoro-1H-indole-3-carboxamide | 250-254 | 539.4 |
| 1095 | 2-{6-[(tert-butylsulfonyl)amino]-2-methylpyridin-3-yl}-6-(difluoromethoxy)-5-fluoro-1-(propan-2-yl)-1H-indole-3-carboxamide | 234-235 | 513.4 |
| 1096 | 2-{6-[(tert-butylsulfonyl)amino]-2-methylpyridin-3-yl}-1-[(1S)-1-cyclopropylethyl]-6-(difluoromethoxy)-5-fluoro-1H-indole-3-carboxamide | 147-151 | 539.2 |

-continued

| Cpd | Name | m.p. | MS |
|---|---|---|---|
| 1100 | 2-{6-[(tert-butylsulfonyl)amino]pyridin-3-yl}-6-cyclopropyl-5-fluoro-1-phenyl-1H-indole-3-carboxamide | 272-274 | 507.3 |
| 1102 | 2-{6-[(tert-butylsulfonyl)amino]pyridin-3-yl}-1-cyclohexyl-5-fluoro-6-(fluoromethoxy)-1H-indole-3-carboxamide | 274-276 | 521.0 |
| 1104 | 2-{6-[(tert-butylsulfonyl)amino]pyridin-3-yl}-1-[(1R)-1-cyclopropylethyl]-6-ethyl-5-fluoro-1H-indole-3-carboxamide | 255.5-259.0 | 487.5 |

Example 15

N-tert-butyl-6-(3,6-diacetyl-5-fluoro-1-(pyrimidin-2-yl)-1H-indol-2-yl)pyridine-3-sulfonamide (Cmp 939)

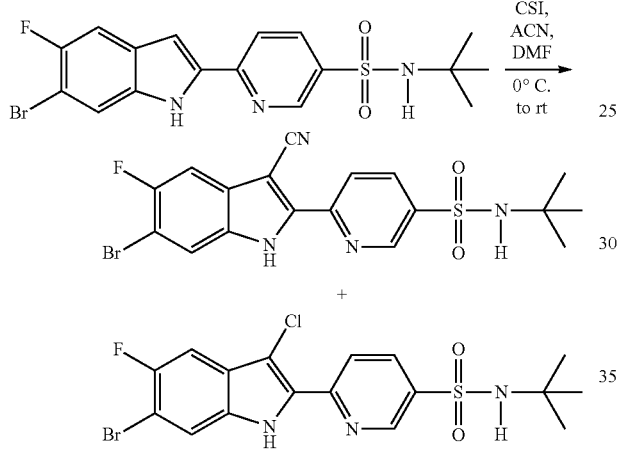

Step A: Into a suspension of 6-(6-bromo-5-fluoro-1H-indol-2-yl)-N-tert-butylpyridine-3-sulfonamide (2.4 g, 5.6 mmol) in acetonitrile (5.6 mL) and DMF (11.2 mL) at 0° C. was added chlorosulfonyl isocyanate (0.97 mL, 11.2 mmol) dropwise. The mixture was stirred at 0° C. for 15 min and then 30 min at room temperature. The reaction was quenched by addition of ice water. The mixture was extracted with ethyl acetate, dried and concentrated. The residue was treated with dichloromethane and filtered. The solid was collected as a mixture of 6-(6-bromo-3-cyano-5-fluoro-1H-indol-2-yl)-N-tert-butylpyridine-3-sulfonamide and 6-(6-bromo-3-chloro-5-fluoro-1H-indol-2-yl)-N-tert-butylpyridine-3-sulfonamide, which was used in the next step without further purification.

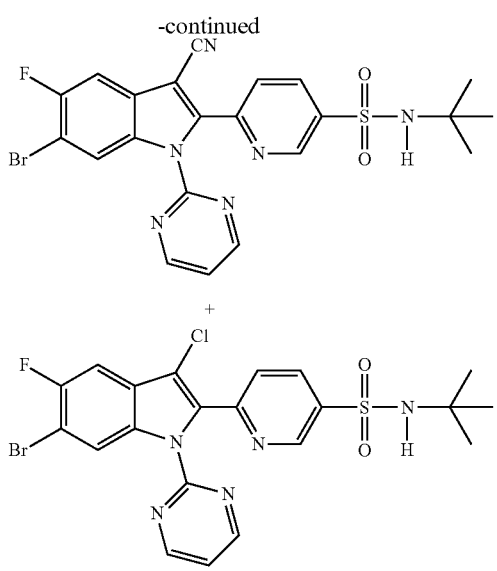

Step B: The mixture prepared as above (0.71 g) was mixed with 2-bromopyrimidine (0.5 g, 3.14 mmol), potassium carbonate (0.65 g, 4.71 mmol) and CuI (60 mg, 0.314 mmol) in DMF (2.0 mL) was stirred at 110° C. for 24 hr under nitrogen atmosphere. The mixture was then treated with ethyl acetate, washed with aqueous ammonium chloride and brine, dried over sodium sulfate and evaporated. The residue was purified with dichloromethane and ethyl acetate (0 to 8%) to give a mixture (0.6 g) of 6-(6-bromo-3-cyano-5-fluoro-1-(pyrimidin-2-yl)-1H-indol-2-yl)-N-tert-butylpyridine-3-sulfonamide (~86%) and 6-(6-bromo-3-chloro-5-fluoro-1-1.0 (pyrimidin-2-yl)-1H-indol-2-yl)-N-tert-butylpyridine-3-sulfonamide (~14%), which was used in the next step reaction without further purification.

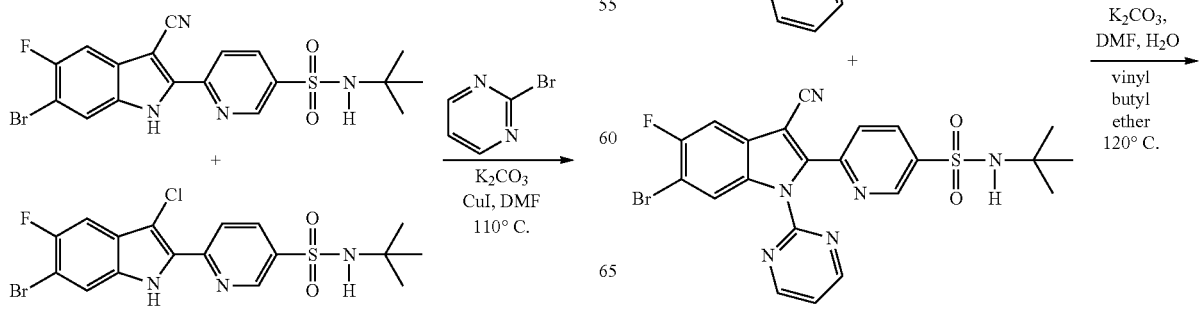

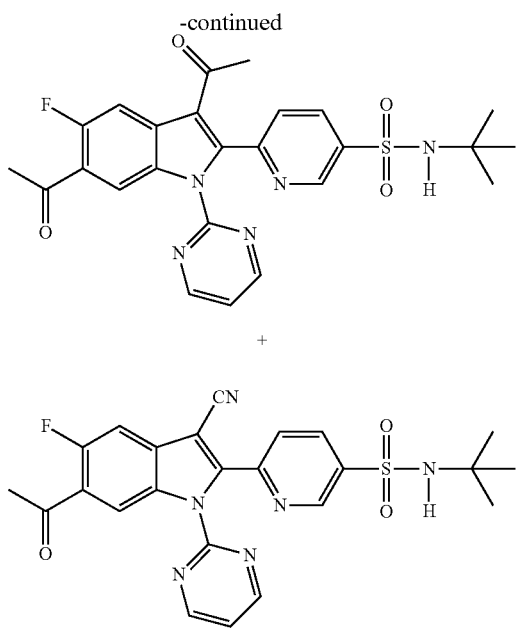

+

Example 16

Cmp 883

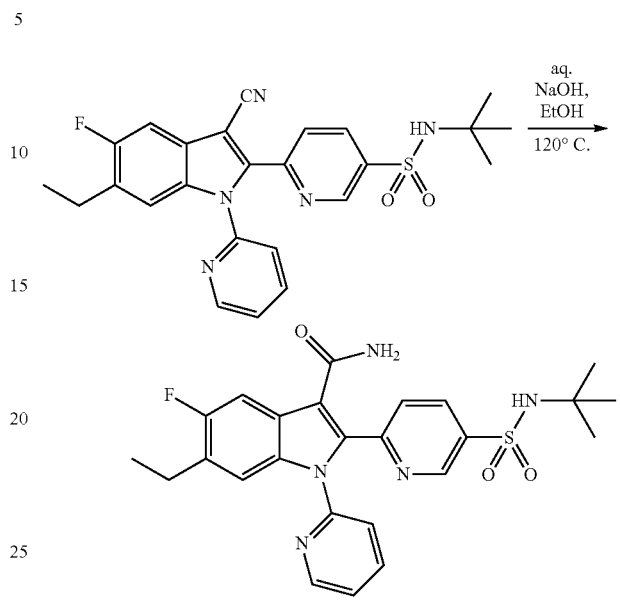

Step C: A mixture of 6-(6-bromo-3-cyano-5-fluoro-1-(pyrimidin-2-yl)-1H-indol-2-yl)-N-tert-butylpyridine-3-sulfonamide and 6-(6-bromo-3-chloro-5-fluoro-1-(pyrimidin-2-yl)-1H-indol-2-yl)-N-tert-butylpyridine-3-sulfonamide (84 mg, 0.156 mmol), Pd(OAc)$_2$ (7.6 mg, 0.034 mmol), 1,3-bis(diphenylphosphino)propane (31 mg, 0.075 mmol), K$_2$CO$_3$ (0.19 g, 1.36 mmol), butyl vinyl ether (0.73 mL, 5.66 mmol) in DMF (3.0 mL) and water (0.35 mL) was stirred at 120° C. overnight under N$_2$ atmosphere. The mixture was then acidified to pH ~1 with 1 N HCl, stirred at room temperature for 1 hr, extracted with ethyl acetate followed by drying with Na$_2$SO$_4$, evaporation and purification by flash chromatography with 5 to 20% ethyl acetate in CH$_2$Cl$_2$ to give N-tert-butyl-6-(3,6-diacetyl-5-fluoro-1-(pyrimidin-2-yl)-1H-indol-2-yl)pyridine-3-sulfonamide (58 mg, 73%). MS m/z 510.1 M+H$^+$; $^1$H NMR (500 MHz, acetone-d$_6$): δ 9.07 (1H, d, J=2.2 Hz), 8.77 (1H, d, J=6.2 Hz), 8.58 (2H, d, 4.9 Hz), 8.28 (1H, dd, J=8.2, 2.2 Hz), 8.12 (1H, d, J=10.2 Hz), 7.78 (1H, dd, J=8.2, 0.7 Hz), 7.21 (1H, t, J=4.9 Hz), 4.80 (1H, br s), 2.75 (3H, d, J=5.4 Hz), 2.21 (3H, s), 1.25 (9H, s).

A pressure vessel was charged with (S)-6-(3-cyano-6-ethyl-5-fluoro-1-(pyridin-2-yl)-1H-indol-2-yl)-N-(1,1,1-trifluoropropan-2-yl)pyridine-3-sulfonamide (600 mg, 1.25 mmol), aq. NaOH (50%, 2 mL) and ethanol (2 mL). The mixture was sealed and heated to 120° C. over night. After cooling the reaction mixture was poured into ice water (20 mL), and extracted with ethyl acetate, dried over MgSO$_4$ and purified by silica gel chromatography to afford 2-(5-(N-tert-butylsulfamoyl)pyridin-2-yl)-6-ethyl-5-fluoro-1-(pyridin-2-yl)-1H-indole-3-carboxamide (315 mg, 51%). MS m/z 496.2 M+H$^+$; $^1$H NMR (500 MHz, CDCl$_3$): δ 8.84 (1H, m), 8.31 (1H, m), 8.02 (1H, q, J=4.0 Hz), 7.79 (1H, m), 7.76 (1H, s), 7.50 (1H, dd, J=3.75 Hz, 3.74 Hz), 7.31 (1H, d, J=3.6 Hz), 7.26 (2H, m), 7.21 (1H, m), 6.58 (1H, s), 2.63 (2H, q, J=1.3 Hz), 1.09 (9H, s), 1.02 (3H, t, J=2.4 Hz).

Additional compounds representative of the present invention may be prepared according to the procedure of Example 16 by substituting the appropriate starting materials, reagents and reaction conditions and include compounds selected from (wherein MS represents mass spec as MH$^+$ (unless otherwise indicated), m.p. represents melting point in ° C. and N/A indicates that the data was not obtained):

| Cpd | Name | m.p. | MS |
|---|---|---|---|
| 846 | 5-methyl-1-(pyrimidin-2-yl)-2-(5-{[(2S)-1,1,1-trifluoropropan-2-yl]sulfamoyl}pyridin-2-yl)-1H-indole-3-carboxamide | N/A | 505.2 |
| 916 | 5-methyl-1-(pyrazin-2-yl)-2-(5-{[(2S)-1,1,1-trifluoropropan-2-yl]sulfamoyl}pyridin-2-yl)-1H-indole-3-carboxamide | 240-245 | 505.2 |
| 918 | 6-fluoro-5-methyl-1-(pyrimidin-2-yl)-2-(5-{[(2S)-1,1,1-trifluoropropan-2-yl]sulfamoyl}pyridin-2-yl)-1H-indole-3-carboxamide | 245-249 | 523.2 |
| 978 | 6-ethyl-5-fluoro-1-(pyrimidin-2-yl)-2-{5-[(1,1,1-trifluoro-2-methylpropan-2-yl)sulfamoyl]pyridin-2-yl}-1H-indole-3-carboxamide | 261-269 | 551.3 |
| 979 | 6-ethyl-5-fluoro-1-(pyrimidin-2-yl)-2-(5-{[1-(trifluoromethyl)cyclopropyl]sulfamoyl}pyridin-2-yl)-1H-indole-3-carboxamide | 240-247 | 549.2 |

-continued

| Cpd | Name | m.p. | MS |
|---|---|---|---|
| 1083 | 2-{6-[(tert-butylsulfonyl)amino]pyridin-3-yl}-1-[(1S)-1-cyclopropylethyl]-6-ethyl-5-fluoro-1H-indole-3-carboxamide | 256.0-259.0 | 487.5 |
| 1088 | 2-{6-[(tert-butylsulfonyl)amino]pyridin-3-yl}-1-cyclohexyl-6-cyclopropyl-4-fluoro-1H-indole-3-carboxamide | 290-294 | 513.7 |
| 1097 | 2-{5-[(tert-butylsulfonyl)amino]pyridin-2-yl}-1-cyclohexyl-6-cyclopropyl-4-fluoro-1H-indole-3-carboxamide | 275-285 decomp. range | 513.4 |
| 1105 | 2-{6-[(tert-butylsulfonyl)amino]pyridin-3-yl}-6-cyclopropyl-4-fluoro-1-(4-fluorophenyl)-1H-indole-3-carboxamide | 290-295 | 525.3 |
| 1106 | 2-{6-[(tert-butylsulfonyl)amino]pyridin-3-yl}-6-ethyl-4-fluoro-1-(4-fluorophenyl)-1H-indole-3-carboxamide | 280-288 | 513.3 |
| 1109 | 2-[5-(tert-butylsulfamoyl)pyridin-2-yl]-6-ethyl-5-fluoro-1-phenyl-1H-indole-3-carboxamide | 237.9-238.9 | 493.3 |
| 1110 | 2-{5-[(tert-butylsulfonyl)amino]pyridin-2-yl}-1-cyclobutyl-6-ethyl-4-fluoro-1H-indole-3-carboxamide | 259-263 | 473.3 |
| 1111 | 2-{6-[(tert-butylsulfonyl)amino]pyridin-3-yl}-6-ethyl-4-fluoro-1-phenyl-1H-indole-3-carboxamide | 288-294 | 495.2 |
| 1115 | 2-[5-(tert-butylsulfamoyl)pyridin-2-yl]-1-cyclohexyl-5-fluoro-6-methyl-1H-indole-3-carboxamide | 274.5-275.6 | 487.4 |
| 1116 | 2-[5-(tert-butylsulfamoyl)pyridin-2-yl]-5-fluoro-6-methyl-1-phenyl-1H-indole-3-carboxamide | 241.2-242.5 | 479.3 |

Example 17

Cmp 810

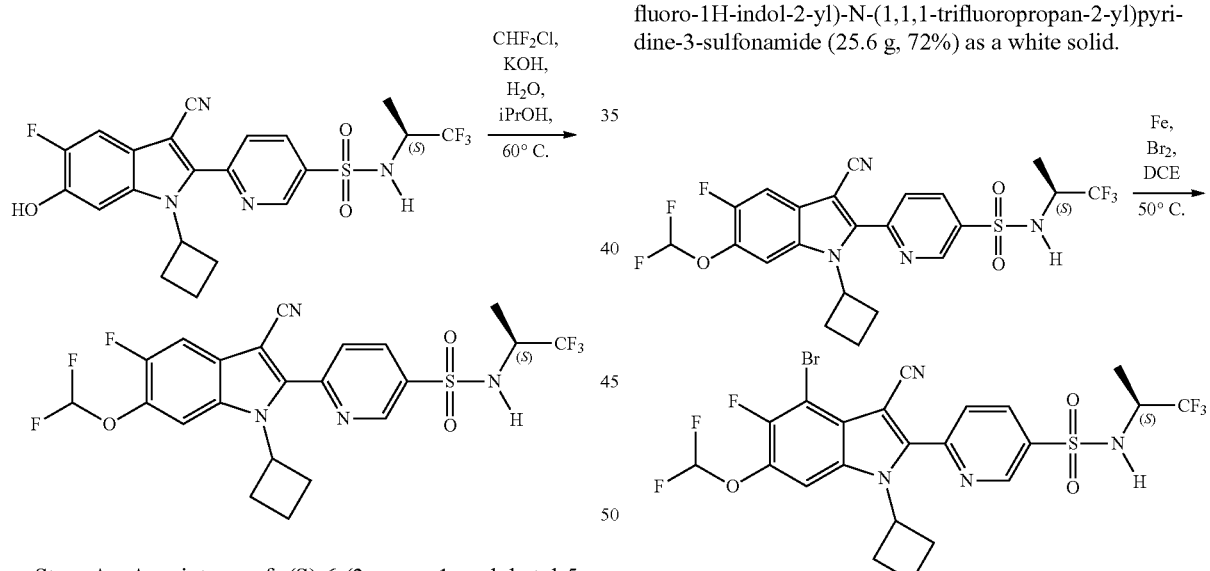

Step A: A mixture of (S)-6-(3-cyano-1-cyclobutyl-5-fluoro-6-hydroxy-1H-indol-2-yl)-N-(1,1,1-trifluoropropan-2-yl)pyridine-3-sulfonamide (31.9 g, 66.2 mmol), 5 N aq. NaOH (25 mL), and isopropanol (140 mL) was stirred at 60° C. Chlorodifluoromethane gas was bubbled into this mixture at a constant rate. Heating continued for 10 hours, with additional 5 N aq. NaOH (3 mL) being added in 30 minute increments. The reaction mixture was diluted in H$_2$O (800 mL) and was acidified with 6 N aq. HCl. This was extracted with EtOAc (2×200 mL). The combined organic extracts were washed with water (2×300 mL), then brine (50 mL). The organic layer was subsequently dried over MgSO$_4$ and filtered, and the filtrate was concentrated under vacuum. The product mixture was redissolved in CH$_2$Cl$_2$ (500 mL), and was absorbed onto silica (100 g). CH$_2$Cl$_2$ was removed under vacuum. The solids were loaded onto a column of 100 g additional silica. Elution with CH$_2$Cl$_2$/hexanes (1:1 to 3:1), and then with ethyl acetate in CH$_2$Cl$_2$ (0% to 5%) yielded 28.6 g crude product. This was washed with Et$_2$O (100 mL) to yield (S)-6-(3-cyano-1-cyclobutyl-6-(difluoromethoxy)-5-fluoro-1H-indol-2-yl)-N-(1,1,1-trifluoropropan-2-yl)pyridine-3-sulfonamide (25.6 g, 72%) as a white solid.

Step B: A mixture of (S)-6-(3-cyano-1-cyclobutyl-6-(difluoromethoxy)-5-fluoro-1H-indol-2-yl)-N-(1,1,1-trifluoropropan-2-yl)pyridine-3-sulfonamide (500 mg, 0.94 mmol), Fe powder (700 mg, 13 mmol), Br$_2$ (300 μL, 5.9 mmol), and 1,2-dichloroethane (3 mL) was heated at 50° C. for 3 hours. The reaction mixture was then poured into aq. NaHSO$_3$ solution. This was extracted into CH$_2$Cl$_2$. The organic layer was dried over MgSO$_4$ and filtered, and the filtrate was concentrated under vacuum. Purification by silica gel chromatography (ethyl acetate in hexanes, 20% to 30%) yielded (S)-6-(4-bromo-3-cyano-1-cyclobutyl-6 (difluoromethoxy)-5-fluoro-1H-indol-2-yl)-N-(1,1,1-trifluoropropan-2-yl)pyridine-3-sulfonamide (266 mg, 46%) as a white solid.

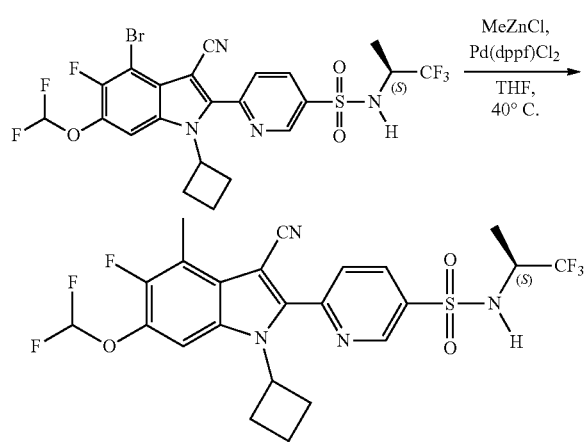

Step C: A solution of MeZnCl (2 M in THF, 370 µL, 0.74 mmol) was added to a mixture of (S)-6-(4-bromo-3-cyano-1-cyclobutyl-6 (difluoromethoxy)-5-fluoro-1H-indol-2-yl)-N-(1,1,1-trifluoropropan-2-yl)pyridine-3-sulfonamide (200 mg, 0.33 mmol), Pd(dppf)Cl$_2$ (25 mg, 0.034 mmol), and THF (1.2 mL). This was heated at 40° C. for 25 hours. The reaction mixture was then poured onto aq. HCl. This was extracted with ethyl acetate and the organic layer was washed with brine. The organic layer was dried over MgSO$_4$ and filtered, and the filtrate was concentrated under vacuum. Purification by silica gel chromatography (20% ethyl acetate in hexanes), followed by washing with hexanes/ether (1:1) yielded (S)-6-(3-cyano-1-cyclobutyl-6 (difluoromethoxy)-5-fluoro-4-methyl-1H-indol-2-yl)-N-(1,1,1-trifluoropropan-2-yl)pyridine-3-sulfonamide (117 mg, 65%) as a white solid. Melting point: 182-186° C.; MS m/z 547.0 M+H$^+$; $^1$H NMR (CDCl$_3$, 500 MHz): δ 9.22 (d, 1H, J=2 Hz), 8.35 (dd, 2H, J=8.5 Hz, 2 Hz), 8.02 (d, 1H, 8.5 Hz), 7.40 (d, 1H, J=6.5 Hz), 6.62 (t, 1H, J=75 Hz), 5.26 (pentet, 1H, J=8.5 Hz), 4.95 (d, 1H, J=9.5 Hz), 4.16 (m, 1H), 2.75 (d, 3H, J=2.0 Hz), 2.47 (m, 2H), 2.38 (m, 2H), 1.87 (m, 2H), 1.47 (d, 3H, J=7 Hz).

Cpd 811 was prepared as in Example 17 except the bromination and freonation steps of that sequence were reversed.

| Cpd | Name | m.p. | MS |
|---|---|---|---|
| 811 | 6-[3-cyano-1-cyclobutyl-6-(difluoromethoxy)-5-fluoro-7-methyl-1H-indol-2-yl]-N-[(2S)-1,1,1-trifluoropropan-2-yl]pyridine-3-sulfonamide | 168-174 | 547.1 |

Example 18

6-(3-cyano-1-cyclobutyl-5-fluoro-6-methyl-1H-indol-2-yl)-N-[(2S)-1,1,1-trifluoro(2-deuterium)propan-2-yl]pyridine-3-sulfonamide (Cmp 1113)

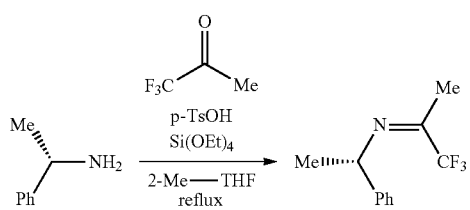

Step A: To a solution of p-toluenesulfonic acid monohydrate (3 g, 16 mmol) and 2-methyltetrahydrofuran (600 mL) were added (S,L)-alpha methylbenzylamine (40 g, 310 mmol), tetraethylorthosilicate (28 mL, 125 mmol), and 1,1,1-trifluoroacetone (65 mL, 690 mmol). The mixture was stirred at reflux for 17 hours and at 0° C. for 1 hour. The mixture was filtered through a thin pad of silica gel, and the filter cake was rinsed with EtOAc. The filtrate was concentrated using a rotary evaporator and used without further purification.

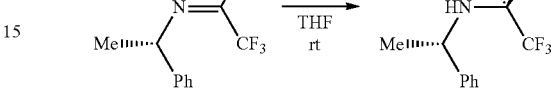

Step B: The residue from above was added as a solution in THF (130 mL), dropwise over 1 hour, to a suspension of lithium aluminum deuteride (34.9 g, 831 mmol) in THF (700 mL) at 0° C. The mixture was stirred at 0° C. for 1 hour and at room temperature for 2 hours. The mixture was then cooled back to 0° C., MTBE (400 mL) was added, followed by the slow, sequential addition of H$_2$O (35 mL), aq. NaOH (5 N, 35 mL), and H$_2$O (105 mL). The mixture was stirred at room temperature for 15 minutes, MgSO$_4$ was added, and the mixture was stirred at room temperature for an additional 15 minutes. The mixture was filtered through Celite and the filter cake was rinsed with EtOAc. The filtrate was concentrated and the residue was transferred to a separatory funnel. MTBE (500 mL) and aq. HCl (3 N, 500 mL) were added and the organic layer was extracted with aq. HCl (3 N, 2×250 mL). The combined aqueous layers were cooled to 0° C., aq. NaOH (50%, 200 mL) was added, the mixture was transferred to a separatory funnel, and the aqueous layer was extracted with CH$_2$Cl$_2$ (3×500 mL). The combined organic layers were dried with Na$_2$SO$_4$ and concentrated using a rotary evaporator. The residue was passed through a silica gel plug, eluting with hexanes, to provide (S)-1,1,1-trifluoro-2-deutero-N—((S)-1-phenylethyl)propan-2-amine (34.2 g, 50% from (S,L-)-alpha-methylbenzylamine).

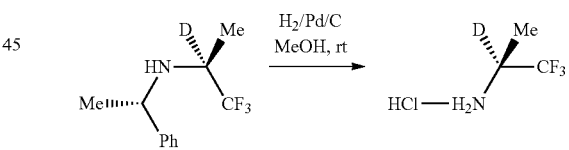

Step C: To a mixture of (S)-1,1,1-trifluoro-2-deutero-N-((S)-1-phenylethyl)propan-2-amine (34.2 g, 157 mmol) dissolved in MeOH (475 mL) was added 10% Pd/C (5 g, 4.7 mmol). The mixture was hydrogenated at room temperature under 1 atmosphere of hydrogen gas for 20 h. The mixture was gravity filtered through Celite, rinsing the filter cake with EtOAc. The filtrate was cooled to 0° C., and HCl (4 M in dioxane, 235 mL) was added. The solution was concentrated using a rotary evaporator to provide (S)-1,1,1-trifluoro-2-deutero-propan-2-amine hydrochloride (22.9 g, 97%). (S)-1,1,1-trifluoro-2-deutero-propan-2-amine hydrochloride (25.0 g, 165.7 mmol) was added to H$_2$O (100 mL), and the mixture was cooled to 0° C. To the mixture was added aq. NaOH (50%, 45 mL), dropwise over 10 minutes, and material was distilled out of this solution at ca. 50° C., providing (S)-1,1,1-trifluoro-2-deutero-propan-2-amine (15.7 g, 67%, 53.3% ee, containing ca. 19 wt % H$_2$O). This material was added to D-tartaric acid (25 g, 170 mmol, 99.8% ee) and MeOH (300 mL), and the mixture was stirred at reflux for 30 minutes. The mixture was cooled slowly to 0° C., allowing crystals to form. The crystals were isolated by filtration, providing (S)-1,1,1-trifluoro-2-deutero-propan-2-amine tartrate salt (28.4 g, 84%, 84.0% ee, containing ca. 4% MeOH and 9 wt % H$_2$O). This material was recrystallized from MeOH (230 mL), providing (S)-1,1,1-trifluoro-2-deutero-propan-2-amine tartrate salt (24.3 g, 85%, 95.7% ee, ca. 9% MeOH and 5 wt % H$_2$O). This material was again recrystallized from MeOH (200 mL), providing (S)-1,1,1-trifluoro-2-deutero-propan-2-amine tartrate salt (20.7 g, 85%, 98.7% ee, ca. 5% MeOH and 10 wt % H$_2$O). This material was added to H$_2$O (150 mL), and the mixture was cooled to 0° C. NaOH (50%, 18 mL) was added, dropwise over 5 minutes, and 6.7 g of material was distilled out of the solution at ca. 49° C. This material was cooled to 0° C. and concentrated aq. HCl (15 mL) was added. The mixture was stirred at room temperature for 25 minutes and then concentrated using a rotary evaporator (azeotropic removal of H$_2$O using MeOH and EtOH), providing (S)-1,1,1-trifluoro-2-deutero-propan-2-amine hydrochloride (8.7 g, 87% from (S)-1,1,1-trifluoro-2-deutero-propan-2-amine tartrate salt, 98.6% ee).

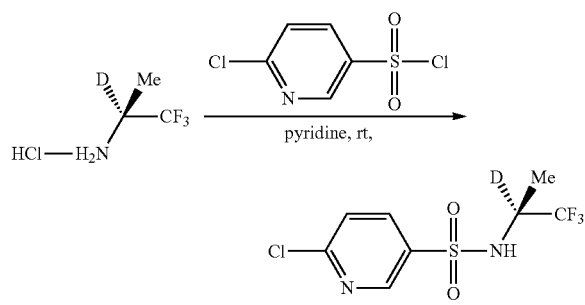

Step D: (S)-1,1,1-trifluoro-2-deutero-propan-2-amine hydrochloride (3 g, 19.9 mmol, 98.6% ee) was converted into (S)-6-chloro-N-(1,1,1-trifluoro-2-deutero-propan-2-yl)pyridine-3-sulfonamide (5.3 g, 91%) in a manner analogous to Example 1B.

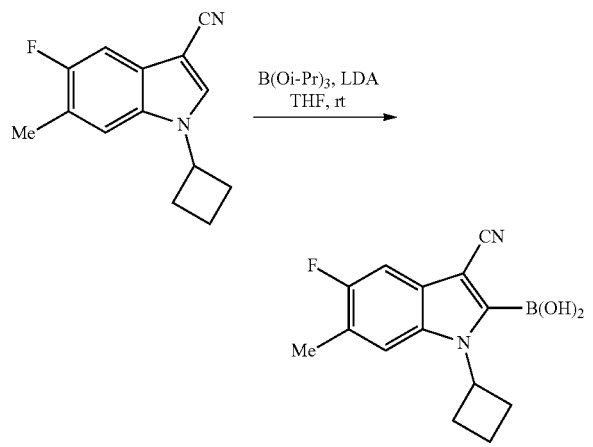

Step E: 1-cyclobutyl-5-fluoro-6-methyl-1H-indole-3-carbonitrile (133 mg, 0.58 mmol) was converted into 3-cyano-1-cyclobutyl-5-fluoro-6-methyl-1H-indol-2-ylboronic acid in a manner analogous to Example 7D and used without further purification.

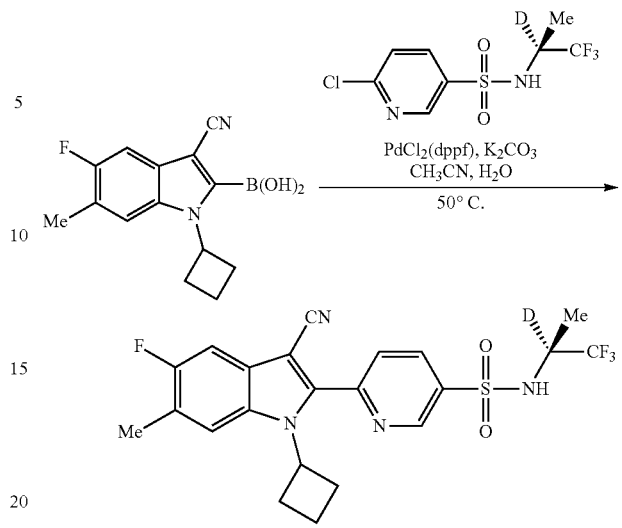

Step F: (S)-6-chloro-N-(1,1,1-trifluoro-2-deutero-propan-2-yl)pyridine-3-sulfonamide (100 mg, 0.35 mmol) and 3-cyano-1-cyclobutyl-5-fluoro-6-methyl-1H-indol-2-ylboronic acid were converted into Compound 1113 (34 mg, 20%) in a manner analogous to Example 7E. Melting point: 215-217° C.; MS m/z 482.0 M-1-H$^+$; $^1$H NMR (500 MHz, acetone-d$_6$) δ 9.21 (1H, dd, J=2.3, 0.7 Hz), 8.49 (1H, dd, J=8.3, 2.4 Hz), 8.08 (1H, dd, J=8.2, 0.8 Hz), 7.77 (1H, d, J=6.2 Hz), 7.72 (1H, br), 7.37 (1H, d, J=9.5 Hz), 5.33 (1H, m), 2.58 (2H, m), 2.41 (3H, d, J=2.0 Hz), 2.40 (2H, m), 1.82 (2H, m), 1.26 (3H, s).

Additional compounds representative of the present invention were prepared according to the procedure of Example 18 by substituting the appropriate starting materials, reagents and reaction conditions and include compounds selected from (wherein MS represents mass spec as MH$^+$, unless otherwise indicated, m.p. represents melting point in ° C., and N/A indicates that the data was not obtained):

| Cpd | Name | m.p. | MS |
| --- | --- | --- | --- |
| 1114 | 6-[3-cyano-1-cyclobutyl-5-fluoro-6-(1,1,1-trideuterium)methyl-1H-indol-2-yl]-N-[(2S)-1,1,1-trifluoro(2-deuterium)propan-2-yl]pyridine-3-sulfonamide | 213-215 | 485.0 |

Example 19

6-[3-cyano-1-(cyclopropylmethyl)-5-fluoro-6-(1,1,1-trideuterium)methyl-1H-indol-2-yl]-N-[(2-deuterium)propan-2-yl]pyridine-3-sulfonamide (Cmp 1119)

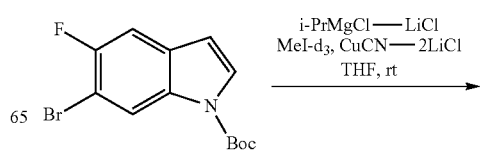

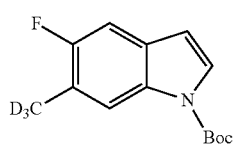

Step A: t-Butyl 6-bromo-5-fluoro-1H-indole-1-carboxylate (30 g, 96 mmol, synthesized in a manner analogous to Example 8A) was added to THF (110 mL), and the mixture was cooled to 0° C. To this mixture was added i-propylmagnesium chloride-lithium chloride complex (90 mL, 117 mmol) portionwise over 10 minutes, and the mixture was stirred at 0° C. for 3 hours. Iodomethane-d₃ (8 mL, 128.6 mmol) was added, followed by a solution of copper (I) cyanide (1.7 g, 19.0 mmol), lithium chloride (1.6 g, 37.7 mmol), and THF (80 mL). The mixture was stirred at room temperature for 18 hours. Diethyl ether (100 mL) and H₂O (100 mL) were added and the mixture was filtered through Celite, rinsing the filter cake with diethyl ether (200 mL). The filtrate was extracted with diethyl ether (2×80 mL). The combined organic extracts were washed with brine (100 mL), dried with Na₂SO₄, and concentrated using a rotary evaporator and used without further purification.

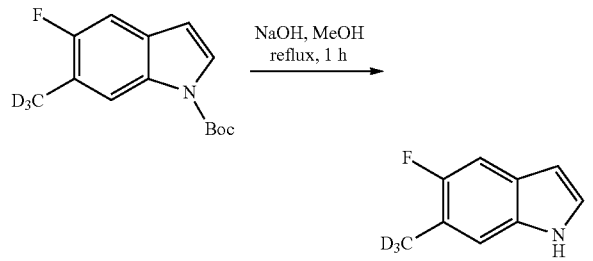

Step B: The residue from above was added to aq. NaOH (50%, 15 mL) and MeOH (190 mL). The mixture was stirred at reflux for 1 hour and then concentrated using a rotary evaporator. The residue was added to CH₂Cl₂ (200 mL), H₂O (200 mL), and the aqueous layer was extracted with CH₂Cl₂ (2×200 mL). The combined organic layers were dried with Na₂SO₄ and concentrated. The residue was purified using silica gel chromatography (2×80 g SiO₂, 0% to 10% EtOAc in hexanes), providing 5-fluoro-6-(methyl-d₃)-1H-indole (13.6 g, 93% from t-butyl 6-bromo-5-fluoro-1H-indole-1-carboxylate).

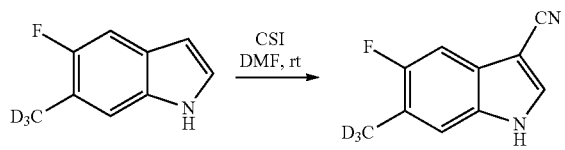 [SMILES: [2H]C([2H])([2H])c1cc2[nH]ccc2cc1F ; [2H]C([2H])([2H])c1cc2[nH]cc(C#N)c2cc1F]

Step C: The compound from above, 5-fluoro-6-(methyl-d₃)-1H-indole (5 g, 32.9 mmol), was converted into 5-fluoro-6-(methyl-d₃)-1H-indole-3-carbonitrile (5.6 g, 95%) in a manner analogous to Example 6B.

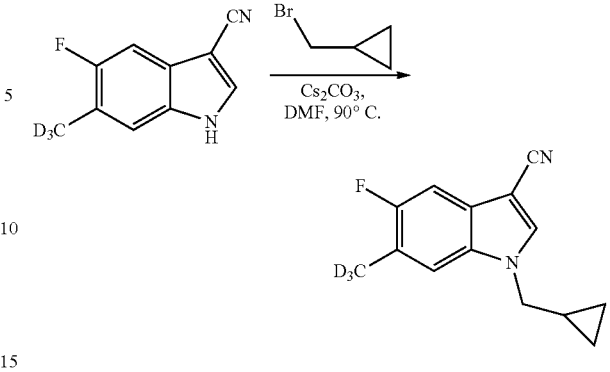

Step D: The compound from above, 5-fluoro-6-(methyl-d₃)-1H-indole-3-carbonitrile (850 mg, 4.8 mmol), was converted into 1-(cyclopropylmethyl)-5-fluoro-6-(methyl-d₃)-1H-indole-3-carbonitrile (901 mg, 81%) in a manner analogous to Example 6C.

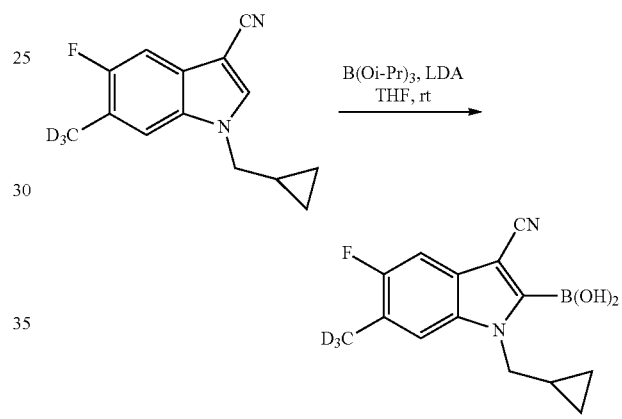

Step E: The compound from above, 1-(cyclopropylmethyl)-5-fluoro-6-(methyl-d₃)-1H-indole-3-carbonitrile (169 mg, 0.73 mmol), was converted into 3-cyano-1-(cyclopropylmethyl)-5-fluoro-6-(methyl-d₃)-1H-indol-2-ylboronic acid in a manner analogous to Example 7D

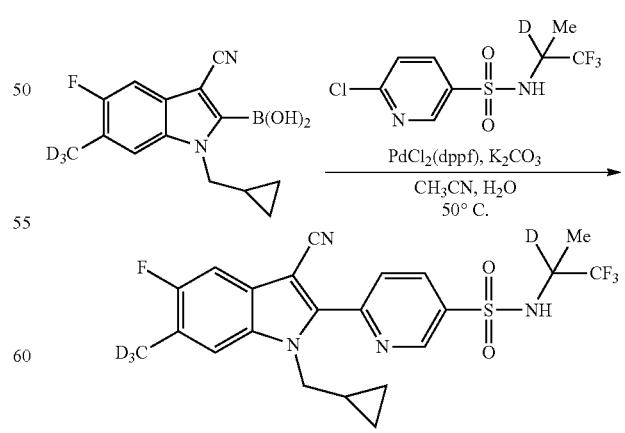

Step F: The compound from above, 3-cyano 1-(cyclopropylmethyl)-5-fluoro-6-(methyl-d₃)-1H-indol-2-ylboronic acid, and 6-chloro-N-(2-deutero-propan-2-yl)pyridine-3-sulfonamide (103 mg, 0.44 mmol, synthesized in a manner analogous to procedure Example 21) were converted into Compound 1119 (101 mg, 53%) in a manner analogous to Example 7E. Melting point: 216-218° C.; MS m/z 431.3 M+H⁺; ¹H NMR (500 MHz, acetone-$d_6$) δ 9.21 (1H, dd, J=2.4, 0.6 Hz), 8.51 (1H, dd, J. 8.3, 2.4 Hz), 8.21 (1H, dd, J=8.4, 0.6 Hz), 7.76 (1H, d, J=6.2 Hz), 7.42 (1H, d, J. 9.6 Hz), 6.86 (1H, br), 4.59 (2H, d, J=7.1 Hz), 1.20 (1H, m), 1.13 (6H, s), 0.38 (2H, m), 0.19 (2H, m).

Additional compounds representative of the present invention were prepared according to the procedure of Example 19 by substituting the appropriate starting materials, reagents and reaction conditions and include compounds selected from (wherein MS represents mass spec as MH⁺, unless otherwise indicated, m.p. represents melting point in ° C., and N/A indicates that the data was not obtained):

| Cpd | Name | m.p. | MS |
|---|---|---|---|
| 1112 | 6-(3-cyano-1-cyclobutyl-5-fluoro-6-methyl-1H-indol-2-yl)-N-[(2-deuterium)propan-2-yl]pyridine-3-sulfonamide | 220-222 | 427.9 |

Example 20

(S)-6-(3-cyano-6-ethyl-5-fluoro-1-(pyrimidin-2-yl)-1H-indol-2-yl)-N-(1,1,1-trifluoropropan-2-yl)pyridine-3-sulfonamide (Cpd 704)

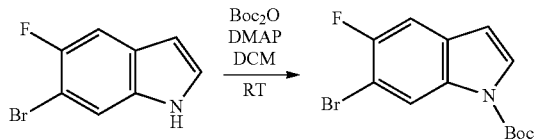

Step A: To a solution of 6-bromo-5-fluoro-1H-indole (1.25 g, 5.3 mmol) in $CH_2Cl_2$ (10 mL) were added di-tert-butyl dicarbonate (1.5 g, 7.0 mmol) and DMAP (13 mg, 0.1 mmol). The reaction mixture was kept stirring for 2 hr at room temperature, then partitioned between $CH_2Cl_2$ and water. The organic layer was washed with water, brine and dried over $Na_2SO_4$ and evaporated. The resulting white solid, tert-butyl 6-bromo-5-fluoro-1H-indole-1-carboxylate, was air dried and used in the next step without further purification. ¹H NMR (500 MHz, $CDCl_3$): δ 8.33 (1H, br s), 7.53 (1H, d, J=3.0 Hz) 7.20 (1H, d, J=8.5 Hz), 6.43 (1H, dd, J=3.5, 0.5 Hz), 1.59 (9H, s).

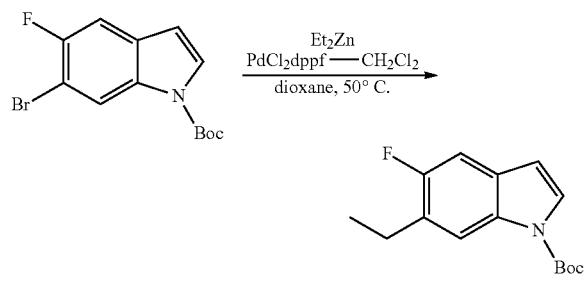

Step B: To a solution of tert-butyl 6-bromo-5-fluoro-1H-indole-1-carboxylate (1.57 g, 5.0 mmol) in dioxane (10 mL) was added a solution of $Et_2Zn$ in heptane (3.5 mL, 1.0M, 3.5 mmol) at room temperature. The mixture was kept stirring for 30 min at 90° C. and then cooled down to 0° C., into which saturated sodium bicarbonate was added dropwise. The mixture was then treated with water and extracted with $CH_2Cl_2$. The organic layer was dried over $Na_2SO_4$ and evaporated. The resulting oil was passed through a silica plug and eluted with 10% ethyl acetate in hexane. The eluent was evaporated to give tert-butyl 6-ethyl-5-fluoro-1H-indole-1-carboxylate as an oil which was solidified upon standing (1.25 g, 95%).

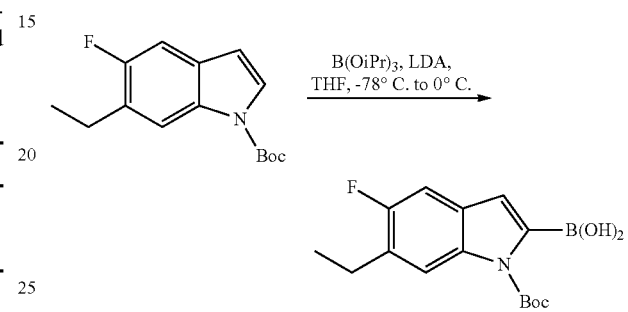

Step C: Into a solution of tert-butyl 6-ethyl-5-fluoro-1H-indole-1-carboxylate (0.93 g, 3.5 mmol) and tri-isopropyl borate (1.2 mL, 5.25 mmol) in THF (7 mL) at −78° C. was added LDA (1.5 M in cyclohexane, 2.8 mL, 4.2 mmol) under nitrogen. The mixture was stirred at −78° C. for 15 min, then 2 hr at 0° C. The reaction was quenched by addition of acetic acid (0.24 mL, 4.2 mmol) over a period of 15 min, followed by removal of solvents by rotary evaporation. The resulting boronic acid (>90% pure by LCMS) was used in the next step without further purification.

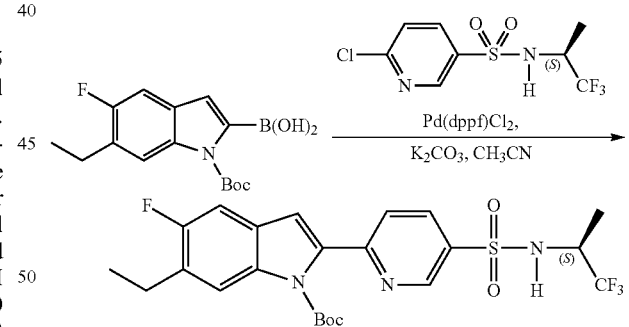

Step D: Into a solution of 1-(tert-butoxycarbonyl)-6-ethyl-5-fluoro-1H-indol-2-ylboronic acid, prepared as above, (S)-6-chloro-N-(1,1,1-trifluoropropan-2-yl)pyridine-3-sulfonamide (0.91 g, 3.15 mmol) and $PdCl_2dppf$ (0.23 g, 0.31 mmol) in acetonitrile (21 mL) was added a solution of potassium carbonate (2.0 M, 7 mL, 14 mmol). The mixture was stirred at 50° C. overnight, cooled to room temperature, and then quenched by addition of HCl (1 N) in ice-water to pH ~8. The mixture was extracted with ethyl acetate. The combined organics were dried over $Na_2SO_4$ and concentrated. The resulting crude mixture was used in the next step without further purification.

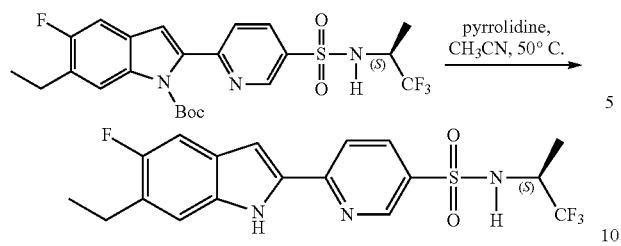

Step E: A mixture of (S)-tert-butyl 6-ethyl-5-fluoro-2-(5-(N-(1,1,1-trifluoropropan-2-yl)sulfamoyl)pyridin-2-yl)-1H-indole-1-carboxylate, prepared as above, and pyrrolidine (1.5 mL, 18 mmol) in acetonitrile (15 mL) was stirred at 50° C. for 2 hr. The solvents were then evaporated and the residue was partitioned between ethyl acetate and HCl (1N). The aqueous phase was further extracted with ethyl acetate. The combined organics were washed with 1N HCl and brine. After concentration, the crude mixture was triturated with $CH_2Cl_2$/hexane to provide (S)-6-(6-ethyl-5-fluoro-1H-indol-2-yl)-N-(1,1,1-trifluoropropan-2-yl)pyridine-3-sulfonamide as light yellow solids (1.16 g, 80% yield from (S)-6-chloro-N-(1,1,1-trifluoropropan-2-yl)pyridine-3-sulfonamide).

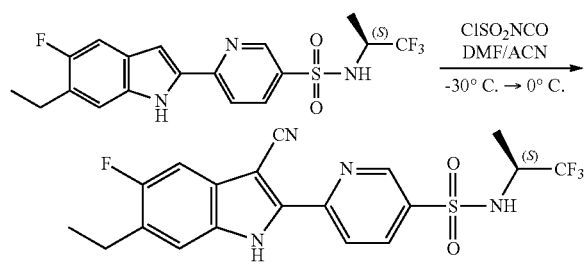

Step F: To a solution of (S)-6-(6-ethyl-5-fluoro-1H-indol-2-yl)-N-(1,1,1-trifluoropropan-2-yl)pyridine-3-sulfonamide (0.22 g, 0.53 mmol) in a mixture of DMF (0.5 mL) and acetonitrile (0.5 mL) was added chlorosulfonyl isocyanate dropwise at −50° C. The reaction mixture was kept stirring at 0° C. for 0.5 hr and then quenched with ice, following by pouring into water. After 0.5 hr stirring at room temperature, the resulting solid was collected by filtration and washed with water, hexane and $CH_2Cl_2$. After air drying, (S)-6-(3-cyano-6-ethyl-5-fluoro-1H-indol-2-yl)-N-(1,1,1-trifluoropropan-2-yl)pyridine-3-sulfonamide was obtained and used in the next step without further purification.

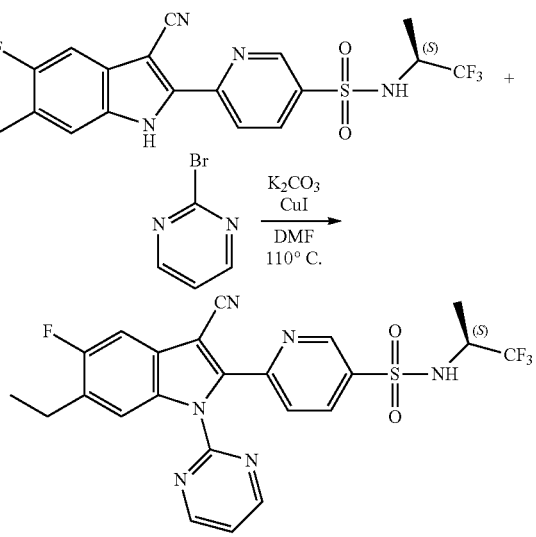

Step G: A mixture of (S)-6-(3-cyano-6-ethyl-5-fluoro-1H-indol-2-yl)-N-(1,1,1-trifluoropropan-2-yl)pyridine-3-sulfonamide (0.22 g, 0.5 mmol), prepared as above, 2-bromopyrimidine (0.167 g, 1.0 mmol), potassium carbonate (0.212 g, 1.5 mmol) and copper (I) iodide (20 mg, 0.1 mmol) were mixed with DMF (2.5 mL). The system was evacuated and replaced with an argon atmosphere. The reaction mixture was stirred at 110° C. for 70 hr, then cooled to 0° C., diluted with ethyl acetate and neutralized with 1N HCl. The ethyl acetate layer was washed with water, brine, dried over $Na_2SO_4$, filtrated through silica gel pad and evaporated. The crude product was triturated with $CH_2Cl_2$ and hexane and was further recrystallized from ethyl acetate and hexane. After air drying, the off-white solid (S)-6-(3-cyano-6-ethyl-5-fluoro-1-(pyrimidin-2-yl)-1H-indol-2-yl)-N-(1,1,1-trifluoropropan-2-yl)pyridine-3-sulfonamide was obtained. Melting point: 195-198° C.; MS m/z 519.1 M-1-H+; $^1$H NMR (500 MHz, acetone-$d_6$): ☐ 8.90 (1H, dd, J=2.5, 1.0 Hz), 8.83 (2H, d, J=4.5 Hz), 8.49 (1H, dd, J=8.0, 2.5 Hz), 8.16 (1 H, t, J=6.5 Hz), 8.15 (1 H, d, J=9.0 Hz), 7.68 (1 H, br s), 7.57-7.54 (2H, m), 4.32 (1 H, br s), 2.85 (2 H, q, J=7.5 Hz), 1.29 (3 H, t, J=7.5 Hz), 1.28 (3 H, d, J=7.2 Hz).

Additional compounds representative of the present invention may be prepared according to the procedure of Example 20 by substituting the appropriate starting materials, reagents and reaction conditions and include compounds selected from (wherein MS represents mass spec as MH+, unless otherwise indicated, m.p. represents melting point in ° C., and N/A indicates that the data was not obtained):

| Cpd | Name | m.p. | MS |
|---|---|---|---|
| 708 | 6-[5-chloro-3-cyano-1-(pyrimidin-2-yl)-1H-indol-2-yl]-N-[(2S)-1,1,1-trifluoropropan-2-yl]pyridine-3-sulfonamide | 193-196 | 507.3 |
| 724 | 6-{3-cyano-5-fluoro-1-[5-(trifluoromethyl)pyridin-2-yl]-1H-indol-2-yl}-N-[(2S)-1,1,1-trifluoropropan-2-yl]pyridine-3-sulfonamide | 216-218 | 558.2 |
| 739 | 6-[3-cyano-5-fluoro-6-methyl-1-(3-methylpyridin-2-yl)-1H-indol-2-yl]-N-[(2S)-1,1,1-trifluoropropan-2-yl]pyridine-3-sulfonamide | 219-221 | 518.2 |
| 740 | 6-{3-cyano-5-fluoro-6-methyl-1-[5-(trifluoromethyl)pyridin-2-yl]-1H-indol-2-yl}-N-[(2S)-1,1,1-trifluoropropan-2-yl]pyridine-3-sulfonamide | 253-255 | 572.2 |

-continued

| Cpd | Name | m.p. | MS |
|---|---|---|---|
| 742 | 6-[3-cyano-5-fluoro-1-(5-fluoropyridin-2-yl)-6-methyl-1H-indol-2-yl]-N-[(2S)-1,1,1-trifluoropropan-2-yl]pyridine-3-sulfonamide | 239-241 | 512.8 |
| 743 | 6-[3-cyano-1-(5-cyanopyridin-2-yl)-5-fluoro-6-methyl-1H-indol-2-yl]-N-[(2S)-1,1,1-trifluoropropan-2-yl]pyridine-3-sulfonamide | 276-277 | 528.9 |
| 744 | 6-[3-cyano-5-fluoro-6-methyl-1-(5-nitropyridin-2-yl)-1H-indol-2-yl]-N-[(2S)-1,1,1-trifluoropropan-2-yl]pyridine-3-sulfonamide | 260-263 | 548.9 |
| 777 | 6-[3-cyano-6-ethyl-5-fluoro-1-(5-fluoropyridin-2-yl)-1H-indol-2-yl]-N-[(2S)-1,1,1-trifluoropropan-2-yl]pyridine-3-sulfonamide | 210-212 | 535.8 |
| 778 | 6-[3-cyano-6-ethyl-5-fluoro-1-(pyridin-2-yl)-1H-indol-2-yl]-N-[(2S)-1,1,1-trifluoropropan-2-yl]pyridine-3-sulfonamide | 205-208 | 517.8 |
| 785 | 6-[5-chloro-3-cyano-6-methyl-1-(pyrimidin-2-yl)-1H-indol-2-yl]-N-[(2S)-1,1,1-trifluoropropan-2-yl]pyridine-3-sulfonamide | 210-212 | 521.2 |
| 803 | 6-[5-chloro-3-cyano-6-methyl-1-(pyridin-2-yl)-1H-indol-2-yl]-N-[(2S)-1,1,1-trifluoropropan-2-yl]pyridine-3-sulfonamide | 210-212 | 519.4 |
| 804 | 6-[5-chloro-3-cyano-1-(5-fluoropyridin-2-yl)-6-methyl-1H-indol-2-yl]-N-[(2S)-1,1,1-trifluoropropan-2-yl]pyridine-3-sulfonamide | 210-212 | 537.9 |
| 814 | 6-[3-cyano-5-fluoro-1-(3-fluoropyridin-2-yl)-6-methyl-1H-indol-2-yl]-N-[(2S)-1,1,1-trifluoropropan-2-yl]pyridine-3-sulfonamide | 193-198 | 521.5 |
| 815 | 6-[3-cyano-5-fluoro-1-(6-fluoropyridin-2-yl)-6-methyl-1H-indol-2-yl]-N-[(2S)-1,1,1-trifluoropropan-2-yl]pyridine-3-sulfonamide | 210-212 | 522.3 |
| 816 | 6-[3-cyano-5-fluoro-1-(4-methoxypyridin-2-yl)-6-methyl-1H-indol-2-yl]-N-[(2S)-1,1,1-trifluoropropan-2-yl]pyridine-3-sulfonamide | 210-213 | 518.2 |
| 817 | 6-[3-cyano-5-fluoro-6-methyl-1-(pyrazin-2-yl)-1H-indol-2-yl]-N-[(2S)-1,1,1-trifluoropropan-2-yl]pyridine-3-sulfonamide | 220-223 | 505.4 |
| 818 | 6-[3-cyano-6-cyclopropyl-5-fluoro-1-(5-fluoropyridin-2-yl)-1H-indol-2-yl]-N-[(2S)-1,1,1-trifluoropropan-2-yl]pyridine-3-sulfonamide | 240-242 | 548.2 |
| 819 | 6-[3-cyano-6-cyclopropyl-5-fluoro-1-(pyridin-2-yl)-1H-indol-2-yl]-N-[(2S)-1,1,1-trifluoropropan-2-yl]pyridine-3-sulfonamide | 220-223 | 530.1 |
| 820 | 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide | 236-240 | 531.2 |
| 823 | N-tert-butyl-6-[3-cyano-5-fluoro-1-(pyrimidin-2-yl)-1H-indol-2-yl]pyridine-3-sulfonamide | N/A | 451.3 |
| 824 | N-tert-butyl-6-[3-cyano-5-fluoro-6-methyl-1-(pyrimidin-2-yl)-1H-indol-2-yl]pyridine-3-sulfonamide | N/A | 465.3 |
| 843 | 6-[3-cyano-5-methyl-1-(pyrimidin-2-yl)-1H-indol-2-yl]-N-[(2S)-1,1,1-trifluoropropan-2-yl]pyridine-3-sulfonamide | 174-179 | 487.2 |
| 844 | 6-[3-cyano-1-(3-fluoropyridin-2-yl)-5-methyl-1H-indol-2-yl]-N-[(2S)-1,1,1-trifluoropropan-2-yl]pyridine-3-sulfonamide | 216-220 | 504.2 |
| 845 | 6-[3-cyano-5-methyl-1-(pyrazin-2-yl)-1H-indol-2-yl]-N-[(2S)-1,1,1-trifluoropropan-2-yl]pyridine-3-sulfonamide | 236-241 | 487.4 |
| 847 | 6-[3-cyano-5-fluoro-1-(pyridin-2-yl)-1H-indol-2-yl]-4-methyl-N-[(2S)-1,1,1-trifluoropropan-2-yl]pyridine-3-sulfonamide | 180-186 | 504.4 |
| 848 | 6-[3-cyano-5-fluoro-1-(pyrimidin-2-yl)-1H-indol-2-yl]-4-methyl-N-[(2S)-1,1,1-trifluoropropan-2-yl]pyridine-3-sulfonamide | 199-204 | 505.1 |
| 851 | 6-[3-cyano-6-ethyl-5-fluoro-1-(pyrimidin-2-yl)-1H-indol-2-yl]-4-methyl-N-[(2S)-1,1,1-trifluoropropan-2-yl]pyridine-3-sulfonamide | 231-236 | 533.5 |
| 852 | 6-[3-cyano-6-ethyl-5-fluoro-1-(pyridin-2-yl)-1H-indol-2-yl]-4-methyl-N-[(2S)-1,1,1-trifluoropropan-2-yl]pyridine-3-sulfonamide | 178-183 | 532.2 |
| 853 | 6-[3-cyano-5-fluoro-6-methyl-1-(pyrimidin-2-yl)-1H-indol-2-yl]-4-methyl-N-[(2S)-1,1,1-trifluoropropan-2-yl]pyridine-3-sulfonamide | 219-226 | 505.1 |
| 854 | 6-[3-cyano-5-fluoro-6-methyl-1-(pyridin-2-yl)-1H-indol-2-yl]-4-methyl-N-[(2S)-1,1,1-trifluoropropan-2-yl]pyridine-3-sulfonamide | 192-197 | 504.0 |
| 855 | N-tert-butyl-6-[3-cyano-6-ethyl-5-fluoro-1-(pyrimidin-2-yl)-1H-indol-2-yl]pyridine-3-sulfonamide | 208-210 | 479.6 |
| 859 | 6-[3-cyano-6-ethyl-5-fluoro-1-(pyrimidin-2-yl)-1H-indol-2-yl]-N-(1,1,1-trifluoro-2-methylpropan-2-yl)pyridine-3-sulfonamide | N/A | 533.1 |

-continued

| Cpd | Name | m.p. | MS |
|---|---|---|---|
| 860 | 6-[3-cyano-6-ethyl-5-fluoro-1-(pyrimidin-2-yl)-1H-indol-2-yl]-N-(1-methylcyclopropyl)pyridine-3-sulfonamide | 169-179 | 477.1 |
| 861 | 6-[3-cyano-6-ethyl-5-fluoro-1-(pyrimidin-2-yl)-1H-indol-2-yl]-N-(1-methylcyclopropyl)-N-(pyrimidin-2-yl)pyridine-3-sulfonamide | 193-200 | 555.1 |
| 864 | 6-[3-cyano-6-ethyl-5-fluoro-1-(pyrimidin-2-yl)-1H-indol-2-yl]-N-[1-(trifluoromethyl)cyclopropyl]pyridine-3-sulfonamide | N/A | 531.5 |
| 865 | 6-[3-cyano-5-fluoro-6-methyl-1-(5-methylpyrazin-2-yl)-1H-indol-2-yl]-N-[(2S)-1,1,1-trifluoropropan-2-yl]pyridine-3-sulfonamide | N/A | 518.5 |
| 866 | 6-[3-cyano-5-fluoro-1-(4-methoxypyrimidin-2-yl)-6-methyl-1H-indol-2-yl]-N-[(2S)-1,1,1-trifluoropropan-2-yl]pyridine-3-sulfonamide | N/A | 534.5 |
| 867 | 6-[3-cyano-6-ethyl-5-fluoro-1-(pyrimidin-2-yl)-1H-indol-2-yl]-5-methyl-N-[(2S)-1,1,1-trifluoropropan-2-yl]pyridine-3-sulfonamide | 192-198 | 533.1 |
| 870 | 6-[3-cyano-6-ethyl-5-fluoro-1-(pyridin-2-yl)-1H-indol-2-yl]-5-methyl-N-[(2S)-1,1,1-trifluoropropan-2-yl]pyridine-3-sulfonamide | 195-198 | 532.1 |
| 873 | 6-[3-cyano-5-fluoro-6-methyl-1-(4-methylpyrimidin-2-yl)-1H-indol-2-yl]-N-[(2S)-1,1,1-trifluoropropan-2-yl]pyridine-3-sulfonamide | N/A | 518.5 |
| 878 | 6-[3-cyano-6-ethyl-5-fluoro-1-(pyrimidin-2-yl)-1H-indol-2-yl]-N-[(2R)-1,1,1-trifluoropropan-2-yl]pyridine-3-sulfonamide | 197-200 | 519.1 |
| 879 | 6-[3-cyano-6-ethyl-5-fluoro-1-(pyridin-2-yl)-1H-indol-2-yl]-N-[(2R)-1,1,1-trifluoropropan-2-yl]pyridine-3-sulfonamide | 178-182 | 518.1 |
| 880 | 6-[3-cyano-6-ethyl-5-fluoro-1-(5-fluoropyridin-2-yl)-1H-indol-2-yl]-N-[(2R)-1,1,1-trifluoropropan-2-yl]pyridine-3-sulfonamide | 209-216 | 536.1 |
| 881 | 6-[3-cyano-6-ethyl-5-fluoro-1-(pyrimidin-2-yl)-1H-indol-2-yl]-2-methyl-N-[(2S)-1,1,1-trifluoropropan-2-yl]pyridine-3-sulfonamide | 258-262 | 533.1 |
| 882 | N-tert-butyl-6-[3-cyano-6-ethyl-5-fluoro-1-(pyridin-2-yl)-1H-indol-2-yl]pyridine-3-sulfonamide | 200-205 | 478.2 |
| 884 | N-tert-butyl-6-(3-cyano-6-ethyl-5-fluoro-1-phenyl-1H-indol-2-yl)pyridine-3-sulfonamide | 175-180 | 477.2 |
| 885 | 6-[3-cyano-5-fluoro-6-methyl-1-(5-methylpyridin-2-yl)-1H-indol-2-yl]-N-[(2S)-1,1,1-trifluoropropan-2-yl]pyridine-3-sulfonamide | 250-254 | 517.5 |
| 886 | 6-[3-cyano-5-fluoro-6-methyl-1-(4-methylpyridin-2-yl)-1H-indol-2-yl]-N-[(2S)-1,1,1-trifluoropropan-2-yl]pyridine-3-sulfonamide | 200-204 | 517.5 |
| 887 | 6-[3-cyano-6-ethyl-5-fluoro-1-(pyridin-2-yl)-1H-indol-2-yl]-2-methyl-N-[(2S)-1,1,1-trifluoropropan-2-yl]pyridine-3-sulfonamide | 219-224 | 531.0 |
| 888 | 6-[3-cyano-5-fluoro-6-methyl-1-(pyrimidin-2-yl)-1H-indol-2-yl]-5-methyl-N-[(2S)-1,1,1-trifluoropropan-2-yl]pyridine-3-sulfonamide | 201-204 | 519.2 |
| 889 | 6-[3-cyano-5-fluoro-6-methyl-1-(pyridin-2-yl)-1H-indol-2-yl]-5-methyl-N-[(2S)-1,1,1-trifluoropropan-2-yl]pyridine-3-sulfonamide | 197-202 | 518.2 |
| 890 | 6-[3-cyano-6-ethyl-5-fluoro-1-(pyrimidin-2-yl)-1H-indol-2-yl]-4-methyl-N-[(2R)-1,1,1-trifluoropropan-2-yl]pyridine-3-sulfonamide | 231-236 | 533.2 |
| 891 | 6-[3-cyano-6-ethyl-5-fluoro-1-(pyridin-2-yl)-1H-indol-2-yl]-4-methyl-N-[(2R)-1,1,1-trifluoropropan-2-yl]pyridine-3-sulfonamide | 178-183 | 532.2 |
| 892 | 6-[3-cyano-5-fluoro-6-methyl-1-(pyridazin-3-yl)-1H-indol-2-yl]-N-[(2S)-1,1,1-trifluoropropan-2-yl]pyridine-3-sulfonamide | 245-250 | 504.5 |
| 893 | 6-[3-cyano-5-fluoro-6-methyl-1-(pyridin-3-yl)-1H-indol-2-yl]-N-[(2S)-1,1,1-trifluoropropan-2-yl]pyridine-3-sulfonamide | 217-221 | 503.5 |
| 894 | 6-[3-cyano-5-fluoro-6-methyl-1-(pyrimidin-5-yl)-1H-indol-2-yl]-N-[(2S)-1,1,1-trifluoropropan-2-yl]pyridine-3-sulfonamide | 198-202 | 504.5 |
| 895 | 6-[6-bromo-3-cyano-5-fluoro-1-(pyrimidin-2-yl)-1H-indol-2-yl]-N-[(2S)-1,1,1-trifluoropropan-2-yl]pyridine-3-sulfonamide | 224-226 | 569.1 |
| 896 | 6-[3-cyano-5-fluoro-6-methyl-1-(pyrimidin-4-yl)-1H-indol-2-yl]-N-[(2S)-1,1,1-trifluoropropan-2-yl]pyridine-3-sulfonamide | 214-219 | 504.5 |
| 897 | 6-[3-cyano-1-(pyrazin-2-yl)-5-(trifluoromethyl)-1H-indol-2-yl]-N-[(2S)-1,1,1-trifluoropropan-2-yl]pyridine-3-sulfonamide | 255-258 | 541.2 |

-continued

| Cpd | Name | m.p. | MS |
|---|---|---|---|
| 898 | 6-[3-cyano-1-(pyrazin-2-yl)-5-(trifluoromethoxy)-1H-indol-2-yl]-N-[(2S)-1,1,1-trifluoropropan-2-yl]pyridine-3-sulfonamide | 191-195 | 557.2 |
| 899 | N-tert-butyl-6-[3-cyano-6-ethyl-5-fluoro-1-(pyrazin-2-yl)-1H-indol-2-yl]pyridine-3-sulfonamide | 196-201 | 479.4 |
| 900 | N-tert-butyl-6-[3-cyano-6-ethyl-5-fluoro-1-(3-fluoropyridin-2-yl)-1H-indol-2-yl]pyridine-3-sulfonamide | 200-203 | 496.2 |
| 901 | 6-[3-cyano-6-fluoro-5-methyl-1-(pyrimidin-2-yl)-1H-indol-2-yl]-N-[(2S)-1,1,1-trifluoropropan-2-yl]pyridine-3-sulfonamide | 125-130 | 505.2 |
| 903 | 6-[5-fluoro-6-methyl-1-(1,3-thiazol-2-yl)-1H-indol-2-yl]-N-[(2S)-1,1,1-trifluoropropan-2-yl]pyridine-3-sulfonamide | 224-230 | 484.5 |
| 907 | 6-[6-acetyl-3-cyano-5-fluoro-1-(pyrimidin-2-yl)-1H-indol-2-yl]-N-[(2S)-1,1,1-trifluoropropan-2-yl]pyridine-3-sulfonamide | 220-221 | 533.0 |
| 908 | 6-[3-cyano-6-ethenyl-5-fluoro-1-(pyrimidin-2-yl)-1H-indol-2-yl]-N-[(2S)-1,1,1-trifluoropropan-2-yl]pyridine-3-sulfonamide | N/A | 517.2 |
| 914 | 6-[1-(5-chloropyrimidin-2-yl)-3-cyano-5-fluoro-6-methyl-1H-indol-2-yl]-N-[(2S)-1,1,1-trifluoropropan-2-yl]pyridine-3-sulfonamide | 213-218 | 538.9 |
| 915 | 6-[3-cyano-5-fluoro-6-methyl-1-(6-methylpyrazin-2-yl)-1H-indol-2-yl]-N-[(2S)-1,1,1-trifluoropropan-2-yl]pyridine-3-sulfonamide | 211-215 | 518.5 |
| 917 | 6-[3-cyano-6-fluoro-5-methyl-1-(pyridin-2-yl)-1H-indol-2-yl]-N-[(2S)-1,1,1-trifluoropropan-2-yl]pyridine-3-sulfonamide | 175-180 | 504.3 |
| 919 | 6-[3-cyano-6-fluoro-5-methyl-1-(pyrazin-2-yl)-1H-indol-2-yl]-N-[(2S)-1,1,1-trifluoropropan-2-yl]pyridine-3-sulfonamide | 233-238 | 505.2 |
| 920 | 6-[3-cyano-1-(4-fluorophenyl)-5-methyl-1H-indol-2-yl]-N-[(2S)-1,1,1-trifluoropropan-2-yl]pyridine-3-sulfonamide | 195-200 | 503.2 |
| 921 | 6-(3-cyano-5-methyl-1-phenyl-1H-indol-2-yl)-N-[(2S)-1,1,1-trifluoropropan-2-yl]pyridine-3-sulfonamide | 160-165 | 485.2 |
| 922 | 6-[3-cyano-1-(pyrimidin-2-yl)-5-(trifluoromethyl)-1H-indol-2-yl]-N-[(2S)-1,1,1-trifluoropropan-2-yl]pyridine-3-sulfonamide | 180-183 | 541.2 |
| 923 | 6-[3-cyano-5-fluoro-6-methyl-1-(6-methylpyridin-2-yl)-1H-indol-2-yl]-N-[(2S)-1,1,1-trifluoropropan-2-yl]pyridine-3-sulfonamide | 219-225 | 517.5 |
| 924 | 6-[3-cyano-5-fluoro-1-(5-fluoropyrimidin-2-yl)-6-methyl-1H-indol-2-yl]-N-[(2S)-1,1,1-trifluoropropan-2-yl]pyridine-3-sulfonamide | 244-248 | 522.5 |
| 925 | 6-[3-cyano-5-fluoro-6-methyl-1-(5-methylpyrimidin-2-yl)-1H-indol-2-yl]-N-[(2S)-1,1,1-trifluoropropan-2-yl]pyridine-3-sulfonamide | 179-184 | 518.5 |
| 926 | 6-[3-cyano-5-fluoro-1-(4-fluoropyridin-2-yl)-6-methyl-1H-indol-2-yl]-N-[(2S)-1,1,1-trifluoropropan-2-yl]pyridine-3-sulfonamide | 229-233 | 521.5 |
| 927 | 6-[3-cyano-5-fluoro-6-(2-methyl-1,3-dioxolan-2-yl)-1-(pyrimidin-2-yl)-1H-indol-2-yl]-N-[(2S)-1,1,1-trifluoropropan-2-yl]pyridine-3-sulfonamide | N/A | 577.2 |
| 929 | 6-[3-cyano-6-ethyl-5-fluoro-1-(pyrazin-2-yl)-1H-indol-2-yl]-N-[(2S)-1,1,1-trifluoropropan-2-yl]pyridine-3-sulfonamide | 225-229 | 519.0 |
| 930 | 6-[3-cyano-6-ethyl-5-fluoro-1-(6-fluoropyridin-2-yl)-1H-indol-2-yl]-N-[(2S)-1,1,1-trifluoropropan-2-yl]pyridine-3-sulfonamide | 205-211 | 536.0 |
| 931 | 6-[3-cyano-6-ethyl-5-fluoro-1-(5-methylpyridin-2-yl)-1H-indol-2-yl]-N-[(2S)-1,1,1-trifluoropropan-2-yl]pyridine-3-sulfonamide | N/A | 532.3 |
| 932 | 6-[3-cyano-6-ethyl-5-fluoro-1-(4-methylpyridin-2-yl)-1H-indol-2-yl]-N-[(2S)-1,1,1-trifluoropropan-2-yl]pyridine-3-sulfonamide | 188-190 | 532.1 |
| 933 | 6-[3-cyano-5-fluoro-6-methyl-1-(pyridin-4-yl)-1H-indol-2-yl]-N-[(2S)-1,1,1-trifluoropropan-2-yl]pyridine-3-sulfonamide | 250-255 | 503.5 |
| 934 | 6-[3-cyano-5-fluoro-6-methyl-1-(1,3-thiazol-2-yl)-1H-indol-2-yl]-N-[(2S)-1,1,1-trifluoropropan-2-yl]pyridine-3-sulfonamide | 203-208 | 509.5 |
| 935 | 6-[3-cyano-6-ethyl-5-fluoro-1-(1,3-thiazol-2-yl)-1H-indol-2-yl]-N-[(2S)-1,1,1-trifluoropropan-2-yl]pyridine-3-sulfonamide | 187-191 | 523.5 |
| 938 | 6-[6-bromo-3-cyano-5-fluoro-1-(pyrimidin-2-yl)-1H-indol-2-yl]-N-tert-butylpyridine-3-sulfonamide | 266-268 | 531.2 |
| 941 | 6-[3-cyano-1-(1,6-dihydropyrimidin-2-yl)-6-ethyl-5-fluoro-1H-indol-2-yl]-N-[(2S)-1,1,1-trifluoropropan-2-yl]pyridine-3-sulfonamide | N/A | 521.3 |

-continued

| Cpd | Name | m.p. | MS |
|---|---|---|---|
| 942 | 6-[1-(5-chloropyrimidin-2-yl)-3-cyano-6-ethyl-5-fluoro-1H-indol-2-yl]-N-[(2S)-1,1,1-trifluoropropan-2-yl]pyridine-3-sulfonamide | 222-229 | 553.3 |
| 943 | 6-[3-cyano-6-ethyl-5-fluoro-1-(2-methylpyrimidin-4-yl)-1H-indol-2-yl]-N-[(2S)-1,1,1-trifluoropropan-2-yl]pyridine-3-sulfonamide | 138-146 | 533.1 |
| 944 | 6-[5-fluoro-1-(2-fluoropyridin-4-yl)-6-methyl-1H-indol-2-yl]-N-[(2S)-1,1,1-trifluoropropan-2-yl]pyridine-3-sulfonamide | 176-180 | 496.5 |
| 945 | 6-[3-cyano-5-fluoro-1-(5-fluoropyridin-3-yl)-6-methyl-1H-indol-2-yl]-N-[(2S)-1,1,1-trifluoropropan-2-yl]pyridine-3-sulfonamide | 199-204 | 521.5 |
| 946 | 6-[3-cyano-6-ethyl-5-fluoro-1-(5-fluoropyrimidin-2-yl)-1H-indol-2-yl]-N-[(2S)-1,1,1-trifluoropropan-2-yl]pyridine-3-sulfonamide | 210-225 | 537.0 |
| 947 | 6-[3-chloro-6-cyclopropyl-5-fluoro-1-(pyrimidin-2-yl)-1H-indol-2-yl]-N-[(2S)-1,1,1-trifluoropropan-2-yl]pyridine-3-sulfonamide | 248-250 | 540.0 |
| 948 | 6-[3-cyano-1-(5-fluoropyrimidin-2-yl)-5-methyl-1H-indol-2-yl]-N-[(2S)-1,1,1-trifluoropropan-2-yl]pyridine-3-sulfonamide | 202-207 | 505.2 |
| 949 | 6-[3-cyano-6-fluoro-1-(5-fluoropyrimidin-2-yl)-5-methyl-1H-indol-2-yl]-N-[(2S)-1,1,1-trifluoropropan-2-yl]pyridine-3-sulfonamide | 226-231 | 523.2 |
| 950 | 6-[3-cyano-1-(pyrimidin-2-yl)-6-(trifluoromethyl)-1H-indol-2-yl]-N-[(2S)-1,1,1-trifluoropropan-2-yl]pyridine-3-sulfonamide | 206-210 | 541.2 |
| 951 | 6-[3-cyano-1-(pyrazin-2-yl)-6-(trifluoromethyl)-1H-indol-2-yl]-N-[(2S)-1,1,1-trifluoropropan-2-yl]pyridine-3-sulfonamide | 208-213 | 541.2 |
| 952 | 6-[3-cyano-1-(pyridin-2-yl)-6-(trifluoromethyl)-1H-indol-2-yl]-N-[(2S)-1,1,1-trifluoropropan-2-yl]pyridine-3-sulfonamide | 173-176 | 540.2 |
| 953 | 6-[3-cyano-6-ethyl-5-fluoro-1-(pyrimidin-2-yl)-1H-indol-2-yl]-N-(cyclobutylmethyl)pyridine-3-sulfonamide | 207-214 | 491.2 |
| 954 | 6-[3-cyano-6-ethyl-5-fluoro-1-(pyridin-3-yl)-1H-indol-2-yl]-N-[(2S)-1,1,1-trifluoropropan-2-yl]pyridine-3-sulfonamide | 205-212 | 518.2 |
| 955 | 6-[3-cyano-6-ethyl-5-fluoro-1-(4-methoxypyridin-2-yl)-1H-indol-2-yl]-N-[(2S)-1,1,1-trifluoropropan-2-yl]pyridine-3-sulfonamide | 227-233 | 548.1 |
| 956 | 6-[3-cyano-6-ethyl-5-fluoro-1-(pyrimidin-2-yl)-1H-indol-2-yl]-N-[(2S)-1,1,1-trifluoro(2-deuterium)propan-2-yl]pyridine-3-sulfonamide | 177-179 | 520.2 |
| 957 | 6-[5-fluoro-6-methyl-1-(1,3-thiazol-4-yl)-1H-indol-2-yl]-N-[(2S)-1,1,1-trifluoropropan-2-yl]pyridine-3-sulfonamide | N/A | 484.5 |
| 958 | 6-[5-fluoro-6-methyl-1-(1,3,4-thiadiazol-2-yl)-1H-indol-2-yl]-N-[(2S)-1,1,1-trifluoropropan-2-yl]pyridine-3-sulfonamide | N/A | 485.5 |
| 959 | 6-[5-fluoro-6-methyl-1-(1,3-thiazol-5-yl)-1H-indol-2-yl]-N-[(2S)-1,1,1-trifluoropropan-2-yl]pyridine-3-sulfonamide | N/A | 484.5 |
| 960 | 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide | 184-189 | 509.5 |
| 961 | 6-[3-cyano-5-fluoro-1-(5-fluoro-6-methylpyridin-2-yl)-6-methyl-1H-indol-2-yl]-N-[(2S)-1,1,1-trifluoropropan-2-yl]pyridine-3-sulfonamide | 240-246 | 535.5 |
| 962 | 6-[1-(6-chloropyridin-2-yl)-3-cyano-5-fluoro-6-methyl-1H-indol-2-yl]-N-[(2S)-1,1,1-trifluoropropan-2-yl]pyridine-3-sulfonamide | 253-257 | 537.9 |
| 963 | 6-[3-cyano-6-ethyl-5-fluoro-1-(pyrimidin-5-yl)-1H-indol-2-yl]-N-[(2S)-1,1,1-trifluoropropan-2-yl]pyridine-3-sulfonamide | 250-257 | 519.2 |
| 964 | 6-[3-cyano-6-ethyl-5-fluoro-1-(pyrimidin-4-yl)-1H-indol-2-yl]-N-[(2S)-1,1,1-trifluoropropan-2-yl]pyridine-3-sulfonamide | 202-206 | 519.2 |
| 965 | 6-[1-(3-chloropyridin-2-yl)-3-cyano-6-ethyl-5-fluoro-1H-indol-2-yl]-N-[(2S)-1,1,1-trifluoropropan-2-yl]pyridine-3-sulfonamide | 200-208 | 552.2 |
| 966 | 6-[1-(5-chloropyridin-2-yl)-3-cyano-6-ethyl-5-fluoro-1H-indol-2-yl]-N-[(2S)-1,1,1-trifluoropropan-2-yl]pyridine-3-sulfonamide | 252-259 | 552.2 |
| 971 | 6-[1-(3-chloropyridin-2-yl)-3-cyano-5-fluoro-6-methyl-1H-indol-2-yl]-N-[(2S)-1,1,1-trifluoropropan-2-yl]pyridine-3-sulfonamide | 221-225 | 537.9 |
| 973 | 6-[3-cyano-5-fluoro-6-methyl-1-(1,3-thiazol-5-yl)-1H-indol-2-yl]-N-[(2S)-1,1,1-trifluoropropan-2-yl]pyridine-3-sulfonamide | 234-238 | 509.5 |

-continued

| Cpd | Name | m.p. | MS |
|---|---|---|---|
| 974 | 6-[3-cyano-6-ethyl-5-fluoro-1-(pyridin-4-yl)-1H-indol-2-yl]-N-[(2S)-1,1,1-trifluoropropan-2-yl]pyridine-3-sulfonamide | 209-215 | 518.3 |
| 975 | 6-[3-cyano-6-ethyl-5-fluoro-1-(pyridazin-3-yl)-1H-indol-2-yl]-N-[(2S)-1,1,1-trifluoropropan-2-yl]pyridine-3-sulfonamide | 240-247 | 519.1 |
| 976 | 6-[3-cyano-6-ethyl-5-fluoro-1-(5-methylpyrimidin-2-yl)-1H-indol-2-yl]-N-[(2S)-1,1,1-trifluoropropan-2-yl]pyridine-3-sulfonamide | 201-206 | 533.2 |
| 977 | 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide | 232-240 | 510.5 |
| 983 | 6-[1-(5-chloropyridin-3-yl)-3-cyano-6-ethyl-5-fluoro-1H-indol-2-yl]-N-[(2S)-1,1,1-trifluoropropan-2-yl]pyridine-3-sulfonamide | 107-109 | 552.3 |
| 984 | 6-{3-cyano-5-fluoro-1-[5-(hydroxymethyl)-1,3-thiazol-2-yl]-6-methyl-1H-indol-2-yl}-N-[(2S)-1,1,1-trifluoropropan-2-yl]pyridine-3-sulfonamide | 180-185 | 539.5 |
| 985 | methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-5-carboxylate | N/A | 567.5 |
| 986 | methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-4-carboxylate | N/A | 567.5 |
| 987 | 6-[5-fluoro-6-methyl-1-(thiophen-3-yl)-1H-indol-2-yl]-N-[(2S)-1,1,1-trifluoropropan-2-yl]pyridine-3-sulfonamide | N/A | 483.5 |
| 988 | 6-[5-fluoro-1-(furan-3-yl)-6-methyl-1H-indol-2-yl]-N-[(2S)-1,1,1-trifluoropropan-2-yl]pyridine-3-sulfonamide | N/A | 467.4 |
| 989 | 6-[5-fluoro-6-methyl-1-(thiophen-2-yl)-1H-indol-2-yl]-N-[(2S)-1,1,1-trifluoropropan-2-yl]pyridine-3-sulfonamide | N/A | 483.5 |
| 990 | 6-[3-cyano-5-fluoro-6-methyl-1-(thiophen-2-yl)-1H-indol-2-yl]-N-[(2S)-1,1,1-trifluoropropan-2-yl]pyridine-3-sulfonamide | 233-240 | 508.5 |
| 991 | 6-[3-cyano-5-fluoro-1-(furan-3-yl)-6-methyl-1H-indol-2-yl]-N-[(2S)-1,1,1-trifluoropropan-2-yl]pyridine-3-sulfonamide | 215-219 | 492.4 |
| 992 | 6-[3-cyano-5-fluoro-6-methyl-1-(thiophen-3-yl)-1H-indol-2-yl]-N-[(2S)-1,1,1-trifluoropropan-2-yl]pyridine-3-sulfonamide | 196-203 | 508.5 |
| 993 | 6-[1-(4-chloropyridin-2-yl)-3-cyano-6-ethyl-5-fluoro-1H-indol-2-yl]-N-[(2S)-1,1,1-trifluoropropan-2-yl]pyridine-3-sulfonamide | 185-190 | 552.2 |
| 1000 | 6-[3-cyano-5-fluoro-6-methyl-1-(3-methylthiophen-2-yl)-1H-indol-2-yl]-N-[(2S)-1,1,1-trifluoropropan-2-yl]pyridine-3-sulfonamide | 197.0-203.8 | 523.5 |
| 1001 | 6-[3-cyano-1-(4,6-difluoropyridin-2-yl)-5-fluoro-6-methyl-1H-indol-2-yl]-N-[(2S)-1,1,1-trifluoropropan-2-yl]pyridine-3-sulfonamide | 190.2-196.8 | 540.5 |
| 1002 | 6-[3-cyano-6-ethyl-5-fluoro-1-(4-fluorophenyl)-1H-indol-2-yl]-N-[(2S)-1,1,1-trifluoropropan-2-yl]pyridine-3-sulfonamide | 236-243 | 535.6 |
| 1003 | 6-[1-(4-chlorophenyl)-3-cyano-6-ethyl-5-fluoro-1H-indol-2-yl]-N-[(2S)-1,1,1-trifluoropropan-2-yl]pyridine-3-sulfonamide | 279-289 | 551.3 553.3 |
| 1004 | 6-[3-cyano-6-ethyl-5-fluoro-1-(4-methylphenyl)-1H-indol-2-yl]-N-[(2S)-1,1,1-trifluoropropan-2-yl]pyridine-3-sulfonamide | N/A | 531.7 |
| 1005 | 6-[3-cyano-6-ethyl-5-fluoro-1-(4-methoxyphenyl)-1H-indol-2-yl]-N-[(2S)-1,1,1-trifluoropropan-2-yl]pyridine-3-sulfonamide | 261-266 | 547.2 |
| 1006 | 6-{3-cyano-6-ethyl-5-fluoro-1-[4-(trifluoromethyl)phenyl]-1H-indol-2-yl}-N-[(2S)-1,1,1-trifluoropropan-2-yl]pyridine-3-sulfonamide | 276-282 | 585.7 |
| 1007 | 6-[3-cyano-1-(4-cyanophenyl)-6-ethyl-5-fluoro-1H-indol-2-yl]-N-[(2S)-1,1,1-trifluoropropan-2-yl]pyridine-3-sulfonamide | 288-293 | 542.2 |
| 1008 | 6-[3-cyano-6-ethyl-5-fluoro-1-(3-fluorophenyl)-1H-indol-2-yl]-N-[(2S)-1,1,1-trifluoropropan-2-yl]pyridine-3-sulfonamide | 210-214 | 535.3 |
| 1009 | 6-[3-cyano-6-ethyl-5-fluoro-1-(3-methylphenyl)-1H-indol-2-yl]-N-[(2S)-1,1,1-trifluoropropan-2-yl]pyridine-3-sulfonamide | 193-198 | 531.4 |
| 1010 | 6-[3-cyano-6-ethyl-5-fluoro-1-(3-methoxyphenyl)-1H-indol-2-yl]-N-[(2S)-1,1,1-trifluoropropan-2-yl]pyridine-3-sulfonamide | 229-233 | 547.2 |
| 1011 | 6-{3-cyano-6-ethyl-5-fluoro-1-[3-(trifluoromethyl)phenyl]-1H-indol-2-yl}-N-[(2S)-1,1,1-trifluoropropan-2-yl]pyridine-3-sulfonamide | 240-245 | 585.3 |

-continued

| Cpd | Name | m.p. | MS |
|---|---|---|---|
| 1012 | 6-[3-cyano-1-(3-cyanophenyl)-6-ethyl-5-fluoro-1H-indol-2-yl]-N-[(2S)-1,1,1-trifluoropropan-2-yl]pyridine-3-sulfonamide | 244-248 | 542.3 |
| 1013 | 6-[3-cyano-5-fluoro-1-(2-fluoropyridin-4-yl)-6-methyl-1H-indol-2-yl]-N-[(2S)-1,1,1-trifluoropropan-2-yl]pyridine-3-sulfonamide | 243.4-246.9 | 522.5 |
| 1014 | 6-[3-cyano-5-fluoro-1-(3-fluoropyridin-4-yl)-6-methyl-1H-indol-2-yl]-N-[(2S)-1,1,1-trifluoropropan-2-yl]pyridine-3-sulfonamide | 204.2-210.5 | 522.5 |
| 1015 | 6-[3-cyano-5-fluoro-1-(6-fluoropyridin-3-yl)-6-methyl-1H-indol-2-yl]-N-[(2S)-1,1,1-trifluoropropan-2-yl]pyridine-3-sulfonamide | 246.8-252.7 | 522.5 |
| 1016 | 6-[3-cyano-5-fluoro-6-methyl-1-(1-methyl-1H-pyrazol-4-yl)-1H-indol-2-yl]-N-[(2S)-1,1,1-trifluoropropan-2-yl]pyridine-3-sulfonamide | 233.7-239.3 | 507.5 |
| 1017 | 6-[3-cyano-5-fluoro-6-methyl-1-(5-methyl-1,3-thiazol-2-yl)-1H-indol-2-yl]-N-[(2S)-1,1,1-trifluoropropan-2-yl]pyridine-3-sulfonamide | 223.1-228.1 | 524.5 |
| 1018 | 6-[1-(3-chlorophenyl)-3-cyano-6-ethyl-5-fluoro-1H-indol-2-yl]-N-[(2S)-1,1,1-trifluoropropan-2-yl]pyridine-3-sulfonamide | 195-198 | 551.3 553.3 |
| 1030 | 6-[3-cyano-5-fluoro-6-methyl-1-(3-methyl-1H-pyrazol-4-yl)-1H-indol-2-yl]-N-[(2S)-1,1,1-trifluoropropan-2-yl]pyridine-3-sulfonamide | 238.8-244.0 | 507.5 |
| 1031 | 6-[3-cyano-5-fluoro-6-methyl-1-(5-methylthiophen-2-yl)-1H-indol-2-yl]-N-[(2S)-1,1,1-trifluoropropan-2-yl]pyridine-3-sulfonamide | 246.8-249.4 | 523.5 |
| 1032 | 6-[1-(5-chlorothiophen-2-yl)-3-cyano-5-fluoro-6-methyl-1H-indol-2-yl]-N-[(2S)-1,1,1-trifluoropropan-2-yl]pyridine-3-sulfonamide | 244.8-247.4 | 544.0 |
| 1033 | 6-[3-cyano-1-(5-cyanothiophen-2-yl)-5-fluoro-6-methyl-1H-indol-2-yl]-N-[(2S)-1,1,1-trifluoropropan-2-yl]pyridine-3-sulfonamide | 182.0-184.6 | 534.5 |
| 1034 | 6-[3-cyano-5-fluoro-6-methyl-1-(5-sulfamoylthiophen-2-yl)-1H-indol-2-yl]-N-[(2S)-1,1,1-trifluoropropan-2-yl]pyridine-3-sulfonamide | 131.6-137.7 | 588.6 |
| 1035 | 6-[1-(5-acetylthiophen-2-yl)-3-cyano-5-fluoro-6-methyl-1H-indol-2-yl]-N-[(2S)-1,1,1-trifluoropropan-2-yl]pyridine-3-sulfonamide | 235.6-238.7 | 551.6 |
| 1038 | 6-[3-cyano-5-fluoro-6-methyl-1-(4-methyl-1,3-thiazol-2-yl)-1H-indol-2-yl]-N-[(2S)-1,1,1-trifluoropropan-2-yl]pyridine-3-sulfonamide | 206.3-211.7 | 524.5 |
| 1055 | 6-[1-(2-acetylthiophen-3-yl)-3-cyano-5-fluoro-6-methyl-1H-indol-2-yl]-N-[(2S)-1,1,1-trifluoropropan-2-yl]pyridine-3-sulfonamide | 208.7-212.4 | 551.6 |
| 1056 | 6-[3-cyano-5-fluoro-6-methyl-1-(4-methylthiophen-3-yl)-1H-indol-2-yl]-N-[(2S)-1,1,1-trifluoropropan-2-yl]pyridine-3-sulfonamide | 223.2-227.1 | 523.5 |
| 1057 | 6-[1-(2-chlorothiophen-3-yl)-3-cyano-5-fluoro-6-methyl-1H-indol-2-yl]-N-[(2S)-1,1,1-trifluoropropan-2-yl]pyridine-3-sulfonamide | 226.7-231.8 | 544.0 |
| 1058 | 6-[3-cyano-5-fluoro-6-methyl-1-(5-methylthiophen-3-yl)-1H-indol-2-yl]-N-[(2S)-1,1,1-trifluoropropan-2-yl]pyridine-3-sulfonamide | 210.5-215.2 | 523.5 |
| 1059 | 6-[5-fluoro-6-methyl-1-(1,3-oxazol-2-yl)-1H-indol-2-yl]-N-[(2S)-1,1,1-trifluoropropan-2-yl]pyridine-3-sulfonamide | N/A | 469.4 |
| 1060 | 6-[1-(5-cyanofuran-2-yl)-5-fluoro-6-methyl-1H-indol-2-yl]-N-[(2S)-1,1,1-trifluoropropan-2-yl]pyridine-3-sulfonamide | N/A | 493.4 |
| 1061 | 6-[3-cyano-1-(3,4-difluorophenyl)-6-ethyl-5-fluoro-1H-indol-2-yl]-N-[(2S)-1,1,1-trifluoropropan-2-yl]pyridine-3-sulfonamide | 229-235 | N/A |
| 1062 | 6-[1-(3-chloro-4-fluorophenyl)-3-cyano-6-ethyl-5-fluoro-1H-indol-2-yl]-N-[(2S)-1,1,1-trifluoropropan-2-yl]pyridine-3-sulfonamide | 228-232 | N/A |
| 1072 | 6-[3-cyano-1-(3-cyanofuran-2-yl)-5-fluoro-6-methyl-1H-indol-2-yl]-N-[(2S)-1,1,1-trifluoropropan-2-yl]pyridine-3-sulfonamide | 238.0-243.6 | 518.5 |
| 1073 | 6-[3-cyano-5-fluoro-6-methyl-1-(1,3-oxazol-2-yl)-1H-indol-2-yl]-N-[(2S)-1,1,1-trifluoropropan-2-yl]pyridine-3-sulfonamide | N/A | 494.4 |
| 1074 | 6-[3-cyano-1-(4-cyano-1,3-oxazol-2-yl)-5-fluoro-6-methyl-1H-indol-2-yl]-N-[(2S)-1,1,1-trifluoropropan-2-yl]pyridine-3-sulfonamide | 212.2-216.9 | 519.4 |
| 1075 | 6-[3-cyano-6-ethyl-5-fluoro-1-(2-fluorophenyl)-1H-indol-2-yl]-N-[(2S)-1,1,1-trifluoropropan-2-yl]pyridine-3-sulfonamide | N/A | 535.5 |

-continued

| Cpd | Name | m.p. | MS |
|---|---|---|---|
| 1078 | 6-{3-cyano-6-[(1,1-dideuterium)ethyl]-5-fluoro-1-(pyrimidin-2-yl)-1H-indol-2-yl}-N-[(2S)-1,1,1-trifluoropropan-2-yl]pyridine-3-sulfonamide | 180-182 | 521.5 |
| 1079 | 6-{3-cyano-6-[(1,1-dideuterium)ethyl]-5-fluoro-1-(pyrimidin-2-yl)-1H-indol-2-yl}-N-[(2S)-1,1,1-trifluoro(2-deuterium)propan-2-yl]pyridine-3-sulfonamide | 180-182 | 522.5 |
| 1098 | 6-[3-cyano-6-cyclopropyl-4-fluoro-1-(pyrimidin-2-yl)-1H-indol-2-yl]-N-(1,1,1-trifluoro-2-methylpropan-2-yl)pyridine-3-sulfonamide | 198-200 | 545.3 |
| 1101 | N-[5-(3-cyano-6-cyclopropyl-5-fluoro-1-phenyl-1H-indol-2-yl)pyridin-2-yl]-2-methylpropane-2-sulfonamide | 249-250 | 489.3 |
| 1107 | 6-[3-cyano-5-fluoro-6-(1,1,1-trideuterium)methyl-1-(pyrimidin-2-yl)-1H-indol-2-yl]-N-[(2S)-1,1,1-trifluoro(2-deuterium)propan-2-yl]pyridine-3-sulfonamide | 200-202 | 508.9 |
| 1108 | N-tert-butyl-6-(3-cyano-5-fluoro-6-methyl-1-phenyl-1H-indol-2-yl)pyridine-3-sulfonamide | 200.6-202.4 | 463.3 |
| 1117 | N-tert-butyl-6-(3-cyano-6-cyclopropyl-5-fluoro-1-phenyl-1H-indol-2-yl)pyridine-3-sulfonamide | 219.2-220.8 | 489.4 |

BIOLOGICAL EXAMPLES

The following biological examples demonstrate the usefulness of the compounds of the present invention for treating viral infections.

Example 1

HCV Replicon Assay

The lack of reliable and readily accessible cell-culture and small animal models permissive for HCV replication has limited the development of new anti-HCV agents. Self-replicating subgenomic HCV systems, termed HCV replicons, have been described and have been widely used to assess the efficacy of anti-HCV inhibitors (see Blight K J, et al., 2000, Efficient initiation of HCV RNA replication in cell culture. Science 290:1972-1974; Blight K J, et al., 2002, Highly permissive cell lines for subgenomic and genomic hepatitis C virus RNA replication. J Virol 76:13001-13014; Ikeda M, et al., 2002. Selectable subgenomic and genome-length dicistronic RNAs derived from an infectious molecular clone of the HCV-N strain of hepatitis C virus replicate efficiently in cultured Huh7 cells. J Virol 76:2997-3006; Lohmann V, et al., 1999, Replication of subgenomic hepatitis C virus RNAs in a hepatoma cell line. Science 285:110-113; Pietschmann T, et al., 2002, Persistent and transient replication of full-length hepatitis C virus genomes in cell culture. J Virol 76:4008-4021; and, Pietschmann T. et al., 2001. Characterization of cell lines carrying self-replicating hepatitis C virus RNAs. J Virol 75:1252-1264).

As described in U.S. Pat. No. 6,630,343, HCV inhibitors are analyzed in the bicistronic replicon by quantitating replicon RNA (GenBank Accession No. AJ242654) reduction and/or the Fluc reporter signal. Replicon-containing cells may be cultured with a test compound of the present invention for up to 3 days. Interferon (IFN) □ is used as a positive control. In general, the replicon $IC_{50}$ values shown in Table 1 represent $IC_{50}$ values determined by replicon RNA reduction.

As shown in Table 1, test compounds of the present invention may demonstrate a replicon RNA reduction $IC_{50}$ value of from greater than about 2 μM to about 5 μM (*), an $IC_{50}$ value of between about 0.5 μM to about 2 μM (), or an $IC_{50}$ value of less than about 0.5 μM (*).

TABLE 1

| Replicon $IC_{50}$ (□M) | |
|---|---|
| Cpd | $IC_{50}$ |
| 1 | *** |
| 2 | *** |
| 3 | *** |
| 4 | * |
| 5 | *** |
| 6 | *** |
| 7 | ** |
| 8 | ** |
| 9 | *** |
| 10 | *** |
| 11 | ** |
| 12 | ** |
| 13 | *** |
| 14 | *** |
| 15 | ** |
| 16 | ** |
| 17 | ** |
| 18 | ** |
| 19 | * |
| 20 | ** |
| 21 | *** |
| 22 | ** |
| 23 | ** |
| 24 | *** |
| 25 | ** |
| 26 | ** |
| 27 | *** |
| 28 | * |
| 29 | *** |
| 30 | *** |
| 31 | *** |
| 32 | *** |
| 33 | *** |
| 34 | *** |
| 35 | *** |
| 36 | *** |
| 37 | *** |
| 38 | *** |
| 39 | * |
| 40 | ** |
| 41 | *** |
| 42 | *** |
| 43 | *** |
| 44 | *** |
| 45 | *** |
| 46 | *** |
| 47 | *** |
| 48 | *** |
| 49 | *** |
| 50 | *** |

TABLE 1-continued

Replicon IC$_{50}$ (µM)

| Cpd | IC$_{50}$ |
|---|---|
| 51 | *** |
| 52 | *** |
| 53 | *** |
| 54 | *** |
| 55 | *** |
| 56 | *** |
| 57 | *** |
| 58 | *** |
| 59 | ** |
| 60 | *** |
| 61 | *** |
| 62 | *** |
| 63 | *** |
| 64 | *** |
| 65 | *** |
| 66 | *** |
| 67 | *** |
| 68 | *** |
| 69 | *** |
| 70 | *** |
| 71 | *** |
| 72 | *** |
| 73 | *** |
| 74 | *** |
| 75 | *** |
| 77 | ** |
| 78 | *** |
| 79 | *** |
| 80 | *** |
| 81 | *** |
| 82 | *** |
| 83 | *** |
| 84 | *** |
| 85 | *** |
| 86 | *** |
| 87 | *** |
| 88 | *** |
| 89 | *** |
| 90 | * |
| 92 | *** |
| 93 | *** |
| 94 | *** |
| 95 | *** |
| 96 | *** |
| 97 | ** |
| 98 | *** |
| 99 | *** |
| 100 | *** |
| 101 | *** |
| 102 | *** |
| 103 | *** |
| 104 | *** |
| 105 | *** |
| 106 | *** |
| 107 | *** |
| 108 | *** |
| 109 | *** |
| 110 | *** |
| 111 | *** |
| 112 | *** |
| 113 | *** |
| 114 | *** |
| 115 | *** |
| 116 | *** |
| 117 | ** |
| 118 | *** |
| 119 | *** |
| 120 | *** |
| 121 | *** |
| 122 | *** |
| 123 | *** |
| 124 | *** |
| 125 | *** |
| 126 | *** |
| 127 | *** |
| 128 | *** |

TABLE 1-continued

Replicon IC$_{50}$ (µM)

| Cpd | IC$_{50}$ |
|---|---|
| 129 | *** |
| 130 | *** |
| 131 | *** |
| 132 | *** |
| 133 | *** |
| 134 | *** |
| 135 | *** |
| 136 | *** |
| 137 | *** |
| 138 | ** |
| 139 | ** |
| 140 | ** |
| 141 | ** |
| 142 | *** |
| 143 | *** |
| 144 | *** |
| 145 | *** |
| 146 | *** |
| 147 | *** |
| 148 | *** |
| 149 | *** |
| 150 | *** |
| 151 | *** |
| 152 | *** |
| 153 | *** |
| 154 | *** |
| 155 | *** |
| 156 | ** |
| 157 | *** |
| 158 | *** |
| 159 | *** |
| 160 | *** |
| 161 | *** |
| 162 | *** |
| 163 | ** |
| 164 | ** |
| 165 | ** |
| 166 | *** |
| 167 | *** |
| 168 | *** |
| 169 | *** |
| 170 | *** |
| 171 | *** |
| 172 | *** |
| 173 | *** |
| 174 | *** |
| 175 | *** |
| 176 | *** |
| 177 | *** |
| 178 | *** |
| 179 | *** |
| 180 | ** |
| 181 | *** |
| 182 | *** |
| 183 | ** |
| 184 | *** |
| 185 | *** |
| 186 | *** |
| 187 | *** |
| 188 | *** |
| 189 | *** |
| 190 | *** |
| 191 | ** |
| 192 | *** |
| 193 | *** |
| 194 | *** |
| 195 | *** |
| 196 | *** |
| 197 | *** |
| 198 | ** |
| 199 | *** |
| 200 | ** |
| 201 | *** |
| 202 | *** |
| 203 | *** |
| 204 | *** |

TABLE 1-continued

Replicon IC$_{50}$ (μM)

| Cpd | IC$_{50}$ |
|---|---|
| 205 | *** |
| 206 | ** |
| 207 | ** |
| 208 | *** |
| 209 | *** |
| 210 | *** |
| 211 | *** |
| 212 | *** |
| 213 | *** |
| 214 | *** |
| 215 | ** |
| 216 | ** |
| 217 | * |
| 218 | *** |
| 219 | *** |
| 220 | *** |
| 221 | *** |
| 222 | *** |
| 223 | *** |
| 224 | *** |
| 225 | *** |
| 226 | *** |
| 227 | *** |
| 228 | *** |
| 229 | *** |
| 230 | *** |
| 231 | *** |
| 232 | *** |
| 233 | *** |
| 234 | *** |
| 235 | *** |
| 236 | *** |
| 237 | *** |
| 238 | *** |
| 239 | ** |
| 240 | *** |
| 241 | *** |
| 242 | ** |
| 243 | ** |
| 244 | * |
| 245 | *** |
| 246 | ** |
| 247 | ** |
| 248 | *** |
| 249 | *** |
| 250 | *** |
| 251 | ** |
| 252 | *** |
| 253 | *** |
| 254 | ** |
| 255 | *** |
| 256 | *** |
| 257 | ** |
| 258 | *** |
| 259 | *** |
| 260 | *** |
| 261 | *** |
| 262 | *** |
| 263 | *** |
| 264 | ** |
| 265 | ** |
| 266 | ** |
| 267 | *** |
| 268 | *** |
| 269 | ** |
| 270 | * |
| 271 | ** |
| 272 | ** |
| 273 | *** |
| 274 | * |
| 275 | * |
| 276 | * |
| 277 | *** |
| 278 | ** |
| 279 | ** |
| 280 | ** |

TABLE 1-continued

Replicon IC$_{50}$ (μM)

| Cpd | IC$_{50}$ |
|---|---|
| 281 | ** |
| 282 | ** |
| 283 | * |
| 284 | ** |
| 285 | ** |
| 286 | ** |
| 287 | ** |
| 288 | ** |
| 289 | ** |
| 290 | * |
| 291 | ** |
| 292 | ** |
| 293 | ** |
| 294 | ** |
| 295 | * |
| 296 | * |
| 297 | ** |
| 298 | ** |
| 299 | * |
| 300 | *** |
| 301 | *** |
| 302 | *** |
| 303 | *** |
| 304 | *** |
| 305 | *** |
| 306 | ** |
| 307 | *** |
| 308 | ** |
| 309 | *** |
| 310 | *** |
| 311 | *** |
| 312 | ** |
| 313 | *** |
| 314 | *** |
| 315 | *** |
| 316 | *** |
| 317 | *** |
| 318 | *** |
| 319 | ** |
| 320 | ** |
| 321 | ** |
| 322 | * |
| 323 | *** |
| 324 | *** |
| 325 | *** |
| 326 | *** |
| 327 | *** |
| 328 | *** |
| 329 | *** |
| 330 | *** |
| 331 | *** |
| 332 | *** |
| 333 | *** |
| 334 | *** |
| 335 | *** |
| 336 | *** |
| 337 | ** |
| 338 | *** |
| 339 | *** |
| 340 | *** |
| 341 | *** |
| 342 | ** |
| 343 | * |
| 344 | *** |
| 345 | *** |
| 346 | *** |
| 347 | ** |
| 348 | ** |
| 349 | ** |
| 350 | ** |
| 351 | *** |
| 352 | *** |
| 353 | *** |
| 354 | *** |
| 355 | *** |
| 356 | *** |

TABLE 1-continued

Replicon IC$_{50}$ (μM)

| Cpd | IC$_{50}$ |
|---|---|
| 357 | *** |
| 358 | *** |
| 359 | *** |
| 360 | *** |
| 361 | *** |
| 362 | *** |
| 363 | *** |
| 364 | *** |
| 365 | *** |
| 367 | ** |
| 368 | *** |
| 369 | *** |
| 370 | *** |
| 371 | *** |
| 372 | *** |
| 373 | *** |
| 374 | *** |
| 375 | *** |
| 376 | *** |
| 377 | *** |
| 378 | *** |
| 379 | *** |
| 380 | *** |
| 381 | *** |
| 382 | *** |
| 383 | *** |
| 384 | *** |
| 385 | *** |
| 386 | *** |
| 387 | *** |
| 388 | ** |
| 389 | ** |
| 390 | ** |
| 391 | *** |
| 392 | *** |
| 393 | *** |
| 394 | *** |
| 395 | *** |
| 396 | *** |
| 397 | *** |
| 398 | *** |
| 399 | *** |
| 400 | *** |
| 401 | *** |
| 402 | *** |
| 403 | ** |
| 404 | *** |
| 405 | *** |
| 406 | *** |
| 407 | *** |
| 408 | *** |
| 409 | *** |
| 410 | *** |
| 411 | ** |
| 412 | *** |
| 413 | *** |
| 414 | *** |
| 415 | *** |
| 416 | *** |
| 417 | ** |
| 418 | ** |
| 419 | ** |
| 420 | ** |
| 421 | *** |
| 422 | *** |
| 423 | *** |
| 424 | *** |
| 425 | ** |
| 426 | *** |
| 427 | *** |
| 428 | *** |
| 429 | *** |
| 430 | *** |
| 431 | *** |
| 432 | *** |
| 433 | *** |

TABLE 1-continued

Replicon IC$_{50}$ (μM)

| Cpd | IC$_{50}$ |
|---|---|
| 434 | *** |
| 435 | *** |
| 436 | *** |
| 437 | *** |
| 438 | *** |
| 439 | *** |
| 440 | *** |
| 441 | *** |
| 442 | *** |
| 443 | *** |
| 444 | *** |
| 445 | *** |
| 446 | *** |
| 447 | *** |
| 448 | ** |
| 449 | *** |
| 450 | *** |
| 451 | *** |
| 452 | *** |
| 453 | *** |
| 454 | *** |
| 455 | *** |
| 456 | *** |
| 457 | *** |
| 458 | *** |
| 459 | *** |
| 460 | *** |
| 461 | *** |
| 462 | *** |
| 463 | *** |
| 464 | ** |
| 465 | *** |
| 466 | *** |
| 467 | *** |
| 468 | *** |
| 469 | ** |
| 470 | *** |
| 471 | *** |
| 472 | *** |
| 473 | *** |
| 474 | *** |
| 475 | *** |
| 476 | *** |
| 477 | *** |
| 478 | *** |
| 479 | *** |
| 480 | *** |
| 481 | *** |
| 482 | *** |
| 483 | *** |
| 484 | *** |
| 485 | *** |
| 486 | *** |
| 487 | *** |
| 488 | *** |
| 489 | ** |
| 490 | * |
| 491 | ** |
| 492 | *** |
| 493 | *** |
| 494 | * |
| 495 | * |
| 496 | ** |
| 497 | *** |
| 498 | ** |
| 499 | *** |
| 500 | *** |
| 501 | *** |
| 502 | *** |
| 503 | ** |
| 504 | *** |
| 505 | *** |
| 506 | *** |
| 507 | ** |
| 508 | *** |
| 509 | *** |

TABLE 1-continued

Replicon IC$_{50}$ (μM)

| Cpd | IC$_{50}$ |
|---|---|
| 510 | ** |
| 511 | *** |
| 512 | *** |
| 513 | *** |
| 514 | *** |
| 515 | *** |
| 516 | *** |
| 517 | *** |
| 518 | *** |
| 519 | *** |
| 520 | ** |
| 521 | *** |
| 522 | *** |
| 523 | ** |
| 524 | *** |
| 525 | ** |
| 526 | *** |
| 527 | *** |
| 528 | *** |
| 529 | *** |
| 530 | *** |
| 531 | *** |
| 532 | *** |
| 533 | *** |
| 534 | *** |
| 535 | *** |
| 536 | *** |
| 537 | *** |
| 538 | *** |
| 539 | *** |
| 540 | *** |
| 541 | *** |
| 542 | *** |
| 543 | *** |
| 544 | *** |
| 545 | *** |
| 546 | ** |
| 547 | *** |
| 548 | ** |
| 549 | *** |
| 550 | *** |
| 551 | *** |
| 552 | ** |
| 553 | *** |
| 554 | *** |
| 555 | *** |
| 556 | *** |
| 557 | *** |
| 558 | *** |
| 559 | *** |
| 560 | *** |
| 561 | ** |
| 562 | *** |
| 563 | ** |
| 564 | *** |
| 565 | *** |
| 566 | ** |
| 567 | *** |
| 568 | * |
| 569 | ** |
| 570 | ** |
| 571 | *** |
| 572 | *** |
| 573 | *** |
| 574 | *** |
| 575 | *** |
| 576 | *** |
| 577 | *** |
| 578 | *** |
| 579 | *** |
| 580 | *** |
| 581 | *** |
| 582 | *** |
| 583 | *** |
| 584 | ** |
| 585 | *** |
| 586 | *** |
| 587 | *** |
| 588 | *** |
| 589 | *** |
| 590 | *** |
| 591 | *** |
| 592 | *** |
| 593 | *** |
| 594 | *** |
| 595 | *** |
| 596 | *** |
| 597 | *** |
| 598 | *** |
| 599 | *** |
| 600 | *** |
| 601 | *** |
| 602 | ** |
| 603 | *** |
| 604 | *** |
| 605 | *** |
| 606 | *** |
| 607 | *** |
| 608 | *** |
| 609 | *** |
| 610 | *** |
| 611 | *** |
| 612 | *** |
| 613 | *** |
| 614 | ** |
| 615 | *** |
| 616 | *** |
| 617 | *** |
| 618 | *** |
| 619 | *** |
| 620 | *** |
| 621 | *** |
| 622 | *** |
| 623 | ** |
| 624 | *** |
| 625 | *** |
| 626 | *** |
| 627 | *** |
| 628 | *** |
| 629 | * |
| 630 | *** |
| 631 | *** |
| 632 | *** |
| 633 | *** |
| 634 | *** |
| 635 | *** |
| 636 | *** |
| 637 | *** |
| 638 | *** |
| 639 | *** |
| 640 | *** |
| 641 | *** |
| 642 | *** |
| 643 | *** |
| 644 | *** |
| 645 | *** |
| 646 | * |
| 647 | ** |
| 648 | *** |
| 649 | *** |
| 650 | *** |
| 651 | *** |
| 652 | *** |
| 653 | *** |
| 654 | *** |
| 655 | *** |
| 656 | *** |
| 657 | *** |
| 658 | *** |
| 659 | *** |
| 660 | *** |
| 661 | *** |

TABLE 1-continued

Replicon IC$_{50}$ (μM)

| Cpd | IC$_{50}$ |
|---|---|
| 662 | *** |
| 663 | ** |
| 664 | *** |
| 665 | ** |
| 666 | *** |
| 667 | *** |
| 668 | *** |
| 669 | *** |
| 670 | *** |
| 671 | *** |
| 672 | *** |
| 673 | *** |
| 674 | *** |
| 675 | *** |
| 676 | *** |
| 677 | *** |
| 678 | *** |
| 679 | *** |
| 680 | *** |
| 681 | *** |
| 682 | *** |
| 683 | *** |
| 684 | ** |
| 685 | ** |
| 686 | *** |
| 687 | *** |
| 688 | *** |
| 689 | ** |
| 690 | ** |
| 691 | *** |
| 692 | *** |
| 693 | *** |
| 694 | * |
| 695 | *** |
| 696 | *** |
| 697 | *** |
| 698 | *** |
| 699 | *** |
| 700 | *** |
| 701 | *** |
| 702 | *** |
| 703 | *** |
| 704 | *** |
| 705 | *** |
| 706 | *** |
| 707 | *** |
| 708 | *** |
| 709 | *** |
| 710 | *** |
| 711 | *** |
| 712 | * |
| 713 | *** |
| 714 | *** |
| 715 | *** |
| 716 | *** |
| 717 | ** |
| 718 | *** |
| 719 | ** |
| 720 | *** |
| 721 | ** |
| 722 | *** |
| 723 | *** |
| 724 | ** |
| 725 | *** |
| 726 | *** |
| 727 | *** |
| 728 | * |
| 729 | *** |
| 730 | *** |
| 731 | *** |
| 732 | *** |
| 733 | *** |
| 734 | *** |
| 735 | *** |
| 736 | *** |
| 737 | *** |

TABLE 1-continued

Replicon IC$_{50}$ (μM)

| Cpd | IC$_{50}$ |
|---|---|
| 738 | *** |
| 739 | *** |
| 740 | *** |
| 741 | ** |
| 742 | *** |
| 743 | *** |
| 744 | *** |
| 745 | *** |
| 746 | *** |
| 747 | *** |
| 748 | *** |
| 749 | *** |
| 750 | *** |
| 751 | *** |
| 752 | *** |
| 753 | *** |
| 754 | *** |
| 755 | *** |
| 756 | *** |
| 757 | ** |
| 758 | *** |
| 760 | *** |
| 761 | *** |
| 762 | *** |
| 763 | ** |
| 764 | *** |
| 765 | *** |
| 766 | *** |
| 767 | *** |
| 768 | *** |
| 769 | *** |
| 770 | *** |
| 771 | *** |
| 772 | *** |
| 773 | ** |
| 774 | *** |
| 775 | ** |
| 776 | *** |
| 774 | *** |
| 775 | ** |
| 776 | *** |
| 777 | *** |
| 778 | *** |
| 780 | *** |
| 781 | *** |
| 782 | *** |
| 783 | * |
| 784 | *** |
| 785 | *** |
| 786 | *** |
| 787 | *** |
| 788 | *** |
| 789 | *** |
| 790 | *** |
| 791 | * |
| 793 | *** |
| 794 | * |
| 795 | *** |
| 796 | *** |
| 797 | *** |
| 798 | ** |
| 799 | *** |
| 800 | *** |
| 801 | *** |
| 802 | *** |
| 803 | *** |
| 804 | *** |
| 805 | ** |
| 806 | *** |
| 807 | *** |
| 808 | *** |
| 809 | *** |
| 810 | *** |
| 811 | *** |
| 812 | * |
| 813 | ** |

TABLE 1-continued

Replicon IC$_{50}$ (μM)

| Cpd | IC$_{50}$ |
|---|---|
| 814 | *** |
| 815 | *** |
| 816 | *** |
| 817 | *** |
| 818 | *** |
| 819 | *** |
| 820 | *** |
| 821 | *** |
| 822 | *** |
| 823 | ** |
| 824 | *** |
| 825 | *** |
| 826 | *** |
| 827 | *** |
| 828 | * |
| 829 | *** |
| 830 | *** |
| 831 | *** |
| 832 | *** |
| 833 | ** |
| 834 | * |
| 835 | *** |
| 836 | ** |
| 837 | *** |
| 838 | *** |
| 839 | *** |
| 840 | *** |
| 841 | *** |
| 842 | *** |
| 843 | *** |
| 844 | *** |
| 845 | *** |
| 846 | *** |
| 847 | *** |
| 848 | *** |
| 849 | *** |
| 850 | *** |
| 851 | *** |
| 852 | *** |
| 853 | *** |
| 854 | *** |
| 855 | *** |
| 856 | *** |
| 857 | *** |
| 858 | ** |
| 859 | ** |
| 860 | *** |
| 861 | * |
| 862 | *** |
| 863 | *** |
| 864 | *** |
| 865 | *** |
| 866 | ** |
| 867 | *** |
| 868 | *** |
| 869 | ** |
| 870 | *** |
| 871 | *** |
| 872 | *** |
| 873 | *** |
| 874 | *** |
| 875 | *** |
| 876 | *** |
| 877 | *** |
| 878 | *** |
| 879 | *** |
| 880 | *** |
| 881 | *** |
| 882 | *** |
| 883 | *** |
| 884 | *** |
| 885 | *** |
| 886 | *** |
| 887 | *** |
| 888 | *** |
| 889 | *** |

TABLE 1-continued

Replicon IC$_{50}$ (μM)

| Cpd | IC$_{50}$ |
|---|---|
| 890 | *** |
| 891 | *** |
| 892 | *** |
| 893 | *** |
| 894 | *** |
| 895 | *** |
| 896 | *** |
| 897 | *** |
| 898 | ** |
| 899 | *** |
| 900 | ** |
| 901 | *** |
| 902 | ** |
| 903 | *** |
| 904 | *** |
| 905 | *** |
| 906 | *** |
| 907 | *** |
| 908 | *** |
| 909 | ** |
| 910 | *** |
| 911 | *** |
| 912 | * |
| 913 | *** |
| 914 | *** |
| 915 | *** |
| 916 | *** |
| 917 | *** |
| 918 | * |
| 919 | *** |
| 920 | *** |
| 921 | *** |
| 922 | *** |
| 923 | *** |
| 924 | *** |
| 925 | *** |
| 926 | *** |
| 927 | *** |
| 928 | *** |
| 929 | *** |
| 930 | *** |
| 931 | *** |
| 932 | *** |
| 933 | *** |
| 934 | *** |
| 935 | *** |
| 936 | *** |
| 937 | *** |
| 938 | *** |
| 939 | * |
| 940 | ** |
| 941 | ** |
| 942 | *** |
| 943 | ** |
| 944 | ** |
| 945 | *** |
| 946 | *** |
| 947 | *** |
| 948 | *** |
| 949 | *** |
| 950 | *** |
| 951 | *** |
| 952 | *** |
| 953 | *** |
| 954 | *** |
| 955 | *** |
| 956 | *** |
| 957 | ** |
| 958 | ** |
| 959 | *** |
| 960 | *** |
| 961 | *** |
| 962 | *** |
| 963 | *** |
| 964 | *** |
| 965 | *** |

TABLE 1-continued

Replicon IC$_{50}$ (μM)

| Cpd | IC$_{50}$ |
|---|---|
| 966 | *** |
| 967 | *** |
| 968 | ** |
| 969 | *** |
| 970 | *** |
| 971 | ** |
| 972 | * |
| 973 | *** |
| 974 | *** |
| 975 | *** |
| 976 | *** |
| 977 | *** |
| 978 | * |
| 979 | * |
| 980 | ** |
| 981 | *** |
| 982 | * |
| 983 | *** |
| 984 | *** |
| 985 | *** |
| 986 | *** |
| 987 | *** |
| 988 | *** |
| 989 | *** |
| 990 | *** |
| 991 | *** |
| 992 | *** |
| 993 | *** |
| 994 | *** |
| 995 | *** |
| 996 | *** |
| 997 | *** |
| 998 | ** |
| 999 | *** |
| 1000 | *** |
| 1001 | *** |
| 1002 | *** |
| 1003 | *** |
| 1004 | *** |
| 1005 | *** |
| 1006 | ** |
| 1007 | *** |
| 1008 | *** |
| 1009 | *** |
| 1010 | *** |
| 1011 | ** |
| 1012 | ** |
| 1013 | *** |
| 1014 | *** |
| 1015 | *** |
| 1016 | *** |
| 1017 | *** |
| 1018 | *** |
| 1019 | *** |
| 1020 | *** |
| 1021 | *** |
| 1022 | *** |
| 1023 | *** |
| 1024 | *** |
| 1025 | *** |
| 1026 | ** |
| 1027 | *** |
| 1028 | * |
| 1029 | * |
| 1030 | ** |
| 1031 | *** |
| 1032 | *** |
| 1033 | *** |
| 1034 | ** |
| 1035 | ** |
| 1036 | * |
| 1037 | *** |
| 1038 | *** |
| 1039 | ** |
| 1040 | *** |
| 1041 | *** |
| 1042 | ** |
| 1043 | *** |
| 1044 | *** |
| 1045 | *** |
| 1046 | * |
| 1047 | ** |
| 1048 | ** |
| 1055 | ** |
| 1056 | *** |
| 1057 | *** |
| 1058 | *** |
| 1059 | *** |
| 1060 | * |
| 1061 | *** |
| 1062 | *** |
| 1063 | *** |
| 1064 | *** |
| 1065 | *** |
| 1072 | ** |
| 1073 | *** |
| 1074 | *** |
| 1075 | *** |
| 1078 | *** |
| 1079 | *** |
| 1080 | ** |
| 1081 | *** |
| 1082 | *** |
| 1083 | *** |
| 1084 | *** |
| 1085 | *** |
| 1086 | *** |
| 1087 | *** |
| 1088 | *** |
| 1092 | *** |
| 1093 | ** |
| 1094 | *** |
| 1095 | ** |
| 1096 | *** |
| 1097 | *** |
| 1098 | ** |
| 1099 | ** |
| 1100 | *** |
| 1101 | ** |
| 1102 | *** |
| 1103 | ** |
| 1104 | *** |
| 1105 | *** |
| 1106 | *** |
| 1107 | *** |
| 1108 | *** |
| 1109 | *** |
| 1110 | *** |
| 1111 | *** |
| 1112 | *** |
| 1113 | *** |
| 1114 | *** |
| 1115 | *** |
| 1116 | *** |
| 1117 | *** |
| 1118 | *** |
| 1119 | *** |

Example 2

Compound Activity Evaluation Using an HCV-Poliovirus Chimera

In an HCV-poliovirus (HCV-PV) chimera, the PV 5' UTR is replaced by the HCV 5' UTR and partial (the first 123 amino acids) core coding sequences (nucleotides 18 to 710 of HCV 1 b) (see Zhao W D and Wimmer E, Genetic analysis of a poliovirus/hepatitis C virus chimera: new structure for domain II of the internal ribosomal entry site of hepatitis C virus, *J. Virol.,* 2001, 75:3719-3730; and, Zhao W D, Wimmer E and Lahser F C, Poliovirus/Hepatitis C virus (internal ribosomal entry site-core) chimeric viruses: improved growth properties through modification of a proteolytic cleavage site and requirement for core RNA sequences but not for core-related polypeptides, *Journal of Virology,* 1999, 73:1546-1554). As a consequence, the expression of poliovirus proteins is under regulation of the HCV IRES. Poliovirus is a picornavirus in which protein translation initiation is mediated by an IRES element located in the 5' UTR. At the 5' end of the HCV-PV chimeric genome, there is the cloverleaf-like RNA structure of PV, which provides a cis-acting replication signal ending with the genome-linked protein VPg. The replication kinetics of the HCV-PV chimera matches that of the parental poliovirus (Mahoney) and can result in cytopathic effects (CPE) in cell culture. Heptazyme (see S C Gordon, B R Bacon, I M Jacobson, M I Shiffman, N H Afdhal, J G McHutchison, T J Kwoh, and F A Dorr, A Phase II, 12-week study of ISIS 14803, an antisense inhibitor of HCV for the treatment of chronic hepatitis C, AASLD Abst. 795*, Hepatology,* 2002, 36:362A.), a ribozyme that targets the HCV IRES, has been shown to be active against the chimeric virus in cell culture (see Macejak D G, K L Jensen, S F Jamison, K Domenico, E C Roberts, N Chaudhary, I von Carlowitz, L Bellon, M J Tong, A Conrad, P A Pavco and L M Blatt, Inhibition of hepatitis C virus (HCV)-RNA-dependent translation and replication of a chimeric HCV poliovirus using synthetic stabilized ribozymes, *Hepatology,* 2000, 31:769-776; and, Macejak D G, K L Jensen, P A Pavco, K M Phipps, B A Heinz, J M Colacino and LM Blatt, Enhanced antiviral effect in cell culture of type 1 interferon and ribozymes targeting HCV RNA, *J Viral Hepatitis,* 2001, 8:400-405).

A compound is tested for activity against the chimeric virus, by seeding into HeLa cells and incubating the cells at 37° C. under 5% $CO_2$ for 24 hours. The cells are then infected with HCV-PV at a multiplicity of infection (MOI) of about 0.1 for 30 min and then treated with a test compound for one day. The activity of a test compound is determined by a change in viral RNA production.

As shown in Table 2, test compounds of the present invention demonstrate HCV-PV $IC_{50}$ values of greater than from about 2 μM to about 5 μM (*), an $IC_{50}$ value of between about 0.5 μM to about 2 μM (), or an $IC_{50}$ value of less than about 0.5 μM (*).

TABLE 2

| HCV PV $IC_{50}$ (μM) | |
|---|---|
| Cpd | $IC_{50}$ |
| 5 | *** |
| 7 | *** |
| 10 | *** |
| 24 | *** |
| 29 | *** |
| 30 | *** |
| 31 | *** |
| 32 | *** |
| 34 | *** |
| 35 | *** |
| 36 | *** |
| 37 | *** |
| 38 | *** |
| 41 | *** |
| 42 | *** |
| 43 | *** |
| 44 | *** |
| 45 | *** |
| 49 | *** |
| 50 | *** |

TABLE 2-continued

| HCV PV $IC_{50}$ (μM) | |
|---|---|
| Cpd | $IC_{50}$ |
| 51 | *** |
| 52 | *** |
| 53 | *** |
| 54 | *** |
| 60 | *** |
| 61 | *** |
| 64 | *** |
| 65 | *** |
| 68 | *** |
| 71 | *** |
| 72 | *** |
| 74 | *** |
| 78 | *** |
| 80 | *** |
| 81 | *** |
| 82 | *** |
| 83 | *** |
| 84 | *** |
| 85 | *** |
| 89 | *** |
| 92 | *** |
| 93 | *** |
| 94 | *** |
| 95 | *** |
| 96 | *** |
| 104 | *** |
| 110 | *** |
| 112 | *** |
| 113 | *** |
| 122 | *** |
| 124 | *** |
| 126 | *** |
| 129 | *** |
| 132 | *** |
| 135 | *** |
| 145 | *** |
| 178 | *** |
| 191 | *** |
| 198 | *** |

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the claims of the invention.

What is claimed is:

1. A compound of Formula (I):

(I)

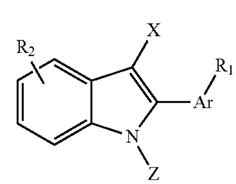

or a free acid, free base, salt, isotopologue, racemate, enantiomer, diastereomer, or stereoisomer form thereof, wherein X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-amino-carbonyl or $C_{1-8}$alkyl-sulfonyl;

Ar is pyridinyl, pyrimidinyl or pyridazinyl;

Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, $C_{1-8}$alkoxy-carbonyl, carboxyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino, $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl, $C_{1-8}$alkyl-carbonyloxy or amino-sulfonyl;

$R_1$ is —$SO_2$—$N(R_5)$—$R_6$;

$R_2$ is one, two, three or four substituents each selected from hydrogen, halogen, hydroxy, cyano, nitro, $C_{1-8}$alkyl, hydroxy-$C_{1-8}$alkyl, halo-$C_{1-8}$alkyl, $C_{2-8}$alkenyl, halo-$C_{2-8}$alkenyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkyl, $C_{1-8}$alkyl-carbonyloxy-$C_{1-8}$alkoxy, amino, $C_{1-8}$alkyl-amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkylthio, $C_{1-8}$alkyl-sulfinyl, $C_{1-8}$alkyl-sulfonyl, $C_{1-8}$alkyl-sulfonyl-amino, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, wherein each instance of aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

$R_5$ is hydrogen;

$R_6$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino.

2. The compound of claim 1, wherein

X is selected from hydrogen, cyano, carboxyl, amino-carbonyl or $C_{1-8}$alkyl-amino-carbonyl;

Z is $C_{1-8}$alkyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with a substituent selected from cyano, halogen, $C_{1-8}$alkyl, $C_{1-8}$alkoxy, amino or $C_{1-8}$alkyl-amino;

$R_2$ is one, two or three substituents each selected from hydrogen, halogen, hydroxy, cyano, $C_{1-8}$alkyl, hydroxy-$C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy, amino, $C_{1-8}$alkyl-amino, amino-$C_{1-8}$alkyl, $C_{1-8}$alkyl-amino-$C_{1-8}$alkyl, $C_{1-8}$alkylthio, $C_{1-8}$alkyl-sulfinyl, $C_{1-8}$alkyl-sulfonyl, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, heteroaryl, heteroaryl-$C_{1-8}$alkyl, heteroaryloxy, heterocyclyl, heterocyclyl-$C_{1-8}$alkyl, heterocyclyl-$C_{1-8}$alkoxy or heterocyclyloxy, wherein heteroaryloxy is optionally substituted with a cyano substituent;

$R_6$ is hydrogen, $C_{1-8}$alkyl, hydroxy-$C_{1-8}$alkyl, halo-$C_{1-8}$alkyl, cyano-$C_{1-8}$alkyl, $C_{3-14}$cycloalkyl or $C_{3-14}$cycloalkyl-$C_{1-8}$alkyl, wherein each instance of $C_{3-14}$cycloalkyl is optionally substituted with one or two substituents each selected from halogen, $C_{1-8}$alkyl or halo-$C_{1-8}$alkyl.

3. The compound of claim 1, wherein

X is cyano;

Z is $C_{1-8}$alkyl, cyclopropyl, cyclobutyl, cyclopentyl, cyclohexyl, cyclohexenyl, cyclopropyl-methyl, phenyl, thiazolyl, pyridinyl, pyrimidinyl, pyrazinyl, pyridazinyl, triazinyl or tetrahydrofuran, wherein phenyl is optionally substituted with a substituent selected from cyano, halogen, $C_{1-8}$alkyl or $C_{1-8}$alkoxy;

$R_2$ is one, two or three substituents each selected from hydrogen, halogen, hydroxy, cyano, $C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkylthio, $C_{1-8}$alkykl-sulfinyl, $C_{1-8}$alkyl-sulfonyl, cyclopropyl, cyclobutyl, cyclobutoxy, pyridinyloxy, pyrimidinyloxy, pyrazinyloxy or morpholinyl, wherein pyridinyl and pyrazinyl are each optionally substituted with a cyano substituent;

$R_6$ is hydrogen, $C_{1-8}$alkyl, hydroxy-$C_{1-8}$alkyl, halo-$C_{1-8}$alkyl, cyano-$C_{1-8}$alkyl, cyclopropyl, cyclobutyl or 1-cyclopropyl-ethyl, wherein each instance of cyclopropyl and cyclobutyl is optionally substituted with one or two substituents each selected from halogen, $C_{1-8}$alkyl or halo-$C_{1-8}$alkyl.

4. The compound of claim 1, wherein the isotopologue is deuterium.

5. The compound of claim 4, wherein $R_2$ is $C_{1-8}$alkyl wherein from 1 to 3 hydrogen atoms are optionally replaced with deuterium;

$R_6$ is $C_{1-8}$alkyl wherein from 1 to 3 hydrogen atoms are optionally replaced with deuterium or halo-$C_{1-8}$alkyl wherein from 1 to 3 hydrogen atoms are optionally replaced with deuterium.

6. A compound of Formula (Ia):

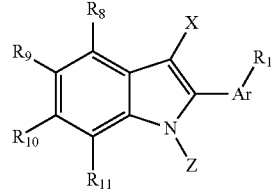

(Ia)

or a free acid, free base, salt, isotopologue, racemate, enantiomer, diastereomer, or stereoisomer form thereof, wherein X is hydrogen, halogen, cyano, nitro, carboxyl, $C_{1-8}$alkyl-carbonyl, $C_{1-8}$alkoxy-carbonyl, formyl, amino, $C_{1-8}$alkyl-amino, amino-carbonyl, $C_{1-8}$alkyl-amino-carbonyl or $C_{1-8}$alkyl-sulfonyl;

Ar is pyridinyl, pyrimidinyl or pyridazinyl;

Z is $C_{1-8}$alkyl, $C_{2-8}$alkenyl-$C_{1-8}$alkyl, $C_{2-8}$alkynyl-$C_{1-8}$alkyl, halo-$C_{1-8}$alkyl, $C_{1-8}$alkoxy-$C_{1-8}$alkyl, $C_{1-8}$alkoxy-carbonyl, carboxyl, $C_{3-14}$cycloalkyl, $C_{3-14}$cycloalkenyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl and heteroaryl is optionally substituted with one, two, three or four substituents each selected from hydroxy, cyano, nitro, halogen, $C_{1-8}$alkyl, $C_{2-8}$alkenyl, $C_{2-8}$alkynyl, hydroxy-$C_{1-8}$alkyl, halo-$C_{1-8}$alkyl, $C_{1-8}$alkoxy, halo-$C_{1-8}$alkoxy, amino, $C_{1-8}$alkyl-amino, $C_{1-8}$alkoxy-$C_{1-8}$alkyl, $C_{1-8}$alkylthio, $C_{1-8}$alkyl-carbonyl, $C_{1-8}$alkoxy-carbonyl, $C_{1-8}$alkyl-carbonyloxy or amino-sulfonyl;

$R_1$ is —$SO_2$—N($R_5$)—$R_6$;

$R_5$ is hydrogen;

$R_6$ is hydrogen, $C_{1-8}$alkyl, hydroxy-$C_{1-8}$alkyl, halo-$C_{1-8}$alkyl, cyano-$C_{1-8}$alkyl, $C_{1-8}$alkoxy-$C_{1-8}$alkyl, amino-$C_{1-8}$alkyl, $C_{1-8}$alkyl-amino-$C_{1-8}$alkyl, $C_{1-8}$alkyl-carbonyl, $C_{1-8}$alkoxy-carbonyl, $C_{3-14}$cycloalkyl, $C_{3-14}$cycloalkyl-$C_{1-8}$alkyl, aryl, aryl-$C_{1-8}$alkyl, heteroaryl, heteroaryl-$C_{1-8}$alkyl, heterocyclyl or heterocyclyl-$C_{1-8}$alkyl, wherein each instance of aryl, heteroaryl, heterocyclyl and $C_{3-14}$cycloalkyl is optionally substituted with one or two substituents each selected from halogen, $C_{1-8}$alkyl, halo-$C_{1-8}$alkyl, $C_{1-8}$alkoxy, halo-$C_{1-8}$alkoxy, amino or $C_{1-8}$alkyl-amino;

$R_8$ is hydrogen, halogen or $C_{1-8}$alkoxy;

$R_9$ is hydrogen, halogen, hydroxy, cyano, nitro, $C_{1-8}$alkyl, halo-$C_{1-8}$alkyl, $C_{1-8}$alkoxy, halo-$C_{1-8}$alkoxy, $C_{1-8}$alkyl-carbonyl, $C_{1-8}$alkoxy-carbonyl, amino, $C_{1-8}$alkyl-amino, amino-$C_{1-8}$alkyl, $C_{1-8}$alkyl-amino-$C_{1-8}$alkyl, $C_{1-8}$alkylthio, $C_{3-14}$cycloalkyl, $C_{3-14}$cycloalkyl-$C_{1-8}$alkoxy, aryl, aryl-$C_{1-8}$alkoxy, heteroaryl, heteroaryl-$C_{1-8}$alkoxy, heterocyclyl or heterocyclyl-$C_{1-8}$alkoxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl;

$R_{10}$ is hydrogen, halogen, hydroxy, cyano, nitro, $C_{1-8}$alkyl, halo-$C_{1-8}$alkyl, $C_{2-8}$alkenyl, halo-$C_{2-8}$alkenyl, hydroxy-$C_{1-8}$alkyl, $C_{1-8}$alkoxy, halo-$C_{1-8}$alkoxy, $C_{1-8}$alkoxy-$C_{1-8}$alkyl, $C_{1-8}$alkyl-carbonyl, $C_{1-8}$alkoxy-carbonyl, $C_{1-8}$alkyl-carbonyloxy, $C_{1-8}$alkyl-carbonyloxy-$C_{1-8}$alkoxy, amino, $C_{1-8}$alkyl-amino, amino-$C_{1-8}$alkyl, $C_{1-8}$alkyl-amino-$C_{1-8}$alkyl, amino-$C_{1-8}$alkoxy, $C_{1-8}$alkyl-amino-$C_{1-8}$alkoxy, $C_{1-8}$alkoxy-$C_{1-8}$alkyl-amino-$C_{1-8}$alkoxy, amino-$C_{1-8}$alkyl-amino-$C_{1-8}$alkoxy, $C_{1-8}$alkyl-amino-$C_{1-8}$alkyl-amino-$C_{1-8}$alkoxy, $C_{1-8}$alkoxy-carbonyl-amino, carboxyl-amino, amino-carbonyl, amino-carbonyl-amino, $C_{1-8}$alkyl-amino-carbonyl-amino, $C_{1-8}$alkylthio, $C_{1-8}$alkyl-sulfinyl, $C_{1-8}$alkyl-sulfonyl, $C_{1-8}$alkyl-sulfonyl-amino, $C_{3-14}$cycloalkyl, $C_{3-14}$cycloalkyl-$C_{1-8}$alkyl, $C_{3-14}$cycloalkyl-$C_{1-8}$alkoxy, $C_{3-14}$cycloalkyloxy, aryl, aryl-$C_{1-8}$alkyl, aryl-$C_{1-8}$alkoxy, aryloxy, aryl-carbonyl-amino, heteroaryl, heteroaryl-$C_{1-8}$alkyl, heteroaryl-$C_{1-8}$alkoxy, heteroaryloxy, heterocyclyl, heterocyclyl-$C_{1-8}$alkyl, heterocyclyl-$C_{1-8}$alkoxy, heterocyclyloxy or heterocyclyl-carbonyloxy, wherein each instance of $C_{3-14}$cycloalkyl, aryl, heteroaryl and heterocyclyl is optionally substituted with one, two, three or four substituents each selected from halogen, cyano, $C_{1-8}$alkyl, $C_{1-8}$alkoxy, $C_{1-8}$alkoxy-$C_{1-8}$alkyl, amino, $C_{1-8}$alkyl-amino, amino-$C_{1-8}$alkyl or $C_{1-8}$alkyl-amino-$C_{1-8}$alkyl; and $R_{11}$ is hydrogen, halogen, hydroxy, cyano, nitro, $C_{1-8}$alkyl, halo-$C_{1-8}$alkyl, $C_{1-8}$alkoxy, halo-$C_{1-8}$alkoxy, $C_{1-8}$alkyl-carbonyl, $C_{1-8}$alkoxy-carbonyl, $C_{1-8}$alkyl-carbonyloxy or $C_{1-8}$alkyl-carbonyloxy-$C_{1-8}$alkyl.

7. The compound of claim 6, wherein
$R_8$ is hydrogen or halogen;
$R_9$ is hydrogen, halogen, hydroxy, cyano, $C_{1-8}$alkyl, halo-$C_{1-8}$alkyl, $C_{1-8}$alkoxy, halo-$C_{1-8}$alkoxy, $C_{1-8}$alkylthio or $C_{3-14}$cycloalkyl;
$R_{10}$ is hydrogen, halogen, hydroxy, cyano, $C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkylthio, $C_{3-14}$cycloalkyl, $C_{3-14}$cycloalkyloxy, heteroaryloxy or heterocyclyl, wherein heteroaryloxy is optionally substituted with a cyano substituent; and
$R_{11}$ is hydrogen or halogen.

8. The compound of claim 6, wherein
$R_9$ is hydrogen, halogen, hydroxy, cyano, $C_{1-8}$alkyl, halo-$C_{1-8}$alkyl, $C_{1-8}$alkoxy, halo-$C_{1-8}$alkoxy, $C_{1-8}$alkylthio or cyclopropyl; and
$R_{10}$ is hydrogen, halogen, hydroxy, cyano, $C_{1-8}$alkyl, halo-$C_{1-8}$alkyl, halo-$C_{2-8}$alkenyl, $C_{1-8}$alkoxy, halo-$C_{1-8}$alkoxy, $C_{1-8}$alkylthio, cyclopropyl, cyclobutyl, cyclobutoxy, pyridinyloxy, pyrimidinyloxy, pyrazinyloxy or morpholinyl, wherein pyridinyl and pyrazinyl are optionally substituted with a cyano substituent.

9. The compound of claim 1, wherein the compound or a free acid, free base, salt, isotopologue, racemate, enantiomer, diastereomer, or stereoisomer form thereof is selected from:
6-[3-cyano-6-(difluoromethoxy)-1-(propan-2-yl)-1H-indol-2-yl]-N-(propan-2-yl)pyridine-3-sulfonamide,
6-[3-cyano-6-(difluoromethoxy)-1-(propan-2-yl)-1H-indol-2-yl]-N-cyclobutylpyridine-3-sulfonamide,
6-[3-cyano-6-(difluoromethoxy)-1-propyl-1H-indol-2-yl]-N-(propan-2-yl)pyridine-3-sulfonamide,
5-[3-cyano-1-cyclobutyl-6-(cyclobutyloxy)-1H-indol-2-yl]-N-(propan-2-yl)pyridine-2-sulfonamide,
6-(3-cyano-1-cyclobutyl-5-fluoro-1H-indol-2-yl)-N-(propan-2-yl)pyridine-3-sulfonamide,
6-[3-cyano-1-(cyclopropylmethyl)-5-fluoro-1H-indol-2-yl]-N-(propan-2-yl)pyridine-3-sulfonamide,
6-(3-cyano-1-cyclobutyl-6-cyclopropyl-1H-indol-2-yl)-N-(propan-2-yl)pyridine-3-sulfonamide,
6-(3-cyano-1-cyclobutyl-5-cyclopropyl-1H-indol-2-yl)-N-(propan-2-yl)pyridine-3-sulfonamide,
N-tert-butyl-6-(3-cyano-1-cyclobutyl-5-fluoro-1H-indol-2-yl)pyridine-3-sulfonamide,
6-[3-cyano-1-cyclobutyl-6-(trifluoromethoxy)-1H-indol-2-yl]-N-(propan-2-yl)pyridine-3-sulfonamide,
6-[3-cyano-1-(cyclopropylmethyl)-6-(trifluoromethoxy)-1H-indol-2-yl]-N-(propan-2-yl)pyridine-3-sulfonamide,
6-[3-cyano-1-(propan-2-yl)-6-(trifluoromethoxy)-1H-indol-2-yl]-N-(propan-2-yl)pyridine-3-sulfonamide,
6-[3-cyano-1-(cyclopropylmethyl)-6-(difluoromethoxy)-1H-indol-2-yl]-N-(propan-2-yl)pyridine-3-sulfonamide,
6-(5-chloro-3-cyano-1-cyclobutyl-1H-indol-2-yl)-N-(propan-2-yl)pyridine-3-sulfonamide,
N-tert-butyl-6-(5-chloro-3-cyano-1-cyclobutyl-1H-indol-2-yl)pyridine-3-sulfonamide, 6-[3-cyano-1-cyclobutyl-6-(propan-2-ylsulfanyl)-1H-indol-2-yl]-N-(propan-2-yl)pyridine-3-sulfonamide,
6-[3-cyano-1-cyclopentyl-6-(trifluoromethoxy)-1H-indol-2-yl]-N-(propan-2-yl)pyridine-3-sulfonamide,
N-tert-butyl-6-[3-cyano-1-cyclopentyl-6-(trifluoromethoxy)-1H-indol-2-yl]pyridine-3-sulfonamide,
6-[3-cyano-1-cyclobutyl-5-(difluoromethoxy)-1H-indol-2-yl]-N-(propan-2-yl)pyridine-3-sulfonamide,
N-tert-butyl-6-[3-cyano-1-cyclobutyl-5-(difluoromethoxy)-1H-indol-2-yl]pyridine-3-sulfonamide,
6-[3-cyano-1-cyclopentyl-5-(difluoromethoxy)-1H-indol-2-yl]-N-(propan-2-yl)pyridine-3-sulfonamide,
6-[3-cyano-1-cyclobutyl-5-(trifluoromethoxy)-1H-indol-2-yl]-N-(propan-2-yl)pyridine-3-sulfonamide,
6-[3-cyano-1-cyclobutyl-6-(trifluoromethoxy)-1H-indol-2-yl]-N-(1,3-difluoropropan-2-yl)pyridine-3-sulfonamide,
6-[3-cyano-1-cyclobutyl-5-(trifluoromethoxy)-1H-indol-2-yl]-N-(1,3-difluoropropan-2-yl)pyridine-3-sulfonamide,
6-[3-cyano-1-cyclobutyl-6-(trifluoromethoxy)-1H-indol-2-yl]-N-(propan-2-yl)pyridine-2-sulfonamide,
5-[3-cyano-1-cyclobutyl-6-(trifluoromethoxy)-1H-indol-2-yl]-N-(propan-2-yl)pyridine-2-sulfonamide,
5-(3-cyano-1-cyclobutyl-6-cyclopropyl-1H-indol-2-yl)-N-(propan-2-yl)pyridine-2-sulfonamide,
5-(5-chloro-3-cyano-1-cyclobutyl-1H-indol-2-yl)-N-(propan-2-yl)pyridine-2-sulfonamide,
6-(3-cyano-1-cyclobutyl-5-fluoro-1H-indol-2-yl)-N-(1,3-difluoropropan-2-yl)pyridine-3-sulfonamide,
6-(5-chloro-3-cyano-1-cyclobutyl-1H-indol-2-yl)-N-(1,3-difluoropropan-2-yl)pyridine-3-sulfonamide,
6-[3-cyano-1-cyclobutyl-6-(difluoromethoxy)-1H-indol-2-yl]-N-(1,3-difluoropropan-2-yl)pyridine-3-sulfonamide,
6-[3-cyano-1-cyclobutyl-5-(difluoromethoxy)-1H-indol-2-yl]-N-(1,3-difluoropropan-2-yl)pyridine-3-sulfonamide,
6-[3-cyano-1-cyclopentyl-5-(difluoromethoxy)-1H-indol-2-yl]-N-(1,3-difluoropropan-2-yl)pyridine-3-sulfonamide,
6-[3-cyano-1-cyclopentyl-5-(trifluoromethoxy)-1H-indol-2-yl]-N-(1,3-difluoropropan-2-yl)pyridine-3-sulfonamide,
6-(3-cyano-1-cyclobutyl-6-cyclopropyl-1H-indol-2-yl)-N-(1,3-difluoropropan-2-yl)pyridine-3-sulfonamide,
6-[3-cyano-6-(difluoromethoxy)-1-(propan-2-yl)-1H-indol-2-yl]-N-(1,3-difluoropropan-2-yl)pyridine-3-sulfonamide,
6-(6-chloro-3-cyano-1-cyclobutyl-1H-indol-2-yl)-N-(1,3-difluoropropan-2-yl)pyridine-3-sulfonamide,
6-(3-cyano-1-cyclopentyl-5-fluoro-1H-indol-2-yl)-N-(1,3-difluoropropan-2-yl)pyridine-3-sulfonamide,
5-[3-cyano-1-cyclopropyl-6-(difluoromethoxy)-1H-indol-2-yl]-N-(propan-2-yl)pyridine-2-sulfonamide,
5-[3-cyano-1-(cyclopropylmethyl)-6-(difluoromethoxy)-1H-indol-2-yl]-N-(propan-2-yl)pyridine-2-sulfonamide,
6-[3-cyano-1-(cyclopropylmethyl)-6-(difluoromethoxy)-1H-indol-2-yl]-N-(1,3-difluoropropan-2-yl)pyridine-3-sulfonamide,
6-[3-cyano-1-cyclopropyl-6-(difluoromethoxy)-1H-indol-2-yl]-N-(1,3-difluoropropan-2-yl)pyridine-3-sulfonamide,
6-[3-cyano-1-cyclobutyl-6-(propan-2-yl)-1H-indol-2-yl]-N-(1,3-difluoropropan-2-yl)pyridine-3-sulfonamide,
6-(3-cyano-1-cyclopentyl-6-methyl-1H-indol-2-yl)-N-(1,3-difluoropropan-2-yl)pyridine-3-sulfonamide,
6-[3-cyano-6-(difluoromethoxy)-1-propyl-1H-indol-2-yl]-N-(1,3-difluoropropan-2-yl)pyridine-3-sulfonamide,
6-[3-cyano-5-fluoro-1-(tetrahydrofuran-3-yl)-1H-indol-2-yl]-N-(1,3-difluoropropan-2-yl)pyridine-3-sulfonamide,
6-[3-cyano-5-fluoro-1-(tetrahydrofuran-3-yl)-1H-indol-2-yl]-N-(propan-2-yl)pyridine-3-sulfonamide,
6-(3-cyano-1-cyclobutyl-6-ethyl-1H-indol-2-yl)-N-(1,3-difluoropropan-2-yl)pyridine-3-sulfonamide,
6-[3-cyano-1-cyclopentyl-6-(difluoromethoxy)-1H-indol-2-yl]-N-(1,3-difluoropropan-2-yl)pyridine-3-sulfonamide,
6-(6-chloro-3-cyano-1-cyclobutyl-5-fluoro-1H-indol-2-yl)-N-(1,3-difluoropropan-2-yl)pyridine-3-sulfonamide,
6-[3-cyano-1-cyclobutyl-6-(difluoromethoxy)-1H-indol-2-yl]-N-(propan-2-yl)pyridine-3-sulfonamide,
6-[3-cyano-1-cyclopentyl-6-(difluoromethoxy)-1H-indol-2-yl]-N-(propan-2-yl)pyridine-3-sulfonamide,
6-[3-cyano-1-cyclopentyl-6-(difluoromethoxy)-1H-indol-2-yl]-N-(1,1,1-trifluoropropan-2-yl)pyridine-3-sulfonamide,
6-{3-cyano-6-methyl-1-[(3R)-tetrahydrofuran-3-yl]-1H-indol-2-yl}-N-(1,3-difluoropropan-2-yl)pyridine-3-sulfonamide,
6-{3-cyano-6-methyl-1-[(3R)-tetrahydrofuran-3-yl]-1H-indol-2-yl}-N-(propan-2-yl)pyridine-3-sulfonamide,
6-(3-cyano-1-cyclobutyl-6-fluoro-1H-indol-2-yl)-N-(1,3-difluoropropan-2-yl)pyridine-3-sulfonamide,
6-[3-cyano-1-(cyclopropylmethyl)-6-fluoro-1H-indol-2-yl]-N-(1,3-difluoropropan-2-yl)pyridine-3-sulfonamide,
6-[3-cyano-1-(cyclopropylmethyl)-5-fluoro-1H-indol-2-yl]-N-(1,3-difluoropropan-2-yl)pyridine-3-sulfonamide,
6-[3-cyano-1-cyclobutyl-6-(2,2-difluoroethoxy)-1H-indol-2-yl]-N-(propan-2-yl)pyridine-3-sulfonamide,
6-[3-cyano-5-fluoro-1-(propan-2-yl)-1H-indol-2-yl]-N-(1,3-difluoropropan-2-yl)pyridine-3-sulfonamide,
6-[3-cyano-6-fluoro-1-(propan-2-yl)-1H-indol-2-yl]-N-(1,3-difluoropropan-2-yl)pyridine-3-sulfonamide,
6-[6-chloro-3-cyano-1-(cyclopropylmethyl)-1H-indol-2-yl]-N-(1,3-difluoropropan-2-yl)pyridine-3-sulfonamide,
6-[6-chloro-3-cyano-1-(propan-2-yl)-1H-indol-2-yl]-N-(1,3-difluoropropan-2-yl)pyridine-3-sulfonamide,
6-(6-chloro-3-cyano-1-cyclopentyl-1H-indol-2-yl)-N-(1,3-difluoropropan-2-yl)pyridine-3-sulfonamide,
6-[5-chloro-3-cyano-1-(propan-2-yl)-1H-indol-2-yl]-N-(1,3-difluoropropan-2-yl)pyridine-3-sulfonamide,
6-(3-cyano-1-cyclopentyl-7-fluoro-1H-indol-2-yl)-N-(propan-2-yl)pyridine-3-sulfonamide,
6-[3-cyano-1-cyclopentyl-6-(difluoromethoxy)-1H-indol-2-yl]-N-(1-fluoro-2-methylpropan-2-yl)pyridine-3-sulfonamide,
6-[3-cyano-1-(cyclopropylmethyl)-6-(trifluoromethoxy)-1H-indol-2-yl]-N-(1,3-difluoropropan-2-yl)pyridine-3-sulfonamide,
6-[3-cyano-1-(propan-2-yl)-6-(trifluoromethoxy)-1H-indol-2-yl]-N-(1,3-difluoropropan-2-yl)pyridine-3-sulfonamide,
6-[3-cyano-1-cyclopentyl-6-(trifluoromethoxy)-1H-indol-2-yl]-N-(1,3-difluoropropan-2-yl)pyridine-3-sulfonamide,
2-(3-cyano-1-cyclobutyl-6-cyclopropyl-1H-indol-2-yl)-N-(propan-2-yl)pyrimidine-5-sulfonamide, 6-(5-chloro-3-cyano-1-cyclopentyl-1H-indol-2-yl)-N-(1,3-difluoropropan-2-yl)pyridine-3-sulfonamide,
6-[5-chloro-3-cyano-1-(cyclopropylmethyl)-1H-indol-2-yl]-N-(1,3-difluoropropan-2-yl)pyridine-3-sulfonamide,
2-(3-cyano-1-cyclopentyl-6-methyl-1H-indol-2-yl)-N-(propan-2-yl)pyrimidine-5-sulfonamide,
6-[3-cyano-6-ethyl-1-(propan-2-yl)-1H-indol-2-yl]-N-(propan-2-yl)pyridine-3-sulfonamide,
6-[3-cyano-1-cyclobutyl-6-(difluoromethoxy)-1H-indol-2-yl]-N-(1-fluoro-2-methylpropan-2-yl)pyridine-3-sulfonamide,
6-[3-cyano-1-cyclobutyl-6-(difluoromethoxy)-1H-indol-2-yl]-N-(1,1,1-trifluoropropan-2-yl)pyridine-3-sulfonamide,
6-(5-chloro-3-cyano-1-cyclohexyl-1H-indol-2-yl)-N-(1,3-difluoropropan-2-yl)pyridine-3-sulfonamide,
6-[3-cyano-6-methyl-1-(propan-2-yl)-1H-indol-2-yl]-N-(1,3-difluoropropan-2-yl)pyridine-3-sulfonamide,
6-[3-cyano-1-(cyclopropylmethyl)-6-methyl-1H-indol-2-yl]-N-(1,3-difluoropropan-2-yl)pyridine-3-sulfonamide,
6-(3-cyano-1-cyclobutyl-6-methyl-1H-indol-2-yl)-N-(1,3-difluoropropan-2-yl)pyridine-3-sulfonamide,
6-[3-cyano-6-cyclopropyl-1-(propan-2-yl)-1H-indol-2-yl]-N-(1,3-difluoropropan-2-yl)pyridine-3-sulfonamide,
6-[3-cyano-6-cyclopropyl-1-(cyclopropylmethyl)-1H-indol-2-yl]-N-(1,3-difluoropropan-2-yl)pyridine-3-sulfonamide,
6-(3-cyano-1-cyclopentyl-6-cyclopropyl-1H-indol-2-yl)-N-(1,3-difluoropropan-2-yl)pyridine-3-sulfonamide,
6-(3-cyano-1-cyclopentyl-6-cyclopropyl-1H-indol-2-yl)-N-(1,1,1-trifluoropropan-2-yl)pyridine-3-sulfonamide,
6-(3-cyano-1-cyclopentyl-7-fluoro-1H-indol-2-yl)-N-(1,3-difluoropropan-2-yl)pyridine-3-sulfonamide,
6-(7-chloro-3-cyano-1-cyclopentyl-1H-indol-2-yl)-N-(1,3-difluoropropan-2-yl)pyridine-3-sulfonamide,
6-(6-chloro-3-cyano-1-cyclohexyl-1H-indol-2-yl)-N-(1,3-difluoropropan-2-yl)pyridine-3-sulfonamide,
6-(3-cyano-1-cyclobutyl-6-cyclopropyl-1H-indol-2-yl)pyridine-3-sulfonamide,
6-(3-cyano-1-cyclohexyl-6-cyclopropyl-1H-indol-2-yl)-N-(1,3-difluoropropan-2-yl)pyridine-3-sulfonamide,
6-[3-cyano-1-cyclobutyl-6-(difluoromethoxy)-1H-indol-2-yl]-N-[1-(trifluoromethyl)cyclopropyl]pyridine-3-sulfonamide,
6-[3-cyano-1-cyclopentyl-6-(difluoromethoxy)-1H-indol-2-yl]-N-[1-(trifluoromethyl)cyclopropyl]pyridine-3-sulfonamide,
6-(3-cyano-6-cyclopropyl-1-phenyl-1H-indol-2-yl)-N-(1,3-difluoropropan-2-yl)pyridine-3-sulfonamide,
6-[3-cyano-5-fluoro-1-(pyridin-2-yl)-1H-indol-2-yl]-N-(1,3-difluoropropan-2-yl)pyridine-3-sulfonamide,
2-(5-chloro-3-cyano-1-cyclohexyl-1H-indol-2-yl)-N-(propan-2-yl)pyrimidine-5-sulfonamide,
2-(3-cyano-1-cyclohexyl-6-methyl-1H-indol-2-yl)-N-(propan-2-yl)pyrimidine-5-sulfonamide,
6-[3-cyano-1-cyclohexyl-6-(difluoromethoxy)-1H-indol-2-yl]-N-(propan-2-yl)pyridine-3-sulfonamide,
6-[3-cyano-1-cyclohexyl-6-(difluoromethoxy)-1H-indol-2-yl]-N-(1,3-difluoropropan-2-yl)pyridine-3-sulfonamide,
6-(3-cyano-1-cyclobutyl-5-fluoro-6-methoxy-1H-indol-2-yl)-N-(propan-2-yl)pyridine-3-sulfonamide,
6-(3-cyano-1-cyclobutyl-5-fluoro-6-methoxy-1H-indol-2-yl)-N-(1,3-difluoropropan-2-yl)pyridine-3-sulfonamide,
6-[3-cyano-1-cyclobutyl-6-(2,2-difluoroethenyl)-1H-indol-2-yl]-N-(1,3-difluoropropan-2-yl)pyridine-3-sulfonamide,
6-(3-cyano-1-cyclohexyl-5-fluoro-1H-indol-2-yl)-N-(1,3-difluoropropan-2-yl)pyridine-3-sulfonamide,
6-[3-cyano-1-cyclohexyl-6-(trifluoromethoxy)-1H-indol-2-yl]-N-(1,3-difluoropropan-2-yl)pyridine-3-sulfonamide,
6-[3-cyano-1-cyclobutyl-6-(difluoromethoxy)-1H-indol-2-yl]-N-[1-(trifluoromethyl)cyclobutyl]pyridine-3-sulfonamide,
6-(3-cyano-1-cyclobutyl-6-cyclopropyl-5-fluoro-1H-indol-2-yl)-N-(1,3-difluoropropan-2-yl)pyridine-3-sulfonamide,
6-(3-cyano-1-cyclobutyl-5-fluoro-6-methyl-1H-indol-2-yl)-N-(1,3-difluoropropan-2-yl)pyridine-3-sulfonamide,
6-(3-cyano-1,6-dicyclopropyl-1H-indol-2-yl)-N-(propan-2-yl)pyridine-3-sulfonamide,
6-[6-chloro-3-cyano-1-(cyclopropylmethyl)-5-fluoro-1H-indol-2-yl]-N-(1,3-difluoropropan-2-yl)pyridine-3-sulfonamide,
6-(3-cyano-6-methyl-1-phenyl-1H-indol-2-yl)-N-(1,3-difluoropropan-2-yl)pyridine-3-sulfonamide,
6-(5-chloro-3-cyano-1-phenyl-1H-indol-2-yl)-N-(1,3-difluoropropan-2-yl)pyridine-3-sulfonamide,
6-(3-cyano-5-fluoro-1-phenyl-1H-indol-2-yl)-N-(1,3-difluoropropan-2-yl)pyridine-3-sulfonamide,
2-(5-chloro-3-cyano-1-cyclobutyl-1H-indol-2-yl)-N-(propan-2-yl)pyrimidine-5-sulfonamide,
2-(6-chloro-3-cyano-1-cyclobutyl-1H-indol-2-yl)-N-(propan-2-yl)pyrimidine-5-sulfonamide,
2-[3-cyano-1-cyclobutyl-6-(trifluoromethoxy)-1H-indol-2-yl]-N-(propan-2-yl)pyrimidine-5-sulfonamide,
2-[3-cyano-1-cyclopentyl-6-(trifluoromethoxy)-1H-indol-2-yl]-N-(propan-2-yl)pyrimidine-5-sulfonamide,
6-(5-chloro-3-cyano-1-cyclopentyl-1H-indol-2-yl)-N-[(1S)-1-cyclopropylethyl]pyridine-3-sulfonamide,
6-(5-chloro-3-cyano-1-cyclobutyl-1H-indol-2-yl)-N-[(1S)-1-cyclopropylethyl]pyridine-3-sulfonamide,
2-[5-chloro-3-cyano-1-(propan-2-yl)-1H-indol-2-yl]-N-(propan-2-yl)pyrimidine-5-sulfonamide,
2-(3-cyano-1-cyclobutyl-5-methyl-1H-indol-2-yl)-N-(propan-2-yl)pyrimidine-5-sulfonamide,
2-(3-cyano-1-cyclobutyl-5-methyl-1H-indol-2-yl)-N-(1,3-difluoropropan-2-yl)pyrimidine-5-sulfonamide,
2-[3-cyano-5-fluoro-1-(propan-2-yl)-1H-indol-2-yl]-N-(propan-2-yl)pyrimidine-5-sulfonamide,
2-[3-cyano-6-cyclopropyl-1-(cyclopropylmethyl)-1H-indol-2-yl]-N-(propan-2-yl)pyrimidine-5-sulfonamide,
2-(3-cyano-1-cyclopentyl-6-cyclopropyl-1H-indol-2-yl)-N-(propan-2-yl)pyrimidine-5-sulfonamide,
2-(3-cyano-1-cyclobutyl-6-cyclopropyl-1H-indol-2-yl)-N-(1,3-difluoropropan-2-yl)pyrimidine-5-sulfonamide,
2-[3-cyano-1-cyclobutyl-6-(difluoromethoxy)-1H-indol-2-yl]-N-(propan-2-yl)pyrimidine-5-sulfonamide,
2-[3-cyano-1-cyclobutyl-6-(difluoromethoxy)-1H-indol-2-yl]-N-(1,1,1-trifluoropropan-2-yl)pyrimidine-5-sulfonamide,
2-[3-cyano-1-cyclobutyl-6-(difluoromethoxy)-1H-indol-2-yl]-N-(1,3-difluoropropan-2-yl)pyrimidine-5-sulfonamide, 2-[3-cyano-1-cyclobutyl-6-(difluoromethoxy)-1H-indol-2-yl]-N-[(1S)-1-cyclopropylethyl]pyrimidine-5-sulfonamide,
2-(3-cyano-1-cyclobutyl-6-cyclopropyl-1H-indol-2-yl)-N-[(1S)-1-cyclopropylethyl]pyrimidine-5-sulfonamide,
2-(3-cyano-1-cyclobutyl-6-methyl-1H-indol-2-yl)-N-(1,3-difluoropropan-2-yl)pyrimidine-5-sulfonamide,
2-[3-cyano-1-(cyclopropylmethyl)-6-methyl-1H-indol-2-yl]-N-(1,3-difluoropropan-2-yl)pyrimidine-5-sulfonamide,
2-[3-cyano-6-methyl-1-(propan-2-yl)-1H-indol-2-yl]-N-(1,3-difluoropropan-2-yl)pyrimidine-5-sulfonamide,
2-(3-cyano-1-cyclopentyl-6-methyl-1H-indol-2-yl)-N-(1,3-difluoropropan-2-yl)pyrimidine-5-sulfonamide,
2-[3-cyano-1-(cyclopropylmethyl)-6-(difluoromethoxy)-1H-indol-2-yl]-N-(1,3-difluoropropan-2-yl)pyrimidine-5-sulfonamide,
2-[3-cyano-6-(difluoromethoxy)-1-(propan-2-yl)-1H-indol-2-yl]-N-(1,3-difluoropropan-2-yl)pyrimidine-5-sulfonamide,
2-(3-cyano-1-cyclobutyl-6-fluoro-1H-indol-2-yl)-N-(propan-2-yl)pyrimidine-5-sulfonamide,
2-[3-cyano-1-(cyclopropylmethyl)-6-fluoro-1H-indol-2-yl]-N-(propan-2-yl)pyrimidine-5-sulfonamide,
2-[3-cyano-6-fluoro-1-(propan-2-yl)-1H-indol-2-yl]-N-(propan-2-yl)pyrimidine-5-sulfonamide,
2-(3-cyano-1-cyclopentyl-6-fluoro-1H-indol-2-yl)-N-(propan-2-yl)pyrimidine-5-sulfonamide,
6-(3-cyano-1-cyclobutyl-5-fluoro-1H-indol-2-yl)-N-[(1S)-1-cyclopropylethyl]pyridine-3-sulfonamide,
6-(3-cyano-1-cyclopentyl-5-fluoro-1H-indol-2-yl)-N-[(1S)-1-cyclopropylethyl]pyridine-3-sulfonamide,
6-(3-cyano-1-cyclobutyl-6-fluoro-1H-indol-2-yl)-N-[(1S)-1-cyclopropylethyl]pyridine-3-sulfonamide,
2-(3-cyano-1-cyclobutyl-6-cyclopropyl-5-fluoro-1H-indol-2-yl)-N-(1,3-difluoropropan-2-yl)pyrimidine-5-sulfonamide,
2-(3-cyano-1-cyclobutyl-5-fluoro-6-methyl-1H-indol-2-yl)-N-(1,3-difluoropropan-2-yl)pyrimidine-5-sulfonamide,
6-(3-cyano-1,6-dicyclopropyl-1H-indol-2-yl)-N-(1,3-difluoropropan-2-yl)pyridine-3-sulfonamide,
2-(3-cyano-1,6-dicyclopropyl-1H-indol-2-yl)-N-(1,3-difluoropropan-2-yl)pyrimidine-5-sulfonamide,
2-(6-chloro-3-cyano-1-cyclobutyl-5-fluoro-1H-indol-2-yl)-N-(1,3-difluoropropan-2-yl)pyrimidine-5-sulfonamide,
2-(3-cyano-1-cyclobutyl-5-fluoro-6-methoxy-1H-indol-2-yl)-N-(1,3-difluoropropan-2-yl)pyrimidine-5-sulfonamide,
6-[3-cyano-1-cyclobutyl-6-(difluoromethoxy)-1H-indol-2-yl]-N-[(1S)-1-cyclopropylethyl]pyridine-3-sulfonamide,
6-[3-cyano-1-cyclobutyl-6-(trifluoromethoxy)-1H-indol-2-yl]-N-[(1S)-1-cyclopropylethyl]pyridine-3-sulfonamide,
6-(3-cyano-1-cyclobutyl-6-cyclopropyl-1H-indol-2-yl)-N-[1-(trifluoromethyl)cyclopropyl]pyridine-3-sulfonamide,
6-(6-chloro-3-cyano-1-cyclobutyl-1H-indol-2-yl)-N-[(1S)-1-cyclopropylethyl]pyridine-3-sulfonamide,
6-(6-chloro-3-cyano-1-cyclopentyl-1H-indol-2-yl)-N-[(1S)-1-cyclopropylethyl]pyridine-3-sulfonamide,
2-[6-chloro-3-cyano-1-(propan-2-yl)-1H-indol-2-yl]-N-(propan-2-yl)pyrimidine-5-sulfonamide,
2-(6-chloro-3-cyano-1-cyclopentyl-1H-indol-2-yl)-N-(1,3-difluoropropan-2-yl)pyrimidine-5-sulfonamide,
6-(3-cyano-1-cyclopentyl-5-methyl-1H-indol-2-yl)-N-(1,3-difluoropropan-2-yl)pyridine-3-sulfonamide,
2-(3-cyano-1-cyclopentyl-5-methyl-1H-indol-2-yl)-N-(propan-2-yl)pyrimidine-5-sulfonamide,
2-(3-cyano-1-cyclopentyl-5-methyl-1H-indol-2-yl)-N-(1,3-difluoropropan-2-yl)pyrimidine-5-sulfonamide,
6-[3-cyano-1-cyclobutyl-6-(methylsulfanyl)-1H-indol-2-yl]-N-(1,3-difluoropropan-2-yl)pyridine-3-sulfonamide,
2-[3-cyano-1-cyclobutyl-6-(methylsulfanyl)-1H-indol-2-yl]-N-(1,3-difluoropropan-2-yl)pyrimidine-5-sulfonamide,
2-(3-cyano-1-cyclobutyl-6-fluoro-1H-indol-2-yl)-N-(1,3-difluoropropan-2-yl)pyrimidine-5-sulfonamide,
2-[3-cyano-1-(cyclopropylmethyl)-6-fluoro-1H-indol-2-yl]-N-(1,3-difluoropropan-2-yl)pyrimidine-5-sulfonamide,
2-[3-cyano-6-fluoro-1-(propan-2-yl)-1H-indol-2-yl]-N-(1,3-difluoropropan-2-yl)pyrimidine-5-sulfonamide,
2-(3-cyano-1-cyclopentyl-6-fluoro-1H-indol-2-yl)-N-(1,3-difluoropropan-2-yl)pyrimidine-5-sulfonamide,
2-[3-cyano-6-methyl-1-(propan-2-yl)-1H-indol-2-yl]-N-(propan-2-yl)pyrimidine-5-sulfonamide,
2-[3-cyano-1-(cyclopropylmethyl)-6-methyl-1H-indol-2-yl]-N-(propan-2-yl)pyrimidine-5-sulfonamide,
2-(3-cyano-1-cyclobutyl-6-methyl-1H-indol-2-yl)-N-(propan-2-yl)pyrimidine-5-sulfonamide,
2-[3-cyano-1-(cyclopropylmethyl)-6-(difluoromethoxy)-1H-indol-2-yl]-N-(propan-2-yl)pyrimidine-5-sulfonamide,
2-[3-cyano-6-(difluoromethoxy)-1-(propan-2-yl)-1H-indol-2-yl]-N-(propan-2-yl)pyrimidine-5-sulfonamide,
2-(3-cyano-1-cyclobutyl-6-methoxy-1H-indol-2-yl)-N-(propan-2-yl)pyrimidine-5-sulfonamide,
2-(3-cyano-1-cyclopentyl-6-cyclopropyl-1H-indol-2-yl)-N-(1,3-difluoropropan-2-yl)pyrimidine-5-sulfonamide,
6-[3-cyano-1-cyclopentyl-6-(difluoromethoxy)-1H-indol-2-yl]-N-[(1S)-1-cyclopropylethyl]pyridine-3-sulfonamide,
2-(5-chloro-3-cyano-1-cyclobutyl-1H-indol-2-yl)-N-(1,3-difluoropropan-2-yl)pyrimidine-5-sulfonamide,
2-(6-chloro-3-cyano-1-cyclobutyl-1H-indol-2-yl)-N-(1,3-difluoropropan-2-yl)pyrimidine-5-sulfonamide,
2-[3-cyano-1-cyclobutyl-6-(trifluoromethoxy)-1H-indol-2-yl]-N-(1,3-difluoropropan-2-yl)pyrimidine-5-sulfonamide,
2-[3-cyano-1-cyclopentyl-6-(trifluoromethoxy)-1H-indol-2-yl]-N-(1,3-difluoropropan-2-yl)pyrimidine-5-sulfonamide,
2-[3-cyano-1-cyclohexyl-6-(difluoromethoxy)-1H-indol-2-yl]-N-(1,3-difluoropropan-2-yl)pyrimidine-5-sulfonamide,
2-(3-cyano-1-cyclobutyl-6-cyclopropyl-1H-indol-2-yl)-N-[(2R)-1,1,1-trifluoropropan-2-yl]pyrimidine-5-sulfonamide,
2-(3-cyano-1-cyclobutyl-6-methyl-1H-indol-2-yl)-N-[(2R)-1,1,1-trifluoropropan-2-yl]pyrimidine-5-sulfonamide,
2-(3-cyano-1-cyclopentyl-6-methyl-1H-indol-2-yl)-N-[(2R)-1,1,1-trifluoropropan-2-yl]pyrimidine-5-sulfonamide,
2-(3-cyano-1-cyclobutyl-6-methoxy-1H-indol-2-yl)-N-[(2R)-1,1,1-trifluoropropan-2-yl]pyrimidine-5-sulfonamide, 2-[3-cyano-1-cyclobutyl-6-(difluoromethoxy)-1H-indol-2-yl]-N-[(2R)-1,1,1-trifluoropropan-2-yl]pyrimidine-5-sulfonamide, 2-[3-cyano-1-cyclobutyl-6-(propan-2-yl)-1H-indol-2-yl]-N-(propan-2-yl)pyrimidine-5-sulfonamide, 2-[3-cyano-1-cyclobutyl-6-(propan-2-yl)-1H-indol-2-yl]-N-(1,3-difluoropropan-2-yl)pyrimidine-5-sulfonamide, 2-[5-chloro-3-cyano-1-(propan-2-yl)-1H-indol-2-yl]-N-(1,3-difluoropropan-2-yl)pyrimidine-5-sulfonamide, 2-(5-chloro-3-cyano-1-cyclopentyl-1H-indol-2-yl)-N-(1,3-difluoropropan-2-yl)pyrimidine-5-sulfonamide, 2-(6-chloro-3-cyano-1-cyclopentyl-1H-indol-2-yl)-N-(propan-2-yl)pyrimidine-5-sulfonamide, 6-(3-cyano-1-cyclopentyl-6-methyl-1H-indol-2-yl)-N-[1-(trifluoromethyl)cyclopropyl]pyridine-3-sulfonamide, 6-[3-cyano-1-cyclobutyl-6-(trifluoromethoxy)-1H-indol-2-yl]-N-[(2R)-1,1,1-trifluoropropan-2-yl]pyridine-3-sulfonamide, 6-(3-cyano-1-cyclobutyl-6-methyl-1H-indol-2-yl)-N-[(2R)-1,1,1-trifluoropropan-2-yl]pyridine-3-sulfonamide, 2-(3-cyano-1-cyclohexyl-6-cyclopropyl-1H-indol-2-yl)-N-(1,3-difluoropropan-2-yl)pyrimidine-5-sulfonamide, 6-[3-cyano-6-(difluoromethoxy)-1-(propan-2-yl)-1H-indol-2-yl]-N-[(2R)-1,1,1-trifluoropropan-2-yl]pyridine-3-sulfonamide, 6-[3-cyano-1-cyclohexyl-6-(difluoromethoxy)-1H-indol-2-yl]-N-[(2R)-1,1,1-trifluoropropan-2-yl]pyridine-3-sulfonamide, 6-[3-cyclobutyl-6-(difluoromethoxy)-1H-indol-2-yl]-N-[(2R)-1,1,1-trifluoropropan-2yl]pyridine-3-sulfonamide, 6-[3-cyano-1-(cyclopropylmethyl)-6-methyl-1H-indol-2-yl]-N-[(2R)-1,1,1-trifluoropropan-2-yl]pyridine-3-sulfonamide, 2-(3-cyano-1-cyclohexyl-5-methyl-1H-indol-2-yl)-N-(1,3-difluoropropan-2-yl)pyrimidine-5-sulfonamide, 6-(3-cyano-1-cyclohexyl-5-methyl-1H-indol-2-yl)-N-(1,3-difluoropropan-2-yl)pyridine-3-sulfonamide, 2-(3-cyano-1-cyclohexyl-5-methyl-1H-indol-2-yl)-N-(propan-2-yl)pyrimidine-5-sulfonamide, 6-(3-cyano-1-cyclobutyl-5-methyl-1H-indol-2-yl)-N-[(1S)-1-cyclopropylethyl]pyridine-3-sulfonamide, 2-(3-cyano-1-cyclobutyl-6-methyl-1H-indol-2-yl)-N-[(1S)-1-cyclopropylethyl]pyrimidine-5-sulfonamide, 2-[3-cyano-1-(cyclopropylmethyl)-6-methyl-1H-indol-2-yl]-N-[(1S)-1-cyclopropylethyl]pyrimidine-5-sulfonamide, 2-(3-cyano-1-cyclopentyl-6-methyl-1H-indol-2-yl)-N-[(1S)-1-cyclopropylethyl]pyrimidine-5-sulfonamide, 2-(3-cyano-1-cyclobutyl-6-methoxy-1H-indol-2-yl)-N-[(1S)-1-cyclopropylethyl]pyrimidine-5-sulfonamide, 2-(3-cyano-1-cyclopentyl-6-methoxy-1H-indol-2-yl)-N-[(1S)-1-cyclopropylethyl]pyrimidine-5-sulfonamide, 2-[3-cyano-6-(difluoromethoxy)-1-(propan-2-yl)-1H-indol-2-yl]-N-[(1S)-1-cyclopropylethyl]pyrimidine-5-sulfonamide, 2-[3-cyano-6-(difluoromethoxy)-1-propyl-1H-indol-2-yl]-N-[(1S)-1-cyclopropylethyl]pyrimidine-5-sulfonamide, 2-[3-cyano-1-cyclopentyl-6-(difluoromethoxy)-1H-indol-2-yl]-N-[(1S)-1-cyclopropylethyl]pyrimidine-5-sulfonamide, 6-[3-cyano-6-methyl-1-(propan-2-yl)-1H-indol-2-yl]-N-[(2R)-1,1,1-trifluoropropan-2-yl]pyridine-3-sulfonamide, 6-(3-cyano-1-cyclopentyl-6-cyclopropyl-1H-indol-2-yl)-N-[(2R)-1,1,1-trifluoropropan-2-yl]pyridine-3-sulfonamide, 6-(3-cyano-1-cyclobutyl-6-cyclopropyl-1H-indol-2-yl)-N-[(2R)-1,1,1-trifluoropropan-2-yl]pyridine-3-sulfonamide, 6-(3-cyano-1-cyclohexyl-6-methyl-1H-indol-2-yl)-N-[(2R)-1,1,1-trifluoropropan-2-yl]pyridine-3-sulfonamide, 6-(3-cyano-1-cyclopentyl-6-methyl-1H-indol-2-yl)-N-[(2R)-1,1,1-trifluoropropan-2-yl]pyridine-3-sulfonamide, 6-(3-cyano-1-cyclobutyl-6-fluoro-1H-indol-2-yl)-N-[(2R)-1,1,1-trifluoropropan-2-yl]pyridine-3-sulfonamide, 6-[3-cyano-1-(cyclopropylmethyl)-6-fluoro-1H-indol-2-yl]-N-[(2R)-1,1,1-trifluoropropan-2-yl]pyridine-3-sulfonamide, 6-(3-cyano-6-fluoro-1-propyl-1H-indol-2-yl)-N-[(2R)-1,1,1-trifluoropropan-2-yl]pyridine-3-sulfonamide, 6-(3-cyano-1-cyclopentyl-6-fluoro-1H-indol-2-yl)-N-[(2R)-1,1,1-trifluoropropan-2-yl]pyridine-3-sulfonamide, 6-(3-cyano-1-cyclobutyl-5-fluoro-1H-indol-2-yl)-N-[(2R)-1,1,1-trifluoropropan-2-yl]pyridine-3-sulfonamide, 6-(3-cyano-1-cyclopentyl-5-fluoro-1H-indol-2-yl)-N-[(2R)-1,1,1-trifluoropropan-2-yl]pyridine-3-sulfonamide, 2-[5-chloro-3-cyano-1-(cyclopropylmethyl)-1H-indol-2-yl]-N-(1,3-difluoropropan-2-yl)pyrimidine-5-sulfonamide, 6-(6-chloro-3-cyano-1-cyclobutyl-1H-indol-2-yl)-N-[(2R)-1,1,1-trifluoropropan-2-yl]pyridine-3-sulfonamide, 6-(6-chloro-3-cyano-1-cyclopentyl-1H-indol-2-yl)-N-[(2R)-1,1,1-trifluoropropan-2-yl]pyridine-3-sulfonamide, 6-(5-chloro-3-cyano-1-cyclopentyl-1H-indol-2-yl)-N-[(2R)-1,1,1-trifluoropropan-2-yl]pyridine-3-sulfonamide, 6-[3-cyano-1-(cyclopropylmethyl)-5-fluoro-6-methoxy-1H-indol-2-yl]-N-(1,3-difluoropropan-2-yl)pyridine-3-sulfonamide, 6-[3-cyano-6-(difluoromethoxy)-1-phenyl-1H-indol-2-yl]-N-(1,3-difluoropropan-2-yl)pyridine-3-sulfonamide, 6-[3-cyano-6-(difluoromethoxy)-1-(2-fluorophenyl)-1H-indol-2-yl]-N-(1,3-difluoropropan-2-yl)pyridine-3-sulfonamide, 6-[3-cyano-6-(difluoromethoxy)-1-(4-fluorophenyl)-1H-indol-2-yl]-N-(1,3-difluoropropan-2-yl)pyridine-3-sulfonamide, 6-(3-cyano-1-cyclobutyl-6-methoxy-1H-indol-2-yl)-N-(1,3-difluoropropan-2-yl)pyridine-3-sulfonamide, 2-(3-cyano-1-cyclobutyl-6-methoxy-1H-indol-2-yl)-N-(1,3-difluoropropan-2-yl)pyrimidine-5-sulfonamide, 2-(3-cyano-1-cyclopentyl-6-methoxy-1H-indol-2-yl)-N-(1,3-difluoropropan-2-yl)pyrimidine-5-sulfonamide, 2-[3-cyano-6-(difluoromethoxy)-1-propyl-1H-indol-2-yl]-N-(1,3-difluoropropan-2-yl)pyrimidine-5-sulfonamide, 2-[3-cyano-1-cyclopentyl-6-(difluoromethoxy)-1H-indol-2-yl]-N-(1,3-difluoropropan-2-yl)pyrimidine-5-sulfonamide, 6-(3-cyano-1-cyclohexyl-6-fluoro-1H-indol-2-yl)-N-(1,3-difluoropropan-2-yl)pyridine-3-sulfonamide, 2-(3-cyano-1-cyclohexyl-6-fluoro-1H-indol-2-yl)-N-(1,3-difluoropropan-2-yl)pyrimidine-5-sulfonamide,
6-(3-cyano-1-cyclobutyl-6-cyclopropyl-1H-indol-2-yl)-N-[(1S)-1-cyclopropylethyl]pyridine-3-sulfonamide,
6-[3-cyano-1-(cyclopropylmethyl)-6-methyl-1H-indol-2-yl]-N-[(1S)-1-cyclopropylethyl]pyridine-3-sulfonamide,
6-(3-cyano-1-cyclobutyl-6-methyl-1H-indol-2-yl)-N-[(1S)-1-cyclopropylethyl]pyridine-3-sulfonamide,
6-[3-cyano-1-cyclobutyl-6-(difluoromethoxy)-1H-indol-2-yl]-N-(1,3-dihydroxypropan-2-yl)pyridine-3-sulfonamide,
2-(3-cyano-1-cyclopentyl-5-fluoro-1H-indol-2-yl)-N-(1,3-difluoropropan-2-yl)pyrimidine-5-sulfonamide,
2-(3-cyano-1-cyclohexyl-6-methyl-1H-indol-2-yl)-N-(1,3-difluoropropan-2-yl)pyrimidine-5-sulfonamide,
2-[3-cyano-5-(difluoromethoxy)-1-ethyl-1H-indol-2-yl]-N-(propan-2-yl)pyrimidine-5-sulfonamide,
6-(5-chloro-3-cyano-1-cyclobutyl-1H-indol-2-yl)-N-(3,3-difluorocyclobutyl)pyridine-3-sulfonamide,
6-(6-chloro-3-cyano-1-cyclobutyl-1H-indol-2-yl)-N-(3,3-difluorocyclobutyl)pyridine-3-sulfonamide,
6-(3-cyano-1-cyclobutyl-6-methyl-1H-indol-2-yl)-N-(3,3-difluorocyclobutyl)pyridine-3-sulfonamide,
6-(3-cyano-1-cyclopentyl-6-methoxy-1H-indol-2-yl)-N-(3,3-difluorocyclobutyl)pyridine-3-sulfonamide,
6-(3-cyano-1-cyclobutyl-6-cyclopropyl-1H-indol-2-yl)-N-(3,3-difluorocyclobutyl)pyridine-3-sulfonamide,
6-[3-cyano-6-methyl-1-(pyridin-2-yl)-1H-indol-2-yl]-N-(1,3-difluoropropan-2-yl)pyridine-3-sulfonamide,
6-[3-cyano-6-(difluoromethoxy)-1-(pyridin-2-yl)-1H-indol-2-yl]-N-(1,3-difluoropropan-2-yl)pyridine-3-sulfonamide,
6-(3-cyano-1-cyclohexyl-5-fluoro-1H-indol-2-yl)-N-[(1S)-1-cyclopropylethyl]pyridine-3-sulfonamide,
2-(3-cyano-1-cyclohexyl-6-fluoro-1H-indol-2-yl)-N-(propan-2-yl)pyrimidine-5-sulfonamide,
6-(3-cyano-1-cyclohexyl-6-fluoro-1H-indol-2-yl)-N-[(2R)-1,1,1-trifluoropropan-2-yl]pyridine-3-sulfonamide,
6-(3-cyano-1-cyclopentyl-6-methyl-1H-indol-2-yl)-N-[1-(trifluoromethyl)cyclobutyl]pyridine-3-sulfonamide,
2-(3-cyano-1-cyclopentyl-6-cyclopropyl-1H-indol-2-yl)-N-[(1S)-1-cyclopropylethyl]pyrimidine-5-sulfonamide,
6-[3-cyano-1-(cyclopropylmethyl)-6-methyl-1H-indol-2-yl]-N-[1-(trifluoromethyl)cyclopropyl]pyridine-3-sulfonamide,
6-(3-cyano-1-cyclobutyl-6-methyl-1H-indol-2-yl)-N-[1-(trifluoromethyl)cyclopropyl]pyridine-3-sulfonamide,
2-[6-chloro-3-cyano-1-(propan-2-yl)-1H-indol-2-yl]-N-(1,3-difluoropropan-2-yl)pyrimidine-5-sulfonamide,
6-(3-cyano-1-cyclobutyl-5-ethyl-1H-indol-2-yl)-N-(1,3-difluoropropan-2-yl)pyridine-3-sulfonamide,
6-[3-cyano-5-fluoro-1-(pyridin-4-yl)-1H-indol-2-yl]-N-(1,3-difluoropropan-2-yl)pyridine-3-sulfonamide,
2-(3-cyano-6-methyl-1-phenyl-1H-indol-2-yl)-N-(1,3-difluoropropan-2-yl)pyrimidine-5-sulfonamide,
6-(3-cyano-1-cyclohexyl-5-fluoro-1H-indol-2-yl)-N-[(2R)-1,1,1-trifluoropropan-2-yl]pyridine-3-sulfonamide,
6-(3-cyano-1-cyclohexyl-6-fluoro-1H-indol-2-yl)-N-[(1S)-1-cyclopropylethyl]pyridine-3-sulfonamide,
6-(3-cyano-1,6-dicyclobutyl-1H-indol-2-yl)-N-[(1S)-1-cyclopropylethyl]pyridine-3-sulfonamide,
2-(3-cyano-1,6-dicyclobutyl-1H-indol-2-yl)-N-(1,3-difluoropropan-2-yl)pyrimidine-5-sulfonamide,
2-(3-cyano-1,6-dicyclobutyl-1H-indol-2-yl)-N-(propan-2-yl)pyrimidine-5-sulfonamide,
6-(3-cyano-1,6-dicyclobutyl-1H-indol-2-yl)-N-(propan-2-yl)pyridine-3-sulfonamide,
6-[3-cyano-1-cyclobutyl-6-(2,2-difluoroethyl)-1H-indol-2-yl]-N-(1,3-difluoropropan-2-yl)pyridine-3-sulfonamide,
6-[3-cyano-1-cyclobutyl-6-(difluoromethoxy)-1H-indol-2-yl]-N-[(2S)-1,1,1-trifluoropropan-2-yl]pyridine-3-sulfonamide,
6-[3-cyano-1-cyclobutyl-6-(difluoromethoxy)-1H-indol-2-yl]-N-(1-cyanoethyl)pyridine-3-sulfonamide,
2-[3-cyano-1-(cyclopropylmethyl)-5-fluoro-1H-indol-2-yl]-N-(1,3-difluoropropan-2-yl)pyrimidine-5-sulfonamide,
2-[3-cyano-1-(cyclopropylmethyl)-5-fluoro-1H-indol-2-yl]-N-(propan-2-yl)pyrimidine-5-sulfonamide,
6-[3-cyano-1-cyclohexyl-6-(trifluoromethoxy)-1H-indol-2-yl]-N-[(2R)-1,1,1-trifluoropropan-2-yl]pyridine-3-sulfonamide,
6-[3-cyano-1-cyclohexyl-6-(trifluoromethoxy)-1H-indol-2-yl]-N-[(1S)-1-cyclopropylethyl]pyridine-3-sulfonamide,
2-[3-cyano-1-cyclohexyl-6-(trifluoromethoxy)-1H-indol-2-yl]-N-(1,3-difluoropropan-2-yl)pyrimidine-5-sulfonamide,
6-(3-cyano-1-cyclopentyl-6-fluoro-1H-indol-2-yl)-N-(1,3-difluoropropan-2-yl)pyridine-3-sulfonamide,
6-[3-cyano-1-(propan-2-yl)-6-(trifluoromethoxy)-1H-indol-2-yl]-N-[(1S)-1-cyclopropylethyl]pyridine-3-sulfonamide,
6-[3-cyano-1-(cyclopropylmethyl)-6-(trifluoromethoxy)-1H-indol-2-yl]-N-[(1S)-1-cyclopropylethyl]pyridine-3-sulfonamide,
6-(3-cyano-1-cyclopentyl-6-ethyl-1H-indol-2-yl)-N-(1,3-difluoropropan-2-yl)pyridine-3-sulfonamide,
6-(3-cyano-1-cyclopentyl-6-ethyl-1H-indol-2-yl)-N-[(2R)-1,1,1-trifluoropropan-2-yl]pyridine-3-sulfonamide,
6-(3-cyano-1-cyclopentyl-6-ethyl-1H-indol-2-yl)-N-[(1S)-1-cyclopropylethyl]pyridine-3-sulfonamide,
6-(3-cyano-1-cyclopentyl-5-methyl-1H-indol-2-yl)-N-[1-(trifluoromethyl)cyclopropyl]pyridine-3-sulfonamide,
2-(5-chloro-3-cyano-1-cyclopentyl-1H-indol-2-yl)-N-(propan-2-yl)pyrimidine-5-sulfonamide,
2-[3-cyano-1-cyclobutyl-6-(fluoromethyl)-1H-indol-2-yl]-N-(propan-2-yl)pyrimidine-5-sulfonamide,
6-(5-chloro-3-cyano-1-cyclobutyl-1H-indol-2-yl)-N-[(2R)-1,1,1-trifluoropropan-2-yl]pyridine-3-sulfonamide,
6-[3-cyano-1-cyclobutyl-6-(fluoromethyl)-1H-indol-2-yl]-N-[(1S)-1-cyclopropylethyl]pyridine-3-sulfonamide,
6-[3-cyano-1-cyclobutyl-6-(fluoromethyl)-1H-indol-2-yl]-N-(1,3-difluoropropan-2-yl)pyridine-3-sulfonamide,
6-[3-cyano-1-cyclobutyl-6-(fluoromethyl)-1H-indol-2-yl]-N-[(2R)-1,1,1-trifluoropropan-2-yl]pyridine-3-sulfonamide,
6-[3-cyano-1-cyclopentyl-6-(trifluoromethoxy)-1H-indol-2-yl]-N-[(1S)-1-cyclopropylethyl]pyridine-3-sulfonamide,
2-[3-cyano-1-cyclobutyl-6-(morpholin-4-yl)-1H-indol-2-yl]-N-(1,3-difluoropropan-2-yl)pyrimidine-5-sulfonamide, 6-[3-cyano-1-cyclobutyl-6-(morpholin-4-yl)-1H-indol-2-yl]-N-(1,3-difluoropropan-2-yl)pyridine-3-sulfonamide, 2-[3-cyano-1-cyclobutyl-6-(difluoromethoxy)-1H-indol-2-yl]-N-[(2S)-1,1,1-trifluoropropan-2-yl]pyrimidine-5-sulfonamide, 2-(3-cyano-1-cyclobutyl-6-cyclopropyl-1H-indol-2-yl)-N-[(2S)-1,1,1-trifluoropropan-2-yl]pyrimidine-5-sulfonamide, 2-(3-cyano-1-cyclobutyl-6-methyl-1H-indol-2-yl)-N-[(2S)-1,1,1-trifluoropropan-2-yl]pyrimidine-5-sulfonamide, 2-[3-cyano-1-cyclopentyl-6-(difluoromethoxy)-1H-indol-2-yl]-N-[(2S)-1,1,1-trifluoropropan-2-yl]pyrimidine-5-sulfonamide, 6-(3-cyano-1-cyclopentyl-5-fluoro-1H-indol-2-yl)-N-[1-(trifluoromethyl)cyclopropyl]pyridine-3-sulfonamide, 6-(3-cyano-1-cyclobutyl-5-methyl-1H-indol-2-yl)-N-[1-(trifluoromethyl)cyclopropyl]pyridine-3-sulfonamide, 6-(3-cyano-1-cyclobutyl-5-fluoro-1H-indol-2-yl)-N-[1-(trifluoromethyl)cyclopropyl]pyridine-3-sulfonamide, 2-[3-cyano-1-cyclobutyl-6-(difluoromethyl)-1H-indol-2-yl]-N-(1,3-difluoropropan-2-yl)pyrimidine-5-sulfonamide, 6-[3-cyano-1-cyclobutyl-6-(difluoromethyl)-1H-indol-2-yl]-N-(1,3-difluoropropan-2-yl)pyridine-3-sulfonamide, 2-[3-cyano-1-cyclobutyl-6-(difluoromethyl)-1H-indol-2-yl]-N-(propan-2-yl)pyrimidine-5-sulfonamide, 6-[3-cyano-1-cyclobutyl-6-(difluoromethyl)-1H-indol-2-yl]-N-(propan-2-yl)pyridine-3-sulfonamide, 6-[3-cyano-1-cyclobutyl-6-(difluoromethyl)-1H-indol-2-yl]-N-[(2R)-1,1,1-trifluoropropan-2-yl]pyridine-3-sulfonamide, 6-[3-cyano-1-cyclobutyl-6-(difluoromethyl)-1H-indol-2-yl]-N-[(1S)-1-cyclopropylethyl]pyridine-3-sulfonamide, 6-[3-cyano-5-fluoro-1-(4-methoxyphenyl)-1H-indol-2-yl]-N-(1,3-difluoropropan-2-yl)pyridine-3-sulfonamide, 2-[3-cyano-5-fluoro-1-(4-methoxyphenyl)-1H-indol-2-yl]-N-(1,3-difluoropropan-2-yl)pyrimidine-5-sulfonamide, 6-(3-cyano-1-cyclobutyl-6-ethyl-1H-indol-2-yl)-N-[(2S)-1,1,1-trifluoropropan-2-yl]pyridine-3-sulfonamide, 6-(3-cyano-1-cyclobutyl-5-ethyl-1H-indol-2-yl)-N-[(2S)-1,1,1-trifluoropropan-2-yl]pyridine-3-sulfonamide, 6-(3-cyano-1-cyclobutyl-5-fluoro-6-methyl-1H-indol-2-yl)-N-[(2S)-1,1,1-trifluoropropan-2-yl]pyridine-3-sulfonamide, 6-[3-cyano-1-cyclohexyl-6-(difluoromethoxy)-1H-indol-2-yl]-N-[(2S)-1,1,1-trifluoropropan-2-yl]pyridine-3-sulfonamide, 6-(3-cyano-1,6-dicyclobutyl-1H-indol-2-yl)-N-(1,3-difluoropropan-2-yl)pyridine-3-sulfonamide, 6-(3-cyano-6-cyclobutyl-1-cyclopentyl-1H-indol-2-yl)-N-[(2R)-1,1,1-trifluoropropan-2-yl]pyridine-3-sulfonamide, 2-[3-cyano-6-cyclopropyl-1-(cyclopropylmethyl)-1H-indol-2-yl]-N-(1,3-difluoropropan-2-yl)pyrimidine-5-sulfonamide, 6-(3-cyano-1-cyclobutyl-5-methyl-1H-indol-2-yl)-N-[(2S)-1,1,1-trifluoropropan-2-yl]pyridine-3-sulfonamide, 6-(3,5-dicyano-1-cyclopentyl-1H-indol-2-yl)-N-[(2S)-1,1,1-trifluoropropan-2-yl]pyridine-3-sulfonamide, 6-[3,6-dicyano-1-(cyclopropylmethyl)-1H-indol-2-yl]-N-(1,3-difluoropropan-2-yl)pyridine-3-sulfonamide, 6-[3,6-dicyano-1-(cyclopropylmethyl)-1H-indol-2-yl]-N-(propan-2-yl)pyridine-3-sulfonamide, 6-[3,6-dicyano-1-(cyclopropylmethyl)-1H-indol-2-yl]-N-[(2S)-1,1,1-trifluoropropan-2-yl]pyridine-3-sulfonamide, N-[(1S)-1-cyclopropylethyl]-6-[3,6-dicyano-1-(cyclopropylmethyl)-1H-indol-2-yl]pyridine-3-sulfonamide, 6-(3-cyano-1-cyclobutyl-6-methyl-1H-indol-2-yl)-N-[(2S)-1,1,1-trifluoropropan-2-yl]pyridine-3-sulfonamide, 6-(3-cyano-1-cyclopentyl-6-methyl-1H-indol-2-yl)-N-[(2S)-1,1,1-trifluoropropan-2-yl]pyridine-3-sulfonamide, 6-[3-cyano-1-(cyclopropylmethyl)-6-methyl-1H-indol-2-yl]-N-[(2S)-1,1,1-trifluoropropan-2-yl]pyridine-3-sulfonamide, 6-(3-cyano-1-cyclohexyl-6-methyl-1H-indol-2-yl)-N-[(2S)-1,1,1-trifluoropropan-2-yl]pyridine-3-sulfonamide, 6-[3-cyano-6-methyl-1-(propan-2-yl)-1H-indol-2-yl]-N-[(2S)-1,1,1-trifluoropropan-2-yl]pyridine-3-sulfonamide, 6-[3-cyano-5-fluoro-1-(4-methylphenyl)-1H-indol-2-yl]-N-(1,3-difluoropropan-2-yl)pyridine-3-sulfonamide, 2-[3-cyano-5-fluoro-1-(4-methylphenyl)-1H-indol-2-yl]-N-(propan-2-yl)pyrimidine-5-sulfonamide, 6-[3-cyano-1-cyclopentyl-6-(trifluoromethoxy)-1H-indol-2-yl]-N-[(2S)-1,1,1-trifluoropropan-2-yl]pyridine-3-sulfonamide, 6-[3-cyano-6-(difluoromethoxy)-1-(propan-2-yl)-1H-indol-2-yl]-N-[(2S)-1,1,1-trifluoropropan-2-yl]pyridine-3-sulfonamide, 6-(6-chloro-3-cyano-1-cyclobutyl-5-fluoro-1H-indol-2-yl)-N-[(2S)-1,1,1-trifluoropropan-2-yl]pyridine-3-sulfonamide, 2-[3-cyano-1-cyclobutyl-6-(fluoromethyl)-1H-indol-2-yl]-N-(1,3-difluoropropan-2-yl)pyrimidine-5-sulfonamide, 6-[3-cyano-1-cyclobutyl-6-(fluoromethyl)-1H-indol-2-yl]-N-[(2S)-1,1,1-trifluoropropan-2-yl]pyridine-3-sulfonamide, 6-[3-cyano-1-cyclobutyl-6-(difluoromethyl)-1H-indol-2-yl]-N-[(2S)-1,1,1-trifluoropropan-2-yl]pyridine-3-sulfonamide, 6-(6-chloro-3-cyano-1-cyclopentyl-1H-indol-2-yl)-N-[(2S)-1,1,1-trifluoropropan-2-yl]pyridine-3-sulfonamide, 6-(5-chloro-3-cyano-1-cyclopentyl-1H-indol-2-yl)-N-[(2S)-1,1,1-trifluoropropan-2-yl]pyridine-3-sulfonamide, N-[(1S)-1-cyclopropylethyl]-2-(3,5-dicyano-1-cyclopentyl-1H-indol-2-yl)pyrimidine-5-sulfonamide, 6-[3-cyano-6-(difluoromethoxy)-1-(4-fluorophenyl)-1H-indol-2-yl]-N-[(2S)-1,1,1-trifluoropropan-2-yl]pyridine-3-sulfonamide, 6-(3-cyano-1-cyclobutyl-6-cyclopropyl-1H-indol-2-yl)-N-[(2S)-1,1,1-trifluoropropan-2-yl]pyridine-3-sulfonamide, 6-[3-cyano-1-cyclobutyl-6-(trifluoromethoxy)-1H-indol-2-yl]-N-[(2S)-1,1,1-trifluoropropan-2-yl]pyridine-3-sulfonamide, 6-(3-cyano-1-cyclopentyl-6-methyl-1H-indol-2-yl)-N-(1,1,1-trifluoro-2-methylpropan-2-yl)pyridine-3-sulfonamide, 6-[3-cyano-1-(cyclopropylmethyl)-5-methyl-1H-indol-2-yl]-N-[(2S)-1,1,1-trifluoropropan-2-yl]pyridine-3-sulfonamide, 6-[3-cyano-1-(cyclopropylmethyl)-5-methyl-1H-indol-2-yl]-N-(1,3-difluoropropan-2-yl)pyridine-3-sulfonamide, 6-(3-cyano-1-cyclopentyl-5-ethyl-1H-indol-2-yl)-N-[(2S)-1,1,1-trifluoropropan-2-yl]pyridine-3-sulfonamide, 6-(6-chloro-3-cyano-1-cyclobutyl-1H-indol-2-yl)-N-[(2S)-1,1,1-trifluoropropan-2-yl]pyridine-3-sulfonamide, 6-(5-chloro-3-cyano-1-cyclobutyl-1H-indol-2-yl)-N-[(2S)-1,1,1-trifluoropropan-2-yl]pyridine-3-sulfonamide, 2-[3-cyano-1-cyclobutyl-5-(fluoromethyl)-1H-indol-2-yl]-N-(1,3-difluoropropan-2-yl)pyrimidine-5-sulfonamide, 6-[3-cyano-1-cyclobutyl-5-(difluoromethyl)-1H-indol-2-yl]-N-(1,3-difluoropropan-2-yl)pyridine-3-sulfonamide, 2-[3-cyano-1-cyclobutyl-5-(difluoromethyl)-1H-indol-2-yl]-N-(1,3-difluoropropan-2-yl)pyrimidine-5-sulfonamide, 2-[3-cyano-1-cyclobutyl-5-(difluoromethyl)-1H-indol-2-yl]-N-[(2S)-1,1,1-trifluoropropan-2-yl]pyrimidine-5-sulfonamide, 6-(3-cyano-1-cyclopentyl-5-ethyl-1H-indol-2-yl)-N-(1,3-difluoropropan-2-yl)pyridine-3-sulfonamide, 6-[3-cyano-1-cyclopentyl-6-(difluoromethoxy)-1H-indol-2-yl]-N-(1,1,1-trifluoro-2-methylpropan-2-yl)pyridine-3-sulfonamide, 6-(3-cyano-1-cyclopentyl-6-cyclopropyl-1H-indol-2-yl)-N-[(2S)-1,1,1-trifluoropropan-2-yl]pyridine-3-sulfonamide, 6-[3-cyano-1-cyclobutyl-6-(2,2-difluoroethyl)-1H-indol-2-yl]-N-[(2S)-1,1,1-trifluoropropan-2-yl]pyridine-3-sulfonamide, 2-[3-cyano-1-cyclobutyl-6-(2,2-difluoroethyl)-1H-indol-2-yl]-N-[(2S)-1,1,1-trifluoropropan-2-yl]pyrimidine-5-sulfonamide, 6-[3-cyano-5-fluoro-1-(pyridin-2-yl)-1H-indol-2-yl]-N-[(2S)-1,1,1-trifluoropropan-2-yl]pyridine-3-sulfonamide, 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, 2-[3-cyano-1-(cyclopropylmethyl)-5-methyl-1H-indol-2-yl]-N-(propan-2-yl)pyrimidine-5-sulfonamide, 2-[3-cyano-1-(cyclopropylmethyl)-5-methyl-1H-indol-2-yl]-N-[(2S)-1,1,1-trifluoropropan-2-yl]pyrimidine-5-sulfonamide, 2-(3-cyano-1-cyclohexyl-5-methyl-1H-indol-2-yl)-N-[(2S)-1,1,1-trifluoropropan-2-yl]pyrimidine-5-sulfonamide, 2-(3-cyano-1-cyclopentyl-5-methyl-1H-indol-2-yl)-N-[(2S)-1,1,1-trifluoropropan-2-yl]pyrimidine-5-sulfonamide, 2-(3,5-dicyano-1-cyclopentyl-1H-indol-2-yl)-N-[(2S)-1,1,1-trifluoropropan-2-yl]pyrimidine-5-sulfonamide, 2-(3-cyano-1-cyclohexyl-5-fluoro-1H-indol-2-yl)-N-[(2S)-1,1,1-trifluoropropan-2-yl]pyrimidine-5-sulfonamide, 6-(3-cyano-1-cyclohexyl-6-fluoro-1H-indol-2-yl)-N-[(2S)-1,1,1-trifluoropropan-2-yl]pyridine-3-sulfonamide, 6-(3-cyano-1-cyclobutyl-6-fluoro-1H-indol-2-yl)-N-[(2S)-1,1,1-trifluoropropan-2-yl]pyridine-3-sulfonamide, 6-(3-cyano-1-cyclopentyl-6-fluoro-1H-indol-2-yl)-N-[(2S)-1,1,1-trifluoropropan-2-yl]pyridine-3-sulfonamide, 6-[3-cyano-1-(cyclopropylmethyl)-6-fluoro-1H-indol-2-yl]-N-[(2S)-1,1,1-trifluoropropan-2-yl]pyridine-3-sulfonamide, 2-[3-cyano-1-(cyclopropylmethyl)-6-(difluoromethoxy)-1H-indol-2-yl]-N-[(2S)-1,1,1-trifluoropropan-2-yl]pyrimidine-5-sulfonamide, 2-[3-cyano-6-(difluoromethoxy)-1-(propan-2-yl)-1H-indol-2-yl]-N-[(2S)-1,1,1-trifluoropropan-2-yl]pyrimidine-5-sulfonamide, 2-[3-cyano-6-(difluoromethoxy)-1-propyl-1H-indol-2-yl]-N-[(2S)-1,1,1-trifluoropropan-2-yl]pyrimidine-5-sulfonamide, 2-(3-cyano-1-cyclopentyl-6-cyclopropyl-1H-indol-2-yl)-N-[(2S)-1,1,1-trifluoropropan-2-yl]pyrimidine-5-sulfonamide, 2-[3-cyano-1-(cyclopropylmethyl)-6-methyl-1H-indol-2-yl]-N-[(2S)-1,1,1-trifluoropropan-2-yl]pyrimidine-5-sulfonamide, 2-[3-cyano-6-methyl-1-(propan-2-yl)-1H-indol-2-yl]-N-[(2S)-1,1,1-trifluoropropan-2-yl]pyrimidine-5-sulfonamide, 2-(3-cyano-1-cyclopentyl-6-methyl-1H-indol-2-yl)-N-[(2S)-1,1,1-trifluoropropan-2-yl]pyrimidine-5-sulfonamide, 2-(3-cyano-1-cyclobutyl-6-methoxy-1H-indol-2-yl)-N-[(2S)-1,1,1-trifluoropropan-2-yl]pyrimidine-5-sulfonamide, 2-(3-cyano-1-cyclopentyl-6-methoxy-1H-indol-2-yl)-N-[(2S)-1,1,1-trifluoropropan-2-yl]pyrimidine-5-sulfonamide, 6-(3-cyano-1-cyclopentyl-5-fluoro-6-methyl-1H-indol-2-yl)-N-(1,3-difluoropropan-2-yl)pyridine-3-sulfonamide, 6-(3-cyano-1-cyclopentyl-5-fluoro-6-methyl-1H-indol-2-yl)-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2R)-1,1,1-trifluoropropan-2-yl]pyridine-3-sulfonamide, 6-(3-cyano-1-cyclohexyl-5-fluoro-1H-indol-2-yl)-N-[(2S)-1,1,1-trifluoropropan-2-yl]pyridine-3-sulfonamide, 2-(3-cyano-1-cyclohexyl-6-fluoro-1H-indol-2-yl)-N-[(2S)-1,1,1-trifluoropropan-2-yl]pyrimidine-5-sulfonamide, 6-[3-cyano-1-(cyclohex-2-en-1-yl)-5-fluoro-1H-indol-2-yl]-N-[(2R)-1,1,1-trifluoropropan-2-yl]pyridine-3-sulfonamide, 6-[3-cyano-1-(cyclohex-2-en-1-yl)-5-fluoro-1H-indol-2-yl]-N-[(2S)-1,1,1-trifluoropropan-2-yl]pyridine-3-sulfonamide, 2-(3-cyano-1-cyclobutyl-5-methyl-1H-indol-2-yl)-N-[(2S)-1,1,1-trifluoropropan-2-yl]pyrimidine-5-sulfonamide, 2-[6-chloro-3-cyano-1-(cyclopropylmethyl)-1H-indol-2-yl]-N-[(2S)-1,1,1-trifluoropropan-2-yl]pyrimidine-5-sulfonamide, 2-(3-cyano-1-cyclobutyl-5-fluoro-1H-indol-2-yl)-N-(propan-2-yl)pyrimidine-5-sulfonamide, 2-(6-chloro-3-cyano-1-cyclopentyl-1H-indol-2-yl)-N-[(2S)-1,1,1-trifluoropropan-2-yl]pyrimidine-5-sulfonamide,
2-[6-chloro-3-cyano-1-(propan-2-yl)-1H-indol-2-yl]-N-[(2S)-1,1,1-trifluoropropan-2-yl]pyrimidine-5-sulfonamide,
2-(5-chloro-3-cyano-1-cyclopentyl-1H-indol-2-yl)-N-[(2S)-1,1,1-trifluoropropan-2-yl]pyrimidine-5-sulfonamide,
2-[5-chloro-3-cyano-1-(propan-2-yl)-1H-indol-2-yl]-N-[(2S)-1,1,1-trifluoropropan-2-yl]pyrimidine-5-sulfonamide,
6-(3-cyano-1-cyclobutyl-7-fluoro-6-methyl-1H-indol-2-yl)-N-[(2S)-1,1,1-trifluoropropan-2-yl]pyridine-3-sulfonamide,
6-(3-cyano-1-cyclobutyl-7-fluoro-6-methyl-1H-indol-2-yl)-N-(1,3-difluoropropan-2-yl)pyridine-3-sulfonamide,
6-(3-cyano-1-cyclopentyl-7-fluoro-6-methyl-1H-indol-2-yl)-N-(1,3-difluoropropan-2-yl)pyridine-3-sulfonamide,
6-(3-cyano-1-cyclopentyl-7-fluoro-6-methyl-1H-indol-2-yl)-N-[(2S)-1,1,1-trifluoropropan-2-yl]pyridine-3-sulfonamide,
6-[3-cyano-6-methyl-1-(propan-2-yl)-1H-indol-2-yl]-N-[(1S)-1-cyclopropylethyl]pyridine-3-sulfonamide,
6-(3-cyano-1-cyclopentyl-6-methyl-1H-indol-2-yl)-N-[(1S)-1-cyclopropylethyl]pyridine-3-sulfonamide,
6-(3-cyano-1-cyclobutyl-6-methoxy-1H-indol-2-yl)-N-[(2S)-1,1,1-trifluoropropan-2-yl]pyridine-3-sulfonamide,
6-(3-cyano-1-cyclobutyl-6-methoxy-1H-indol-2-yl)-N-[(2R)-1,1,1-trifluoropropan-2-yl]pyridine-3-sulfonamide,
6-(3-cyano-1-cyclobutyl-6-methoxy-1H-indol-2-yl)-N-[(1S)-1-cyclopropylethyl]pyridine-3-sulfonamide,
6-(3-cyano-1-cyclopentyl-6-methoxy-1H-indol-2-yl)-N-[(2S)-1,1,1-trifluoropropan-2-yl]pyridine-3-sulfonamide,
6-(3-cyano-1-cyclopentyl-6-methoxy-1H-indol-2-yl)-N-[(2R)-1,1,1-trifluoropropan-2-yl]pyridine-3-sulfonamide,
6-(3-cyano-1-cyclopentyl-6-methoxy-1H-indol-2-yl)-N-[(1S)-1-cyclopropylethyl]pyridine-3-sulfonamide,
6-(3-cyano-1-cyclopentyl-6-cyclopropyl-1H-indol-2-yl)-N-[(1S)-1-cyclopropylethyl]pyridine-3-sulfonamide,
6-(3-cyano-1-cyclobutyl-5-fluoro-1H-indol-2-yl)-N-[(2S)-1,1,1-trifluoropropan-2-yl]pyridine-3-sulfonamide,
6-(3-cyano-1-cyclopentyl-5-fluoro-1H-indol-2-yl)-N-[(2S)-1,1,1-trifluoropropan-2-yl]pyridine-3-sulfonamide,
6-[3-cyano-1-(cyclopropylmethyl)-5-fluoro-1H-indol-2-yl]-N-[(2S)-1,1,1-trifluoropropan-2-yl]pyridine-3-sulfonamide,
6-[6-chloro-3-cyano-1-(pyridin-2-yl)-1H-indol-2-yl]-N-[(2S)-1,1,1-trifluoropropan-2-yl]pyridine-3-sulfonamide,
6-[6-chloro-3-cyano-1-(pyridin-2-yl)-1H-indol-2-yl]-N-(1,3-difluoropropan-2-yl)pyridine-3-sulfonamide,
6-[3-cyano-5-fluoro-1-(pyridin-2-yl)-1H-indol-2-yl]-N-(propan-2-yl)pyridine-3-sulfonamide,
6-(3-cyano-6-methyl-1-phenyl-1H-indol-2-yl)-N-[(2S)-1,1,1-trifluoropropan-2-yl]pyridine-3-sulfonamide,
6-(5-chloro-3-cyano-1-phenyl-1H-indol-2-yl)-N-[(2S)-1,1,1-trifluoropropan-2-yl]pyridine-3-sulfonamide,
6-[5-chloro-3-cyano-1-(pyridin-2-yl)-1H-indol-2-yl]-N-[(2S)-1,1,1-trifluoropropan-2-yl]pyridine-3-sulfonamide,
6-[5-chloro-3-cyano-1-(pyridin-2-yl)-1H-indol-2-yl]-N-(1,3-difluoropropan-2-yl)pyridine-3-sulfonamide,
6-(5-chloro-3-cyano-1-cyclobutyl-6-methyl-1H-indol-2-yl)-N-(1,3-difluoropropan-2-yl)pyridine-3-sulfonamide,
6-(5-chloro-3-cyano-1-cyclobutyl-6-methyl-1H-indol-2-yl)-N-[(2R)-1,1,1-trifluoropropan-2-yl]pyridine-3-sulfonamide,
6-(5-chloro-3-cyano-1-cyclobutyl-6-methyl-1H-indol-2-yl)-N-[(2S)-1,1,1-trifluoropropan-2-yl]pyridine-3-sulfonamide,
2-(5-chloro-3-cyano-1-cyclobutyl-6-methyl-1H-indol-2-yl)-N-(1,3-difluoropropan-2-yl)pyrimidine-5-sulfonamide,
2-(5-chloro-3-cyano-1-cyclobutyl-6-methyl-1H-indol-2-yl)-N-[(2S)-1,1,1-trifluoropropan-2-yl]pyrimidine-5-sulfonamide,
2-[6-chloro-3-cyano-1-(pyridin-2-yl)-1H-indol-2-yl]-N-[(2S)-1,1,1-trifluoropropan-2-yl]pyrimidine-5-sulfonamide,
2-[6-chloro-3-cyano-1-(pyridin-2-yl)-1H-indol-2-yl]-N-(1,3-difluoropropan-2-yl)pyrimidine-5-sulfonamide,
2-(3-cyano-1-cyclobutyl-5-fluoro-1H-indol-2-yl)-N-[(2S)-1,1,1-trifluoropropan-2-yl]pyrimidine-5-sulfonamide,
2-(3-cyano-1-cyclobutyl-5-fluoro-1H-indol-2-yl)-N-(1,3-difluoropropan-2-yl)pyrimidine-5-sulfonamide,
6-(3-cyano-1-cyclobutyl-5-methoxy-1H-indol-2-yl)-N-[(2S)-1,1,1-trifluoropropan-2-yl]pyridine-3-sulfonamide,
2-(5-chloro-3-cyano-1-cyclobutyl-1H-indol-2-yl)-N-[(2S)-1,1,1-trifluoropropan-2-yl]pyrimidine-5-sulfonamide,
2-[3-cyano-1-cyclobutyl-6-(propan-2-yl)-1H-indol-2-yl]-N-[(2S)-1,1,1-trifluoropropan-2-yl]pyrimidine-5-sulfonamide,
6-[3-cyano-1,6-di(propan-2-yl)-1H-indol-2-yl]-N-(1,3-difluoropropan-2-yl)pyridine-3-sulfonamide,
6-[3-cyano-1-cyclopentyl-6-(propan-2-yl)-1H-indol-2-yl]-N-(1,3-difluoropropan-2-yl)pyridine-3-sulfonamide,
6-[3-cyano-1-(cyclopropylmethyl)-5-methyl-1H-indol-2-yl]-N-[(2R)-1,1,1-trifluoropropan-2-yl]pyridine-3-sulfonamide,
6-[3-cyano-1-cyclohexyl-6-(trifluoromethoxy)-1H-indol-2-yl]-N-[(2S)-1,1,1-trifluoropropan-2-yl]pyridine-3-sulfonamide,
6-[3-cyano-1-(cyclopropylmethyl)-6-(propan-2-yl)-1H-indol-2-yl]-N-(1,3-difluoropropan-2-yl)pyridine-3-sulfonamide,
6-(5-chloro-3-cyano-1-cyclohexyl-1H-indol-2-yl)-N-[(2R)-1,1,1-trifluoropropan-2-yl]pyridine-3-sulfonamide,
6-(5-chloro-3-cyano-1-cyclohexyl-1H-indol-2-yl)-N-[(2S)-1,1,1-trifluoropropan-2-yl]pyridine-3-sulfonamide,
2-(5-chloro-3-cyano-1-cyclohexyl-1H-indol-2-yl)-N-(1,3-difluoropropan-2-yl)pyrimidine-5-sulfonamide,
2-(5-chloro-3-cyano-1-cyclohexyl-1H-indol-2-yl)-N-[(2S)-1,1,1-trifluoropropan-2-yl]pyrimidine-5-sulfonamide,
6-(3,6-dicyano-1-cyclobutyl-1H-indol-2-yl)-N-(1,3-difluoropropan-2-yl)pyridine-3-sulfonamide, 2-(3,6-dicyano-1-cyclobutyl-1H-indol-2-yl)-N-(1,3-difluoropropan-2-yl)pyrimidine-5-sulfonamide,
6-(3,6-dicyano-1-cyclobutyl-1H-indol-2-yl)-N-[(2S)-1,1,1-trifluoropropan-2-yl]pyridine-3-sulfonamide,
6-(3,6-dicyano-1-cyclopentyl-1H-indol-2-yl)-N-(1,3-difluoropropan-2-yl)pyridine-3-sulfonamide,
2-(3,6-dicyano-1-cyclopentyl-1H-indol-2-yl)-N-(1,3-difluoropropan-2-yl)pyrimidine-5-sulfonamide,
6-(3,6-dicyano-1-cyclopentyl-1H-indol-2-yl)-N-[(2S)-1,1,1-trifluoropropan-2-yl]pyridine-3-sulfonamide,
2-[3-cyano-1-cyclohexyl-6-(difluoromethoxy)-1H-indol-2-yl]-N-[(1S)-1-cyclopropylethyl]pyrimidine-5-sulfonamide,
2-[3-cyano-1-cyclohexyl-6-(difluoromethoxy)-1H-indol-2-yl]-N-[(2S)-1,1,1-trifluoropropan-2-yl]pyrimidine-5-sulfonamide,
2-[3-cyano-1-cyclohexyl-6-(difluoromethoxy)-1H-indol-2-yl]-N-(propan-2-yl)pyrimidine-5-sulfonamide,
2-[3-cyano-5-fluoro-1-(pyridin-2-yl)-1H-indol-2-yl]-N-[(2S)-1,1,1-trifluoropropan-2-yl]pyrimidine-5-sulfonamide,
2-[3-cyano-6-methyl-1-(pyridin-2-yl)-1H-indol-2-yl]-N-[(2S)-1,1,1-trifluoropropan-2-yl]pyrimidine-5-sulfonamide,
6-[3-cyano-6-methyl-1-(pyridin-2-yl)-1H-indol-2-yl]-N-[(2S)-1,1,1-trifluoropropan-2-yl]pyridine-3-sulfonamide,
2-[3-cyano-6-(difluoromethoxy)-1-(4-fluorophenyl)-1H-indol-2-yl]-N-(1,3-difluoropropan-2-yl)pyrimidine-5-sulfonamide,
6-(3-cyano-1-cyclobutyl-6-methyl-1H-indol-2-yl)-N-(1,1,1-trifluoro-2-methylpropan-2-yl)pyridine-3-sulfonamide,
6-[3-cyano-1-cyclobutyl-6-(difluoromethoxy)-1H-indol-2-yl]-N-(1,1,1-trifluoro-2-methylpropan-2-yl)pyridine-3-sulfonamide,
6-(3-cyano-1-cyclobutyl-5-methyl-1H-indol-2-yl)-N-(1,1,1-trifluoro-2-methylpropan-2-yl)pyridine-3-sulfonamide,
6-(3-cyano-1-cyclobutyl-6-ethyl-1H-indol-2-yl)-N-(1,1,1-trifluoro-2-methylpropan-2-yl)pyridine-3-sulfonamide,
6-(3-cyano-1-cyclopentyl-6-fluoro-5-methyl-1H-indol-2-yl)-N-(1,3-difluoropropan-2-yl)pyridine-3-sulfonamide,
6-(3-cyano-1-cyclopentyl-6-fluoro-5-methyl-1H-indol-2-yl)-N-[(2S)-1,1,1-trifluoropropan-2-yl]pyridine-3-sulfonamide,
6-(3-cyano-1-cyclobutyl-5-methyl-1H-indol-2-yl)-N-[(2R)-1,1,1-trifluoropropan-2-yl]pyridine-3-sulfonamide,
6-[3-cyano-5-methyl-1-(propan-2-yl)-1H-indol-2-yl]-N-[(2R)-1,1,1-trifluoropropan-2-yl]pyridine-3-sulfonamide,
6-(3-cyano-1-cyclopentyl-5-methyl-1H-indol-2-yl)-N-[(2R)-1,1,1-trifluoropropan-2-yl]pyridine-3-sulfonamide,
6-(3-cyano-1-cyclohexyl-5-methyl-1H-indol-2-yl)-N-[(2R)-1,1,1-trifluoropropan-2-yl]pyridine-3-sulfonamide,
6-[6-chloro-3-cyano-1-(pyridin-2-yl)-1H-indol-2-yl]-N-[(1S)-1-cyclopropylethyl]pyridine-3-sulfonamide,
6-[6-chloro-3-cyano-1-(pyridin-2-yl)-1H-indol-2-yl]-N-[(2R)-1,1,1-trifluoropropan-2-yl]pyridine-3-sulfonamide,
6-[5-chloro-3-cyano-1-(pyridin-2-yl)-1H-indol-2-yl]-N-[(1S)-1-cyclopropylethyl]pyridine-3-sulfonamide,
6-[5-chloro-3-cyano-1-(pyridin-2-yl)-1H-indol-2-yl]-N-[(2R)-1,1,1-trifluoropropan-2-yl]pyridine-3-sulfonamide,
6-(3-cyano-1-cyclobutyl-6-fluoro-5-methyl-1H-indol-2-yl)-N-[(2S)-1,1,1-trifluoropropan-2-yl]pyridine-3-sulfonamide,
6-(3-cyano-1-cyclobutyl-6-fluoro-5-methyl-1H-indol-2-yl)-N-(1,3-difluoropropan-2-yl)pyridine-3-sulfonamide,
2-(3-cyano-1-cyclobutyl-6-fluoro-1H-indol-2-yl)-N-[(2S)-1,1,1-trifluoropropan-2-yl]pyrimidine-5-sulfonamide,
2-(3-cyano-1-cyclopentyl-6-fluoro-1H-indol-2-yl)-N-[(2S)-1,1,1-trifluoropropan-2-yl]pyrimidine-5-sulfonamide,
2-(3-cyano-1-cyclobutyl-6-fluoro-1H-indol-2-yl)-N-[(1S)-1-cyclopropylethyl]pyrimidine-5-sulfonamide,
2-(3-cyano-1-cyclopentyl-6-fluoro-1H-indol-2-yl)-N-[(1S)-1-cyclopropylethyl]pyrimidine-5-sulfonamide,
2-[3-cyano-1-(cyclopropylmethyl)-6-fluoro-1H-indol-2-yl]-N-[(1S)-1-cyclopropylethyl]pyrimidine-5-sulfonamide,
2-(3-cyano-1-cyclohexyl-6-fluoro-1H-indol-2-yl)-N-[(1S)-1-cyclopropylethyl]pyrimidine-5-sulfonamide,
6-(3-cyano-1-cyclobutyl-5-methoxy-1H-indol-2-yl)-N-[(2R)-1,1,1-trifluoropropan-2-yl]pyridine-3-sulfonamide,
6-[3-cyano-6-cyclopropyl-1-(pyridin-2-yl)-1H-indol-2-yl]-N-(1,3-difluoropropan-2-yl)pyridine-3-sulfonamide,
6-[3-cyano-6-cyclopropyl-1-(pyridin-2-yl)-1H-indol-2-yl]-N-[(2S)-1,1,1-trifluoropropan-2-yl]pyridine-3-sulfonamide,
6-[3-cyano-5-methyl-1-(pyridin-2-yl)-1H-indol-2-yl]-N-[(2S)-1,1,1-trifluoropropan-2-yl]pyridine-3-sulfonamide,
6-[3-cyano-5-methyl-1-(pyridin-2-yl)-1H-indol-2-yl]-N-(1,3-difluoropropan-2-yl)pyridine-3-sulfonamide,
6-(6-chloro-3-cyano-1-cyclobutyl-5-methyl-1H-indol-2-yl)-N-(1,3-difluoropropan-2-yl)pyridine-3-sulfonamide,
6-(6-chloro-3-cyano-1-cyclobutyl-5-methyl-1H-indol-2-yl)-N-[(2S)-1,1,1-trifluoropropan-2-yl]pyridine-3-sulfonamide,
2-(6-chloro-3-cyano-1-cyclobutyl-5-methyl-1H-indol-2-yl)-N-(propan-2-yl)pyrimidine-5-sulfonamide,
6-(3-cyano-1-cyclopentyl-5,7-difluoro-6-methyl-1H-indol-2-yl)-N-[(2S)-1,1,1-trifluoropropan-2-yl]pyridine-3-sulfonamide,
6-(3-cyano-1-cyclopentyl-5,7-difluoro-6-methyl-1H-indol-2-yl)-N-(1,3-difluoropropan-2-yl)pyridine-3-sulfonamide,
6-(6-chloro-3-cyano-1-cyclobutyl-5-methyl-1H-indol-2-yl)-N-[(2R)-1,1,1-trifluoropropan-2-yl]pyridine-3-sulfonamide,
6-(1-cyclobutyl-6-methyl-1H-indol-2-yl)-N-(1,3-difluoropropan-2-yl)pyridine-3-sulfonamide,
6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide,
6-(3-cyano-1-cyclohexyl-6-methyl-1H-indol-2-yl)-N-(1,3-difluoropropan-2-yl)pyridine-3-sulfonamide,
6-(6-chloro-3-cyano-1-cyclohexyl-1H-indol-2-yl)-N-[(2R)-1,1,1-trifluoropropan-2-yl]pyridine-3-sulfonamide, 6-(6-chloro-3-cyano-1-cyclohexyl-1H-indol-2-yl)-N-[(2S)-1,1,1-trifluoropropan-2-yl]pyridine-3-sulfonamide, 2-(6-chloro-3-cyano-1-cyclohexyl-1H-indol-2-yl)-N-[(2S)-1,1,1-trifluoropropan-2-yl]pyrimidine-5-sulfonamide, 2-(6-chloro-3-cyano-1-cyclohexyl-1H-indol-2-yl)-N-(1,3-difluoropropan-2-yl)pyrimidine-5-sulfonamide, 6-(3-cyano-1-cyclohexyl-6-methoxy-1H-indol-2-yl)-N-[(2R)-1,1,1-trifluoropropan-2-yl]pyridine-3-sulfonamide, 6-(3-cyano-1-cyclohexyl-6-methoxy-1H-indol-2-yl)-N-[(2S)-1,1,1-trifluoropropan-2-yl]pyridine-3-sulfonamide, 2-(3-cyano-1-cyclohexyl-6-methoxy-1H-indol-2-yl)-N-(1,3-difluoropropan-2-yl)pyrimidine-5-sulfonamide, 6-(6-chloro-3-cyano-1-cyclopentyl-5-methyl-1H-indol-2-yl)-N-(1,3-difluoropropan-2-yl)pyridine-3-sulfonamide, 6-(6-chloro-3-cyano-1-cyclopentyl-5-methyl-1H-indol-2-yl)-N-[(2S)-1,1,1-trifluoropropan-2-yl]pyridine-3-sulfonamide, 2-(6-chloro-3-cyano-1-cyclopentyl-5-methyl-1H-indol-2-yl)-N-(propan-2-yl)pyrimidine-5-sulfonamide, 2-[3-cyano-1-(cyclopropylmethyl)-5-methyl-1H-indol-2-yl]-N-(1,3-difluoropropan-2-yl)pyrimidine-5-sulfonamide, 6-[3-cyano-1-(cyclopropylmethyl)-5-methyl-1H-indol-2-yl]-N-[(1S)-1-cyclopropylethyl]pyridine-3-sulfonamide, 2-(3-cyano-1-cyclohexyl-5-fluoro-1H-indol-2-yl)-N-(propan-2-yl)pyrimidine-5-sulfonamide, 2-(3-cyano-1-cyclohexyl-5-fluoro-1H-indol-2-yl)-N-(1,3-difluoropropan-2-yl)pyrimidine-5-sulfonamide, 2-(3-cyano-1-cyclohexyl-5-fluoro-1H-indol-2-yl)-N-[(1S)-1-cyclopropylethyl]pyrimidine-5-sulfonamide, 2-[3-cyano-5-fluoro-1-(propan-2-yl)-1H-indol-2-yl]-N-[(1S)-1-cyclopropylethyl]pyrimidine-5-sulfonamide, 2-(3-cyano-1-cyclopentyl-5-fluoro-1H-indol-2-yl)-N-[(1S)-1-cyclopropylethyl]pyrimidine-5-sulfonamide, 2-[3-cyano-1-(cyclopropylmethyl)-5-fluoro-1H-indol-2-yl]-N-[(1S)-1-cyclopropylethyl]pyrimidine-5-sulfonamide, 6-(3-cyano-1-cyclobutyl-5,7-difluoro-6-methyl-1H-indol-2-yl)-N-[(2S)-1,1,1-trifluoropropan-2-yl]pyridine-3-sulfonamide, 6-(3-cyano-1-cyclobutyl-5,7-difluoro-6-methyl-1H-indol-2-yl)-N-(1,3-difluoropropan-2-yl)pyridine-3-sulfonamide, 6-[3-cyano-6-(difluoromethoxy)-1-(pyridin-2-yl)-1H-indol-2-yl]-N-[(2R)-1,1,1-trifluoropropan-2-yl]pyridine-3-sulfonamide, 6-[3-cyano-1-cyclopentyl-5-(difluoromethyl)-1H-indol-2-yl]-N-(1,3-difluoropropan-2-yl)pyridine-3-sulfonamide, 2-[3-cyano-1-cyclopentyl-5-(difluoromethyl)-1H-indol-2-yl]-N-(1,3-difluoropropan-2-yl)pyrimidine-5-sulfonamide, 6-[3-cyano-1-cyclopentyl-5-(difluoromethyl)-1H-indol-2-yl]-N-[(2S)-1,1,1-trifluoropropan-2-yl]pyridine-3-sulfonamide, 6-[3-cyano-1-cyclopentyl-5-(difluoromethyl)-1H-indol-2-yl]-N-[(2R)-1,1,1-trifluoropropan-2-yl]pyridine-3-sulfonamide, 6-(3-cyano-1-cyclobutyl-5-fluoro-6-methyl-1H-indol-2-yl)-N-(1,1,1-trifluoro-2-methylpropan-2-yl)pyridine-3-sulfonamide, 6-[3-cyano-5-fluoro-6-methyl-1-(pyridin-2-yl)-1H-indol-2-yl]-N-(1,3-difluoropropan-2-yl)pyridine-3-sulfonamide, 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-(1,3-difluoropropan-2-yl)pyridine-3-sulfonamide, N-tert-butyl-6-[3-cyano-1-cyclobutyl-6-(difluoromethoxy)-1H-indol-2-yl]pyridine-3-sulfonamide, 2-(3-cyano-1-cyclobutyl-5-fluoro-1H-indol-2-yl)-N-[(1S)-1-cyclopropylethyl]pyrimidine-5-sulfonamide, 2-(3-cyano-1-cyclobutyl-5-methyl-1H-indol-2-yl)-N-[(1S)-1-cyclopropylethyl]pyrimidine-5-sulfonamide, 2-[3-cyano-5-fluoro-1-(propan-2-yl)-1H-indol-2-yl]-N-[(2S)-1,1,1-trifluoropropan-2-yl]pyrimidine-5-sulfonamide, 2-(3-cyano-1-cyclopentyl-5-fluoro-1H-indol-2-yl)-N-[(2S)-1,1,1-trifluoropropan-2-yl]pyrimidine-5-sulfonamide, 2-[3-cyano-1-(cyclopropylmethyl)-5-fluoro-1H-indol-2-yl]-N-[(2S)-1,1,1-trifluoropropan-2-yl]pyrimidine-5-sulfonamide, 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, 6-(3-cyano-1-cyclobutyl-5-methoxy-1H-indol-2-yl)-N-(1,3-difluoropropan-2-yl)pyridine-3-sulfonamide, 2-(3-cyano-1-cyclobutyl-5-methoxy-1H-indol-2-yl)-N-(1,3-difluoropropan-2-yl)pyrimidine-5-sulfonamide, 6-[3-cyano-1-cyclobutyl-6-(difluoromethoxy)-1H-indol-2-yl]pyridine-3-sulfonamide, 6-[3-cyano-6-(difluoromethoxy)-1-phenyl-1H-indol-2-yl]-N-[(2S)-1,1,1-trifluoropropan-2-yl]pyridine-3-sulfonamide, 6-[3-cyano-6-(difluoromethoxy)-1-phenyl-1H-indol-2-yl]-N-[(2R)-1,1,1-trifluoropropan-2-yl]pyridine-3-sulfonamide, 6-(3-cyano-1-cyclobutyl-4,6-difluoro-5-methyl-1H-indol-2-yl)-N-[(2S)-1,1,1-trifluoropropan-2-yl]pyridine-3-sulfonamide, 6-(3-cyano-1-cyclobutyl-4,6-difluoro-5-methyl-1H-indol-2-yl)-N-(1,3-difluoropropan-2-yl)pyridine-3-sulfonamide, 2-(3-cyano-1-cyclobutyl-7-fluoro-6-methyl-1H-indol-2-yl)-N-(1,3-difluoropropan-2-yl)pyrimidine-5-sulfonamide, 6-(3-cyano-1-cyclopentyl-4,6-difluoro-5-methyl-1H-indol-2-yl)-N-(1,3-difluoropropan-2-yl)pyridine-3-sulfonamide, 6-(3-cyano-1-cyclopentyl-4,6-difluoro-5-methyl-1H-indol-2-yl)-N-[(2S)-1,1,1-trifluoropropan-2-yl]pyridine-3-sulfonamide, 6-(3-cyano-1-cyclohexyl-5-methyl-1H-indol-2-yl)-N-[(2S)-1,1,1-trifluoropropan-2-yl]pyridine-3-sulfonamide, 2-[3-cyano-1-(cyclopropylmethyl)-5-methyl-1H-indol-2-yl]-N-[(1S)-1-cyclopropylethyl]pyrimidine-5-sulfonamide, 2-(3-cyano-1-cyclopentyl-5-methyl-1H-indol-2-yl)-N-[(1S)-1-cyclopropylethyl]pyrimidine-5-sulfonamide, 2-[3-cyano-5-methyl-1-(propan-2-yl)-1H-indol-2-yl]-N-[(1S)-1-cyclopropylethyl]pyrimidine-5-sulfonamide, 6-[3-cyano-5-methyl-1-(propan-2-yl)-1H-indol-2-yl]-N-[(1S)-1-cyclopropylethyl]pyridine-3-sulfonamide, 2-[3-cyano-5-methyl-1-(propan-2-yl)-1H-indol-2-yl]-N-(propan-2-yl)pyrimidine-5-sulfonamide, 2-[3-cyano-5-methyl-1-(propan-2-yl)-1H-indol-2-yl]-N-[(2S)-1,1,1-trifluoropropan-2-yl]pyrimidine-5-sulfonamide, 2-[3-cyano-5-methyl-1-(propan-2-yl)-1H-indol-2-yl]-N-(1,3-difluoropropan-2-yl)pyrimidine-5-sulfonamide, 1-cyclobutyl-6-(difluoromethoxy)-2-(5-sulfamoylpyridin-2-yl)-1H-indole-3-carboxamide, 2-(3-cyano-1-cyclobutyl-5-methoxy-1H-indol-2-yl)-N-[(2S)-1,1,1-trifluoropropan-2-yl]pyrimidine-5-sulfonamide, 2-(3-cyano-1-cyclobutyl-5-methoxy-1H-indol-2-yl)-N-[(1S)-1-cyclopropylethyl]pyrimidine-5-sulfonamide, 6-(3-cyano-1-cyclopentyl-5-methoxy-1H-indol-2-yl)-N-(1,3-difluoropropan-2-yl)pyridine-3-sulfonamide, 2-(3-cyano-1-cyclopentyl-5-methoxy-1H-indol-2-yl)-N-(1,3-difluoropropan-2-yl)pyrimidine-5-sulfonamide, 6-[3-cyano-1-cyclopentyl-6-(difluoromethoxy)-5-fluoro-1H-indol-2-yl]-N-(1,3-difluoropropan-2-yl)pyridine-3-sulfonamide, 6-[3-cyano-1-cyclopentyl-6-(difluoromethoxy)-5-fluoro-1H-indol-2-yl]-N-[(2S)-1,1,1-trifluoropropan-2-yl]pyridine-3-sulfonamide, 6-(3-cyano-1-cyclopentyl-5-fluoro-6-hydroxy-1H-indol-2-yl)-N-(1,3-difluoropropan-2-yl)pyridine-3-sulfonamide, 6-(3-cyano-1-cyclopentyl-5-fluoro-6-hydroxy-1H-indol-2-yl)-N-[(2S)-1,1,1-trifluoropropan-2-yl]pyridine-3-sulfonamide, 6-(3-cyano-1-cyclobutyl-5,7-difluoro-6-methyl-1H-indol-2-yl)-N-(1,1,1-trifluoro-2-methylpropan-2-yl)pyridine-3-sulfonamide, 6-(3-cyano-1-cyclobutyl-7-fluoro-6-methyl-1H-indol-2-yl)-N-(1,1,1-trifluoro-2-methylpropan-2-yl)pyridine-3-sulfonamide, 6-(3-cyano-1-cyclopentyl-7-fluoro-6-methyl-1H-indol-2-yl)-N-(1,1,1-trifluoro-2-methylpropan-2-yl)pyridine-3-sulfonamide, 6-(3-cyano-1-cyclopentyl-5,7-difluoro-6-methyl-1H-indol-2-yl)-N-(1,1,1-trifluoro-2-methylpropan-2-yl)pyridine-3-sulfonamide, 1-cyclobutyl-6-(difluoromethoxy)-2-{5-[(1,3-difluoropropan-2-yl)sulfamoyl]pyridin-2-yl}-1H-indole-3-carboxamide, 1-cyclobutyl-6-cyclopropyl-2-{5-[(1,3-difluoropropan-2-yl)sulfamoyl]pyridin-2-yl}-1H-indole-3-carboxamide, 6-[3-cyano-6-(difluoromethoxy)-1-(pyridin-2-yl)-1H-indol-2-yl]-N-(1,1,1-trifluoro-2-methylpropan-2-yl)pyridine-3-sulfonamide, 6-[3-cyano-6-cyclopropyl-1-(pyridin-2-yl)-1H-indol-2-yl]-N-(1,1,1-trifluoro-2-methylpropan-2-yl)pyridine-3-sulfonamide, 6-(3-cyano-6-methyl-1-phenyl-1H-indol-2-yl)-N-(1,1,1-trifluoro-2-methylpropan-2-yl)pyridine-3-sulfonamide, 2-(3-cyano-1-cyclopentyl-7-fluoro-6-methyl-1H-indol-2-yl)-N-(1,3-difluoropropan-2-yl)pyrimidine-5-sulfonamide, 6-(3-cyano-1-cyclobutyl-6-methyl-1H-indol-2-yl)-N-[1-(trifluoromethyl)cyclobutyl]pyridine-3-sulfonamide, 6-[3-cyano-1-cyclobutyl-6-(difluoromethoxy)-1H-indol-2-yl]-N-[1-(trifluoromethyl)cyclobutyl]pyridine-3-sulfonamide, 6-[3-cyano-1-cyclopentyl-6-(difluoromethoxy)-1H-indol-2-yl]-N-[(2S)-1,1,1-trifluoropropan-2-yl]pyridine-3-sulfonamide, 6-[3-cyano-1-cyclobutyl-6-(2,2-difluoroethyl)-1H-indol-2-yl]-N-[(1S)-1-cyclopropylethyl]pyridine-3-sulfonamide, 2-[3-cyano-1-cyclobutyl-6-(2,2-difluoroethyl)-1H-indol-2-yl]-N-(1,3-difluoropropan-2-yl)pyrimidine-5-sulfonamide, 2-[3-cyano-1-cyclobutyl-6-(2,2-difluoroethyl)-1H-indol-2-yl]-N-[(1S)-1-cyclopropylethyl]pyrimidine-5-sulfonamide, 6-[3-cyano-1-cyclopentyl-6-(2,2-difluoroethyl)-1H-indol-2-yl]-N-(1,3-difluoropropan-2-yl)pyridine-3-sulfonamide, 6-[3-cyano-1-cyclopentyl-6-(2,2-difluoroethyl)-1H-indol-2-yl]-N-[(1S)-1-cyclopropylethyl]pyridine-3-sulfonamide, 6-[3-cyano-1-cyclopentyl-6-(2,2-difluoroethyl)-1H-indol-2-yl]-N-[(2S)-1,1,1-trifluoropropan-2-yl]pyridine-3-sulfonamide, 6-[3-cyano-1-cyclopentyl-6-(2,2-difluoroethyl)-1H-indol-2-yl]-N-(1,1,1-trifluoro-2-methylpropan-2-yl)pyridine-3-sulfonamide, 2-[3-cyano-1-cyclopentyl-6-(2,2-difluoroethyl)-1H-indol-2-yl]-N-[(1S)-1-cyclopropylethyl]pyrimidine-5-sulfonamide, 2-[3-cyano-1-cyclopentyl-6-(2,2-difluoroethyl)-1H-indol-2-yl]-N-(propan-2-yl)pyrimidine-5-sulfonamide, 2-[3-cyano-1-cyclopentyl-6-(2,2-difluoroethyl)-1H-indol-2-yl]-N-(1,3-difluoropropan-2-yl)pyrimidine-5-sulfonamide, 2-[3-cyano-1-cyclopentyl-6-(2,2-difluoroethyl)-1H-indol-2-yl]-N-[(2S)-1,1,1-trifluoropropan-2-yl]pyrimidine-5-sulfonamide, 6-[3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-1-(pyrimidin-2-yl)-1H-indol-2-yl]-N-(1,1,1-trifluoro-2-methylpropan-2-yl)pyridine-3-sulfonamide, 2-(3-cyano-1-cyclopentyl-5-fluoro-1H-indol-2-yl)-N-(propan-2-yl)pyrimidine-5-sulfonamide, 6-[3-cyano-5-fluoro-1-(propan-2-yl)-1H-indol-2-yl]-N-[(1S)-1-cyclopropylethyl]pyridine-3-sulfonamide, 2-(3-cyano-1-cyclohexyl-6-methyl-1H-indol-2-yl)-N-[(2S)-1,1,1-trifluoropropan-2-yl]pyrimidine-5-sulfonamide, 6-(3-cyano-1-cyclohexyl-5-methyl-1H-indol-2-yl)-N-[(1S)-1-cyclopropylethyl]pyridine-3-sulfonamide, 6-(3-cyano-1-cyclopentyl-5-methyl-1H-indol-2-yl)-N-(1,1,1-trifluoro-2-methylpropan-2-yl)pyridine-3-sulfonamide, 6-[3-cyano-5-fluoro-1-(pyrimidin-2-yl)-1H-indol-2-yl]-N-(1,3-difluoropropan-2-yl)pyridine-3-sulfonamide, 6-(3-cyano-1-cyclobutyl-5-fluoro-6-methyl-1H-indol-2-yl)-N-[(2R)-1,1,1-trifluoropropan-2-yl]pyridine-3-sulfonamide, 2-[3-cyano-6-(difluoromethoxy)-1-phenyl-1H-indol-2-yl]-N-(1,3-difluoropropan-2-yl)pyrimidine-5-sulfonamide, 2-[3-cyano-6-(difluoromethoxy)-1-phenyl-1H-indol-2-yl]-N-[(2S)-1,1,1-trifluoropropan-2-yl]pyrimidine-5-sulfonamide, 6-[3-cyano-6-(difluoromethoxy)-1-phenyl-1H-indol-2-yl]-N-(1,1,1-trifluoro-2-methylpropan-2-yl)pyridine-3-sulfonamide, 6-(3-cyano-1-cyclobutyl-5-fluoro-6-methyl-1H-indol-2-yl)-N-[1-(trifluoromethyl)cyclopropyl]pyridine-3-sulfonamide, 6-(3-cyano-1-cyclopentyl-4-fluoro-5-methyl-1H-indol-2-yl)-N-(1,1,1-trifluoro-2-methylpropan-2-yl)pyridine-3-sulfonamide, 6-(3-cyano-1-cyclopentyl-4-fluoro-5-methyl-1H-indol-2-yl)-N-[(2S)-1,1,1-trifluoropropan-2-yl]pyridine-3-sulfonamide, 6-[3-cyano-1-(cyclopropylmethyl)-6-(2,2-difluoroethyl)-1H-indol-2-yl]-N-(1,3-difluoropropan-2-yl)pyridine-3-sulfonamide, 6-[3-cyano-1-(cyclopropylmethyl)-6-(2,2-difluoroethyl)-1H-indol-2-yl]-N-[(1S)-1-cyclopropylethyl]pyridine-3-sulfonamide, 6-[3-cyano-1-(cyclopropylmethyl)-6-(2,2-difluoroethyl)-1H-indol-2-yl]-N-[(2S)-1,1,1-trifluoropropan-2-yl]pyridine-3-sulfonamide, 2-[3-cyano-1-(cyclopropylmethyl)-6-(2,2-difluoroethyl)-1H-indol-2-yl]-N-[(1S)-1-cyclopropylethyl]pyrimidine-5-sulfonamide, 2-[3-cyano-1-(cyclopropylmethyl)-6-(2,2-difluoroethyl)-1H-indol-2-yl]-N-(propan-2-yl)pyrimidine-5-sulfonamide, 2-[3-cyano-1-(cyclopropylmethyl)-6-(2,2-difluoroethyl)-1H-indol-2-yl]-N-(1,3-difluoropropan-2-yl)pyrimidine-5-sulfonamide, 2-[3-cyano-1-(cyclopropylmethyl)-6-(2,2-difluoroethyl)-1H-indol-2-yl]-N-[(2S)-1,1,1-trifluoropropan-2-yl]pyrimidine-5-sulfonamide, 6-[3-cyano-6-(difluoromethoxy)-1-(pyridin-2-yl)-1H-indol-2-yl]-N-[1-(trifluoromethyl)cyclopropyl]pyridine-3-sulfonamide, N-tert-butyl-6-[3-cyano-6-(difluoromethoxy)-1-phenyl-1H-indol-2-yl]pyridine-3-sulfonamide, 6-(3-cyano-1-cyclopentyl-4-fluoro-6-methyl-1H-indol-2-yl)-N-[(2S)-1,1,1-trifluoropropan-2-yl]pyridine-3-sulfonamide, 6-(3-cyano-1-cyclopentyl-4-fluoro-6-methyl-1H-indol-2-yl)-N-(1,1,1-trifluoro-2-methylpropan-2-yl)pyridine-3-sulfonamide, 6-(3-cyano-1-cyclobutyl-4-fluoro-6-methyl-1H-indol-2-yl)-N-[(2S)-1,1,1-trifluoropropan-2-yl]pyridine-3-sulfonamide, 6-(3-cyano-1-cyclopentyl-4-fluoro-6-methyl-1H-indol-2-yl)-N-[1-(trifluoromethyl)cyclopropyl]pyridine-3-sulfonamide, 6-(3-cyano-1-cyclobutyl-4-fluoro-6-methyl-1H-indol-2-yl)-N-[1-(trifluoromethyl)cyclopropyl]pyridine-3-sulfonamide, 6-(3-cyano-1-cyclobutyl-6-cyclopropyl-5-fluoro-1H-indol-2-yl)-N-[(2S)-1,1,1-trifluoropropan-2-yl]pyridine-3-sulfonamide, 6-(3-cyano-1-cyclobutyl-6-cyclopropyl-5-fluoro-1H-indol-2-yl)-N-[(2R)-1,1,1-trifluoropropan-2-yl]pyridine-3-sulfonamide, 6-(3-cyano-1-cyclopentyl-6-ethyl-5-fluoro-1H-indol-2-yl)-N-[(2R)-1,1,1-trifluoropropan-2-yl]pyridine-3-sulfonamide, 6-(3-cyano-1-cyclopentyl-6-ethyl-5-fluoro-1H-indol-2-yl)-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, 6-[3-cyano-6-(difluoromethoxy)-1-(pyrimidin-2-yl)-1H-indol-2-yl]-N-(1,3-difluoropropan-2-yl)pyridine-3-sulfonamide, 6-[5-chloro-3-cyano-1-cyclobutyl-6-(difluoromethoxy)-1H-indol-2-yl]-N-[(2S)-1,1,1-trifluoropropan-2-yl]pyridine-3-sulfonamide, 6-(3-cyano-1-cyclopentyl-6-ethyl-5-fluoro-1H-indol-2-yl)-N-[1-(trifluoromethyl)cyclopropyl]pyridine-3-sulfonamide, 2-(3-cyano-1-cyclopentyl-6-ethyl-5-fluoro-1H-indol-2-yl)-N-(1,3-difluoropropan-2-yl)pyrimidine-5-sulfonamide, 6-(3-cyano-1-cyclopentyl-6-ethyl-5-fluoro-1H-indol-2-yl)-N-(1,3-difluoropropan-2-yl)pyridine-3-sulfonamide, 6-(3-cyano-1-cyclobutyl-6-ethyl-5-fluoro-1H-indol-2-yl)-N-[(2S)-1,1,1-trifluoropropan-2-yl]pyridine-3-sulfonamide, 6-(3-cyano-1-cyclobutyl-6-ethyl-5-fluoro-1H-indol-2-yl)-N-[(2R)-1,1,1-trifluoropropan-2-yl]pyridine-3-sulfonamide, 6-(3-cyano-1-cyclobutyl-6-ethyl-5-fluoro-1H-indol-2-yl)-N-[1-(trifluoromethyl)cyclopropyl]pyridine-3-sulfonamide, N-tert-butyl-6-(3-cyano-1-cyclopentyl-5-fluoro-6-methyl-1H-indol-2-yl)pyridine-3-sulfonamide, 6-(3-cyano-1-cyclopentyl-5-fluoro-6-methyl-1H-indol-2-yl)-N-[1-(trifluoromethyl)cyclopropyl]pyridine-3-sulfonamide, 6-(3-cyano-1-cyclopentyl-5-fluoro-6-methyl-1H-indol-2-yl)-N-(1-methylcyclopropyl)pyridine-3-sulfonamide, 6-[1-cyclobutyl-6-(difluoromethoxy)-5-methyl-1H-indol-2-yl]-N-[(2S)-1,1,1-trifluoropropan-2-yl]pyridine-3-sulfonamide, 6-[3-cyano-1-cyclobutyl-6-(difluoromethoxy)-5-ethyl-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-[(2R)-1,1,1-trifluoropropan-2-yl]pyridine-3-sulfonamide, 6-[3-cyano-6-(difluoromethoxy)-1-(4-fluorophenyl)-1H-indol-2-yl]-N-[(2R)-1,1,1-trifluoropropan-2-yl]pyridine-3-sulfonamide, 6-[3-cyano-6-cyclopropyl-1-(pyrimidin-2-yl)-1H-indol-2-yl]-N-[(2S)-1,1,1-trifluoropropan-2-yl]pyridine-3-sulfonamide, N-tert-butyl-6-(3-cyano-1-cyclobutyl-5-fluoro-6-methyl-1H-indol-2-yl)pyridine-3-sulfonamide, 6-(3-cyano-1-cyclobutyl-5-fluoro-6-methyl-1H-indol-2-yl)-N-cyclopropylpyridine-3-sulfonamide, 6-(3-cyano-1-cyclopentyl-5,7-difluoro-6-methyl-1H-indol-2-yl)-N-[(2R)-1,1,1-trifluoropropan-2-yl]pyridine-3-sulfonamide, 6-(3-cyano-1-cyclopentyl-5,7-difluoro-6-methyl-1H-indol-2-yl)-N-[1-(trifluoromethyl)cyclopropyl]pyridine-3-sulfonamide, 6-(3-cyano-1-cyclobutyl-5-fluoro-6-methyl-1H-indol-2-yl)-N-(propan-2-yl)pyridine-3-sulfonamide, 2-(3-cyano-1-cyclopentyl-5,7-difluoro-6-methyl-1H-indol-2-yl)-N-(1,3-difluoropropan-2-yl)pyrimidine-5-sulfonamide, 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, 6-[5-chloro-3-cyano-1-cyclobutyl-6-(difluoromethoxy)-1H-indol-2-yl]-N-(1-methylcyclopropyl)pyridine-3-sulfonamide, 2-[5-chloro-3-cyano-1-cyclobutyl-6-(difluoromethoxy)-1H-indol-2-yl]-N-(1,3-difluoropropan-2-yl)pyrimidine-5-sulfonamide, 6-[3-cyano-1-cyclobutyl-6-(difluoromethoxy)-5-methyl-1H-indol-2-yl]-N-[(2S)-1,1,1-trifluoropropan-2-yl]pyridine-3-sulfonamide, 6-(3-cyano-1-cyclopentyl-6-cyclopropyl-5-fluoro-1H-indol-2-yl)-N-[(2S)-1,1,1-trifluoropropan-2-yl]pyridine-3-sulfonamide, 6-(3-cyano-1-cyclopentyl-6-cyclopropyl-5-fluoro-1H-indol-2-yl)-N-[(2R)-1,1,1-trifluoropropan-2-yl]pyridine-3-sulfonamide, 6-[3-cyano-6-(difluoromethoxy)-1-(pyrimidin-2-yl)-1H-indol-2-yl]-N-(1,1,1-trifluoro-2-methylpropan-2-yl)pyridine-3-sulfonamide, 6-[3-cyano-6-(difluoromethoxy)-1-(4-fluorophenyl)-1H-indol-2-yl]-N-[1-(trifluoromethyl)cyclopropyl]pyridine-3-sulfonamide, 6-[3-cyano-1-cyclobutyl-6-(difluoromethoxy)-5-methyl-1H-indol-2-yl]-N-[(2R)-1,1,1-trifluoropropan-2-yl]pyridine-3-sulfonamide, 6-(3-cyano-1-cyclobutyl-5,7-difluoro-6-methyl-1H-indol-2-yl)-N-[(2R)-1,1,1-trifluoropropan-2-yl]pyridine-3-sulfonamide, 6-(3-cyano-1-cyclobutyl-5,7-difluoro-6-methyl-1H-indol-2-yl)-N-[1-(trifluoromethyl)cyclopropyl]pyridine-3-sulfonamide, 2-(3-cyano-1-cyclobutyl-5,7-difluoro-6-methyl-1H-indol-2-yl)-N-(1,3-difluoropropan-2-yl)pyrimidine-5-sulfonamide, 6-(3-cyano-1-cyclopentyl-5-methoxy-6-methyl-1H-indol-2-yl)-N-[(2S)-1,1,1-trifluoropropan-2-yl]pyridine-3-sulfonamide, 6-[3-cyano-6-(difluoromethoxy)-5-fluoro-1-(pyridin-2-yl)-1H-indol-2-yl]-N-[(2R)-1,1,1-trifluoropropan-2-yl]pyridine-3-sulfonamide, 6-[3-cyano-6-methyl-1-(pyridin-2-yl)-1H-indol-2-yl]-N-[(2R)-1,1,1-trifluoropropan-2-yl]pyridine-3-sulfonamide, 6-(3-cyano-1-cyclopentyl-6-ethyl-5-fluoro-1H-indol-2-yl)-N-(1,1,1-trifluoro-2-methylpropan-2-yl)pyridine-3-sulfonamide, 6-[3-cyano-5-fluoro-1-(pyrimidin-2-yl)-1H-indol-2-yl]-N-[(2R)-1,1,1-trifluoropropan-2-yl]pyridine-3-sulfonamide, 6-[3-cyano-1-cyclobutyl-6-(difluoromethoxy)-5-hydroxy-1H-indol-2-yl]-N-[(2S)-1,1,1-trifluoropropan-2-yl]pyridine-3-sulfonamide, 6-(5-bromo-3-cyano-1-cyclopentyl-6-methyl-1H-indol-2-yl)-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-(1,1,1-trifluoro-2-methylpropan-2-yl)pyridine-3-sulfonamide, 6-[3-cyano-6-methyl-1-(pyrimidin-2-yl)-1H-indol-2-yl]-N-[(2S)-1,1,1-trifluoropropan-2-yl]pyridine-3-sulfonamide, 6-(3-cyano-1-cyclohexyl-5-fluoro-6-methyl-1H-indol-2-yl)-N-[(2S)-1,1,1-trifluoropropan-2-yl]pyridine-3-sulfonamide, 2-(3-cyano-1-cyclohexyl-5-fluoro-6-methyl-1H-indol-2-yl)-N-[(2S)-1,1,1-trifluoropropan-2-yl]pyrimidine-5-sulfonamide, 6-(3-cyano-1-cyclohexyl-5-fluoro-6-methyl-1H-indol-2-yl)-N-[(2R)-1,1,1-trifluoropropan-2-yl]pyridine-3-sulfonamide, 6-(3-cyano-1-cyclopentyl-5-fluoro-6-methyl-1H-indol-2-yl)-N-(1,1,1-trifluoro-2-methylpropan-2-yl)pyridine-3-sulfonamide, 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, 2-[5-(tert-butylsulfamoyl)pyridin-2-yl]-1-cyclopentyl-5-fluoro-6-methyl-1H-indole-3-carboxamide, 6-(5-bromo-3-cyano-1-cyclobutyl-6-hydroxy-1H-indol-2-yl)-N-[(2S)-1,1,1-trifluoropropan-2-yl]pyridine-3-sulfonamide, 6-[3-cyano-1-cyclobutyl-6-(difluoromethoxy)-5-(methylsulfanyl)-1H-indol-2-yl]-N-[(2S)-1,1,1-trifluoropropan-2-yl]pyridine-3-sulfonamide, 6-[3-cyano-6-methyl-1-(pyridin-2-yl)-1H-indol-2-yl]-N-(1,1,1-trifluoro-2-methylpropan-2-yl)pyridine-3-sulfonamide, 6-[3-cyano-6-(difluoromethoxy)-1-(4-fluorophenyl)-1H-indol-2-yl]-N-(1,1,1-trifluoro-2-methylpropan-2-yl)pyridine-3-sulfonamide, 6-[3-cyano-6-methyl-1-(pyridin-2-yl)-1H-indol-2-yl]-N-[(2R)-1,1,1-trifluoropropan-2-yl]pyridine-3-sulfonamide, 6-[3-cyano-6-methyl-1-(pyridin-2-yl)-1H-indol-2-yl]-N-(1,1,1-trifluoro-2-methylpropan-2-yl)pyridine-3-sulfonamide, 6-[3-cyano-6-(difluoromethoxy)-1-(pyrimidin-2-yl)-1H-indol-2-yl]-N-[1-(trifluoromethyl)cyclopropyl]pyridine-3-sulfonamide, 6-(3-cyano-1-cyclopentyl-5-hydroxy-6-methyl-1H-indol-2-yl)-N-[(2S)-1,1,1-trifluoropropan-2-yl]pyridine-3-sulfonamide, 6-(5-bromo-3-cyano-1-cyclopentyl-6-methyl-1H-indol-2-yl)-N-[(2R)-1,1,1-trifluoropropan-2-yl]pyridine-3-sulfonamide, 6-(3-cyano-1-cyclopentyl-5-hydroxy-6-methyl-1H-indol-2-yl)-N-[(2R)-1,1,1-trifluoropropan-2-yl]pyridine-3-sulfonamide, 6-(3-cyano-1-cyclopentyl-5-methoxy-6-methyl-1H-indol-2-yl)-N-[(2R)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2R)-1,1,1-trifluoropropan-2-yl]pyridine-3-sulfonamide, 6-[3-cyano-1-cyclobutyl-5-(2,2-difluoroethyl)-1H-indol-2-yl]-N-(1-methylcyclopropyl)pyridine-3-sulfonamide, 6-[3-cyano-1-cyclobutyl-6-(2,2-difluoroethyl)-5-fluoro-1H-indol-2-yl]-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-N-[(2R)-1,1,1-trifluoropropan-2-yl]pyridine-3-sulfonamide, 1-cyclopentyl-5-fluoro-6-methyl-2-(5-{[(2R)-1,1,1-trifluoropropan-2-yl]sulfamoyl}pyridin-2-yl)-1H-indole-3-carboxamide, 1-cyclopentyl-5-fluoro-6-methyl-2-(5-{[(2S)-1,1,1-trifluoropropan-2-yl]sulfamoyl}pyridin-2-yl)-1H-indole-3-carboxamide, 1-cyclopentyl-5-fluoro-6-methyl-2-{5-[(1,1,1-trifluoro-2-methylpropan-2-yl)sulfamoyl]pyridin-2-yl}-1H-indole-3-carboxamide, 6-[3-cyano-1-cyclobutyl-5-(2,2-difluoroethyl)-1H-indol-2-yl]-N-[(2S)-1,1,1-trifluoropropan-2-yl]pyridine-3-sulfonamide, 1-cyclobutyl-6-(difluoromethoxy)-5-fluoro-2-(5-{[(2S)-1,1,1-trifluoropropan-2-yl]sulfamoyl}pyridin-2-yl)-1H-indole-3-carboxamide, 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide,
6-(3-cyano-1-cyclohexyl-5-fluoro-6-methyl-1H-indol-2-yl)-N-(1,1,1-trifluoro-2-methylpropan-2-yl)pyridine-3-sulfonamide,
1-cyclohexyl-5-fluoro-6-methyl-2-(5-{[(2S)-1,1,1-trifluoropropan-2-yl]sulfamoyl}pyridin-2-yl)-1H-indole-3-carboxamide,
1-cyclohexyl-5-fluoro-6-methyl-2-(5-{[(2S)-1,1,1-trifluoropropan-2-yl]sulfamoyl}pyrimidin-2-yl)-1H-indole-3-carboxamide,
6-[5-chloro-3-cyano-1-(pyrimidin-2-yl)-1H-indol-2-yl]-N-[(2S)-1,1,1-trifluoropropan-2-yl]pyridine-3-sulfonamide,
N-tert-butyl-6-(3-cyano-1-cyclohexyl-5-fluoro-6-methyl-1H-indol-2-yl)pyridine-3-sulfonamide,
6-(3-cyano-1-cyclobutyl-5-fluoro-6-hydroxy-1H-indol-2-yl)-N-[(2S)-1,1,1-trifluoropropan-2-yl]pyridine-3-sulfonamide,
6-[3-cyano-1-cyclobutyl-6-(difluoromethoxy)-5-fluoro-1H-indol-2-yl]-N-(difluoromethyl)-N-[(2S)-1,1,1-trifluoropropan-2-yl]pyridine-3-sulfonamide,
6-[3-cyano-1-cyclopentyl-6-(difluoromethoxy)-5-fluoro-1H-indol-2-yl]-N-[(2R)-1,1,1-trifluoropropan-2-yl]pyridine-3-sulfonamide,
1-cyclohexyl-5-fluoro-6-methyl-2-{5-[(1,1,1-trifluoro-2-methylpropan-2-yl)sulfamoyl]pyridin-2-yl}-1H-indole-3-carboxamide,
1-cyclohexyl-5-fluoro-6-methyl-2-(5-sulfamoylpyridin-2-yl)-1H-indole-3-carboxamide,
1-cyclohexyl-5-fluoro-6-methyl-2-(5-{[(2R)-1,1,1-trifluoropropan-2-yl]sulfamoyl}pyridin-2-yl)-1H-indole-3-carboxamide
methyl 1-cyclohexyl-5-fluoro-2-(5-{[(2S)-1,1,1-trifluoropropan-2-yl]sulfamoyl}pyridin-2-yl)-1H-indole-3-carboxylate
1-cyclopentyl-6-(difluoromethoxy)-5-fluoro-2-(5-{[(2R)-1,1,1-trifluoropropan-2-yl]sulfamoyl}pyridin-2-yl)-1H-indole-3-carboxamide
N-tert-butyl-6-(3-cyano-1-cyclobutyl-5-fluoro-6-hydroxy-1H-indol-2-yl)pyridine-3-sulfonamide
6-[3-cyano-1-cyclobutyl-6-(difluoromethoxy)-5-fluoro-1H-indol-2-yl]pyridine-3-sulfonamide
2-[5-(tert-butylsulfamoyl)pyridin-2-yl]-1-cyclobutyl-6-(difluoromethoxy)-5-fluoro-1H-indole-3-carboxamide
6-{3-cyano-5-fluoro-1-[5-(trifluoromethyl)pyridin-2-yl]-1H-indol-2-yl}-N-[(2S)-1,1,1-trifluoropropan-2-yl]pyridine-3-sulfonamide
6-(3-cyano-1-cyclobutyl-5-fluoro-6-methoxy-1H-indol-2-yl)-N-[(2S)-1,1,1-trifluoropropan-2-yl]pyridine-3-sulfonamide
6-(3-cyano-1-cyclobutyl-6-ethoxy-5-fluoro-1H-indol-2-yl)-N-[(2S)-1,1,1-trifluoropropan-2-yl]pyridine-3-sulfonamide
6-[1-cyclobutyl-6-(difluoromethoxy)-5-fluoro-1H-indol-2-yl]-N-[(2S)-1,1,1-trifluoropropan-2-yl]pyridine-3-sulfonamide
6-(1-cyclobutyl-5-fluoro-6-hydroxy-1H-indol-2-yl)-N-[(2S)-1,1,1-trifluoropropan-2-yl]pyridine-3-sulfonamide,
1-cyclobutyl-6-(difluoromethoxy)-5-fluoro-2-{5-[(1,1,1-trifluoro-2-methylpropan-2-yl)sulfamoyl]pyridin-2-yl}-1H-indole-3-carboxamide,
1-cyclopentyl-5-fluoro-6-methyl-2-(5-{[1-(trifluoromethyl)cyclopropyl]sulfamoyl}pyridin-2-yl)-1H-indole-3-carboxamide,
1-cyclobutyl-6-cyclopropyl-5-fluoro-2-(5-{[(2S)-1,1,1-trifluoropropan-2-yl]sulfamoyl}pyridin-2-yl)-1H-indole-3-carboxamide,
1-cyclobutyl-5-fluoro-6-methyl-2-(5-{[(2R)-1,1,1-trifluoropropan-2-yl]sulfamoyl}pyridin-2-yl)-1H-indole-3-carboxamide,
5-chloro-1-cyclobutyl-6-methyl-2-(5-{[(2S)-1,1,1-trifluoropropan-2-yl]sulfamoyl}pyrimidin-2-yl)-1H-indole-3-carboxamide,
5-chloro-1-cyclobutyl-6-methyl-2-(5-{[(2S)-1,1,1-trifluoropropan-2-yl]sulfamoyl}pyridin-2-yl)-1H-indole-3-carboxamide,
5-chloro-1-cyclobutyl-6-methyl-2-(5-{[(2R)-1,1,1-trifluoropropan-2-yl]sulfamoyl}pyridin-2-yl)-1H-indole-3-carboxamide,
6-chloro-1-cyclobutyl-5-fluoro-2-(5-{[(2S)-1,1,1-trifluoropropan-2-yl]sulfamoyl}pyridin-2-yl)-1H-indole-3-carboxamide,
1-cyclobutyl-5-fluoro-6-methyl-2-(5-{[(2S)-1,1,1-trifluoropropan-2-yl]sulfamoyl}pyridin-2-yl)-1H-indole-3-carboxamide,
6-[3-cyano-1-cyclobutyl-6-(difluoromethoxy)-5-fluoro-1H-indol-2-yl]-N-[(2S)-1,1,1-trifluorobutan-2-yl]pyridine-3-sulfonamide,
6-[3-cyano-5-fluoro-6-methyl-1-(3-methylpyridin-2-yl)-1H-indol-2-yl]-N-[(2S)-1,1,1-trifluoropropan-2-yl]pyridine-3-sulfonamide,
6-{3-cyano-5-fluoro-6-methyl-1-[5-(trifluoromethyl)pyridin-2-yl]-1H-indol-2-yl}-N-[(2S)-1,1,1-trifluoropropan-2-yl]pyridine-3-sulfonamide,
1-cyclohexyl-5-fluoro-2-(5-{[(2S)-1,1,1-trifluoropropan-2-yl]sulfamoyl}pyridin-2-yl)-1H-indole-3-carboxylic acid,
6-[3-cyano-5-fluoro-1-(5-fluoropyridin-2-yl)-6-methyl-1H-indol-2-yl]-N-[(2S)-1,1,1-trifluoropropan-2-yl]pyridine-3-sulfonamide,
6-[3-cyano-1-(5-cyanopyridin-2-yl)-5-fluoro-6-methyl-1H-indol-2-yl]-N-[(2S)-1,1,1-trifluoropropan-2-yl]pyridine-3-sulfonamide,
6-[3-cyano-5-fluoro-6-methyl-1-(5-nitropyridin-2-yl)-1H-indol-2-yl]-N-[(2S)-1,1,1-trifluoropropan-2-yl]pyridine-3-sulfonamide,
5-chloro-1-cyclobutyl-2-[5-(propan-2-ylsulfamoyl)pyrimidin-2-yl]-1H-indole-3-carboxamide,
1-cyclohexyl-6-(difluoromethoxy)-2-(5-{[(2S)-1,1,1-trifluoropropan-2-yl]sulfamoyl}pyrimidin-2-yl)-1H-indole-3-carboxamide,
1-cyclohexyl-6-(difluoromethoxy)-2-[5-(propan-2-ylsulfamoyl)pyrimidin-2-yl]-1H-indole-3-carboxamide,
5-fluoro-1-(pyridin-2-yl)-2-(5-{[(2S)-1,1,1-trifluoropropan-2-yl]sulfamoyl}pyridin-2-yl)-1H-indole-3-carboxamide,
6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide,
6-[3-cyano-5-fluoro-6-methyl-1-(tetrahydro-2H-pyran-4-yl)-1H-indol-2-yl]-N-(1,1,1-trifluoro-2-methylpropan-2-yl)pyridine-3-sulfonamide,
6-[3-cyano-5-fluoro-6-methyl-1-(tetrahydro-2H-pyran-4-yl)-1H-indol-2-yl]-N-[(2S)-1,1,1-trifluoropropan-2-yl]pyridine-3-sulfonamide,
N-tert-butyl-6-[3-cyano-5-fluoro-6-methyl-1-(tetrahydro-2H-pyran-4-yl)-1H-indol-2-yl]pyridine-3-sulfonamide,
2-[3-cyano-5-fluoro-6-methyl-1-(tetrahydro-2H-pyran-4-yl)-1H-indol-2-yl]-N-[(2S)-1,1,1-trifluoropropan-2-yl]pyrimidine-5-sulfonamide, methyl 1-cyclopentyl-5-fluoro-6-methyl-2-{5-[(1,1,1-trifluoro-2-methylpropan-2-yl)sulfamoyl]pyridin-2-yl}-1H-indole-3-carboxylate,
methyl 2-[5-(tert-butylsulfamoyl)pyridin-2-yl]-1-cyclopentyl-5-fluoro-6-methyl-1H-indole-3-carboxylate,
methyl 1-cyclopentyl-5-fluoro-6-methyl-2-(5-{[(2S)-1,1,1-trifluoropropan-2-yl]sulfamoyl}pyridin-2-yl)-1H-indole-3-carboxylate,
6-(3-cyano-1-cyclobutyl-5-methoxy-6-methyl-1H-indol-2-yl)-N-[(2S)-1,1,1-trifluoropropan-2-yl]pyridine-3-sulfonamide,
1-cyclopentyl-5-fluoro-6-methyl-2-(5-{[(2S)-1,1,1-trifluoropropan-2-yl]sulfamoyl}pyridin-2-yl)-1H-indole-3-carboxylic acid,
6-(1-cyclopentyl-5-fluoro-6-methyl-1H-indol-2-yl)-N-[(2S)-1,1,1-trifluoropropan-2-yl]pyridine-3-sulfonamide,
1-cyclopentyl-5-fluoro-N,6-dimethyl-2-(5-{[(2S)-1,1,1-trifluoropropan-2-yl]sulfamoyl}pyridin-2-yl)-1H-indole-3-carboxamide,
1-cyclopentyl-N-ethyl-5-fluoro-6-methyl-2-(5-{[(2S)-1,1,1-trifluoropropan-2-yl]sulfamoyl}pyridin-2-yl)-1H-indole-3-carboxamide,
1-cyclopentyl-5-fluoro-6-methyl-N-(propan-2-yl)-2-(5-{[(2S)-1,1,1-trifluoropropan-2-yl]sulfamoyl}pyridin-2-yl)-1H-indole-3-carboxamide,
N-tert-butyl-6-(3-cyano-1-cyclobutyl-6-ethyl-5-fluoro-1H-indol-2-yl)pyridine-3-sulfonamide,
1-cyclopentyl-5-fluoro-6-methyl-2-{5-[(1,1,1-trifluoro-2-methylpropan-2-yl)sulfamoyl]pyridin-2-yl}-1H-indole-3-carboxylic acid,
2-[5-(tert-butylsulfamoyl)pyridin-2-yl]-1-cyclopentyl-5-fluoro-6-methyl-1H-indole-3-carboxylic acid
5-fluoro-6-methyl-1-(tetrahydro-2H-pyran-4-yl)-2-(5-{[(2R)-1,1,1-trifluoropropan-2-yl]sulfamoyl}pyridin-2-yl)-1H-indole-3-carboxamide,
5-fluoro-6-methyl-1-(tetrahydro-2H-pyran-4-yl)-2-{5-[(1,1,1-trifluoro-2-methylpropan-2-yl)sulfamoyl]pyridin-2-yl}-1H-indole-3-carboxamide,
5-fluoro-6-methyl-1-(tetrahydro-2H-pyran-4-yl)-2-(5-{[(2S)-1,1,1-trifluoropropan-2-yl]sulfamoyl}pyridin-2-yl)-1H-indole-3-carboxamide,
methyl 2-[5-(tert-butylsulfamoyl)pyridin-2-yl]-1-cyclobutyl-5-fluoro-6-methyl-1H-indole-3-carboxylate,
methyl 1-cyclobutyl-5-fluoro-6-methyl-2-(5-{[(2S)-1,1,1-trifluoropropan-2-yl]sulfamoyl}pyridin-2-yl)-1H-indole-3-carboxylate,
6-[3-cyano-1-cyclobutyl-5-fluoro-6-(methylsulfanyl)-1H-indol-2-yl]-N-[(2S)-1,1,1-trifluoropropan-2-yl]pyridine-3-sulfonamide,
6-[3-cyano-1-(cyclopropylmethyl)-6-(difluoromethoxy)-4-fluoro-1H-indol-2-yl]-N-[(2S)-1,1,1-trifluoropropan-2-yl]pyridine-3-sulfonamide,
methyl 1-cyclobutyl-5-fluoro-6-methyl-2-(5-{[(2S)-1,1,1-trifluoropropan-2-yl]sulfamoyl}pyrimidin-2-yl)-1H-indole-3-carboxylate,
1-cyclobutyl-5-fluoro-6-methyl-2-(5-{[(2S)-1,1,1-trifluoropropan-2-yl]sulfamoyl}pyrimidin-2-yl)-1H-indole-3-carboxylic acid,
2-[5-(tert-butylsulfamoyl)pyridin-2-yl]-1-cyclobutyl-5-fluoro-6-methyl-1H-indole-3-carboxylic acid,
6-[3-cyano-6-ethyl-5-fluoro-1-(5-fluoropyridin-2-yl)-1H-indol-2-yl]-N-[(2S)-1,1,1-trifluoropropan-2-yl]pyridine-3-sulfonamide,
6-[3-cyano-6-ethyl-5-fluoro-1-(pyridin-2-yl)-1H-indol-2-yl]-N-[(2S)-1,1,1-trifluoropropan-2-yl]pyridine-3-sulfonamide,
6-chloro-1-cyclobutyl-2-[5-(propan-2-ylsulfamoyl)pyrimidin-2-yl]-1H-indole-3-carboxamide,
1-cyclobutyl-2-[5-(propan-2-ylsulfamoyl)pyrimidin-2-yl]-6-(trifluoromethoxy)-1H-indole-3-carboxamide,
1-cyclopentyl-2-[5-(propan-2-ylsulfamoyl)pyrimidin-2-yl]-6-(trifluoromethoxy)-1H-indole-3-carboxamide,
1-cyclopentyl-5-fluoro-N,N,6-trimethyl-2-(5-{[(2S)-1,1,1-trifluoropropan-2-yl]sulfamoyl}pyridin-2-yl)-1H-indole-3-carboxamide,
6-[3-cyano-6-(difluoromethoxy)-4-fluoro-1-(propan-2-yl)-1H-indol-2-yl]-N-[(2S)-1,1,1-trifluoropropan-2-yl]pyridine-3-sulfonamide,
6-[5-chloro-3-cyano-6-methyl-1-(pyrimidin-2-yl)-1H-indol-2-yl]-N-[(2S)-1,1,1-trifluoropropan-2-yl]pyridine-3-sulfonamide,
6-[3-cyano-6-(difluoromethoxy)-5-fluoro-1-propyl-1H-indol-2-yl]-N-[(2S)-1,1,1-trifluoropropan-2-yl]pyridine-3-sulfonamide,
6-[3-cyano-1-(cyclopropylmethyl)-6-(difluoromethoxy)-5-fluoro-1H-indol-2-yl]-N-[(2S)-1,1,1-trifluoropropan-2-yl]pyridine-3-sulfonamide,
6-[3-cyano-6-(difluoromethoxy)-5-fluoro-1-propyl-1H-indol-2-yl]-N-[(2R)-1,1,1-trifluoropropan-2-yl]pyridine-3-sulfonamide,
6-[3-cyano-1-(cyclopropylmethyl)-6-(difluoromethoxy)-5-fluoro-1H-indol-2-yl]-N-[(2R)-1,1,1-trifluoropropan-2-yl]pyridine-3-sulfonamide,
6-[3-cyano-1-cyclobutyl-6-(difluoromethoxy)-5-fluoro-1H-indol-2-yl]-N-(1,1,1-trifluorobutan-2-yl)pyridine-3-sulfonamide,
6-[3-cyano-1-cyclobutyl-6-(difluoromethoxy)-5-fluoro-1H-indol-2-yl]-N-phenylpyridine-3-sulfonamide,
1-cyclobutyl-5-fluoro-6-methyl-2-(5-{[(2S)-1,1,1-trifluoropropan-2-yl]sulfamoyl}pyridin-2-yl)-1H-indole-3-carboxylic acid,
2-[5-(tert-butylsulfamoyl)pyridin-2-yl]-1-cyclobutyl-5-fluoro-6-methyl-1H-indole-3-carboxylic acid,
2-[5-(tert-butylsulfamoyl)pyridin-2-yl]-1-cyclobutyl-5-fluoro-N,6-dimethyl-1H-indole-3-carboxamide,
6-(3-cyano-1-cyclobutyl-5-hydroxy-6-methyl-1H-indol-2-yl)-N-[(2S)-1,1,1-trifluoropropan-2-yl]pyridine-3-sulfonamide,
6-[3-cyano-1-cyclobutyl-6-(difluoromethoxy)-4-fluoro-1H-indol-2-yl]-N-[(2S)-1,1,1-trifluoropropan-2-yl]pyridine-3-sulfonamide,
2-[5-(tert-butylsulfamoyl)pyridin-2-yl]-1-cyclopentyl-5-fluoro-N,6-dimethyl-1H-indole-3-carboxamide,
2-[5-(tert-butylsulfamoyl)pyridin-2-yl]-1-cyclobutyl-5-fluoro-6-methyl-1H-indole-3-carboxamide,
1-cyclobutyl-5-fluoro-N,6-dimethyl-2-(5-{[(2S)-1,1,1-trifluoropropan-2-yl]sulfamoyl}pyridin-2-yl)-1H-indole-3-carboxamide,
2-[5-(tert-butylsulfamoyl)pyrimidin-2-yl]-1-cyclobutyl-5-fluoro-N,6-dimethyl-1H-indole-3-carboxamide,
6-[5-chloro-3-cyano-6-methyl-1-(pyridin-2-yl)-1H-indol-2-yl]-N-[(2S)-1,1,1-trifluoropropan-2-yl]pyridine-3-sulfonamide,
6-[5-chloro-3-cyano-1-(5-fluoropyridin-2-yl)-6-methyl-1H-indol-2-yl]-N-[(2S)-1,1,1-trifluoropropan-2-yl]pyridine-3-sulfonamide,
N-tert-butyl-6-(3-cyano-1-cyclobutyl-5-hydroxy-6-methyl-1H-indol-2-yl)pyridine-3-sulfonamide,
1-cyclopentyl-6-(difluoromethoxy)-5-fluoro-2-(5-{[(2S)-1,1,1-trifluoropropan-2-yl]sulfamoyl}pyridin-2-yl)-1H-indole-3-carboxamide, 6-(3-cyano-1-cyclobutyl-5-hydroxy-6-methyl-1H-indol-2-yl)-N-[(2R)-1,1,1-trifluoropropan-2-yl]pyridine-3-sulfonamide, 6-[3-cyano-1-cyclobutyl-6-(difluoromethoxy)-5-fluoro-1H-indol-2-yl]-N-[1-(trifluoromethyl)cyclopropyl]pyridine-3-sulfonamide, 1-cyclobutyl-6-(difluoromethoxy)-5-fluoro-2-(5-{[1-(trifluoromethyl)cyclopropyl]sulfamoyl}pyridin-2-yl)-1H-indole-3-carboxamide, 6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-7-methyl-1H-indol-2-yl]-N-[(2S)-1,1,1-trifluoropropan-2-yl]pyridine-3-sulfonamide, 6-[3-cyano-1-(cyclopropylmethyl)-6-(difluoromethoxy)-5-fluoro-1H-indol-2-yl]pyridine-3-sulfonamide, 6-(3-cyano-1-cyclobutyl-5-fluoro-6-hydroxy-1H-indol-2-yl)-N-[1-(trifluoromethyl)cyclopropyl]pyridine-3-sulfonamide, 6-[3-cyano-5-fluoro-1-(3-fluoropyridin-2-yl)-6-methyl-1H-indol-2-yl]-N-[(2S)-1,1,1-trifluoropropan-2-yl]pyridine-3-sulfonamide, 6-[3-cyano-5-fluoro-1-(6-fluoropyridin-2-yl)-6-methyl-1H-indol-2-yl]-N-[(2S)-1,1,1-trifluoropropan-2-yl]pyridine-3-sulfonamide, 6-[3-cyano-5-fluoro-1-(4-methoxypyridin-2-yl)-6-methyl-1H-indol-2-yl]-N-[(2S)-1,1,1-trifluoropropan-2-yl]pyridine-3-sulfonamide, 6-[3-cyano-5-fluoro-6-methyl-1-(pyrazin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(5-fluoropyridin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(pyridin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2S)-1,1,1-trifluorobutan-2-yl]pyridine-3-sulfonamide, 6-[3-cyano-1-cyclobutyl-6-(difluoromethoxy)-5-fluoro-1H-indol-2-yl]-4-methyl-N-[(2S)-1,1,1-trifluoropropan-2-yl]pyridine-3-sulfonamide, N-tert-butyl-6-[3-cyano-5-fluoro-1-(pyrimidin-2-yl)-1H-indol-2-yl]pyridine-3-sulfonamide, N-tert-butyl-6-[3-cyano-5-fluoro-6-methyl-1-(pyrimidin-2-yl)-1H-indol-2-yl]pyridine-3-sulfonamide, 1-cyclobutyl-6-(difluoromethoxy)-4-fluoro-2-(5-{[(2S)-1,1,1-trifluoropropan-2-yl]sulfamoyl}pyridin-2-yl)-1H-indole-3-carboxamide, 6-(3-cyano-1-cyclobutyl-5-fluoro-6-methyl-1H-indol-2-yl)-N-[(2S)-1,1,1-trifluorobutan-2-yl]pyridine-3-sulfonamide, 6-[3-cyano-1-cyclobutyl-6-(difluoromethoxy)-5-fluoro-1H-indol-2-yl]-5-methyl-N-[(2S)-1,1,1-trifluoropropan-2-yl]pyridine-3-sulfonamide, 2-[5-(tert-butylsulfamoyl)pyridin-2-yl]-1-cyclobutyl-5-hydroxy-6-methyl-1H-indole-3-carboxamide, 1-cyclopentyl-6-cyclopropyl-5-fluoro-2-(5-{[(2R)-1,1,1-trifluoropropan-2-yl]sulfamoyl}pyridin-2-yl)-1H-indole-3-carboxamide, 1-cyclopentyl-6-ethyl-5-fluoro-2-(5-{[(2S)-1,1,1-trifluoropropan-2-yl]sulfamoyl}pyridin-2-yl)-1H-indole-3-carboxamide, 6-(3-cyano-1-cyclopentyl-6-cyclopropyl-5-fluoro-1H-indol-2-yl)-N-(1,1,1-trifluoro-2-methylpropan-2-yl)pyridine-3-sulfonamide, N-tert-butyl-6-(3-cyano-1-cyclopentyl-6-cyclopropyl-5-fluoro-1H-indol-2-yl)pyridine-3-sulfonamide, 1-cyclobutyl-5-hydroxy-6-methyl-2-(5-{[(2S)-1,1,1-trifluoropropan-2-yl]sulfamoyl}pyridin-2-yl)-1H-indole-3-carboxamide, 1-cyclopentyl-5-methoxy-6-methyl-2-(5-{[(2R)-1,1,1-trifluoropropan-2-yl]sulfamoyl}pyridin-2-yl)-1H-indole-3-carboxamide, 1-cyclohexyl-5-fluoro-6-methyl-2-(5-{[1-(trifluoromethyl)cyclopropyl]sulfamoyl}pyridin-2-yl)-1H-indole-3-carboxylic acid, 6-(3-cyano-1-cyclopentyl-5-fluoro-6-methyl-1H-indol-2-yl)-5-methyl-N-[(2S)-1,1,1-trifluoropropan-2-yl]pyridine-3-sulfonamide, 1-cyclopentyl-6-cyclopropyl-5-fluoro-2-(5-{[(2S)-1,1,1-trifluoropropan-2-yl]sulfamoyl}pyridin-2-yl)-1H-indole-3-carboxamide, 6-(difluoromethoxy)-4-fluoro-1-(propan-2-yl)-2-(5-{[(2S)-1,1,1-trifluoropropan-2-yl]sulfamoyl}pyridin-2-yl)-1H-indole-3-carboxamide, 1-(cyclopropylmethyl)-6-(difluoromethoxy)-4-fluoro-2-(5-{[(2S)-1,1,1-trifluoropropan-2-yl]sulfamoyl}pyridin-2-yl)-1H-indole-3-carboxamide, 1-cyclopentyl-5-hydroxy-6-methyl-2-(5-{[(2S)-1,1,1-trifluoropropan-2-yl]sulfamoyl}pyridin-2-yl)-1H-indole-3-carboxamide, 6-(3-cyano-1-cyclopentyl-5-fluoro-6-methyl-1H-indol-2-yl)-4-methyl-N-[(2S)-1,1,1-trifluoropropan-2-yl]pyridine-3-sulfonamide, 6-[3-cyano-5-methyl-1-(pyrimidin-2-yl)-1H-indol-2-yl]-N-[(2S)-1,1,1-trifluoropropan-2-yl]pyridine-3-sulfonamide, 6-[3-cyano-1-(3-fluoropyridin-2-yl)-5-methyl-1H-indol-2-yl]-N-[(2S)-1,1,1-trifluoropropan-2-yl]pyridine-3-sulfonamide, 6-[3-cyano-5-methyl-1-(pyrazin-2-yl)-1H-indol-2-yl]-N-[(2S)-1,1,1-trifluoropropan-2-yl]pyridine-3-sulfonamide, 5-methyl-1-(pyrimidin-2-yl)-2-(5-{[(2S)-1,1,1-trifluoropropan-2-yl]sulfamoyl}pyridin-2-yl)-1H-indole-3-carboxamide, 6-[3-cyano-5-fluoro-1-(pyridin-2-yl)-1H-indol-2-yl]-4-methyl-N-[(2S)-1,1,1-trifluoropropan-2-yl]pyridine-3-sulfonamide, 6-[3-cyano-5-fluoro-1-(pyrimidin-2-yl)-1H-indol-2-yl]-4-methyl-N-[(2S)-1,1,1-trifluoropropan-2-yl]pyridine-3-sulfonamide, 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, 1-cyclopentyl-6-cyclopropyl-5-fluoro-2-{5-[(1,1,1-trifluoro-2-methylpropan-2-yl)sulfamoyl]pyridin-2-yl}-1H-indole-3-carboxamide, 6-[3-cyano-6-ethyl-5-fluoro-1-(pyrimidin-2-yl)-1H-indol-2-yl]-4-methyl-N-[(2S)-1,1,1-trifluoropropan-2-yl]pyridine-3-sulfonamide, 6-[3-cyano-6-ethyl-5-fluoro-1-(pyridin-2-yl)-1H-indol-2-yl]-4-methyl-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-4-methyl-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-4-methyl-N-[(2S)-1,1,1-trifluoropropan-2-yl]pyridine-3-sulfonamide, N-tert-butyl-6-[3-cyano-6-ethyl-5-fluoro-1-(pyrimidin-2-yl)-1H-indol-2-yl]pyridine-3-sulfonamide, 6-(3-cyano-1-cyclohexyl-5-fluoro-6-methyl-1H-indol-2-yl)-N-[1-(trifluoromethyl)cyclopropyl]pyridine-3-sulfonamide, 1-cyclohexyl-5-fluoro-6-methyl-2-(5-{[1-(trifluoromethyl)cyclopropyl]sulfamoyl}pyridin-2-yl)-1H-indole-3-carboxamide, 6-(3-cyano-1-cyclobutyl-6-ethyl-4-methoxy-1H-indol-2-yl)-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-(1,1,1-trifluoro-2-methylpropan-2-yl)pyridine-3-sulfonamide, 6-[3-cyano-6-ethyl-5-fluoro-1-(pyrimidin-2-yl)-1H-indol-2-yl]-N-(1-methylcyclopropyl)pyridine-3-sulfonamide, 6-[3-cyano-1-cyclopentyl-6-(difluoromethoxy)-5-fluoro-1H-indol-2-yl]-N-(1,1,1-trifluoro-2-methylpropan-2-yl)pyridine-3-sulfonamide, 1-cyclopentyl-6-(difluoromethoxy)-5-fluoro-2-{5-[(1,1,1-trifluoro-2-methylpropan-2-yl)sulfamoyl]pyridin-2-yl}-1H-indole-3-carboxamide 6-[3-cyano-6-ethyl-5-fluoro-1-(pyrimidin-2-yl)-1H-indol-2-yl]-N-[1-(trifluoromethyl)cyclopropyl]pyridine-3-sulfonamide 6-[3-cyano-5-fluoro-6-methyl-1-(5-methylpyrazin-2-yl)-1H-indol-2-yl]-N-[(2S)-1,1,1-trifluoropropan-2-yl]pyridine-3-sulfonamide 6-[3-cyano-5-fluoro-1-(4-methoxypyrimidin-2-yl)-6-methyl-1H-indol-2-yl]-N-[(2S)-1,1,1-trifluoropropan-2-yl]pyridine-3-sulfonamide 6-[3-cyano-6-ethyl-5-fluoro-1-(pyrimidin-2-yl)-1H-indol-2-yl]-5-methyl-N-[(2S)-1,1,1-trifluoropropan-2-yl]pyridine-3-sulfonamide 6-(3-cyano-1-cyclopentyl-5-fluoro-6-methyl-1H-indol-2-yl)-2-methyl-N-[(2S)-1,1,1-trifluoropropan-2-yl]pyridine-3-sulfonamide N-tert-butyl-6-[6-ethyl-5-fluoro-3-(methylsulfonyl)-1-(pyrimidin-2-yl)-1H-indol-2-yl]pyridine-3-sulfonamide 6-[3-cyano-6-ethyl-5-fluoro-1-(pyridin-2-yl)-1H-indol-2-yl]-5-methyl-N-[(2S)-1,1,1-trifluoropropan-2-yl]pyridine-3-sulfonamide, 1-cyclopentyl-6-ethyl-5-fluoro-2-{5-[(1,1,1-trifluoro-2-methylpropan-2-yl)sulfamoyl]pyridin-2-yl}-1H-indole-3-carboxamide, 1-cyclopentyl-6-ethyl-5-fluoro-2-(5-{[1-(trifluoromethyl)cyclopropyl]sulfamoyl}pyridin-2-yl)-1H-indole-3-carboxamide, 6-[3-cyano-5-fluoro-6-methyl-1-(4-methylpyrimidin-2-yl)-1H-indol-2-yl]-N-[(2S)-1,1,1-trifluoropropan-2-yl]pyridine-3-sulfonamide, 5-fluoro-6-methyl-1-(pyridin-2-yl)-2-(5-{[(2S)-1,1,1-trifluoropropan-2-yl]sulfamoyl}pyridin-2-yl)-1H-indole-3-carboxamide, 5-fluoro-6-methyl-1-(pyrazin-2-yl)-2-(5-{[(2S)-1,1,1-trifluoropropan-2-yl]sulfamoyl}pyridin-2-yl)-1H-indole-3-carboxamide, 5-fluoro-1-(5-fluoropyridin-2-yl)-6-methyl-2-(5-{[(2S)-1,1,1-trifluoropropan-2-yl]sulfamoyl}pyridin-2-yl)-1H-indole-3-carboxamide, 5-fluoro-1-(6-fluoropyridin-2-yl)-6-methyl-2-(5-{[(2S)-1,1,1-trifluoropropan-2-yl]sulfamoyl}pyridin-2-yl)-1H-indole-3-carboxamide, 6-[3-cyano-6-ethyl-5-fluoro-1-(pyrimidin-2-yl)-1H-indol-2-yl]-N-[(2R)-1,1,1-trifluoropropan-2-yl]pyridine-3-sulfonamide, 6-[3-cyano-6-ethyl-5-fluoro-1-(pyridin-2-yl)-1H-indol-2-yl]-N-[(2R)-1,1,1-trifluoropropan-2-yl]pyridine-3-sulfonamide, 6-[3-cyano-6-ethyl-5-fluoro-1-(5-fluoropyridin-2-yl)-1H-indol-2-yl]-N-[(2R)-1,1,1-trifluoropropan-2-yl]pyridine-3-sulfonamide, 6-[3-cyano-6-ethyl-5-fluoro-1-(pyrimidin-2-yl)-1H-indol-2-yl]-2-methyl-N-[(2S)-1,1,1-trifluoropropan-2-yl]pyridine-3-sulfonamide, N-tert-butyl-6-[3-cyano-6-ethyl-5-fluoro-1-(pyridin-2-yl)-1H-indol-2-yl]pyridine-3-sulfonamide, 2-[5-(tert-butylsulfamoyl)pyridin-2-yl]-6-ethyl-5-fluoro-1-(pyridin-2-yl)-1H-indole-3-carboxamide, N-tert-butyl-6-(3-cyano-6-ethyl-5-fluoro-1-phenyl-1H-indol-2-yl)pyridine-3-sulfonamide, 6-[3-cyano-5-fluoro-6-methyl-1-(5-methylpyridin-2-yl)-1H-indol-2-yl]-N-[(2S)-1,1,1-trifluoropropan-2-yl]pyridine-3-sulfonamide, 6-[3-cyano-5-fluoro-6-methyl-1-(4-methylpyridin-2-yl)-1H-indol-2-yl]-N-[(2S)-1,1,1-trifluoropropan-2-yl]pyridine-3-sulfonamide, 6-[3-cyano-6-ethyl-5-fluoro-1-(pyridin-2-yl)-1H-indol-2-yl]-2-methyl-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-5-methyl-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-5-methyl-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-4-methyl-N-[(2R)-1,1,1-trifluoropropan-2-yl]pyridine-3-sulfonamide, 6-[3-cyano-6-ethyl-5-fluoro-1-(pyridin-2-yl)-1H-indol-2-yl]-4-methyl-N-[(2R)-1,1,1-trifluoropropan-2-yl]pyridine-3-sulfonamide, 6-[3-cyano-5-fluoro-6-methyl-1-(pyridazin-3-yl)-1H-indol-2-yl]-N-[(2S)-1,1,1-trifluoropropan-2-yl]pyridine-3-sulfonamide, 6-[3-cyano-5-fluoro-6-methyl-1-(pyridin-3-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-5-yl)-1H-indol-2-yl]-N-[(2S)-1,1,1-trifluoropropan-2-yl]pyridine-3-sulfonamide, 6-[6-bromo-3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-4-yl)-1H-indol-2-yl]-N-[(2S)-1,1,1-trifluoropropan-2-yl]pyridine-3-sulfonamide, 6-[3-cyano-1-(pyrazin-2-yl)-5-(trifluoromethyl)-1H-indol-2-yl]-N-[(2S)-1,1,1-trifluoropropan-2-yl]pyridine-3-sulfonamide, 6-[3-cyano-1-(pyrazin-2-yl)-5-(trifluoromethoxy)-1H-indol-2-yl]-N-[(2S)-1,1,1-trifluoropropan-2-yl]pyridine-3-sulfonamide, N-tert-butyl-6-[3-cyano-6-ethyl-5-fluoro-1-(pyrazin-2-yl)-1H-indol-2-yl]pyridine-3-sulfonamide, N-tert-butyl-6-[3-cyano-6-ethyl-5-fluoro-1-(3-fluoropyridin-2-yl)-1H-indol-2-yl]pyridine-3-sulfonamide, 6-[3-cyano-6-fluoro-5-methyl-1-(pyrimidin-2-yl)-1H-indol-2-yl]-N-[(2S)-1,1,1-trifluoropropan-2-yl]pyridine-3-sulfonamide, 5-fluoro-1-(3-fluoropyridin-2-yl)-6-methyl-2-(5-{[(2S)-1,1,1-trifluoropropan-2-yl]sulfamoyl}pyridin-2-yl)-1H-indole-3-carboxamide, 6-[5-fluoro-6-methyl-1-(1,3-thiazol-2-yl)-1H-indol-2-yl]-N-[(2S)-1,1,1-trifluoropropan-2-yl]pyridine-3-sulfonamide, 5-fluoro-6-methyl-1-(5-methylpyrazin-2-yl)-2-(5-{[(2S)-1,1,1-trifluoropropan-2-yl]sulfamoyl}pyridin-2-yl)-1H-indole-3-carboxamide 5-fluoro-6-methyl-1-(4-methylpyrimidin-2-yl)-2-(5-{[(2S)-1,1,1-trifluoropropan-2-yl]sulfamoyl}pyridin-2-yl)-1H-indole-3-carboxamide 5-fluoro-1-(4-methoxypyrimidin-2-yl)-6-methyl-2-(5-{[(2S)-1,1,1-trifluoropropan-2-yl]sulfamoyl}pyridin-2-yl)-1H-indole-3-carboxamide 6-[6-acetyl-3-cyano-5-fluoro-1-(pyrimidin-2-yl)-1H-indol-2-yl]-N-[(2S)-1,1,1-trifluoropropan-2-yl]pyridine-3-sulfonamide 6-[3-cyano-6-ethenyl-5-fluoro-1-(pyrimidin-2-yl)-1H-indol-2-yl]-N-[(2S)-1,1,1-trifluoropropan-2-yl]pyridine-3-sulfonamide 6-ethyl-5-fluoro-1-(pyridin-2-yl)-2-(5-{[(2S)-1,1,1-trifluoropropan-2-yl]sulfamoyl}pyridin-2-yl)-1H-indole-3-carboxamide 6-(3-cyano-1-cyclopropyl-6-ethyl-5-fluoro-1H-indol-2-yl)-N-[(2S)-1,1,1-trifluoropropan-2-yl]pyridine-3-sulfonamide 6-[3-cyano-5-fluoro-6-(1-hydroxyethyl)-1-(pyrimidin-2-yl)-1H-indol-2-yl]-N-[(2S)-1,1,1-trifluoropropan-2-yl]pyridine-3-sulfonamide 5-fluoro-6-methyl-1-(pyridazin-3-yl)-2-(5-{[(2S)-1,1,1-trifluoropropan-2-yl]sulfamoyl}pyridin-2-yl)-1H-indole-3-carboxamide 5-fluoro-6-methyl-1-(pyridin-3-yl)-2-(5-{[(2S)-1,1,1-trifluoropropan-2-yl]sulfamoyl}pyridin-2-yl)-1H-indole-3-carboxamide 6-[1-(5-chloropyrimidin-2-yl)-3-cyano-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(6-methylpyrazin-2-yl)-1H-indol-2-yl]-N-[(2S)-1,1,1-trifluoropropan-2-yl]pyridine-3-sulfonamide, 5-methyl-1-(pyrazin-2-yl)-2-(5-{[(2S)-1,1,1-trifluoropropan-2-yl]sulfamoyl}pyridin-2-yl)-1H-indole-3-carboxamide, 6-[3-cyano-6-fluoro-5-methyl-1-(pyridin-2-yl)-1H-indol-2-yl]-N-[(2S)-1,1,1-trifluoropropan-2-yl]pyridine-3-sulfonamide, 6-fluoro-5-methyl-1-(pyrimidin-2-yl)-2-(5-{[(2S)-1,1,1-trifluoropropan-2-yl]sulfamoyl}pyridin-2-yl)-1H-indole-3-carboxamide, 6-[3-cyano-6-fluoro-5-methyl-1-(pyrazin-2-yl)-1H-indol-2-yl]-N-[(2S)-1,1,1-trifluoropropan-2-yl]pyridine-3-sulfonamide, 6-[3-cyano-1-(4-fluorophenyl)-5-methyl-1H-indol-2-yl]-N-[(2S)-1,1,1-trifluoropropan-2-yl]pyridine-3-sulfonamide, 6-(3-cyano-5-methyl-1-phenyl-1H-indol-2-yl)-N-[(2S)-1,1,1-trifluoropropan-2-yl]pyridine-3-sulfonamide, 6-[3-cyano-1-(pyrimidin-2-yl)-5-(trifluoromethyl)-1H-indol-2-yl]-N-[(2S)-1,1,1-trifluoropropan-2-yl]pyridine-3-sulfonamide, 6-[3-cyano-5-fluoro-6-methyl-1-(6-methylpyridin-2-yl)-1H-indol-2-yl]-N-[(2S)-1,1,1-trifluoropropan-2-yl]pyridine-3-sulfonamide, 6-[3-cyano-5-fluoro-1-(5-fluoropyrimidin-2-yl)-6-methyl-1H-indol-2-yl]-N-[(2S)-1,1,1-trifluoropropan-2-yl]pyridine-3-sulfonamide, 6-[3-cyano-5-fluoro-6-methyl-1-(5-methylpyrimidin-2-yl)-1H-indol-2-yl]-N-[(2S)-1,1,1-trifluoropropan-2-yl]pyridine-3-sulfonamide, 6-[3-cyano-5-fluoro-1-(4-fluoropyridin-2-yl)-6-methyl-1H-indol-2-yl]-N-[(2S)-1,1,1-trifluoropropan-2-yl]pyridine-3-sulfonamide, 6-[3-cyano-5-fluoro-6-(2-methyl-1,3-dioxolan-2-yl)-1-(pyrimidin-2-yl)-1H-indol-2-yl]-N-[(2S)-1,1,1-trifluoropropan-2-yl]pyridine-3-sulfonamide, 1-cyclohexyl-6-(difluoromethoxy)-5-fluoro-2-{5-[(1,1,1-trifluoro-2-methylpropan-2-yl)sulfamoyl]pyridin-2-yl}-1H-indole-3-carboxylic acid, 6-[3-cyano-6-ethyl-5-fluoro-1-(pyrazin-2-yl)-1H-indol-2-yl]-N-[(2S)-1,1,1-trifluoropropan-2-yl]pyridine-3-sulfonamide, 6-[3-cyano-6-ethyl-5-fluoro-1-(6-fluoropyridin-2-yl)-1H-indol-2-yl]-N-[(2S)-1,1,1-trifluoropropan-2-yl]pyridine-3-sulfonamide, 6-[3-cyano-6-ethyl-5-fluoro-1-(5-methylpyridin-2-yl)-1H-indol-2-yl]-N-[(2S)-1,1,1-trifluoropropan-2-yl]pyridine-3-sulfonamide, 6-[3-cyano-6-ethyl-5-fluoro-1-(4-methylpyridin-2-yl)-1H-indol-2-yl]-N-[(2S)-1,1,1-trifluoropropan-2-yl]pyridine-3-sulfonamide, 6-[3-cyano-5-fluoro-6-methyl-1-(pyridin-4-yl)-1H-indol-2-yl]-N-[(2S)-1,1,1-trifluoropropan-2-yl]pyridine-3-sulfonamide, 6-[3-cyano-5-fluoro-6-methyl-1-(1,3-thiazol-2-yl)-1H-indol-2-yl]-N-[(2S)-1,1,1-trifluoropropan-2-yl]pyridine-3-sulfonamide, 6-[3-cyano-6-ethyl-5-fluoro-1-(1,3-thiazol-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(propan-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide, 6-[6-bromo-3-cyano-5-fluoro-1-(pyrimidin-2-yl)-1H-indol-2-yl]-N-tert-butylpyridine-3-sulfonamide, N-tert-butyl-6-[3,6-diacetyl-5-fluoro-1-(pyrimidin-2-yl)-1H-indol-2-yl]pyridine-3-sulfonamide, 6-[3-cyano-6-(difluoromethoxy)-5-fluoro-1-(2-hydroxyethyl)-1H-indol-2-yl]-N-[(2S)-1,1,1-trifluoropropan-2-yl]pyridine-3-sulfonamide, 6-[3-cyano-1-(1,6-dihydropyrimidin-2-yl)-6-ethyl-5-fluoro-1H-indol-2-yl]-N-[(2S)-1,1,1-trifluoropropan-2-yl]pyridine-3-sulfonamide, 6-[1-(5-chloropyrimidin-2-yl)-3-cyano-6-ethyl-5-fluoro-1H-indol-2-yl]-N-[(2S)-1,1,1-trifluoropropan-2-yl]pyridine-3-sulfonamide, 6-[3-cyano-6-ethyl-5-fluoro-1-(2-methylpyrimidin-4-yl)-1H-indol-2-yl]-N-[(2S)-1,1,1-trifluoropropan-2-yl]pyridine-3-sulfonamide, 6-[5-fluoro-1-(2-fluoropyridin-4-yl)-6-methyl-1H-indol-2-yl]-N-[(2S)-1,1,1-trifluoropropan-2-yl]pyridine-3-sulfonamide, 6-[3-cyano-5-fluoro-1-(5-fluoropyridin-3-yl)-6-methyl-1H-indol-2-yl]-N-[(2S)-1,1,1-trifluoropropan-2-yl]pyridine-3-sulfonamide, 6-[3-cyano-6-ethyl-5-fluoro-1-(5-fluoropyrimidin-2-yl)-1H-indol-2-yl]-N-[(2S)-1,1,1-trifluoropropan-2-yl]pyridine-3-sulfonamide, 6-[3-chloro-6-cyclopropyl-5-fluoro-1-(pyrimidin-2-yl)-1H-indol-2-yl]-N-[(2S)-1,1,1-trifluoropropan-2-yl]pyridine-3-sulfonamide, 6-[3-cyano-1-(5-fluoropyrimidin-2-yl)-5-methyl-1H-indol-2-yl]-N-[(2S)-1,1,1-trifluoropropan-2-yl]pyridine-3-sulfonamide, 6-[3-cyano-6-fluoro-1-(5-fluoropyrimidin-2-yl)-5-methyl-1H-indol-2-yl]-N-[(2S)-1,1,1-trifluoropropan-2-yl]pyridine-3-sulfonamide, 6-[3-cyano-1-(pyrimidin-2-yl)-6-(trifluoromethyl)-1H-indol-2-yl]-N-[(2S)-1,1,1-trifluoropropan-2-yl]pyridine-3-sulfonamide, 6-[3-cyano-1-(pyrazin-2-yl)-6-(trifluoromethyl)-1H-indol-2-yl]-N-[(2S)-1,1,1-trifluoropropan-2-yl]pyridine-3-sulfonamide, 6-[3-cyano-1-(pyridin-2-yl)-6-(trifluoromethyl)-1H-indol-2-yl]-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-(cyclobutylmethyl)pyridine-3-sulfonamide, 6-[3-cyano-6-ethyl-5-fluoro-1-(pyridin-3-yl)-1H-indol-2-yl]-N-[(2S)-1,1,1-trifluoropropan-2-yl]pyridine-3-sulfonamide, 6-[3-cyano-6-ethyl-5-fluoro-1-(4-methoxypyridin-2-yl)-1H-indol-2-yl]-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-[(2S)-1,1,1-trifluoro(2-deuterium)propan-2-yl]pyridine-3-sulfonamide, 6-[5-fluoro-6-methyl-1-(1,3-thiazol-4-yl)-1H-indol-2-yl]-N-[(2S)-1,1,1-trifluoropropan-2-yl]pyridine-3-sulfonamide, 6-[5-fluoro-6-methyl-1-(1,3,4-thiadiazol-2-yl)-1H-indol-2-yl]-N-[(2S)-1,1,1-trifluoropropan-2-yl]pyridine-3-sulfonamide, 6-[5-fluoro-6-methyl-1-(1,3-thiazol-5-yl)-1H-indol-2-yl]-N-[(2S)-1,1,1-trifluoropropan-2-yl]pyridine-3-sulfonamide, 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, 6-[3-cyano-5-fluoro-1-(5-fluoro-6-methylpyridin-2-yl)-6-methyl-1H-indol-2-yl]-N-[(2S)-1,1,1-trifluoropropan-2-yl]pyridine-3-sulfonamide, 6-[1-(6-chloropyridin-2-yl)-3-cyano-5-fluoro-6-methyl-1H-indol-2-yl]-N-[(2S)-1,1,1-trifluoropropan-2-yl]pyridine-3-sulfonamide, 6-[3-cyano-6-ethyl-5-fluoro-1-(pyrimidin-5-yl)-1H-indol-2-yl]-N-[(2S)-1,1,1-trifluoropropan-2-yl]pyridine-3-sulfonamide, 6-[3-cyano-6-ethyl-5-fluoro-1-(pyrimidin-4-yl)-1H-indol-2-yl]-N-[(2S)-1,1,1-trifluoropropan-2-yl]pyridine-3-sulfonamide, 6-[1-(3-chloropyridin-2-yl)-3-cyano-6-ethyl-5-fluoro-1H-indol-2-yl]-N-[(2S)-1,1,1-trifluoropropan-2-yl]pyridine-3-sulfonamide, 6-[1-(5-chloropyridin-2-yl)-3-cyano-6-ethyl-5-fluoro-1H-indol-2-yl]-N-[(2S)-1,1,1-trifluoropropan-2-yl]pyridine-3-sulfonamide, 6-[3-cyano-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, 6-[3-chloro-5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, 6-[5-fluoro-6-(prop-2-en-1-yl)-1-(pyrimidin-2-yl)-1H-indol-2-yl]-N-[(2S)-1,1,1-trifluoropropan-2-yl]pyridine-3-sulfonamide, 6-[3-cyano-5-fluoro-6-(2-hydroxyethyl)-1-(pyrimidin-2-yl)-1H-indol-2-yl]-N-[(2S)-1,1,1-trifluoropropan-2-yl]pyridine-3-sulfonamide, 6-[1-(3-chloropyridin-2-yl)-3-cyano-5-fluoro-6-methyl-1H-indol-2-yl]-N-[(2S)-1,1,1-trifluoropropan-2-yl]pyridine-3-sulfonamide, 6-[3-chloro-5-fluoro-6-methyl-1-(1,3,4-thiadiazol-2-yl)-1H-indol-2-yl]-N-[(2S)-1,1,1-trifluoropropan-2-yl]pyridine-3-sulfonamide, 6-[3-cyano-5-fluoro-6-methyl-1-(1,3-thiazol-5-yl)-1H-indol-2-yl]-N-[(2S)-1,1,1-trifluoropropan-2-yl]pyridine-3-sulfonamide, 6-[3-cyano-6-ethyl-5-fluoro-1-(pyridin-4-yl)-1H-indol-2-yl]-N-[(2S)-1,1,1-trifluoropropan-2-yl]pyridine-3-sulfonamide, 6-[3-cyano-6-ethyl-5-fluoro-1-(pyridazin-3-yl)-1H-indol-2-yl]-N-[(2S)-1,1,1-trifluoropropan-2-yl]pyridine-3-sulfonamide, 6-[3-cyano-6-ethyl-5-fluoro-1-(5-methylpyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide, 6-ethyl-5-fluoro-1-(pyrimidin-2-yl)-2-{5-[(1,1,1-trifluoro-2-methylpropan-2-yl)sulfamoyl]pyridin-2-yl}-1H-indole-3-carboxamide, 6-ethyl-5-fluoro-1-(pyrimidin-2-yl)-2-(5-{[1-(trifluoromethyl)cyclopropyl]sulfamoyl}pyridin-2-yl)-1H-indole-3-carboxamide, 6-ethyl-5-fluoro-1-(4-methylpyridin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(5-fluoropyridin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(2-methylpyrimidin-4-yl)-2-(5-{[(2S)-1,1,1-trifluoropropan-2-yl]sulfamoyl}pyridin-2-yl)-1H-indole-3-carboxamide, 6-[1-(5-chloropyridin-3-yl)-3-cyano-6-ethyl-5-fluoro-1H-indol-2-yl]-N-[(2S)-1,1,1-trifluoropropan-2-yl]pyridine-3-sulfonamide, 6-{3-cyano-5-fluoro-1-[5-(hydroxymethyl)-1,3-thiazol-2-yl]-6-methyl-1H-indol-2-yl}-N-[(2S)-1,1,1-trifluoropropan-2-yl]pyridine-3-sulfonamide, methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-5-carboxylate, methyl 2-[3-cyano-5-fluoro-6-methyl-2-(5-{[(2S)-1,1,1-trifluoropropan-2-yl]sulfamoyl}pyridin-2-yl)-1H-indol-1-yl]-1,3-thiazole-4-carboxylate, 6-[5-fluoro-6-methyl-1-(thiophen-3-yl)-1H-indol-2-yl]-N-[(2S)-1,1,1-trifluoropropan-2-yl]pyridine-3-sulfonamide, 6-[5-fluoro-1-(furan-3-yl)-6-methyl-1H-indol-2-yl]-N-[(2S)-1,1,1-trifluoropropan-2-yl]pyridine-3-sulfonamide, 6-[5-fluoro-6-methyl-1-(thiophen-2-yl)-1H-indol-2-yl]-N-[(2S)-1,1,1-trifluoropropan-2-yl]pyridine-3-sulfonamide, 6-[3-cyano-5-fluoro-6-methyl-1-(thiophen-2-yl)-1H-indol-2-yl]-N-[(2S)-1,1,1-trifluoropropan-2-yl]pyridine-3-sulfonamide, 6-[3-cyano-5-fluoro-1-(furan-3-yl)-6-methyl-1H-indol-2-yl]-N-[(2S)-1,1,1-trifluoropropan-2-yl]pyridine-3-sulfonamide, 6-[3-cyano-5-fluoro-6-methyl-1-(thiophen-3-yl)-1H-indol-2-yl]-N-[(2S)-1,1,1-trifluoropropan-2-yl]pyridine-3-sulfonamide, 6-[1-(4-chloropyridin-2-yl)-3-cyano-6-ethyl-5-fluoro-1H-indol-2-yl]-N-[(2S)-1,1,1-trifluoropropan-2-yl]pyridine-3-sulfonamide, 6-ethyl-5-fluoro-1-(pyrazin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(6-fluoropyridin-2-yl)-2-(5-{[(2S)-1,1,1-trifluoropropan-2-yl]sulfamoyl}pyridin-2-yl)-1H-indole-3-carboxamide, 5-chloro-1-cyclobutyl-2-(5-{[(2S)-1,1,1-trifluoropropan-2-yl]sulfamoyl}pyridin-2-yl)-1H-indole-3-carboxamide, 1-cyclobutyl-5-fluoro-2-(5-{[(2S)-1,1,1-trifluoropropan-2-yl]sulfamoyl}pyridin-2-yl)-1H-indole-3-carboxamide, 6-[3-cyano-5-fluoro-6-methyl-1-(3-methylthiophen-2-yl)-1H-indol-2-yl]-N-[(2S)-1,1,1-trifluoropropan-2-yl]pyridine-3-sulfonamide, 6-[3-cyano-1-(4,6-difluoropyridin-2-yl)-5-fluoro-6-methyl-1H-indol-2-yl]-N-[(2S)-1,1,1-trifluoropropan-2-yl]pyridine-3-sulfonamide, 6-[3-cyano-6-ethyl-5-fluoro-1-(4-fluorophenyl)-1H-indol-2-yl]-N-[(2S)-1,1,1-trifluoropropan-2-yl]pyridine-3-sulfonamide, 6-[1-(4-chlorophenyl)-3-cyano-6-ethyl-5-fluoro-1H-indol-2-yl]-N-[(2S)-1,1,1-trifluoropropan-2-yl]pyridine-3-sulfonamide, 6-[3-cyano-6-ethyl-5-fluoro-1-(4-methylphenyl)-1H-indol-2-yl]-N-[(2S)-1,1,1-trifluoropropan-2-yl]pyridine-3-sulfonamide, 6-[3-cyano-6-ethyl-5-fluoro-1-(4-methoxyphenyl)-1H-indol-2-yl]-N-[(2S)-1,1,1-trifluoropropan-2-yl]pyridine-3-sulfonamide, 6-{3-cyano-6-ethyl-5-fluoro-1-[4-(trifluoromethyl)phenyl]-1H-indol-2-yl}-N-[(2S)-1,1,1-trifluoropropan-2-yl]pyridine-3-sulfonamide, 6-[3-cyano-1-(4-cyanophenyl)-6-ethyl-5-fluoro-1H-indol-2-yl]-N-[(2S)-1,1,1-trifluoropropan-2-yl]pyridine-3-sulfonamide, 6-[3-cyano-6-ethyl-5-fluoro-1-(3-fluorophenyl)-1H-indol-2-yl]-N-[(2S)-1,1,1-trifluoropropan-2-yl]pyridine-3-sulfonamide, 6-[3-cyano-6-ethyl-5-fluoro-1-(3-methylphenyl)-1H-indol-2-yl]-N-[(2S)-1,1,1-trifluoropropan-2-yl]pyridine-3-sulfonamide, 6-[3-cyano-6-ethyl-5-fluoro-1-(3-methoxyphenyl)-1H-indol-2-yl]-N-[(2S)-1,1,1-trifluoropropan-2-yl]pyridine-3-sulfonamide, 6-{3-cyano-6-ethyl-5-fluoro-1-[3-(trifluoromethyl)phenyl]-1H-indol-2-yl}-N-[(2S)-1,1,1-trifluoropropan-2-yl]pyridine-3-sulfonamide, 6-[3-cyano-1-(3-cyanophenyl)-6-ethyl-5-fluoro-1H-indol-2-yl]-N-[(2S)-1,1,1-trifluoropropan-2-yl]pyridine-3-sulfonamide, 6-[3-cyano-5-fluoro-1-(2-fluoropyridin-4-yl)-6-methyl-1H-indol-2-yl]-N-[(2S)-1,1,1-trifluoropropan-2-yl]pyridine-3-sulfonamide, 6-[3-cyano-5-fluoro-1-(3-fluoropyridin-4-yl)-6-methyl-1H-indol-2-yl]-N-[(2S)-1,1,1-trifluoropropan-2-yl]pyridine-3-sulfonamide, 6-[3-cyano-5-fluoro-1-(6-fluoropyridin-3-yl)-6-methyl-1H-indol-2-yl]-N-[(2S)-1,1,1-trifluoropropan-2-yl]pyridine-3-sulfonamide, 6-[3-cyano-5-fluoro-6-methyl-1-(1-methyl-1H-pyrazol-4-yl)-1H-indol-2-yl]-N-[(2S)-1,1,1-trifluoropropan-2-yl]pyridine-3-sulfonamide, 6-[3-cyano-5-fluoro-6-methyl-1-(5-methyl-1,3-thiazol-2-yl)-1H-indol-2-yl]-N-[(2S)-1,1,1-trifluoropropan-2-yl]pyridine-3-sulfonamide, 6-[1-(3-chlorophenyl)-3-cyano-6-ethyl-5-fluoro-1H-indol-2-yl]-N-[(2S)-1,1,1-trifluoropropan-2-yl]pyridine-3-sulfonamide, 6-ethyl-5-fluoro-1-(4-fluorophenyl)-2-(5-{[(2S)-1,1,1-trifluoropropan-2-yl]sulfamoyl}pyridin-2-yl)-1H-indole-3-carboxamide, 1-(4-chlorophenyl)-6-ethyl-5-fluoro-2-(5-{[(2S)-1,1,1-trifluoropropan-2-yl]sulfamoyl}pyridin-2-yl)-1H-indole-3-carboxamide, 6-ethyl-5-fluoro-1-(4-methylphenyl)-2-(5-{[(2S)-1,1,1-trifluoropropan-2-yl]sulfamoyl}pyridin-2-yl)-1H-indole-3-carboxamide, 6-ethyl-5-fluoro-1-[4-(trifluoromethyl)phenyl]-2-(5-{[(2S)-1,1,1-trifluoropropan-2-yl]sulfamoyl}pyridin-2-yl)-1H-indole-3-carboxamide, 6-ethyl-5-fluoro-1-(3-fluorophenyl)-2-(5-{[(2S)-1,1,1-trifluoropropan-2-yl]sulfamoyl}pyridin-2-yl)-1H-indole-3-carboxamide, 6-ethyl-5-fluoro-1-(3-methylphenyl)-2-(5-{[(2S)-1,1,1-trifluoropropan-2-yl]sulfamoyl}pyridin-2-yl)-1H-indole-3-carboxamide, 6-ethyl-5-fluoro-1-(3-methoxyphenyl)-2-(5-{[(2S)-1,1,1-trifluoropropan-2-yl]sulfamoyl}pyridin-2-yl)-1H-indole-3-carboxamide, 6-ethyl-5-fluoro-1-[3-(trifluoromethyl)phenyl]-2-(5-{[(2S)-1,1,1-trifluoropropan-2-yl]sulfamoyl}pyridin-2-yl)-1H-indole-3-carboxamide, 1-(3-chlorophenyl)-6-ethyl-5-fluoro-2-(5-{[(2S)-1,1,1-trifluoropropan-2-yl]sulfamoyl}pyridin-2-yl)-1H-indole-3-carboxamide, 6-[3-cyano-5-fluoro-6-methyl-1-(3-methyl-1H-pyrazol-4-yl)-1H-indol-2-yl]-N-[(2S)-1,1,1-trifluoropropan-2-yl]pyridine-3-sulfonamide, 6-[3-cyano-5-fluoro-6-methyl-1-(5-methylthiophen-2-yl)-1H-indol-2-yl]-N-[(2S)-1,1,1-trifluoropropan-2-yl]pyridine-3-sulfonamide, 6-[1-(5-chlorothiophen-2-yl)-3-cyano-5-fluoro-6-methyl-1H-indol-2-yl]-N-[(2S)-1,1,1-trifluoropropan-2-yl]pyridine-3-sulfonamide, 6-[3-cyano-1-(5-cyanothiophen-2-yl)-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(5-sulfamoylthiophen-2-yl)-1H-indol-2-yl]-N-[(2S)-1,1,1-trifluoropropan-2-yl]pyridine-3-sulfonamide, 6-[1-(5-acetylthiophen-2-yl)-3-cyano-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(4-methyl-1,3-thiazol-2-yl)-1H-indol-2-yl]-N-[(2S)-1,1,1-trifluoropropan-2-yl]pyridine-3-sulfonamide, 6-ethyl-5-fluoro-1-(5-methylpyridin-2-yl)-2-(5-{[(2S)-1,1,1-trifluoropropan-2-yl]sulfamoyl}pyridin-2-yl)-1H-indole-3-carboxamide, 6-ethyl-5-fluoro-1-(pyridin-3-yl)-2-(5-{[(2S)-1,1,1-trifluoropropan-2-yl]sulfamoyl}pyridin-2-yl)-1H-indole-3-carboxamide, 6-ethyl-5-fluoro-1-(pyrimidin-4-yl)-2-(5-{[(2S)-1,1,1-trifluoropropan-2-yl]sulfamoyl}pyridin-2-yl)-1H-indole-3-carboxamide, 1-(3-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, 1-(5-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, 1-(5-chloropyridin-3-yl)-6-ethyl-5-fluoro-2-(5-{[(2S)-1,1,1-trifluoropropan-2-yl]sulfamoyl}pyridin-2-yl)-1H-indole-3-carboxamide 6-ethyl-5-fluoro-1-(pyridin-4-yl)-2-(5-{[(2S)-1,1,1-trifluoropropan-2-yl]sulfamoyl}pyridin-2-yl)-1H-indole-3-carboxamide, 6-ethyl-5-fluoro-1-(pyridazin-3-yl)-2-(5-{[(2S)-1,1,1-trifluoropropan-2-yl]sulfamoyl}pyridin-2-yl)-1H-indole-3-carboxamide, 6-ethyl-5-fluoro-1-(5-methylpyrimidin-2-yl)-2-(5-{[(2S)-1,1,1-trifluoropropan-2-yl]sulfamoyl}pyridin-2-yl)-1H-indole-3-carboxamide, 1-(4-chloropyridin-2-yl)-6-ethyl-5-fluoro-2-(5-{[(2S)-1,1,1-trifluoropropan-2-yl]sulfamoyl}pyridin-2-yl)-1H-indole-3-carboxamide, 6-[1-(2-acetylthiophen-3-yl)-3-cyano-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(4-methylthiophen-3-yl)-1H-indol-2-yl]-N-[(2S)-1,1,1-trifluoropropan-2-yl]pyridine-3-sulfonamide, 6-[1-(2-chlorothiophen-3-yl)-3-cyano-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(5-methylthiophen-3-yl)-1H-indol-2-yl]-N-[(2S)-1,1,1-trifluoropropan-2-yl]pyridine-3-sulfonamide, 6-[5-fluoro-6-methyl-1-(1,3-oxazol-2-yl)-1H-indol-2-yl]-N-[(2S)-1,1,1-trifluoropropan-2-yl]pyridine-3-sulfonamide, 6-[1-(5-cyanofuran-2-yl)-5-fluoro-6-methyl-1H-indol-2-yl]-N-[(2S)-1,1,1-trifluoropropan-2-yl]pyridine-3-sulfonamide, 6-[3-cyano-1-(3,4-difluorophenyl)-6-ethyl-5-fluoro-1H-indol-2-yl]-N-[(2S)-1,1,1-trifluoropropan-2-yl]pyridine-3-sulfonamide, 6-[1-(3-chloro-4-fluorophenyl)-3-cyano-6-ethyl-5-fluoro-1H-indol-2-yl]-N-[(2S)-1,1,1-trifluoropropan-2-yl]pyridine-3-sulfonamide, 6-[3-cyano-1-(3-cyanofuran-2-yl)-5-fluoro-6-methyl-1H-indol-2-yl]-N-[(2S)-1,1,1-trifluoropropan-2-yl]pyridine-3-sulfonamide, 6-[3-cyano-5-fluoro-6-methyl-1-(1,3oxazol-2-yl)-1H-indol-2-yl]-N-[(2S)-1,1,1-trifluoropropan-2-yl]pyridine-3-sulfonamide, 6-[3-cyano-1-(4-cyano-1,3-oxazol-2-yl)-5fluoro-6-methyl-1H-indol-2-yl]-N-[(2S)-1,1,1-trifluoropropan-2-yl]pyridine-3sulfonamide, 6-[3-cyano-6-ethyl-5-fluoro-1-(2-fluorophenyl)-1H-indol-2-yl]-N-[(2S)-1,1,1-trifluoropropan-2-yl]pyridine-3-sulfonamide, 6-{3-cyano-6-[(1,1-dideuterium)ethyl]-5-fluoro-1-(pyrimidin-2-yl)-1H-indol-2-yl}-N-[(2S)-1,1,1-trifluoropropan-2-yl]pyridine-3-sulfonamide, 6-{3-cyano-6-[(1,1-D)ethyl]-5-fluoro-1-(pyrimidin-2-yl]-N-[(2S)-1,1,1-trifluoro(2-deuterium)propan-2-yl]pyridine-3-sulfonamide, 6-[3-cyano-6-cyclopropyl-4-fluoro-1-(pyrimidin-2-yl)-1H-indol-2-yl]-N-(1,1,1-trifluoro-2-methylpropan-2-yl)pyridine-3-sulfonamide, 6-[3-cyano-5-fluoro-6-(1,1,1-trideuterium)methyl-1-(pyrimidin-2-yl)-1H-indol-2-yl]-N-[(2S)-1,1,1-trifluoro(2-deuterium)propan-2-yl]pyridine-3-sulfonamide, N-tert-butyl-6-(3-cyano-5-fluoro-6-methyl-1-phenyl-1H-indol-2-yl)pyridine-3-sulfonamide, 2-[5-(tert-butylsulfamoyl)pyridin-2-yl]-6-ethyl-5-fluoro-1-phenyl-1H-indole-3-carboxamide, 6-(3-cyano-1-cyclobutyl-5-fluoro-6-methyl-1H-indol-2-yl)-N-[(2-deuterium)propan-2-yl]pyridine-3-sulfonamide, 6-(3-cyano-1-cyclobutyl-5-fluoro-6-methyl-1H-indol-2-yl)-N-[(2S)-1,1,1-trifluoro(2-deuterium)propan-2-yl]pyridine-3-sulfonamide, 6-[3-cyano-1-cyclobutyl-5-fluoro-6-(1,1,1-trideuterium)methyl-1H-indol-2-yl]-N-[(2S)-1,1,1-trifluoro(2-deuterium)propan-2-yl]pyridine-3-sulfonamide, 2-[5-(tert-butylsulfamoyl)pyridin-2-yl]-1-cyclohexyl-5-fluoro-6-methyl-1H-indole-3-carboxamide, 2-[5-(tert-butylsulfamoyl)pyridin-2-yl]-5-fluoro-6-methyl-1-phenyl-1H-indole-3-carboxamide, N-tert-butyl-6-(3-cyano-6-cyclopropyl-5-fluoro-1-phenyl-1H-indol-2-yl)pyridine-3-sulfonamide, 6-[3-cyano-1-(cyclopropylmethyl)-5-fluoro-6-(1,1,1-trideuterium)methyl-1H-indol-2-yl]-N-[(2-deuterium)propan-2-yl]pyridine-3-sulfonamide.

10. The compound of claim 9, wherein the compound or a free acid, free base, salt, isotopologue, racemate, enantiomer, diastereomer, or stereoisomer form thereof is selected from:

6-(3-cyano-1-cyclobutyl-6-cyclopropyl-1H-indol-2-yl)-N-(propan-2-yl)pyridine-3-sulfonamide, 6-[3-cyano-1-cyclobutyl-6-(difluoromethoxy)-1H-indol-2-yl]-N-(1,3-difluoropropan-2-yl)pyridine-3-sulfonamide, 6-(3-cyano-1-cyclobutyl-6-cyclopropyl-1H-indol-2-yl)-N-(1,3-difluoropropan-2-yl)pyridine-3-sulfonamide, 6-(3-cyano-1-cyclopentyl-6-methyl-1H-indol-2-yl)-N-(1,3-difluoropropan-2-yl)pyridine-3-sulfonamide, 6-[3-cyano-1-cyclobutyl-6-(difluoromethoxy)-1H-indol-2-yl]-N-(propan-2-yl)pyridine-3-sulfonamide, 6-(3-cyano-1-cyclobutyl-6-cyclopropyl-5-fluoro-1H-indol-2-yl)-N-(1,3-difluoropropan-2-yl)pyridine-3-sulfonamide, 6-(3-cyano-1-cyclobutyl-5-fluoro-6-methyl-1H-indol-2-yl)-N-(1,3-difluoropropan-2-yl)pyridine-3-sulfonamide, 6-(3-cyano-1-cyclopentyl-6-methyl-1H-indol-2-yl)-N-[1-(trifluoromethyl)cyclopropyl]pyridine-3-sulfonamide, 6-[3-cyano-1-cyclobutyl-6-(difluoromethoxy)-1H-indol-2-yl]-N-[(2S)-1,1,1-trifluoropropan-2-yl]pyridine-3-sulfonamide, 6-(3-cyano-1-cyclopentyl-6-methyl-1H-indol-2-yl)-N-(1,1,1-trifluoro-2-methylpropan-2-yl)pyridine-3-sulfonamide, 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, 6-(3-cyano-1-cyclopentyl-5-fluoro-6-methyl-1H-indol-2-yl)-N-(1,3-difluoropropan-2-yl)pyridine-3-sulfonamide, 6-(3-cyano-1-cyclopentyl-5-fluoro-6-methyl-1H-indol-2-yl)-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2R)-1,1,1-trifluoropropan-2-yl]pyridine-3-sulfonamide, 6-(3-cyano-1-cyclobutyl-7-fluoro-6-methyl-1H-indol-2-yl)-N-[(2S)-1,1,1-trifluoropropan-2-yl]pyridine-3-sulfonamide, 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, 6-(3-cyano-1-cyclobutyl-5,7-difluoro-6-methyl-1H-indol-2-yl)-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, 6-[3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, 6-(3-cyano-1-cyclobutyl-6-ethyl-5-fluoro-1H-indol-2-yl)-N-[(2S)-1,1,1-trifluoropropan-2-yl]pyridine-3-sulfonamide, 6-[3-cyano-6-cyclopropyl-1-(pyrimidin-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(pyridine-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, 2-[5-(tert-butylsulfamoyl)pyridin-2-yl]-1-cyclopentyl-5-fluoro-6-methyl-1H-indole-3-carboxamide, 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, 1-cyclohexyl-5-fluoro-6-methyl-2-(5-{[(2R)-1,1,1-trifluoropropan-2-yl]sulfamoyl}pyridin-2-yl)-1H-indole-3-carboxamide, 6-[3-cyano-5-fluoro-6-methyl-1-(tetrahydro-2H-pyran-4-yl)-1H-indol-2-yl]-N-[(2R)-1,1,1-trifluoropropan-2-yl]pyridine-3-sulfonamide, 6-[3-cyano-1-cyclobutyl-6-(difluoromethoxy)-5-fluoro-4-methyl-1H-indol-2-yl]-N-[(2S)-1,1,1-trifluoropropan-2-yl]pyridine-3-sulfonamide, 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2S)-1,1,1-trifluorobutan-2-yl]pyridine-3-sulfonamide, 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, 6-[3-cyano-6-(difluoromethoxy)-5-fluoro-1-(2-methylpropyl)-1H-indol-2-yl]-N-[(2S)-1,1,1-trifluoropropan-2-yl]pyridine-3-sulfonamide, 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide, or 6-[3-cyano-5-fluoro-6-methyl-1-(1,3,4-thiadiazol-2-yl)-1H-indol-2-yl]-N-[(2S)-1,1,1-trifluoropropan-2-yl]pyridine-3-sulfonamide.

11. The compound of claim 10, wherein the compound or free acid, free base, salt, isotopologue, racemate, enantiomer, diastereomer, or stereoisomer form thereof is selected from:

6-[3-cyano-1-cyclobutyl-6-(difluoromethoxy)-1H-indol-2-yl]-N-[(2S)-1,1,1-trifluoropropan-2-yl]pyridine-3-sulfonamide, 6-[3-cyano-6-(difluoromethoxy)-1-(pyridin-2-yl)-1H-indol-2-yl]-N-[(2S)-1,1,1-trifluoropropan-2-yl]pyridine-3-sulfonamide, 6-(3-cyano-1-cyclopentyl-5-fluoro-6-methyl-1H-indol-2-yl)-N-[(2R)-1,1,1-trifluoropropan-2-yl]pyridine-3-sulfonamide, 6-[3-cyano-6-(difluoromethoxy)-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyridin-2-yl)-1H-indol-2-yl]-N-[(2S)-1,1,1-trifluoropropan-2-yl]pyridine-3-sulfonamide, 6-[3-cyano-1-cyclobutyl-6-(difluoromethoxy)-5-fluoro-1H-indol-2-yl]-N-[(2S)-1,1,1-trifluoropropan-2-yl]pyridine-3-sulfonamide, 6-[3-cyano-5-fluoro-1-(pyrimidin-2-yl)-1H-indol-2-yl]-N-[(2S)-1,1,1-trifluoropropan-2-yl]pyridine-3-sulfonamide, 6-[3-cyano-5-fluoro-6-methyl-1-(pyrimidin-2-yl)-1H-indol-2-yl]-N-[(2S)-1,1,1-trifluoropropan-2-yl]pyridine-3-sulfonamide, 6-[3-cyano-6-cyclopropyl-1-(pyrimidin-2-yl)-1H-indol-2-yl]-N-[(2S)-1,1,1-trifluoropropan-2-yl]pyridine-3-sulfonamide, 6-[3-cyano-6-(difluoromethoxy)-5-fluoro-1-(pyrimidin-2-yl)-1H-indol-2-yl]-N-[(2S)-1,1,1-trifluoropropan-2-yl]pyridine-3-sulfonamide, 6-[3-cyano-6-ethyl-5-fluoro-1-(pyrimidin-2-yl)-1H-indol-2-yl]-N-[(2S)-1,1,1-trifluoropropan-2-yl]pyridine-3-sulfonamide, 6-[3-cyano-6-cyclopropyl-5-fluoro-1-(pyrimidin-2-yl)-1H-indol-2-yl]-N-[(2S)-1,1,1-trifluoropropan-2-yl]pyridine-3-sulfonamide, 6-ethyl-5-fluoro-1-(pyrimidin-2-yl)-2-(5-{[(2S)-1,1,1-trifluoropropan-2-yl]sulfamoyl}pyridin-2-yl)-1H-indole-3-carboxamide, or 6-[3-cyano-5-fluoro-6-methyl-1-(1,3-thiazol-4-yl)-1H-indol-2-yl]-N-[(2S)-1,1,1-trifluoropropan-2-yl]pyridine-3-sulfonamide.

12. A method for inhibiting HCV viral replication in replicon-containing cells comprising the steps of:
1) culturing replicon-containing cells with a compound of claim 1 for a period of time sufficient to reduce the replicon RNA value, and
2) comparing the replicon RNA value in replicon-containing cells cultured with the compound of claim 1 with the replicon RNA value in replicon-containing cells that have not been cultured with the compound of claim 1; wherein the replicon is a hepatitis C virus replicon.

13. A method for treating a hepatitis C viral infection in a subject in need thereof comprising administering an effective amount of a compound of claim 1 to the subject.

14. The method of claim 13, wherein the effective amount of a compound of claim 1 or a form thereof is in a range of from about 0.001 mg/Kg/day to about 500 mg/Kg/day.

15. A pharmaceutical composition comprising an effective amount of a compound of claim 1 or a form thereof in admixture with a pharmaceutically acceptable excipient.

* * * * *